US012790388B2

(12) United States Patent
Agrawal et al.

(10) Patent No.: US 12,790,388 B2
(45) Date of Patent: Nov. 10, 2026

(54) ANTI-HUMAN PAC1 ANTIBODIES OR ANTIGEN-BINDING FRAGMENTS THEREOF AND METHODS OF USE THEREOF FOR INHIBITING VASODILATION AND AMELIORATING A HEADACHE CONDITION

(71) Applicant: AMGEN INC., Thousand Oaks, CA (US)

(72) Inventors: Neeraj Jagdish Agrawal, Natick, MA (US); Kevin Graham, Thousand Oaks, CA (US); Agnes Eva Hamburger, Newbury Park, CA (US); Christopher Mohr, Newbury Park, CA (US); Derek E. Piper, Santa Clara, CA (US); Kenneth William Walker, Newbury Park, CA (US); Zhulun Wang, Los Altos, CA (US); Cen Xu, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 18/545,688

(22) Filed: Dec. 19, 2023

(65) Prior Publication Data

US 2024/0150448 A1 May 9, 2024

Related U.S. Application Data

(60) Continuation of application No. 17/558,032, filed on Dec. 21, 2021, now Pat. No. 11,891,435, which is a (Continued)

(51) Int. Cl.

| | |
|---|---|
| ***C07K 16/00*** | (2006.01) |
| ***A61K 38/22*** | (2006.01) |
| ***A61K 39/00*** | (2006.01) |
| ***A61K 39/395*** | (2006.01) |
| ***A61K 49/00*** | (2006.01) |

(Continued)

(52) U.S. Cl.

CPC .......... *C07K 16/18* (2013.01); *A61K 38/2278* (2013.01); *A61P 25/06* (2018.01); *C07K 16/2869* (2013.01); *A61K 38/1796* (2013.01); *A61K 38/22* (2013.01); *A61K 2039/505* (2013.01); *A61K 2039/545* (2013.01); *A61K 47/6843* (2017.08); *A61K 47/6849* (2017.08); *A61K 51/10* (2013.01); *A61K 2300/00* (2013.01); *C07K 14/47* (2013.01); *C07K 14/575* (2013.01); *C07K 14/57563* (2013.01); *C07K 14/72* (2013.01); *C07K 16/00* (2013.01); *C07K 16/26* (2013.01); *C07K 2317/21* (2013.01); *C07K 2317/24* (2013.01); *C07K 2317/31* (2013.01); *C07K 2317/33* (2013.01); *C07K 2317/34* (2013.01); *C07K 2317/51* (2013.01); *C07K 2317/515* (2013.01); *C07K 2317/52* (2013.01); *C07K 2317/522* (2013.01); *C07K 2317/56* (2013.01); *C07K 2317/565* (2013.01); *C07K 2317/622* (2013.01); *C07K 2317/70* (2013.01); *C07K 2317/72* (2013.01); *C07K 2317/76* (2013.01); *C07K 2317/90* (2013.01); *C07K 2317/92* (2013.01); *C12N 2501/30* (2013.01); *G01N 33/6854* (2013.01); *G01N 33/6896* (2013.01); *G01N 33/74* (2013.01); *G01N 2333/575* (2013.01); *G01N 2333/5757* (2013.01); *Y02A 50/30* (2018.01)

(58) Field of Classification Search

CPC ............ C07K 2317/76; C07K 2317/24; C07K 2317/92; C07K 16/2869; C07K 2317/565; C07K 2317/21; C07K 16/18; C07K 2317/622; C07K 2317/56; C07K 2317/35; C07K 2317/524; C07K 2317/526; C07K 2317/55; C07K 2317/569; C07K 14/47; C07K 14/575; C07K 14/705; C07K 14/70503; C07K 14/72; C07K 14/4702; C07K 14/52; A61K 39/3955; A61K 48/00; A61K 38/22; A61K 38/17; A61K 47/6803; A61P 25/06; A61P 25/04; A61P 25/28; A61P 31/00

See application file for complete search history.

(56) References Cited

U.S. PATENT DOCUMENTS

| | | | |
|---|---|---|---|
| 5,486,472 | A | 1/1996 | Suzuki |
| 5,858,787 | A | 1/1999 | Onda |

(Continued)

FOREIGN PATENT DOCUMENTS

| | | | |
|---|---|---|---|
| CN | 102939303 | A | 2/2013 |
| EP | 0522159 | B1 | 12/2001 |

(Continued)

OTHER PUBLICATIONS

Azimova et al., “Innovative methods of migraine treatment,” RJM, 29: 27-30 (2015).

(Continued)

*Primary Examiner* — Chang-Yu Wang
(74) *Attorney, Agent, or Firm* — Angela L. Purcell

(57) ABSTRACT

The present invention relates to neutralizing antibodies of the human pituitary adenylate cyclase activating polypeptide type I receptor (PAC1) and pharmaceutical compositions comprising such antibodies. Methods of treating or preventing headache conditions, such as migraine and cluster headache, using the neutralizing antibodies are also described.

20 Claims, 15 Drawing Sheets

Specification includes a Sequence Listing.

Related U.S. Application Data continuation of application No. 16/919,032, filed on Jul. 1, 2020, now Pat. No. 11,248,043, which is a division of application No. 16/246,326, filed on Jan. 11, 2019, now Pat. No. 10,738,110.

(60) Provisional application No. 62/617,157, filed on Jan. 12, 2018.

(51) Int. Cl.

| | |
|---|---|
| ***A61P 25/06*** | (2006.01) |
| ***C07K 16/18*** | (2006.01) |
| ***C07K 16/28*** | (2006.01) |
| *A61K 38/17* | (2006.01) |
| *A61K 47/68* | (2017.01) |
| *A61K 51/10* | (2006.01) |
| *C07K 14/47* | (2006.01) |
| *C07K 14/575* | (2006.01) |
| *C07K 14/72* | (2006.01) |
| *C07K 16/26* | (2006.01) |
| *G01N 33/68* | (2006.01) |
| *G01N 33/74* | (2006.01) |

(56) References Cited

U.S. PATENT DOCUMENTS

| | | | | |
|---|---|---|---|---|
| 5,892,004 | A | 4/1999 | Ohtaki | |
| 5,973,117 | A | 10/1999 | Onda | |
| 6,017,533 | A | 1/2000 | Moro | |
| 6,242,563 | B1 | 6/2001 | Dong | |
| 6,399,316 | B1 | 6/2002 | Onda | |
| 6,462,016 | B1 | 10/2002 | Wakita | |
| 8,741,291 | B2 | 6/2014 | Bhat | |
| 8,986,697 | B2 | 3/2015 | Ma | |
| 9,181,349 | B2 | 11/2015 | Baurin | |
| 9,365,653 | B2 * | 6/2016 | Xu | C07K 16/2869 |
| 9,546,203 | B2 * | 1/2017 | Kannan | A61P 37/02 |
| 9,676,851 | B2 * | 6/2017 | Xu | C07K 16/28 |
| 9,822,178 | B2 * | 11/2017 | Xu | A61P 25/06 |
| 10,053,507 | B2 * | 8/2018 | Xu | C07K 16/28 |
| 10,738,110 | B2 * | 8/2020 | Agrawal | C07K 16/2869 |
| 10,934,362 | B2 * | 3/2021 | Kannan | C07K 16/18 |
| 11,248,043 | B2 * | 2/2022 | Agrawal | A61P 25/06 |
| 11,891,435 | B2 * | 2/2024 | Agrawal | A61P 25/06 |
| 2002/0155533 | A1 | 10/2002 | Onda | |
| 2002/0182729 | A1 | 12/2002 | DiCicco-Bloom | |
| 2005/0129687 | A1 | 6/2005 | Margaret | |
| 2005/0142133 | A1 | 6/2005 | Lazar | |
| 2006/0062785 | A1 | 3/2006 | Freson | |
| 2006/0160996 | A9 | 7/2006 | Lazar | |
| 2007/0054843 | A1 | 3/2007 | Yeomans | |
| 2009/0215895 | A1 | 8/2009 | Ferrante | |
| 2009/0291900 | A1 | 11/2009 | Yeomans | |
| 2010/0112601 | A1 | 5/2010 | Shirakawa | |
| 2011/0021426 | A1 | 1/2011 | Toll | |
| 2013/0196908 | A1 | 8/2013 | Toll | |
| 2015/0010560 | A1 * | 1/2015 | Xu | C07K 16/2869 435/69.6 |
| 2016/0039939 | A1 * | 2/2016 | Xu | C07K 16/28 435/254.2 |
| 2017/0247451 | A1 * | 8/2017 | Xu | C07K 16/28 |
| 2017/0306033 | A1 * | 10/2017 | Kannan | A61P 25/06 |
| 2018/0085458 | A1 | 3/2018 | Nyborg | |
| 2018/0094055 | A1 * | 4/2018 | Xu | C07K 16/2869 |
| 2018/0362645 | A1 * | 12/2018 | Xu | C07K 16/28 |
| 2019/0218279 | A1 * | 7/2019 | Agrawal | A61K 38/2278 |
| 2021/0017261 | A1 * | 1/2021 | Agrawal | A61P 25/06 |
| 2022/0195022 | A1 * | 6/2022 | Agrawal | A61K 38/2278 |
| 2022/0363770 | A1 * | 11/2022 | Chen | C07K 16/28 |

FOREIGN PATENT DOCUMENTS

| | | | |
|---|---|---|---|
| EP | 2048162 | A1 | 4/2009 |
| EP | 1098906 | B1 | 11/2009 |
| EP | 1928484 | B1 | 2/2010 |
| EP | 2161282 | A1 | 3/2010 |
| JP | 2008536855 | A | 9/2008 |
| WO | 0005260 | A2 | 2/2000 |
| WO | 2004062684 | A2 | 7/2004 |
| WO | 2004099249 | A2 | 11/2004 |
| WO | 2005073164 | A1 | 8/2005 |
| WO | 2006113308 | A1 | 10/2006 |
| WO | 2007022070 | A2 | 2/2007 |
| WO | 2007025249 | A2 | 3/2007 |
| WO | 2009033489 | A2 | 3/2009 |
| WO | 2010066125 | A1 | 6/2010 |
| WO | 2011017122 | A1 | 2/2011 |
| WO | 2011076781 | A1 | 6/2011 |
| WO | 2012125850 | A1 | 9/2012 |
| WO | 2013093809 | A1 | 6/2013 |
| WO | 2013177062 | A2 | 11/2013 |
| WO | 2014144632 | A2 | 9/2014 |
| WO | 2016044224 | A1 | 3/2016 |
| WO | 2016168757 | A1 | 10/2016 |
| WO | 2016168760 | A1 | 10/2016 |
| WO | 2016168762 | A2 | 10/2016 |
| WO | 2016168768 | A2 | 10/2016 |
| WO | 2017106578 | A1 | 6/2017 |

OTHER PUBLICATIONS

Bostrom et al., "Improving antibody binding affinity and specificity for therapeutic development," Methods Mol Biol., 525: 353-376 (2009).

Gonzales et al., "Minimizing the Immunogenicity of Antibodies for Clinical Application," Tumor Biol., 26(1): 31-43 (2005).

ISR and Written Opinion for PCT/US2016/067054 dated May 17, 2017.

Russian Patent Office, Office Action in RU 2020126721 dated Feb. 1, 2022.

Sela-Culang et al., "The structural basis of antibody-antigen recognition," Frontiers in Immunology, vol. 4(302), pp. 1-13 (2013).

Wark et al., "Latest technologies for the enhancement of antibody affinity," Advanced Drug Delivery Reviews, 58 (5-6): 657-670 (2006).

Yarilin A. A., "V-domains of immunoglobulins. Antigen-binding sites", Osnovy immunologii, Moskva, Medicina, pp. 171-174 (1999).

Alaoui-Ismalli and Falb, "Design of second generation therapeutic recombinant bone morphogenetic proteins", Cytokine & Growth Factors Rev., vol. 20, pp. 501-507 (2009).

Ashina, Messoud, "Migraine", New Engl. J. Med., vol. 383, pp. 1866-1876 (2020).

Bee et al., "Determining the Binding Affinity of Therapeutic Monoclonal Antibodies towards Their Native Unpurified Antigens in Human Serum", PLOS ONE, vol. 8 (11:e80501), pp. 1-14 (2013).

Bendig, Mary M., "Humanization of rodent monoclonal antibodies by CDR grafting", Methods: A Companion to Methods in Enzymology, vol. 9, pp. 83-93 (1995).

Bourgault et al., "Molecular and conformational determinants of pituitary adenylate cyclase-activating polypeptide (PACAP) for activation of the PAC1 receptor", J. Med. Chem., vol. 52 (10), pp. 3308-3316 (2009).

Bowie et al., "Deciphering the message in protein sequences: tolerance to amino acid substitutions", Science, vol. 247 (4948), pp. 1306-1310 (1990).

Burgess et al., "Possible dissociation of the heparin-binding and mitogenic activities of heparin-binding (acidic fibroblast) growth factor-1 from its receptor-binding activities by site-directed mutagenesis of a single lysine residue", J. Cell Biol., vol. 111, pp. 2129-2138 (1990).

Casset et al., "A peptide mimetic of an anti-CD4 monoclonal antibody by rational design", Biochem. Biophys. Res. Commun., vol. 307 (1), pp. 198-205 (2003).

Chen et al., "Selection and analysis of an optimized anti-VEGF antibody: crystal structure of an affinity-matured Fab in complex with antigen," J. Mol. Biol., vol. 293 (4), pp. 865-881 (1999).

(56) References Cited

OTHER PUBLICATIONS

Colman, "Effects of Amino Acid Sequence Changes on Antibody-Antigen Interactions", Res. Immunol., vol. 145 (1), pp. 33-36 (1994).
De Pascalis et al., "Grafting of 'abbreviated' complementarity-determining regions containing specificity-determining residues essential for ligand contact to engineer a less immunogenic humanized monoclonal antibody", J. Immunol., vol. 169 (6), pp. 3076-3084 (2002).
Drake et al., "Biacore surface matrix effects on the binding kinetics and affinity of an antigen/antibody complex," Anal. Biochem., vol. 429 (1), pp. 58-69 (2012).
Drake et al., "Characterizing high-affinity antigen/antibody complexes by kinetic- and equilibrium-based methods," Anal. Biochem., vol. 328 (1), pp. 35-43 (2004).
Goetzl et al., "PACAP and VIP Receptors", pp. 2249-2253 (2015).
Guirland et al., "Direct CAMP Signaling through G-Protein-Coupled Receptors Mediates Growth Cone Attraction Induced by Pituitary Adenylate Cyclase-Activating Polypeptide", J. Neurosci., vol. 23 (6), pp. 2274-2283 (2003).
Guo et al., "Protein tolerance to random amino acid change", Proc. Natl. Acad, Sci., vol. 101 (25), pp. 9205-9210 (2004).
Heinrich et al., "Comparison of the results obtained by ELISA and surface plasmon resonance for the determination of antibody affinity", J. Immunol. Methods, vol. 352 (1-2), pp. 13-22 (2010).
Holmes et al., "Structural consequences of humanizing an antibody", J. Immunol., vol. 158, pp. 2192-2201 (1997).
Honegger et al., "Yet Another Numbering Scheme for Immunoglobulin Variable Domains: An Automatic Modeling and Analysis Tool", J. Mol. Biol., vol. 309 (3), pp. 657-670 (2001).
Inooka et al., "Conformation of a peptide ligand bound to its G-protein coupled receptor," Nat. Struct. Biol., vol. 8 (2), pp. 161-165 (2001).
International Search Report and Written Opinion for PCT/US2014/029128 dated Oct. 8, 2014.
International Search Report and Written Opinion for PCT/US2019/013227 dated Jun. 28, 2019.
Jacobsen et al., "Engineering an IgG scaffold lacking effector function with optimized developability", J. Biol. Chem., vol. 292 (5), pp. 1865-1875 (2017).
Kunik et al., "Structural consensus among antibodies defines the antigen binding site," PLoS Comput Biol., vol. 8 (2; e1002388), pp. 1-12 (2012).
Laburthe, Marc et al., "Class II G protein-coupled receptors for VIP and PACAP: structure, models of activation and pharmacology", Peptides, vol. 28, pp. 1631-1639 (2007).
Lerner et al., "Maxadilan, a PAC1 receptor agonist from sand flies", Peptides, vol. 28 (9), pp. 1651-1654 (2007).
Maccallum et al., "Antibody-antigen Interactions: Contact Analysis and Binding Site Topography", J. Mol. Biol., vol. 262 (5), pp. 732-745 (1996).
Moretti et al., "PACAP and type I PACAP receptors in human prostate cancer tissue", Ann N Y Acad Sci., vol. 1070, pp. 440-449 (2006).
Moro et al., "Functional characterization of structural alterations in the sequence of the vasodilatory peptide maxadilan yields a pituitary adenylate cyclase-activating peptide type 1 receptor-specific antagonist", J. Biol. Chem., vol. 274 (33), pp. 23103-23110 (1999).
Paul, "Structure and Function of Immunoglobulins", Fundamental Immunology, 3rd ed., Raven Press, Chapter 9, pp. 292-295 (1993).
Pawson and Nash, "Assembly of cell regulatory systems through protein interaction domains", Science, vol. 300, pp. 445-452 (2003).
Pérez De La Lastra et al., "Epitope mapping of 10 monoclonal antibodies against the pig analogue of human membrane cofactor protein (MCP)", Immunol., vol. 96 (4), pp. 663-670 (1999).
Pietrobon and Moskowitz, "Pathophysiology of Migraine", Ann. Rev. Physiol., vol. 75, pp. 365-391 (2013).
Rudikoff et al., "Single Amino Acid Substitution Altering Antigen-Binding Specificity", Proc. Natl. Acad. Sci. USA., vol. 79, pp. 1979-1983 (1982).
Saldanha J. W., "Molecular Engineering I: Humanization", Handbook of Therapeutic Antibodies, Ch. 6, pp. 119-144 (2007).
Sazinsky et al., "Aglycosylated Immunoglobulin G1 Variants Productively Engage Activating Fc Receptors", Proc. Natl. Acad. Sci. USA, vol. 105 (51), pp. 20167-20172 (2008).
Schulz et al., "Immunocytochemical identification of VPAC1, VPAC2, and PAC1 receptors in normal and neoplastic human tissues with subtype-specific antibodies," Clin. Cancer Res., vol. 10 (24), pp. 8235-8242 (2004).
Schwarzhoff et al., "Specific monoclonal antibodies neutralize the action of PACAP 1-27 or PACAP 1-38 on intestinal muscle strips in vitro," Regul. Pept., vol. 55 (1), pp. 57-66 (1995).
Schytz et al., "PACAP38 induces migraine-like attacks in patients with migraine without aura," Brain, vol. 132, pp. 16-25 (2009).
Schytz et al., "The PACAP receptor: a novel target for migraine treatment," Neurotherap., vol. 7 (2), pp. 191-196 (2010).
Silberstein, Stephen, "Current management: migraine headache", CNS Spectrums, vol. 22, pp. 4-12 (2017).
Suzuki et al., "Production of Immunoreactive Pituitary Adenylate Cyclase Activating Polypeptide (PACAP) by Human Neuroblastoma Cells, IMR-32: Detection and Characterization with Monoclonal and Polyclonal Antibodies against Different Epitopes of Pacap", J. Biochem., vol. 113 (5), pp. 549-556 (1993).
Syed et al., "Pituitary Adenylate Cyclase-Activating Polypeptide (PACAP) Potently Dilates Middle Meningeal Arteries: Implications for Migraine", J. Mol. Neurosci., vol. 48 (3), pp. 574-583 (2012).
Tuka et al., "Peripheral and central alterations of pituitary adenylate cyclase activating polypeptide-like immunoreactivity in the rat in response to activation of the trigeminovascular system", Peptides, vol. 33 (2), pp. 307-316 (2012).
Vajdos et al., "Comprehensive Functional Maps of the Antigen-binding Site of an Anti-ErbB2 Antibody Obtained with Shotgun Scanning Mutagenesis", J Mol Biol., vol. 320 (2), pp. 415-428 (2002).
Vaudry et al., "Pituitary adenylate cyclase-activating polypeptide and its receptors: 20 years after the discovery", Pharmacol. Rev., vol. 61 (3), pp. 283-357 (2009).
Vaudry et al., "Pituitary adenylate cyclase-activating polypeptide and its receptors: from structure to functions", Pharmacol Rev., vol. 52 (2), pp. 269-324 (2000).
Wu et al., "Humanization of a murine monoclonal antibody by simultaneous optimization of framework and CDR residues," J. Mol. Biol., vol. 294 (1), pp. 151-162 (1999).
Zagami et al., "Pituitary adenylate cyclase activating polypeptide and migraine", Ann. Clin. Transl. Neurol., vol. 1 (12), pp. 1036-1040 (2014).
Zvirbliene et al., "Production and characterization of monoclonal antibodies to pituitary adenylate cyclase activating polypeptide type I receptor", Hybridoma, vol. 18 (4), pp. 335-342 (1999).
Holm et al., "Functional mapping and single chain construction of the anti-cytokeratin 8 monoclonal antibody TS1", Mol. Immunol., vol. 44(6), pp. 1075-1084(2007).

* cited by examiner

SEQUENCE LISTING

```
Sequence total quantity: 569
SEQ ID NO: 1            moltype = AA  length = 468
FEATURE                 Location/Qualifiers
REGION                  1..468
                        note = Human PAC1
source                  1..468
                        mol_type = protein
                        organism = synthetic construct
SEQUENCE: 1
MAGVVHVSLA ALLLLPMAPA MHSDCIFKKE QAMCLEKIQR ANELMGFNDS SPGCPGMWDN  60
ITCWKPAHVG EMVLVSCPEL FRIFNPDQVW ETETIGESDF GDSNSLDLSD MGVVSRNCTE  120
DGWSEPFPHY FDACGFDEYE SETGDQDYYY LSVKALYTVG YSTSLVTLTT AMVILCRFRK  180
LHCTRNFIHM NLFVSFMLRA ISVFIKDWIL YAEQDSNHCF ISTVECKAVM VFFHYCVVSN  240
YFWLFIEGLY LFTLLVETFF PERRYFYWYT IIGWGTPTVC VTVWATLRLY FDDTGCWDMN  300
DSTALWWVIK GPVVGSIMVN FVLFIGIIVI LVQKLQSPDM GGNESSIYLR LARSTLLLIP  360
LFGIHYTVFA FSPENVSKRE RLVFELGLGS FQGFVVAVLY CFLNGEVQAE IKRKWRSWKV  420
NRYFAVDFKH RHPSLASSGV NGGTQLSILS KSSSQIRMSG LPADNLAT              468

SEQ ID NO: 2            moltype = AA  length = 226
FEATURE                 Location/Qualifiers
REGION                  1..226
                        note = Human PAC1 ECD
source                  1..226
                        mol_type = protein
                        organism = synthetic construct
SEQUENCE: 2
QVQLVESGGG VVQPGRSLRL SCAASGFTFS RFAMHWVRQA PGKGLEWVAV ISYDGGNKYY  60
AESVKGRFTI SRDNSKNTLY LQMNSLRAED TALFYCARGY DVLTGYPDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSNFGTQT YTCNVDHKPS NTKVDKTVER KGDEVD                226

SEQ ID NO: 3            moltype = AA  length = 214
FEATURE                 Location/Qualifiers
REGION                  1..214
                        note = Human PAC1 ECD
source                  1..214
                        mol_type = protein
                        organism = synthetic construct
SEQUENCE: 3
DIQLTQSPSF LSASVGDRVT ITCRASQSIG RSLHWYQQKP GKAPKLLIKY ASQSLSGVPS  60
RFSGSGSGTE FTLTISSLQP EDFATYYCHQ SSRLPFTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                            214

SEQ ID NO: 4            moltype = AA  length = 105
FEATURE                 Location/Qualifiers
REGION                  1..105
                        note = Human PAC1 ECD
source                  1..105
                        mol_type = protein
                        organism = synthetic construct
SEQUENCE: 4
GSMAHSDGIF KKEQAMCLEK IQRANELMGF NDSSPGCPGM WDNITCWKPA HVGEMVLVSC  60
PELFRIFNPD QDMGVVSRNC TEDGWSEPFP HYFDACGFDE YESET                 105

SEQ ID NO: 5            moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 5
RASQSVGRSL H                                                     11

SEQ ID NO: 6            moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 6
RASQSIGRSL H                                                     11

SEQ ID NO: 7            moltype = AA  length = 11
FEATURE                 Location/Qualifiers
REGION                  1..11
```

```
                        note = Synthetic polypeptide
source                  1..11
                        mol_type = protein
                        organism = synthetic construct
SEQUENCE: 7
RASKSVGRSL H                                                   11

SEQ ID NO: 8            moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 8
RASQSVWRSL H                                                   11

SEQ ID NO: 9            moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 9
RASQSVGRNL H                                                   11

SEQ ID NO: 10           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 10
RASKSVWRSL H                                                   11

SEQ ID NO: 11           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 11
RASKSVGRNL H                                                   11

SEQ ID NO: 12           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 12
RASKSVGWSL H                                                   11

SEQ ID NO: 13           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 13
RASKSVGYSL H                                                   11

SEQ ID NO: 14           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 14
RASKAVGWSL H                                                   11

SEQ ID NO: 15           moltype = AA  length = 11
FEATURE                 Location/Qualifiers
```

```
REGION                  1..11
                        note = Synthetic polypeptide
source                  1..11
                        mol_type = protein
                        organism = synthetic construct
SEQUENCE: 15
RASKSVGQSL H                                                        11

SEQ ID NO: 16           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 16
RASRSVGLAL H                                                        11

SEQ ID NO: 17           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 17
RASQSISRYL N                                                        11

SEQ ID NO: 18           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 18
RASQYIVRYL N                                                        11

SEQ ID NO: 19           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 19
RASQTIVRYL N                                                        11

SEQ ID NO: 20           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 20
RASQKIARYL V                                                        11

SEQ ID NO: 21           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 21
RASQPIAQYL N                                                        11

SEQ ID NO: 22           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 22
RASQPISRYL S                                                        11

SEQ ID NO: 23           moltype = AA  length = 11
```

```
FEATURE                Location/Qualifiers
REGION                 1..11
                       note = Synthetic polypeptide
source                 1..11
                       mol_type = protein
                       organism = synthetic construct
SEQUENCE: 23
RASQQIARYL N                                                        11

SEQ ID NO: 24          moltype = AA  length = 11
FEATURE                Location/Qualifiers
REGION                 1..11
                       note = Synthetic polypeptide
source                 1..11
                       mol_type = protein
                       organism = synthetic construct
SEQUENCE: 24
RASQRIARYL N                                                        11

SEQ ID NO: 25          moltype = AA  length = 11
FEATURE                Location/Qualifiers
REGION                 1..11
                       note = Synthetic polypeptide
source                 1..11
                       mol_type = protein
                       organism = synthetic construct
SEQUENCE: 25
RASQMIARYL N                                                        11

SEQ ID NO: 26          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 26
YASQSLS                                                             7

SEQ ID NO: 27          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 27
AASSLQS                                                             7

SEQ ID NO: 28          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 28
AGQRLQS                                                             7

SEQ ID NO: 29          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 29
AAHHLQS                                                             7

SEQ ID NO: 30          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 30
AANMLQS                                                             7
```

```
SEQ ID NO: 31           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 31
ASYNLQS                                                              7

SEQ ID NO: 32           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 32
AGRYLQS                                                              7

SEQ ID NO: 33           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 33
AGRILQS                                                              7

SEQ ID NO: 34           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 34
AGSILQS                                                              7

SEQ ID NO: 35           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 35
GARNLQS                                                              7

SEQ ID NO: 36           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 36
HQSSRLPFT                                                            9

SEQ ID NO: 37           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 37
HQSSMLPFT                                                            9

SEQ ID NO: 38           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 38
HQSSFLPFT                                                            9
```

```
SEQ ID NO: 39           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 39
QQSYSPPFT                                                          9

SEQ ID NO: 40           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 40
QQAIGMPYT                                                          9

SEQ ID NO: 41           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 41
QQAIQEPYT                                                          9

SEQ ID NO: 42           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 42
QQAIINPYT                                                          9

SEQ ID NO: 43           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 43
QQAINQPYT                                                          9

SEQ ID NO: 44           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 44
QQSIQQPYT                                                          9

SEQ ID NO: 45           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 45
QQAIQQPYT                                                          9

SEQ ID NO: 46           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 46
```

```
QQAIMAPYT                                               9

SEQ ID NO: 47          moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 47
QQAIQNPYT                                               9

SEQ ID NO: 48          moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 48
QQAIVQPYT                                               9

SEQ ID NO: 49          moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 49
QQAISIPYT                                               9

SEQ ID NO: 50          moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 50
QQAIIQPYT                                               9

SEQ ID NO: 51          moltype = AA  length = 9
FEATURE                Location/Qualifiers
REGION                 1..9
                       note = Synthetic polypeptide
source                 1..9
                       mol_type = protein
                       organism = synthetic construct
SEQUENCE: 51
QQSIQTPYT                                               9

SEQ ID NO: 52          moltype = AA  length = 108
FEATURE                Location/Qualifiers
REGION                 1..108
                       note = Synthetic polypeptide
source                 1..108
                       mol_type = protein
                       organism = synthetic construct
SEQUENCE: 52
EIVLTQSPAT LSLSPGERAT LSCRASQSVG RSLHWYQQKP GQAPRLLIKY ASQSLSGIPA  60
RFSGSGSGTD FTLTISSLEP EDFAVYYCHQ SSRLPFTFGP GTKVDIKR               108

SEQ ID NO: 53          moltype = AA  length = 108
FEATURE                Location/Qualifiers
REGION                 1..108
                       note = Synthetic polypeptide
source                 1..108
                       mol_type = protein
                       organism = synthetic construct
SEQUENCE: 53
DIQLTQSPSF LSASVGDRVT ITCRASQSIG RSLHWYQQKP GKAPKLLIKY ASQSLSGVPS  60
RFSGSGSGTE FTLTISSLQP EDFATYYCHQ SSRLPFTFGP GTKVDIKR               108

SEQ ID NO: 54          moltype = AA  length = 107
FEATURE                Location/Qualifiers
REGION                 1..107
                       note = Synthetic polypeptide
source                 1..107
```

```
                         mol_type = protein
                         organism = synthetic construct
SEQUENCE: 54
EIVLTQSPAT LSLSPGERAT LSCRASKSVG RSLHWYQQKP GQAPRLLIKY ASQSLSGIPA  60
RFSGSGSGTD FTLTISSLEP EDFAVYYCHQ SSRLPFTFGP GTKVDIK                107

SEQ ID NO: 55            moltype = AA  length = 107
FEATURE                  Location/Qualifiers
REGION                   1..107
                         note = Synthetic polypeptide
source                   1..107
                         mol_type = protein
                         organism = synthetic construct
SEQUENCE: 55
EIVLTQSPAT LSLSPGERAT LSCRASQSVG RSLHWYQQKP GQAPRLLIKY ASQSLSGIPA  60
RFSGSGSGTD FTLTISSLEP EDFAVYYCHQ SSRLPFTFGP GTKVDIK                107

SEQ ID NO: 56            moltype = AA  length = 107
FEATURE                  Location/Qualifiers
REGION                   1..107
                         note = Synthetic polypeptide
source                   1..107
                         mol_type = protein
                         organism = synthetic construct
SEQUENCE: 56
EIVLTQSPAT LSLSPGERAT LSCRASQSVW RSLHWYQQKP GQAPRLLIKY ASQSLSGIPA  60
RFSGSGSGTD FTLTISSLEP EDFAVYYCHQ SSRLPFTFGP GTKVDIK                107

SEQ ID NO: 57            moltype = AA  length = 107
FEATURE                  Location/Qualifiers
REGION                   1..107
                         note = Synthetic polypeptide
source                   1..107
                         mol_type = protein
                         organism = synthetic construct
SEQUENCE: 57
EIVLTQSPAT LSLSPGERAT LSCRASQSVG RNLHWYQQKP GQAPRLLIKY ASQSLSGIPA  60
RFSGSGSGTD FTLTISSLEP EDFAVYYCHQ SSRLPFTFGP GTKVDIK                107

SEQ ID NO: 58            moltype = AA  length = 107
FEATURE                  Location/Qualifiers
REGION                   1..107
                         note = Synthetic polypeptide
source                   1..107
                         mol_type = protein
                         organism = synthetic construct
SEQUENCE: 58
EIVLTQSPAT LSLSPGERAT LSCRASQSVG RSLHWYQQKP GQAPRLLIKY ASQSLSGIPA  60
RFSGSGSGTD FTLTISSLEP EDFAVYYCHQ SSMLPFTFGP GTKVDIK                107

SEQ ID NO: 59            moltype = AA  length = 107
FEATURE                  Location/Qualifiers
REGION                   1..107
                         note = Synthetic polypeptide
source                   1..107
                         mol_type = protein
                         organism = synthetic construct
SEQUENCE: 59
EIVLTQSPAT LSLSPGERAT LSCRASKSVW RSLHWYQQKP GQAPRLLIKY ASQSLSGIPA  60
RFSGSGSGTD FTLTISSLEP EDFAVYYCHQ SSRLPFTFGP GTKVDIK                107

SEQ ID NO: 60            moltype = AA  length = 107
FEATURE                  Location/Qualifiers
REGION                   1..107
                         note = Synthetic polypeptide
source                   1..107
                         mol_type = protein
                         organism = synthetic construct
SEQUENCE: 60
EIVLTQSPAT LSLSPGERAT LSCRASKSVG RNLHWYQQKP GQAPRLLIKY ASQSLSGIPA  60
RFSGSGSGTD FTLTISSLEP EDFAVYYCHQ SSRLPFTFGP GTKVDIK                107

SEQ ID NO: 61            moltype = AA  length = 107
FEATURE                  Location/Qualifiers
REGION                   1..107
                         note = Synthetic polypeptide
source                   1..107
                         mol_type = protein
                         organism = synthetic construct
```

```
SEQUENCE: 61
EIVLTQSPAT LSLSPGERAT LSCRASKSVG RSLHWYQQKP GQAPRLLIKY ASQSLSGIPA  60
RFSGSGSGTD FTLTISSLEP EDFAVYYCHQ SSMLPFTFGP GTKVDIK               107

SEQ ID NO: 62          moltype = AA  length = 108
FEATURE                Location/Qualifiers
REGION                 1..108
                       note = Synthetic polypeptide
source                 1..108
                       mol_type = protein
                       organism = synthetic construct
SEQUENCE: 62
EIVLTQSPAT LSLSPGERAT LSCRASKSVG WSLHWYQQKP GQAPRLLIKY ASQSLSGIPA  60
RFSGSGSGTD FTLTISSLEP EDFAVYYCHQ SSRLPFTFGP GTKVDIKR              108

SEQ ID NO: 63          moltype = AA  length = 108
FEATURE                Location/Qualifiers
REGION                 1..108
                       note = Synthetic polypeptide
source                 1..108
                       mol_type = protein
                       organism = synthetic construct
SEQUENCE: 63
EIVLTQSPAT LSLSPGERAT LSCRASKSVG YSLHWYQQKP GQAPRLLIKY ASQSLSGIPA  60
RFSGSGSGTD FTLTISSLEP EDFAVYYCHQ SSRLPFTFGP GTKVDIKR              108

SEQ ID NO: 64          moltype = AA  length = 108
FEATURE                Location/Qualifiers
REGION                 1..108
                       note = Synthetic polypeptide
source                 1..108
                       mol_type = protein
                       organism = synthetic construct
SEQUENCE: 64
EIVLTQSPAT LSLSPGERAT LSCRASKAVG WSLHWYQQKP GQAPRLLIKY ASQSLSGIPA  60
RFSGSGSGTD FTLTISSLEP EDFAVYYCHQ SSRLPFTFGP GTKVDIKR              108

SEQ ID NO: 65          moltype = AA  length = 108
FEATURE                Location/Qualifiers
REGION                 1..108
                       note = Synthetic polypeptide
source                 1..108
                       mol_type = protein
                       organism = synthetic construct
SEQUENCE: 65
EIVLTQSPAT LSLSPGERAT LSCRASKSVG QSLHWYQQKP GQAPRLLIKY ASQSLSGIPA  60
RFSGSGSGTD FTLTISSLEP EDFAVYYCHQ SSRLPFTFGP GTKVDIKR              108

SEQ ID NO: 66          moltype = AA  length = 108
FEATURE                Location/Qualifiers
REGION                 1..108
                       note = Synthetic polypeptide
source                 1..108
                       mol_type = protein
                       organism = synthetic construct
SEQUENCE: 66
EIVLTQSPAT LSLSPGERAT LSCRASRSVG LALHWYQQKP GQAPRLLIKY ASQSLSGIPA  60
RFSGSGSGTD FTLTISSLEP EDFAVYYCHQ SSFLPFTFGP GTKVDIKR              108

SEQ ID NO: 67          moltype = AA  length = 108
FEATURE                Location/Qualifiers
REGION                 1..108
                       note = Synthetic polypeptide
source                 1..108
                       mol_type = protein
                       organism = synthetic construct
SEQUENCE: 67
DIQMTQSPSS LSASVGDRIT ITCRASQSIS RYLNWYQQKP GKAPKLLIYA ASSLQSGIPS  60
RFSGSGSGTD FTLTINSLQP EDFATYFCQQ SYSPPFTFGP GTKVDIKR              108

SEQ ID NO: 68          moltype = AA  length = 107
FEATURE                Location/Qualifiers
REGION                 1..107
                       note = Synthetic polypeptide
source                 1..107
                       mol_type = protein
                       organism = synthetic construct
SEQUENCE: 68
DIQMTQSPSS LSASVGDRIT ITCRASQSIS RYLNWYQQKP GKAPKLLIFA GQRLQSGIPS  60
```

```
RFSGSGSGTD FTLTINSLQP EDFATYFCQQ AIGMPYTFGP GTKVDIK                107

SEQ ID NO: 69           moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 69
DIQMTQSPSS LSASVGDRIT ITCRASQYIV RYLNWYQQKP GKAPKLLIYA AHHLQSGIPS  60
RFSGSGSGTD FTLTINSLQP EDFATYFCQQ AIQEPYTFGP GTKVDIK                107

SEQ ID NO: 70           moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 70
DIQMTQSPSS LSASVGDRIT ITCRASQTIV RYLNWYQQKP GKAPKLLIFA GQRLQSGIPS  60
RFSGSGSGTD FTLTINSLQP EDFATYFCQQ AIINPYTFGP GTKVDIK                107

SEQ ID NO: 71           moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 71
DIQMTQSPSS LSASVGDRIT ITCRASQYIV RYLNWYQQKP GKAPKLLIYA ANMLQSGIPS  60
RFSGSGSGTD FTLTINSLQP EDFATYFCQQ AINQPYTFGP GTKVDIK                107

SEQ ID NO: 72           moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 72
DIQMTQSPSS LSASVGDRIT ITCRASQKIA RYLVWYQQKP GKAPKLLIYA ANMLQSGIPS  60
RFSGSGSGTD FTLTINSLQP EDFATYFCQQ SIQQPYTFGP GTKVDIK                107

SEQ ID NO: 73           moltype = AA  length = 108
FEATURE                 Location/Qualifiers
REGION                  1..108
                        note = Synthetic polypeptide
source                  1..108
                        mol_type = protein
                        organism = synthetic construct
SEQUENCE: 73
DIQMTQSPSS LSASVGDRIT ITCRASQSIS RYLNWYQQKP GKAPKLLIFA GQRLQSGIPS  60
RFSGSGSGTD FTLTINSLQP EDFATYFCQQ AIQQPYTFGP GTKVDIKR               108

SEQ ID NO: 74           moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 74
DIQMTQSPSS LSASVGDRIT ITCRASQYIV RYLNWYQQKP GKAPKLLIYA SYNLQSGIPS  60
RFSGSGSGTD FTLTINSLQP EDFATYFCQQ AIMAPYTFGP GTKVDIK                107

SEQ ID NO: 75           moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 75
DIQMTQSPSS LSASVGDRIT ITCRASQPIA QYLNWYQQKP GKAPKLLIYA GRYLQSGIPS  60
RFSGSGSGTD FTLTINSLQP EDFATYFCQQ AIQNPYTFGP GTKVDIK                107
```

```
SEQ ID NO: 76          moltype = AA  length = 107
FEATURE                Location/Qualifiers
REGION                 1..107
                       note = Synthetic polypeptide
source                 1..107
                       mol_type = protein
                       organism = synthetic construct
SEQUENCE: 76
DIQMTQSPSS LSASVGDRIT ITCRASQSIS RYLNWYQQKP GKAPKLLIFA GQRLQSGIPS  60
RFSGSGSGTD FTLTINSLQP EDFATYFCQQ AIVQPYTFGP GTKVDIK              107

SEQ ID NO: 77          moltype = AA  length = 107
FEATURE                Location/Qualifiers
REGION                 1..107
                       note = Synthetic polypeptide
source                 1..107
                       mol_type = protein
                       organism = synthetic construct
SEQUENCE: 77
DIQMTQSPSS LSASVGDRIT ITCRASQPIS RYLSWYQQKP GKAPKLLIFA GQRLQSGIPS  60
RFSGSGSGTD FTLTINSLQP EDFATYFCQQ AISIPYTFGP GTKVDIK              107

SEQ ID NO: 78          moltype = AA  length = 107
FEATURE                Location/Qualifiers
REGION                 1..107
                       note = Synthetic polypeptide
source                 1..107
                       mol_type = protein
                       organism = synthetic construct
SEQUENCE: 78
DIQMTQSPSS LSASVGDRIT ITCRASQQIA RYLNWYQQKP GKAPKLLIYA SYNLQSGIPS  60
RFSGSGSGTD FTLTINSLQP EDFATYFCQQ AIIQPYTFGP GTKVDIK              107

SEQ ID NO: 79          moltype = AA  length = 107
FEATURE                Location/Qualifiers
REGION                 1..107
                       note = Synthetic polypeptide
source                 1..107
                       mol_type = protein
                       organism = synthetic construct
SEQUENCE: 79
DIQMTQSPSS LSASVGDRIT ITCRASQSIS RYLNWYQQKP GKAPKLLIYA SYNLQSGIPS  60
RFSGSGSGTD FTLTINSLQP EDFATYFCQQ AIQNPYTFGP GTKVDIK              107

SEQ ID NO: 80          moltype = AA  length = 107
FEATURE                Location/Qualifiers
REGION                 1..107
                       note = Synthetic polypeptide
source                 1..107
                       mol_type = protein
                       organism = synthetic construct
SEQUENCE: 80
DIQMTQSPSS LSASVGDRIT ITCRASQTIV RYLNWYQQKP GKAPKLLIFA GQRLQSGIPS  60
RFSGSGSGTD FTLTINSLQP EDFATYFCQQ SIQTPYTFGP GTKVDIK              107

SEQ ID NO: 81          moltype = AA  length = 107
FEATURE                Location/Qualifiers
REGION                 1..107
                       note = Synthetic polypeptide
source                 1..107
                       mol_type = protein
                       organism = synthetic construct
SEQUENCE: 81
DIQMTQSPSS LSASVGDRIT ITCRASQSIS RYLNWYQQKP GKAPKLLIYA GRILQSGIPS  60
RFSGSGSGTD FTLTINSLQP EDFATYFCQQ AIINPYTFGP GTKVDIK              107

SEQ ID NO: 82          moltype = AA  length = 107
FEATURE                Location/Qualifiers
REGION                 1..107
                       note = Synthetic polypeptide
source                 1..107
                       mol_type = protein
                       organism = synthetic construct
SEQUENCE: 82
DIQMTQSPSS LSASVGDRIT ITCRASQRIA RYLNWYQQKP GKAPKLLIFA GSILQSGIPS  60
RFSGSGSGTD FTLTINSLQP EDFATYFCQQ AIQNPYTFGP GTKVDIK              107

SEQ ID NO: 83          moltype = AA  length = 107
FEATURE                Location/Qualifiers
```

```
REGION                  1..107
                        note = Synthetic polypeptide
source                  1..107
                        mol_type = protein
                        organism = synthetic construct
SEQUENCE: 83
DIQMTQSPSS LSASVGDRIT ITCRASQSIS RYLNWYQQKP GKAPKLLIYA SYNLQSGIPS  60
RFSGSGSGTD FTLTINSLQP EDFATYFCQQ SIQQPYTFGP GTKVDIK               107

SEQ ID NO: 84           moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 84
DIQMTQSPSS LSASVGDRIT ITCRASQYIV RYLNWYQQKP GKAPKLLIYA SYNLQSGIPS  60
RFSGSGSGTD FTLTINSLQP EDFATYFCQQ AIQQPYTFGP GTKVDIK               107

SEQ ID NO: 85           moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 85
DIQMTQSPSS LSASVGDRIT ITCRASQMIA RYLNWYQQKP GKAPKLLIYA SYNLQSGIPS  60
RFSGSGSGTD FTLTINSLQP EDFATYFCQQ AIINPYTFGP GTKVDIK               107

SEQ ID NO: 86           moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 86
DIQMTQSPSS LSASVGDRIT ITCRASQYIV RYLNWYQQKP GKAPKLLIYG ARNLQSGIPS  60
RFSGSGSGTD FTLTINSLQP EDFATYFCQQ SIQTPYTFGP GTKVDIK               107

SEQ ID NO: 87           moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 87
DIQMTQSPSS LSASVGDRIT ITCRASQSIS RYLNWYQQKP GKAPKLLIYA ASSLQSGIPS  60
RFSGSGSGTD FTLTINSLQP EDFATYFCQQ SYSPPFTFGP GTKVDIK               107

SEQ ID NO: 88           moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 88
RFAMH                                                             5

SEQ ID NO: 89           moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 89
HFAMH                                                             5

SEQ ID NO: 90           moltype = AA  length = 5
FEATURE                 Location/Qualifiers
REGION                  1..5
                        note = Synthetic polypeptide
source                  1..5
                        mol_type = protein
```

```
                        organism = synthetic construct
SEQUENCE: 90
RYAMH                                                                       5

SEQ ID NO: 91           moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 91
KYAMH                                                                       5

SEQ ID NO: 92           moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 92
KFAMH                                                                       5

SEQ ID NO: 93           moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 93
HYAMH                                                                       5

SEQ ID NO: 94           moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 94
YFAMH                                                                       5

SEQ ID NO: 95           moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 95
FYAMH                                                                       5

SEQ ID NO: 96           moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 96
YYAMH                                                                       5

SEQ ID NO: 97           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 97
SNSATWN                                                                     7

SEQ ID NO: 98           moltype = AA  length = 7
FEATURE                 Location/Qualifiers
REGION                  1..7
                        note = Synthetic polypeptide
source                  1..7
```

```
                        mol_type = protein
                        organism = synthetic construct
SEQUENCE: 98
NRLATWN                                                                7

SEQ ID NO: 99           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 99
SRQATWN                                                                7

SEQ ID NO: 100          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 100
NKQATWN                                                                7

SEQ ID NO: 101          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 101
SNHATWN                                                                7

SEQ ID NO: 102          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 102
SRYATWN                                                                7

SEQ ID NO: 103          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 103
SHVATWN                                                                7

SEQ ID NO: 104          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 104
NHQATWN                                                                7

SEQ ID NO: 105          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 105
SRDATWN                                                                7

SEQ ID NO: 106          moltype = AA  length = 17
FEATURE                 Location/Qualifiers
REGION                  1..17
                        note = Synthetic polypeptide
```

```
source                  1..17
                        mol_type = protein
                        organism = synthetic construct
SEQUENCE: 106
VISYDGGNKY YAESVKG                                                    17

SEQ ID NO: 107          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 107
VISYNGGNKY YAESVKG                                                    17

SEQ ID NO: 108          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 108
VISYIGGNKY YAESVKG                                                    17

SEQ ID NO: 109          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 109
VISYQGGNKY YAESVKG                                                    17

SEQ ID NO: 110          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 110
VISYYGGNKY YAESVKG                                                    17

SEQ ID NO: 111          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 111
VISYDGRNKY YAESVKG                                                    17

SEQ ID NO: 112          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 112
VISYDGNNKY YAESVKG                                                    17

SEQ ID NO: 113          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 113
VISYDGGNKY YARSVKG                                                    17

SEQ ID NO: 114          moltype = AA  length = 17
FEATURE                 Location/Qualifiers
REGION                  1..17
```

```
                        note = Synthetic polypeptide
source                  1..17
                        mol_type = protein
                        organism = synthetic construct
SEQUENCE: 114
VISYNGRNKY YAESVKG                                                    17

SEQ ID NO: 115          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 115
VISYIGRNKY YAESVKG                                                    17

SEQ ID NO: 116          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 116
VISYQGRNKY YAESVKG                                                    17

SEQ ID NO: 117          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 117
VISYYGRNKY YAESVKG                                                    17

SEQ ID NO: 118          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 118
VISYNGNNKY YAESVKG                                                    17

SEQ ID NO: 119          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 119
VISYIGNNKY YAESVKG                                                    17

SEQ ID NO: 120          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 120
VISYQGNNKY YAESVKG                                                    17

SEQ ID NO: 121          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 121
VISYYGNNKY YAESVKG                                                    17

SEQ ID NO: 122          moltype = AA  length = 17
FEATURE                 Location/Qualifiers
```

```
REGION                  1..17
                        note = Synthetic polypeptide
source                  1..17
                        mol_type = protein
                        organism = synthetic construct
SEQUENCE: 122
VISYNGGNKY YARSVKG                                                    17

SEQ ID NO: 123          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 123
VISYIGGNKY YARSVKG                                                    17

SEQ ID NO: 124          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 124
VISYQGGNKY YARSVKG                                                    17

SEQ ID NO: 125          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 125
VISYYGGNKY YARSVKG                                                    17

SEQ ID NO: 126          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 126
VISYDGRNKY YARSVKG                                                    17

SEQ ID NO: 127          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 127
VISYDGNNKY YARSVKG                                                    17

SEQ ID NO: 128          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 128
VISYNGRNKY YARSVKG                                                    17

SEQ ID NO: 129          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 129
VISYIGRNKY YARSVKG                                                    17

SEQ ID NO: 130          moltype = AA  length = 17
```

```
FEATURE                 Location/Qualifiers
REGION                  1..17
                        note = Synthetic polypeptide
source                  1..17
                        mol_type = protein
                        organism = synthetic construct
SEQUENCE: 130
VISYQGRNKY YARSVKG                                                         17

SEQ ID NO: 131          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 131
VISYYGRNKY YARSVKG                                                         17

SEQ ID NO: 132          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 132
VISYNGNNKY YARSVKG                                                         17

SEQ ID NO: 133          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 133
VISYIGNNKY YARSVKG                                                         17

SEQ ID NO: 134          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 134
VISYQGNNKY YARSVKG                                                         17

SEQ ID NO: 135          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 135
VISYYGNNKY YARSVKG                                                         17

SEQ ID NO: 136          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 136
VISFDGGNKY YAESVKG                                                         17

SEQ ID NO: 137          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 137
VISYDGANKY YAESVKG                                                         17
```

```
SEQ ID NO: 138          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 138
VISFNGGNKY YAESVKG                                                 17

SEQ ID NO: 139          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 139
VISYNGANKY YAESVKG                                                 17

SEQ ID NO: 140          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 140
VISFDGRNKY YAESVKG                                                 17

SEQ ID NO: 141          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 141
VISFDGGNKY YARSVKG                                                 17

SEQ ID NO: 142          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 142
VISYDGANKY YARSVKG                                                 17

SEQ ID NO: 143          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 143
VISFKGSNKY YAESVKG                                                 17

SEQ ID NO: 144          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 144
VISFSGSNKY YAESVKG                                                 17

SEQ ID NO: 145          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 145
VISYRGGNKY YAESVKG                                                 17
```

```
SEQ ID NO: 146          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 146
VISYSGANKY YAESVKG                                                 17

SEQ ID NO: 147          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 147
VISFKGANKY YAESVKG                                                 17

SEQ ID NO: 148          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 148
VISYRGANKY YAESVKG                                                 17

SEQ ID NO: 149          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 149
VISFYGSNKY YAESVKG                                                 17

SEQ ID NO: 150          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 150
VISFFGGNKY YAESVKG                                                 17

SEQ ID NO: 151          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 151
VISFMGTNKY YAESVKG                                                 17

SEQ ID NO: 152          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 152
VISHRGTNKY YAESVKG                                                 17

SEQ ID NO: 153          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 153
```

```
VINYRGHGKY YAESVKG                                               17

SEQ ID NO: 154          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 154
VISFSGGSKY YAESVKG                                               17

SEQ ID NO: 155          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 155
VISYTGQFKY YAESVKG                                               17

SEQ ID NO: 156          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 156
VISYTGAQKY YAESVKG                                               17

SEQ ID NO: 157          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 157
VISYSGASKY YAESVKG                                               17

SEQ ID NO: 158          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 158
VISYSGAFKY YAESVKG                                               17

SEQ ID NO: 159          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 159
VITYTGGAKY YAESVKG                                               17

SEQ ID NO: 160          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 160
VINFQGTTKY YAESVKG                                               17

SEQ ID NO: 161          moltype = AA  length = 17
FEATURE                 Location/Qualifiers
REGION                  1..17
                        note = Synthetic polypeptide
source                  1..17
                        mol_type = protein
                        organism = synthetic construct
```

```
SEQUENCE: 161
VISYSGDLKY YAESVKG                                         17

SEQ ID NO: 162          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 162
VINYFGDAKY YAESVKG                                         17

SEQ ID NO: 163          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 163
VISSFGSNKY YAESVKG                                         17

SEQ ID NO: 164          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 164
VISYSGSNKY YAESVKG                                         17

SEQ ID NO: 165          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 165
VISHYGTNKY YAESVKG                                         17

SEQ ID NO: 166          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 166
VISYQGSNKY YAESVKG                                         17

SEQ ID NO: 167          moltype = AA  length = 18
FEATURE                 Location/Qualifiers
REGION                  1..18
                        note = Synthetic polypeptide
source                  1..18
                        mol_type = protein
                        organism = synthetic construct
SEQUENCE: 167
RTYYRSKWSN HYAVSVKS                                        18

SEQ ID NO: 168          moltype = AA  length = 18
FEATURE                 Location/Qualifiers
REGION                  1..18
                        note = Synthetic polypeptide
source                  1..18
                        mol_type = protein
                        organism = synthetic construct
SEQUENCE: 168
RTYYRGKWKN HYAVSVKS                                        18

SEQ ID NO: 169          moltype = AA  length = 18
FEATURE                 Location/Qualifiers
REGION                  1..18
                        note = Synthetic polypeptide
source                  1..18
                        mol_type = protein
```

```
                        organism = synthetic construct
SEQUENCE: 169
RTYYRGQWKN HYAVSVKS                                                 18

SEQ ID NO: 170          moltype = AA  length = 18
FEATURE                 Location/Qualifiers
REGION                  1..18
                        note = Synthetic polypeptide
source                  1..18
                        mol_type = protein
                        organism = synthetic construct
SEQUENCE: 170
RTYFRRTWKN HYAVSVKS                                                 18

SEQ ID NO: 171          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 171
GYDVLTGYPD Y                                                        11

SEQ ID NO: 172          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 172
GYDILTGYPD Y                                                        11

SEQ ID NO: 173          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 173
GYDFLTGYPD Y                                                        11

SEQ ID NO: 174          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 174
GYDLLTGYPD Y                                                        11

SEQ ID NO: 175          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 175
GYDMLTGYPD Y                                                        11

SEQ ID NO: 176          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 176
GYDLLSGYPD Y                                                        11

SEQ ID NO: 177          moltype = AA  length = 11
FEATURE                 Location/Qualifiers
REGION                  1..11
                        note = Synthetic polypeptide
source                  1..11
```

```
                        mol_type = protein
                        organism = synthetic construct
SEQUENCE: 177
GYDPLTGYPD Y                                                  11

SEQ ID NO: 178          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 178
GTWKQLWFLD H                                                  11

SEQ ID NO: 179          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 179
GTWNQDWFLD H                                                  11

SEQ ID NO: 180          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 180
GTWDQDWFLD H                                                  11

SEQ ID NO: 181          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 181
GTWEQDWFLD H                                                  11

SEQ ID NO: 182          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 182
GMWNQNWFLD H                                                  11

SEQ ID NO: 183          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 183
GTWIGDWFMD H                                                  11

SEQ ID NO: 184          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 184
GTWIQDWFLD H                                                  11

SEQ ID NO: 185          moltype = AA  length = 11
FEATURE                 Location/Qualifiers
REGION                  1..11
                        note = Synthetic polypeptide
```

```
source                  1..11
                        mol_type = protein
                        organism = synthetic construct
SEQUENCE: 185
GMWSGDWFLD H                                                  11

SEQ ID NO: 186          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 186
GMWSEDWFLD H                                                  11

SEQ ID NO: 187          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 187
GMWQGNWFLD H                                                  11

SEQ ID NO: 188          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 188
GQWNEDWFLD H                                                  11

SEQ ID NO: 189          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 189
GRWEGDWFFD H                                                  11

SEQ ID NO: 190          moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 190
GVWIGNWFLD H                                                  11

SEQ ID NO: 191          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 191
QVQLVESGGG VVQPGRSLRL SCAASGFTFS RFAMHWVRQA PGKGLEWVAV ISYDGGNKYY  60
AESVKGRFTI SRDNSKNTLY LQMNSLRAED TALFYCARGY DVLTGYPDYW GQGTLVTVSS  120

SEQ ID NO: 192          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 192
QVQLVESGAE VVKPGASVKV SCKASGFTFS RFAMHWVRQA PGQGLEWMGV ISYDGGNKYY  60
AESVKGRVTM TRDTSTSTLY MELSSLRSED TAVYYCARGY DVLTGYPDYW GQGTLVTVSS  120

SEQ ID NO: 193          moltype = AA  length = 120
```

```
FEATURE                Location/Qualifiers
REGION                 1..120
                       note = Synthetic polypeptide
source                 1..120
                       mol_type = protein
                       organism = synthetic construct
SEQUENCE: 193
QVQLVESGGG VVQPGRSLRL SCAASGFTFS RFAMHWVRQA PGKGLEWVAV ISYNGGNKYY  60
AESVKGRFTI SRDNSKNTLY LQMNSLRAED TALFYCARGY DVLTGYPDYW GQGTLVTVSS  120

SEQ ID NO: 194         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 194
QVQLVESGGG VVQPGRSLRL SCAASGFTFS RFAMHWVRQA PGKGLEWVAV ISYIGGNKYY  60
AESVKGRFTI SRDNSKNTLY LQMNSLRAED TALFYCARGY DVLTGYPDYW GQGTLVTVSS  120

SEQ ID NO: 195         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 195
QVQLVESGGG VVQPGRSLRL SCAASGFTFS RFAMHWVRQA PGKGLEWVAV ISYQGGNKYY  60
AESVKGRFTI SRDNSKNTLY LQMNSLRAED TALFYCARGY DVLTGYPDYW GQGTLVTVSS  120

SEQ ID NO: 196         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 196
QVQLVESGGG VVQPGRSLRL SCAASGFTFS RFAMHWVRQA PGKGLEWVAV ISYYGGNKYY  60
AESVKGRFTI SRDNSKNTLY LQMNSLRAED TALFYCARGY DVLTGYPDYW GQGTLVTVSS  120

SEQ ID NO: 197         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 197
QVQLVESGGG VVQPGRSLRL SCAASGFTFS RFAMHWVRQA PGKGLEWVAV ISYDGRNKYY  60
AESVKGRFTI SRDNSKNTLY LQMNSLRAED TALFYCARGY DVLTGYPDYW GQGTLVTVSS  120

SEQ ID NO: 198         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 198
QVQLVESGGG VVQPGRSLRL SCAASGFTFS RFAMHWVRQA PGKGLEWVAV ISYDGNNKYY  60
AESVKGRFTI SRDNSKNTLY LQMNSLRAED TALFYCARGY DVLTGYPDYW GQGTLVTVSS  120

SEQ ID NO: 199         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 199
QVQLVESGGG VVQPGRSLRL SCAASGFTFS RFAMHWVRQA PGKGLEWVAV ISYDGGNKYY  60
ARSVKGRFTI SRDNSKNTLY LQMNSLRAED TALFYCARGY DVLTGYPDYW GQGTLVTVSS  120

SEQ ID NO: 200         moltype = AA  length = 120
FEATURE                Location/Qualifiers
REGION                 1..120
```

```
                         note = Synthetic polypeptide
source                   1..120
                         mol_type = protein
                         organism = synthetic construct
SEQUENCE: 200
QVQLVESGGG VVQPGRSLRL SCAASGFTFS RFAMHWVRQA PGKGLEWVAV ISYDGGNKYY  60
AESVKGRFTI SRDNSKNTLY LQMNSLRAED TALFYCARGY DILTGYPDYW GQGTLVTVSS  120

SEQ ID NO: 201           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 201
QVQLVESGGG VVQPGRSLRL SCAASGFTFS RFAMHWVRQA PGKGLEWVAV ISYNGRNKYY  60
AESVKGRFTI SRDNSKNTLY LQMNSLRAED TALFYCARGY DVLTGYPDYW GQGTLVTVSS  120

SEQ ID NO: 202           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 202
QVQLVESGGG VVQPGRSLRL SCAASGFTFS RFAMHWVRQA PGKGLEWVAV ISYIGRNKYY  60
AESVKGRFTI SRDNSKNTLY LQMNSLRAED TALFYCARGY DVLTGYPDYW GQGTLVTVSS  120

SEQ ID NO: 203           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 203
QVQLVESGGG VVQPGRSLRL SCAASGFTFS RFAMHWVRQA PGKGLEWVAV ISYQGRNKYY  60
AESVKGRFTI SRDNSKNTLY LQMNSLRAED TALFYCARGY DVLTGYPDYW GQGTLVTVSS  120

SEQ ID NO: 204           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 204
QVQLVESGGG VVQPGRSLRL SCAASGFTFS RFAMHWVRQA PGKGLEWVAV ISYYGRNKYY  60
AESVKGRFTI SRDNSKNTLY LQMNSLRAED TALFYCARGY DVLTGYPDYW GQGTLVTVSS  120

SEQ ID NO: 205           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 205
QVQLVESGGG VVQPGRSLRL SCAASGFTFS RFAMHWVRQA PGKGLEWVAV ISYNGNNKYY  60
AESVKGRFTI SRDNSKNTLY LQMNSLRAED TALFYCARGY DVLTGYPDYW GQGTLVTVSS  120

SEQ ID NO: 206           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 206
QVQLVESGGG VVQPGRSLRL SCAASGFTFS RFAMHWVRQA PGKGLEWVAV ISYIGNNKYY  60
AESVKGRFTI SRDNSKNTLY LQMNSLRAED TALFYCARGY DVLTGYPDYW GQGTLVTVSS  120

SEQ ID NO: 207           moltype = AA  length = 120
FEATURE                  Location/Qualifiers
REGION                   1..120
                         note = Synthetic polypeptide
source                   1..120
```

```
                        mol_type = protein
                        organism = synthetic construct
SEQUENCE: 207
QVQLVESGGG VVQPGRSLRL SCAASGFTFS RFAMHWVRQA PGKGLEWVAV ISYQGNNKYY  60
AESVKGRFTI SRDNSKNTLY LQMNSLRAED TALFYCARGY DVLTGYPDYW GQGTLVTVSS  120

SEQ ID NO: 208          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 208
QVQLVESGGG VVQPGRSLRL SCAASGFTFS RFAMHWVRQA PGKGLEWVAV ISYYGNNKYY  60
AESVKGRFTI SRDNSKNTLY LQMNSLRAED TALFYCARGY DVLTGYPDYW GQGTLVTVSS  120

SEQ ID NO: 209          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 209
QVQLVESGGG VVQPGRSLRL SCAASGFTFS RFAMHWVRQA PGKGLEWVAV ISYNGGNKYY  60
ARSVKGRFTI SRDNSKNTLY LQMNSLRAED TALFYCARGY DVLTGYPDYW GQGTLVTVSS  120

SEQ ID NO: 210          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 210
QVQLVESGGG VVQPGRSLRL SCAASGFTFS RFAMHWVRQA PGKGLEWVAV ISYIGGNKYY  60
ARSVKGRFTI SRDNSKNTLY LQMNSLRAED TALFYCARGY DVLTGYPDYW GQGTLVTVSS  120

SEQ ID NO: 211          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 211
QVQLVESGGG VVQPGRSLRL SCAASGFTFS RFAMHWVRQA PGKGLEWVAV ISYQGGNKYY  60
ARSVKGRFTI SRDNSKNTLY LQMNSLRAED TALFYCARGY DVLTGYPDYW GQGTLVTVSS  120

SEQ ID NO: 212          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 212
QVQLVESGGG VVQPGRSLRL SCAASGFTFS RFAMHWVRQA PGKGLEWVAV ISYYGGNKYY  60
ARSVKGRFTI SRDNSKNTLY LQMNSLRAED TALFYCARGY DVLTGYPDYW GQGTLVTVSS  120

SEQ ID NO: 213          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 213
QVQLVESGGG VVQPGRSLRL SCAASGFTFS RFAMHWVRQA PGKGLEWVAV ISYNGGNKYY  60
AESVKGRFTI SRDNSKNTLY LQMNSLRAED TALFYCARGY DILTGYPDYW GQGTLVTVSS  120

SEQ ID NO: 214          moltype = AA  length = 120
FEATURE                 Location/Qualifiers
REGION                  1..120
                        note = Synthetic polypeptide
source                  1..120
                        mol_type = protein
                        organism = synthetic construct
```

```
SEQUENCE: 214
QVQLVESGGG VVQPGRSLRL SCAASGFTFS RFAMHWVRQA PGKGLEWVAV ISYIGGNKYY  60
AESVKGRFTI SRDNSKNTLY LQMNSLRAED TALFYCARGY DILTGYPDYW GQGTLVTVSS  120

SEQ ID NO: 215         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 215
QVQLVESGGG VVQPGRSLRL SCAASGFTFS RFAMHWVRQA PGKGLEWVAV ISYQGGNKYY  60
AESVKGRFTI SRDNSKNTLY LQMNSLRAED TALFYCARGY DILTGYPDYW GQGTLVTVSS  120

SEQ ID NO: 216         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 216
QVQLVESGGG VVQPGRSLRL SCAASGFTFS RFAMHWVRQA PGKGLEWVAV ISYYGGNKYY  60
AESVKGRFTI SRDNSKNTLY LQMNSLRAED TALFYCARGY DILTGYPDYW GQGTLVTVSS  120

SEQ ID NO: 217         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 217
QVQLVESGGG VVQPGRSLRL SCAASGFTFS RFAMHWVRQA PGKGLEWVAV ISYDGRNKYY  60
ARSVKGRFTI SRDNSKNTLY LQMNSLRAED TALFYCARGY DVLTGYPDYW GQGTLVTVSS  120

SEQ ID NO: 218         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 218
QVQLVESGGG VVQPGRSLRL SCAASGFTFS RFAMHWVRQA PGKGLEWVAV ISYDGNNKYY  60
ARSVKGRFTI SRDNSKNTLY LQMNSLRAED TALFYCARGY DVLTGYPDYW GQGTLVTVSS  120

SEQ ID NO: 219         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 219
QVQLVESGGG VVQPGRSLRL SCAASGFTFS RFAMHWVRQA PGKGLEWVAV ISYDGRNKYY  60
AESVKGRFTI SRDNSKNTLY LQMNSLRAED TALFYCARGY DILTGYPDYW GQGTLVTVSS  120

SEQ ID NO: 220         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 220
QVQLVESGGG VVQPGRSLRL SCAASGFTFS RFAMHWVRQA PGKGLEWVAV ISYDGNNKYY  60
AESVKGRFTI SRDNSKNTLY LQMNSLRAED TALFYCARGY DILTGYPDYW GQGTLVTVSS  120

SEQ ID NO: 221         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 221
QVQLVESGGG VVQPGRSLRL SCAASGFTFS RFAMHWVRQA PGKGLEWVAV ISYDGGNKYY  60
```

```
ARSVKGRFTI SRDNSKNTLY LQMNSLRAED TALFYCARGY DILTGYPDYW GQGTLVTVSS  120

SEQ ID NO: 222         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 222
QVQLVESGGG VVQPGRSLRL SCAASGFTFS RFAMHWVRQA PGKGLEWVAV ISYNGRNKYY  60
ARSVKGRFTI SRDNSKNTLY LQMNSLRAED TALFYCARGY DVLTGYPDYW GQGTLVTVSS  120

SEQ ID NO: 223         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 223
QVQLVESGGG VVQPGRSLRL SCAASGFTFS RFAMHWVRQA PGKGLEWVAV ISYIGRNKYY  60
ARSVKGRFTI SRDNSKNTLY LQMNSLRAED TALFYCARGY DVLTGYPDYW GQGTLVTVSS  120

SEQ ID NO: 224         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 224
QVQLVESGGG VVQPGRSLRL SCAASGFTFS RFAMHWVRQA PGKGLEWVAV ISYQGRNKYY  60
ARSVKGRFTI SRDNSKNTLY LQMNSLRAED TALFYCARGY DVLTGYPDYW GQGTLVTVSS  120

SEQ ID NO: 225         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 225
QVQLVESGGG VVQPGRSLRL SCAASGFTFS RFAMHWVRQA PGKGLEWVAV ISYYGRNKYY  60
ARSVKGRFTI SRDNSKNTLY LQMNSLRAED TALFYCARGY DVLTGYPDYW GQGTLVTVSS  120

SEQ ID NO: 226         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 226
QVQLVESGGG VVQPGRSLRL SCAASGFTFS RFAMHWVRQA PGKGLEWVAV ISYNGNNKYY  60
ARSVKGRFTI SRDNSKNTLY LQMNSLRAED TALFYCARGY DVLTGYPDYW GQGTLVTVSS  120

SEQ ID NO: 227         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 227
QVQLVESGGG VVQPGRSLRL SCAASGFTFS RFAMHWVRQA PGKGLEWVAV ISYIGNNKYY  60
ARSVKGRFTI SRDNSKNTLY LQMNSLRAED TALFYCARGY DVLTGYPDYW GQGTLVTVSS  120

SEQ ID NO: 228         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 228
QVQLVESGGG VVQPGRSLRL SCAASGFTFS RFAMHWVRQA PGKGLEWVAV ISYQGNNKYY  60
ARSVKGRFTI SRDNSKNTLY LQMNSLRAED TALFYCARGY DVLTGYPDYW GQGTLVTVSS  120
```

```
SEQ ID NO: 229          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 229
QVQLVESGGG VVQPGRSLRL SCAASGFTFS RFAMHWVRQA PGKGLEWVAV ISYYGNNKYY  60
ARSVKGRFTI SRDNSKNTLY LQMNSLRAED TALFYCARGY DVLTGYPDYW GQGTLVTVSS  120

SEQ ID NO: 230          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 230
QVQLVESGGG VVQPGRSLRL SCAASGFTFS RFAMHWVRQA PGKGLEWVAV ISYNGRNKYY  60
AESVKGRFTI SRDNSKNTLY LQMNSLRAED TALFYCARGY DILTGYPDYW GQGTLVTVSS  120

SEQ ID NO: 231          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 231
QVQLVESGGG VVQPGRSLRL SCAASGFTFS RFAMHWVRQA PGKGLEWVAV ISYIGRNKYY  60
AESVKGRFTI SRDNSKNTLY LQMNSLRAED TALFYCARGY DILTGYPDYW GQGTLVTVSS  120

SEQ ID NO: 232          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 232
QVQLVESGGG VVQPGRSLRL SCAASGFTFS RFAMHWVRQA PGKGLEWVAV ISYQGRNKYY  60
AESVKGRFTI SRDNSKNTLY LQMNSLRAED TALFYCARGY DILTGYPDYW GQGTLVTVSS  120

SEQ ID NO: 233          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 233
QVQLVESGGG VVQPGRSLRL SCAASGFTFS RFAMHWVRQA PGKGLEWVAV ISYYGRNKYY  60
AESVKGRFTI SRDNSKNTLY LQMNSLRAED TALFYCARGY DILTGYPDYW GQGTLVTVSS  120

SEQ ID NO: 234          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 234
QVQLVESGGG VVQPGRSLRL SCAASGFTFS RFAMHWVRQA PGKGLEWVAV ISYNGNNKYY  60
AESVKGRFTI SRDNSKNTLY LQMNSLRAED TALFYCARGY DILTGYPDYW GQGTLVTVSS  120

SEQ ID NO: 235          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 235
QVQLVESGGG VVQPGRSLRL SCAASGFTFS RFAMHWVRQA PGKGLEWVAV ISYIGNNKYY  60
AESVKGRFTI SRDNSKNTLY LQMNSLRAED TALFYCARGY DILTGYPDYW GQGTLVTVSS  120

SEQ ID NO: 236          moltype = AA  length = 120
FEATURE                 Location/Qualifiers
```

```
REGION                  1..120
                        note = Synthetic polypeptide
source                  1..120
                        mol_type = protein
                        organism = synthetic construct
SEQUENCE: 236
QVQLVESGGG VVQPGRSLRL SCAASGFTFS RFAMHWVRQA PGKGLEWVAV ISYQGNNKYY  60
AESVKGRFTI SRDNSKNTLY LQMNSLRAED TALFYCARGY DILTGYPDYW GQGTLVTVSS  120

SEQ ID NO: 237          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 237
QVQLVESGGG VVQPGRSLRL SCAASGFTFS RFAMHWVRQA PGKGLEWVAV ISYYGNNKYY  60
AESVKGRFTI SRDNSKNTLY LQMNSLRAED TALFYCARGY DILTGYPDYW GQGTLVTVSS  120

SEQ ID NO: 238          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 238
QVQLVESGGG VVQPGRSLRL SCAASGFTFS RFAMHWVRQA PGKGLEWVAV ISYDGRNKYY  60
ARSVKGRFTI SRDNSKNTLY LQMNSLRAED TALFYCARGY DILTGYPDYW GQGTLVTVSS  120

SEQ ID NO: 239          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 239
QVQLVESGGG VVQPGRSLRL SCAASGFTFS RFAMHWVRQA PGKGLEWVAV ISYDGNNKYY  60
ARSVKGRFTI SRDNSKNTLY LQMNSLRAED TALFYCARGY DILTGYPDYW GQGTLVTVSS  120

SEQ ID NO: 240          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 240
QVQLVESGGG VVQPGRSLRL SCAASGFTFS RFAMHWVRQA PGKGLEWVAV ISYNGRNKYY  60
ARSVKGRFTI SRDNSKNTLY LQMNSLRAED TALFYCARGY DILTGYPDYW GQGTLVTVSS  120

SEQ ID NO: 241          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 241
QVQLVESGGG VVQPGRSLRL SCAASGFTFS RFAMHWVRQA PGKGLEWVAV ISYIGRNKYY  60
ARSVKGRFTI SRDNSKNTLY LQMNSLRAED TALFYCARGY DILTGYPDYW GQGTLVTVSS  120

SEQ ID NO: 242          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 242
QVQLVESGGG VVQPGRSLRL SCAASGFTFS RFAMHWVRQA PGKGLEWVAV ISYQGRNKYY  60
ARSVKGRFTI SRDNSKNTLY LQMNSLRAED TALFYCARGY DILTGYPDYW GQGTLVTVSS  120

SEQ ID NO: 243          moltype = AA  length = 120
FEATURE                 Location/Qualifiers
REGION                  1..120
                        note = Synthetic polypeptide
```

```
source                  1..120
                        mol_type = protein
                        organism = synthetic construct
SEQUENCE: 243
QVQLVESGGG VVQPGRSLRL SCAASGFTFS RFAMHWVRQA PGKGLEWVAV ISYYGRNKYY  60
ARSVKGRFTI SRDNSKNTLY LQMNSLRAED TALFYCARGY DILTGYPDYW GQGTLVTVSS  120

SEQ ID NO: 244          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 244
QVQLVESGGG VVQPGRSLRL SCAASGFTFS RFAMHWVRQA PGKGLEWVAV ISYNGNNKYY  60
ARSVKGRFTI SRDNSKNTLY LQMNSLRAED TALFYCARGY DILTGYPDYW GQGTLVTVSS  120

SEQ ID NO: 245          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 245
QVQLVESGGG VVQPGRSLRL SCAASGFTFS RFAMHWVRQA PGKGLEWVAV ISYIGNNKYY  60
ARSVKGRFTI SRDNSKNTLY LQMNSLRAED TALFYCARGY DILTGYPDYW GQGTLVTVSS  120

SEQ ID NO: 246          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 246
QVQLVESGGG VVQPGRSLRL SCAASGFTFS RFAMHWVRQA PGKGLEWVAV ISYQGNNKYY  60
ARSVKGRFTI SRDNSKNTLY LQMNSLRAED TALFYCARGY DILTGYPDYW GQGTLVTVSS  120

SEQ ID NO: 247          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 247
QVQLVESGGG VVQPGRSLRL SCAASGFTFS RFAMHWVRQA PGKGLEWVAV ISYYGNNKYY  60
ARSVKGRFTI SRDNSKNTLY LQMNSLRAED TALFYCARGY DILTGYPDYW GQGTLVTVSS  120

SEQ ID NO: 248          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 248
QVQLVESGGG VVQPGRSLRL SCAASGFTFS HFAMHWVRQA PGKGLEWVAV ISYDGGNKYY  60
AESVKGRFTI SRDNSKNTLY LQMNSLRAED TALFYCARGY DVLTGYPDYW GQGTLVTVSS  120

SEQ ID NO: 249          moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 249
QVQLVESGGG VVQPGRSLRL SCAASGFTFS RYAMHWVRQA PGKGLEWVAV ISYDGGNKYY  60
AESVKGRFTI SRDNSKNTLY LQMNSLRAED TALFYCARGY DVLTGYPDYW GQGTLVTVSS  120

SEQ ID NO: 250          moltype = AA  length = 120
FEATURE                 Location/Qualifiers
REGION                  1..120
                        note = Synthetic polypeptide
source                  1..120
                        mol_type = protein
```

```
                         organism = synthetic construct
SEQUENCE: 250
QVQLVESGGG VVQPGRSLRL SCAASGFTFS RFAMHWVRQA PGKGLEWVAV ISFDGGNKYY  60
AESVKGRFTI SRDNSKNTLY LQMNSLRAED TALFYCARGY DVLTGYPDYW GQGTLVTVSS  120

SEQ ID NO: 251           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 251
QVQLVESGGG VVQPGRSLRL SCAASGFTFS RFAMHWVRQA PGKGLEWVAV ISYDGANKYY  60
AESVKGRFTI SRDNSKNTLY LQMNSLRAED TALFYCARGY DVLTGYPDYW GQGTLVTVSS  120

SEQ ID NO: 252           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 252
QVQLVESGGG VVQPGRSLRL SCAASGFTFS RFAMHWVRQA PGKGLEWVAV ISYDGGNKYY  60
AESVKGRFTI SRDNSKNTLY LQMNSLRAED TALFYCARGY DFLTGYPDYW GQGTLVTVSS  120

SEQ ID NO: 253           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 253
QVQLVESGGG VVQPGRSLRL SCAASGFTFS HFAMHWVRQA PGKGLEWVAV ISYNGGNKYY  60
AESVKGRFTI SRDNSKNTLY LQMNSLRAED TALFYCARGY DVLTGYPDYW GQGTLVTVSS  120

SEQ ID NO: 254           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 254
QVQLVESGGG VVQPGRSLRL SCAASGFTFS RYAMHWVRQA PGKGLEWVAV ISYNGGNKYY  60
AESVKGRFTI SRDNSKNTLY LQMNSLRAED TALFYCARGY DVLTGYPDYW GQGTLVTVSS  120

SEQ ID NO: 255           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 255
QVQLVESGGG VVQPGRSLRL SCAASGFTFS RFAMHWVRQA PGKGLEWVAV ISFNGGNKYY  60
AESVKGRFTI SRDNSKNTLY LQMNSLRAED TALFYCARGY DVLTGYPDYW GQGTLVTVSS  120

SEQ ID NO: 256           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 256
QVQLVESGGG VVQPGRSLRL SCAASGFTFS RFAMHWVRQA PGKGLEWVAV ISYNGANKYY  60
AESVKGRFTI SRDNSKNTLY LQMNSLRAED TALFYCARGY DVLTGYPDYW GQGTLVTVSS  120

SEQ ID NO: 257           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 257
```

```
QVQLVESGGG VVQPGRSLRL SCAASGFTFS RFAMHWVRQA PGKGLEWVAV ISYNGGNKYY  60
AESVKGRFTI SRDNSKNTLY LQMNSLRAED TALFYCARGY DFLTGYPDYW GQGTLVTVSS  120

SEQ ID NO: 258         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 258
QVQLVESGGG VVQPGRSLRL SCAASGFTFS HFAMHWVRQA PGKGLEWVAV ISYDGRNKYY  60
AESVKGRFTI SRDNSKNTLY LQMNSLRAED TALFYCARGY DVLTGYPDYW GQGTLVTVSS  120

SEQ ID NO: 259         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 259
QVQLVESGGG VVQPGRSLRL SCAASGFTFS RYAMHWVRQA PGKGLEWVAV ISYDGRNKYY  60
AESVKGRFTI SRDNSKNTLY LQMNSLRAED TALFYCARGY DVLTGYPDYW GQGTLVTVSS  120

SEQ ID NO: 260         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 260
QVQLVESGGG VVQPGRSLRL SCAASGFTFS RFAMHWVRQA PGKGLEWVAV ISFDGRNKYY  60
AESVKGRFTI SRDNSKNTLY LQMNSLRAED TALFYCARGY DVLTGYPDYW GQGTLVTVSS  120

SEQ ID NO: 261         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 261
QVQLVESGGG VVQPGRSLRL SCAASGFTFS RFAMHWVRQA PGKGLEWVAV ISYDGRNKYY  60
AESVKGRFTI SRDNSKNTLY LQMNSLRAED TALFYCARGY DFLTGYPDYW GQGTLVTVSS  120

SEQ ID NO: 262         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 262
QVQLVESGGG VVQPGRSLRL SCAASGFTFS HFAMHWVRQA PGKGLEWVAV ISYDGGNKYY  60
ARSVKGRFTI SRDNSKNTLY LQMNSLRAED TALFYCARGY DVLTGYPDYW GQGTLVTVSS  120

SEQ ID NO: 263         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 263
QVQLVESGGG VVQPGRSLRL SCAASGFTFS RYAMHWVRQA PGKGLEWVAV ISYDGGNKYY  60
ARSVKGRFTI SRDNSKNTLY LQMNSLRAED TALFYCARGY DVLTGYPDYW GQGTLVTVSS  120

SEQ ID NO: 264         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 264
QVQLVESGGG VVQPGRSLRL SCAASGFTFS RFAMHWVRQA PGKGLEWVAV ISFDGGNKYY  60
ARSVKGRFTI SRDNSKNTLY LQMNSLRAED TALFYCARGY DVLTGYPDYW GQGTLVTVSS  120
```

```
SEQ ID NO: 265         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 265
QVQLVESGGG VVQPGRSLRL SCAASGFTFS RFAMHWVRQA PGKGLEWVAV ISYDGANKYY  60
ARSVKGRFTI SRDNSKNTLY LQMNSLRAED TALFYCARGY DVLTGYPDYW GQGTLVTVSS  120

SEQ ID NO: 266         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 266
QVQLVESGGG VVQPGRSLRL SCAASGFTFS RFAMHWVRQA PGKGLEWVAV ISYDGGNKYY  60
ARSVKGRFTI SRDNSKNTLY LQMNSLRAED TALFYCARGY DFLTGYPDYW GQGTLVTVSS  120

SEQ ID NO: 267         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 267
QVQLVESGGG VVQPGRSLRL SCAASGFTFS HFAMHWVRQA PGKGLEWVAV ISYDGGNKYY  60
AESVKGRFTI SRDNSKNTLY LQMNSLRAED TALFYCARGY DILTGYPDYW GQGTLVTVSS  120

SEQ ID NO: 268         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 268
QVQLVESGGG VVQPGRSLRL SCAASGFTFS RYAMHWVRQA PGKGLEWVAV ISYDGGNKYY  60
AESVKGRFTI SRDNSKNTLY LQMNSLRAED TALFYCARGY DILTGYPDYW GQGTLVTVSS  120

SEQ ID NO: 269         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 269
QVQLVESGGG VVQPGRSLRL SCAASGFTFS RFAMHWVRQA PGKGLEWVAV ISFDGGNKYY  60
AESVKGRFTI SRDNSKNTLY LQMNSLRAED TALFYCARGY DILTGYPDYW GQGTLVTVSS  120

SEQ ID NO: 270         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 270
QVQLVESGGG VVQPGRSLRL SCAASGFTFS RFAMHWVRQA PGKGLEWVAV ISYDGANKYY  60
AESVKGRFTI SRDNSKNTLY LQMNSLRAED TALFYCARGY DILTGYPDYW GQGTLVTVSS  120

SEQ ID NO: 271         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 271
QVQLVESGGG VVQPGRSLRL SCAASGFTFS KYAMHWVRQA PGKGLEWVAV ISFKGSNKYY  60
AESVKGRFTI SRDNSKNTLY LQMNSLRAED TALFYCARGY DLLTGYPDYW GQGTLVTVSS  120

SEQ ID NO: 272         moltype = AA  length = 120
```

```
FEATURE                Location/Qualifiers
REGION                 1..120
                       note = Synthetic polypeptide
source                 1..120
                       mol_type = protein
                       organism = synthetic construct
SEQUENCE: 272
QVQLVESGGG VVQPGRSLRL SCAASGFTFS RYAMHWVRQA PGKGLEWVAV ISYQGGNKYY  60
AESVKGRFTI SRDNSKNTLY LQMNSLRAED TALFYCARGY DLLTGYPDYW GQGTLVTVSS  120

SEQ ID NO: 273         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 273
QVQLVESGGG VVQPGRSLRL SCAASGFTFS HFAMHWVRQA PGKGLEWVAV ISFSGSNKYY  60
AESVKGRFTI SRDNSKNTLY LQMNSLRAED TALFYCARGY DMLTGYPDYW GQGTLVTVSS  120

SEQ ID NO: 274         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 274
QVQLVESGGG VVQPGRSLRL SCAASGFTFS KFAMHWVRQA PGKGLEWVAV ISYRGGNKYY  60
AESVKGRFTI SRDNSKNTLY LQMNSLRAED TALFYCARGY DLLTGYPDYW GQGTLVTVSS  120

SEQ ID NO: 275         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 275
QVQLVESGGG VVQPGRSLRL SCAASGFTFS RYAMHWVRQA PGKGLEWVAV ISYSGANKYY  60
AESVKGRFTI SRDNSKNTLY LQMNSLRAED TALFYCARGY DLLSGYPDYW GQGTLVTVSS  120

SEQ ID NO: 276         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 276
QVQLVESGGG VVQPGRSLRL SCAASGFTFS HYAMHWVRQA PGKGLEWVAV ISFKGANKYY  60
AESVKGRFTI SRDNSKNTLY LQMNSLRAED TALFYCARGY DLLTGYPDYW GQGTLVTVSS  120

SEQ ID NO: 277         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 277
QVQLVESGGG VVQPGRSLRL SCAASGFTFS HYAMHWVRQA PGKGLEWVAV ISYRGANKYY  60
AESVKGRFTI SRDNSKNTLY LQMNSLRAED TALFYCARGY DLLTGYPDYW GQGTLVTVSS  120

SEQ ID NO: 278         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 278
QVQLVESGGG VVQPGRSLRL SCAASGFTFS HYAMHWVRQA PGKGLEWVAV ISFYGSNKYY  60
AESVKGRFTI SRDNSKNTLY LQMNSLRAED TALFYCARGY DFLTGYPDYW GQGTLVTVSS  120

SEQ ID NO: 279         moltype = AA  length = 120
FEATURE                Location/Qualifiers
REGION                 1..120
```

```
                         note = Synthetic polypeptide
source                   1..120
                         mol_type = protein
                         organism = synthetic construct
SEQUENCE: 279
QVQLVESGGG VVQPGRSLRL SCAASGFTFS HFAMHWVRQA PGKGLEWVAV ISFFGGNKYY  60
AESVKGRFTI SRDNSKNTLY LQMNSLRAED TALFYCARGY DFLTGYPDYW GQGTLVTVSS  120

SEQ ID NO: 280           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 280
QVQLVESGGG VVQPGRSLRL SCAASGFTFS HYAMHWVRQA PGKGLEWVAV ISFMGTNKYY  60
AESVKGRFTI SRDNSKNTLY LQMNSLRAED TALFYCARGY DFLTGYPDYW GQGTLVTVSS  120

SEQ ID NO: 281           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 281
QVQLVESGGG VVQPGRSLRL SCAASGFTFS YFAMHWVRQA PGKGLEWVAV ISHRGTNKYY  60
AESVKGRFTI SRDNSKNTLY LQMNSLRAED TALFYCARGY DLLSGYPDYW GQGTLVTVSS  120

SEQ ID NO: 282           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 282
QVQLVESGGG VVQPGRSLRL SCAASGFTFS RFAMHWVRQA PGKGLEWVGV INYRGHGKYY  60
AESVKGRFTV SRDNSKNTLY LQMNSLRAED TALFYCARGY DVLTGYPDYW GQGTLVTVSS  120

SEQ ID NO: 283           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 283
QVQLVESGGG VVQPGRSLRL SCAASGFTFS RFAMHWVRQA PGKGLEWVGV ISFSGGSKYY  60
AESVKGRFTL SRDNSKNTLY LQMNSLRAED TALFYCARGY DVLTGYPDYW GQGTLVTVSS  120

SEQ ID NO: 284           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 284
QVQLVESGGG VVQPGRSLRL SCAASGFTFS RFAMHWVRQA PGKGLEWVGV ISYTGQFKYY  60
AESVKGRFTV SRDNSKNTLY LQMNSLRAED TALFYCARGY DVLTGYPDYW GQGTLVTVSS  120

SEQ ID NO: 285           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 285
QVQLVESGGG VVQPGRSLRL SCAASGFTFS RFAMHWVRQA PGKGLEWVGV ISYTGAQKYY  60
AESVKGRFTM SRDNSKNTLY LQMNSLRAED TALFYCARGY DVLTGYPDYW GQGTLVTVSS  120

SEQ ID NO: 286           moltype = AA  length = 120
FEATURE                  Location/Qualifiers
REGION                   1..120
                         note = Synthetic polypeptide
source                   1..120
```

```
                         mol_type = protein
                         organism = synthetic construct
SEQUENCE: 286
QVQLVESGGG VVQPGRSLRL SCAASGFTFS RFAMHWVRQA PGKGLEWVGV ISYSGASKYY  60
AESVKGRFTM SRDNSKNTLY LQMNSLRAED TALFYCARGY DVLTGYPDYW GQGTLVTVSS  120

SEQ ID NO: 287           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 287
QVQLVESGGG VVQPGRSLRL SCAASGFTFS RFAMHWVRQA PGKGLEWVAV ISYSGAFKYY  60
AESVKGRFTV SRDNSKNTLY LQMNSLRAED TALFYCARGY DVLTGYPDYW GQGTLVTVSS  120

SEQ ID NO: 288           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 288
QVQLVESGGG VVQPGRSLRL SCAASGFTFS RFAMHWVRQA PGKGLEWVGV ITYTGGAKYY  60
AESVKGRFTI SRDNSKNTLY LQMNSLRAED TALFYCARGY DVLTGYPDYW GQGTLVTVSS  120

SEQ ID NO: 289           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 289
QVQLVESGGG VVQPGRSLRL SCAASGFTFS RFAMHWVRQA PGKGLEWVGV INFQGTTKYY  60
AESVKGRFTI SRDNSKNTLY LQMNSLRAED TALFYCARGY DVLTGYPDYW GQGTLVTVSS  120

SEQ ID NO: 290           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 290
QVQLVESGGG VVQPGRSLRL SCAASGFTFS RFAMHWVRQA PGKGLEWVGV ISYSGDLKYY  60
AESVKGRFTV SRDNSKNTLY LQMNSLRAED TALFYCARGY DVLTGYPDYW GQGTLVTVSS  120

SEQ ID NO: 291           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 291
QVQLVESGGG VVQPGRSLRL SCAASGFTFS RFAMHWVRQA PGKGLEWVGV INYFGDAKYY  60
AESVKGRFTI SRDNSKNTLY LQMNSLRAED TALFYCARGY DVLTGYPDYW GQGTLVTVSS  120

SEQ ID NO: 292           moltype = AA  length = 120
FEATURE                  Location/Qualifiers
REGION                   1..120
                         note = Synthetic polypeptide
source                   1..120
                         mol_type = protein
                         organism = synthetic construct
SEQUENCE: 292
QVQLVESGGG VVQPGRSLRL SCAASGFTFS FYAMHWVRQA PGKGLEWVAV ISSFGSNKYY  60
AESVKGRFTI SRDNSKNTLY LQMNSLRAED TALFYCARGY DLLTGYPDYW GQGTLVTVSS  120

SEQ ID NO: 293           moltype = AA  length = 120
FEATURE                  Location/Qualifiers
REGION                   1..120
                         note = Synthetic polypeptide
source                   1..120
                         mol_type = protein
                         organism = synthetic construct
```

```
SEQUENCE: 293
QVQLVESGGG VVQPGRSLRL SCAASGFTFS YYAMHWVRQA PGKGLEWVAV ISYSGSNKYY  60
AESVKGRFTI SRDNSKNTLY LQMNSLRAED TALFYCARGY DLLTGYPDYW GQGTLVTVSS  120

SEQ ID NO: 294         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 294
QVQLVESGGG VVQPGRSLRL SCAASGFTFS YYAMHWVRQA PGKGLEWVAV ISHYGTNKYY  60
AESVKGRFTI SRDNSKNTLY LQMNSLRAED TALFYCARGY DPLTGYPDYW GQGTLVTVSS  120

SEQ ID NO: 295         moltype = AA  length = 120
FEATURE                Location/Qualifiers
REGION                 1..120
                       note = Synthetic polypeptide
source                 1..120
                       mol_type = protein
                       organism = synthetic construct
SEQUENCE: 295
QVQLVESGGG VVQPGRSLRL SCAASGFTFS HYAMHWVRQA PGKGLEWVAV ISYQGSNKYY  60
AESVKGRFTI SRDNSKNTLY LQMNSLRAED TALFYCARGY DLLTGYPDYW GQGTLVTVSS  120

SEQ ID NO: 296         moltype = AA  length = 123
FEATURE                Location/Qualifiers
REGION                 1..123
                       note = Synthetic polypeptide
source                 1..123
                       mol_type = protein
                       organism = synthetic construct
SEQUENCE: 296
QVQLQQSGPG LVKPSQTLSL TCAISGDSVS SNSATWNWIR QSPSRGLEWL GRTYYRSKWS  60
NHYAVSVKSR ITINPDTSKS QFSLQLNSVT PEDTAVYYCA RGTWKQLWFL DHWGQGTLVT  120
VSS                                                               123

SEQ ID NO: 297         moltype = AA  length = 123
FEATURE                Location/Qualifiers
REGION                 1..123
                       note = Synthetic polypeptide
source                 1..123
                       mol_type = protein
                       organism = synthetic construct
SEQUENCE: 297
QVQLQQSGPG LVKPSQTLSL TCAISGDSVS NRLATWNWIR QSPSRGLEWL GRTYYRGKWK  60
NHYAVSVKSR ITINPDTSKS QFSLQLNSVT PEDTAVYYCA RGTWNQDWFL DHWGQGTLVT  120
VSS                                                               123

SEQ ID NO: 298         moltype = AA  length = 123
FEATURE                Location/Qualifiers
REGION                 1..123
                       note = Synthetic polypeptide
source                 1..123
                       mol_type = protein
                       organism = synthetic construct
SEQUENCE: 298
QVQLQQSGPG LVKPSQTLSL TCAISGDSVS NRLATWNWIR QSPSRGLEWL GRTYYRGKWK  60
NHYAVSVKSR ITINPDTSKS QFSLQLNSVT PEDTAVYYCA RGTWDQDWFL DHWGQGTLVT  120
VSS                                                               123

SEQ ID NO: 299         moltype = AA  length = 123
FEATURE                Location/Qualifiers
REGION                 1..123
                       note = Synthetic polypeptide
source                 1..123
                       mol_type = protein
                       organism = synthetic construct
SEQUENCE: 299
QVQLQQSGPG LVKPSQTLSL TCAISGDSVS SRQATWNWIR QSPSRGLEWL GRTYYRGKWK  60
NHYAVSVKSR ITINPDTSKS QFSLQLNSVT PEDTAVYYCA RGTWEQDWFL DHWGQGTLVT  120
VSS                                                               123

SEQ ID NO: 300         moltype = AA  length = 123
FEATURE                Location/Qualifiers
REGION                 1..123
                       note = Synthetic polypeptide
source                 1..123
```

```
                         mol_type = protein
                         organism = synthetic construct
SEQUENCE: 300
QVQLQQSGPG LVKPSQTLSL TCAISGDSVS NKQATWNWIR QSPSRGLEWL GRTYYRGKWK  60
NHYAVSVKSR ITINPDTSKS QFSLQLNSVT PEDTAVYYCA RGMWNQNWFL DHWGQGTLVT  120
VSS                                                                123

SEQ ID NO: 301           moltype = AA  length = 123
FEATURE                  Location/Qualifiers
REGION                   1..123
                         note = Synthetic polypeptide
source                   1..123
                         mol_type = protein
                         organism = synthetic construct
SEQUENCE: 301
QVQLQQSGPG LVKPSQTLSL TCAISGDSVS NKQATWNWIR QSPSRGLEWL GRTYYRGQWK  60
NHYAVSVKSR ITINPDTSKS QFSLQLNSVT PEDTAVYYCA RGTWIGDWFM DHWGQGTLVT  120
VSS                                                                123

SEQ ID NO: 302           moltype = AA  length = 123
FEATURE                  Location/Qualifiers
REGION                   1..123
                         note = Synthetic polypeptide
source                   1..123
                         mol_type = protein
                         organism = synthetic construct
SEQUENCE: 302
QVQLQQSGPG LVKPSQTLSL TCAISGDSVS NKQATWNWIR QSPSRGLEWL GRTYYRGKWK  60
NHYAVSVKSR ITINPDTSKS QFSLQLNSVT PEDTAVYYCA RGTWIQDWFL DHWGQGTLVT  120
VSS                                                                123

SEQ ID NO: 303           moltype = AA  length = 123
FEATURE                  Location/Qualifiers
REGION                   1..123
                         note = Synthetic polypeptide
source                   1..123
                         mol_type = protein
                         organism = synthetic construct
SEQUENCE: 303
QVQLQQSGPG LVKPSQTLSL TCAISGDSVS SNHATWNWIR QSPSRGLEWL GRTYYRGKWK  60
NHYAVSVKSR ITINPDTSKS QFSLQLNSVT PEDTAVYYCA RGTWDQDWFL DHWGQGTLVT  120
VSS                                                                123

SEQ ID NO: 304           moltype = AA  length = 123
FEATURE                  Location/Qualifiers
REGION                   1..123
                         note = Synthetic polypeptide
source                   1..123
                         mol_type = protein
                         organism = synthetic construct
SEQUENCE: 304
QVQLQQSGPG LVKPSQTLSL TCAISGDSVS SRYATWNWIR QSPSRGLEWL GRTYYRGQWK  60
NHYAVSVKSR ITINPDTSKS QFSLQLNSVT PEDTAVYYCA RGMWNQNWFL DHWGQGTLVT  120
VSS                                                                123

SEQ ID NO: 305           moltype = AA  length = 123
FEATURE                  Location/Qualifiers
REGION                   1..123
                         note = Synthetic polypeptide
source                   1..123
                         mol_type = protein
                         organism = synthetic construct
SEQUENCE: 305
QVQLQQSGPG LVKPSQTLSL TCAISGDSVS NKQATWNWIR QSPSRGLEWL GRTYYRGKWK  60
NHYAVSVKSR ITINPDTSKS QFSLQLNSVT PEDTAVYYCA RGMWSGDWFL DHWGQGTLVT  120
VSS                                                                123

SEQ ID NO: 306           moltype = AA  length = 123
FEATURE                  Location/Qualifiers
REGION                   1..123
                         note = Synthetic polypeptide
source                   1..123
                         mol_type = protein
                         organism = synthetic construct
SEQUENCE: 306
QVQLQQSGPG LVKPSQTLSL TCAISGDSVS SHVATWNWIR QSPSRGLEWL GRTYYRGKWK  60
NHYAVSVKSR ITINPDTSKS QFSLQLNSVT PEDTAVYYCA RGMWSEDWFL DHWGQGTLVT  120
VSS                                                                123
```

```
SEQ ID NO: 307          moltype = AA  length = 123
FEATURE                 Location/Qualifiers
REGION                  1..123
                        note = Synthetic polypeptide
source                  1..123
                        mol_type = protein
                        organism = synthetic construct
SEQUENCE: 307
QVQLQQSGPG LVKPSQTLSL TCAISGDSVS SRQATWNWIR QSPSRGLEWL GRTYYRGKWK  60
NHYAVSVKSR ITINPDTSKS QFSLQLNSVT PEDTAVYYCA RGMWQGNWFL DHWGQGTLVT  120
VSS                                                                123

SEQ ID NO: 308          moltype = AA  length = 123
FEATURE                 Location/Qualifiers
REGION                  1..123
                        note = Synthetic polypeptide
source                  1..123
                        mol_type = protein
                        organism = synthetic construct
SEQUENCE: 308
QVQLQQSGPG LVKPSQTLSL TCAISGDSVS NHQATWNWIR QSPSRGLEWL GRTYYRGKWK  60
NHYAVSVKSR ITINPDTSKS QFSLQLNSVT PEDTAVYYCA RGTWIQDWFL DHWGQGTLVT  120
VSS                                                                123

SEQ ID NO: 309          moltype = AA  length = 123
FEATURE                 Location/Qualifiers
REGION                  1..123
                        note = Synthetic polypeptide
source                  1..123
                        mol_type = protein
                        organism = synthetic construct
SEQUENCE: 309
QVQLQQSGPG LVKPSQTLSL TCAISGDSVS SRDATWNWIR QSPSRGLEWL GRTYYRGKWK  60
NHYAVSVKSR ITINPDTSKS QFSLQLNSVT PEDTAVYYCA RGQWNEDWFL DHWGQGTLVT  120
VSS                                                                123

SEQ ID NO: 310          moltype = AA  length = 123
FEATURE                 Location/Qualifiers
REGION                  1..123
                        note = Synthetic polypeptide
source                  1..123
                        mol_type = protein
                        organism = synthetic construct
SEQUENCE: 310
QVQLQQSGPG LVKPSQTLSL TCAISGDSVS NRLATWNWIR QSPSRGLEWL GRTYYRGKWK  60
NHYAVSVKSR ITINPDTSKS QFSLQLNSVT PEDTAVYYCA RGRWEGDWFF DHWGQGTLVT  120
VSS                                                                123

SEQ ID NO: 311          moltype = AA  length = 123
FEATURE                 Location/Qualifiers
REGION                  1..123
                        note = Synthetic polypeptide
source                  1..123
                        mol_type = protein
                        organism = synthetic construct
SEQUENCE: 311
QVQLQQSGPG LVKPSQTLSL TCAISGDSVS NKQATWNWIR QSPSRGLEWL GRTYFRRTWK  60
NHYAVSVKSR ITINPDTSKS QFSLQLNSVT PEDTAVYYCA RGMWSEDWFL DHWGQGTLVT  120
VSS                                                                123

SEQ ID NO: 312          moltype = AA  length = 123
FEATURE                 Location/Qualifiers
REGION                  1..123
                        note = Synthetic polypeptide
source                  1..123
                        mol_type = protein
                        organism = synthetic construct
SEQUENCE: 312
QVQLQQSGPG LVKPSQTLSL TCAISGDSVS NRLATWNWIR QSPSRGLEWL GRTYYRGKWK  60
NHYAVSVKSR ITINPDTSKS QFSLQLNSVT PEDTAVYYCA RGVWIGNWFL DHWGQGTLVT  120
VSS                                                                123

SEQ ID NO: 313          moltype = AA  length = 106
FEATURE                 Location/Qualifiers
REGION                  1..106
                        note = Synthetic polypeptide
source                  1..106
                        mol_type = protein
                        organism = synthetic construct
```

```
SEQUENCE: 313
GQPKANPTVT LFPPSSEELQ ANKATLVCLI SDFYPGAVTV AWKADGSPVK AGVETTKPSK  60
QSNNKYAASS YLSLTPEQWK SHRSYSCQVT HEGSTVEKTV APTECS                106

SEQ ID NO: 314          moltype = AA  length = 106
FEATURE                 Location/Qualifiers
REGION                  1..106
                        note = Synthetic polypeptide
source                  1..106
                        mol_type = protein
                        organism = synthetic construct
SEQUENCE: 314
GQPKAAPSVT LFPPSSEELQ ANKATLVCLI SDFYPGAVTV AWKADSSPVK AGVETTTPSK  60
QSNNKYAASS YLSLTPEQWK SHRSYSCQVT HEGSTVEKTV APTECS                106

SEQ ID NO: 315          moltype = AA  length = 105
FEATURE                 Location/Qualifiers
REGION                  1..105
                        note = Synthetic polypeptide
source                  1..105
                        mol_type = protein
                        organism = synthetic construct
SEQUENCE: 315
QPKAAPSVTL FPPSSEELQA NKATLVCLIS DFYPGAVTVA WKADSSPVKA GVETTTPSKQ  60
SNNKYAASSY LSLTPEQWKS HRSYSCQVTH EGSTVEKTVA PTECS                 105

SEQ ID NO: 316          moltype = AA  length = 106
FEATURE                 Location/Qualifiers
REGION                  1..106
                        note = Synthetic polypeptide
source                  1..106
                        mol_type = protein
                        organism = synthetic construct
SEQUENCE: 316
GQPKAAPSVT LFPPSSEELQ ANKATLVCLI SDFYPGAVTV AWKADSSPVK AGVETTTPSK  60
QSNNKYAASS YLSLTPEQWK SHKSYSCQVT HEGSTVEKTV APTECS                106

SEQ ID NO: 317          moltype = AA  length = 106
FEATURE                 Location/Qualifiers
REGION                  1..106
                        note = Synthetic polypeptide
source                  1..106
                        mol_type = protein
                        organism = synthetic construct
SEQUENCE: 317
GQPKAAPSVT LFPPSSEELQ ANKATLVCLV SDFYPGAVTV AWKADGSPVK VGVETTKPSK  60
QSNNKYAASS YLSLTPEQWK SHRSYSCRVT HEGSTVEKTV APAECS                106

SEQ ID NO: 318          moltype = AA  length = 106
FEATURE                 Location/Qualifiers
REGION                  1..106
                        note = Synthetic polypeptide
source                  1..106
                        mol_type = protein
                        organism = synthetic construct
SEQUENCE: 318
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                106

SEQ ID NO: 319          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 319
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC               107

SEQ ID NO: 320          moltype = AA  length = 330
FEATURE                 Location/Qualifiers
REGION                  1..330
                        note = Synthetic polypeptide
source                  1..330
                        mol_type = protein
                        organism = synthetic construct
SEQUENCE: 320
ASTKGPSVFP LAPSSKSTSG GTAALGCLVK DYFPEPVTVS WNSGALTSGV HTFPAVLQSS  60
```

```
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 321         moltype = AA  length = 330
FEATURE                Location/Qualifiers
REGION                 1..330
                       note = Synthetic polypeptide
source                 1..330
                       mol_type = protein
                       organism = synthetic construct
SEQUENCE: 321
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 322         moltype = AA  length = 330
FEATURE                Location/Qualifiers
REGION                 1..330
                       note = Synthetic polypeptide
source                 1..330
                       mol_type = protein
                       organism = synthetic construct
SEQUENCE: 322
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 323         moltype = AA  length = 330
FEATURE                Location/Qualifiers
REGION                 1..330
                       note = Synthetic polypeptide
source                 1..330
                       mol_type = protein
                       organism = synthetic construct
SEQUENCE: 323
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 324         moltype = AA  length = 330
FEATURE                Location/Qualifiers
REGION                 1..330
                       note = Synthetic polypeptide
source                 1..330
                       mol_type = protein
                       organism = synthetic construct
SEQUENCE: 324
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYG  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 325         moltype = AA  length = 330
FEATURE                Location/Qualifiers
REGION                 1..330
                       note = Synthetic polypeptide
source                 1..330
                       mol_type = protein
                       organism = synthetic construct
SEQUENCE: 325
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPCEEQYG  180
STYRCVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
```

-continued

```
QQGNVFSCSV MHEALHNHYT QKSLSLSPGK                              330

SEQ ID NO: 326          moltype = AA  length = 326
FEATURE                 Location/Qualifiers
REGION                  1..326
                        note = Synthetic polypeptide
source                  1..326
                        mol_type = protein
                        organism = synthetic construct
SEQUENCE: 326
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPGK                                  326

SEQ ID NO: 327          moltype = AA  length = 330
FEATURE                 Location/Qualifiers
REGION                  1..330
                        note = Synthetic polypeptide
source                  1..330
                        mol_type = protein
                        organism = synthetic construct
SEQUENCE: 327
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPCEEQYG  180
STYRCVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                              330

SEQ ID NO: 328          moltype = DNA  length = 326
FEATURE                 Location/Qualifiers
misc_feature            1..326
                        note = Synthetic polynucleotide
source                  1..326
                        mol_type = other DNA
                        organism = synthetic construct
SEQUENCE: 328
gagatcgtac ttactcagtc acccgccaca ttgtccctga gcccgggtga acgggcgacc  60
ctcagctgcc gagcatccca gtccgtcgga cgatcattgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgaggt tgcctttcac gtttggacca  300
gggaccaagg tggacattaa gcgtac                                  326

SEQ ID NO: 329          moltype = DNA  length = 326
FEATURE                 Location/Qualifiers
misc_feature            1..326
                        note = Synthetic polynucleotide
source                  1..326
                        mol_type = other DNA
                        organism = synthetic construct
SEQUENCE: 329
gatatccagc tcactcaatc gccatcattt ctctccgctt cggtaggcga ccgggtcacg  60
atcacatgca gggcgtcgca aagcattggg aggtcgttgc attggtatca gcagaaaccc  120
ggaaaggccc cgaaacttct gatcaaatac gcatcacaaa gcttgagcgg tgtgccgtcg  180
cgcttctccg gttccggaag cggaacggaa ttcacgctta caatctcctc actgcagccc  240
gaggatttcg cgacctatta ctgtcaccag tcatccagac tcccgtttac ttttggccct  300
gggaccaagg tggacattaa gcgtac                                  326

SEQ ID NO: 330          moltype = DNA  length = 321
FEATURE                 Location/Qualifiers
misc_feature            1..321
                        note = Synthetic polynucleotide
source                  1..321
                        mol_type = other DNA
                        organism = synthetic construct
SEQUENCE: 330
gagatcgtac ttactcagtc acccgccaca ttgtccctga gcccgggtga acgggcgacc  60
ctcagctgcc gagcatccaa gtccgtcgga cgatcattgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgaggt tgcctttcac gtttggacca  300
gggaccaagg tggacattaa g                                       321

SEQ ID NO: 331          moltype = DNA  length = 321
FEATURE                 Location/Qualifiers
```

```
misc_feature           1..321
                       note = Synthetic polynucleotide
source                 1..321
                       mol_type = other DNA
                       organism = synthetic construct
SEQUENCE: 331
gagatcgtac ttactcagtc acccgccaca ttgtccctga gcccgggtga acgggcgacc  60
ctcagctgcc gagcatccca gtccgtcgga cgatcattgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgaggt tgcctttcac gtttggacca  300
gggaccaagg tggacattaa g                                            321

SEQ ID NO: 332         moltype = DNA  length = 321
FEATURE                Location/Qualifiers
misc_feature           1..321
                       note = Synthetic polynucleotide
source                 1..321
                       mol_type = other DNA
                       organism = synthetic construct
SEQUENCE: 332
gagatcgtac ttactcagtc acccgccaca ttgtccctga gcccgggtga acgggcgacc  60
ctcagctgcc gagcatccca gtccgtctgg cgatcattgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgaggt tgcctttcac gtttggacca  300
gggaccaagg tggacattaa g                                            321

SEQ ID NO: 333         moltype = DNA  length = 321
FEATURE                Location/Qualifiers
misc_feature           1..321
                       note = Synthetic polynucleotide
source                 1..321
                       mol_type = other DNA
                       organism = synthetic construct
SEQUENCE: 333
gagatcgtac ttactcagtc acccgccaca ttgtccctga gcccgggtga acgggcgacc  60
ctcagctgcc gagcatccca gtccgtcgga cgaaacttgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgaggt tgcctttcac gtttggacca  300
gggaccaagg tggacattaa g                                            321

SEQ ID NO: 334         moltype = DNA  length = 321
FEATURE                Location/Qualifiers
misc_feature           1..321
                       note = Synthetic polynucleotide
source                 1..321
                       mol_type = other DNA
                       organism = synthetic construct
SEQUENCE: 334
gagatcgtac ttactcagtc acccgccaca ttgtccctga gcccgggtga acgggcgacc  60
ctcagctgcc gagcatccca gtccgtcgga cgatcattgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgatgt tgcctttcac gtttggacca  300
gggaccaagg tggacattaa g                                            321

SEQ ID NO: 335         moltype = DNA  length = 321
FEATURE                Location/Qualifiers
misc_feature           1..321
                       note = Synthetic polynucleotide
source                 1..321
                       mol_type = other DNA
                       organism = synthetic construct
SEQUENCE: 335
gagatcgtac ttactcagtc acccgccaca ttgtccctga gcccgggtga acgggcgacc  60
ctcagctgcc gagcatccaa gtccgtctgg cgatcattgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgaggt tgcctttcac gtttggacca  300
gggaccaagg tggacattaa g                                            321

SEQ ID NO: 336         moltype = DNA  length = 321
FEATURE                Location/Qualifiers
misc_feature           1..321
                       note = Synthetic polynucleotide
source                 1..321
                       mol_type = other DNA
```

```
                         organism = synthetic construct
SEQUENCE: 336
gagatcgtac ttactcagtc acccgccaca ttgtccctga gcccgggtga acgggcgacc  60
ctcagctgcc gagcatccaa gtccgtcgga cgaaacttgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgaggt tgcctttcac gtttggacca  300
gggaccaagg tggacattaa g                                            321

SEQ ID NO: 337           moltype = DNA  length = 321
FEATURE                  Location/Qualifiers
misc_feature             1..321
                         note = Synthetic polynucleotide
source                   1..321
                         mol_type = other DNA
                         organism = synthetic construct
SEQUENCE: 337
gagatcgtac ttactcagtc acccgccaca ttgtccctga gcccgggtga acgggcgacc  60
ctcagctgcc gagcatccaa gtccgtcgga cgatcattgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgatgt tgcctttcac gtttggacca  300
gggaccaagg tggacattaa g                                            321

SEQ ID NO: 338           moltype = DNA  length = 325
FEATURE                  Location/Qualifiers
misc_feature             1..325
                         note = Synthetic polynucleotide
source                   1..325
                         mol_type = other DNA
                         organism = synthetic construct
SEQUENCE: 338
gagatcgtac ttactcagtc acccgccaca ttgtccctga gcccgggtga acgggcgacc  60
ctcagctgcc gagcatccaa atccgtcggg tggagcttgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgaggt tgcctttcac gtttggacca  300
gggaccaagg tggacattaa gcgta                                        325

SEQ ID NO: 339           moltype = DNA  length = 325
FEATURE                  Location/Qualifiers
misc_feature             1..325
                         note = Synthetic polynucleotide
source                   1..325
                         mol_type = other DNA
                         organism = synthetic construct
SEQUENCE: 339
gagatcgtac ttactcagtc acccgccaca ttgtccctga gcccgggtga acgggcgacc  60
ctcagctgcc gagcatccaa atccgtcggg tacagcttgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgaggt tgcctttcac gtttggacca  300
gggaccaagg tggacattaa gcgta                                        325

SEQ ID NO: 340           moltype = DNA  length = 325
FEATURE                  Location/Qualifiers
misc_feature             1..325
                         note = Synthetic polynucleotide
source                   1..325
                         mol_type = other DNA
                         organism = synthetic construct
SEQUENCE: 340
gagatcgtac ttactcagtc acccgccaca ttgtccctga gcccgggtga acgggcgacc  60
ctcagctgcc gagcatccaa agccgtcggg tggagcttgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgaggt tgcctttcac gtttggacca  300
gggaccaagg tggacattaa gcgta                                        325

SEQ ID NO: 341           moltype = DNA  length = 325
FEATURE                  Location/Qualifiers
misc_feature             1..325
                         note = Synthetic polynucleotide
source                   1..325
                         mol_type = other DNA
                         organism = synthetic construct
SEQUENCE: 341
gagatcgtac ttactcagtc acccgccaca ttgtccctga gcccgggtga acgggcgacc  60
ctcagctgcc gagcatccaa atcagtcggt cagtctttgc actggtacca acaaaaaccg  120
```

```
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgcgtt tgcctttcac gtttggacca  300
gggaccaagg tggacattaa gcgta                                          325

SEQ ID NO: 342         moltype = DNA  length = 325
FEATURE                Location/Qualifiers
misc_feature           1..325
                       note = Synthetic polynucleotide
source                 1..325
                       mol_type = other DNA
                       organism = synthetic construct
SEQUENCE: 342
gagatcgtac ttactcagtc acccgccaca ttgtccctga gcccgggtga acgggcgacc  60
ctcagctgcc gagcatcccg ttcagtcggt ctggctttgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgttct tgcctttcac gtttggacca  300
gggaccaagg tggacattaa gcgta                                          325

SEQ ID NO: 343         moltype = DNA  length = 326
FEATURE                Location/Qualifiers
misc_feature           1..326
                       note = Synthetic polynucleotide
source                 1..326
                       mol_type = other DNA
                       organism = synthetic construct
SEQUENCE: 343
gacatccaga tgacccagtc tccatcctcc ctgtctgcat ctgtaggaga cagaatcacc  60
atcacttgcc gggcaagtca gagcattagc aggtatttaa attggtatca acagaaacca  120
gggaaagccc ctaaactcct gatctatgct gcatccagtt tgcaaagtgg gatcccatca  180
aggttcagcg gcagtggatc tgggacagat ttcactctca ccatcaacag tctgcaacct  240
gaagattttg caacttactt ctgtcaacag agttacagtc cccattcac tttcggccct  300
gggaccaaag tggatatcaa acgtac                                         326

SEQ ID NO: 344         moltype = DNA  length = 321
FEATURE                Location/Qualifiers
misc_feature           1..321
                       note = Synthetic polynucleotide
source                 1..321
                       mol_type = other DNA
                       organism = synthetic construct
SEQUENCE: 344
gacatccaga tgacccagtc tccatcctcc ctgtctgcat ctgtaggaga cagaatcacc  60
atcacttgcc gggcaagtca gagcattagc aggtatttaa attggtatca acagaaacca  120
gggaaagccc ctaaactcct gatcttcgct ggtcagcgtt tgcaaagtgg gatcccatca  180
aggttcagcg gcagtggatc tgggacagat ttcactctca ccatcaacag tctgcaacct  240
gaagattttg caacttactt ctgtcaacag gctatcggta tgccatacac tttcggccct  300
gggaccaaag tggatatcaa a                                              321

SEQ ID NO: 345         moltype = DNA  length = 321
FEATURE                Location/Qualifiers
misc_feature           1..321
                       note = Synthetic polynucleotide
source                 1..321
                       mol_type = other DNA
                       organism = synthetic construct
SEQUENCE: 345
gacatccaga tgacccagtc tccatcctcc ctgtctgcat ctgtaggaga cagaatcacc  60
atcacttgcc gggcaagtca gtacattgtt cgttacttaa actggtatca acagaaacca  120
gggaaagccc ctaaactcct gatctacgct gctcatcatt tgcaaagtgg gatcccatca  180
aggttcagcg gcagtggatc tgggacagat ttcactctca ccatcaacag tctgcaacct  240
gaagattttg caacttactt ctgtcaacag gctatccagg aaccatacac tttcggccct  300
gggaccaaag tggatatcaa a                                              321

SEQ ID NO: 346         moltype = DNA  length = 321
FEATURE                Location/Qualifiers
misc_feature           1..321
                       note = Synthetic polynucleotide
source                 1..321
                       mol_type = other DNA
                       organism = synthetic construct
SEQUENCE: 346
gacatccaga tgacccagtc tccatcctcc ctgtctgcat ctgtaggaga cagaatcacc  60
atcacttgcc gggcaagtca gactattgtt cgttacttaa actggtatca acagaaacca  120
gggaaagccc ctaaactcct gatcttcgct ggtcagcgtt tgcaaagtgg gatcccatca  180
aggttcagcg gcagtggatc tgggacagat ttcactctca ccatcaacag tctgcaacct  240
gaagattttg caacttactt ctgtcaacag gctatcatca acccatacac tttcggccct  300
gggaccaaag tggatatcaa a                                              321
```

```
SEQ ID NO: 347          moltype = DNA  length = 321
FEATURE                 Location/Qualifiers
misc_feature            1..321
                        note = Synthetic polynucleotide
source                  1..321
                        mol_type = other DNA
                        organism = synthetic construct
SEQUENCE: 347
gacatccaga tgacccagtc tccatcctcc ctgtctgcat ctgtaggaga cagaatcacc  60
atcacttgcc gggcaagtca gtacattgtt cgttacttaa actggtatca acagaaacca  120
gggaaagccc ctaaactcct gatctacgct gctaacatgt tgcaaagtgg gatcccatca  180
aggttcagcg gcagtggatc tgggacagat ttcactctca ccatcaacag tctgcaacct  240
gaagattttg caacttactt ctgtcaacag gctatcaacc agccatacac tttcggccct  300
gggaccaaag tggatatcaa a                                            321

SEQ ID NO: 348          moltype = DNA  length = 321
FEATURE                 Location/Qualifiers
misc_feature            1..321
                        note = Synthetic polynucleotide
source                  1..321
                        mol_type = other DNA
                        organism = synthetic construct
SEQUENCE: 348
gacatccaga tgacccagtc tccatcctcc ctgtctgcat ctgtaggaga cagaatcacc  60
atcacttgcc gggcaagtca gaaaattgct cgttacttag tttggtatca acagaaacca  120
gggaaagccc ctaaactcct gatctacgct gctaacatgt tgcaaagtgg gatcccatca  180
aggttcagcg gcagtggatc tgggacagat ttcactctca ccatcaacag tctgcaacct  240
gaagattttg caacttactt ctgtcaacag tctatccagc agccatacac tttcggccct  300
gggaccaaag tggatatcaa a                                            321

SEQ ID NO: 349          moltype = DNA  length = 324
FEATURE                 Location/Qualifiers
misc_feature            1..324
                        note = Synthetic polynucleotide
source                  1..324
                        mol_type = other DNA
                        organism = synthetic construct
SEQUENCE: 349
gacatccaga tgacccagtc tccatcctcc ctgtctgcat ctgtaggaga cagaatcacc  60
atcacttgcc gggcaagtca gagcattagc aggtatttaa attggtatca acagaaacca  120
gggaaagccc ctaaactcct gatcttcgct ggtcagcgtt tgcaaagtgg gatcccatca  180
aggttcagcg gcagtggatc tgggacagat ttcactctca ccatcaacag tctgcaacct  240
gaagattttg caacttactt ctgtcaacag gctatccagc agccatacac tttcggccct  300
gggaccaaag tggatatcaa acgt                                         324

SEQ ID NO: 350          moltype = DNA  length = 321
FEATURE                 Location/Qualifiers
misc_feature            1..321
                        note = Synthetic polynucleotide
source                  1..321
                        mol_type = other DNA
                        organism = synthetic construct
SEQUENCE: 350
gacatccaga tgacccagtc tccatcctcc ctgtctgcat ctgtaggaga cagaatcacc  60
atcacttgcc gggcaagtca gtacattgtt cgttacttaa actggtatca acagaaacca  120
gggaaagccc ctaaactcct gatctacgct tcttacaact tgcaaagtgg gatcccatca  180
aggttcagcg gcagtggatc tgggacagat ttcactctca ccatcaacag tctgcaacct  240
gaagattttg caacttactt ctgtcaacag gctatcatgg ctccatacac tttcggccct  300
gggaccaaag tggatatcaa a                                            321

SEQ ID NO: 351          moltype = DNA  length = 321
FEATURE                 Location/Qualifiers
misc_feature            1..321
                        note = Synthetic polynucleotide
source                  1..321
                        mol_type = other DNA
                        organism = synthetic construct
SEQUENCE: 351
gacatccaga tgacccagtc tccatcctcc ctgtctgcat ctgtaggaga cagaatcacc  60
atcacttgcc gggcaagtca gcctattgct cagtacttaa actggtatca acagaaacca  120
gggaaagccc ctaaactcct gatctacgct ggtcgttact tgcaaagtgg gatcccatca  180
aggttcagcg gcagtggatc tgggacagat ttcactctca ccatcaacag tctgcaacct  240
gaagattttg caacttactt ctgtcaacag gctatccaga acccatacac tttcggccct  300
gggaccaaag tggatatcaa a                                            321

SEQ ID NO: 352          moltype = DNA  length = 321
FEATURE                 Location/Qualifiers
misc_feature            1..321
```

```
                         note = Synthetic polynucleotide
source                   1..321
                         mol_type = other DNA
                         organism = synthetic construct
SEQUENCE: 352
gacatccaga tgacccagtc tccatcctcc ctgtctgcat ctgtaggaga cagaatcacc  60
atcacttgcc gggcaagtca gagcattagc aggtatttaa attggtatca acagaaacca  120
gggaaagccc ctaaactcct gatcttcgct ggtcagcgtt tgcaaagtgg gatcccatca  180
aggttcagcg gcagtggatc tgggacagat ttcactctca ccatcaacag tctgcaacct  240
gaagattttg caacttactt ctgtcaacag gctatcgttc agccatacac tttcggccct  300
gggaccaaag tggatatcaa a                                            321

SEQ ID NO: 353           moltype = DNA  length = 321
FEATURE                  Location/Qualifiers
misc_feature             1..321
                         note = Synthetic polynucleotide
source                   1..321
                         mol_type = other DNA
                         organism = synthetic construct
SEQUENCE: 353
gacatccaga tgacccagtc tccatcctcc ctgtctgcat ctgtaggaga cagaatcacc  60
atcacttgcc gggcaagtca gccgatttct cgttacttat cttggtatca acagaaacca  120
gggaaagccc ctaaactcct gatcttcgct ggtcagcgtt tgcaaagtgg gatcccatca  180
aggttcagcg gcagtggatc tgggacagat ttcactctca ccatcaacag tctgcaacct  240
gaagattttg caacttactt ctgtcaacag gctatctcta tcccatacac tttcggccct  300
gggaccaaag tggatatcaa a                                            321

SEQ ID NO: 354           moltype = DNA  length = 321
FEATURE                  Location/Qualifiers
misc_feature             1..321
                         note = Synthetic polynucleotide
source                   1..321
                         mol_type = other DNA
                         organism = synthetic construct
SEQUENCE: 354
gacatccaga tgacccagtc tccatcctcc ctgtctgcat ctgtaggaga cagaatcacc  60
atcacttgcc gggcaagtca gcagattgct cgttacttaa actggtatca acagaaacca  120
gggaaagccc ctaaactcct gatctacgct tcttacaact tgcaaagtgg gatcccatca  180
aggttcagcg gcagtggatc tgggacagat ttcactctca ccatcaacag tctgcaacct  240
gaagattttg caacttactt ctgtcaacag gctatcatcc agccatacac tttcggccct  300
gggaccaaag tggatatcaa a                                            321

SEQ ID NO: 355           moltype = DNA  length = 321
FEATURE                  Location/Qualifiers
misc_feature             1..321
                         note = Synthetic polynucleotide
source                   1..321
                         mol_type = other DNA
                         organism = synthetic construct
SEQUENCE: 355
gacatccaga tgacccagtc tccatcctcc ctgtctgcat ctgtaggaga cagaatcacc  60
atcacttgcc gggcaagtca gagcattagc aggtatttaa attggtatca acagaaacca  120
gggaaagccc ctaaactcct gatctacgct tcttacaact tgcaaagtgg gatcccatca  180
aggttcagcg gcagtggatc tgggacagat ttcactctca ccatcaacag tctgcaacct  240
gaagattttg caacttactt ctgtcaacag gctatccaga acccatacac tttcggccct  300
gggaccaaag tggatatcaa a                                            321

SEQ ID NO: 356           moltype = DNA  length = 321
FEATURE                  Location/Qualifiers
misc_feature             1..321
                         note = Synthetic polynucleotide
source                   1..321
                         mol_type = other DNA
                         organism = synthetic construct
SEQUENCE: 356
gacatccaga tgacccagtc tccatcctcc ctgtctgcat ctgtaggaga cagaatcacc  60
atcacttgcc gggcaagtca gactattgtt cgttacttaa actggtatca acagaaacca  120
gggaaagccc ctaaactcct gatcttcgct ggtcagcgtt tgcaaagtgg gatcccatca  180
aggttcagcg gcagtggatc tgggacagat ttcactctca ccatcaacag tctgcaacct  240
gaagattttg caacttactt ctgtcaacag tctatccaga ctccatacac tttcggccct  300
gggaccaaag tggatatcaa a                                            321

SEQ ID NO: 357           moltype = DNA  length = 321
FEATURE                  Location/Qualifiers
misc_feature             1..321
                         note = Synthetic polynucleotide
source                   1..321
                         mol_type = other DNA
                         organism = synthetic construct
```

```
SEQUENCE: 357
gacatccaga tgacccagtc tccatcctcc ctgtctgcat ctgtaggaga cagaatcacc  60
atcacttgcc gggcaagtca gagcattagc aggtatttaa attggtatca acagaaacca  120
gggaaagccc ctaaactcct gatctacgct ggtcgtatct tgcaaagtgg gatcccatca  180
aggttcagcg gcagtggatc tgggacagat ttcactctca ccatcaacag tctgcaacct  240
gaagattttg caacttactt ctgtcaacag gctatcatca acccatacac tttcggccct  300
gggaccaaag tggatatcaa a                                           321

SEQ ID NO: 358          moltype = DNA  length = 321
FEATURE                 Location/Qualifiers
misc_feature            1..321
                        note = Synthetic polynucleotide
source                  1..321
                        mol_type = other DNA
                        organism = synthetic construct
SEQUENCE: 358
gacatccaga tgacccagtc tccatcctcc ctgtctgcat ctgtaggaga cagaatcacc  60
atcacttgcc gggcaagtca gcgtattgct cgttacttaa actggtatca acagaaacca  120
gggaaagccc ctaaactcct gatcttcgct ggttctatct tgcaaagtgg gatcccatca  180
aggttcagcg gcagtggatc tgggacagat ttcactctca ccatcaacag tctgcaacct  240
gaagattttg caacttactt ctgtcaacag gctatccaga acccatacac tttcggccct  300
gggaccaaag tggatatcaa a                                           321

SEQ ID NO: 359          moltype = DNA  length = 321
FEATURE                 Location/Qualifiers
misc_feature            1..321
                        note = Synthetic polynucleotide
source                  1..321
                        mol_type = other DNA
                        organism = synthetic construct
SEQUENCE: 359
gacatccaga tgacccagtc tccatcctcc ctgtctgcat ctgtaggaga cagaatcacc  60
atcacttgcc gggcaagtca gagcattagc aggtatttaa attggtatca acagaaacca  120
gggaaagccc ctaaactcct gatctacgct tcttacaact tgcaaagtgg gatcccatca  180
aggttcagcg gcagtggatc tgggacagat ttcactctca ccatcaacag tctgcaacct  240
gaagattttg caacttactt ctgtcaacag tctatccagc agccatacac tttcggccct  300
gggaccaaag tggatatcaa a                                           321

SEQ ID NO: 360          moltype = DNA  length = 321
FEATURE                 Location/Qualifiers
misc_feature            1..321
                        note = Synthetic polynucleotide
source                  1..321
                        mol_type = other DNA
                        organism = synthetic construct
SEQUENCE: 360
gacatccaga tgacccagtc tccatcctcc ctgtctgcat ctgtaggaga cagaatcacc  60
atcacttgcc gggcaagtca gtacattgtt cgttacttaa actggtatca acagaaacca  120
gggaaagccc ctaaactcct gatctacgct tcttacaact tgcaaagtgg gatcccatca  180
aggttcagcg gcagtggatc tgggacagat ttcactctca ccatcaacag tctgcaacct  240
gaagattttg caacttactt ctgtcaacag gctatccagc agccatacac tttcggccct  300
gggaccaaag tggatatcaa a                                           321

SEQ ID NO: 361          moltype = DNA  length = 321
FEATURE                 Location/Qualifiers
misc_feature            1..321
                        note = Synthetic polynucleotide
source                  1..321
                        mol_type = other DNA
                        organism = synthetic construct
SEQUENCE: 361
gacatccaga tgacccagtc tccatcctcc ctgtctgcat ctgtaggaga cagaatcacc  60
atcacttgcc gggcaagtca gatgattgct cgttacttaa actggtatca acagaaacca  120
gggaaagccc ctaaactcct gatctacgct tcttacaact tgcaaagtgg gatcccatca  180
aggttcagcg gcagtggatc tgggacagat ttcactctca ccatcaacag tctgcaacct  240
gaagattttg caacttactt ctgtcaacag gctatcatca acccatacac tttcggccct  300
gggaccaaag tggatatcaa a                                           321

SEQ ID NO: 362          moltype = DNA  length = 321
FEATURE                 Location/Qualifiers
misc_feature            1..321
                        note = Synthetic polynucleotide
source                  1..321
                        mol_type = other DNA
                        organism = synthetic construct
SEQUENCE: 362
gacatccaga tgacccagtc tccatcctcc ctgtctgcat ctgtaggaga cagaatcacc  60
atcacttgcc gggcaagtca gtacattgtt cgttacttaa actggtatca acagaaacca  120
gggaaagccc ctaaactcct gatctacggt gctcgtaact tgcaaagtgg gatcccatca  180
```

```
aggttcagcg gcagtggatc tgggacagat ttcactctca ccatcaacag tctgcaacct  240
gaagattttg caacttactt ctgtcaacag tctatccaga ctccatacac tttcggccct  300
gggaccaaag tggatatcaa a                                            321

SEQ ID NO: 363         moltype = DNA  length = 321
FEATURE                Location/Qualifiers
misc_feature           1..321
                       note = Synthetic polynucleotide
source                 1..321
                       mol_type = other DNA
                       organism = synthetic construct
SEQUENCE: 363
gacatccaga tgacccagtc tccatcctcc ctgtctgcat ctgtaggaga cagaatcacc  60
atcacttgcc gggcaagtca gagcattagc aggtatttaa attggtatca acagaaacca  120
gggaaagccc ctaaactcct gatctatgct gcatccagtt tgcaaagtgg gatcccatca  180
aggttcagcg gcagtggatc tgggacagat ttcactctca ccatcaacag tctgcaacct  240
gaagattttg caacttactt ctgtcaacag agttacagtc cccattcac tttcggccct  300
gggaccaaag tggatatcaa a                                            321

SEQ ID NO: 364         moltype = DNA  length = 362
FEATURE                Location/Qualifiers
misc_feature           1..362
                       note = Synthetic polynucleotide
source                 1..362
                       mol_type = other DNA
                       organism = synthetic construct
SEQUENCE: 364
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctcctca  360
gc                                                                 362

SEQ ID NO: 365         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 365
caagttcagt tggtggagtc tggagccgaa gtagtaaagc caggagcttc agtgaaagtc  60
tcttgtaaag caagtggatt cacgtttagc cgctttgcca tgcattgggt gcggcaagct  120
cccggtcagg ggttggagtg gatgggagtt attagctatg acgggggcaa taagtactac  180
gccgagtctg ttaagggtcg ggtcacaatg acacgggaca cctcaaccag tacactctat  240
atggaactgt ctagcctgag atccgaggac accgctgtgt attattgcgc taggggggtac  300
gatgtattga cgggttatcc tgattactgg gggcagggga cactcgtaac cgtctctagt  360

SEQ ID NO: 366         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 366
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata acggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 367         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 367
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata tcggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360
```

```
SEQ ID NO: 368         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 368
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatc agggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 369         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 369
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatt acggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 370         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 370
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggacgcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 371         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 371
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggaaacaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 372         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 372
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggaggaaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 373         moltype = DNA  length = 360
FEATURE                Location/Qualifiers
misc_feature           1..360
```

```
                         note = Synthetic polynucleotide
source                   1..360
                         mol_type = other DNA
                         organism = synthetic construct
SEQUENCE: 373
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 374           moltype = DNA  length = 360
FEATURE                  Location/Qualifiers
misc_feature             1..360
                         note = Synthetic polynucleotide
source                   1..360
                         mol_type = other DNA
                         organism = synthetic construct
SEQUENCE: 374
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata acggacgcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 375           moltype = DNA  length = 360
FEATURE                  Location/Qualifiers
misc_feature             1..360
                         note = Synthetic polynucleotide
source                   1..360
                         mol_type = other DNA
                         organism = synthetic construct
SEQUENCE: 375
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata tcggacgcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 376           moltype = DNA  length = 360
FEATURE                  Location/Qualifiers
misc_feature             1..360
                         note = Synthetic polynucleotide
source                   1..360
                         mol_type = other DNA
                         organism = synthetic construct
SEQUENCE: 376
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatc agggacgcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 377           moltype = DNA  length = 360
FEATURE                  Location/Qualifiers
misc_feature             1..360
                         note = Synthetic polynucleotide
source                   1..360
                         mol_type = other DNA
                         organism = synthetic construct
SEQUENCE: 377
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatt acggacgcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 378           moltype = DNA  length = 360
FEATURE                  Location/Qualifiers
misc_feature             1..360
                         note = Synthetic polynucleotide
source                   1..360
                         mol_type = other DNA
                         organism = synthetic construct
```

```
SEQUENCE: 378
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata acggaaacaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 379          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 379
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata tcggaaacaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 380          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 380
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatc agggaaacaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 381          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 381
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatt acggaaacaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 382          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 382
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata acggaggaaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 383          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 383
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata tcggaggaaa taaatactat  180
```

```
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 384         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 384
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatc agggaggaaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 385         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 385
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatt acggaggaaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 386         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 386
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata acggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 387         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 387
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata tcggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 388         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 388
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatc agggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360
```

```
SEQ ID NO: 389          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 389
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatt acggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 390          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 390
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggacgcaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 391          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 391
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggaaacaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 392          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 392
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggacgcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 393          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 393
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggaaacaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 394          moltype = DNA  length = 360
FEATURE                 Location/Qualifiers
misc_feature            1..360
                        note = Synthetic polynucleotide
```

```
source                 1..360
                       mol_type = other DNA
                       organism = synthetic construct
SEQUENCE: 394
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggaggaaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 395         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 395
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata acggacgcaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 396         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 396
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata tcggacgcaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 397         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 397
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatc agggacgcaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 398         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 398
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatt acggacgcaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 399         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 399
```

```
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata acggaaacaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 400          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 400
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata tcggaaacaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 401          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 401
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatc agggaaacaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 402          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 402
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatt acggaaacaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 403          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 403
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata acggacgcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 404          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 404
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata tcggacgcaa taaatactat  180
gcagagtccg tgaagggccg gttcaccatc tccagagaca attccaagaa caccctgtat  240
```

```
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 405         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 405
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatc agggacgcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 406         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 406
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatt acggacgcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 407         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 407
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata acggaaacaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 408         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 408
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata tcggaaacaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 409         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 409
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatc agggaaacaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 410         moltype = DNA  length = 360
```

```
FEATURE                 Location/Qualifiers
misc_feature            1..360
                        note = Synthetic polynucleotide
source                  1..360
                        mol_type = other DNA
                        organism = synthetic construct
SEQUENCE: 410
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatt acggaaacaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 411          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 411
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggacgcaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 412          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 412
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggaaacaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 413          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 413
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata acggacgcaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 414          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 414
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata tcggacgcaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 415          moltype = DNA  length = 360
FEATURE                 Location/Qualifiers
misc_feature            1..360
                        note = Synthetic polynucleotide
source                  1..360
```

```
                         mol_type = other DNA
                         organism = synthetic construct
SEQUENCE: 415
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatc agggacgcaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 416           moltype = DNA  length = 360
FEATURE                  Location/Qualifiers
misc_feature             1..360
                         note = Synthetic polynucleotide
source                   1..360
                         mol_type = other DNA
                         organism = synthetic construct
SEQUENCE: 416
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatt acggacgcaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 417           moltype = DNA  length = 360
FEATURE                  Location/Qualifiers
misc_feature             1..360
                         note = Synthetic polynucleotide
source                   1..360
                         mol_type = other DNA
                         organism = synthetic construct
SEQUENCE: 417
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata acggaaacaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 418           moltype = DNA  length = 360
FEATURE                  Location/Qualifiers
misc_feature             1..360
                         note = Synthetic polynucleotide
source                   1..360
                         mol_type = other DNA
                         organism = synthetic construct
SEQUENCE: 418
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata tcggaaacaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 419           moltype = DNA  length = 360
FEATURE                  Location/Qualifiers
misc_feature             1..360
                         note = Synthetic polynucleotide
source                   1..360
                         mol_type = other DNA
                         organism = synthetic construct
SEQUENCE: 419
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatc agggaaacaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 420           moltype = DNA  length = 360
FEATURE                  Location/Qualifiers
misc_feature             1..360
                         note = Synthetic polynucleotide
source                   1..360
                         mol_type = other DNA
                         organism = synthetic construct
SEQUENCE: 420
caggtgcagc tggtggagtc tgggggaggc gtggtccagc ctgggaggtc cctgcgactc  60
```

```
tcctgtgcag cctctggatt caccttcagt agatttgcca tgcactgggt ccgccaggct  120
ccaggcaagg ggctggagtg ggtggcagtt atatcatatt acggaaacaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 421         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 421
caggtgcagc tggtggagtc tgggggaggc gtggtccagc ctgggaggtc cctgcgactc  60
tcctgtgcag cctctggatt caccttcagt cactttgcca tgcactgggt ccgccaggct  120
ccaggcaagg ggctggagtg ggtggcagtt atatcatatg atggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 422         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 422
caggtgcagc tggtggagtc tgggggaggc gtggtccagc ctgggaggtc cctgcgactc  60
tcctgtgcag cctctggatt caccttcagt agatacgcca tgcactgggt ccgccaggct  120
ccaggcaagg ggctggagtg ggtggcagtt atatcatatg atggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 423         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 423
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcattcg atggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 424         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 424
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggagccaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 425         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 425
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
```

```
gatttcttga ctggttaccc cgactactgg ggccagggaa ccctggtcac cgtctctagt  360

SEQ ID NO: 426          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 426
caggtgcagc tggtggagtc tgggggaggc gtggtccagc ctgggaggtc cctgcgactc  60
tcctgtgcag cctctggatt caccttcagt cactttgcca tgcactgggt ccgccaggct  120
ccaggcaagg ggctggagtg ggtggcagtt atatcatata acggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 427          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 427
caggtgcagc tggtggagtc tgggggaggc gtggtccagc ctgggaggtc cctgcgactc  60
tcctgtgcag cctctggatt caccttcagt agatacgcca tgcactgggt ccgccaggct  120
ccaggcaagg ggctggagtg ggtggcagtt atatcatata acggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 428          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 428
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcattca acggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 429          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 429
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata acggagccaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 430          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 430
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata acggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatttcttga ctggttaccc cgactactgg ggccagggaa ccctggtcac cgtctctagt  360

SEQ ID NO: 431          moltype = DNA  length = 360
FEATURE                 Location/Qualifiers
```

```
misc_feature           1..360
                       note = Synthetic polynucleotide
source                 1..360
                       mol_type = other DNA
                       organism = synthetic construct
SEQUENCE: 431
caggtgcagc tggtggagtc tgggggaggc gtggtccagc ctgggaggtc cctgcgactc  60
tcctgtgcag cctctggatt caccttcagt cactttgcca tgcactgggt ccgccaggct  120
ccaggcaagg ggctggagtg ggtggcagtt atatcatatg atggacgcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 432         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 432
caggtgcagc tggtggagtc tgggggaggc gtggtccagc ctgggaggtc cctgcgactc  60
tcctgtgcag cctctggatt caccttcagt agatacgcca tgcactgggt ccgccaggct  120
ccaggcaagg ggctggagtg ggtggcagtt atatcatatg atggacgcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 433         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 433
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcattcg atggacgcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 434         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 434
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggacgcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatttcttga ctggttaccc cgactactgg ggccagggaa ccctggtcac cgtctctagt  360

SEQ ID NO: 435         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 435
caggtgcagc tggtggagtc tgggggaggc gtggtccagc ctgggaggtc cctgcgactc  60
tcctgtgcag cctctggatt caccttcagt cactttgcca tgcactgggt ccgccaggct  120
ccaggcaagg ggctggagtg ggtggcagtt atatcatatg atggaggaaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 436         moltype = DNA  length = 360
FEATURE                Location/Qualifiers
misc_feature           1..360
                       note = Synthetic polynucleotide
source                 1..360
                       mol_type = other DNA
```

```
                          organism = synthetic construct
SEQUENCE: 436
caggtgcagc tggtggagtc tgggggaggc gtggtccagc ctgggaggtc cctgcgactc  60
tcctgtgcag cctctggatt caccttcagt agatacgcca tgcactgggt ccgccaggct  120
ccaggcaagg ggctggagtg ggtggcagtt atatcatatg atggaggaaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 437            moltype = DNA  length = 360
FEATURE                   Location/Qualifiers
misc_feature              1..360
                          note = Synthetic polynucleotide
source                    1..360
                          mol_type = other DNA
                          organism = synthetic construct
SEQUENCE: 437
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcattcg atggaggaaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 438            moltype = DNA  length = 360
FEATURE                   Location/Qualifiers
misc_feature              1..360
                          note = Synthetic polynucleotide
source                    1..360
                          mol_type = other DNA
                          organism = synthetic construct
SEQUENCE: 438
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggagccaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360

SEQ ID NO: 439            moltype = DNA  length = 360
FEATURE                   Location/Qualifiers
misc_feature              1..360
                          note = Synthetic polynucleotide
source                    1..360
                          mol_type = other DNA
                          organism = synthetic construct
SEQUENCE: 439
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggaggaaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatttcttga ctggttaccc cgactactgg ggccagggaa ccctggtcac cgtctctagt  360

SEQ ID NO: 440            moltype = DNA  length = 360
FEATURE                   Location/Qualifiers
misc_feature              1..360
                          note = Synthetic polynucleotide
source                    1..360
                          mol_type = other DNA
                          organism = synthetic construct
SEQUENCE: 440
caggtgcagc tggtggagtc tgggggaggc gtggtccagc ctgggaggtc cctgcgactc  60
tcctgtgcag cctctggatt caccttcagt cactttgcca tgcactgggt ccgccaggct  120
ccaggcaagg ggctggagtg ggtggcagtt atatcatatg atggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 441            moltype = DNA  length = 360
FEATURE                   Location/Qualifiers
misc_feature              1..360
                          note = Synthetic polynucleotide
source                    1..360
                          mol_type = other DNA
                          organism = synthetic construct
SEQUENCE: 441
caggtgcagc tggtggagtc tgggggaggc gtggtccagc ctgggaggtc cctgcgactc  60
tcctgtgcag cctctggatt caccttcagt agatacgcca tgcactgggt ccgccaggct  120
```

```
ccaggcaagg ggctggagtg ggtggcagtt atatcatatg atggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 442         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 442
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcattcg atggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 443         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 443
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggagccaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360

SEQ ID NO: 444         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 444
caggtgcagc tggtggagtc tgggggaggc gtggtccagc ctgggaggtc cctgcgactc  60
tcctgtgcag cctctggatt caccttcagt aagtacgcca tgcactgggt ccgccaggct  120
ccaggcaagg ggctggagtg ggtggcagtt atatcattca agggaagcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatctgttga ctggttaccc cgactactgg ggccagggaa ccctggtcac cgtctctagt  360

SEQ ID NO: 445         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 445
caggtgcagc tggtggagtc tgggggaggc gtggtccagc ctgggaggtc cctgcgactc  60
tcctgtgcag cctctggatt caccttcagt agatacgcca tgcactgggt ccgccaggct  120
ccaggcaagg ggctggagtg ggtggcagtt atatcatatc agggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatctgttga ctggttaccc cgactactgg ggccagggaa ccctggtcac cgtctctagt  360

SEQ ID NO: 446         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 446
caggtgcagc tggtggagtc tgggggaggc gtggtccagc ctgggaggtc cctgcgactc  60
tcctgtgcag cctctggatt caccttcagt cactttgcca tgcactgggt ccgccaggct  120
ccaggcaagg ggctggagtg ggtggcagtt atatcattca gcggaagcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatgttga ctggttaccc cgactactgg ggccagggaa ccctggtcac cgtctctagt  360
```

```
SEQ ID NO: 447          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 447
caggtgcagc tggtggagtc tgggggaggc gtggtccagc ctgggaggtc cctgcgactc  60
tcctgtgcag cctctggatt caccttcagt aagtttgcca tgcactgggt ccgccaggct  120
ccaggcaagg ggctggagtg ggtggcagtt atatcatatc gcggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatctgttga ctggttaccc cgactactgg ggccagggaa ccctggtcac cgtctctagt  360

SEQ ID NO: 448          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 448
caggtgcagc tggtggagtc tgggggaggc gtggtccagc ctgggaggtc cctgcgactc  60
tcctgtgcag cctctggatt caccttcagt agatacgcca tgcactgggt ccgccaggct  120
ccaggcaagg ggctggagtg ggtggcagtt atatcatata gcggagccaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatctgttga gcggttaccc cgactactgg ggccagggaa ccctggtcac cgtctctagt  360

SEQ ID NO: 449          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 449
caggtgcagc tggtggagtc tgggggaggc gtggtccagc ctgggaggtc cctgcgactc  60
tcctgtgcag cctctggatt caccttcagt cactacgcca tgcactgggt ccgccaggct  120
ccaggcaagg ggctggagtg ggtggcagtt atatcattca agggagccaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatctgttga ctggttaccc cgactactgg ggccagggaa ccctggtcac cgtctctagt  360

SEQ ID NO: 450          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 450
caggtgcagc tggtggagtc tgggggaggc gtggtccagc ctgggaggtc cctgcgactc  60
tcctgtgcag cctctggatt caccttcagt cactacgcca tgcactgggt ccgccaggct  120
ccaggcaagg ggctggagtg ggtggcagtt atatcatatc gcggagccaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatctgttga ctggttaccc cgactactgg ggccagggaa ccctggtcac cgtctctagt  360

SEQ ID NO: 451          moltype = DNA  length = 360
FEATURE                 Location/Qualifiers
misc_feature            1..360
                        note = Synthetic polynucleotide
source                  1..360
                        mol_type = other DNA
                        organism = synthetic construct
SEQUENCE: 451
caggtgcagc tggtggagtc tgggggaggc gtggtccagc ctgggaggtc cctgcgactc  60
tcctgtgcag cctctggatt caccttcagt cactacgcca tgcactgggt ccgccaggct  120
ccaggcaagg ggctggagtg ggtggcagtt atatcattct acggaagcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatttcttga ctggttaccc cgactactgg ggccagggaa ccctggtcac cgtctctagt  360

SEQ ID NO: 452          moltype = DNA  length = 360
FEATURE                 Location/Qualifiers
misc_feature            1..360
```

```
                         note = Synthetic polynucleotide
source                   1..360
                         mol_type = other DNA
                         organism = synthetic construct
SEQUENCE: 452
caggtgcagc tggtggagtc tgggggaggc gtggtccagc ctgggaggtc cctgcgactc  60
tcctgtgcag cctctggatt caccttcagt cactttgcca tgcactgggt ccgccaggct  120
ccaggcaagg ggctggagtg ggtggcagtt atatcattct tcggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatttcttga ctggttaccc cgactactgg ggccagggaa ccctggtcac cgtctctagt  360

SEQ ID NO: 453           moltype = DNA  length = 360
FEATURE                  Location/Qualifiers
misc_feature             1..360
                         note = Synthetic polynucleotide
source                   1..360
                         mol_type = other DNA
                         organism = synthetic construct
SEQUENCE: 453
caggtgcagc tggtggagtc tgggggaggc gtggtccagc ctgggaggtc cctgcgactc  60
tcctgtgcag cctctggatt caccttcagt cactacgcca tgcactgggt ccgccaggct  120
ccaggcaagg ggctggagtg ggtggcagtt atatcattca tgggaaccaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatttcttga ctggttaccc cgactactgg ggccagggaa ccctggtcac cgtctctagt  360

SEQ ID NO: 454           moltype = DNA  length = 360
FEATURE                  Location/Qualifiers
misc_feature             1..360
                         note = Synthetic polynucleotide
source                   1..360
                         mol_type = other DNA
                         organism = synthetic construct
SEQUENCE: 454
caggtgcagc tggtggagtc tgggggaggc gtggtccagc ctgggaggtc cctgcgactc  60
tcctgtgcag cctctggatt caccttcagt tactttgcca tgcactgggt ccgccaggct  120
ccaggcaagg ggctggagtg ggtggcagtt atatcacacc gcggaaccaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatctgttga gcggttaccc cgactactgg ggccagggaa ccctggtcac cgtctctagt  360

SEQ ID NO: 455           moltype = DNA  length = 360
FEATURE                  Location/Qualifiers
misc_feature             1..360
                         note = Synthetic polynucleotide
source                   1..360
                         mol_type = other DNA
                         organism = synthetic construct
SEQUENCE: 455
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtgggtgtt atcaactatc gtggacatgg taaatactat  180
gcagagtccg tgaagggccg gttcaccgtg tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtgtctagt  360

SEQ ID NO: 456           moltype = DNA  length = 360
FEATURE                  Location/Qualifiers
misc_feature             1..360
                         note = Synthetic polynucleotide
source                   1..360
                         mol_type = other DNA
                         organism = synthetic construct
SEQUENCE: 456
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtgggtgtt atatcttttt ctggaggttc taaatactat  180
gcagagtccg tgaagggccg gttcaccttg tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtgtctagt  360

SEQ ID NO: 457           moltype = DNA  length = 360
FEATURE                  Location/Qualifiers
misc_feature             1..360
                         note = Synthetic polynucleotide
source                   1..360
                         mol_type = other DNA
                         organism = synthetic construct
```

SEQUENCE: 457
caggtgcagc tggtggagtc tgggggaggc gtggtccagc ctgggaggtc cctgcgactc 60
tcctgtgcag cctctggatt caccttcagt agatttgcca tgcactgggt ccgccaggct 120
ccaggcaagg ggctggagtg ggtgggtgtt atctcttata ctggacagtt caaatactat 180
gcagagtccg tgaagggccg gttcaccgtg tccagagaca attccaagaa caccctgtat 240
ctgcaaatga acagcctgag agctgaggac acggctctgt tttactgtgc gagaggatac 300
gatgttttga ctggttaccc cgactactgg ggccagggaa ccctggtcac cgtgtctagt 360

SEQ ID NO: 458 moltype = DNA length = 360
FEATURE Location/Qualifiers
misc_feature 1..360
note = Synthetic polynucleotide
source 1..360
mol_type = other DNA
organism = synthetic construct
SEQUENCE: 458
caggtgcagc tggtggagtc tgggggaggc gtggtccagc ctgggaggtc cctgcgactc 60
tcctgtgcag cctctggatt caccttcagt agatttgcca tgcactgggt ccgccaggct 120
ccaggcaagg ggctggagtg ggtgggtgtt atatcttata ctggagctca gaaatactat 180
gcagagtccg tgaagggccg gttcaccatg tccagagaca attccaagaa caccctgtat 240
ctgcaaatga acagcctgag agctgaggac acggctctgt tttactgtgc gagaggatac 300
gatgttttga ctggttaccc cgactactgg ggccagggaa ccctggtcac cgtgtctagt 360

SEQ ID NO: 459 moltype = DNA length = 360
FEATURE Location/Qualifiers
misc_feature 1..360
note = Synthetic polynucleotide
source 1..360
mol_type = other DNA
organism = synthetic construct
SEQUENCE: 459
caggtgcagc tggtggagtc tgggggaggc gtggtccagc ctgggaggtc cctgcgactc 60
tcctgtgcag cctctggatt caccttcagt agatttgcca tgcactgggt ccgccaggct 120
ccaggcaagg ggctggagtg ggtgggtgtt atatcttatt ctggagcttc taaatactat 180
gcagagtccg tgaagggccg gttcaccatg tccagagaca attccaagaa caccctgtat 240
ctgcaaatga acagcctgag agctgaggac acggctctgt tttactgtgc gagaggatac 300
gatgttttga ctggttaccc cgactactgg ggccagggaa ccctggtcac cgtgtctagt 360

SEQ ID NO: 460 moltype = DNA length = 360
FEATURE Location/Qualifiers
misc_feature 1..360
note = Synthetic polynucleotide
source 1..360
mol_type = other DNA
organism = synthetic construct
SEQUENCE: 460
caggtgcagc tggtggagtc tgggggaggc gtggtccagc ctgggaggtc cctgcgactc 60
tcctgtgcag cctctggatt caccttcagt agatttgcca tgcactgggt ccgccaggct 120
ccaggcaagg ggctggagtg ggtggctgtt atatcttatt ctggagcttt caaatactat 180
gcagagtccg tgaagggccg gttcaccgtg tccagagaca attccaagaa caccctgtat 240
ctgcaaatga acagcctgag agctgaggac acggctctgt tttactgtgc gagaggatac 300
gatgttttga ctggttaccc cgactactgg ggccagggaa ccctggtcac cgtgtctagt 360

SEQ ID NO: 461 moltype = DNA length = 360
FEATURE Location/Qualifiers
misc_feature 1..360
note = Synthetic polynucleotide
source 1..360
mol_type = other DNA
organism = synthetic construct
SEQUENCE: 461
caggtgcagc tggtggagtc tgggggaggc gtggtccagc ctgggaggtc cctgcgactc 60
tcctgtgcag cctctggatt caccttcagt agatttgcca tgcactgggt ccgccaggct 120
ccaggcaagg ggctggagtg ggtgggtgtt ataacttata ctggaggtgc taaatactat 180
gcagagtccg tgaagggccg gttcaccatc tccagagaca attccaagaa caccctgtat 240
ctgcaaatga acagcctgag agctgaggac acggctctgt tttactgtgc gagaggatac 300
gatgttttga ctggttaccc cgactactgg ggccagggaa ccctggtcac cgtgtctagt 360

SEQ ID NO: 462 moltype = DNA length = 360
FEATURE Location/Qualifiers
misc_feature 1..360
note = Synthetic polynucleotide
source 1..360
mol_type = other DNA
organism = synthetic construct
SEQUENCE: 462
caggtgcagc tggtggagtc tgggggaggc gtggtccagc ctgggaggtc cctgcgactc 60
tcctgtgcag cctctggatt caccttcagt agatttgcca tgcactgggt ccgccaggct 120
ccaggcaagg ggctggagtg ggtgggtgtt atcaactttc agggaactac taaatactat 180

```
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtgtctagt  360

SEQ ID NO: 463         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 463
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtgggtgtt atatcttatt ctggagatct gaaatactat  180
gcagagtccg tgaagggccg gttcaccgtg tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtgtctagt  360

SEQ ID NO: 464         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 464
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtgggtgtt atcaactatt tcggagacgc taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtgtctagt  360

SEQ ID NO: 465         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 465
caggtgcagc tggtggagtc tgggggaggc gtggtccagc ctgggaggtc cctgagactc  60
tcctgtgcag cctctggatt caccttcagt ttctacgcca tgcactgggt ccgccaggct  120
ccaggcaagg ggctggagtg ggtggcagtt atctcatctt tcggaagtaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatctgctga ctggttaccc cgactactgg ggccagggaa ccctggtcac cgtgtctagt  360

SEQ ID NO: 466         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 466
caggtgcagc tggtggagtc tgggggaggc gtggtccagc ctgggaggtc cctgcgactc  60
tcctgtgcag cctctggatt caccttcagt tactacgcca tgcactgggt ccgccaggct  120
ccaggcaagg ggctggagtg ggtggcagtt atctcatact ctggaagtaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatctgctga ctggttaccc cgactactgg ggccagggaa ccctggtcac cgtgtctagt  360

SEQ ID NO: 467         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 467
caggtgcagc tggtggagtc tgggggaggc gtggtccagc ctgggaggtc cctgcgactc  60
tcctgtgcag cctctggatt caccttcagt tactacgcca tgcactgggt ccgccaggct  120
ccaggcaagg ggctggagtg ggtggcagtt atctcacatt acggaactaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatcctctga ctggttaccc cgactactgg ggccagggaa ccctggtcac cgtgtctagt  360
```

-continued

```
SEQ ID NO: 468         moltype = DNA  length = 360
FEATURE                Location/Qualifiers
misc_feature           1..360
                       note = Synthetic polynucleotide
source                 1..360
                       mol_type = other DNA
                       organism = synthetic construct
SEQUENCE: 468
caggtgcagc tggtggagtc tgggggaggc gtggtccagc ctgggaggtc cctgcgactc  60
tcctgtgcag cctctggatt caccttcagt cattacgcca tgcactgggt ccgccaggct  120
ccaggcaagg ggctggagtg ggtggcagtt atctcatacc agggaagtaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatctgctga ctggttaccc cgactactgg ggccagggaa ccctggtcac cgtgtctagt  360

SEQ ID NO: 469         moltype = DNA  length = 370
FEATURE                Location/Qualifiers
misc_feature           1..370
                       note = Synthetic polynucleotide
source                 1..370
                       mol_type = other DNA
                       organism = synthetic construct
SEQUENCE: 469
caggtacagc tgcagcagtc aggtccagga ctggtgaagc cctcgcagac cctctcactc  60
acctgtgcca tctccgggga cagtgtctct agcaacagtg ctacttggaa ctggatcagg  120
cagtccccat cgagaggcct tgagtggctg ggaaggacat attacaggtc caagtggtct  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaacgt ggaaacagct atggttcctt gaccactggg gccagggaac cctggtcacc  360
gtctctagtg                                                        370

SEQ ID NO: 470         moltype = DNA  length = 369
FEATURE                Location/Qualifiers
misc_feature           1..369
                       note = Synthetic polynucleotide
source                 1..369
                       mol_type = other DNA
                       organism = synthetic construct
SEQUENCE: 470
caggtacagc tgcagcagtc aggtccagga ctggtgaagc cctcgcagac cctctcactc  60
acctgtgcca tctccgggga cagtgtctct aaccgtctgg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaactt ggaaccagga ctggttcctg gaccactggg gccagggaac cctggtcacc  360
gtctctagt                                                         369

SEQ ID NO: 471         moltype = DNA  length = 369
FEATURE                Location/Qualifiers
misc_feature           1..369
                       note = Synthetic polynucleotide
source                 1..369
                       mol_type = other DNA
                       organism = synthetic construct
SEQUENCE: 471
caggtacagc tgcagcagtc aggtccagga ctggtgaagc cctcgcagac cctctcactc  60
acctgtgcca tctccgggga cagtgtctct aaccgtctgg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaactt gggaccagga ctggttcctg gaccactggg gccagggaac cctggtcacc  360
gtctctagt                                                         369

SEQ ID NO: 472         moltype = DNA  length = 369
FEATURE                Location/Qualifiers
misc_feature           1..369
                       note = Synthetic polynucleotide
source                 1..369
                       mol_type = other DNA
                       organism = synthetic construct
SEQUENCE: 472
caggtacagc tgcagcagtc aggtccagga ctggtgaagc cctcgcagac cctctcactc  60
acctgtgcca tctccgggga cagtgtctct tctcgtcagg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaactt gggaacagga ctggttcctg gaccactggg gccagggaac cctggtcacc  360
gtctctagt                                                         369
```

```
SEQ ID NO: 473          moltype = DNA  length = 369
FEATURE                 Location/Qualifiers
misc_feature            1..369
                        note = Synthetic polynucleotide
source                  1..369
                        mol_type = other DNA
                        organism = synthetic construct
SEQUENCE: 473
caggtacagc tgcagcagtc aggtccagga ctggtgaagc cctcgcagac cctctcactc  60
acctgtgcca tctccgggga cagtgtctct aacaaacagg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaatgt ggaaccagaa ctggttcctg gaccactggg gccagggaac cctggtcacc  360
gtctctagt                                                          369

SEQ ID NO: 474          moltype = DNA  length = 369
FEATURE                 Location/Qualifiers
misc_feature            1..369
                        note = Synthetic polynucleotide
source                  1..369
                        mol_type = other DNA
                        organism = synthetic construct
SEQUENCE: 474
caggtacagc tgcagcagtc aggtccagga ctggtgaagc cctcgcagac cctctcactc  60
acctgtgcca tctccgggga cagtgtctct aacaaacagg ctacttggaa ctggatcagg  120
cagtccccat cgagaggcct tgagtggctg ggaaggacat actacagggg tcagtggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaactt ggatcggtga ctggttcatg gaccactggg gccagggaac cctggtcacc  360
gtctctagt                                                          369

SEQ ID NO: 475          moltype = DNA  length = 369
FEATURE                 Location/Qualifiers
misc_feature            1..369
                        note = Synthetic polynucleotide
source                  1..369
                        mol_type = other DNA
                        organism = synthetic construct
SEQUENCE: 475
caggtacagc tgcagcagtc aggtccagga ctggtgaagc cctcgcagac cctctcactc  60
acctgtgcca tctccgggga cagtgtctct aacaaacagg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaactt ggatccagga ctggttcctg gaccactggg gccagggaac cctggtcacc  360
gtctctagt                                                          369

SEQ ID NO: 476          moltype = DNA  length = 369
FEATURE                 Location/Qualifiers
misc_feature            1..369
                        note = Synthetic polynucleotide
source                  1..369
                        mol_type = other DNA
                        organism = synthetic construct
SEQUENCE: 476
caggtacagc tgcagcagtc aggtccagga ctggtgaagc cctcgcagac cctctcactc  60
acctgtgcca tctccgggga cagtgtctct tctaaccatg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaactt gggaccagga ctggttcctg gaccactggg gccagggaac cctggtcacc  360
gtctctagt                                                          369

SEQ ID NO: 477          moltype = DNA  length = 369
FEATURE                 Location/Qualifiers
misc_feature            1..369
                        note = Synthetic polynucleotide
source                  1..369
                        mol_type = other DNA
                        organism = synthetic construct
SEQUENCE: 477
caggtacagc tgcagcagtc aggtccagga ctggtgaagc cctcgcagac cctctcactc  60
acctgtgcca tctccgggga cagtgtctct tctcgttacg ctacttggaa ctggatcagg  120
cagtccccat cgagaggcct tgagtggctg ggaaggacat actacagggg tcagtggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaatgt ggaaccagaa ctggttcctg gaccactggg gccagggaac cctggtcacc  360
gtctctagt                                                          369
```

```
SEQ ID NO: 478          moltype = DNA  length = 369
FEATURE                 Location/Qualifiers
misc_feature            1..369
                        note = Synthetic polynucleotide
source                  1..369
                        mol_type = other DNA
                        organism = synthetic construct
SEQUENCE: 478
caggtacagc tgcagcagtc aggtccagga ctggtgaagc cctcgcagac cctctcactc  60
acctgtgcca tctccgggga cagtgtctct aacaaacagg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaatgt ggtctggtga ctggttcctg gaccactggg gccagggaac cctggtcacc  360
gtctctagt                                                          369

SEQ ID NO: 479          moltype = DNA  length = 369
FEATURE                 Location/Qualifiers
misc_feature            1..369
                        note = Synthetic polynucleotide
source                  1..369
                        mol_type = other DNA
                        organism = synthetic construct
SEQUENCE: 479
caggtacagc tgcagcagtc aggtccagga ctggtgaagc cctcgcagac cctctcactc  60
acctgtgcca tctccgggga cagtgtctct tctcatgttg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaatgt ggtctgaaga ctggttcctg gaccactggg gccagggaac cctggtcacc  360
gtctctagt                                                          369

SEQ ID NO: 480          moltype = DNA  length = 369
FEATURE                 Location/Qualifiers
misc_feature            1..369
                        note = Synthetic polynucleotide
source                  1..369
                        mol_type = other DNA
                        organism = synthetic construct
SEQUENCE: 480
caggtacagc tgcagcagtc aggtccagga ctggtgaagc cctcgcagac cctctcactc  60
acctgtgcca tctccgggga cagtgtctct tctcgtcagg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaatgt ggcagggtaa ctggttcctg gaccactggg gccagggaac cctggtcacc  360
gtctctagt                                                          369

SEQ ID NO: 481          moltype = DNA  length = 369
FEATURE                 Location/Qualifiers
misc_feature            1..369
                        note = Synthetic polynucleotide
source                  1..369
                        mol_type = other DNA
                        organism = synthetic construct
SEQUENCE: 481
caggtacagc tgcagcagtc aggtccagga ctggtgaagc cctcgcagac cctctcactc  60
acctgtgcca tctccgggga cagtgtctct aaccatcagg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaactt ggatccagga ctggttcctg gaccactggg gccagggaac cctggtcacc  360
gtctctagt                                                          369

SEQ ID NO: 482          moltype = DNA  length = 369
FEATURE                 Location/Qualifiers
misc_feature            1..369
                        note = Synthetic polynucleotide
source                  1..369
                        mol_type = other DNA
                        organism = synthetic construct
SEQUENCE: 482
caggtacagc tgcagcagtc aggtccagga ctggtgaagc cctcgcagac cctctcactc  60
acctgtgcca tctccgggga cagtgtctct tctcgtgacg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggacagt ggaacgaaga ctggttcctg gaccactggg gccagggaac cctggtcacc  360
```

```
gtctctagt                                                         369

SEQ ID NO: 483         moltype = DNA  length = 369
FEATURE                Location/Qualifiers
misc_feature           1..369
                       note = Synthetic polynucleotide
source                 1..369
                       mol_type = other DNA
                       organism = synthetic construct
SEQUENCE: 483
caggtacagc tgcagcagtc aggtccagga ctggtgaagc cctcgcagac cctctcactc  60
acctgtgcca tctccgggga cagtgtctct aaccgtctgg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggacgtt gggaaggtga ctggttcttc gaccactggg gccagggaac cctggtcacc  360
gtctctagt                                                         369

SEQ ID NO: 484         moltype = DNA  length = 369
FEATURE                Location/Qualifiers
misc_feature           1..369
                       note = Synthetic polynucleotide
source                 1..369
                       mol_type = other DNA
                       organism = synthetic construct
SEQUENCE: 484
caggtacagc tgcagcagtc aggtccagga ctggtgaagc cctcgcagac cctctcactc  60
acctgtgcca tctccgggga cagtgtctct aacaaacagg ctacttggaa ctggatcagg  120
cagtccccat cgagaggcct tgagtggctg ggaaggacat acttcaggcg tacttggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaatgt ggtctgaaga ctggttcctg gaccactggg gccagggaac cctggtcacc  360
gtctctagt                                                         369

SEQ ID NO: 485         moltype = DNA  length = 369
FEATURE                Location/Qualifiers
misc_feature           1..369
                       note = Synthetic polynucleotide
source                 1..369
                       mol_type = other DNA
                       organism = synthetic construct
SEQUENCE: 485
caggtacagc tgcagcagtc aggtccagga ctggtgaagc cctcgcagac cctctcactc  60
acctgtgcca tctccgggga cagtgtctct aaccgtctgg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggagttt ggatcggtaa ctggttcctg gaccactggg gccagggaac cctggtcacc  360
gtctctagt                                                         369

SEQ ID NO: 486         moltype = AA  length = 22
FEATURE                Location/Qualifiers
REGION                 1..22
                       note = Synthetic polypeptide
source                 1..22
                       mol_type = protein
                       organism = synthetic construct
SEQUENCE: 486
MDMRVPAQLL GLLLLWLRGA RC                                          22

SEQ ID NO: 487         moltype = AA  length = 19
FEATURE                Location/Qualifiers
REGION                 1..19
                       note = Synthetic polypeptide
source                 1..19
                       mol_type = protein
                       organism = synthetic construct
SEQUENCE: 487
MAWALLLLTL LTQGTGSWA                                              19

SEQ ID NO: 488         moltype = AA  length = 19
FEATURE                Location/Qualifiers
REGION                 1..19
                       note = Synthetic polypeptide
source                 1..19
                       mol_type = protein
                       organism = synthetic construct
SEQUENCE: 488
MTCSPLLLTL LIHCTGSWA                                              19
```

```
SEQ ID NO: 489         moltype = AA  length = 20
FEATURE                Location/Qualifiers
REGION                 1..20
                       note = Synthetic polypeptide
source                 1..20
                       mol_type = protein
                       organism = synthetic construct
SEQUENCE: 489
MEAPAQLLFL LLLWLPDTTG                                              20

SEQ ID NO: 490         moltype = AA  length = 19
FEATURE                Location/Qualifiers
REGION                 1..19
                       note = Synthetic polypeptide
source                 1..19
                       mol_type = protein
                       organism = synthetic construct
SEQUENCE: 490
MEWTWRVLFL VAAATGAHS                                               19

SEQ ID NO: 491         moltype = AA  length = 20
FEATURE                Location/Qualifiers
REGION                 1..20
                       note = Synthetic polypeptide
source                 1..20
                       mol_type = protein
                       organism = synthetic construct
SEQUENCE: 491
METPAQLLFL LLLWLPDTTG                                              20

SEQ ID NO: 492         moltype = AA  length = 20
FEATURE                Location/Qualifiers
REGION                 1..20
                       note = Synthetic polypeptide
source                 1..20
                       mol_type = protein
                       organism = synthetic construct
SEQUENCE: 492
METPAQLLFL LLLWLPDTTG                                              20

SEQ ID NO: 493         moltype = AA  length = 19
FEATURE                Location/Qualifiers
REGION                 1..19
                       note = Synthetic polypeptide
source                 1..19
                       mol_type = protein
                       organism = synthetic construct
SEQUENCE: 493
MKHLWFFLLL VAAPRWVLS                                               19

SEQ ID NO: 494         moltype = AA  length = 19
FEATURE                Location/Qualifiers
REGION                 1..19
                       note = Synthetic polypeptide
source                 1..19
                       mol_type = protein
                       organism = synthetic construct
SEQUENCE: 494
MEWSWVFLFF LSVTTGVHS                                               19

SEQ ID NO: 495         moltype = AA  length = 22
FEATURE                Location/Qualifiers
REGION                 1..22
                       note = Synthetic polypeptide
source                 1..22
                       mol_type = protein
                       organism = synthetic construct
SEQUENCE: 495
MDIRAPTQLL GLLLLWLPGA KC                                           22

SEQ ID NO: 496         moltype = AA  length = 22
FEATURE                Location/Qualifiers
REGION                 1..22
                       note = Synthetic polypeptide
source                 1..22
                       mol_type = protein
                       organism = synthetic construct
SEQUENCE: 496
```

```
MDIRAPTQLL GLLLLWLPGA RC                                          22

SEQ ID NO: 497          moltype = AA  length = 22
FEATURE                 Location/Qualifiers
REGION                  1..22
                        note = Synthetic polypeptide
source                  1..22
                        mol_type = protein
                        organism = synthetic construct
SEQUENCE: 497
MDTRAPTQLL GLLLLWLPGA TF                                          22

SEQ ID NO: 498          moltype = AA  length = 22
FEATURE                 Location/Qualifiers
REGION                  1..22
                        note = Synthetic polypeptide
source                  1..22
                        mol_type = protein
                        organism = synthetic construct
SEQUENCE: 498
MDTRAPTQLL GLLLLWLPGA RC                                          22

SEQ ID NO: 499          moltype = AA  length = 19
FEATURE                 Location/Qualifiers
REGION                  1..19
                        note = Synthetic polypeptide
source                  1..19
                        mol_type = protein
                        organism = synthetic construct
SEQUENCE: 499
METGLRWLLL VAVLKGVQC                                              19

SEQ ID NO: 500          moltype = AA  length = 21
FEATURE                 Location/Qualifiers
REGION                  1..21
                        note = Synthetic polypeptide
source                  1..21
                        mol_type = protein
                        organism = synthetic construct
SEQUENCE: 500
METGLRWLLL VAVLKGVQCQ E                                           21

SEQ ID NO: 501          moltype = AA  length = 22
FEATURE                 Location/Qualifiers
REGION                  1..22
                        note = Synthetic polypeptide
source                  1..22
                        mol_type = protein
                        organism = synthetic construct
SEQUENCE: 501
MDMRAPTQLL GLLLLWLPGA RC                                          22

SEQ ID NO: 502          moltype = AA  length = 110
FEATURE                 Location/Qualifiers
REGION                  1..110
                        note = Synthetic polypeptide
source                  1..110
                        mol_type = protein
                        organism = synthetic construct
SEQUENCE: 502
QSVLTQPPSV SAAPGQKVTI SCSGSSSNIG NNYVSWYQQL PGTAPKLLIY DNNKRPSGIP  60
DRFSGSKSGT STTLGITGLQ TGDEADYYCG TWDSRLSAVV FGGGTKLTVL            110

SEQ ID NO: 503          moltype = AA  length = 130
FEATURE                 Location/Qualifiers
REGION                  1..130
                        note = Synthetic polypeptide
source                  1..130
                        mol_type = protein
                        organism = synthetic construct
SEQUENCE: 503
QVQLVESGGG VVQPGRSLRL SCAASGFTFS SFGMHWVRQA PGKGLEWVAV ISFDGSIKYS  60
VDSVKGRFTI SRDNSKNTLF LQMNSLRAED TAVYYCARDR LNYYDSSGYY HYKYYGMAVW  120
GQGTTVTVSS                                                        130

SEQ ID NO: 504          moltype = AA  length = 214
FEATURE                 Location/Qualifiers
REGION                  1..214
                        note = Synthetic polypeptide
```

```
source                  1..214
                        mol_type = protein
                        organism = synthetic construct
SEQUENCE: 504
EIVLTQSPAT LSLSPGERAT LSCRASQSVG RSLHWYQQKP GQAPRLLIKY ASQSLSGIPA  60
RFSGSGSGTD FTLTISSLEP EDFAVYYCHQ SSRLPFTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 505          moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 505
DIQLTQSPSF LSASVGDRVT ITCRASQSIG RSLHWYQQKP GKAPKLLIKY ASQSLSGVPS  60
RFSGSGSGTE FTLTISSLQP EDFATYYCHQ SSRLPFTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 506          moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 506
EIVLTQSPAT LSLSPGERAT LSCRASKSVG RSLHWYQQKP GQAPRLLIKY ASQSLSGIPA  60
RFSGSGSGTD FTLTISSLEP EDFAVYYCHQ SSRLPFTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 507          moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 507
EIVLTQSPAT LSLSPGERAT LSCRASKSVG WSLHWYQQKP GQAPRLLIKY ASQSLSGIPA  60
RFSGSGSGTD FTLTISSLEP EDFAVYYCHQ SSRLPFTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 508          moltype = AA  length = 142
FEATURE                 Location/Qualifiers
REGION                  1..142
                        note = Synthetic polypeptide
source                  1..142
                        mol_type = protein
                        organism = synthetic construct
SEQUENCE: 508
LTISSLEPED FAVYYCHQSS RLPFTFGPGT KVDIKRTVAA PSVFIFPPSD EQLKSGTASV  60
VCLLNNFYPR EAKVQWKVDN ALQSGNSQES VTEQDSKDST YSLSSTLTLS KADYEKHKVY  120
ACEVTHQGLS SPVTKSFNRG EC                                           142

SEQ ID NO: 509          moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 509
DIQMTQSPSS LSASVGDRIT ITCRASQSIS RYLNWYQQKP GKAPKLLIYA ASSLQSGIPS  60
RFSGSGSGTD FTLTINSLQP EDFATYFCQQ SYSPPFTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 510          moltype = AA  length = 214
FEATURE                 Location/Qualifiers
REGION                  1..214
                        note = Synthetic polypeptide
source                  1..214
                        mol_type = protein
```

```
                         organism = synthetic construct
SEQUENCE: 510
DIQMTQSPSS LSASVGDRIT ITCRASQMIA RYLNWYQQKP GKAPKLLIYA SYNLQSGIPS  60
RFSGSGSGTD FTLTINSLQP EDFATYFCQQ AIINPYTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 511          moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 511
DIQMTQSPSS LSASVGDRIT ITCRASQKIA RYLVWYQQKP GKAPKLLIYA ANMLQSGIPS  60
RFSGSGSGTD FTLTINSLQP EDFATYFCQQ SIQQPYTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 512          moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 512
DIQMTQSPSS LSASVGDRIT ITCRASQSIS RYLNWYQQKP GKAPKLLIYA GRILQSGIPS  60
RFSGSGSGTD FTLTINSLQP EDFATYFCQQ AIINPYTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 513          moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 513
DIQMTQSPSS LSASVGDRIT ITCRASQSIS RYLNWYQQKP GKAPKLLIYA SYNLQSGIPS  60
RFSGSGSGTD FTLTINSLQP EDFATYFCQQ SIQQPYTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 514          moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 514
DIQMTQSPSS LSASVGDRIT ITCRASQYIV RYLNWYQQKP GKAPKLLIYA SYNLQSGIPS  60
RFSGSGSGTD FTLTINSLQP EDFATYFCQQ AIMAPYTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 515          moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 515
DIQMTQSPSS LSASVGDRIT ITCRASQSIS RYLNWYQQKP GKAPKLLIFA GQRLQSGIPS  60
RFSGSGSGTD FTLTINSLQP EDFATYFCQQ AIGMPYTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 516          moltype = AA  length = 214
FEATURE                 Location/Qualifiers
REGION                  1..214
                        note = Synthetic polypeptide
source                  1..214
                        mol_type = protein
                        organism = synthetic construct
```

```
SEQUENCE: 516
DIQMTQSPSS LSASVGDRIT ITCRASQYIV RYLNWYQQKP GKAPKLLIYA ANMLQSGIPS  60
RFSGSGSGTD FTLTINSLQP EDFATYFCQQ AINQPYTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 517          moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 517
DIQMTQSPSS LSASVGDRIT ITCRASQPIS RYLSWYQQKP GKAPKLLIFA GQRLQSGIPS  60
RFSGSGSGTD FTLTINSLQP EDFATYFCQQ AISIPYTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 518          moltype = AA  length = 214
FEATURE                 Location/Qualifiers
REGION                  1..214
                        note = Synthetic polypeptide
source                  1..214
                        mol_type = protein
                        organism = synthetic construct
SEQUENCE: 518
DIQMTQSPSS LSASVGDRIT ITCRASQQIA RYLNWYQQKP GKAPKLLIYA SYNLQSGIPS  60
RFSGSGSGTD FTLTINSLQP EDFATYFCQQ AIIQPYTFGP GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 519          moltype = AA  length = 450
FEATURE                 Location/Qualifiers
REGION                  1..450
                        note = Synthetic polypeptide
source                  1..450
                        mol_type = protein
                        organism = synthetic construct
SEQUENCE: 519
QVQLVESGGG VVQPGRSLRL SCAASGFTFS RFAMHWVRQA PGKGLEWVAV ISYDGGNKYY  60
AESVKGRFTI SRDNSKNTLY LQMNSLRAED TALFYCARGY DVLTGYPDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPCEEQYG  300
STYRCVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 520          moltype = AA  length = 450
FEATURE                 Location/Qualifiers
REGION                  1..450
                        note = Synthetic polypeptide
source                  1..450
                        mol_type = protein
                        organism = synthetic construct
SEQUENCE: 520
QVQLVESGAE VVKPGASVKV SCKASGFTFS RFAMHWVRQA PGQGLEWMGV ISYDGGNKYY  60
AESVKGRVTM TRDTSTSTLY MELSSLRSED TAVYYCARGY DVLTGYPDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYG  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 521          moltype = AA  length = 450
FEATURE                 Location/Qualifiers
REGION                  1..450
                        note = Synthetic polypeptide
source                  1..450
                        mol_type = protein
                        organism = synthetic construct
SEQUENCE: 521
QVQLVESGGG VVQPGRSLRL SCAASGFTFS RFAMHWVRQA PGKGLEWVAV ISYIGGNKYY  60
AESVKGRFTI SRDNSKNTLY LQMNSLRAED TALFYCARGY DVLTGYPDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPCEEQYG  300
```

```
STYRCVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 522          moltype = AA  length = 450
FEATURE                 Location/Qualifiers
REGION                  1..450
                        note = Synthetic polypeptide
source                  1..450
                        mol_type = protein
                        organism = synthetic construct
SEQUENCE: 522
QVQLVESGGG VVQPGRSLRL SCAASGFTFS RFAMHWVRQA PGKGLEWVAV ISYQGRNKYY  60
AESVKGRFTI SRDNSKNTLY LQMNSLRAED TALFYCARGY DVLTGYPDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPCEEQYG  300
STYRCVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 523          moltype = AA  length = 450
FEATURE                 Location/Qualifiers
REGION                  1..450
                        note = Synthetic polypeptide
source                  1..450
                        mol_type = protein
                        organism = synthetic construct
SEQUENCE: 523
QVQLVESGGG VVQPGRSLRL SCAASGFTFS RFAMHWVRQA PGKGLEWVAV ISYQGNNKYY  60
ARSVKGRFTI SRDNSKNTLY LQMNSLRAED TALFYCARGY DVLTGYPDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPCEEQYG  300
STYRCVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 524          moltype = AA  length = 450
FEATURE                 Location/Qualifiers
REGION                  1..450
                        note = Synthetic polypeptide
source                  1..450
                        mol_type = protein
                        organism = synthetic construct
SEQUENCE: 524
QVQLVESGGG VVQPGRSLRL SCAASGFTFS KFAMHWVRQA PGKGLEWVAV ISYRGGNKYY  60
AESVKGRFTI SRDNSKNTLY LQMNSLRAED TALFYCARGY DLLTGYPDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPCEEQYG  300
STYRCVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 525          moltype = AA  length = 450
FEATURE                 Location/Qualifiers
REGION                  1..450
                        note = Synthetic polypeptide
source                  1..450
                        mol_type = protein
                        organism = synthetic construct
SEQUENCE: 525
QVQLVESGGG VVQPGRSLRL SCAASGFTFS RFAMHWVRQA PGKGLEWVAV ISYIGGNKYY  60
AESVKGRFTI SRDNSKNTLY LQMNSLRAED TALFYCARGY DILTGYPDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPCEEQYG  300
STYRCVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 526          moltype = AA  length = 450
FEATURE                 Location/Qualifiers
REGION                  1..450
                        note = Synthetic polypeptide
source                  1..450
                        mol_type = protein
                        organism = synthetic construct
```

```
SEQUENCE: 526
QVQLVESGGG VVQPGRSLRL SCAASGFTFS RFAMHWVRQA PGKGLEWVAV ISYNGRNKYY  60
ARSVKGRFTI SRDNSKNTLY LQMNSLRAED TALFYCARGY DILTGYPDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPCEEQYG  300
STYRCVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 527          moltype = AA  length = 450
FEATURE                 Location/Qualifiers
REGION                  1..450
                        note = Synthetic polypeptide
source                  1..450
                        mol_type = protein
                        organism = synthetic construct
SEQUENCE: 527
QVQLVESGGG VVQPGRSLRL SCAASGFTFS RFAMHWVRQA PGKGLEWVGV INYRGHGKYY  60
AESVKGRFTV SRDNSKNTLY LQMNSLRAED TALFYCARGY DVLTGYPDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPCEEQYG  300
STYRCVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 528          moltype = AA  length = 450
FEATURE                 Location/Qualifiers
REGION                  1..450
                        note = Synthetic polypeptide
source                  1..450
                        mol_type = protein
                        organism = synthetic construct
SEQUENCE: 528
QVQLVESGGG VVQPGRSLRL SCAASGFTFS RFAMHWVRQA PGKGLEWVGV ISFSGGSKYY  60
AESVKGRFTL SRDNSKNTLY LQMNSLRAED TALFYCARGY DVLTGYPDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPCEEQYG  300
STYRCVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 529          moltype = AA  length = 450
FEATURE                 Location/Qualifiers
REGION                  1..450
                        note = Synthetic polypeptide
source                  1..450
                        mol_type = protein
                        organism = synthetic construct
SEQUENCE: 529
QVQLVESGGG VVQPGRSLRL SCAASGFTFS RFAMHWVRQA PGKGLEWVGV ISYTGQFKYY  60
AESVKGRFTV SRDNSKNTLY LQMNSLRAED TALFYCARGY DVLTGYPDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPCEEQYG  300
STYRCVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 530          moltype = AA  length = 453
FEATURE                 Location/Qualifiers
REGION                  1..453
                        note = Synthetic polypeptide
source                  1..453
                        mol_type = protein
                        organism = synthetic construct
SEQUENCE: 530
QVQLQQSGPG LVKPSQTLSL TCAISGDSVS SNSATWNWIR QSPSRGLEWL GRTYYRSKWS  60
NHYAVSVKSR ITINPDTSKS QFSLQLNSVT PEDTAVYYCA RGTWKQLWFL DHWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPCEE  300
QYGSTYRCVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 531          moltype = AA  length = 453
```

```
FEATURE                Location/Qualifiers
REGION                 1..453
                       note = Synthetic polypeptide
source                 1..453
                       mol_type = protein
                       organism = synthetic construct
SEQUENCE: 531
QVQLQQSGPG LVKPSQTLSL TCAISGDSVS NRLATWNWIR QSPSRGLEWL GRTYYRGKWK  60
NHYAVSVKSR ITINPDTSKS QFSLQLNSVT PEDTAVYYCA RGVWIGNWFL DHWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPCEE  300
QYGSTYRCVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 532         moltype = AA  length = 453
FEATURE                Location/Qualifiers
REGION                 1..453
                       note = Synthetic polypeptide
source                 1..453
                       mol_type = protein
                       organism = synthetic construct
SEQUENCE: 532
QVQLQQSGPG LVKPSQTLSL TCAISGDSVS NKQATWNWIR QSPSRGLEWL GRTYYRGKWK  60
NHYAVSVKSR ITINPDTSKS QFSLQLNSVT PEDTAVYYCA RGMWNQNWFL DHWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPCEE  300
QYGSTYRCVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 533         moltype = AA  length = 453
FEATURE                Location/Qualifiers
REGION                 1..453
                       note = Synthetic polypeptide
source                 1..453
                       mol_type = protein
                       organism = synthetic construct
SEQUENCE: 533
QVQLQQSGPG LVKPSQTLSL TCAISGDSVS SRQATWNWIR QSPSRGLEWL GRTYYRGKWK  60
NHYAVSVKSR ITINPDTSKS QFSLQLNSVT PEDTAVYYCA RGMWQGNWFL DHWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPCEE  300
QYGSTYRCVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 534         moltype = AA  length = 453
FEATURE                Location/Qualifiers
REGION                 1..453
                       note = Synthetic polypeptide
source                 1..453
                       mol_type = protein
                       organism = synthetic construct
SEQUENCE: 534
QVQLQQSGPG LVKPSQTLSL TCAISGDSVS NRLATWNWIR QSPSRGLEWL GRTYYRGKWK  60
NHYAVSVKSR ITINPDTSKS QFSLQLNSVT PEDTAVYYCA RGRWEGDWFF DHWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPCEE  300
QYGSTYRCVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 535         moltype = AA  length = 453
FEATURE                Location/Qualifiers
REGION                 1..453
                       note = Synthetic polypeptide
source                 1..453
                       mol_type = protein
                       organism = synthetic construct
SEQUENCE: 535
QVQLQQSGPG LVKPSQTLSL TCAISGDSVS NRLATWNWIR QSPSRGLEWL GRTYYRGKWK  60
NHYAVSVKSR ITINPDTSKS QFSLQLNSVT PEDTAVYYCA RGTWNQDWFL DHWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
```

```
LGGPSVFLFP PKPKDTLMIS RTPEVTCVVV DVSHEDPEVK FNWYVDGVEV HNAKTKPCEE  300
QYGSTYRCVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 536          moltype = AA  length = 453
FEATURE                 Location/Qualifiers
REGION                  1..453
                        note = Synthetic polypeptide
source                  1..453
                        mol_type = protein
                        organism = synthetic construct
SEQUENCE: 536
QVQLQQSGPG LVKPSQTLSL TCAISGDSVS SRYATWNWIR QSPSRGLEWL GRTYYRGQWK  60
NHYAVSVKSR ITINPDTSKS QFSLQLNSVT PEDTAVYYCA RGMWNQNWFL DHWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPCEE  300
QYGSTYRCVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 537          moltype = DNA  length = 645
FEATURE                 Location/Qualifiers
misc_feature            1..645
                        note = Synthetic polynucleotide
source                  1..645
                        mol_type = other DNA
                        organism = synthetic construct
SEQUENCE: 537
gagatcgtac ttactcagtc acccgccaca ttgtccctga gcccgggtga acgggcgacc  60
ctcagctgcc gagcatccca gtccgtcgga cgatcattgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgaggt tgcctttcac gtttggacca  300
gggaccaagg tggacattaa gcgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                 645

SEQ ID NO: 538          moltype = DNA  length = 642
FEATURE                 Location/Qualifiers
misc_feature            1..642
                        note = Synthetic polynucleotide
source                  1..642
                        mol_type = other DNA
                        organism = synthetic construct
SEQUENCE: 538
gatatccagc tcactcaatc gccatcattt ctctccgctt cggtaggcga ccgggtcacg  60
atcacatgca gggcgtcgca aagcattggg aggtcgttgc attggtatca gcagaaaccc  120
ggaaaggccc cgaaacttct gatcaaatac gcatcacaaa gcttgagcgg tgtgccgtcg  180
cgcttctccg gttccggaag cggaacggaa ttcacgctta caatctcctc actgcagccc  240
gaggatttcg cgacctatta ctgtcaccag tcatccagac tcccgtttac ttttggccct  300
gggaccaagg tggacattaa gcgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                    642

SEQ ID NO: 539          moltype = DNA  length = 642
FEATURE                 Location/Qualifiers
misc_feature            1..642
                        note = Synthetic polynucleotide
source                  1..642
                        mol_type = other DNA
                        organism = synthetic construct
SEQUENCE: 539
gagatcgtac ttactcagtc acccgccaca ttgtccctga gcccgggtga acgggcgacc  60
ctcagctgcc gagcatccaa gtccgtcgga cgatcattgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgaggt tgcctttcac gtttggacca  300
gggaccaagg tggacattaa gcgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
```

```
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 540         moltype = DNA  length = 642
FEATURE                Location/Qualifiers
misc_feature           1..642
                       note = Synthetic polynucleotide
source                 1..642
                       mol_type = other DNA
                       organism = synthetic construct
SEQUENCE: 540
gagatcgtac ttactcagtc acccgccaca ttgtccctga gcccgggtga acgggcgacc  60
ctcagctgcc gagcatccaa atccgtcggg tggagcttgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgaggt tgcctttcac gtttggacca  300
gggaccaagg tggacattaa gcgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 541         moltype = DNA  length = 642
FEATURE                Location/Qualifiers
misc_feature           1..642
                       note = Synthetic polynucleotide
source                 1..642
                       mol_type = other DNA
                       organism = synthetic construct
SEQUENCE: 541
gagatcgtac ttactcagtc acccgccaca ttgtccctga gcccgggtga acgggcgacc  60
ctcagctgcc gagcatccaa atccgtcggg tacagcttgc actggtacca acaaaaaccg  120
ggccaggccc ccagacttct gatcaagtat gcgtcacaga gcttgtcggg tattcccgct  180
cgcttttcgg ggtcgggatc cgggacagat ttcacgctca caatctcctc gctggaaccc  240
gaggacttcg cggtctacta ttgtcatcag tcatcgaggt tgcctttcac gtttggacca  300
gggaccaagg tggacattaa gcgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 542         moltype = DNA  length = 642
FEATURE                Location/Qualifiers
misc_feature           1..642
                       note = Synthetic polynucleotide
source                 1..642
                       mol_type = other DNA
                       organism = synthetic construct
SEQUENCE: 542
gacatccaga tgacccagtc tccatcctcc ctgtctgcat ctgtaggaga cagaatcacc  60
atcacttgcc gggcaagtca gagcattagc aggtatttaa attggtatca acagaaacca  120
gggaaagccc ctaaactcct gatctatgct gcatccagtt tgcaaagtgg gatcccatca  180
aggttcagcg gcagtggatc tgggacagat ttcactctca ccatcaacag tctgcaacct  240
gaagattttg caacttactt ctgtcaacag agttacagtc ccccattcac tttcggccct  300
gggaccaaag tggatatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 543         moltype = DNA  length = 642
FEATURE                Location/Qualifiers
misc_feature           1..642
                       note = Synthetic polynucleotide
source                 1..642
                       mol_type = other DNA
                       organism = synthetic construct
SEQUENCE: 543
gacatccaga tgacccagtc tccatcctcc ctgtctgcat ctgtaggaga cagaatcacc  60
atcacttgcc gggcaagtca gatgattgct cgttacttaa actggtatca acagaaacca  120
gggaaagccc ctaaactcct gatctacgct tcttacaact tgcaaagtgg gatcccatca  180
aggttcagcg gcagtggatc tgggacagat ttcactctca ccatcaacag tctgcaacct  240
gaagattttg caacttactt ctgtcaacag gctatcatca acccatacac tttcggccct  300
gggaccaaag tggatatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
```

```
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 544         moltype = DNA  length = 642
FEATURE                Location/Qualifiers
misc_feature           1..642
                       note = Synthetic polynucleotide
source                 1..642
                       mol_type = other DNA
                       organism = synthetic construct
SEQUENCE: 544
gacatccaga tgacccagtc tccatcctcc ctgtctgcat ctgtaggaga cagaatcacc  60
atcacttgcc gggcaagtca gaaaattgct cgttacttag tttggtatca acagaaacca  120
gggaaagccc ctaaactcct gatctacgct gctaacatgt tgcaaagtgg gatcccatca  180
aggttcagcg gcagtggatc tgggacagat ttcactctca ccatcaacag tctgcaacct  240
gaagattttg caacttactt ctgtcaacag tctatccagc agccatacac tttcggccct  300
gggaccaaag tggatatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 545         moltype = DNA  length = 642
FEATURE                Location/Qualifiers
misc_feature           1..642
                       note = Synthetic polynucleotide
source                 1..642
                       mol_type = other DNA
                       organism = synthetic construct
SEQUENCE: 545
gacatccaga tgacccagtc tccatcctcc ctgtctgcat ctgtaggaga cagaatcacc  60
atcacttgcc gggcaagtca gagcattagc aggtatttaa attggtatca acagaaacca  120
gggaaagccc ctaaactcct gatctacgct ggtcgtatct tgcaaagtgg gatcccatca  180
aggttcagcg gcagtggatc tgggacagat ttcactctca ccatcaacag tctgcaacct  240
gaagattttg caacttactt ctgtcaacag gctatcatca acccatacac tttcggccct  300
gggaccaaag tggatatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 546         moltype = DNA  length = 642
FEATURE                Location/Qualifiers
misc_feature           1..642
                       note = Synthetic polynucleotide
source                 1..642
                       mol_type = other DNA
                       organism = synthetic construct
SEQUENCE: 546
gacatccaga tgacccagtc tccatcctcc ctgtctgcat ctgtaggaga cagaatcacc  60
atcacttgcc gggcaagtca gagcattagc aggtatttaa attggtatca acagaaacca  120
gggaaagccc ctaaactcct gatctacgct tcttacaact tgcaaagtgg gatcccatca  180
aggttcagcg gcagtggatc tgggacagat ttcactctca ccatcaacag tctgcaacct  240
gaagattttg caacttactt ctgtcaacag tctatccagc agccatacac tttcggccct  300
gggaccaaag tggatatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 547         moltype = DNA  length = 642
FEATURE                Location/Qualifiers
misc_feature           1..642
                       note = Synthetic polynucleotide
source                 1..642
                       mol_type = other DNA
                       organism = synthetic construct
SEQUENCE: 547
gacatccaga tgacccagtc tccatcctcc ctgtctgcat ctgtaggaga cagaatcacc  60
atcacttgcc gggcaagtca gtacattgtt cgttacttaa actggtatca acagaaacca  120
gggaaagccc ctaaactcct gatctacgct tcttacaact tgcaaagtgg gatcccatca  180
aggttcagcg gcagtggatc tgggacagat ttcactctca ccatcaacag tctgcaacct  240
gaagattttg caacttactt ctgtcaacag gctatcatgg ctccatacac tttcggccct  300
gggaccaaag tggatatcaa acgtacggtg gctgcaccat ctgtcttcat cttcccgcca  360
tctgatgagc agttgaaatc tggaactgcc tctgttgtgt gcctgctgaa taacttctat  420
```

```
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                    642

SEQ ID NO: 548         moltype = DNA  length = 642
FEATURE                Location/Qualifiers
misc_feature           1..642
                       note = Synthetic polynucleotide
source                 1..642
                       mol_type = other DNA
                       organism = synthetic construct
SEQUENCE: 548
gacatccaga tgacccagtc tccatcctcc ctgtctgcat ctgtaggaga cagaatcacc  60
atcacttgcc gggcaagtca gagcattagc aggtatttaa attggtatca acagaaacca  120
gggaaagccc ctaaactcct gatcttcgct ggtcagcgtt tgcaaagtgg gatcccatca  180
aggttcagcg gcagtggatc tgggacagat ttcactctca ccatcaacag tctgcaacct  240
gaagattttg caacttactt ctgtcaacag gctatcggta tgccatacac tttcggccct  300
gggaccaaag tggatatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                    642

SEQ ID NO: 549         moltype = DNA  length = 642
FEATURE                Location/Qualifiers
misc_feature           1..642
                       note = Synthetic polynucleotide
source                 1..642
                       mol_type = other DNA
                       organism = synthetic construct
SEQUENCE: 549
gacatccaga tgacccagtc tccatcctcc ctgtctgcat ctgtaggaga cagaatcacc  60
atcacttgcc gggcaagtca gtacattgtt cgttacttaa actggtatca acagaaacca  120
gggaaagccc ctaaactcct gatctacgct gctaacatgt tgcaaagtgg gatcccatca  180
aggttcagcg gcagtggatc tgggacagat ttcactctca ccatcaacag tctgcaacct  240
gaagattttg caacttactt ctgtcaacag gctatcaacc agccatacac tttcggccct  300
gggaccaaag tggatatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                    642

SEQ ID NO: 550         moltype = DNA  length = 642
FEATURE                Location/Qualifiers
misc_feature           1..642
                       note = Synthetic polynucleotide
source                 1..642
                       mol_type = other DNA
                       organism = synthetic construct
SEQUENCE: 550
gacatccaga tgacccagtc tccatcctcc ctgtctgcat ctgtaggaga cagaatcacc  60
atcacttgcc gggcaagtca gccgatttct cgttacttat cttggtatca acagaaacca  120
gggaaagccc ctaaactcct gatcttcgct ggtcagcgtt tgcaaagtgg gatcccatca  180
aggttcagcg gcagtggatc tgggacagat ttcactctca ccatcaacag tctgcaacct  240
gaagattttg caacttactt ctgtcaacag gctatctcta tcccatacac tttcggccct  300
gggaccaaag tggatatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                    642

SEQ ID NO: 551         moltype = DNA  length = 642
FEATURE                Location/Qualifiers
misc_feature           1..642
                       note = Synthetic polynucleotide
source                 1..642
                       mol_type = other DNA
                       organism = synthetic construct
SEQUENCE: 551
gacatccaga tgacccagtc tccatcctcc ctgtctgcat ctgtaggaga cagaatcacc  60
atcacttgcc gggcaagtca gcagattgct cgttacttaa actggtatca acagaaacca  120
gggaaagccc ctaaactcct gatctacgct tcttacaact tgcaaagtgg gatcccatca  180
aggttcagcg gcagtggatc tgggacagat ttcactctca ccatcaacag tctgcaacct  240
gaagattttg caacttactt ctgtcaacag gctatcatcc agccatacac tttcggccct  300
gggaccaaag tggatatcaa acgtacggtg gctgcaccat ctgtcttcat cttcccgcca  360
```

```
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                    642

SEQ ID NO: 552          moltype = DNA  length = 1350
FEATURE                 Location/Qualifiers
misc_feature            1..1350
                        note = Synthetic polynucleotide
source                  1..1350
                        mol_type = other DNA
                        organism = synthetic construct
SEQUENCE: 552
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatg atggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgtgcgagga gcagtacggc  900
agcacgtacc gttgcgtcag cgtcctcacc gtcctgcacc aggactggct gaatggcaag  960
gagtacaagt gcaaggtgtc caacaaagcc ctcccagccc ccatcgagaa aaccatctcc  1020
aaagccaaag ggcagccccg agaaccacag gtgtacaccc tgcccccatc ccgggaggag  1080
atgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa                                  1350

SEQ ID NO: 553          moltype = DNA  length = 1350
FEATURE                 Location/Qualifiers
misc_feature            1..1350
                        note = Synthetic polynucleotide
source                  1..1350
                        mol_type = other DNA
                        organism = synthetic construct
SEQUENCE: 553
caagttcagt tggtggagtc tggagccgaa gtagtaaagc caggagcttc agtgaaagtc  60
tcttgtaaag caagtggatt cacgtttagc cgctttgcca tgcattgggt gcggcaagct  120
cccggtcagg ggttggagtg gatgggagtt attagctatg acgggggcaa taagtactac  180
gccgagtctg ttaagggtcg ggtcacaatg acacgggaca cctcaaccag tacactctat  240
atggaactgt ctagcctgag atccgaggac accgctgtgt attattgcgc taggggggtac  300
gatgtattga cgggttatcc tgattactgg gggcagggga cactcgtaac cgtctctagt  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacggc  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggaggag  1080
atgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa                                  1350

SEQ ID NO: 554          moltype = DNA  length = 1350
FEATURE                 Location/Qualifiers
misc_feature            1..1350
                        note = Synthetic polynucleotide
source                  1..1350
                        mol_type = other DNA
                        organism = synthetic construct
SEQUENCE: 554
caggtgcagc tggtggagtc tgggggaggc gtggtccagc ctgggaggtc cctgcgactc  60
```

```
tcctgtgcag cctctggatt caccttcagt agatttgcca tgcactgggt ccgccaggct  120
ccaggcaagg ggctggagtg ggtggcagtt atatcatata tcggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgtgcgagga gcagtacggc  900
agcacgtacc gttgcgtcag cgtcctcacc gtcctgcacc aggactggct gaatggcaag  960
gagtacaagt gcaaggtgtc caacaaagcc ctcccagccc ccatcgagaa aaccatctcc  1020
aaagccaaag ggcagccccg agaaccacag gtgtacaccc tgcccccatc ccgggaggag  1080
atgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa                                    1350

SEQ ID NO: 555          moltype = DNA  length = 1350
FEATURE                 Location/Qualifiers
misc_feature            1..1350
                        note = Synthetic polynucleotide
source                  1..1350
                        mol_type = other DNA
                        organism = synthetic construct
SEQUENCE: 555
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatc agggacgcaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgtgcgagga gcagtacggc  900
agcacgtacc gttgcgtcag cgtcctcacc gtcctgcacc aggactggct gaatggcaag  960
gagtacaagt gcaaggtgtc caacaaagcc ctcccagccc ccatcgagaa aaccatctcc  1020
aaagccaaag ggcagccccg agaaccacag gtgtacaccc tgcccccatc ccgggaggag  1080
atgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa                                    1350

SEQ ID NO: 556          moltype = DNA  length = 1350
FEATURE                 Location/Qualifiers
misc_feature            1..1350
                        note = Synthetic polynucleotide
source                  1..1350
                        mol_type = other DNA
                        organism = synthetic construct
SEQUENCE: 556
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatatc agggaaacaa taaatactat  180
gcacgctccg tgaagggccg gttcaccatc tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtctctagt  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgtgcgagga gcagtacggc  900
agcacgtacc gttgcgtcag cgtcctcacc gtcctgcacc aggactggct gaatggcaag  960
```

```
gagtacaagt gcaaggtgtc caacaaagcc ctcccagccc ccatcgagaa aaccatctcc  1020
aaagccaaag ggcagccccg agaaccacag gtgtacaccc tgcccccatc ccgggaggag  1080
atgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa                                   1350

SEQ ID NO: 557          moltype = DNA  length = 1350
FEATURE                 Location/Qualifiers
misc_feature            1..1350
                        note = Synthetic polynucleotide
source                  1..1350
                        mol_type = other DNA
                        organism = synthetic construct
SEQUENCE: 557
caggtgcagc tggtggagtc tgggggaggc gtggtccagc ctgggaggtc cctgcgactc  60
tcctgtgcag cctctggatt caccttcagt aagtttgcca tgcactgggt ccgccaggct  120
ccaggcaagg ggctggagtg ggtggcagtt atatcatatc gcggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatctgttga ctggttaccc cgactactgg ggccagggaa ccctggtcac cgtctctagt  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgtgcgagga gcagtacggc  900
agcacgtacc gttgcgtcag cgtcctcacc gtcctgcacc aggactggct gaatggcaag  960
gagtacaagt gcaaggtgtc caacaaagcc ctcccagccc ccatcgagaa aaccatctcc  1020
aaagccaaag ggcagccccg agaaccacag gtgtacaccc tgcccccatc ccgggaggag  1080
atgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa                                   1350

SEQ ID NO: 558          moltype = DNA  length = 1350
FEATURE                 Location/Qualifiers
misc_feature            1..1350
                        note = Synthetic polynucleotide
source                  1..1350
                        mol_type = other DNA
                        organism = synthetic construct
SEQUENCE: 558
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtggcagtt atatcatata tcggaggaaa taaatactat  180
gcagagtccg tgaagggccg gttcaccatc tccagagaca attccaagaa caccctgtat  240
ctgcaaatga acagcctgag agctgaggac acggctctgt tttactgtgc gagaggatac  300
gatatcttga ctggttaccc cgactactgg ggccagggaa ccctggtcac cgtctctagt  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgtgcgagga gcagtacggc  900
agcacgtacc gttgcgtcag cgtcctcacc gtcctgcacc aggactggct gaatggcaag  960
gagtacaagt gcaaggtgtc caacaaagcc ctcccagccc ccatcgagaa aaccatctcc  1020
aaagccaaag ggcagccccg agaaccacag gtgtacaccc tgcccccatc ccgggaggag  1080
atgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa                                   1350

SEQ ID NO: 559          moltype = DNA  length = 1350
FEATURE                 Location/Qualifiers
misc_feature            1..1350
                        note = Synthetic polynucleotide
source                  1..1350
                        mol_type = other DNA
                        organism = synthetic construct
```

SEQUENCE: 559
caggtgcagc tggtggagtc tgggggaggc gtggtccagc ctgggaggtc cctgcgactc 60
tcctgtgcag cctctggatt caccttcagt agatttgcca tgcactgggt ccgccaggct 120
ccaggcaagg ggctggagtg ggtggcagtt atatcatata acggacgcaa taaatactat 180
gcacgctccg tgaagggccg gttcaccatc tccagagaca attccaagaa caccctgtat 240
ctgcaaatga acagcctgag agctgaggac acggctctgt tttactgtgc gagaggatac 300
gatatcttga ctggttaccc cgactactgg ggccagggaa ccctggtcac cgtctctagt 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagaa agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgtgcgagga gcagtacggc 900
agcacgtacc gttgcgtcag cgtcctcacc gtcctgcacc aggactggct gaatggcaag 960
gagtacaagt gcaaggtgtc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctat agcaagctca ccgtggacaa gagcaggtgg 1260
cagcagggga acgtcttctc atgctccgtg atgcatgagg ctctgcacaa ccactacacg 1320
cagaagagcc tctccctgtc tccgggtaaa 1350

SEQ ID NO: 560 moltype = DNA length = 1350
FEATURE Location/Qualifiers
misc_feature 1..1350
note = Synthetic polynucleotide
source 1..1350
mol_type = other DNA
organism = synthetic construct
SEQUENCE: 560
caggtgcagc tggtggagtc tgggggaggc gtggtccagc ctgggaggtc cctgcgactc 60
tcctgtgcag cctctggatt caccttcagt agatttgcca tgcactgggt ccgccaggct 120
ccaggcaagg ggctggagtg ggtgggtgtt atcaactatc gtggacatgg taaatactat 180
gcagagtccg tgaagggccg gttcaccgtg tccagagaca attccaagaa caccctgtat 240
ctgcaaatga acagcctgag agctgaggac acggctctgt tttactgtgc gagaggatac 300
gatgttttga ctggttaccc cgactactgg ggccagggaa ccctggtcac cgtgtctagt 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagaa agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgtgcgagga gcagtacggc 900
agcacgtacc gttgcgtcag cgtcctcacc gtcctgcacc aggactggct gaatggcaag 960
gagtacaagt gcaaggtgtc caacaaagcc ctcccagccc ccatcgagaa aaccatctcc 1020
aaagccaaag ggcagccccg agaaccacag gtgtacaccc tgcccccatc ccgggaggag 1080
atgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctat agcaagctca ccgtggacaa gagcaggtgg 1260
cagcagggga acgtcttctc atgctccgtg atgcatgagg ctctgcacaa ccactacacg 1320
cagaagagcc tctccctgtc tccgggtaaa 1350

SEQ ID NO: 561 moltype = DNA length = 1350
FEATURE Location/Qualifiers
misc_feature 1..1350
note = Synthetic polynucleotide
source 1..1350
mol_type = other DNA
organism = synthetic construct
SEQUENCE: 561
caggtgcagc tggtggagtc tgggggaggc gtggtccagc ctgggaggtc cctgcgactc 60
tcctgtgcag cctctggatt caccttcagt agatttgcca tgcactgggt ccgccaggct 120
ccaggcaagg ggctggagtg ggtgggtgtt atatcttttt ctggaggttc taaatactat 180
gcagagtccg tgaagggccg gttcaccttg tccagagaca attccaagaa caccctgtat 240
ctgcaaatga acagcctgag agctgaggac acggctctgt tttactgtgc gagaggatac 300
gatgttttga ctggttaccc cgactactgg ggccagggaa ccctggtcac cgtgtctagt 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagaa agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840

```
tacgtggacg gcgtggaggt gcataatgcc aagacaaagc cgtgcgagga gcagtacggc  900
agcacgtacc gttgcgtcag cgtcctcacc gtcctgcacc aggactggct gaatggcaag  960
gagtacaagt gcaaggtgtc caacaaagcc ctcccagccc ccatcgagaa aaccatctcc  1020
aaagccaaag ggcagccccg agaaccacag gtgtacaccc tgcccccatc ccgggaggag  1080
atgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa                                   1350
```

```
SEQ ID NO: 562          moltype = DNA  length = 1350
FEATURE                 Location/Qualifiers
misc_feature            1..1350
                        note = Synthetic polynucleotide
source                  1..1350
                        mol_type = other DNA
                        organism = synthetic construct
SEQUENCE: 562
caggtgcagc tggtggagtc tgggggaggc gtggtccagc ctgggaggtc cctgcgactc  60
tcctgtgcag cctctggatt caccttcagt agatttgcca tgcactgggt ccgccaggct  120
ccaggcaagg ggctggagtg ggtgggtgtt atctcttata ctggacagtt caaatactat  180
gcagagtccg tgaagggccg gttcaccgtg tccagagaca attccaagaa caccctgtat  240
ctgcaaatga acagcctgag agctgaggac acggctctgt tttactgtgc gagaggatac  300
gatgttttga ctggttaccc cgactactgg ggccagggaa ccctggtcac cgtgtctagt  360
gcctccacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgtgcgagga gcagtacggc  900
agcacgtacc gttgcgtcag cgtcctcacc gtcctgcacc aggactggct gaatggcaag  960
gagtacaagt gcaaggtgtc caacaaagcc ctcccagccc ccatcgagaa aaccatctcc  1020
aaagccaaag ggcagccccg agaaccacag gtgtacaccc tgcccccatc ccgggaggag  1080
atgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa                                   1350
```

```
SEQ ID NO: 563          moltype = DNA  length = 1359
FEATURE                 Location/Qualifiers
misc_feature            1..1359
                        note = Synthetic polynucleotide
source                  1..1359
                        mol_type = other DNA
                        organism = synthetic construct
SEQUENCE: 563
caggtacagc tgcagcagtc aggtccagga ctggtgaagc cctcgcagac cctctcactc  60
acctgtgcca tctccgggga cagtgtctct agcaacagtg ctacttggaa ctggatcagg  120
cagtccccat cgagaggcct tgagtggctg ggaaggacat attacaggtc caagtggtct  180
aatcattatg cagtatctgt gaaaagtcga atcaccatca accccgacac gtccaagagc  240
cagttctccc tgcagctgaa ctctgtgact cccgaggaca cggctgtgta ttactgtgca  300
agaggaacgt ggaaacagct atggttcctt gaccactggg gccagggaac cctggtcacc  360
gtgtctagtg cctccaccaa gggcccatcg gtcttccccc tggcaccctc ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gtgcgaggag  900
cagtacggca gcacgtaccg ttgcgtcagc gtcctcaccg tcctgcacca ggactggctg  960
aatggcaagg agtacaagtg caaggtgtcc aacaaagccc tcccagcccc catcgagaaa  1020
accatctcca aagccaaagg gcagccccga gaaccacagg tgtacaccct gcccccatcc  1080
cgggaggaga tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctata gcaagctcac cgtggacaag  1260
agcaggtggc agcaggggaa cgtcttctca tgctccgtga tgcatgaggc tctgcacaac  1320
cactacacgc agaagagcct ctccctgtct ccgggcaaa                         1359
```

```
SEQ ID NO: 564          moltype = DNA  length = 1359
FEATURE                 Location/Qualifiers
misc_feature            1..1359
                        note = Synthetic polynucleotide
source                  1..1359
```

```
                        mol_type = other DNA
                        organism = synthetic construct
SEQUENCE: 564
caggtacagc tgcagcagtc aggtccagga ctggtgaagc cctcgcagac cctctcactc  60
acctgtgcca tctccgggga cagtgtctct aaccgtctgg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggagttt ggatcggtaa ctggttcctg gaccactggg gccagggaac cctggtcacc  360
gtgtcctcag cctccaccaa gggcccatcg gtcttccccc tggcaccctc ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gtgcgaggag  900
cagtacggca gcacgtaccg ttgcgtcagc gtcctcaccg tcctgcacca ggactggctg  960
aatggcaagg agtacaagtg caaggtgtcc aacaaagccc tcccagcccc catcgagaaa  1020
accatctcca aagccaaagg gcagccccga gaaccacagg tgtacaccct gcccccatcc  1080
cgggaggaga tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctata gcaagctcac cgtggacaag  1260
agcaggtggc agcaggggaa cgtcttctca tgctccgtga tgcatgaggc tctgcacaac  1320
cactacacgc agaagagcct ctccctgtct ccgggtaaa                         1359

SEQ ID NO: 565          moltype = DNA  length = 1359
FEATURE                 Location/Qualifiers
misc_feature            1..1359
                        note = Synthetic polynucleotide
source                  1..1359
                        mol_type = other DNA
                        organism = synthetic construct
SEQUENCE: 565
caggtacagc tgcagcagtc aggtccagga ctggtgaagc cctcgcagac cctctcactc  60
acctgtgcca tctccgggga cagtgtctct aacaaacagg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaatgt ggaaccagaa ctggttcctg gaccactggg gccagggaac cctggtcacc  360
gtgtcctcag cctccaccaa gggcccatcg gtcttccccc tggcaccctc ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gtgcgaggag  900
cagtacggca gcacgtaccg ttgcgtcagc gtcctcaccg tcctgcacca ggactggctg  960
aatggcaagg agtacaagtg caaggtgtcc aacaaagccc tcccagcccc catcgagaaa  1020
accatctcca aagccaaagg gcagccccga gaaccacagg tgtacaccct gcccccatcc  1080
cgggaggaga tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctata gcaagctcac cgtggacaag  1260
agcaggtggc agcaggggaa cgtcttctca tgctccgtga tgcatgaggc tctgcacaac  1320
cactacacgc agaagagcct ctccctgtct ccgggtaaa                         1359

SEQ ID NO: 566          moltype = DNA  length = 1359
FEATURE                 Location/Qualifiers
misc_feature            1..1359
                        note = Synthetic polynucleotide
source                  1..1359
                        mol_type = other DNA
                        organism = synthetic construct
SEQUENCE: 566
caggtacagc tgcagcagtc aggtccagga ctggtgaagc cctcgcagac cctctcactc  60
acctgtgcca tctccgggga cagtgtctct tctcgtcagg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaatgt ggcagggtaa ctggttcctg gaccactggg gccagggaac cctggtcacc  360
gtgtcctcag cctccaccaa gggcccatcg gtcttccccc tggcaccctc ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
```

```
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gtgcgaggag  900
cagtacggca gcacgtaccg ttgcgtcagc gtcctcaccg tcctgcacca ggactggctg  960
aatggcaagg agtacaagtg caaggtgtcc aacaaagccc tcccagcccc catcgagaaa  1020
accatctcca aagccaaagg gcagccccga gaaccacagg tgtacaccct gcccccatcc  1080
cgggaggaga tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctata gcaagctcac cgtggacaag  1260
agcaggtggc agcaggggaa cgtcttctca tgctccgtga tgcatgaggc tctgcacaac  1320
cactacacgc agaagagcct ctccctgtct ccgggtaaa                         1359

SEQ ID NO: 567          moltype = DNA  length = 1359
FEATURE                 Location/Qualifiers
misc_feature            1..1359
                        note = Synthetic polynucleotide
source                  1..1359
                        mol_type = other DNA
                        organism = synthetic construct
SEQUENCE: 567
caggtacagc tgcagcagtc aggtccagga ctggtgaagc cctcgcagac cctctcactc  60
acctgtgcca tctccgggga cagtgtctct aaccgtctgg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggacgtt gggaaggtga ctggttcttc gaccactggg gccagggaac cctggtcacc  360
gtgtcctcag cctccaccaa gggcccatcg gtcttccccc tggcaccctc ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gtgcgaggag  900
cagtacggca gcacgtaccg ttgcgtcagc gtcctcaccg tcctgcacca ggactggctg  960
aatggcaagg agtacaagtg caaggtgtcc aacaaagccc tcccagcccc catcgagaaa  1020
accatctcca aagccaaagg gcagccccga gaaccacagg tgtacaccct gcccccatcc  1080
cgggaggaga tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctata gcaagctcac cgtggacaag  1260
agcaggtggc agcaggggaa cgtcttctca tgctccgtga tgcatgaggc tctgcacaac  1320
cactacacgc agaagagcct ctccctgtct ccgggtaaa                         1359

SEQ ID NO: 568          moltype = DNA  length = 1359
FEATURE                 Location/Qualifiers
misc_feature            1..1359
                        note = Synthetic polynucleotide
source                  1..1359
                        mol_type = other DNA
                        organism = synthetic construct
SEQUENCE: 568
caggtacagc tgcagcagtc aggtccagga ctggtgaagc cctcgcagac cctctcactc  60
acctgtgcca tctccgggga cagtgtctct aaccgtctgg ctacttggaa ctggatcagg  120
cagtccccat cgagaggcct tgagtggctg ggaaggacat actacagggg taaatggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaactt ggaaccagga ctggttcctg gaccactggg gccagggaac cctggtcacc  360
gtgtcctcag cctccaccaa gggcccatcg gtcttccccc tggcaccctc ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gtgcgaggag  900
cagtacggca gcacgtaccg ttgcgtcagc gtcctcaccg tcctgcacca ggactggctg  960
aatggcaagg agtacaagtg caaggtgtcc aacaaagccc tcccagcccc catcgagaaa  1020
accatctcca aagccaaagg gcagccccga gaaccacagg tgtacaccct gcccccatcc  1080
cgggaggaga tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctata gcaagctcac cgtggacaag  1260
agcaggtggc agcaggggaa cgtcttctca tgctccgtga tgcatgaggc tctgcacaac  1320
cactacacgc agaagagcct ctccctgtct ccgggtaaa                         1359

SEQ ID NO: 569          moltype = DNA  length = 1359
FEATURE                 Location/Qualifiers
misc_feature            1..1359
```

```
                     note = Synthetic polynucleotide
source               1..1359
                     mol_type = other DNA
                     organism = synthetic construct
SEQUENCE: 569
caggtacagc tgcagcagtc aggtccagga ctggtgaagc cctcgcagac cctctcactc  60
acctgtgcca tctccgggga cagtgtctct tctcgttacg ctacttggaa ctggatcagg  120
cagtccccat cgagaggcct tgagtggctg ggaaggacat actacagggg tcagtggaaa  180
aatcattatg cagtatctgt gaaaagtcga ataaccatca accccgacac gtccaagagc  240
cagttctccc tgcagctgaa ctctgtgact cccgaggaca cggctgtgta ttactgtgca  300
agaggaatgt ggaaccagaa ctggttcctg gaccactggg gccagggaac cctggtcacc  360
gtgtcctcag cctccaccaa gggcccatcg gtcttccccc tggcaccctc ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaactc  720
ctggggggac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gtgcgaggag  900
cagtacggca gcacgtaccg ttgcgtcagc gtcctcaccg tcctgcacca ggactggctg  960
aatggcaagg agtacaagtg caaggtgtcc aacaaagccc tcccagcccc catcgagaaa  1020
accatctcca aagccaaagg gcagccccga gaaccacagg tgtacaccct gcccccatcc  1080
cgggaggaga tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctata gcaagctcac cgtggacaag  1260
agcaggtggc agcaggggaa cgtcttctca tgctccgtga tgcatgaggc tctgcacaac  1320
cactacacgc agaagagcct ctccctgtct ccgggtaaa                        1359
```

ANTI-HUMAN PAC1 ANTIBODIES OR ANTIGEN-BINDING FRAGMENTS THEREOF AND METHODS OF USE THEREOF FOR INHIBITING VASODILATION AND AMELIORATING A HEADACHE CONDITION

CROSS-REFERENCE TO RELATED APPLICATIONS

This application is a continuation of U.S. application Ser. No. 17/558,032, filed Dec. 21, 2021, now U.S. Pat. No. 11,891,435, which is a continuation of U.S. application Ser. No. 16/919,032, now U.S. Pat. No. 11,248,043, filed Jul. 1, 2020, which is a divisional of U.S. application Ser. No. 16/246,326, now U.S. Pat. No. 10,738,110, filed Jan. 11, 2019, which claims the benefit of U.S. Provisional Application No. 62/617,157, filed Jan. 12, 2018, all of which are hereby incorporated by reference in their entireties.

DESCRIPTION OF THE TEXT FILE SUBMITTED ELECTRONICALLY

The present application contains a Sequence Listing, which has been submitted electronically in XML format and is hereby incorporated by reference in its entirety. The computer readable format copy of the Sequence Listing, which was created on Dec. 18, 2023, is named A-2189-US05-CNT_ST26 and is 815 kilobytes in size.

FIELD OF THE INVENTION

The present invention relates to the field of biopharmaceuticals. In particular, the invention relates to antibodies that specifically bind to human pituitary adenylate cyclase-activating polypeptide type I receptor (PAC1) and potently inhibit its biological activity. The invention also relates to pharmaceutical compositions comprising the antibodies as well as methods of producing and using such antibodies.

BACKGROUND OF THE INVENTION

Migraines are episodic headaches that can involve significant pain, are often accompanied by nausea, vomiting, and extreme sensitivity to light (photophobia) and sound (phonophobia), and are sometimes preceded by sensory warning symptoms or signs (auras). Migraine is a highly prevalent disease worldwide with approximately 12% of the European population, and 18% of women, 6% of men in the United States suffering from migraine attacks (Lipton et al, Neurology, Vol. 68:343-349, 2007; Lipton et al., Headache, Vol. 41:646-657, 2001). A study to assess the prevalence of migraine in the United States reported that nearly half the migraine patient population had three or more migraines per month (Lipton et al, Neurology, Vol. 68:343-349, 2007). Additionally, migraines are associated with a number of psychiatric and medical comorbidities such as depression and vascular disorders (Buse et al., J. Neurol. Neurosurg. Psychiatry, Vol. 81:428-432, 2010; Bigal et al., Neurology, Vol. 72:1864-1871, 2009). Most of the current migraine therapies are either not well tolerated or ineffective (Loder et al., Headache, Vol. 52:930-945, 2012; Lipton et al, 2001); thus, migraine remains an unmet medical need.

A major component of migraine pathogenesis involves the activation of the trigeminovascular system. The release of trigeminal and parasympathetic neurotransmitters from perivascular nerve fibers (Sánchez-del-Rio and Reuter, Curr. Opin. Neurol., Vol. 17(3):289-93, 2004) results in vasodilation of the cranial blood vessels and has been suggested to be associated with the onset of migraine headaches (Edvinsson, Cephalagia, Vol. 33(13): 1070-1072, 2013; Goadsby et al., New Engl J Med., Vol. 346(4):257-270, 2002).

Pituitary adenylate cyclase-activating polypeptides (PACAP) are 38-amino acid (PACAP38), or 27-amino acid (PACAP27) peptides that were first isolated from an ovine hypothalamic extract on the basis of their ability to stimulate cyclic AMP (cAMP) formation in anterior pituitary cells (Miyata et al., Biochem Biophys Res Commun., Vol. 164: 567-574, 1989; Miyata et al., Biochem Biophys Res Commun., Vol. 170:643-648, 1990). PACAP belongs to the VIP/secretin/glucagon superfamily. The sequence of PACAP27 corresponds to the 27 N-terminal amino acids of PACAP38 and shares 68% identity with vasoactive intestinal polypeptide (VIP) (Pantaloni et al., J. Biol. Chem., Vol. 271: 22146-22151, 1996; Pisegna and Wank, Proc. Natl. Acad. Sci. USA, Vol. 90: 6345-49, 1993; Campbell and Scanes, Growth Regul., Vol. 2:175-191, 1992). The major form of PACAP peptide in the human body is PACAP38, and the pharmacology of PACAP38 has not been shown to be different from the pharmacology of PACAP27. Three PACAP receptors have been reported: one receptor that binds PACAP with high affinity and has a much lower affinity for VIP (PAC1 receptor), and two receptors that recognize PACAP and VIP equally well (VPAC1 and VPAC2 receptors) (Vaudry et al., Pharmacol Rev., Vol. 61:283-357, 2009).

Human experimental migraine models using PACAP as a challenge agent to induce migraine-like headaches support the approach for antagonism of the PACAP/PAC1 signaling pathway as a treatment for migraine prophylaxis. PACAP38 is elevated in plasma during spontaneous migraine attacks in migraine patients, and these elevated PACAP38 levels can be normalized with sumatriptan, an acute migraine therapy (Tuka et al., Cephalalgia, Vol. 33: 1085-1095, 2013; Zagami et al., Ann. Clin. Transl. Neurol., Vol. 1: 1036-1040, 2014). Infusion of PACAP38 causes headaches in healthy subjects and migraine-like headaches in migraine patients (Schytz et al., Brain, Vol. 132:16-25, 2009; Amin et al., Brain, Vol. 137: 779-794, 2014; Guo et al., Cephalalgia, Vol. 37:125-135, 2017). However, in the same model, VIP does not cause migraine-like headaches in migraine patients (Rahmann et al., Cephalalgia, Vol. 28:226-236, 2008). The lack of migraine-like headache induction from VIP infusion suggests that PACAP38 peptide's effects are mediated through the PAC1 receptor, rather than VPAC1 or VPAC2 receptors, because VIP has a much higher affinity at the latter two receptors. This notion is further supported by animal studies in which PAC1 receptor antagonists inhibit nociceptive neuronal activity in the trigeminocervical complex in an in vivo model of migraine (Akerman et al., Sci. Transl. Med., Vol. 7: 308ra157, 2015; Hoffmann et al., Cephalalgia, Vol. 37 (1S): 3, Abstract OC-BA-004, 2017). Taken together, these data suggest that pharmacological agents that inhibit PACAP-activation of the PAC1 receptor have the potential to treat migraine.

SUMMARY OF THE INVENTION

The present invention is based, in part, on the design and generation of high affinity antibodies that specifically bind to and potently inhibit human PAC1. The antibodies of the invention have enhanced inhibitory potency against human PAC1 as compared to previously described anti-PAC1 antibodies, with IC50 values in the picomolar range. The isolated antibodies and antigen-binding fragments thereof can be used to inhibit, interfere with, or modulate the biological activity of human PAC1, including inhibiting or reducing PACAP-induced activation of PAC1, inhibiting or reducing vasodilation, and ameliorating or treating symptoms of migraine and other vascular headaches.

In some embodiments, the isolated antibodies and antigen-binding fragments thereof specifically bind to human PAC1 at an epitope that comprises one or more amino acids selected from Asp59, Asn60, Ile61, Arg116, Asn117, Thr119, Glu120, Asp121, Gly122, Trp123, Ser124, Glu125, Pro126, Phe127, Pro128, His129, Tyr130, Phe131, Asp132, and Gly135 of SEQ ID NO: 1. In certain embodiments, the epitope comprises at least amino acids Asn60, Ile61, Glu120, and Asp121 of human PAC1. In these and other embodiments, the antibodies and antigen-binding fragments of the invention comprise specific amino acids at particular positions within the light chain and heavy chain variable regions that interact with these epitope residues. For instance, in one embodiment, the antibodies or antigen-binding fragments comprise a light chain variable region in which the amino acid at position 29 according to AHo numbering is a basic amino acid (e.g. arginine or lysine) that interacts with amino acids Glu120 or Asp121 of human PAC1. In another embodiment, the antibodies or antigen-binding fragments comprise a heavy chain variable region in which the amino acid at position 61 according to AHo numbering is a hydrophobic, basic, or neutral hydrophilic amino acid (e.g. isoleucine, valine, leucine, glutamine, asparagine, arginine, or lysine) that interacts with amino acids Asn60 or Ile61 of human PAC1. In yet another embodiment, the antibodies or antigen-binding fragments comprise a heavy chain variable region in which the amino acid at position 66 according to AHo numbering is a basic or neutral hydrophilic amino acid (e.g. glutamine, asparagine, arginine, or lysine) that interacts with amino acids Asn60 or Ile61 of human PAC1.

The anti-PAC1 antibodies and antigen-binding fragments of the invention can inhibit ligand-induced activation of the PAC1 receptor. For instance, in some embodiments, the anti-PAC1 antibodies and antigen-binding fragments inhibit PACAP-induced activation of human PAC1 with an IC50 less than 500 pM as measured by a cell-based cAMP assay. In other embodiments, the anti-PAC1 antibodies and antigen-binding fragments inhibit PACAP-induced activation of human PAC1 with an IC50 less than 300 pM as measured by a cell-based cAMP assay. In certain embodiments, the anti-PAC1 antibodies and antigen-binding fragments inhibit PACAP-induced activation of the human PAC1 receptor with an IC50 between about 50 pM and about 500 pM as measured by a cell-based cAMP assay.

In some embodiments, the anti-PAC1 antibodies and antigen binding fragments of the invention cross-react with PAC1 receptors from other species. In one embodiment, the anti-PAC1 antibodies or antigen-binding fragments specifically bind to and inhibit PACAP-induced activation of the cynomolgus monkey PAC1 receptor. In such an embodiment, the anti-PAC1 antibodies or antigen-binding fragments may inhibit PACAP-induced activation of the cynomolgus monkey PAC1 receptor with an IC50 between about 0.1 nM and about 1 nM or between about 50 pM and about 500 pM as measured by a cell-based cAMP assay. In another embodiment, the anti-PAC1 antibodies or antigen-binding fragments specifically bind to and inhibit PACAP-induced activation of the rat PAC1 receptor. The anti-PAC1 antibodies or antigen-binding fragments may inhibit PACAP-induced activation of the rat PAC1 receptor with an IC50 less than 10 nM, for example with an IC50 between about 0.1 nM and about 10 nM or between about 100 pM and about 2 nM as measured by a cell-based cAMP assay.

In certain embodiments, the anti-PAC1 antibodies or antigen-binding fragments of the invention comprise a light chain variable region comprising complementarity determining regions CDRL1, CDRL2, and CDRL3 and a heavy chain variable region comprising complementarity determining regions CDRH1, CDRH2, and CDRH3. The light chain and heavy chain variable regions or CDRs may be from any of the anti-PAC1 antibodies described herein. For instance, in some embodiments, the anti-PAC1 antibodies or antigen-binding fragments comprise a CDRL1 comprising a sequence selected from SEQ ID NOs: 5-16; a CDRL2 comprising the sequence of SEQ ID NO: 26; a CDRL3 comprising a sequence selected from SEQ ID NOs: 36-38; a CDRH1 comprising a sequence selected from SEQ ID NOs: 88-96; a CDRH2 comprising a sequence selected from SEQ ID NOs: 106-166; and a CDRH3 comprising a sequence selected from SEQ ID NOs: 171-177. In other embodiments, the anti-PAC1 antibodies or antigen-binding fragments comprise a CDRL1 comprising a sequence selected from SEQ ID NOs: 17-25; a CDRL2 comprising a sequence selected from SEQ ID NOs: 27-35; a CDRL3 comprising a sequence selected from SEQ ID NOs: 39-51; a CDRH1 comprising a sequence selected from SEQ ID NOs: 97-105; a CDRH2 comprising a sequence selected from SEQ ID NOs: 167-170; and a CDRH3 comprising a sequence selected from SEQ ID NOs: 178-190.

In some embodiments, the anti-PAC1 antibodies or antigen-binding fragments of the invention comprise a light chain variable region that comprises a sequence that is at least 90% identical or at least 95% identical to a sequence selected from SEQ ID NOs: 54-66 and SEQ ID NOs: 68-87. In these and other embodiments, the anti-PAC1 antibodies or antigen-binding fragments of the invention comprise a heavy chain variable region that comprises a sequence that is at least 90% identical or at least 95% identical to a sequence selected from SEQ ID NOs: 191-312. In one embodiment, the anti-PAC1 antibodies or antigen-binding fragments comprise a light chain variable region comprising a sequence selected from SEQ ID NOs: 54-66 and a heavy chain variable region comprising a sequence selected from SEQ ID NOs: 191-295. In another embodiment, the anti-PAC1 antibodies or antigen-binding fragments comprise a light chain variable region comprising a sequence selected from SEQ ID NOs: 68-87 and a heavy chain variable region comprising a sequence selected from SEQ ID NOs: 296-312.

In any of the embodiments described herein, including the embodiments described above, the anti-PAC1 antibody or antigen-binding fragment of the invention is a monoclonal antibody or antigen-binding fragment thereof. In some embodiments, the monoclonal antibody or antigen-binding fragment thereof is a chimeric antibody or antigen-binding fragment thereof. In other embodiments, the monoclonal antibody or antigen-binding fragment thereof is a humanized antibody or antigen-binding fragment thereof. In yet other embodiments, the monoclonal antibody or antigen-binding fragment thereof is a fully human antibody or antigen-binding fragment thereof. The monoclonal antibody can be of any isotype, such as a human IgG1, IgG2, IgG3, or IgG4. In one particular embodiment, the monoclonal antibody is a human IgG1 antibody. In another particular embodiment, the monoclonal antibody is a human IgG2 antibody. The monoclonal antibody may comprise a light chain that comprises a human kappa constant region. In some embodiments, the human kappa constant region comprises the sequence of SEQ ID NO: 318 or SEQ ID NO: 319. Thus, the anti-PAC1 antibodies or antigen-binding fragments of the invention may comprise a light chain that comprises any of the light chain variable region sequences listed in Table 1A fused to a human kappa constant region comprising the sequence of SEQ ID NO: 318 or SEQ ID NO: 319. In other embodiments, the monoclonal antibody may comprise a light chain that comprises a human lambda constant region. In certain embodiments, the human lambda constant region comprises the sequence of SEQ ID NO: 315. Thus, in some embodiments, the anti-PAC1 antibodies or antigen-binding fragments of the invention may comprise a light chain that comprises any of the light chain variable region sequences listed in Table 1A fused to a human lambda constant region comprising the sequence of SEQ ID NO: 315.

In certain embodiments, the anti-PAC1 antibodies or antigen-binding fragments of the invention may contain one or more modifications that affect the glycosylation of the antibody or antigen-binding fragment. In some embodiments, the antibody or antigen-binding fragment comprises one or more mutations to reduce or eliminate glycosylation. In such embodiments, the aglycosylated antibody may comprise a mutation at amino acid position N297 (according to the EU numbering scheme), such as a N297G mutation, in its heavy chain. The aglycosylated antibody may comprise further mutations to stabilize the antibody structure. Such mutations can include pairs of cysteine substitutions, such as A287C and L306C, V259C and L306C, R292C and V302C, and V323C and I332C (amino acid positions according to the EU numbering scheme). In one embodiment, the aglycosylated antibody comprises R292C and V302C mutations (according to the EU numbering scheme) in its heavy chain. In certain embodiments, the aglycosylated anti-PAC1 antibody comprises a heavy chain constant region comprising the amino acid sequence of SEQ ID NO: 324 or SEQ ID NO: 325.

The present invention also includes isolated polynucleotides and expression vectors encoding the anti-PAC1 antibodies and antigen-binding fragments described herein as well as host cells, such as CHO cells, comprising the encoding polynucleotides and expression vectors. In certain embodiments, the present invention includes methods for producing the anti-PAC1 antibodies and antigen-binding fragments described herein. In one embodiment, the method comprises culturing a host cell comprising an expression vector encoding the anti-PAC1 antibody or antigen-binding fragment under conditions that allow expression of the antibody or antigen-binding fragment, and recovering the antibody or antigen-binding fragment from the culture medium or host cell.

The anti-PAC1 antibodies or antigen-binding fragments described herein can be used in the manufacture of a pharmaceutical composition or medicament for the treatment or prevention of conditions associated with PAC1 biological activity, such as headache, migraine, cluster headache, and vasomotor symptoms. Thus, the present invention also provides a pharmaceutical composition comprising an anti-PAC1 antibody or antigen-binding fragment described herein and a pharmaceutically acceptable excipient. The pharmaceutical compositions can be used in any of the methods described herein.

In certain embodiments, the present invention provides methods for treating or preventing a headache condition in a patient in need thereof comprising administering to the patient an effective amount of an anti-PAC1 antibody or antigen-binding fragment described herein. In some embodiments, the headache condition to be treated or prevented with the methods of the invention is migraine. The migraine can be episodic migraine or chronic migraine. In other embodiments, the headache condition to be treated or prevented with the methods of the invention is cluster headache. In certain embodiments, the methods provide prophylactic treatment for these conditions.

In some embodiments of the methods of the invention, the methods comprise administering a second headache therapeutic agent to the patient in combination with an anti-PAC1 antibody or antigen-binding fragment of the invention. The second headache therapeutic agent can be an acute headache therapeutic agent, such as a serotonin receptor agonist (e.g. agonist of a $5HT_{1B}$, $5HT_{1D}$, and/or $5HT_{1F}$ serotonin receptor). In some embodiments, the acute headache therapeutic agent is a triptan, ergotamine, non-steroidal anti-inflammatory drug, or an opioid. In other embodiments, the second headache therapeutic agent to be administered in combination with an anti-PAC1 antibody or antigen-binding fragment of the invention is a prophylactic headache therapeutic agent, such as an antiepileptic, a beta-blocker, an antidepressant, or onabotulinum toxin A. The second headache therapeutic agent may be administered to the patient before, after, or concurrently with an anti-PAC1 antibody or antigen-binding fragment of the invention.

In certain embodiments of the methods of the invention, the methods comprise administering a CGRP pathway antagonist to the patient in combination with an anti-PAC1 antibody or antigen-binding fragment of the invention. The CGRP pathway antagonist can be an antagonist of the human CGRP receptor, such as an antibody that specifically binds to the human CGRP receptor. In one embodiment, the CGRP pathway antagonist administered in combination with an anti-PAC1 antibody or antigen-binding fragment of the invention is erenumab. In other embodiments, the CGRP pathway antagonist can be an antagonist of the CGRP ligand, such as an antibody that specifically binds to human α-CGRP and/or I3-CGRP. In one such embodiment, the CGRP pathway antagonist administered in combination with an anti-PAC1 antibody or antigen-binding fragment of the invention is fremanezumab. In another such embodiment, the CGRP pathway antagonist administered in combination with an anti-PAC1 antibody or antigen-binding fragment of the invention is galcanezumab. In yet another such embodiment, the CGRP pathway antagonist administered in combination with an anti-PAC1 antibody or antigen-binding fragment of the invention is eptinezumab.

The present invention also includes methods of inhibiting vasodilation in a patient in need thereof. In one embodiment, the method comprises administering to the patient an effective amount of any of the anti-PAC1 antibodies or antigen-binding fragments described herein. In some embodiments, the patient in need of treatment has a headache condition, such as migraine or cluster headache. In other embodiments, the patient in need of treatment has vasomotor symptoms (e.g. hot flashes, facial flushing, sweating, and night sweats), such as those associated with menopause.

The use of the anti-PAC1 antibodies or antigen-binding fragments in any of the methods disclosed herein or for preparation of medicaments for administration according to any of the methods disclosed herein is specifically contemplated. For instance, the present invention includes an anti-PAC1 antibody or antigen-binding fragment for use in a method for treating or preventing a headache condition in a patient in need thereof. The headache condition includes migraine (e.g. episodic and chronic migraine) and cluster headache. In some embodiments, the present invention provides an anti-PAC1 antibody or antigen-binding fragment for use in a method for inhibiting vasodilation in a patient in need thereof. In such embodiments, the patient may be diagnosed with or have a headache condition. In other embodiments, the present invention provides an anti-PAC1 antibody or antigen-binding fragment for use in a method for inhibiting activation of human PAC1 receptor in a patient having a headache condition. The headache condition may be migraine (e.g. episodic or chronic migraine) or cluster headache.

The present invention also includes the use of an anti-PAC1 antibody or antigen-binding fragment in the preparation of a medicament for treating or preventing a headache condition in a patient in need thereof. The headache condition includes migraine (e.g. episodic and chronic migraine) and cluster headache. In certain embodiments, the present invention encompasses the use of an anti-PAC1 antibody or antigen-binding fragment in the preparation of a medicament for inhibiting vasodilation in a patient in need thereof. In such embodiments, the patient may be diagnosed with or have a headache condition. In other embodiments, the present invention includes the use of an anti-PAC1 antibody or antigen-binding fragment in the preparation of a medicament for inhibiting activation of human PAC1 receptor in a patient having a headache condition. The headache condition may be migraine (e.g. episodic or chronic migraine) or cluster headache.

BRIEF DESCRIPTION OF THE DRAWINGS

FIG. 10A shows the % change from baseline in dermal blood flow induced by intradermal injection of maxadilan at the indicated days following antibody treatment. *$p<0.05$, $p<0.01$, *$p<0.001$ compared to Day 0 within the same treatment group by one-way ANOVA followed by Bonferroni's Multiple Comparison Test. Eight animals per group except for Day 36 in which four animals were tested with antibody 420653 at 3 mg/kg as denoted by the A symbol. FIG. 10B shows the inhibitory effect of antibody treatment on maxadilan-induced increase in dermal blood flow expressed as % inhibition. #$p<0.05$, ##$p<0.01$, ###$p<0.001$ comparison between antibody 420653 at 3 mg/kg and antibody 29G4v22 at 10 mg/kg at each time point by two-tailed Unpaired t-test.

DETAILED DESCRIPTION

Figure 1A:
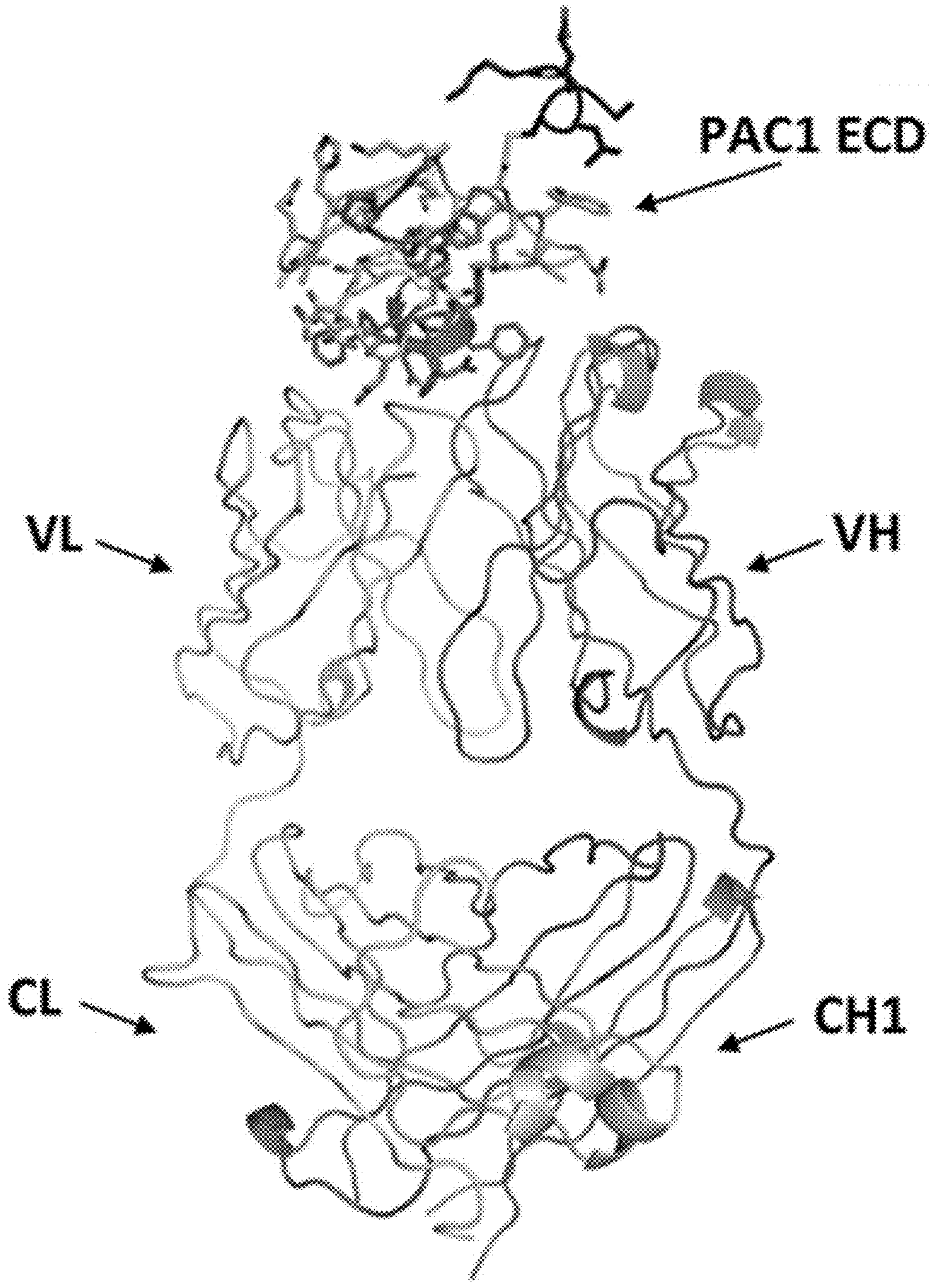
FIG. 1A is a front view of the crystal structure of the complex between human PAC1 extracellular domain (ECD) and the Fab fragment of the 29G4v9 antibody. VL=light chain variable region; CL=light chain constant region; VH=heavy chain variable region; and CH1=heavy chain CH1 constant region.

The present invention relates to isolated antibodies and antigen-binding fragments thereof that specifically bind to pituitary adenylate cyclase-activating polypeptide type I receptor (PAC1), particularly human PAC1. The antibodies of the invention have enhanced inhibitory potency against human PAC1 as compared to previously described anti-PAC1 antagonist antibodies. The antibodies of the invention also cross-react with the rat PAC1 receptor and the cynomolgus monkey PAC1 receptor, thereby allowing for preclinical in vivo evaluation of the antibodies in these species.

Human PAC1 is a 468 amino acid protein (NCBI Reference Sequence NP 001109.2) encoded by the ADCYAP IRI gene on chromosome 7. The human PAC1 receptor is a G protein-coupled receptor that is positively coupled to adenylate cyclase. Activation of the human PAC1 receptor by its endogenous ligands (e.g. PACAP38 or PACAP27) results in an increase in intracellular cyclic AMP (cAMP). The amino acid sequence for human PAC1 is provided below as SEQ ID NO: 1.

Amino acids 1 to 23 of the human PAC1 protein (SEQ ID NO: 1) constitute a signal peptide, which is generally removed from the mature protein. The mature human PAC1 protein has the basic structure of a G protein-coupled receptor consisting of a seven-transmembrane domain, an extracellular domain composed of an N-terminal region and three extracellular loops, three intracellular loops, and a C-terminal cytoplasmic domain. The N-terminal extracellular domain is approximately at amino acids 24-153 of SEQ ID NO: 1, and the first of seven transmembrane domains begins at amino acid 154 of SEQ ID NO: 1. The C-terminal cytoplasmic domain is located approximately at amino acids 397-468 of SEQ ID NO: 1. See Blechman and Levkowitz, Front. Endocrinol., Vol. 4 (55): 1-19, 2013 for location of domains within the amino acid sequence. The terms "human PAC1," "human PAC1 receptor," "hPAC1," and "hPAC1 receptor" are used interchangeably and can refer to a polypeptide of SEQ ID NO: 1, a polypeptide of SEQ ID NO: 1 minus the signal peptide (amino acids 1 to 23), allelic variants of human PAC1, or splice variants of human PAC1.

The present invention provides antibodies that specifically bind to human PAC1. An "antibody" is a protein that comprises an antigen-binding fragment that specifically binds to an antigen, and a scaffold or framework portion that allows the antigen-binding fragment to adopt a conformation that promotes binding of the antibody to the antigen. As used herein, the term "antibody" generally refers to a tetrameric immunoglobulin protein comprising two light chain polypeptides (about 25 kDa each) and two heavy chain polypeptides (about 50-70 kDa each).

The term "light chain" or "immunoglobulin light chain" refers to a polypeptide comprising, from amino terminus to carboxyl terminus, a single immunoglobulin light chain variable region (VL) and a single immunoglobulin light chain constant domain (CL). The immunoglobulin light chain constant domain (CL) can be a human kappa (κ) or human lambda (λ) constant domain. The term "heavy chain" or "immunoglobulin heavy chain" refers to a polypeptide comprising, from amino terminus to carboxyl terminus, a single immunoglobulin heavy chain variable region (VH), an immunoglobulin heavy chain constant domain 1 (CH1), an immunoglobulin hinge region, an immunoglobulin heavy chain constant domain 2 (CH2), an immunoglobulin heavy chain constant domain 3 (CH3), and optionally an immunoglobulin heavy chain constant domain 4 (CH4). Heavy chains are classified as mu (μ), delta (Δ), gamma (γ), alpha (α), and epsilon (ε), and define the antibody's isotype as IgM, IgD, IgG, IgA, and IgE, respectively. The IgG-class and IgA-class antibodies are further divided into subclasses, namely, IgG1, IgG2, IgG3, and IgG4, and IgA1 and IgA2, respectively. The heavy chains in IgG, IgA, and IgD anti-

```
1    MAGVVHVSLA ALLLLPMAPA MHSDCIFKKE QAMCLEKIQR ANELMGFNDS SPGCPGMWDN

61   ITCWKPAHVG EMVLVSCPEL FRIFNPDQVW ETETIGESDF GDSNSLDLSD MGVVSRNCTE

121  DGWSEPFPHY FDACGFDEYE SETGDQDYYY LSVKALYTVG YSTSLVTLTT AMVILCRFRK

181  LHCTRNFIHM NLFVSFMLRA ISVFIKDWIL YAEQDSNHCF ISTVECKAVM VFFHYCVVSN

241  YFWLFIEGLY LFTLLVETFF PERRYFYWYT IIGWGTPTVC VTVWATLRLY FDDTGCWDMN

301  DSTALWWVIK GPVVGSIMVN FVLFIGIIVI LVQKLQSPDM GGNESSIYLR LARSTLLLIP

361  LFGIHYTVFA FSPENVSKRE RLVFELGLGS FQGFVVAVLY CFLNGEVQAE IKRKWRSWKV

421  NRYFAVDFKH RHPSLASSGV NGGTQLSILS KSSSQIRMSG LPADNLAT
```

bodies have three constant domains (CH1, CH2, and CH3), whereas the heavy chains in IgM and IgE antibodies have four constant domains (CH1, CH2, CH3, and CH4). The immunoglobulin heavy chain constant domains can be from any immunoglobulin isotype, including subtypes. The antibody chains are linked together via inter-polypeptide disulfide bonds between the CL domain and the CH1 domain (i.e. between the light and heavy chain) and between the hinge regions of the two antibody heavy chains.

The present invention also includes antigen-binding fragments of the anti-PAC1 antibodies described herein. An "antigen-binding fragment," used interchangeably herein with "binding fragment" or "fragment," is a portion of an antibody that lacks at least some of the amino acids present in a full-length heavy chain and/or light chain, but which is still capable of specifically binding to an antigen. An antigen-binding fragment includes, but is not limited to, a single-chain variable fragment (scFv), a nanobody (e.g. VH domain of camelid heavy chain antibodies; VHH fragment, see Cortez-Retamozo et al., Cancer Research, Vol. 640: 2853-57, 2004), a Fab fragment, a Fab' fragment, a F(ab')2 fragment, a Fv fragment, a Fd fragment, and a complementarity determining region (CDR) fragment, and can be derived from any mammalian source, such as human, mouse, rat, rabbit, or camelid. Antigen-binding fragments may compete for binding of a target antigen with an intact antibody and the fragments may be produced by the modification of intact antibodies (e.g. enzymatic or chemical cleavage) or synthesized de novo using recombinant DNA technologies or peptide synthesis. In some embodiments, the antigen-binding fragment comprises at least one CDR from an antibody that binds to the antigen, for example, the heavy chain CDR3 from an antibody that binds to the antigen. In other embodiments, the antigen-binding fragment comprises all three CDRs from the heavy chain of an antibody that binds to the antigen or all three CDRs from the light chain of an antibody that binds to the antigen. In still other embodiments, the antigen-binding fragment comprises all six CDRs from an antibody that binds to the antigen (three from the heavy chain and three from the light chain).

The term "isolated molecule" (where the molecule is, for example, a polypeptide, a polynucleotide, an antibody, or antigen-binding fragment) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

In certain embodiments of the invention, the antibodies or antigen-binding fragments thereof specifically bind to human PAC1. An antibody or antigen-binding fragment thereof "specifically binds" to a target antigen when it has a significantly higher binding affinity for, and consequently is capable of distinguishing, that antigen compared to its affinity for other unrelated proteins, under similar binding assay conditions. Antibodies or antigen-binding fragments that specifically bind an antigen may have an equilibrium dissociation constant ($K_D$)$\leq 1\times10^{-6}$ M. The antibody or binding fragment specifically binds antigen with "high affinity" when the $K_D$ is $\leq 1\times10^{-8}$ M. In one embodiment, the antibodies or binding fragments of the invention bind to human PAC1 with a $K_D$ of $\leq 5\times10^{-9}$ M. In another embodiment, the antibodies or binding fragments of the invention bind to human PAC1 with a $K_D$ of $\leq 1\times10^{-9}$ M. In yet another embodiment, the antibodies or binding fragments of the invention bind to human PAC1 with a $K_D$ of $\leq$5×10 40 M. In another embodiment, the antibodies or binding fragments of the invention bind to human PAC1 with a $K_D$ of $\leq 1\times10^{-10}$ M. In certain embodiments, the antibodies or binding fragments of the invention bind to human PAC1 with a $K_D$ of $\leq 5\times10^{-11}$ M. In other embodiments, the antibodies or binding fragments of the invention bind to human PAC1 with a $K_D$ of $\leq 1\times10^{-11}$ M. In one particular embodiment, the antibodies or binding fragments of the invention bind to human PAC1 with a $K_D$ of $\leq 5\times10^{-12}$ M. In another particular embodiment, the antibodies or binding fragments of the invention bind to human PAC1 with a $K_D$ of $\leq 1\times10^{-12}$ M.

Affinity is determined using a variety of techniques, an example of which is an affinity ELISA assay. In various embodiments, affinity is determined by a surface plasmon resonance assay (e.g., BIAcore®-based assay). Using this methodology, the association rate constant ($k_a$ in $M^{-1}$ $s^{-1}$) and the dissociation rate constant ($k_d$ ins 1) can be measured. The equilibrium dissociation constant ($K_D$ in M) can then be calculated from the ratio of the kinetic rate constants ($k_d/k_a$). In some embodiments, affinity is determined by a kinetic method, such as a Kinetic Exclusion Assay (KinExA) as described in Rathanaswami et al. Analytical Biochemistry, Vol. 373:52-60, 2008. Using a KinExA assay, the equilibrium dissociation constant ($K_D$ in M) and the association rate constant ($k_a$ in $M^{-1}$ $s^{-1}$) can be measured. The dissociation rate constant ($k_d$ in $s^{-1}$) can be calculated from these values ($K_D\times k_a$). In other embodiments, affinity is determined by a bio-layer interferometry method, such as that described in Kumaraswamy et al., Methods Mol. Biol., Vol. 1278:165-82, 2015 and employed in Octet® systems (Pall ForteBio). The kinetic ($k_a$ and $k_d$) and affinity ($K_D$) constants can be calculated in real-time using the bio-layer interferometry method. In some embodiments, the antibodies or binding fragments described herein exhibit desirable characteristics such as binding avidity as measured by $k_d$ (dissociation rate constant) for human PAC1 of about $10^{-2}$, $10^{-3}$, $10^{-4}$, $10^{-5}$, $10^{-6}$, $10^{-7}$, $10^{-8}$, $10^{-9}$, $10^{-10}$ $s^{-1}$ or lower (lower values indicating higher binding avidity), and/or binding affinity as measured by $K_D$ (equilibrium dissociation constant) for human PAC1 of about $10^{-8}$, $10^{-9}$, $10^{-10}$, $10^{-11}$, $10^{-12}$ or lower (lower values indicating higher binding affinity).

Preferably, the antibodies or binding fragments of the invention do not significantly bind to or cross-react with other members of the secretin/glucagon receptor family, such as human VPAC1 receptor (NCBI Reference Sequence NP_004615.2) and human VPAC2 receptor (NCBI Reference Sequence NP_003373.2). As used herein, an antibody or binding fragment does "not significantly bind" to a target antigen when it has a binding affinity for that antigen that is comparable to its affinity for other unrelated proteins, under similar binding assay conditions. Antibodies or binding fragments that do not significantly bind to a target antigen may also include those proteins that do not generate a statistically different signal than a negative control in an affinity assay, such as those described herein, for the target antigen. By way of example, an antibody, which produces a signal value in an ELISA- or a BIAcore®-based assay for determining binding to human VPAC1 that is not statistically different from the signal value produced with a negative control (e.g. buffer solution without antibody), would be considered to not significantly bind to human VPAC1. Antibodies or binding fragments that do not significantly bind an antigen may have an equilibrium dissociation constant ($K_D$) for that antigen greater than $1\times10^{-6}$ M, greater than $1\times10^{-5}$ M, greater than $1\times10^{-4}$ M, or greater than $1\times10^{-3}$ M. Thus, in certain embodiments, the antibodies and binding fragments of the invention selectively bind to human PAC1 relative to human VPAC1 and human VPAC2. In other words, the antibodies and binding fragments of the invention do not significantly bind to human VPAC1 or human VPAC2.

The antibodies and antigen-binding fragments of the invention may inhibit, interfere with, or modulate one or more biological activities of the human PAC1 receptor. Biological activities of the human PAC1 receptor include, but are not limited to, induction of PACAP-mediated receptor signal transduction pathways, induction of vasodilation, and inhibition of vasoconstriction. In some embodiments, the antibodies or binding fragments of the invention inhibit binding of PACAP (e.g. PACAP38 or PACAP27) to the human PAC1 receptor. "Inhibition of binding" occurs when an excess of antibodies or binding fragments reduces the quantity of human PAC1 receptor bound to PACAP, or vice versa, for example, by at least about 40%, about 50%, about 60%, about 70%, about 80%, about 85%, about 90%, about 95%, about 97%, about 99% or more, for example by measuring binding in an in vitro competitive binding assay. Inhibitory constants (Ki), which are indicative of how potent the antibodies or antigen-binding fragments of the invention are at preventing binding of PACAP to human PAC1 receptor, can be calculated from such competitive binding assays. By way of example, a radioactive isotope (e.g. 125I) is attached to the receptor ligand (e.g. PACAP38) and the assay measures the binding of the radiolabeled ligand to human PAC1 receptor in increasing concentrations of the anti-PAC1 antibody or binding fragment thereof. The Ki value can be calculated using the equation Ki=IC50/(1+([L]/Kd)), where [L] is the concentration of the radioligand used (e.g., $^{125}$I-labeled PACAP38) and Kd is the dissociation constant of the radioligand. See, e.g., Keen M, MacDermot J (1993) Analysis of receptors by radioligand binding. In: Wharton J, Polak J M (eds) Receptor autoradiography, principles and practice. Oxford University Press, Oxford. The lower the value of Ki for an antagonist, the more potent the antagonist is. In some embodiments, the antibodies or antigen-binding fragments thereof of the invention compete for binding to the human PAC1 receptor with a radiolabeled PACAP ligand with a Ki of ≤1 nM. In other embodiments, the antibodies or antigen-binding fragments thereof of the invention compete for binding to the human PAC1 receptor with a radiolabeled PACAP ligand with a Ki of ≤500 pM. In yet other embodiments, the antibodies or antigen-binding fragments thereof of the invention compete for binding to the human PAC1 receptor with a radiolabeled PACAP ligand with a Ki of ≤200 pM. In certain other embodiments, the antibodies or antigen-binding fragments thereof of the invention compete for binding to the human PAC1 receptor with a radiolabeled PACAP ligand with a Ki of ≤100 pM.

In certain embodiments, the antibodies and antigen-binding fragments of the invention inhibit ligand-induced activation of the human PAC1 receptor. The ligand can be an endogenous ligand of the receptor, such as PACAP38 or PACAP27, or the ligand can be another known agonist of the receptor, such as maxadilan. Maxadilan is a 65 amino acid peptide originally isolated from the sand fly that is exquisitely selective for PAC1 compared with VPAC1 or VPAC2, and can thus be used as a PAC1-selective agonist (Lerner et al., J Biol Chem., Vol. 266(17):11234-11236, 1991; Lerner et al., Peptides, Vol. 28(9): 1651-1654, 2007). Various assays for assessing activation of PAC1 receptors are known in the art and include cell-based assays measuring ligand-induced calcium mobilization and cAMP production. An exemplary cell-based cAMP assay is described in Example 3. Other suitable PAC1 receptor activation assays are described in Dickson et al., Ann. N. Y. Acad. Sci., Vol. 1070:239-42, 2006; Bourgault et al., J. Med. Chem., Vol. 52: 3308-3316, 2009; and U.S. Patent Publication No. 2011/0229423, all of which are hereby incorporated by reference in their entireties.

The inhibitory activity of the antibodies or antigen-binding fragments on PAC1 receptor activation can be quantitated by calculating an IC50 in any functional assay for the receptor, such as those described above. An "IC50" is the dose/concentration required to achieve 50% inhibition of a biological or biochemical function. With radioactive ligands, IC50 is the concentration of a competing ligand that displaces 50% of the specific binding of the radioligand. The IC50 of any particular substance or antagonist can be determined by constructing a dose-response curve and examining the effect of different concentrations of the drug or antagonist on reversing agonist activity in a particular functional assay. IC50 values can be calculated for a given antagonist or drug by determining the concentration needed to inhibit half of the maximum biological response of the agonist. Thus, the IC50 value for any anti-PAC1 antibody or binding fragment thereof of the invention can be calculated by determining the concentration of the antibody or binding fragment needed to inhibit half of the maximum biological response of the ligand (e.g. PACAP27, PACAP38, or maxadilan) in activating the human PAC1 receptor in any functional assay, such as the cAMP assay described in the Examples. An anti-PAC1 antibody or binding fragment thereof that inhibits ligand-induced (e.g. PACAP-induced) activation of the PAC1 receptor is understood to be a neutralizing or antagonist antibody or binding fragment of the PAC1 receptor.

In certain embodiments, the antibodies or antigen-binding fragments of the invention inhibit PACAP-induced (PACAP38- or PACAP27-induced) activation of the human PAC1 receptor. For instance, the antibodies or antigen-binding fragments may inhibit PACAP-induced activation of the human PAC1 receptor with an IC50 less than about 10 nM, less than about 8 nM, less than about 5 nM, less than about 3 nM, less than about 1 nM, less than about 800 pM, less than about 500 pM, less than about 400 pM, less than about 300 pM, less than about 200 pM, or less than about 100 pM as measured by a cell-based calcium mobilization assay or cAMP assay. In one particular embodiment, the antibodies or antigen-binding fragments of the invention inhibit PACAP-induced activation of the human PAC1 receptor with an IC50 less than about 5 nM as measured by a cell-based cAMP assay. In another particular embodiment, the antibodies or antigen-binding fragments of the invention inhibit PACAP-induced activation of the human PAC1 receptor with an IC50 less than about 1 nM as measured by a cell-based cAMP assay. In still another particular embodiment, the antibodies or antigen-binding fragments of the invention inhibit PACAP-induced activation of the human PAC1 receptor with an IC50 less than about 500 pM as measured by a cell-based cAMP assay. In another embodiment, the antibodies or antigen-binding fragments of the invention inhibit PACAP-induced activation of the human PAC1 receptor with an IC50 less than about 300 pM as measured by a cell-based cAMP assay. In some embodiments, the antibodies or antigen-binding fragments of the invention inhibit PACAP-induced activation of the human PAC1 receptor with an IC50 between about 0.1 nM and about 1 nM as measured by a cell-based cAMP assay. In other embodiments, the antibodies or antigen-binding fragments of the invention inhibit PACAP-induced activation of the human PAC1 receptor with an IC50 between about 50 pM and about 500 pM as measured by a cell-based cAMP assay.

In some embodiments, the antibodies or antigen-binding fragments of the invention bind to and inhibit PAC1 receptors from other species. For instance, the antibodies or antigen-binding fragments bind to and inhibit the cynomolgus monkey PAC1 receptor (NCBI Reference Sequence XP 015303041.1). In such embodiments, the antibodies or antigen-binding fragments inhibit PACAP-induced activation of the cynomolgus monkey PAC1 receptor with an IC50 less than about 10 nM, less than about 8 nM, less than about 5 nM, less than about 3 nM, less than about 1 nM, less than about 800 pM, less than about 500 pM, less than about 400 pM, less than about 300 pM, less than about 200 pM, or less than about 100 pM as measured by a cell-based calcium mobilization assay or cAMP assay. In one embodiment, the antibodies or antigen-binding fragments of the invention inhibit PACAP-induced activation of the cynomolgus monkey PAC1 receptor with an IC50 less than about 1 nM as measured by a cell-based cAMP assay. In another embodiment, the antibodies or antigen-binding fragments of the invention inhibit PACAP-induced activation of the cynomolgus monkey PAC1 receptor with an IC50 less than about 500 pM as measured by a cell-based cAMP assay. In yet another embodiment, the antibodies or antigen-binding fragments of the invention inhibit PACAP-induced activation of the cynomolgus monkey PAC1 receptor with an IC50 between about 0.1 nM and about 1 nM as measured by a cell-based cAMP assay. In still another embodiment, the antibodies or antigen-binding fragments of the invention inhibit PACAP-induced activation of the cynomolgus monkey PAC1 receptor with an IC50 between about 50 pM and about 500 pM as measured by a cell-based cAMP assay.

In certain embodiments, the antibodies or antigen-binding fragments bind to and inhibit the rat PAC1 receptor (NCBI Reference Sequence NP_598195.1). In these embodiments, the antibodies or antigen-binding fragments may inhibit PACAP-induced activation of the rat PAC1 receptor with an IC50 less than about 10 nM, less than about 8 nM, less than about 5 nM, less than about 3 nM, less than about 1 nM, less than about 800 pM, less than about 500 pM, less than about 400 pM, less than about 300 pM, less than about 200 pM, or less than about 100 pM as measured by a cell-based calcium mobilization assay or cAMP assay. In one embodiment, the antibodies or antigen-binding fragments of the invention inhibit PACAP-induced activation of the rat PAC1 receptor with an IC50 less than about 10 nM as measured by a cell-based cAMP assay. In another embodiment, the antibodies or antigen-binding fragments of the invention inhibit PACAP-induced activation of the rat PAC1 receptor with an IC50 less than about 5 nM as measured by a cell-based cAMP assay. In yet another embodiment, the antibodies or antigen-binding fragments of the invention inhibit PACAP-induced activation of the rat PAC1 receptor with an IC50 less than about 500 pM as measured by a cell-based cAMP assay. In still another embodiment, the antibodies or antigen-binding fragments of the invention inhibit PACAP-induced activation of the rat PAC1 receptor with an IC50 less than about 300 pM as measured by a cell-based cAMP assay. In some embodiments, the antibodies or antigen-binding fragments of the invention inhibit PACAP-induced activation of the rat PAC1 receptor with an IC50 between about 0.1 nM and about 10 nM as measured by a cell-based cAMP assay. In still another embodiment, the antibodies or antigen-binding fragments of the invention inhibit PACAP-induced activation of the rat PAC1 receptor with an IC50 between about 100 pM and about 2 nM as measured by a cell-based cAMP assay. In some embodiments in which the antibodies or binding fragments of the invention cross-react with PAC1 receptors from other species, the antibodies or binding fragments may inhibit PACAP-induced activation of the PAC1 receptor with comparable potencies. For example, an antibody or binding fragment of the invention may inhibit PACAP-induced activation of the human PAC1 receptor with an IC50 similar to the IC50 for the antibody or binding fragment to inhibit PACAP-induced activation of the cynomolgus monkey or rat PAC1 receptor. Cross-reactivity to PAC1 receptors of other species of the antibodies or binding fragments of the invention can be advantageous as the antibodies or binding fragments can be evaluated in additional pre-clinical animal models for therapeutic efficacy.

Generally, the antibodies or antigen-binding fragments of the invention do not significantly inhibit ligand-induced activation (e.g. PACAP38-, PACAP27-, or VIP-induced) of the human VPAC1 receptor or VPAC2 receptor. As used herein, an antibody or antigen-binding fragment would "not significantly inhibit" the activation of a receptor or binding of a ligand to its receptor if there is no statistical difference between ligand-induced receptor activation or ligand binding to the receptor in the presence or absence of the antibody or antigen-binding fragment. For example, if the amount of cAMP production induced by PACAP or VIP in cells expressing human VPAC1 receptor in the presence of an antibody or binding fragment is not statistically different than the amount produced in the absence of the antibody or binding fragment, then the antibody or binding fragment would be considered to not significantly inhibit PACAP/VIP-induced activation of the human VPAC1 receptor. Similarly, if the amount of PACAP or VIP bound to the human VPAC1 receptor in the presence of excess antibody or binding fragment is not statistically different than the amount of PACAP or VIP bound to the receptor in the absence of the antibody or binding fragment, then the antibody or binding fragment would be considered to not significantly inhibit the binding of PACAP or VIP to the human VPAC1 receptor. In certain embodiments, the antibodies or binding fragments of the invention inhibit PACAP-induced activation of the human PAC1 receptor, but do not significantly inhibit PACAP-induced activation of the human VPAC1 receptor or the human VPAC2 receptor. Thus, the antibodies and binding fragments of the invention selectively inhibit the human PAC1 receptor relative to the human VPAC1 receptor and the human VPAC2 receptor.

The antibodies and binding fragments of the invention may, in some embodiments, bind to a particular region or epitope of human PAC1. As used herein, an "epitope" refers to any determinant capable of being specifically bound by an antibody or fragment thereof. An epitope is a region of an antigen that is bound by, or interacts with, an antibody or binding fragment that targets that antigen, and when the antigen is a protein, includes specific amino acids that directly contact, or interact with, the antibody or binding fragment. An epitope can be formed both by contiguous amino acids or non-contiguous amino acids juxtaposed by tertiary folding of a protein. A "linear epitope" is an epitope where an amino acid primary sequence comprises the recognized epitope. A linear epitope typically includes at least 3 or 4 amino acids, and more usually, at least 5, at least 6, or at least 7 amino acids, for example, about 8 to about 10 amino acids in a unique sequence. A "conformational epitope," in contrast to a linear epitope, is a group of discontinuous amino acids (e.g., in a polypeptide, amino acid residues that are not contiguous in the polypeptide's primary sequence but that, in the context of the polypeptide's tertiary and quaternary structure, are near enough to each other to be bound by an antibody or binding fragment thereof). Epitope determinants can include chemically active surface groupings of molecules such as amino acids, sugar side chains, phosphoryl or sulfonyl groups, and can have specific three-dimensional structural characteristics, and/or specific charge characteristics. Generally, antibodies or binding fragments specific for a particular target molecule will preferentially recognize an epitope on the target molecule in a complex mixture of proteins and/or macromolecules.

In certain embodiments, the antibodies or antigen-binding fragments of the invention bind to human PAC1 at an epitope within the N-terminal extracellular domain (ECD) of human PAC1 (SEQ ID NO: 4). In related embodiments, the antibodies or antigen-binding fragments bind to human PAC1 at an epitope within amino acids 24-153 of SEQ ID NO: 1. In other related embodiments, the antibodies or antigen-binding fragments bind to human PAC1 at an epitope within amino acids 50-140 of SEQ ID NO: 1. As described in Example 1, a crystal structure of the complex of the human PAC1 N-terminal ECD and the Fab region of an anti-PAC1 neutralizing antibody revealed key amino acids within the human PAC1 ECD that comprised the binding interface with the anti-PAC1 Fab. These core interface amino acids, all of which contained at least one non-hydrogen atom at a distance of 5 Å or less from a non-hydrogen atom in the Fab, include Asp59, Asn60, Ile61, Arg116, Asn117, Thr119, Asp121, Gly122, Trp123, Ser124, Glu125, Pro126, Phe127, Pro128, His129, Tyr130, Phe131, Asp132, and Gly135 (amino acid position numbers relative to SEQ ID NO: 1). Thus, in some embodiments, the antibodies or binding fragments of the invention bind to human PAC1 at an epitope comprising one or more amino acids selected from Asp59, Asn60, Ile61, Arg116, Asn117, Thr119, Glu120, Asp121, Gly122, Trp123, Ser124, Glu125, Pro126, Phe127, Pro128, His129, Tyr130, Phe131, Asp132, and Gly135 of SEQ ID NO: 1. In other embodiments, the antibodies or binding fragments bind to human PAC1 at an epitope comprising at least amino acids Asn60, Ile61, Glu120, and Asp121 of SEQ ID NO: 1. In yet other embodiments, the antibodies or binding fragments bind to human PAC1 at an epitope comprising at least amino acids Asn60, Ile61, Glu120, Asp121, Phe127, and Phe131 of SEQ ID NO: 1. In certain other embodiments, the antibodies or binding fragments bind to human PAC1 at an epitope comprising all of the amino acids selected from Asp59, Asn60, Ile61, Arg116, Asn117, Thr119, Glu120, Asp121, Gly122, Trp123, Ser124, Glu125, Pro126, Phe127, Pro128, His129, Tyr130, Phe131, Asp132, and Gly of SEQ ID NO: 1.

The crystal structure of the human PAC1 ECD-Fab complex described in Example 1 also revealed important residues in the CDRs of the heavy and light chains of the Fab that interacted with the amino acids in the human PAC1 ECD, thereby identifying key amino acids in the paratope of the antibody. A "paratope" is the region of an antibody that recognizes and binds to the target antigen. Paratope residues include Gln27, Gly30, Arg31, and Ser32 in the light chain variable region (SEQ ID NO: 3) and Arg31, Phe32, Tyr53, Asp54, Gly56 in the heavy chain variable region (SEQ ID NO: 2). Specific mutations of several of these residues in the paratope were designed to improve the interaction with the core interface residues (i.e. residues in the epitope) in the human PAC1 ECD resulting in enhanced binding affinity and inhibitory potency as compared to the parental antibody (see Examples 1-3). Gln27, Gly30, Arg31, and Ser32 in the light chain variable region of SEQ ID NO: 3 or SEQ ID NO: 52 correspond to amino acids positions 29, 32, 39, and 40 in AHo numbering, respectively, and Arg31, Phe32, Tyr53, Asp54, Gly56 in the heavy chain variable region of SEQ ID NO: 2 or SEQ ID NO: 191 correspond to amino acid positions 33, 39, 60, 61, and 66 in AHo numbering, respectively. The AHo numbering scheme is a structure-based numbering scheme, which introduces gaps in the CDR regions to minimize deviation from the average structure of the aligned domains (Honegger and Pluckthun, J. Mol. Biol. 309(3):657-670; 2001). In the AHo numbering scheme, structurally equivalent positions in different antibodies will have the same residue number.

In some embodiments, the present invention provides an antibody or antigen-binding fragment thereof that specifically binds to human PAC1 (SEQ ID NO: 1), wherein the antibody or antigen-binding fragment thereof comprises: (i) a light chain variable region in which the amino acid at position 29 according to AHo numbering is a basic amino acid that interacts with amino acids Glu120 or Asp121 of human PAC1, and (ii) a heavy chain variable region in which the amino acid at position 61 according to AHo numbering is a hydrophobic, basic, or neutral hydrophilic amino acid that interacts with amino acids Asn60 or Ile61 of human PAC1. As used herein, one amino acid is said to "interact" with another amino acid when one or more atoms in one amino acid forms non-covalent bonds with one or more atoms in the other amino acid through, for example, van der Waals, hydrophobic, or electrostatic forces. Basic amino acids include arginine, lysine, and histidine, whereas neutral hydrophilic amino acids include asparagine, glutamine, serine, and threonine. Hydrophobic amino acids include phenylalanine, tryptophan, tyrosine, alanine, isoleucine, leucine, and valine. In certain embodiments, the amino acid at position 29 according to AHo numbering in the light chain variable region is lysine or arginine. In one particular embodiment, the amino acid at position 29 according to AHo numbering in the light chain variable region is lysine. In related embodiments, the amino acid at position 61 according to AHo numbering in the heavy chain variable region is isoleucine, leucine, valine, glutamine, asparagine, arginine, or lysine. In one embodiment, the amino acid at position 61 according to AHo numbering in the heavy chain variable region is isoleucine. In another embodiment, the amino acid at position 61 according to AHo numbering in the heavy chain variable region is glutamine or asparagine. In yet another embodiment, the amino acid at position 61 according to AHo numbering in the heavy chain variable region is arginine.

In some embodiments, the amino acid at position 66 according to AHo numbering in the heavy chain variable region of the antibody or antigen-binding fragment thereof is a basic or neutral hydrophilic amino acid that interacts with amino acids Asn60 or Ile61 of human PAC1 (SEQ ID NO: 1). The amino acid at position 66 according AHo numbering in the heavy chain variable region may be glutamine, asparagine, arginine, or lysine. In one embodiment, the amino acid at position 66 according AHo numbering in the heavy chain variable region is arginine. In another embodiment, the amino acid at position 66 according AHo numbering in the heavy chain variable region is asparagine.

The paratope-epitope interactions described above were found to correlate with improvements in inhibitory potency with IC50 values in the picomolar range. See Example 3. Thus, antibodies or antigen-binding fragments thereof having the above-specified amino acids at positions 29 in the light chain variable region and positions 61 and/or 66 in the heavy chain variable region according to AHo numbering and interacting with the specified residues in the human PAC1 receptor (Glu120, Asp121, Asn60, and/or Ile61 of SEQ ID NO: 1) would be expected to have enhanced inhibitory potency, e.g. inhibit PACAP-induced activation of human PAC1 with an IC50 less than 500 pM as measured by a cell-based cAMP assay. In some embodiments, such antibodies or antigen-binding fragments may inhibit PACAP-induced activation of human PAC1 with an IC50 less than 300 pM as measured by a cell-based cAMP assay. In these and other embodiments, the antibodies or antigen-binding fragments thereof may have a light chain variable region comprising a sequence that is at least 90% identical to the sequence of SEQ ID NO: 52 and a heavy chain variable region comprising a sequence that is at least 90% identical to the sequence of SEQ ID NO: 191.

The antibodies or antigen-binding fragments of the invention may comprise one or more complementarity determining regions (CDR) from the light and heavy chain variable regions of antibodies that specifically bind to human PAC1 as described herein. The term "CDR" refers to the complementarity determining region (also termed "minimal recognition units" or "hypervariable region") within antibody variable sequences. There are three heavy chain variable region CDRs (CDRH1, CDRH2 and CDRH3) and three light chain variable region CDRs (CDRL1, CDRL2 and CDRL3). The term "CDR region" as used herein refers to a group of three CDRs that occur in a single variable region (i.e. the three light chain CDRs or the three heavy chain CDRs). The CDRs in each of the two chains typically are aligned by the framework regions (FRs) to form a structure that binds specifically with a specific epitope or domain on the target protein (e.g., human PAC1). From N-terminus to C-terminus, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, MD), or Chothia & Lesk, 1987, *J. Mol. Biol.* 196:901-917; Chothia et al., 1989, Nature 342: 878-883. Complementarity determining regions (CDRs) and framework regions (FR) of a given antibody may be identified using this system. Other numbering systems for the amino acids in immunoglobulin chains include IMGT® (the international ImMunoGeneTics information system; Lefranc et al., Dev. Comp. Immunol. 29:185-203; 2005) and AHo (Honegger and Pluckthun, J. Mol. Biol. 309(3):657-670; 2001).

In certain embodiments, the anti-PAC1 antibodies or antigen-binding fragments thereof of the invention comprise at least one light chain variable region comprising a CDRL1, CDRL2, and CDRL3, and at least one heavy chain variable region comprising a CDRH1, CDRH2, and CDRH3 from any of the anti-PAC1 antibodies described herein. Light chain and heavy chain variable regions and associated CDRs of exemplary human anti-PAC1 antibodies are set forth below in Tables 1A and 1B, respectively.

TABLE 1A

Exemplary Anti-Human PAC1 Antibody Light Chain Variable Region Amino Acid Sequences

| Ab ID. | VL Group | VL Amino Acid Sequence | CDRL1 | CDRL2 | CDRL3 |
|---|---|---|---|---|---|
| | | 29G4 variants | | | |
| 29G4v10 | LV-01 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIKR (SEQ ID NO: 52) | RASQSVGRSLH (SEQ ID NO: 5) | YASQSLS (SEQ ID NO: 26) | HQSSRLPFT (SEQ ID NO: 36) |
| 29G4v22 | LV-02 | DIQLTQSPSFLSASVGDRVTITCRASQSIGRSLHWYQQKPGKAPKLLEKYASQSLSGVPSRFSGSGSGTEFTLTISSLQPEDFATYYCHQSSRLPFTFGPGTKVDIKR (SEQ ID NO: 53) | RASQSIGRSLH (SEQ ID NO: 6) | YASQSLS (SEQ ID NO: 26) | HQSSRLPFT (SEQ ID NO: 36) |
| iPS:420649 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420653 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |

TABLE 1A-continued

Exemplary Anti-Human PAC1 Antibody Light Chain Variable Region Amino Acid Sequences

| Ab ID. | VL Group | VL Amino Acid Sequence | CDRL1 | CDRL2 | CDRL3 |
|---|---|---|---|---|---|
| iPS:420657 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420661 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420665 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420672 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420679 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420686 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420690 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420697 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420704 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420711 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |

TABLE 1A-continued

Exemplary Anti-Human PAC1 Antibody Light Chain Variable Region Amino Acid Sequences

| Ab ID. | VL Group | VL Amino Acid Sequence | CDRL1 | CDRL2 | CDRL3 |
|---|---|---|---|---|---|
| iPS:420718 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420725 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420732 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420739 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420746 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420753 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420760 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420767 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420774 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420781 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |

TABLE 1A-continued

Exemplary Anti-Human PAC1 Antibody Light Chain Variable Region Amino Acid Sequences

| Ab ID. | VL Group | VL Amino Acid Sequence | CDRL1 | CDRL2 | CDRL3 |
|---|---|---|---|---|---|
| iPS:420788 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420795 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420802 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420809 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420816 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420823 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420830 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420837 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420841 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420845 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |

TABLE 1A-continued

| Exemplary Anti-Human PAC1 Antibody Light Chain Variable Region Amino Acid Sequences | | | | | |
|---|---|---|---|---|---|
| Ab ID. | VL Group | VL Amino Acid Sequence | CDRL1 | CDRL2 | CDRL3 |
| iPS:420849 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iP:420853 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420857 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420861 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420865 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420869 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420873 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420877 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420881 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420885 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |

TABLE 1A-continued

Exemplary Anti-Human PAC1 Antibody Light Chain Variable Region Amino Acid Sequences

| Ab ID. | VL Group | VL Amino Acid Sequence | CDRL1 | CDRL2 | CDRL3 |
|---|---|---|---|---|---|
| iPS:420889 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420893 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420897 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:420901 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420908 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420915 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420922 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQ SVGRSLH (SEQ ID NO: 5) | YASQSLS (SEQ ID NO: 26) | HQSSRLPFT (SEQ ID NO: 36) |
| iPS:420929 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420936 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420943 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |

TABLE 1A-continued

| Exemplary Anti-Human PAC1 Antibody Light Chain Variable Region Amino Acid Sequences | | | | | |
|---|---|---|---|---|---|
| Ab ID. | VL Group | VL Amino Acid Sequence | CDRL1 | CDRL2 | CDRL3 |
| iPS:420950 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420957 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420964 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420971 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420978 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420985 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420992 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:420999 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421006 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421013 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |

TABLE 1A-continued

Exemplary Anti-Human PAC1 Antibody Light Chain Variable Region Amino Acid Sequences

| Ab ID. | VL Group | VL Amino Acid Sequence | CDRL1 | CDRL2 | CDRL3 |
|---|---|---|---|---|---|
| iPS:421020 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421027 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421031 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421035 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421039 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421043 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421047 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421051 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421055 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421059 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |

TABLE 1A-continued

| Exemplary Anti-Human PAC1 Antibody Light Chain Variable Region Amino Acid Sequences | | | | | |
|---|---|---|---|---|---|
| Ab ID. | VL Group | VL Amino Acid Sequence | CDRL1 | CDRL2 | CDRL3 |
| iPS:421063 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421067 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421071 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421075 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421079 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421083 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421087 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421091 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421098 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421105 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |

TABLE 1A-continued

Exemplary Anti-Human PAC1 Antibody Light Chain Variable Region Amino Acid Sequences

| Ab ID. | VL Group | VL Amino Acid Sequence | CDRL1 | CDRL2 | CDRL3 |
|---|---|---|---|---|---|
| iPS:421112 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421119 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421126 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421133 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421140 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421147 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421151 | LV-05 | EIVLTQSPATLSLSPGERATLSCRASQSVWRSLHWYQQKPGQAPRLLIKYASQSLSGIPARFSGSGSGTDFTLTISSLEPEDFAVYYCHQSSRLPFTFGPGTKVDIK (SEQ ID NO: 56) | RASQSVWRSLH (SEQ ID NO: 8) | YASQSLS (SEQ ID NO: 26) | HQSSRLPFT (SEQ ID NO: 36) |
| iPS:391478 | LV-06 | EIVLTQSPATLSLSPGERATLSCRASQSVGRNLHWYQQKPGQAPRLLIKYASQSLSGIPARFSGSGSGTDFTLTISSLEPEDFAVYYCHQSSRLPFTFGPGTKVDIK (SEQ ID NO: 57) | RASQSVGRNLH (SEQ ID NO: 9) | YASQSLS (SEQ ID NO: 26) | HQSSRLPFT (SEQ ID NO: 36) |
| iPS:421157 | LV-07 | EIVLTQSPATLSLSPGERATLSCRASQSVGRSLHWYQQKPGQAPRLLIKYASQSLSGIPARFSGSGSGTDFTLTISSLEPEDFAVYYCHQSSMLPFTFGPGTKVDIK (SEQ ID NO: 58) | RASQSVGRSLH (SEQ ID NO: 5) | YASQSLS (SEQ ID NO: 26) | HQSSMLPFT (SEQ ID NO: 37) |
| iPS:421163 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |

TABLE 1A-continued

| Exemplary Anti-Human PAC1 Antibody Light Chain Variable Region Amino Acid Sequences | | | | | |
|---|---|---|---|---|---|
| Ab ID. | VL Group | VL Amino Acid Sequence | CDRL1 | CDRL2 | CDRL3 |
| iPS:391578 | LV-04 | EIVLTQSPATLSLSPGERATLSCRA SQSVGRSLHWYQQKPGQAPRLLI KYASQSLSGIPARFSGSGSGTDFTL TISSLEPEDFAVYYCHQSSRLPFTF GPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421170 | LV-04 | EIVLTQSPATLSLSPGERATLSCRA SQSVGRSLHWYQQKPGQAPRLLI KYASQSLSGIPARFSGSGSGTDFTL TISSLEPEDFAVYYCHQSSRLPFTF GPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421176 | LV-04 | EIVLTQSPATLSLSPGERATLSCRA SQSVGRSLHWYQQKPGQAPRLLI KYASQSLSGIPARFSGSGSGTDFTL TISSLEPEDFAVYYCHQSSRLPFTF GPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421182 | LV-04 | EIVLTQSPATLSLSPGERATLSCRA SQSVGRSLHWYQQKPGQAPRLLI KYASQSLSGIPARFSGSGSGTDFTL TISSLEPEDFAVYYCHQSSRLPFTF GPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421189 | LV-08 | EIVLTQSPATLSLSPGERATLSCRA SKSVWRSLHWYQQKPGQAPRLLI KYASQSLSGIPARFSGSGSGTDFTL TISSLEPEDFAVYYCHQSSRLPFTF GPGTKVDIK (SEQ ID NO: 59) | RASKSVWRSLH (SEQ ID NO: 10) | YASQSLS (SEQ ID NO: 26) | HQSSRLPFT (SEQ ID NO: 36) |
| iPS:421195 | LV-09 | EIVLTQSPATLSLSPGERATLSCRA SKSVGRNLHWYQQKPGQAPRLLI KYASQSLSGIPARFSGSGSGTDFTL TISSLEPEDFAVYYCHQSSRLPFTF GPGTKVDIK (SEQ ID NO: 60) | RASKSVGRNLH (SEQ ID NO: 11) | YASQSLS (SEQ ID NO: 26) | HQSSRLPFT (SEQ ID NO: 36) |
| iPS:421201 | LV-10 | EIVLTQSPATLSLSPGERATLSCRA SKSVGRSLHWYQQKPGQAPRLLI KYASQSLSGIPARFSGSGSGTDFTL TISSLEPEDFAVYYCHQSSMLPFTF GPGTKVDIK (SEQ ID NO: 61) | RASKSVGRSLH (SEQ ID NO: 7) | YASQSLS (SEQ ID NO: 26) | HQSSMLPFT (SEQ ID NO: 37) |
| iPS:421207 | LV-03 | EIVLTQSPATLSLSPGERATLSCRA SKSVGRSLHWYQQKPGQAPRLLI KYASQSLSGIPARFSGSGSGTDFTL TISSLEPEDFAVYYCHQSSRLPFTF GPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421211 | LV-03 | EIVLTQSPATLSLSPGERATLSCRA SKSVGRSLHWYQQKPGQAPRLLI KYASQSLSGIPARFSGSGSGTDFTL TISSLEPEDFAVYYCHQSSRLPFTF GPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421215 | LV-03 | EIVLTQSPATLSLSPGERATLSCRA SKSVGRSLHWYQQKPGQAPRLLI KYASQSLSGIPARFSGSGSGTDFTL TISSLEPEDFAVYYCHQSSRLPFTF GPGTKVDIK (SEQ ID NO: 54) | RASKSVGRSLH (SEQ ID NO: 7) | YASQSLS (SEQ ID NO: 26) | HQSSRLPFT (SEQ ID NO: 36) |

TABLE 1A-continued

| Exemplary Anti-Human PAC1 Antibody Light Chain Variable Region Amino Acid Sequences | | | | | |
|---|---|---|---|---|---|
| Ab ID. | VL Group | VL Amino Acid Sequence | CDRL1 | CDRL2 | CDRL3 |
| iPS:421219 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421223 | LV-03 | EIVLTQSPATLSLSPGERATLSCRASKSVGRSLHWYQQKPGQAPRLLIKYASQSLSGIPARFSGSGSGTDFTLTISSLEPEDFAVYYCHQSSRLPFTFGPGTKVDIK (SEQ ID NO: 54) | RASKSVGRSLH (SEQ ID NO: 7) | YASQSLS (SEQ ID NO: 26) | HQSSRLPFT (SEQ ID NO: 36) |
| iPS:421227 | LV-05 | EIVLTQSPATLSLSPGERATLSCRASQSVWRSLHWYQQKPGQAPRLLIKYASQSLSGIPARFSGSGSGTDFTLTISSLEPEDFAVYYCHQSSRLPFTFGPGTKVDIK (SEQ ID NO: 56) | RASQSVWRSLH (SEQ ID NO: 8) | YASQSLS (SEQ ID NO: 26) | HQSSRLPFT (SEQ ID NO: 36) |
| iPS:421231 | LV-06 | EIVLTQSPATLSLSPGERATLSCRASQSVGRNLHWYQQKPGQAPRLLIKYASQSLSGIPARFSGSGSGTDFTLTISSLEPEDFAVYYCHQSSRLPFTFGPGTKVDIK (SEQ ID NO: 57) | RASQSVGRNLH (SEQ ID NO: 9) | YASQSLS (SEQ ID NO: 26) | HQSSRLPFT (SEQ ID NO: 36) |
| iPS:421235 | LV-07 | EIVLTQSPATLSLSPGERATLSCRASQSVGRSLHWYQQKPGQAPRLLIKYASQSLSGIPARFSGSGSGTDFTLTISSLEPEDFAVYYCHQSSMLPFTFGPGTKVDIK (SEQ ID NO: 58) | RASQSVGRSLH (SEQ ID NO: 5) | YASQSLS (SEQ ID NO: 26) | HQSSMLPFT (SEQ ID NO: 37) |
| iPS:421239 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421246 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421253 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421260 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421267 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |

TABLE 1A-continued

Exemplary Anti-Human PAC1 Antibody Light Chain Variable Region Amino Acid Sequences

| Ab ID. | VL Group | VL Amino Acid Sequence | CDRL1 | CDRL2 | CDRL3 |
|---|---|---|---|---|---|
| iPS:421274 | LV-05 | EIVLTQSPATLSLSPGERATLSCRA SQSVWRSLHWYQQKPGQAPRLLI KYASQSLSGIPARFSGSGSGTDFTL TISSLEPEDFAVYYCHQSSRLPFTF GPGTKVDIK (SEQ ID NO: 56) | RASQSVWRSLH (SEQ ID NO: 8) | YASQSLS (SEQ ID NO: 26) | HQSSRLPFT (SEQ ID NO: 36) |
| iPS:421278 | LV-06 | EIVLTQSPATLSLSPGERATLSCRA SQSVGRNLHWYQQKPGQAPRLLI KYASQSLSGIPARFSGSGSGTDFTL TISSLEPEDFAVYYCHQSSRLPFTF GPGTKVDIK (SEQ ID NO: 57) | RASQSVGRNLH (SEQ ID NO: 9) | YASQSLS (SEQ ID NO: 26) | HQSSRLPFT (SEQ ID NO: 36) |
| iPS:421282 | LV-07 | EIVLTQSPATLSLSPGERATLSCRA SQSVGRSLHWYQQKPGQAPRLLI KYASQSLSGIPARFSGSGSGTDFTL TISSLEPEDFAVYYCHQSSMLPFTF GPGTKVDIK (SEQ ID NO: 58) | RASQSVGRSLH (SEQ ID NO: 5) | YASQSLS (SEQ ID NO: 26) | HQSSMLPFT (SEQ ID NO: 37) |
| iPS:421286 | LV-04 | EIVLTQSPATLSLSPGERATLSCRA SQSVGRSLHWYQQKPGQAPRLLI KYASQSLSGIPARFSGSGSGTDFTL TISSLEPEDFAVYYCHQSSRLPFTF GPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421293 | LV-04 | EIVLTQSPATLSLSPGERATLSCRA SQSVGRSLHWYQQKPGQAPRLLI KYASQSLSGIPARFSGSGSGTDFTL TISSLEPEDFAVYYCHQSSRLPFTF GPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421300 | LV-04 | EIVLTQSPATLSLSPGERATLSCRA SQSVGRSLHWYQQKPGQAPRLLI KYASQSLSGIPARFSGSGSGTDFTL TISSLEPEDFAVYYCHQSSRLPFTF GPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421307 | LV-04 | EIVLTQSPATLSLSPGERATLSCRA SQSVGRSLHWYQQKPGQAPRLLI KYASQSLSGIPARFSGSGSGTDFTL TISSLEPEDFAVYYCHQSSRLPFTF GPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421314 | LV-05 | EIVLTQSPATLSLSPGERATLSCRA SQSVWRSLHWYQQKPGQAPRLLI KYASQSLSGIPARFSGSGSGTDFTL TISSLEPEDFAVYYCHQSSRLPFTF GPGTKVDIK (SEQ ID NO: 56) | RASQSVWRSLH (SEQ ID NO: 8) | YASQSLS (SEQ ID NO: 26) | HQSSRLPFT (SEQ ID NO: 36) |
| iPS:421318 | LV-06 | EIVLTQSPATLSLSPGERATLSCRA SQSVGRNLHWYQQKPGQAPRLLI KYASQSLSGIPARFSGSGSGTDFTL TISSLEPEDFAVYYCHQSSRLPFTF GPGTKVDIK (SEQ ID NO: 57) | RASQSVGRNLH (SEQ ID NO: 9) | YASQSLS (SEQ ID NO: 26) | HQSSRLPFT (SEQ ID NO: 36) |
| iPS:421322 | LV-07 | EIVLTQSPATLSLSPGERATLSCRA SQSVGRSLHWYQQKPGQAPRLLI KYASQSLSGIPARFSGSGSGTDFTL TISSLEPEDFAVYYCHQSSMLPFTF GPGTKVDIK (SEQ ID NO: 58) | RASQSVGRSLH (SEQ ID NO: 5) | YASQSLS (SEQ ID NO: 26) | HQSSMLPFT (SEQ ID NO: 37) |

TABLE 1A-continued

Exemplary Anti-Human PAC1 Antibody Light Chain Variable Region Amino Acid Sequences

| Ab ID. | VL Group | VL Amino Acid Sequence | CDRL1 | CDRL2 | CDRL3 |
|---|---|---|---|---|---|
| iPS:421326 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421333 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421340 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421347 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421354 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421361 | LV-05 | EIVLTQSPATLSLSPGERATLSCRASQSVWRSLHWYQQKPGQAPRLLIKYASQSLSGIPARFSGSGSGTDFTLTISSLEPEDFAVYYCHQSSRLPFTFGPGTKVDIK (SEQ ID NO: 56) | RASQSVWRSLH (SEQ ID NO: 8) | YASQSLS (SEQ ID NO: 26) | HQSSRLPFT (SEQ ID NO: 36) |
| iPS:421365 | LV-06 | EIVLTQSPATLSLSPGERATLSCRASQSVGRNLHWYQQKPGQAPRLLIKYASQSLSGIPARFSGSGSGTDFTLTISSLEPEDFAVYYCHQSSRLPFTFGPGTKVDIK (SEQ ID NO: 57) | RASQSVGRNLH (SEQ ID NO: 9) | YASQSLS (SEQ ID NO: 26) | HQSSRLPFT (SEQ ID NO: 36) |
| iPS:421369 | LV-07 | EIVLTQSPATLSLSPGERATLSCRASQSVGRSLHWYQQKPGQAPRLLIKYASQSLSGIPARFSGSGSGTDFTLTISSLEPEDFAVYYCHQSSMLPFTFGPGTKVDIK (SEQ ID NO: 58) | RASQSVGRSLH (SEQ ID NO: 5) | YASQSLS (SEQ ID NO: 26) | HQSSMLPFT (SEQ ID NO: 37) |
| iPS:421373 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421380 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |

TABLE 1A-continued

Exemplary Anti-Human PAC1 Antibody Light Chain Variable Region Amino Acid Sequences

| Ab ID. | VL Group | VL Amino Acid Sequence | CDRL1 | CDRL2 | CDRL3 |
|---|---|---|---|---|---|
| iPS:421387 | LV-04 | EIVLTQSPATLSLSPGERATLSCRA<br>SQSVGRSLHWYQQKPGQAPRLLI<br>KYASQSLSGIPARFSGSGSGTDFTL<br>TISSLEPEDFAVYYCHQSSRLPFTF<br>GPGTKVDIK<br>(SEQ ID NO: 55) | RASQSVGRSLH (SEQ ID NO: 5) | YASQSLS (SEQ ID NO: 26) | HQSSRLPFT (SEQ ID NO: 36) |
| iPS:421394 | LV-04 | EIVLTQSPATLSLSPGERATLSCRA<br>SQSVGRSLHWYQQKPGQAPRLLI<br>KYASQSLSGIPARFSGSGSGTDFTL<br>TISSLEPEDFAVYYCHQSSRLPFTF<br>GPGTKVDIK<br>(SEQ ID NO: 55) | RASQSVGRSLH (SEQ ID NO: 5) | YASQSLS (SEQ ID NO: 26) | HQSSRLPFT (SEQ ID NO: 36) |
| iPS:421855 | LV-04 | EIVLTQSPATLSLSPGERATLSCRA<br>SQSVGRSLHWYQQKPGQAPRLLI<br>KYASQSLSGIPARFSGSGSGTDFTL<br>TISSLEPEDFAVYYCHQSSRLPFTF<br>GPGTKVDIK<br>(SEQ ID NO: 55) | RASQSVGRSLH (SEQ ID NO: 5) | YASQSLS (SEQ ID NO: 26) | HQSSRLPFT (SEQ ID NO: 36) |
| iPS:421861 | LV-04 | EIVLTQSPATLSLSPGERATLSCRA<br>SQSVGRSLHWYQQKPGQAPRLLI<br>KYASQSLSGIPARFSGSGSGTDFTL<br>TISSLEPEDFAVYYCHQSSRLPFTF<br>GPGTKVDIK<br>(SEQ ID NO: 55) | RASQSVGRSLH (SEQ ID NO: 5) | YASQSLS (SEQ ID NO: 26) | HQSSRLPFT (SEQ ID NO: 36) |
| iPS:421867 | LV-04 | EIVLTQSPATLSLSPGERATLSCRA<br>SQSVGRSLHWYQQKPGQAPRLLI<br>KYASQSLSGIPARFSGSGSGTDFTL<br>TISSLEPEDFAVYYCHQSSRLPFTF<br>GPGTKVDIK<br>(SEQ ID NO: 55) | RASQSVGRSLH (SEQ ID NO: 5) | YASQSLS (SEQ ID NO: 26) | HQSSRLPFT (SEQ ID NO: 36) |
| iPS:421873 | LV-04 | EIVLTQSPATLSLSPGERATLSCRA<br>SQSVGRSLHWYQQKPGQAPRLLI<br>KYASQSLSGIPARFSGSGSGTDFTL<br>TISSLEPEDFAVYYCHQSSRLPFTF<br>GPGTKVDIK<br>(SEQ ID NO: 55) | RASQSVGRSLH (SEQ ID NO: 5) | YASQSLS (SEQ ID NO: 26) | HQSSRLPFT (SEQ ID NO: 36) |
| iPS:421879 | LV-04 | EIVLTQSPATLSLSPGERATLSCRA<br>SQSVGRSLHWYQQKPGQAPRLLI<br>KYASQSLSGIPARFSGSGSGTDFTL<br>TISSLEPEDFAVYYCHQSSRLPFTF<br>GPGTKVDIK<br>(SEQ ID NO: 55) | RASQSVGRSLH (SEQ ID NO: 5) | YASQSLS (SEQ ID NO: 26) | HQSSRLPFT (SEQ ID NO: 36) |
| iPS:421885 | LV-04 | EIVLTQSPATLSLSPGERATLSCRA<br>SQSVGRSLHWYQQKPGQAPRLLI<br>KYASQSLSGIPARFSGSGSGTDFTL<br>TISSLEPEDFAVYYCHQSSRLPFTF<br>GPGTKVDIK<br>(SEQ ID NO: 55) | RASQSVGRSLH (SEQ ID NO: 5) | YASQSLS (SEQ ID NO: 26) | HQSSRLPFT (SEQ ID NO: 36) |
| iPS:421891 | LV-04 | EIVLTQSPATLSLSPGERATLSCRA<br>SQSVGRSLHWYQQKPGQAPRLLI<br>KYASQSLSGIPARFSGSGSGTDFTL<br>TISSLEPEDFAVYYCHQSSRLPFTF<br>GPGTKVDIK<br>(SEQ ID NO: 55) | RASQSVGRSLH (SEQ ID NO: 5) | YASQSLS (SEQ ID NO: 26) | HQSSRLPFT (SEQ ID NO: 36) |
| iPS:421897 | LV-04 | EIVLTQSPATLSLSPGERATLSCRA<br>SQSVGRSLHWYQQKPGQAPRLLI<br>KYASQSLSGIPARFSGSGSGTDFTL<br>TISSLEPEDFAVYYCHQSSRLPFTF<br>GPGTKVDIK<br>(SEQ ID NO: 55) | RASQSVGRSLH (SEQ ID NO: 5) | YASQSLS (SEQ ID NO: 26) | HQSSRLPFT (SEQ ID NO: 36) |

TABLE 1A-continued

Exemplary Anti-Human PAC1 Antibody Light Chain Variable Region Amino Acid Sequences

| Ab ID. | VL Group | VL Amino Acid Sequence | CDRL1 | CDRL2 | CDRL3 |
|---|---|---|---|---|---|
| iPS:421903 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421909 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:421915 | LV-04 | EIVLTQSPATLSLSPGERATLSCRASQSVGRSLHWYQQKPGQAPRLLIKYASQSLSGIPARFSGSGSGTDFTLTISSLEPEDFAVYYCHQSSRLPFTFGPGTKVDIK (SEQ ID NO: 55) | RASQSVGRSLH (SEQ ID NO: 5) | YASQSLS (SEQ ID NO: 26) | HQSSRLPFT (SEQ ID NO: 36) |
| iPS:480711 | LV-11 | EIVLTQSPATLSLSPGERATLSCRASKSVGWSLHWYQQKPGQAPRLLIKYASQSLSGIPARFSGSGSGTDFTLTISSLEPEDFAVYYCHQSSRLPFTFGPGTKVDIKR (SEQ ID NO: 62) | RASKSVGWSLH (SEQ ID NO: 12) | YASQSLS (SEQ ID NO: 26) | HQSSRLPFT (SEQ ID NO: 36) |
| iPS:480706 | LV-11 | EIVLTQSPATLSLSPGERATLSCRASKSVGWSLHWYQQKPGQAPRLLIKYASQSLSGIPARFSGSGSGTDFTLTISSLEPEDFAVYYCHQSSRLPFTFGPGTKVDIKR (SEQ ID NO: 62) | RASKSVGWSLH (SEQ ID NO: 12) | YASQSLS (SEQ ID NO: 26) | HQSSRLPFT (SEQ ID NO: 36) |
| iPS:480713 | LV-12 | EIVLTQSPATLSLSPGERATLSCRASKSVGYSLHWYQQKPGQAPRLLIKYASQSLSGIPARFSGSGSGTDFTLTISSLEPEDFAVYYCHQSSRLPFTFGPGTKVDIKR (SEQ ID NO: 63) | RASKSVGYSLH (SEQ ID NO: 13) | YASQSLS (SEQ ID NO: 26) | HQSSRLPFT (SEQ ID NO: 36) |
| iPS:480705 | LV-11 | EIVLTQSPATLSLSPGERATLSCRASKSVGWSLHWYQQKPGQAPRLLIKYASQSLSGIPARFSGSGSGTDFTLTISSLEPEDFAVYYCHQSSRLPFTFGPGTKVDIKR (SEQ ID NO: 62) | RASKSVGWSLH (SEQ ID NO: 12) | YASQSLS (SEQ ID NO: 26) | HQSSRLPFT (SEQ ID NO: 36) |
| iPS:480707 | LV-11 | EIVLTQSPATLSLSPGERATLSCRASKSVGWSLHWYQQKPGQAPRLLIKYASQSLSGIPARFSGSGSGTDFTLTISSLEPEDFAVYYCHQSSRLPFTFGPGTKVDIKR (SEQ ID NO: 62) | RASKSVGWSLH (SEQ ID NO: 12) | YASQSLS (SEQ ID NO: 26) | HQSSRLPFT (SEQ ID NO: 36) |
| iPS:480708 | LV-11 | EIVLTQSPATLSLSPGERATLSCRASKSVGWSLHWYQQKPGQAPRLLIKYASQSLSGIPARFSGSGSGTDFTLTISSLEPEDFAVYYCHQSSRLPFTFGPGTKVDIKR (SEQ ID NO: 62) | RASKSVGWSLH (SEQ ID NO: 12) | YASQSLS (SEQ ID NO: 26) | HQSSRLPFT (SEQ ID NO: 36) |
| iPS:480709 | LV-13 | EIVLTQSPATLSLSPGERATLSCRASKAVGWSLHWYQQKPGQAPRLLIKYASQSLSGIPARFSGSGSGTDFTLTISSLEPEDFAVYYCHQSSRLPFTFGPGTKVDIKR (SEQ ID NO: 64) | RASKAVGWSLH (SEQ ID NO: 14) | YASQSLS (SEQ ID NO: 26) | HQSSRLPFT (SEQ ID NO: 36) |

TABLE 1A-continued

| Exemplary Anti-Human PAC1 Antibody Light Chain Variable Region Amino Acid Sequences | | | | | |
|---|---|---|---|---|---|
| Ab ID. | VL Group | VL Amino Acid Sequence | CDRL1 | CDRL2 | CDRL3 |
| iPS:480712 | LV-11 | EIVLTQSPATLSLSPGERATLSCRA SKSVGWSLHWYQQKPGQAPRLLI KYASQSLSGIPARFSGSGSGTDFTL TISSLEPEDFAVYYCHQSSRLPFTF GPGTKVDIKR (SEQ ID NO: 62) | RASKSVGWSLH (SEQ ID NO: 12) | YASQSLS (SEQ ID NO: 26) | HQSSRLPFT (SEQ ID NO: 36) |
| iPS:480704 | LV-11 | EIVLTQSPATLSLSPGERATLSCRA SKSVGWSLHWYQQKPGQAPRLLI KYASQSLSGIPARFSGSGSGTDFTL TISSLEPEDFAVYYCHQSSRLPFTF GPGTKVDIKR (SEQ ID NO: 62) | RASKSVGWSLH (SEQ ID NO: 12) | YASQSLS (SEQ ID NO: 26) | HQSSRLPFT (SEQ ID NO: 36) |
| iPS:480710 | LV-11 | EIVLTQSPATLSLSPGERATLSCRA SKSVGWSLHWYQQKPGQAPRLLI KYASQSLSGIPARFSGSGSGTDFTL TISSLEPEDFAVYYCHQSSRLPFTF GPGTKVDIKR (SEQ ID NO: 62) | RASKSVGWSLH (SEQ ID NO: 12) | YASQSLS (SEQ ID NO: 26) | HQSSRLPFT (SEQ ID NO: 36) |
| iPS:480716 | LV-14 | EIVLTQSPATLSLSPGERATLSCRA SKSVGQSLHWYQQKPGQAPRLLI KYASQSLSGIPARFSGSGSGTDFTL TISSLEPEDFAVYYCHQSSRLPFTF GPGTKVDIKR (SEQ ID NO: 65) | RASKSVGQSLH (SEQ ID NO: 15) | YASQSLS (SEQ ID NO: 26) | HQSSRLPFT (SEQ ID NO: 36) |
| iPS:480715 | LV-14 | EIVLTQSPATLSLSPGERATLSCRA SKSVGQSLHWYQQKPGQAPRLLI KYASQSLSGIPARFSGSGSGTDFTL TISSLEPEDFAVYYCHQSSRLPFTF GPGTKVDIKR (SEQ ID NO: 65) | RASKSVGQSLH (SEQ ID NO: 15) | YASQSLS (SEQ ID NO: 26) | HQSSRLPFT (SEQ ID NO: 36) |
| iPS:480717 | LV-14 | EIVLTQSPATLSLSPGERATLSCRA SKSVGQSLHWYQQKPGQAPRLLI KYASQSLSGIPARFSGSGSGTDFTL TISSLEPEDFAVYYCHQSSRLPFTF GPGTKVDIKR (SEQ ID NO: 65) | RASKSVGQSLH (SEQ ID NO: 15) | YASQSLS (SEQ ID NO: 26) | HQSSRLPFT (SEQ ID NO: 36) |
| iPS:480714 | LV-15 | EIVLTQSPATLSLSPGERATLSCRA SRSVGLALHWYQQKPGQAPRLLI KYASQSLSGIPARFSGSGSGTDFTL TISSLEPEDFAVYYCHQSSFLPFTF GPGTKVDIKR (SEQ ID NO: 66) | RASRSVGLALH (SEQ ID NO: 16) | YASQSLS (SEQ ID NO: 26) | HQSSFLPFT (SEQ ID NO: 38) |
| 19H8 variants | | | | | |
| 19H8 | LV-16 | DIQMTQSPSSLSASVGDRITITCRA SQSISRYLNWYQQKPGKAPKLLIY AASSLQSGIPSRFSGSGSGTDFTLTI NSLQPEDFATYFCQQSYSPPFTFGP GTKVDIKR (SEQ ID NO: 67) | RASQSISRYLN (SEQ ID NO: 17) | AASSLQS (SEQ ID NO: 27) | QQSYSPPFT (SEQ ID NO: 39) |
| iPS:448202 | LV-17 | DIQMTQSPSSLSASVGDRITITCRA SQSISRYLNWYQQKPGKAPKLLIF AGQRLQSGIPSRFSGSGSGTDFTLT INSLQPEDFATYFCQQAIG1VIPYTF GPGTKVDIK (SEQ ID NO: 68) | RASQSISRYLN (SEQ ID NO: 17) | AGQRLQS (SEQ ID NO: 28) | QQAIGMPYT (SEQ ID NO: 40) |
| iPS:449375 | LV-18 | DIQMTQSPSSLSASVGDRITITCRA SQYIVRYLNWYQQKPGKAPKLLI YAAHHLQSGIPSRFSGSGSGTDFT LTINSLQPEDFATYFCQQAIQEPYT FGPGTKVDIK (SEQ ID NO: 69) | RASQYIVRYLN (SEQ ID NO: 18) | AAHHLQS (SEQ ID NO: 29) | QQAIQEPYT (SEQ ID NO: 41) |

TABLE 1A-continued

Exemplary Anti-Human PAC1 Antibody Light Chain Variable Region Amino Acid Sequences

| Ab ID. | VL Group | VL Amino Acid Sequence | CDRL1 | CDRL2 | CDRL3 |
|---|---|---|---|---|---|
| iPS:448083 | LV-19 | DIQMTQSPSSLSASVGDRITITCRASQTIVRYLNWYQQKPGKAPKLLIFAGQRLQSGIPSRFSGSGSGTDFTLTINSLQPEDFATYFCQQAIINPYTFGPGTKVDIK (SEQ ID NO: 70) | RASQTIVRYLN (SEQ ID NO: 19) | AGQRLQS (SEQ ID NO: 28) | QQAIINPYT (SEQ ID NO: 42) |
| iPS:452128 | LV-20 | DIQMTQSPSSLSASVGDRITITCRASQYIVRYLNWYQQKPGKAPKLLIYAANMLQSGIPSRFSGSGSGTDFTLTINSLQPEDFATYFCQQAINQPYTFGPGTKVDIK (SEQ ID NO: 71) | RASQYIVRYLN (SEQ ID NO: 18) | AANMLQS (SEQ ID NO: 30) | QQAINQPYT (SEQ ID NO: 43) |
| iPS:448195 | LV-21 | DIQMTQSPSSLSASVGDRITITCRASQKIARYLVWYQQKPGKAPKLLIYAANMLQSGIPSRFSGSGSGTDFTLTINSLQPEDFATYFCQQSIQQPYTFGPGTKVDIK (SEQ ID NO: 72) | RASQKIARYLV (SEQ ID NO: 20) | AANMLQS (SEQ ID NO: 30) | QQSIQQPYT (SEQ ID NO: 44) |
| iPS:448466 | LV-22 | DIQMTQSPSSLSASVGDRITITCRASQSISRYLNWYQQKPGKAPKLLIFAGQRLQSGIPSRFSGSGSGTDFTLTINSLQPEDFATYFCQQAIQQPYTFGPGTKVDIKR (SEQ ID NO: 73) | RASQSISRYLN (SEQ ID NO: 17) | AGQRLQS (SEQ ID NO: 28) | QQAIQQPYT (SEQ ID NO: 45) |
| iPS:448689 | LV-23 | DIQMTQSPSSLSASVGDRITITCRASQYIVRYLNWYQQKPGKAPKLLIYASYNLQSGIPSRFSGSGSGTDFTLTINSLQPEDFATYFCQQAIMAPYTFGPGTKVDIK (SEQ ID NO: 74) | RASQYIVRYLN (SEQ ID NO: 18) | ASYNLQS (SEQ ID NO: 31) | QQAIMAPYT (SEQ ID NO: 46) |
| iPS:449034 | LV-24 | DIQMTQSPSSLSASVGDRITITCRASQPIAQYLNWYQQKPGKAPKLLIYAGRYLQSGIPSRFSGSGSGTDFTLTINSLQPEDFATYFCQQAIQNPYTFGPGTKVDIK (SEQ ID NO: 75) | RASQPIAQYLN (SEQ ID NO: 21) | AGRYLQS (SEQ ID NO: 32) | QQAIQNPYT (SEQ ID NO: 47) |
| iPS:448075 | LV-25 | DIQMTQSPSSLSASVGDRITITCRASQSISRYLNWYQQKPGKAPKLLIFAGQRLQSGIPSRFSGSGSGTDFTLTINSLQPEDFATYFCQQAIVQPYTFGPGTKVDIK (SEQ ID NO: 76) | RASQSISRYLN (SEQ ID NO: 17) | AGQRLQS (SEQ ID NO: 28) | QQAIVQPYT (SEQ ID NO: 48) |
| iPS:448924 | LV-26 | DIQMTQSPSSLSASVGDRITITCRASQPISRYLSWYQQKPGKAPKLLIFAGQRLQSGIPSRFSGSGSGTDFTLTINSLQPEDFATYFCQQAISIPYTFGPGTKVDIK (SEQ ID NO: 77) | RASQPISRYLS (SEQ ID NO: 22) | AGQRLQS (SEQ ID NO: 28) | QQAISIPYT (SEQ ID NO: 49) |
| iPS:448752 | LV-27 | DIQMTQSPSSLSASVGDRITITCRASQQIARYLNWYQQKPGKAPKLLIYASYNLQSGIPSRFSGSGSGTDFTLTINSLQPEDFATYFCQQAIIQPYTFGPGTKVDIK (SEQ ID NO: 78) | RASQQIARYLN (SEQ ID NO: 23) | ASYNLQS (SEQ ID NO: 31) | QQAIIQPYT (SEQ ID NO: 50) |
| iPS:448772 | LV-28 | DIQMTQSPSSLSASVGDRITITCRASQSISRYLNWYQQKPGKAPKLLIYASYNLQSGIPSRFSGSGSGTDFTLTINSLQPEDFATYFCQQAIQNPYTFGPGTKVDIK (SEQ ID NO: 79) | RASQSISRYLN (SEQ ID NO: 17) | ASYNLQS (SEQ ID NO: 31) | QQAIQNPYT (SEQ ID NO: 47) |

TABLE 1A-continued

| Exemplary Anti-Human PAC1 Antibody Light Chain Variable Region Amino Acid Sequences | | | | | |
|---|---|---|---|---|---|
| Ab ID. | VL Group | VL Amino Acid Sequence | CDRL1 | CDRL2 | CDRL3 |
| iPS:448117 | LV-29 | DIQMTQSPSSLSASVGDRITITCRA SQTIVRYLNWYQQKPGKAPKLLIF AGQRLQSGIPSRFSGSGSGTDFTLT INSLQPEDFATYFCQQSIQTPYTFG PGTKVDIK (SEQ ID NO: 80) | RASQTIVRYLN (SEQ ID NO: 19) | AGQRLQS (SEQ ID NO: 28) | QQSIQTPYT (SEQ ID NO: 51) |
| iPS:448788 | LV-30 | DIQMTQSPSSLSASVGDRITITCRA SQSISRYLNWYQQKPGKAPKLLIY AGRILQSGIPSRFSGSGSGTDFTLTI NSLQPEDFATYFCQQAIINPYTFGP GTKVDIK (SEQ ID NO: 81) | RASQSISRYLN (SEQ ID NO: 17) | AGRILQS (SEQ ID NO: 33) | QQAIINPYT (SEQ ID NO: 42) |
| iPS:448593 | LV-28 | DIQMTQSPSSLSASVGDRITITCRA SQSISRYLNWYQQKPGKAPKLLIY ASYNLQSGIPSRFSGSGSGTDFTLT INSLQPEDFATYFCQQAIQNPYTFG PGTKVDIK (SEQ ID NO: 79) | RASQSISRYLN (SEQ ID NO: 17) | ASYNLQS (SEQ ID NO: 31) | QQAIQNPYT (SEQ ID NO: 47) |
| iPS:448238 | LV-31 | DIQMTQSPSSLSASVGDRITITCRA SQRIARYLNWYQQKPGKAPKLLIF AGSILQSGIPSRFSGSGSGTDFTLTI NSLQPEDFATYFCQQAIQNPYTFG PGTKVDIK (SEQ ID NO: 82) | RASQRIARYLN (SEQ ID NO: 24) | AGSILQS (SEQ ID NO: 34) | QQAIQNPYT (SEQ ID NO: 47) |
| iPS:448901 | LV-32 | DIQMTQSPSSLSASVGDRITITCRA SQSISRYLNWYQQKPGKAPKLLIY ASYNLQSGIPSRFSGSGSGTDFTLT INSLQPEDFATYFCQQSIQQPYTFG PGTKVDIK (SEQ ID NO: 83) | RASQSISRYLN (SEQ ID NO: 17) | ASYNLQS (SEQ ID NO: 31) | QQSIQQPYT (SEQ ID NO: 44) |
| iPS:448655 | LV-33 | DIQMTQSPSSLSASVGDRITITCRA SQYIVRYLNWYQQKPGKAPKLLI YASYNLQSGIPSRFSGSGSGTDFTL TINSLQPEDFATYFCQQAIQQPYTF GPGTKVDIK (SEQ ID NO: 84) | RASQYIVRYLN (SEQ ID NO: 18) | ASYNLQS (SEQ ID NO: 31) | QQAIQQPYT (SEQ ID NO: 45) |
| iPS:448730 | LV-34 | DIQMTQSPSSLSASVGDRITITCRA SQMIARYLNWYQQKPGKAPKLLI YASYNLQSGIPSRFSGSGSGTDFTL TINSLQPEDFATYFCQQAIINPYTF GPGTKVDIK (SEQ ID NO: 85) | RASQMIARYLN (SEQ ID NO: 25) | ASYNLQS (SEQ ID NO: 31) | QQAIINPYT (SEQ ID NO: 42) |
| iPS:449027 | LV-35 | DIQMTQSPSSLSASVGDRITITCRA SQYIVRYLNWYQQKPGKAPKLLI YGARNLQSGIPSRFSGSGSGTDFTL TINSLQPEDFATYFCQQSIQTPYTF GPGTKVDIK (SEQ ID NO: 86) | RASQYIVRYLN (SEQ ID NO: 18) | GARNLQS (SEQ ID NO: 35) | QQSIQTPYT (SEQ ID NO: 51) |
| 3574 | LV-36 | DIQMTQSPSSLSASVGDRITITCRA SQSISRYLNWYQQKPGKAPKLLIY AASSLQSGIPSRFSGSGSGTDFTLTI NSLQPEDFATYFCQQSYSPPFTFGP GTKVDIK (SEQ ID NO: 87) | RASQSISRYLN (SEQ ID NO: 17) | AASSLQS (SEQ ID NO: 27) | QQSYSPPFT (SEQ ID NO: 39) |
| 3575 | LV-27 | DIQMTQSPSSLSASVGDRITITCRA SQQIARYLNWYQQKPGKAPKLLI YASYNLQSGIPSRFSGSGSGTDFTL TINSLQPEDFATYFCQQAIIQPYTF GPGTKVDIK (SEQ ID NO: 78) | RASQQIARYLN (SEQ ID NO: 23) | ASYNLQS (SEQ ID NO: 31) | QQAIIQPYT (SEQ ID NO: 50) |

TABLE 1B

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| 29G4 variants | | | | | |
| 29G4v10 | HV-01 | QVQLVESGGGVVQPGRSLR LSCAASGFTFSRFAMHWVR QAPGKGLEWVAVISYDGGN KYYAESVKGRFTISRDNSKN TLYLQMNSLRAEDTALFYC ARGYDVLTGYPDYWGQGTL VTVSS (SEQ ID NO: 191) | RFAMH (SEQ ID NO: 88) | VISYDGGNKYYAESVKG (SEQ ID NO: 106) | GYDVLTGYPDY (SEQ ID NO: 171) |
| 29G4v22 | HV-02 | QVQLVESGAEVVKPGASVK VSCKASGFTESRFAMHWVR QAPGQGLEWMGVISYDGGN KYYAESVKGRVTMTRDTST STLYMELSSLRSEDTAVYYC ARGYDVLTGYPDYWGQGTL VTVSS (SEQ ID NO: 192) | RFAMH (SEQ ID NO: 88) | VISYDGGNKYYAESVKG (SEQ ID NO: 106) | GYDVLTGYPDY (SEQ ID NO: 171) |
| iPS:420649 | HV-03 | QVQLVESGGGVVQPGRSLR LSCAASGFTFSRFAMHWVR QAPGKGLEWVAVISYNGGN KYYAESVKGRFTISRDNSKN TLYLQMNSLRAEDTALFYC ARGYDVLTGYPDYWGQGTL VTVSS (SEQ ID NO: 193) | RFAMH (SEQ ID NO: 88) | VISYNGGNKYYAESVKG (SEQ ID NO: 107) | GYDVLTGYPDY (SEQ ID NO: 171) |
| iPS:420653 | HV-04 | QVQLVESGGGVVQPGRSLR LSCAASGFTFSRFAMHWVR QAPGKGLEWVAVISYIGGN KYYAESVKGRFTISRDNSKN TLYLQMNSLRAEDTALFYC ARGYDVLTGYPDYWGQGTL VTVSS (SEQ ID NO: 194) | RFAMH (SEQ ID NO: 88) | VISYIGGNKYYAESVKG (SEQ ID NO: 108) | GYDVLTGYPDY (SEQ ID NO: 171) |
| iPS:420657 | HV-05 | QVQLVESGGGVVQPGRSLR LSCAASGFTFSRFAMHWVR QAPGKGLEWVAVISYQGGN KYYAESVKGRFTISRDNSKN TLYLQMNSLRAEDTALFYC ARGYDVLTGYPDYWGQGTL VTVSS (SEQ ID NO: 195) | RFAMH (SEQ ID NO: 88) | VISYQGGNKYYAESVKG (SEQ ID NO: 109) | GYDVLTGYPDY (SEQ ID NO: 171) |
| iPS:420661 | HV-06 | QVQLVESGGGVVQPGRSLR LSCAASGFTFSRFAMHWVR QAPGKGLEWVAVISYYGGN KYYAESVKGRFTISRDNSKN TLYLQMNSLRAEDTALFYC ARGYDVLTGYPDYWGQGTL VVTVSS (SEQ ID NO: 196) | RFAMH (SEQ ID NO: 88) | VISYYGGNKYYAESVKG (SEQ ID NO: 110) | GYDVLTGYPDY (SEQ ID NO: 171) |
| iPS:420665 | HV-07 | QVQLVESGGGVVQPGRSLR LSCAASGFTFSRFAMHWVR QAPGKGLEWVAVISYDGRN KYYAESVKGRFTISRDNSKN TLYLQMNSLRAEDTALFYC ARGYDVLTGYPDYWGQGTL VTVSS (SEQ ID NO: 197) | RFAMH (SEQ ID NO: 88) | VISYDGRNKYYAESVKG (SEQ ID NO: 111) | GYDVLTGYPDY (SEQ ID NO: 171) |
| iPS:420672 | HV-08 | QVQLVESGGGVVQPGRSLR LSCAASGFTFSRFAMHWVR QAPGKGLEWVAVISYDGNN KYYAESVKGRFTISRDNSKN TLYLQMNSLRAEDTALFYC ARGYDVLTGYPDYWGQGTL VTVSS (SEQ ID NO: 198) | RFAMH (SEQ ID NO: 88) | VISYDGNNKYYAESVKG (SEQ ID NO: 112) | GYDVLTGYPDY (SEQ ID NO: 171) |
| iPS:420679 | HV-09 | QVQLVESGGGVVQPGRSLR LSCAASGFTFSRFAMHWVR QAPGKGLEWVAVISYDGGN KYYARSVKGRFTISRDNSKN TLYLQMNSLRAEDTALFYC ARGYDVLTGYPDYWGQGTL VTVSS (SEQ ID NO: 199) | RFAMH (SEQ ID NO: 88) | VISYDGGNKYYARSVKG (SEQ ID NO: 113) | GYDVLTGYPDY (SEQ ID NO: 171) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| iPS:420686 | HV-10 | QVQLVESGGGVVQPGRSLR LSCAASGFTFSRFAMHWVR QAPGKGLEWVAVISYDGGN KYYAESVKGRFTISRDNSKN TLYLQMNSLRAEDTALFYC ARGYDILTGYPDYWGQGTL VTVSS (SEQ ID NO: 200) | RFAMH (SEQ ID NO: 88) | VISYDGGNKYYAESVKG (SEQ ID NO: 106) | GYDILTGYPDY (SEQ ID NO: 172) |
| iPS:420690 | HV-11 | QVQLVESGGGVVQPGRSLR LSCAASGFTFSRFAMHWVR QAPGKGLEWVAVISYNGRN KYYAESVKGRFTISRDNSKN TLYLQMNSLRAEDTALFYC ARGYDVLTGYPDYWGQGTL VTVSS (SEQ ID NO: 201) | RFAMH (SEQ ID NO: 88) | VISYNGRNKYYAESVKG (SEQ ID NO: 114) | GYDVLTGYPDY (SEQ ID NO: 171) |
| iPS:420697 | HV-12 | QVQLVESGGGVVQPGRSLR LSCAASGFTFSRFAMHWVR QAPGKGLEWVAVISYIGRNK YYAESVKGRFTISRDNSKNT LYLQMNSLRAEDTALFYCA RGYDVLTGYPDYWGQGTLV TVSS (SEQ ID NO: 202) | RFAMH (SEQ ID NO: 88) | VISYIGRNKYYAESVKG (SEQ ID NO: 115) | GYDVLTGYPDY (SEQ ID NO: 171) |
| iPS:420704 | HV-13 | QVQLVESGGGVVQPGRSLR LSCAASGFTFSRFAMHWVR QAPGKGLEWVAVISYQGRN KYYAESVKGRFTISRDNSKN TLYLQMNSLRAEDTALFYC ARGYDVLTGYPDYWGQGTL VTVSS (SEQ ID NO: 203) | RFAMH (SEQ ID NO: 88) | VISYQGRNKYYAESVKG (SEQ ID NO: 116) | GYDVLTGYPDY (SEQ ID NO: 171) |
| iPS:420711 | HV-14 | QVQLVESGGGVVQPGRSLR LSCAASGFTFSRFAMHWVR QAPGKGLEWVAVISYYGRN KYYAESVKGRFTISRDNSKN TLYLQMNSLRAEDTALFYC ARGYDVLTGYPDYWGQGTL VTVSS (SEQ ID NO: 204) | RFAMH (SEQ ID NO: 88) | VISYYGRNKYYAESVKG (SEQ ID NO: 117) | GYDVLTGYPDY (SEQ ID NO: 171) |
| iPS:420718 | HV-15 | QVQLVESGGGVVQPGRSLR LSCAASGFTFSRFAMHWVR QAPGKGLEWVAVISYNGNN KYYAESVKGRFTISRDNSKN TLYLQMNSLRAEDTALFYC ARGYDVLTGYPDYWGQGTL VTVSS (SEQ ID NO: 205) | RFAMH (SEQ ID NO: 88) | VISYNGNNKYYAESVKG (SEQ ID NO: 118) | GYDVLTGYPDY (SEQ ID NO: 171) |
| iPS:420725 | HV-16 | QVQLVESGGGVVQPGRSLR LSCAASGFTFSRFAMHWVR QAPGKGLEWVAVISYIGNN KYYAESVKGRFTISRDNSKN TLYLQMNSLRAEDTALFYC ARGYDVLTGYPDYWGQGTL VTVSS (SEQ ID NO: 206) | RFAMH (SEQ ID NO: 88) | VISYIGNNKYYAESVKG (SEQ ID NO: 119) | GYDVLTGYPDY (SEQ ID NO: 171) |
| iPS:420732 | HV-17 | QVQLVESGGGVVQPGRSLR LSCAASGFTFSRFAMHWVR QAPGKGLEWVAVISYQGNN KYYAESVKGRFTISRDNSKN TLYLQMNSLRAEDTALFYC ARGYDVLTGYPDYWGQGTL VTVSS (SEQ ID NO: 207) | RFAMH (SEQ ID NO: 88) | VISYQGNNKYYAESVKG (SEQ ID NO: 120) | GYDVLTGYPDY (SEQ ID NO: 171) |
| iPS:420739 | HV-18 | QVQLVESGGGVVQPGRSLR LSCAASGFTFSRFAMHWVR QAPGKGLEWVAVISYYGNN KYYAESVKGRFTISRDNSKN TLYLQMNSLRAEDTALFYC ARGYDVLTGYPDYWGQGTL VTVSS (SEQ ID NO: 208) | RFAMH (SEQ ID NO: 88) | VISYYGNNKYYAESVKG (SEQ ID NO: 121) | GYDVLTGYPDY (SEQ ID NO: 171) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| iPS:420746 | HV-19 | QVQLVESGGGVVQPGRSLR LSCAASGFTFSRFAMHWVR QAPGKGLEWVAVISYNGGN KYYARSVKGRFTISRDNSKN TLYLQMNSLRAEDTALFYC ARGYDVLTGYPDYWGQGTL VTVSS (SEQ ID NO: 209) | RFAMH (SEQ ID NO: 88) | VISYNGGNKYYARSVKG (SEQ ID NO: 122) | GYDVLTGYPDY (SEQ ID NO: 171) |
| iPS:420753 | HV-20 | QVQLVESGGGVVQPGRSLR LSCAASGFTFSRFAMHWVR QAPGKGLEWVAVISYIGGN KYYARSVKGRFTISRDNSKN TLYLQMNSLRAEDTALFYC ARGYDVLTGYPDYWGQGTL VTVSS (SEQ ID NO: 210) | RFAMH (SEQ ID NO: 88) | VISYIGGNKYYARSVKG (SEQ ID NO: 123) | GYDVLTGYPDY (SEQ ID NO: 171) |
| iPS:420760 | HV-21 | QVQLVESGGGVVQPGRSLR LSCAASGFTFSRFAMHWVR QAPGKGLEWVAVISYQGGN KYYARSVKGRFTISRDNSKN TLYLQMNSLRAEDTALFYC ARGYDVLTGYPDYWGQGTL VTVSS (SEQ ID NO: 211) | RFAMH (SEQ ID NO: 88) | VISYQGGNKYYARSVKG (SEQ ID NO: 124) | GYDVLTGYPDY (SEQ ID NO: 171) |
| iPS:420767 | HV-22 | QVQLVESGGGVVQPGRSLR LSCAASGFTFSRFAMHWVR QAPGKGLEWVAVISYYGGN KYYARSVKGRFTISRDNSKN TLYLQMNSLRAEDTALFYC ARGYDVLTGYPDYWGQGTL VTVSS (SEQ ID NO: 212) | RFAMH (SEQ ID NO: 88) | VISYYGGNKYYARSVKG (SEQ ID NO: 125) | GYDVLTGYPDY (SEQ ID NO: 171) |
| iPS:420774 | HV-23 | QVQLVESGGGVVQPGRSLR LSCAASGFTFSRFAMHWVR QAPGKGLEWVAVISYNGGN KYYAESVKGRFTISRDNSKN TLYLQMNSLRAEDTALFYC ARGYDILTGYPDYWGQGTL VTVSS (SEQ ID NO: 213) | RFAMH (SEQ ID NO: 88) | VISYNGGNKYYAESVKG (SEQ ID NO: 107) | GYDILTGYPDY (SEQ ID NO: 172) |
| iPS:420781 | HV-24 | QVQLVESGGGVVQPGRSLR LSCAASGFTFSRFAMHWVR QAPGKGLEWVAVISYIGGN KYYAESVKGRFTISRDNSKN TLYLQMNSLRAEDTALFYC ARGYDILTGYPDYWGQGTL VTVSS (SEQ ID NO: 214) | RFAMH (SEQ ID NO: 88) | VISYIGGNKYYAESVKG (SEQ ID NO: 108) | GYDILTGYPDY (SEQ ID NO: 172) |
| iPS:420788 | HV-25 | QVQLVESGGGVVQPGRSLR LSCAASGFTFSRFAMHWVR QAPGKGLEWVAVISYQGGN KYYAESVKGRFTISRDNSKN TLYLQMNSLRAEDTALFYC ARGYDILTGYPDYWGQGTL VTVSS (SEQ ID NO: 215) | RFAMH (SEQ ID NO: 88) | VISYQGGNKYYAESVKG (SEQ ID NO: 109) | GYDILTGYPDY (SEQ ID NO: 172) |
| iPS:420795 | HV-26 | QVQLVESGGGVVQPGRSLR LSCAASGFTFSRFAMHWVR QAPGKGLEWVAVISYYGGN KYYAESVKGRFTISRDNSKN TLYLQMNSLRAEDTALFYC ARGYDILTGYPDYWGQGTL VTVSS (SEQ ID NO: 216) | RFAMH (SEQ ID NO: 88) | VISYYGGNKYYAESVKG (SEQ ID NO: 110) | GYDILTGYPDY (SEQ ID NO: 172) |
| iPS:420802 | HV-27 | QVQLVESGGGVVQPGRSLR LSCAASGFTFSRFAMHWVR QAPGKGLEWVAVISYDGRN KYYARSVKGRFTISRDNSKN TLYLQMNSLRAEDTALFYC ARGYDVLTGYPDYWGQGTL VTVSS (SEQ ID NO: 217) | RFAMH (SEQ ID NO: 88) | VISYDGRNKYYARSVKG (SEQ ID NO: 126) | GYDVLTGYPDY (SEQ ID NO: 171) |

TABLE 1B-continued

| Exemplary Anti-Human PAC1 Antibody Heavy Chain Variable Region Amino Acid Sequences | | | | | |
|---|---|---|---|---|---|
| Ab ID. | VH Group | VH Amino Acid Sequence | CDRH1 | CDRH2 | CDRH3 |
| iPS:420809 | HV-28 | QVQLVESGGGVVQPGRSLR LSCAASGFTFSRFAMHWVR QAPGKGLEWVAVISYDGNN KYYARSVKGRFTISRDNSKN TLYLQMNSLRAEDTALFYC ARGYDVLTGYPDYWGQGTL VTVSS (SEQ ID NO: 218) | RFAMH (SEQ ID NO: 88) | VISYDGNNKYYARSVKG (SEQ ID NO: 127) | GYDVLTGYPDY (SEQ ID NO: 171) |
| iPS:420816 | HV-29 | QVQLVESGGGVVQPGRSLR LSCAASGFTFSRFAMHWVR QAPGKGLEWVAVISYDGRN KYYAESVKGRFTISRDNSKN TLYLQMNSLRAEDTALFYC ARGYDILTGYPDYWGQGTL VTVSS (SEQ ID NO: 219) | RFAMH (SEQ ID NO: 88) | VISYDGRNKYYAESVKG (SEQ ID NO: 111) | GYDILTGYPDY (SEQ ID NO: 172) |
| iPS:420823 | HV-30 | QVQLVESGGGVVQPGRSLR LSCAASGFTFSRFAMHWVR QAPGKGLEWVAVISYDGNN KYYAESVKGRFTISRDNSKN TLYLQMNSLRAEDTALFYC ARGYDILTGYPDYWGQGTL VTVSS (SEQ ID NO: 220) | RFAMH (SEQ ID NO: 88) | VISYDGNNKYYAESVKG (SEQ ID NO: 112) | GYDILTGYPDY (SEQ ID NO: 172) |
| IPS:420830 | HV-31 | QVQLVESGGGVVQPGRSLR LSCAASGFTFSRFAMHWVR QAPGKGLEWVAVISYDGGN KYYARSVKGRFTISRDNSKN TLYLQMNSLRAEDTALFYC ARGYDILTGYPDYWGQGTL VTVSS (SEQ ID NO: 221) | RFAMH (SEQ ID NO: 88) | VISYDGGNKYYARSVKG (SEQ ID NO: 113) | GYDILTGYPDY (SEQ ID NO: 172) |
| IPS:420837 | HV-11 | QVQLVESGGGVVQPGRSLR LSCAASGFTFSRFAMHWVR QAPGKGLEWVAVISYNGRN KYYAESVKGRFTISRDNSKN TLYLQMNSLRAEDTALFYC ARGYDVLTGYPDYWGQGTL VTVSS (SEQ ID NO: 201) | RFAMH (SEQ ID NO: 88) | VISYNGRNKYYAESVKG (SEQ ID NO: 114) | GYDVLTGYPDY (SEQ ID NO: 171) |
| IPS:420841 | HV-12 | QVQLVESGGGVVQPGRSLR LSCAASGFTFSRFAMHWVR QAPGKGLEWVAVISYIGRNK YYAESVKGRFTISRDNSKNT LYLQMNSLRAEDTALFYCA RGYDVLTGYPDYWGQGTLV TVSS (SEQ ID NO: 202) | RFAMH (SEQ ID NO: 88) | VISYIGRNKYYAESVKG (SEQ ID NO: 115) | GYDVLTGYPDY (SEQ ID NO: 171) |
| IPS:420845 | HV-13 | QVQLVESGGGVVQPGRSLR LSCAASGFTFSRFAMHWVR QAPGKGLEWVAVISYQGRN KYYAESVKGRFTISRDNSKN TLYLQMNSLRAEDTALFYC ARGYDVLTGYPDYWGQGTL VTVSS (SEQ ID NO: 203) | RFAMH (SEQ ID NO: 88) | VISYQGRNKYYAESVKG (SEQ ID NO: 116) | GYDVLTGYPDY (SEQ ID NO: 171) |
| IPS:420849 | HV-14 | QVQLVESGGGVVQPGRSLR LSCAASGFTFSRFAMHWVR QAPGKGLEWVAVISYYGRN KYYAESVKGRFTISRDNSKN TLYLQMNSLRAEDTALFYC ARGYDVLTGYPDYWGQGTL VTVSS (SEQ ID NO: 204) | RFAMH (SEQ ID NO: 88) | VISYYGRNKYYAESVKG (SEQ ID NO: 117) | GYDVLTGYPDY (SEQ ID NO: 171) |
| IPS:420853 | HV-15 | QVQLVESGGGVVQPGRSLR LSCAASGFTFSRFAMHWVR QAPGKGLEWVAVISYNGNN KYYAESVKGRFTISRDNSKN TLYLQMNSLRAEDTALFYC ARGYDVLTGYPDYWGQGTL VTVSS (SEQ ID NO: 205) | RFAMH (SEQ ID NO: 88) | VISYNGNNKYYAESVKG (SEQ ID NO: 118) | GYDVLTGYPDY (SEQ ID NO: 171) |

TABLE 1B-continued

| Exemplary Anti-Human PAC1 Antibody Heavy Chain Variable Region Amino Acid Sequences | | | | | |
|---|---|---|---|---|---|
| Ab ID. | VH Group | VH Amino Acid Sequence | CDRH1 | CDRH2 | CDRH3 |
| IPS:420857 | HV-16 | QVQLVESGGGVVQPGRSLR LSCAASGFTFSRFAMHWVR QAPGKGLEWVAVISYIGNN KYYAESVKGRFTISRDNSKN TLYLQMNSLRAEDTALFYC ARGYDVLTGYPDYWGQGTL VTVSS (SEQ ID NO: 206) | RFAMH (SEQ ID NO: 88) | VISYIGNNKYYAESVKG (SEQ ID NO: 119) | GYDVLTGYPDY (SEQ ID NO: 171) |
| IPS:420861 | HV-17 | QVQLVESGGGVVQPGRSLR LSCAASGFTFSRFAMHWVR QAPGKGLEWVAVISYQGNN KYYAESVKGRFTISRDNSKN TLYLQMNSLRAEDTALFYC ARGYDVLTGYPDYWGQGTL VTVSS (SEQ ID NO: 207) | RFAMH (SEQ ID NO: 88) | VISYQGNNKYYAESVKG (SEQ ID NO: 120) | GYDVLTGYPDY (SEQ ID NO: 171) |
| IPS:420865 | HV-18 | QVQLVESGGGVVQPGRSLR LSCAASGFTFSRFAMHWVR QAPGKGLEWVAVISYYGNN KYYAESVKGRFTISRDNSKN TLYLQMNSLRAEDTALFYC ARGYDVLTGYPDYWGQGTL VTVSS (SEQ ID NO: 208) | RFAMH (SEQ ID NO: 88) | VISYYGNNKYYAESVKG (SEQ ID NO: 121) | GYDVLTGYPDY (SEQ ID NO: 171) |
| iPS:420869 | HV-19 | QVQLVESGGGVVQPGRSLR LSCAASGFTFSRFAMHWVR QAPGKGLEWVAVISYNGGN KYYARSVKGRFTISRDNSKN TLYLQMNSLRAEDTALFYC ARGYDVLTGYPDYWGQGTL VTVSS (SEQ ID NO: 209) | RFAMH (SEQ ID NO: 88) | VISYNGGNKYYARSVKG (SEQ ID NO: 122) | GYDVLTGYPDY (SEQ ID NO: 171) |
| iPS:420873 | HV-20 | QVQLVESGGGVVQPGRSLR LSCAASGFTFSRFAMHWVR QAPGKGLEWVAVISYIGGN KYYARSVKGRFTISRDNSKN TLYLQMNSLRAEDTALFYC ARGYDVLTGYPDYWGQGTL VTVSS (SEQ ID NO: 210) | RFAMH (SEQ ID NO: 88) | VISYIGGNKYYARSVKG (SEQ ID NO: 123) | GYDVLTGYPDY (SEQ ID NO: 171) |
| iPS:420877 | HV-21 | QVQLVESGGGVVQPGRSLR LSCAASGFTFSRFAMHWVR QAPGKGLEWVAVISYQGGN KYYARSVKGRFTISRDNSKN TLYLQMNSLRAEDTALFYC ARGYDVLTGYPDYWGQGTL VTVSS (SEQ ID NO: 211) | RFAMH (SEQ ID NO: 88) | VISYQGGNKYYARSVKG (SEQ ID NO: 124) | GYDVLTGYPDY (SEQ ID NO: 171) |
| iPS:420881 | HV-22 | QVQLVESGGGVVQPGRSLR LSCAASGFTFSRFAMHWVR QAPGKGLEWVAVISYYGGN KYYARSVKGRFTISRDNSKN TLYLQMNSLRAEDTALFYC ARGYDVLTGYPDYWGQGTL VTVSS (SEQ ID NO: 212) | RFAMH (SEQ ID NO: 88) | VISYYGGNKYYARSVKG (SEQ ID NO: 125) | GYDVLTGYPDY (SEQ ID NO: 171) |
| iPS:420885 | HV-23 | QVQLVESGGGVVQPGRSLR LSCAASGFTFSRFAMHWVR QAPGKGLEWVAVISYNGGN KYYAESVKGRFTISRDNSKN TLYLQMNSLRAEDTALFYC ARGYDILTGYPDYWGQGTL VTVSS (SEQ ID NO: 213) | RFAMH (SEQ ID NO: 88) | VISYNGGNKYYAESVKG (SEQ ID NO: 107) | GYDILTGYPDY (SEQ ID NO: 172) |
| iPS:420889 | HV-24 | QVQLVESGGGVVQPGRSLR LSCAASGFTFSRFAMHWVR QAPGKGLEWVAVISYIGGN KYYAESVKGRFTISRDNSKN TLYLQMNSLRAEDTALFYC ARGYDILTGYPDYWGQGTL VTVSS (SEQ ID NO: 214) | RFAMH (SEQ ID NO: 88) | VISYIGGNKYYAESVKG (SEQ ID NO: 108) | GYDILTGYPDY (SEQ ID NO: 172) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| iPS:420893 | HV-25 | QVQLVESGGGVVQPGRSLR LSCAASGFTFSRFAMHWVR QAPGKGLEWVAVISYQGGN KYYAESVKGRFTISRDNSKN TLYLQMNSLRAEDTALFYC ARGYDILTGYPDYWGQGTL VTVSS (SEQ ID NO: 215) | RFAMH (SEQ ID NO: 88) | VISYQGGNKYYAESVKG (SEQ ID NO: 109) | GYDILTGYPDY (SEQ ID NO: 172) |
| iPS:420897 | HV-26 | QVQLVESGGGVVQPGRSLR LSCAASGFTFSRFAMHWVR QAPGKGLEWVAVISYYGGN KYYAESVKGRFTISRDNSKN TLYLQMNSLRAEDTALFYC ARGYDILTGYPDYWGQGTL VVTVSS (SEQ ID NO: 216) | RFAMH (SEQ ID NO: 88) | VISYYGGNKYYAESVKG (SEQ ID NO: 110) | GYDILTGYPDY (SEQ ID NO: 172) |
| IPS:420901 | HV-32 | QVQLVESGGGVVQPGRSLR LSCAASGFTFSRFAMHWVR QAPGKGLEWVAVISYNGRN KYYARSVKGRFTISRDNSKN TLYLQMNSLRAEDTALFYC ARGYDVLTGYPDYWGQGTL VTVSS (SEQ ID NO: 222) | RFAMH (SEQ ID NO: 88) | VISYNGRNKYYARSVKG (SEQ ID NO: 128) | GYDVLTGYPDY (SEQ ID NO: 171) |
| IPS:420908 | HV-33 | QVQLVESGGGVVQPGRSLR LSCAASGFTFSRFAMHWVR QAPGKGLEWVAVISYIGRNK YYARSVKGRFTISRDNSKNT LYLQMNSLRAEDTALFYCA RGYDVLTGYPDYWGQGTLV TVSS (SEQ ID NO: 223) | RFAMH (SEQ ID NO: 88) | VISYIGRNKYYARSVKG (SEQ ID NO: 129) | GYDVLTGYPDY (SEQ ID NO: 171) |
| IPS:420915 | HV-34 | QVQLVESGGGVVQPGRSLR LSCAASGFTFSRFAMHWVR QAPGKGLEWVAVISYQGRN KYYARSVKGRFTISRDNSKN TLYLQMNSLRAEDTALFYC ARGYDVLTGYPDYWGQGTL VTVSS (SEQ ID NO: 224) | RFAMH (SEQ ID NO: 88) | VISYQGRNKYYARSVKG (SEQ ID NO: 130) | GYDVLTGYPDY (SEQ ID NO: 171) |
| IPS:420922 | HV-35 | QVQLVESGGGVVQPGRSLR LSCAASGFTFSRFAMHWVR QAPGKGLEWVAVISYYGRN KYYARSVKGRFTISRDNSKN TLYLQMNSLRAEDTALFYC ARGYDVLTGYPDYWGQGTL VTVSS (SEQ ID NO: 225) | RFAMH (SEQ ID NO: 88) | VISYYGRNKYYARSVKG (SEQ ID NO: 131) | GYDVLTGYPDY (SEQ ID NO: 171) |
| IPS:420929 | HV-36 | QVQLVESGGGVVQPGRSLR LSCAASGFTFSRFAMHWVR QAPGKGLEWVAVISYNGNN KYYARSVKGRFTISRDNSKN TLYLQMNSLRAEDTALFYC ARGYDVLTGYPDYWGQGTL VTVSS (SEQ ID NO: 226) | RFAMH (SEQ ID NO: 88) | VISYNGNNTKYYARSVKG (SEQ ID NO: 132) | GYDVLTGYPDY (SEQ ID NO: 171) |
| IPS:420936 | HV-37 | QVQLVESGGGVVQPGRSLR LSCAASGFTFSRFAMHWVR QAPGKGLEWVAVISYIGNN KYYARSVKGRFTISRDNSKN TLYLQMNSLRAEDTALFYC ARGYDVLTGYPDYWGQGTL VTVSS (SEQ ID NO: 227) | RFAMH (SEQ ID NO: 88) | VISYIGNNTKYYARSVKG (SEQ ID NO: 133) | GYDVLTGYPDY (SEQ ID NO: 171) |
| IPS:420943 | HV-38 | QVQLVESGGGVVQPGRSLR LSCAASGFTFSRFAMHWVR QAPGKGLEWVAVISYQGNN KYYARSVKGRFTISRDNSKN TLYLQMNSLRAEDTALFYC ARGYDVLTGYPDYWGQGTL VTVSS (SEQ ID NO: 228) | RFAMH (SEQ ID NO: 88) | VISYQGNNTKYYARSVKG (SEQ ID NO: 134) | GYDVLTGYPDY (SEQ ID NO: 171) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| IPS:420950 | HV-39 | QVQLVESGGGVVQPGRSLR LSCAASGFTFSRFAMHWVR QAPGKGLEWVAVISYYGNN KYYARSVKGRFTISRDNSKN TLYLQMNSLRAEDTALFYC ARGYDVLTGYPDYWGQGTL VTVSS (SEQ ID NO: 229) | RFAMH (SEQ ID NO: 88) | VISYYGNNTKYYARSVKG (SEQ ID NO: 135) | GYDVLTGYPDY (SEQ ID NO: 171) |
| iPS:420957 | HV-40 | QVQLVESGGGVVQPGRSLR LSCAASGFTFSRFAMHWVR QAPGKGLEWVAVISYNGRN KYYAESVKGRFTISRDNSKN TLYLQMNSLRAEDTALFYC ARGYDILTGYPDYWGQGTL VTVSS (SEQ ID NO: 230) | RFAMH (SEQ ID NO: 88) | VISYNGRNKYYAESVKG (SEQ ID NO: 114) | GYDILTGYPDY (SEQ ID NO: 172) |
| iPS:420964 | HV-41 | QVQLVESGGGVVQPGRSLR LSCAASGFTFSRFAMHWVR QAPGKGLEWVAVISYIGRNK YYAESVKGRFTISRDNSKNT LYLQMNSLRAEDTALFYCA RGYDILTGYPDYWGQGTLV TVSS (SEQ ID NO: 231) | RFAMH (SEQ ID NO: 88) | VISYIGRNKYYAESVKG (SEQ ID NO: 115) | GYDILTGYPDY (SEQ ID NO: 172) |
| iPS:420971 | HV-42 | QVQLVESGGGVVQPGRSLR LSCAASGFTFSRFAMHWVR QAPGKGLEWVAVISYQGRN KYYAESVKGRFTISRDNSKN TLYLQMNSLRAEDTALFYC ARGYDILTGYPDYWGQGTL VTVSS (SEQ ID NO: 232) | RFAMH (SEQ ID NO: 88) | VISYQGRNKYYAESVKG (SEQ ID NO: 116) | GYDILTGYPDY (SEQ ID NO: 172) |
| iPS:420978 | HV-43 | QVQLVESGGGVVQPGRSLR LSCAASGFTFSRFAMHWVR QAPGKGLEWVAVISYYGRN KYYAESVKGRFTISRDNSKN TLYLQMNSLRAEDTALFYC ARGYDILTGYPDYWGQGTL VTVSS (SEQ ID NO: 233) | RFAMH (SEQ ID NO: 88) | VISYYGRNKYYAESVKG (SEQ ID NO: 117) | GYDILTGYPDY (SEQ ID NO: 172) |
| iPS:420985 | HV-44 | QVQLVESGGGVVQPGRSLR LSCAASGFTFSRFAMHWVR QAPGKGLEWVAVISYNGNN KYYAESVKGRFTISRDNSKN TLYLQMNSLRAEDTALFYC ARGYDILTGYPDYWGQGTL VTVSS (SEQ ID NO: 234) | RFAMH (SEQ ID NO: 88) | VISYNGNNKYYAESVKG (SEQ ID NO: 118) | GYDILTGYPDY (SEQ ID NO: 172) |
| iPS:420992 | HV-45 | QVQLVESGGGVVQPGRSLR LSCAASGFTFSRFAMHWVR QAPGKGLEWVAVISYIGNN KYYAESVKGRFTISRDNSKN TLYLQMNSLRAEDTALFYC ARGYDILTGYPDYWGQGTL VTVSS (SEQ ID NO: 235) | RFAMH (SEQ ID NO: 88) | VISYIGNNKYYAESVKG (SEQ ID NO: 119) | GYDILTGYPDY (SEQ ID NO: 172) |
| iPS:420999 | HV-46 | QVQLVESGGGVVQPGRSLR LSCAASGFTFSRFAMHWVR QAPGKGLEWVAVISYQGNN KYYAESVKGRFTISRDNSKN TLYLQMNSLRAEDTALFYC ARGYDILTGYPDYWGQGTL VTVSS (SEQ ID NO: 236) | RFAMH (SEQ ID NO: 88) | VISYQGNNKYYAESVKG (SEQ ID NO: 120) | GYDILTGYPDY (SEQ ID NO: 172) |
| iPS:421006 | HV-47 | QVQLVESGGGVVQPGRSLR LSCAASGFTFSRFAMHWVR QAPGKGLEWVAVISYYGNN KYYAESVKGRFTISRDNSKN TLYLQMNSLRAEDTALFYC ARGYDILTGYPDYWGQGTL VTVSS (SEQ ID NO: 237) | RFAMH (SEQ ID NO: 88) | VISYYGNNKYYAESVKG (SEQ ID NO: 121) | GYDILTGYPDY (SEQ ID NO: 172) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| iPS:421013 | HV-48 | QVQLVESGGGVVQPGRSLR LSCAASGFTFSRFAMHWVR QAPGKGLEWVAVISYDGRN KYYARSVKGRFTISRDNSKN TLYLQMNSLRAEDTALFYC ARGYDILTGYPDYWGQGTL VTVSS (SEQ ID NO: 238) | RFAMH (SEQ ID NO: 88) | VISYDGRNKYYARSVKG (SEQ ID NO: 126) | GYDILTGYPDY (SEQ ID NO: 172) |
| iPS:421020 | HV-49 | QVQLVESGGGVVQPGRSLR LSCAASGFTFSRFAMHWVR QAPGKGLEWVAVISYDGNN KYYARSVKGRFTISRDNSKN TLYLQMNSLRAEDTALFYC ARGYDILTGYPDYWGQGTL VTVSS (SEQ ID NO: 239) | RFAMH (SEQ ID NO: 88) | VISYDGNNKYYARSVKG (SEQ ID NO: 127) | GYDILTGYPDY (SEQ ID NO: 172) |
| iPS:421027 | HV-32 | QVQLVESGGGVVQPGRSLR LSCAASGFTFSRFAMHWVR QAPGKGLEWVAVISYNGRN KYYARSVKGRFTISRDNSKN TLYLQMNSLRAEDTALFYC ARGYDVLTGYPDYWGQGTL VTVSS (SEQ ID NO: 222) | RFAMH (SEQ ID NO: 88) | VISYNGRNKYYARSVKG (SEQ ID NO: 128) | GYDVLTGYPDY (SEQ ID NO: 171) |
| IPS:421031 | HV-33 | QVQLVESGGGVVQPGRSLR LSCAASGFTFSRFAMHWVR QAPGKGLEWVAVISYIGRNK YYARSVKGRFTISRDNSKNT LYLQMNSLRAEDTALFYCA RGYDVLTGYPDYWGQGTLV TVSS (SEQ ID NO: 223) | RFAMH (SEQ ID NO: 88) | VISYIGRNKYYARSVKG (SEQ ID NO: 129) | GYDVLTGYPDY (SEQ ID NO: 171) |
| IPS:421035 | HV-34 | QVQLVESGGGVVQPGRSLR LSCAASGFTFSRFAMHWVR QAPGKGLEWVAVISYQGRN KYYARSVKGRFTISRDNSKN TLYLQMNSLRAEDTALFYC ARGYDVLTGYPDYWGQGTL VTVSS (SEQ ID NO: 224) | RFAMH (SEQ ID NO: 88) | VISYQGRNKYYARSVKG (SEQ ID NO: 130) | GYDVLTGYPDY (SEQ ID NO: 171) |
| IPS:421039 | HV-35 | QVQLVESGGGVVQPGRSLR LSCAASGFTFSRFAMHWVR QAPGKGLEWVAVISYYGRN KYYARSVKGRFTISRDNSKN TLYLQMNSLRAEDTALFYC ARGYDVLTGYPDYWGQGTL VTVSS (SEQ ID NO: 225) | RFAMH (SEQ ID NO: 88) | VISYYGRNKYYARSVKG (SEQ ID NO: 131) | GYDVLTGYPDY (SEQ ID NO: 171) |
| iPS:421043 | HV-36 | QVQLVESGGGVVQPGRSLR LSCAASGFTFSRFAMHWVR QAPGKGLEWVAVISYNGNN KYYARSVKGRFTISRDNSKN TLYLQMNSLRAEDTALFYC ARGYDVLTGYPDYWGQGTL VTVSS (SEQ ID NO: 226) | RFAMH (SEQ ID NO: 88) | VISYNGNNKYYARSVKG (SEQ ID NO: 132) | GYDVLTGYPDY (SEQ ID NO: 171) |
| iPS:421047 | HV-37 | QVQLVESGGGVVQPGRSLR LSCAASGFTFSRFAMHWVR QAPGKGLEWVAVISYIGNN KYYARSVKGRFTISRDNSKN TLYLQMNSLRAEDTALFYC ARGYDVLTGYPDYWGQGTL VTVSS (SEQ ID NO: 227) | RFAMH (SEQ ID NO: 88) | VISYIGNNKYYARSVKG (SEQ ID NO: 133) | GYDVLTGYPDY (SEQ ID NO: 171) |
| IPS:421051 | HV-38 | QVQLVESGGGVVQPGRSLR LSCAASGFTFSRFAMHWVR QAPGKGLEWVAVISYQGNN KYYARSVKGRFTISRDNSKN TLYLQMNSLRAEDTALFYC ARGYDVLTGYPDYWGQGTL VTVSS (SEQ ID NO: 228) | RFAMH (SEQ ID NO: 88) | VISYQGNNKYYARSVKG (SEQ ID NO: 134) | GYDVLTGYPDY (SEQ ID NO: 171) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| IPS:421055 | HV-39 | QVQLVESGGGVVQPGRSLRLSCAASGFTFSRFAMHWVRQAPGKGLEWVAVISYYGNNKYYARSVKGRFTISRDNSKNTLYLQMNSLRAEDTALFYCARGYDVLTGYPDYWGQGTLVTVSS (SEQ ID NO: 229) | RFAMH (SEQ ID NO: 88) | VISYYGNNKYYARSVKG (SEQ ID NO: 135) | GYDVLTGYPDY (SEQ ID NO: 171) |
| iPS:421059 | HV-40 | QVQLVESGGGVVQPGRSLRLSCAASGFTFSRFAMHWVRQAPGKGLEWVAVISYNGRNKYYAESVKGRFTISRDNSKNTLYLQMNSLRAEDTALFYCARGYDILTGYPDYWGQGTLVTVSS (SEQ ID NO: 230) | RFAMH (SEQ ID NO: 88) | VISYNGRNKYYAESVKG (SEQ ID NO: 114) | GYDILTGYPDY (SEQ ID NO: 172) |
| iPS:421063 | HV-41 | QVQLVESGGGVVQPGRSLRLSCAASGFTFSRFAMHWVRQAPGKGLEWVAVISYIGRNKYYAESVKGRFTISRDNSKNTLYLQMNSLRAEDTALFYCARGYDILTGYPDYWGQGTLVTVSS (SEQ ID NO: 231) | RFAMH (SEQ ID NO: 88) | VISYIGRNKYYAESVKG (SEQ ID NO: 115) | GYDILTGYPDY (SEQ ID NO: 172) |
| iPS:421067 | HV-42 | QVQLVESGGGVVQPGRSLRLSCAASGFTFSRFAMHWVRQAPGKGLEWVAVISYQGRNKYYAESVKGRFTISRDNSKNTLYLQMNSLRAEDTALFYCARGYDILTGYPDYWGQGTLVTVSS (SEQ ID NO: 232) | RFAMH (SEQ ID NO: 88) | VISYQGRNKYYAESVKG (SEQ ID NO: 116) | GYDILTGYPDY (SEQ ID NO: 172) |
| iPS:421071 | HV-43 | QVQLVESGGGVVQPGRSLRLSCAASGFTFSRFAMHWVRQAPGKGLEWVAVISYYGRNKYYAESVKGRFTISRDNSKNTLYLQMNSLRAEDTALFYCARGYDILTGYPDYWGQGTLVTVSS (SEQ ID NO: 233) | RFAMH (SEQ ID NO: 88) | VISYYGRNKYYAESVKG (SEQ ID NO: 117) | GYDILTGYPDY (SEQ ID NO: 172) |
| iPS:421075 | HV-44 | QVQLVESGGGVVQPGRSLRLSCAASGFTFSRFAMHWVRQAPGKGLEWVAVISYNGNNKYYAESVKGRFTISRDNSKNTLYLQMNSLRAEDTALFYCARGYDILTGYPDYWGQGTLVTVSS (SEQ ID NO: 234) | RFAMH (SEQ ID NO: 88) | VISYNGNNKYYAESVKG (SEQ ID NO: 118) | GYDILTGYPDY (SEQ ID NO: 172) |
| iPS:421079 | HV-45 | QVQLVESGGGVVQPGRSLRLSCAASGFTFSRFAMHWVRQAPGKGLEWVAVISYIGNNKYYAESVKGRFTISRDNSKNTLYLQMNSLRAEDTALFYCARGYDILTGYPDYWGQGTLVTVSS (SEQ ID NO: 235) | RFAMH (SEQ ID NO: 88) | VISYIGNNKYYAESVKG (SEQ ID NO: 119) | GYDILTGYPDY (SEQ ID NO: 172) |
| iPS:421083 | HV-46 | QVQLVESGGGVVQPGRSLRLSCAASGFTFSRFAMHWVRQAPGKGLEWVAVISYQGNNKYYAESVKGRFTISRDNSKNTLYLQMNSLRAEDTALFYCARGYDILTGYPDYWGQGTLVTVSS (SEQ ID NO: 236) | RFAMH (SEQ ID NO: 88) | VISYQGNNKYYAESVKG (SEQ ID NO: 120) | GYDILTGYPDY (SEQ ID NO: 172) |
| iPS:421087 | HV-47 | QVQLVESGGGVVQPGRSLRLSCAASGFTFSRFAMHWVRQAPGKGLEWVAVISYYGNNKYYAESVKGRFTISRDNSKNTLYLQMNSLRAEDTALFYCARGYDILTGYPDYWGQGTLVTVSS (SEQ ID NO: 237) | RFAMH (SEQ ID NO: 88) | VISYYGNNKYYAESVKG (SEQ ID NO: 121) | GYDILTGYPDY (SEQ ID NO: 172) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| iPS:421091 | HV-50 | QVQLVESGGGVVQPGRSLR LSCAASGFTFSRFAMHWVR QAPGKGLEWVAVISYNGRN KYYARSVKGRFTISRDNSKN TLYLQMNSLRAEDTALFYC ARGYDILTGYPDYWGQGTL VTVSS (SEQ ID NO: 240) | RFAMH (SEQ ID NO: 88) | VISYNGRNKYYARSVKG (SEQ ID NO: 128) | GYDILTGYPDY (SEQ ID NO: 172) |
| iPS:421098 | HV-51 | QVQLVESGGGVVQPGRSLR LSCAASGFTFSRFAMHWVR QAPGKGLEWVAVISYIGRNK YYARSVKGRFTISRDNSKNT LYLQMNSLRAEDTALFYCA RGYDILTGYPDYWGQGTLV TVSS (SEQ ID NO: 241) | RFAMH (SEQ ID NO: 88) | VISYIGRNKYYARSVKG (SEQ ID NO: 129) | GYDILTGYPDY (SEQ ID NO: 172) |
| iPS:421105 | HV-52 | QVQLVESGGGVVQPGRSLR LSCAASGFTFSRFAMHWVR QAPGKGLEWVAVISYQGRN KYYARSVKGRFTISRDNSKN TLYLQMNSLRAEDTALFYC ARGYDILTGYPDYWGQGTL VTVSS (SEQ ID NO: 242) | RFAMH (SEQ ID NO: 88) | VISYQGRNKYYARSVKG (SEQ ID NO: 130) | GYDILTGYPDY (SEQ ID NO: 172) |
| iPS:421112 | HV-53 | QVQLVESGGGVVQPGRSLR LSCAASGFTFSRFAMHWVR QAPGKGLEWVAVISYYGRN KYYARSVKGRFTISRDNSKN TLYLQMNSLRAEDTALFYC ARGYDILTGYPDYWGQGTL VTVSS (SEQ ID NO: 243) | RFAMH (SEQ ID NO: 88) | VISYYGRNKYYARSVKG (SEQ ID NO: 131) | GYDILTGYPDY (SEQ ID NO: 172) |
| iPS:421119 | HV-54 | QVQLVESGGGVVQPGRSLR LSCAASGFTFSRFAMHWVR QAPGKGLEWVAVISYNGNN KYYARSVKGRFTISRDNSKN TLYLQMNSLRAEDTALFYC ARGYDILTGYPDYWGQGTL VTVSS (SEQ ID NO: 244) | RFAMH (SEQ ID NO: 88) | VISYNGNNTKYYARSVKG (SEQ ID NO: 132) | GYDILTGYPDY (SEQ ID NO: 172) |
| iPS:421126 | HV-55 | QVQLVESGGGVVQPGRSLR LSCAASGFTFSRFAMHWVR QAPGKGLEWVAVISYIGNN KYYARSVKGRFTISRDNSKN TLYLQMNSLRAEDTALFYC ARGYDILTGYPDYWGQGTL VTVSS (SEQ ID NO: 245) | RFAMH (SEQ ID NO: 88) | VISYIGNNTKYYARSVKG (SEQ ID NO: 133) | GYDILTGYPDY (SEQ ID NO: 172) |
| iPS:421133 | HV-56 | QVQLVESGGGVVQPGRSLR LSCAASGFTFSRFAMHWVR QAPGKGLEWVAVISYQGNN KYYARSVKGRFTISRDNSKN TLYLQMNSLRAEDTALFYC ARGYDILTGYPDYWGQGTL VTVSS (SEQ ID NO: 246) | RFAMH (SEQ ID NO: 88) | VISYQGNNTKYYARSVKG (SEQ ID NO: 134) | GYDILTGYPDY (SEQ ID NO: 172) |
| iPS:421140 | HV-57 | QVQLVESGGGVVQPGRSLR LSCAASGFTFSRFAMHWVR QAPGKGLEWVAVISYYGNN KYYARSVKGRFTISRDNSKN TLYLQMNSLRAEDTALFYC ARGYDILTGYPDYWGQGTL VTVSS (SEQ ID NO: 247) | RFAMH (SEQ ID NO: 88) | VISYYGNNTKYYARSVKG (SEQ ID NO: 135) | GYDILTGYPDY (SEQ ID NO: 172) |
| iPS:421147 | HV-57 | QVQLVESGGGVVQPGRSLR LSCAASGFTFSRFAMHWVR QAPGKGLEWVAVISYYGNN KYYARSVKGRFTISRDNSKN TLYLQMNSLRAEDTALFYC ARGYDILTGYPDYWGQGTL VTVSS (SEQ ID NO: 247) | RFAMH (SEQ ID NO: 88) | VISYYGNNTKYYARSVKG (SEQ ID NO: 135) | GYDILTGYPDY (SEQ ID NO: 172) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
| --- | --- | --- | --- | --- | --- |
| iPS:421151 | HV-01 | QVQLVESGGGVVQPGRSLR LSCAASGFTFSRFAMHWVR QAPGKGLEWVAVISYDGGN KYYAESVKGRFTISRDNSKN TLYLQMNSLRAEDTALFYC ARGYDVLTGYPDYWGQGTL VTVSS (SEQ ID NO: 191) | RFAMH (SEQ ID NO: 88) | VISYDGGNKYYAESVKG (SEQ ID NO: 106) | GYDVLTGYPDY (SEQ ID NO: 171) |
| iPS:391478 | HV-01 | QVQLVESGGGVVQPGRSLR LSCAASGFTFSRFAMHWVR QAPGKGLEWVAVISYDGGN KYYAESVKGRFTISRDNSKN TLYLQMNSLRAEDTALFYC ARGYDVLTGYPDYWGQGTL VTVSS (SEQ ID NO: 191) | RFAMH (SEQ ID NO: 88) | VISYDGGNKYYAESVKG (SEQ ID NO: 106) | GYDVLTGYPDY (SEQ ID NO: 171) |
| iPS:421157 | HV-01 | QVQLVESGGGVVQPGRSLR LSCAASGFTFSRFAMHWVR QAPGKGLEWVAVISYDGGN KYYAESVKGRFTISRDNSKN TLYLQMNSLRAEDTALFYC ARGYDVLTGYPDYWGQGTL VTVSS (SEQ ID NO: 191) | RFAMH (SEQ ID NO: 88) | VISYDGGNKYYAESVKG (SEQ ID NO: 106) | GYDVLTGYPDY (SEQ ID NO: 171) |
| iPS:421163 | HV-58 | QVQLVESGGGVVQPGRSLR LSCAASGFTFSHFAMHWVR QAPGKGLEWVAVISYDGGN KYYAESVKGRFTISRDNSKN TLYLQMNSLRAEDTALFYC ARGYDVLTGYPDYWGQGTL VTVSS (SEQ ID NO: 248) | HFAMH (SEQ ID NO: 89) | VISYDGGNKYYAESVKG (SEQ ID NO: 106) | GYDVLTGYPDY (SEQ ID NO: 171) |
| iPS:391578 | HV-59 | QVQLVESGGGVVQPGRSLR LSCAASGFTFSRYAMHWVR QAPGKGLEWVAVISYDGGN KYYAESVKGRFTISRDNSKN TLYLQMNSLRAEDTALFYC ARGYDVLTGYPDYWGQGTL VTVSS (SEQ ID NO: 249) | RYAMH (SEQ ID NO: 90) | VISYDGGNKYYAESVKG (SEQ ID NO: 106) | GYDVLTGYPDY (SEQ ID NO: 171) |
| iPS:421170 | HV-60 | QVQLVESGGGVVQPGRSLR LSCAASGFTFSRFAMHWVR QAPGKGLEWVAVISFDGGN KYYAESVKGRFTISRDNSKN TLYLQMNSLRAEDTALFYC ARGYDVLTGYPDYWGQGTL VTVSS (SEQ ID NO: 250) | RFAMH (SEQ ID NO: 88) | VISFDGGNKYYAESVKG (SEQ ID NO: 136) | GYDVLTGYPDY (SEQ ID NO: 171) |
| iPS:421176 | HV-61 | QVQLVESGGGVVQPGRSLR LSCAASGFTFSRFAMHWVR QAPGKGLEWVAVISYDGAN KYYAESVKGRFTISRDNSKN TLYLQMNSLRAEDTALFYC ARGYDVLTGYPDYWGQGTL VTVSS (SEQ ID NO: 251) | RFAMH (SEQ ID NO: 88) | VISYDGANKYYAESVKG (SEQ ID NO: 137) | GYDVLTGYPDY (SEQ ID NO: 171) |
| iPS:421182 | HV-62 | QVQLVESGGGVVQPGRSLR LSCAASGFTFSRFAMHWVR QAPGKGLEWVAVISYDGGN KYYAESVKGRFTISRDNSKN TLYLQMNSLRAEDTALFYC ARGYDFLTGYPDYWGQGTL VTVSS (SEQ ID NO: 252) | RFAMH (SEQ ID NO: 88) | VISYDGGNKYYAESVKG (SEQ ID NO: 106) | GYDFLTGYPDY (SEQ ID NO: 173) |
| iPS:421189 | HV-01 | QVQLVESGGGVVQPGRSLR LSCAASGFTFSRFAMHWVR QAPGKGLEWVAVISYDGGN KYYAESVKGRFTISRDNSKN TLYLQMNSLRAEDTALFYC ARGYDVLTGYPDYWGQGTL VTVSS (SEQ ID NO: 191) | RFAMH (SEQ ID NO: 88) | VISYDGGNKYYAESVKG (SEQ ID NO: 106) | GYDVLTGYPDY (SEQ ID NO: 171) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| iPS:421195 | HV-01 | QVQLVESGGGVVQPGRSLR LSCAASGFTFSRFAMHWVR QAPGKGLEWVAVISYDGGN KYYAESVKGRFTISRDNSKN TLYLQMNSLRAEDTALFYC ARGYDVLTGYPDYWGQGTL VTVSS (SEQ ID NO: 191) | RFAMH (SEQ ID NO: 88) | VISYDGGNKYYAESVKG (SEQ ID NO: 106) | GYDVLTGYPDY (SEQ ID NO: 171) |
| iPS:421201 | HV-01 | QVQLVESGGGVVQPGRSLR LSCAASGFTFSRFAMHWVR QAPGKGLEWVAVISYDGGN KYYAESVKGRFTISRDNSKN TLYLQMNSLRAEDTALFYC ARGYDVLTGYPDYWGQGTL VTVSS (SEQ ID NO: 191) | RFAMH (SEQ ID NO: 88) | VISYDGGNKYYAESVKG (SEQ ID NO: 106) | GYDVLTGYPDY (SEQ ID NO: 171) |
| iPS:421207 | HV-58 | QVQLVESGGGVVQPGRSLR LSCAASGFTFSHFAMHWVR QAPGKGLEWVAVISYDGGN KYYAESVKGRFTISRDNSKN TLYLQMNSLRAEDTALFYC ARGYDVLTGYPDYWGQGTL VTVSS (SEQ ID NO: 248) | HFAMH (SEQ ID NO: 89) | VISYDGGNKYYAESVKG (SEQ ID NO: 106) | GYDVLTGYPDY (SEQ ID NO: 171) |
| iPS:421211 | HV-59 | QVQLVESGGGVVQPGRSLR LSCAASGFTFSRYAMHWVR QAPGKGLEWVAVISYDGGN KYYAESVKGRFTISRDNSKN TLYLQMNSLRAEDTALFYC ARGYDVLTGYPDYWGQGTL VTVSS (SEQ ID NO: 249) | RYAMH (SEQ ID NO: 90) | VISYDGGNKYYAESVKG (SEQ ID NO: 106) | GYDVLTGYPDY (SEQ ID NO: 171) |
| iPS:421215 | HV-60 | QVQLVESGGGVVQPGRSLR LSCAASGFTFSRFAMHWVR QAPGKGLEWVAVISFDGGN KYYAESVKGRFTISRDNSKN TLYLQMNSLRAEDTALFYC ARGYDVLTGYPDYWGQGTL VTVSS (SEQ ID NO: 250) | RFAMH (SEQ ID NO: 88) | VISFDGGNKYYAESVKG (SEQ ID NO: 136) | GYDVLTGYPDY (SEQ ID NO: 171) |
| iPS:421219 | HV-61 | QVQLVESGGGVVQPGRSLR LSCAASGFTFSRFAMHWVR QAPGKGLEWVAVISYDGAN KYYAESVKGRFTISRDNSKN TLYLQMNSLRAEDTALFYC ARGYDVLTGYPDYWGQGTL VTVSS (SEQ ID NO: 251) | RFAMH (SEQ ID NO: 88) | VISYDGANKYYAESVKG (SEQ ID NO: 137) | GYDVLTGYPDY (SEQ ID NO: 171) |
| iPS:421223 | HV-62 | QVQLVESGGGVVQPGRSLR LSCAASGFTFSRFAMHWVR QAPGKGLEWVAVISYDGGN KYYAESVKGRFTISRDNSKN TLYLQMNSLRAEDTALFYC ARGYDFLTGYPDYWGQGTL VTVSS (SEQ ID NO: 252) | RFAMH (SEQ ID NO: 88) | VISYDGGNKYYAESVKG (SEQ ID NO: 106) | GYDFLTGYPDY (SEQ ID NO: 173) |
| iPS:421227 | HV-03 | QVQLVESGGGVVQPGRSLR LSCAASGFTFSRFAMHWVR QAPGKGLEWVAVISYNGGN KYYAESVKGRFTISRDNSKN TLYLQMNSLRAEDTALFYC ARGYDVLTGYPDYWGQGTL VTVSS (SEQ ID NO: 193) | RFAMH (SEQ ID NO: 88) | VISYNGGNKYYAESVKG (SEQ ID NO: 107) | GYDVLTGYPDY (SEQ ID NO: 171) |
| iPS:421231 | HV-03 | QVQLVESGGGVVQPGRSLR LSCAASGFTFSRFAMHWVR QAPGKGLEWVAVISYNGGN KYYAESVKGRFTISRDNSKN TLYLQMNSLRAEDTALFYC ARGYDVLTGYPDYWGQGTL VTVSS (SEQ ID NO: 193) | RFAMH (SEQ ID NO: 88) | VISYNGGNKYYAESVKG (SEQ ID NO: 107) | GYDVLTGYPDY (SEQ ID NO: 171) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| iPS:421235 | HV-03 | QVQLVESGGGVVQPGRSLR LSCAASGFTFSRFAMHWVR QAPGKGLEWVAVISYNGGN KYYAESVKGRFTISRDNSKN TLYLQMNSLRAEDTALFYC ARGYDVLTGYPDYWGQGTL VTVSS (SEQ ID NO: 193) | RFAMH (SEQ ID NO: 88) | VISYNGGNKYYAESVKG (SEQ ID NO: 107) | GYDVLTGYPDY (SEQ ID NO: 171) |
| iPS:421239 | HV-63 | QVQLVESGGGVVQPGRSLR LSCAASGFTFSHFAMHWVR QAPGKGLEWVAVISYNGGN KYYAESVKGRFTISRDNSKN TLYLQMNSLRAEDTALFYC ARGYDVLTGYPDYWGQGTL VTVSS (SEQ ID NO: 253) | HFAMH (SEQ ID NO: 89) | VISYNGGNKYYAESVKG (SEQ ID NO: 107) | GYDVLTGYPDY (SEQ ID NO: 171) |
| iPS:421246 | HV-64 | QVQLVESGGGVVQPGRSLR LSCAASGFTFSRYAMHWVR QAPGKGLEWVAVISYNGGN KYYAESVKGRFTISRDNSKN TLYLQMNSLRAEDTALFYC ARGYDVLTGYPDYWGQGTL VTVSS (SEQ ID NO: 254) | RYAMH (SEQ ID NO: 90) | VISYNGGNKYYAESVKG (SEQ ID NO: 107) | GYDVLTGYPDY (SEQ ID NO: 171) |
| iPS:421253 | HV-65 | QVQLVESGGGVVQPGRSLR LSCAASGFTFSRFAMHWVR QAPGKGLEWVAVISFNGGN KYYAESVKGRFTISRDNSKN TLYLQMNSLRAEDTALFYC ARGYDVLTGYPDYWGQGTL VTVSS (SEQ ID NO: 255) | RFAMH (SEQ ID NO: 88) | VISFNGGNKYYAESVKG (SEQ ID NO: 138) | GYDVLTGYPDY (SEQ ID NO: 171) |
| iPS:421260 | HV-66 | QVQLVESGGGVVQPGRSLR LSCAASGFTFSRFAMHWVR QAPGKGLEWVAVISYNGAN KYYAESVKGRFTISRDNSKN TLYLQMNSLRAEDTALFYC ARGYDVLTGYPDYWGQGTL VTVSS (SEQ ID NO: 256) | RFAMH (SEQ ID NO: 88) | VISYNGANKYYAESVKG (SEQ ID NO: 139) | GYDVLTGYPDY (SEQ ID NO: 171) |
| iPS:421267 | HV-67 | QVQLVESGGGVVQPGRSLR LSCAASGFTFSRFAMHWVR QAPGKGLEWVAVISYNGGN KYYAESVKGRFTISRDNSKN TLYLQMNSLRAEDTALFYC ARGYDFLTGYPDYWGQGTL VTVSS (SEQ ID NO: 257) | RFAMH (SEQ ID NO: 88) | VISYNGGNKYYAESVKG (SEQ ID NO: 107) | GYDFLTGYPDY (SEQ ID NO: 173) |
| iPS:421274 | HV-07 | QVQLVESGGGVVQPGRSLR LSCAASGFTFSRFAMHWVR QAPGKGLEWVAVISYDGRN KYYAESVKGRFTISRDNSKN TLYLQMNSLRAEDTALFYC ARGYDVLTGYPDYWGQGTL VTVSS (SEQ ID NO: 197) | RFAMH (SEQ ID NO: 88) | VISYDGRNKYYAESVKG (SEQ ID NO: 111) | GYDVLTGYPDY (SEQ ID NO: 171) |
| iPS:421278 | HV-07 | QVQLVESGGGVVQPGRSLR LSCAASGFTFSRFAMHWVR QAPGKGLEWVAVISYDGRN KYYAESVKGRFTISRDNSKN TLYLQMNSLRAEDTALFYC ARGYDVLTGYPDYWGQGTL VTVSS (SEQ ID NO: 197) | RFAMH (SEQ ID NO: 88) | VISYDGRNKYYAESVKG (SEQ ID NO: 111) | GYDVLTGYPDY (SEQ ID NO: 171) |
| iPS:421282 | HV-07 | QVQLVESGGGVVQPGRSLR LSCAASGFTFSRFAMHWVR QAPGKGLEWVAVISYDGRN KYYAESVKGRFTISRDNSKN TLYLQMNSLRAEDTALFYC ARGYDVLTGYPDYWGQGTL VTVSS (SEQ ID NO: 197) | RFAMH (SEQ ID NO: 88) | VISYDGRNKYYAESVKG (SEQ ID NO: 111) | GYDVLTGYPDY (SEQ ID NO: 171) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| iPS:421286 | HV-68 | QVQLVESGGGVVQPGRSLR LSCAASGFTFSHFAMHWVR QAPGKGLEWVAVISYDGRN KYYAESVKGRFTISRDNSKN TLYLQMNSLRAEDTALFYC ARGYDVLTGYPDYWGQGTL VTVSS (SEQ ID NO: 258) | HFAMH (SEQ ID NO: 89) | VISYDGRNKYYAESVKG (SEQ ID NO: 111) | GYDVLTGYPDY (SEQ ID NO: 171) |
| iPS:421293 | HV-69 | QVQLVESGGGVVQPGRSLR LSCAASGFTFSRYAMHWVR QAPGKGLEWVAVISYDGRN KYYAESVKGRFTISRDNSKN TLYLQMNSLRAEDTALFYC ARGYDVLTGYPDYWGQGTL VTVSS (SEQ ID NO: 259) | RYAMH (SEQ ID NO: 90) | VISYDGRNKYYAESVKG (SEQ ID NO: 111) | GYDVLTGYPDY (SEQ ID NO: 171) |
| iPS:421300 | HV-70 | QVQLVESGGGVVQPGRSLR LSCAASGFTFSRFAMHWVR QAPGKGLEWVAVISFDGRN KYYAESVKGRFTISRDNSKN TLYLQMNSLRAEDTALFYC ARGYDVLTGYPDYWGQGTL VTVSS (SEQ ID NO: 260) | RFAMH (SEQ ID NO: 88) | VISFDGRNKYYAESVKG (SEQ ID NO: 140) | GYDVLTGYPDY (SEQ ID NO: 171) |
| iPS:421307 | HV-71 | QVQLVESGGGVVQPGRSLR LSCAASGFTFSRFAMHWVR QAPGKGLEWVAVISYDGRN KYYAESVKGRFTISRDNSKN TLYLQMNSLRAEDTALFYC ARGYDFLTGYPDYWGQGTL VTVSS (SEQ ID NO: 261) | RFAMH (SEQ ID NO: 88) | VISYDGRNKYYAESVKG (SEQ ID NO: 111) | GYDFLTGYPDY (SEQ ID NO: 173) |
| iPS:421314 | HV-09 | QVQLVESGGGVVQPGRSLR LSCAASGFTFSRFAMHWVR QAPGKGLEWVAVISYDGGN KYYARSVKGRFTISRDNSKN TLYLQMNSLRAEDTALFYC ARGYDVLTGYPDYWGQGTL VTVSS (SEQ ID NO: 199) | RFAMH (SEQ ID NO: 88) | VISYDGGNKYYARSVKG (SEQ ID NO: 113) | GYDVLTGYPDY (SEQ ID NO: 171) |
| iPS:421318 | HV-09 | QVQLVESGGGVVQPGRSLR LSCAASGFTFSRFAMHWVR QAPGKGLEWVAVISYDGGN KYYARSVKGRFTISRDNSKN TLYLQMNSLRAEDTALFYC ARGYDVLTGYPDYWGQGTL VTVSS (SEQ ID NO: 199) | RFAMH (SEQ ID NO: 88) | VISYDGGNKYYARSVKG (SEQ ID NO: 113) | GYDVLTGYPDY (SEQ ID NO: 171) |
| iPS:421322 | HV-09 | QVQLVESGGGVVQPGRSLR LSCAASGFTFSRFAMHWVR QAPGKGLEWVAVISYDGGN KYYARSVKGRFTISRDNSKN TLYLQMNSLRAEDTALFYC ARGYDVLTGYPDYWGQGTL VTVSS (SEQ ID NO: 199) | RFAMH (SEQ ID NO: 88) | VISYDGGNKYYARSVKG (SEQ ID NO: 113) | GYDVLTGYPDY (SEQ ID NO: 171) |
| iPS:421326 | HV-72 | QVQLVESGGGVVQPGRSLR LSCAASGFTFSHFAMHWVR QAPGKGLEWVAVISYDGGN KYYARSVKGRFTISRDNSKN TLYLQMNSLRAEDTALFYC ARGYDVLTGYPDYWGQGTL VTVSS (SEQ ID NO: 262) | HFAMH (SEQ ID NO: 89) | VISYDGGNKYYARSVKG (SEQ ID NO: 113) | GYDVLTGYPDY (SEQ ID NO: 171) |
| iPS:421333 | HV-73 | QVQLVESGGGVVQPGRSLR LSCAASGFTFSRYAMHWVR QAPGKGLEWVAVISYDGGN KYYARSVKGRFTISRDNSKN TLYLQMNSLRAEDTALFYC ARGYDVLTGYPDYWGQGTL VTVSS (SEQ ID NO: 263) | RYAMH (SEQ ID NO: 90) | VISYDGGNKYYARSVKG (SEQ ID NO: 113) | GYDVLTGYPDY (SEQ ID NO: 171) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| iPS:421340 | HV-74 | QVQLVESGGGVVQPGRSLR LSCAASGFTFSRFAMHWVR QAPGKGLEWVAVISFDGGN KYYARSVKGRFTISRDNSKN TLYLQMNSLRAEDTALFYC ARGYDVLTGYPDYWGQGTL VTVSS (SEQ ID NO: 264) | RFAMH (SEQ ID NO: 88) | VISFDGGNKYYARSVKG (SEQ ID NO: 141) | GYDVLTGYPDY (SEQ ID NO: 171) |
| iPS:421347 | HV-75 | QVQLVESGGGVVQPGRSLR LSCAASGFTFSRFAMHWVR QAPGKGLEWVAVISYDGAN KYYARSVKGRFTISRDNSKN TLYLQMNSLRAEDTALFYC ARGYDVLTGYPDYWGQGTL VTVSS (SEQ ID NO: 265) | RFAMH (SEQ ID NO: 88) | VISYDGANKYYARSVKG (SEQ ID NO: 142) | GYDVLTGYPDY (SEQ ID NO: 171) |
| iPS:421354 | HV-76 | QVQLVESGGGVVQPGRSLR LSCAASGFTFSRFAMHWVR QAPGKGLEWVAVISYDGGN KYYARSVKGRFTISRDNSKN TLYLQMNSLRAEDTALFYC ARGYDFLTGYPDYWGQGTL VTVSS (SEQ ID NO: 266) | RFAMH (SEQ ID NO: 88) | VISYDGGNKYYARSVKG (SEQ ID NO: 113) | GYDFLTGYPDY (SEQ ID NO: 173) |
| iPS:421361 | HV-10 | QVQLVESGGGVVQPGRSLR LSCAASGFTFSRFAMHWVR QAPGKGLEWVAVISYDGGN KYYAESVKGRFTISRDNSKN TLYLQMNSLRAEDTALFYC ARGYDILTGYPDYWGQGTL VTVSS (SEQ ID NO: 200) | RFAMH (SEQ ID NO: 88) | VISYDGGNKYYAESVKG (SEQ ID NO: 106) | GYDILTGYPDY (SEQ ID NO: 172) |
| iPS:421365 | HV-10 | QVQLVESGGGVVQPGRSLR LSCAASGFTFSRFAMHWVR QAPGKGLEWVAVISYDGGN KYYAESVKGRFTISRDNSKN TLYLQMNSLRAEDTALFYC ARGYDILTGYPDYWGQGTL VTVSS (SEQ ID NO: 200) | RFAMH (SEQ ID NO: 88) | VISYDGGNKYYAESVKG (SEQ ID NO: 106) | GYDILTGYPDY (SEQ ID NO: 172) |
| iPS:421369 | HV-10 | QVQLVESGGGVVQPGRSLR LSCAASGFTFSRFAMHWVR QAPGKGLEWVAVISYDGGN KYYAESVKGRFTISRDNSKN TLYLQMNSLRAEDTALFYC ARGYDILTGYPDYWGQGTL VTVSS (SEQ ID NO: 200) | RFAMH (SEQ ID NO: 88) | VISYDGGNKYYAESVKG (SEQ ID NO: 106) | GYDILTGYPDY (SEQ ID NO: 172) |
| iPS:421373 | HV-77 | QVQLVESGGGVVQPGRSLR LSCAASGFTFSHFAMHWVR QAPGKGLEWVAVISYDGGN KYYAESVKGRFTISRDNSKN TLYLQMNSLRAEDTALFYC ARGYDILTGYPDYWGQGTL VTVSS (SEQ ID NO: 267) | HFAMH (SEQ ID NO: 89) | VISYDGGNKYYAESVKG (SEQ ID NO: 106) | GYDILTGYPDY (SEQ ID NO: 172) |
| iPS:421380 | HV-78 | QVQLVESGGGVVQPGRSLR LSCAASGFTFSRYAMHWVR QAPGKGLEWVAVISYDGGN KYYAESVKGRFTISRDNSKN TLYLQMNSLRAEDTALFYC ARGYDILTGYPDYWGQGTL VTVSS (SEQ ID NO: 268) | RYAMH (SEQ ID NO: 90) | VISYDGGNKYYAESVKG (SEQ ID NO: 106) | GYDILTGYPDY (SEQ ID NO: 172) |
| iPS:421387 | HV-79 | QVQLVESGGGVVQPGRSLR LSCAASGFTFSRFAMHWVR QAPGKGLEWVAVISFDGGN KYYAESVKGRFTISRDNSKN TLYLQMNSLRAEDTALFYC ARGYDILTGYPDYWGQGTL VTVSS (SEQ ID NO: 269) | RFAMH (SEQ ID NO: 88) | VISFDGGNKYYAESVKG (SEQ ID NO: 136) | GYDILTGYPDY (SEQ ID NO: 172) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| iPS:421394 | HV-80 | QVQLVESGGGVVQPGRSLR LSCAASGFTFSRFAMHWVR QAPGKGLEWVAVISYDGAN KYYAESVKGRFTISRDNSKN TLYLQMNSLRAEDTALFYC ARGYDILTGYPDYWGQGTL VTVSS (SEQ ID NO: 270) | RFAMH (SEQ ID NO: 88) | VISYDGANKYYAESVKG (SEQ ID NO: 137) | GYDILTGYPDY (SEQ ID NO: 172) |
| iPS:421855 | HV-81 | QVQLVESGGGVVQPGRSLR LSCAASGFTFSKYAMHWVR QAPGKGLEWVAVISFKGSN KYYAESVKGRFTISRDNSKN TLYLQMNSLRAEDTALFYC ARGYDLLTGYPDYWGQGTL VTVSS (SEQ ID NO: 271) | KYAMH (SEQ ID NO: 91) | VISFKGSNKYYAESVKG (SEQ ID NO: 143) | GYDLLTGYPDY (SEQ ID NO: 174) |
| iPS:421861 | HV-82 | QVQLVESGGGVVQPGRSLR LSCAASGFTFSRYAMHWVR QAPGKGLEWVAVISYQGGN KYYAESVKGRFTISRDNSKN TLYLQMNSLRAEDTALFYC ARGYDLLTGYPDYWGQGTL VTVSS (SEQ ID NO: 272) | RYAMH (SEQ ID NO: 90) | VISFKGSNKYYAESVKG (SEQ ID NO: 109) | GYDLLTGYPDY (SEQ ID NO: 174) |
| iPS:421867 | HV-83 | QVQLVESGGGVVQPGRSLR LSCAASGFTFSHFAMHWVR QAPGKGLEWVAVISFSGSNK YYAESVKGRFTISRDNSKNT LYLQMNSLRAEDTALFYCA RGYDMLTGYPDYWGQGTL VTVSS (SEQ ID NO: 273) | HFAMH (SEQ ID NO: 89) | VISFSGSNKYYAESVKG (SEQ ID NO: 144) | GYDMLTGYPDY (SEQ ID NO: 175) |
| iPS:421873 | HV-84 | QVQLVESGGGVVQPGRSLR LSCAASGFTFSKFAMHWVR QAPGKGLEWVAVISYRGGN KYYAESVKGRFTISRDNSKN TLYLQMNSLRAEDTALFYC ARGYDLLTGYPDYWGQGTL VTVSS (SEQ ID NO: 274) | KFAMH (SEQ ID NO: 92) | VISYRGGNKYYAESVKG (SEQ ID NO: 145) | GYDLLTGYPDY (SEQ ID NO: 174) |
| iPS:421879 | HV-85 | QVQLVESGGGVVQPGRSLR LSCAASGFTFSRYAMHWVR QAPGKGLEWVAVISYSGAN KYYAESVKGRFTISRDNSKN TLYLQMNSLRAEDTALFYC ARGYDLLSGYPDYWGQGTL VTVSS (SEQ ID NO: 275) | RYAMH (SEQ ID NO: 90) | VISYSGANKYYAESVKG (SEQ ID NO: 146) | GYDLLSGYPDY (SEQ ID NO: 176) |
| iPS:421885 | HV-86 | QVQLVESGGGVVQPGRSLR LSCAASGFTFSHYAMHWVR QAPGKGLEWVAVISFKGAN KYYAESVKGRFTISRDNSKN TLYLQMNSLRAEDTALFYC ARGYDLLTGYPDYWGQGTL VTVSS (SEQ ID NO: 276) | HYAMH (SEQ ID NO: 93) | VISFKGANKYYAESVKG (SEQ ID NO: 147) | GYDLLTGYPDY (SEQ ID NO: 174) |
| iPS:421891 | HV-87 | QVQLVESGGGVVQPGRSLR LSCAASGFTFSHYAMHWVR QAPGKGLEWVAVISYRGAN KYYAESVKGRFTISRDNSKN TLYLQMNSLRAEDTALFYC ARGYDLLTGYPDYWGQGTL VTVSS (SEQ ID NO: 277) | HYAMH (SEQ ID NO: 93) | VISYRGANKYYAESVKG (SEQ ID NO: 148) | GYDLLTGYPDY (SEQ ID NO: 174) |
| iPS:421897 | HV-88 | QVQLVESGGGVVQPGRSLR LSCAASGFTFSHYAMHWVR QAPGKGLEWVAVISFYGSN KYYAESVKGRFTISRDNSKN TLYLQMNSLRAEDTALFYC ARGYDFLTGYPDYWGQGTL VTVSS (SEQ ID NO: 278) | HYAMH (SEQ ID NO: 93) | VISFYGSNKYYAESVKG (SEQ ID NO: 149) | GYDFLTGYPDY (SEQ ID NO: 173) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| iPS:421903 | HV-89 | QVQLVESGGGVVQPGRSLR LSCAASGFTFSHFAMHWVR QAPGKGLEWVAVISFFGGN KYYAESVKGRFTISRDNSKN TLYLQMNSLRAEDTALFYC ARGYDFLTGYPDYWGQGTL TVSS (SEQ ID NO: 279) | HFAMH (SEQ ID NO: 89) | VISFFGGNKYYAESVKG (SEQ ID NO: 150) | GYDFLTGYPDY (SEQ ID NO: 173) |
| iPS:421909 | HV-90 | QVQLVESGGGVVQPGRSLR LSCAASGFTFSHYAMHWVR QAPGKGLEWVAVISFMGTN KYYAESVKGRFTISRDNSKN TLYLQMNSLRAEDTALFYC ARGYDFLTGYPDYWGQGTL VTVSS (SEQ ID NO: 280) | HYAMH (SEQ ID NO: 93) | VISFMGTNKYYAESVKG (SEQ ID NO: 151) | GYDFLTGYPDY (SEQ ID NO: 173) |
| iPS:421915 | HV-91 | QVQLVESGGGVVQPGRSLR LSCAASGFTFSYFAMHWVR QAPGKGLEWVAVISHRGTN KYYAESVKGRFTISRDNSKN TLYLQMNSLRAEDTALFYC ARGYDLLSGYPDYWGQGTL VTVSS (SEQ ID NO: 281) | YFAMH (SEQ ID NO: 94) | VISHRGTNKYYAESVKG (SEQ ID NO: 152) | GYDLLSGYPDY (SEQ ID NO: 176) |
| iPS:480711 | HV-92 | QVQLVESGGGVVQPGRSLR LSCAASGFTFSRFAMHWVR QAPGKGLEWVGVINYRGHG KYYAESVKGRFTVSRDNSK NTLYLQMNSLRAEDTALFY CARGYDVLTGYPDYWGQG TLVTVSS (SEQ ID NO: 282) | RFAMH (SEQ ID NO: 88) | VINYRGHGKYYAESVKG (SEQ ID NO: 153) | GYDVLTGYPDY (SEQ ID NO: 171) |
| iPS:480706 | HV-93 | QVQLVESGGGVVQPGRSLR LSCAASGFTFSRFAMHWVR QAPGKGLEWVGVISFSGGSK YYAESVKGRFTLSRDNSKNT LYLQMNSLRAEDTALFYCA RGYDVLTGYPDYWGQGTLV TVSS (SEQ ID NO: 283) | RFAMH (SEQ ID NO: 88) | VISFSGGSKYYAESVKG (SEQ ID NO: 154) | GYDVLTGYPDY (SEQ ID NO: 171) |
| iPS:480713 | HV-94 | QVQLVESGGGVVQPGRSLR LSCAASGFTFSRFAMHWVR QAPGKGLEWVGVISYTGQF KYYAESVKGRFTVSRDNSK NTLYLQMNSLRAEDTALFY CARGYDVLTGYPDYWGQG TLVTVSS (SEQ ID NO: 284) | RFAMH (SEQ ID NO: 88) | VISYTGQFKYYAESVKG (SEQ ID NO: 155) | GYDVLTGYPDY (SEQ ID NO: 171) |
| iPS:480705 | HV-95 | QVQLVESGGGVVQPGRSLR LSCAASGFTFSRFAMHWVR QAPGKGLEWVGVISYTGAQ KYYAESVKGRFTMSRDNSK NTLYLQMNSLRAEDTALFY CARGYDVLTGYPDYWGQG TLVTVSS (SEQ ID NO: 285) | RFAMH (SEQ ID NO: 88) | VISYTGAQKYYAESVKG (SEQ ID NO: 156) | GYDVLTGYPDY (SEQ ID NO: 171) |
| iPS:48070 | HV-96 | QVQLVESGGGVVQPGRSLR LSCAASGFTFSRFAMHWVR QAPGKGLEWVGVISYSGAS KYYAESVKGRFTMSRDNSK NTLYLQMNSLRAEDTALFY CARGYDVLTGYPDYWGQG TLVTVSS (SEQ ID NO: 286) | RFAMH (SEQ ID NO: 88) | VISYSGASKYYAESVKG (SEQ ID NO: 157) | GYDVLTGYPDY (SEQ ID NO: 171) |
| iPS:480708 | HV-97 | QVQLVESGGGVVQPGRSLR LSCAASGFTFSRFAMHWVR QAPGKGLEWVAVISYSGAF KYYAESVKGRFTVSRDNSK NTLYLQMNSLRAEDTALFY CARGYDVLTGYPDYWGQG TLVTVSS (SEQ ID NO: 287) | RFAMH (SEQ ID NO: 88) | VISYSGAFKYYAESVKG (SEQ ID NO: 158) | GYDVLTGYPDY (SEQ ID NO: 171) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| iPS:480709 | HV-98 | QVQLVESGGGVVQPGRSLRLSCAASGFTFSRFAMHWVRQAPGKGLEWVGVITYTGGAKYYAESVKGRFTISRDNSKNTLYLQMNSLRAEDTALFYCARGYDVLTGYPDYWGQGTLVTVSS (SEQ ID NO: 288) | RFAMH (SEQ ID NO: 88) | VITYTGGAKYYAESVKG (SEQ ID NO: 159) | GYDVLTGYPDY (SEQ ID NO: 171) |
| iPS:480712 | HV-99 | QVQLVESGGGVVQPGRSLRLSCAASGFTFSRFAMHWVRQAPGKGLEWVGVINFQGTTKYYAESVKGRFTISRDNSKNTLYLQMNSLRAEDTALFYCARGYDVLTGYPDYWGQGTLVTVSS (SEQ ID NO: 289) | RFAMH (SEQ ID NO: 88) | VINFQGTTKYYAESVKG (SEQ ID NO: 160) | GYDVLTGYPDY (SEQ ID NO: 171) |
| iPS:480704 | HV-100 | QVQLVESGGGVVQPGRSLRLSCAASGFTFSRFAMHWVRQAPGKGLEWVGVISYSGDLKYYAESVKGRFTVSRDNSKNTLYLQMNSLRAEDTALFYCARGYDVLTGYPDYWGQGTLVTVSS (SEQ ID NO: 290) | RFAMH (SEQ ID NO: 88) | VISYSGDLKYYAESVKG (SEQ ID NO: 161) | GYDVLTGYPDY (SEQ ID NO: 171) |
| iPS:480710 | HV-101 | QVQLVESGGGVVQPGRSLRLSCAASGFTFSRFAMHWVRQAPGKGLEWVGVINYFGDAKYYAESVKGRFTISRDNSKNTLYLQMNSLRAEDTALFYCARGYDVLTGYPDYWGQGTLVTVSS (SEQ ID NO: 291) | RFAMH (SEQ ID NO: 88) | VINYFGDAKYYAESVKG (SEQ ID NO: 162) | GYDVLTGYPDY (SEQ ID NO: 171) |
| iPS:480716 | HV-102 | QVQLVESGGGVVQPGRSLRLSCAASGFTFSFYAMHWVRQAPGKGLEWVAVISSFGSNKYYAESVKGRFTISRDNSKNTLYLQMNSLRAEDTALFYCARGYDLLTGYPDYWGQGTLVTVSS (SEQ ID NO: 292) | FYAMH (SEQ ID NO: 95) | VISSFGSNKYYAESVKG (SEQ ID NO: 163) | GYDLLTGYPDY (SEQ ID NO: 174) |
| iPS:480715 | HV-103 | QVQLVESGGGVVQPGRSLRLSCAASGFTFSYYAMHWVRQAPGKGLEWVAVISYSGSNKYYAESVKGRFTISRDNSKNTLYLQMNSLRAEDTALFYCARGYDLLTGYPDYWGQGTLVTVSS (SEQ ID NO: 293) | YYAMEE (SEQ ID NO: 96) | VISYSGSNKYYAESVKG (SEQ ID NO: 164) | GYDLLTGYPDY (SEQ ID NO: 174) |
| iPS:480717 | HV-104 | QVQLVESGGGVVQPGRSLRLSCAASGFTFSYYAMHWVRQAPGKGLEWVAVISHYGTNKYYAESVKGRFTISRDNSKNTLYLQMNSLRAEDTALFYCARGYDPLTGYPDYWGQGTLVTVSS (SEQ ID NO: 294) | YYAMEE (SEQ ID NO: 96) | VISHYGTNKYYAESVKG (SEQ ID NO: 165) | GYDPLTGYPDY (SEQ ID NO: 177) |
| iPS:480714 | HV-105 | QVQLVESGGGVVQPGRSLRLSCAASGFTFSHYAMHWVRQAPGKGLEWVAVISYQGSNKYYAESVKGRFTISRDNSKNTLYLQMNSLRAEDTALFYCARGYDLLTGYPDYWGQGTLVTVSS (SEQ ID NO: 295) | HYAMH (SEQ ID NO: 93) | VISYQGSNKYYAESVKG (SEQ ID NO: 166) | GYDLLTGYPDY (SEQ ID NO: 174) |
| 19H8 variants | | | | | |
| 19H8 | HV-106 | QVQLQQSGPGLVKPSQTLSLTCAISGDSVSSNSATWNWIRQSPSRGLEWLGRTYYRSKWSNHYAVSVKSRITINPDTSKSQFSLQLNSVTPEDTAVYYCARGTWKQLWFLDHWGQGTLVTVSS (SEQ ID NO: 296) | SNSATWN (SEQ ID NO: 97) | RTYYRSKWSNHYAVSVKS (SEQ ID NO: 167) | GTWKQLWFLDH (SEQ ID NO: 178) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| iPS:448202 | HV-107 | QVQLQQSGPGLVKPSQTLSLTCAISGDSVSNRLATWNWIRQSPSRGLEWLGRTYYRGKWKNHYAVSVKSRITINPDTSKSQFSLQLNSVTPEDTAVYYCARGTWNQDWFLDHWGQGTLVTVSS (SEQ ID NO: 297) | NRLATWN (SEQ ID NO: 98) | RTYYRGKWKNHYAVSVKS (SEQ ID NO: 168) | GTWNQDWFLDH (SEQ ID NO: 179) |
| iPS:449375 | HV-108 | QVQLQQSGPGLVKPSQTLSLTCAISGDSVSNRLATWNWIRQSPSRGLEWLGRTYYRGKWKNHYAVSVKSRITINPDTSKSQFSLQLNSVTPEDTAVYYCARGTWDQDWFLDHWGQGTLVTVSS (SEQ ID NO: 298) | NRLATWN (SEQ ID NO: 98) | RTYYRGKWKNHYAVSVKS (SEQ ID NO: 168) | GTWDQDWFLDH (SEQ ID NO: 180) |
| iPS:448083 | HV-109 | QVQLQQSGPGLVKPSQTLSLTCAISGDSVSSRQATWNWIRQSPSRGLEWLGRTYYRGKWKNHYAVSVKSRITINPDTSKSQFSLQLNSVTPEDTAVYYCARGTWEQDWFLDHWGQGTLVTVSS (SEQ ID NO: 299) | SRQATWN (SEQ ID NO: 99) | RTYYRGKWKNHYAVSVKS (SEQ ID NO: 168) | GTWEQDWFLDH (SEQ ID NO: 181) |
| iPS:452128 | HV-110 | QVQLQQSGPGLVKPSQTLSLTCAISGDSVSNKQATWNWIRQSPSRGLEWLGRTYYRGKWKNHYAVSVKSRITINPDTSKSQFSLQLNSVTPEDTAVYYCARGMWNQNWFLDHWGQGTLVTVSS (SEQ ID NO: 300) | NKQATWN (SEQ ID NO: 100) | RTYYRGKWKNHYAVSVKS (SEQ ID NO: 168) | GMWNQNWFLDH (SEQ ID NO: 182) |
| iPS:448195 | HV-110 | QVQLQQSGPGLVKPSQTLSLTCAISGDSVSNKQATWNWIRQSPSRGLEWLGRTYYRGKWKNHYAVSVKSRITINPDTSKSQFSLQLNSVTPEDTAVYYCARGMWNQNVVFLDHWGQGTLVTVSS (SEQ ID NO: 300) | NKQATWN (SEQ ID NO: 100) | RTYYRGKWKNHYAVSVKS (SEQ ID NO: 168) | GMWNQNWFLDH (SEQ ID NO: 182) |
| iPS:448466 | HV-111 | QVQLQQSGPGLVKPSQTLSLTCAISGDSVSNKQATWNWIRQSPSRGLEWLGRTYYRGQWKNHYAVSVKSRITINPDTSKSQFSLQLNSVTPEDTAVYYCARGTWIGDWFMDHWGQGTLVTVSS (SEQ ID NO: 301) | NKQATWN (SEQ ID NO: 100) | RTYYRGQWKNHYAVSVKS (SEQ ID NO: 169) | GTWIGDWFMDH (SEQ ID NO: 183) |
| iPS:448689 | HV-107 | QVQLQQSGPGLVKPSQTLSLTCAISGDSVSNRLATWNWIRQSPSRGLEWLGRTYYRGKWKNHYAVSVKSRITINPDTSKSQFSLQLNSVTPEDTAVYYCARGTWNQDWFLDHWGQGTLVTVSS (SEQ ID NO: 297) | NRLATWN (SEQ ID NO: 98) | RTYYRGKWKNHYAVSVKS (SEQ ID NO: 168) | GTWNQDWFLDH (SEQ ID NO: 179) |
| iPS:449034 | HV-112 | QVQLQQSGPGLVKPSQTLSLTCAISGDSVSNKQATWNWIRQSPSRGLEWLGRTYYRGKWKNHYAVSVKSRITINPDTSKSQFSLQLNSVTPEDTAVYYCARGTWIQDWFLDHWGQGTLVTVSS (SEQ ID NO: 302) | NKQATWN (SEQ ID NO: 100) | RTYYRGKWKNHYAVSVKS (SEQ ID NO: 168) | GTWIQDWFLDH (SEQ ID NO: 184) |
| iPS:448075 | HV-113 | QVQLQQSGPGLVKPSQTLSLTCAISGDSVSSNHATWNWIRQSPSRGLEWLGRTYYRGKWKNHYAVSVKSRITINPDTSKSQFSLQLNSVTPEDTAVYYCARGTWDQDWFLDHWGQGTLVTVSS (SEQ ID NO: 303) | SNHATWN (SEQ ID NO: 101) | RTYYRGKWKNHYAVSVKS (SEQ ID NO: 168) | GTWDQDWFLDH (SEQ ID NO: 180) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| iPS:448924 | HV-114 | QVQLQQSGPGLVKPSQTLSLTCAISGDSVSSRYATWNWIRQSPSRGLEWLGRTYYRGQWKNHYAVSVKSRITINPDTSKSQFSLQLNSVTPEDTAVYYCARGMWNQNWFLDHWGQGTLVTVSS (SEQ ID NO: 304) | SRYATWN (SEQ ID NO: 102) | RTYYRGQWKNHYAVSVKS (SEQ ID NO: 169) | GMWNQNWFLDH (SEQ ID NO: 182) |
| iPS:448752 | HV-110 | QVQLQQSGPGLVKPSQTLSLTCAISGDSVSNKQATWNWIRQSPSRGLEWLGRTYYRGKWKNHYAVSVKSRITINPDTSKSQFSLQLNSVTPEDTAVYYCARGMWNQNWFLDHWGQGTLVTVSS (SEQ ID NO: 300) | NKQATWN (SEQ ID NO: 100) | RTYYRGKWKNHYAVSVKS (SEQ ID NO: 168) | GMWNQNWFLDH (SEQ ID NO: 182) |
| iPS:448772 | HV-115 | QVQLQQSGPGLVKPSQTLSLTCAISGDSVSNKQATWNWIRQSPSRGLEWLGRTYYRGKWKNHYAVSVKSRITINPDTSKSQFSLQLNSVTPEDTAVYYCARGMWSGDWFLDHWGQGTLVTVSS (SEQ ID NO: 305) | NKQATWN (SEQ ID NO: 100) | RTYYRGKWKNHYAVSVKS (SEQ ID NO: 168) | GMWSGDWFLDH (SEQ ID NO: 185) |
| iPS:448117 | HV-116 | QVQLQQSGPGLVKPSQTLSLTCAISGDSVSSHVATWNWIRQSPSRGLEWLGRTYYRGKWKNHYAVSVKSRITINPDTSKSQFSLQLNSVTPEDTAVYYCARGMWSEDWFLDHWGQGTLVTVSS (SEQ ID NO: 306) | SHVATWN (SEQ ID NO: 103) | RTYYRGKWKNHYAVSVKS (SEQ ID NO: 168) | GMWSEDWFLDH (SEQ ID NO: 186) |
| iPS:448788 | HV-117 | QVQLQQSGPGLVKPSQTLSLTCAISGDSVSSRQATWNWIRQSPSRGLEWLGRTYYRGKWKNHYAVSVKSRITINPDTSKSQFSLQLNSVTPEDTAVYYCARGMWQGNWFLDHWGQGTLVTVSS (SEQ ID NO: 307) | SRQATWN (SEQ ID NO: 99) | RTYYRGKWKNHYAVSVKS (SEQ ID NO: 168) | GMWQGNWFLDH (SEQ ID NO: 187) |
| iPS:448593 | HV-118 | QVQLQQSGPGLVKPSQTLSLTCAISGDSVSNHQATWNWIRQSPSRGLEWLGRTYYRGKWKNHYAVSVKSRITINPDTSKSQFSLQLNSVTPEDTAVYYCARGTWIQDWFLDHWGQGTLVTVSS (SEQ ID NO: 308) | NHQATWN (SEQ ID NO: 104) | RTYYRGKWKNHYAVSVKS (SEQ ID NO: 168) | GTWIQDWFLDH (SEQ ID NO: 184) |
| iPS:448238 | HV-119 | QVQLQQSGPGLVKPSQTLSLTCAISGDSVSSRDATWNWIRQSPSRGLEWLGRTYYRGKWKNHYAVSVKSRITINPDTSKSQFSLQLNSVTPEDTAVYYCARGQWNEDWFLDHWGQGTLVTVSS (SEQ ID NO: 309) | SRDATWN (SEQ ID NO: 105) | RTYYRGKWKNHYAVSVKS (SEQ ID NO: 168) | GQWNEDWFLDH (SEQ ID NO: 188) |
| iPS:448901 | HV-120 | QVQLQQSGPGLVKPSQTLSLTCAISGDSVSNRLATWNWIRQSPSRGLEWLGRTYYRGKWKNHYAVSVKSRITINPDTSKSQFSLQLNSVTPEDTAVYYCARGRWEGDWFFDHWGQGTLVTVSS (SEQ ID NO: 310) | NRLATWN (SEQ ID NO: 98) | RTYYRGKWKNHYAVSVKS (SEQ ID NO: 168) | GRWEGDWFFDH (SEQ ID NO: 189) |
| iPS:448655 | HV-121 | QVQLQQSGPGLVKPSQTLSLTCAISGDSVSNKQATWNWIRQSPSRGLEWLGRTYFRRTWKNHYAVSVKSRITINPDTSKSQFSLQLNSVTPEDTAVYYCARGMWSEDWFLDHWGQGTLVTVSS (SEQ ID NO: 311) | NKQATWN (SEQ ID NO: 100) | RTYFRRTWKNHYAVSVKS (SEQ ID NO: 170) | GMWSEDWFLDH (SEQ ID NO: 186) |

TABLE 1B-continued

Exemplary Anti-Human PAC1 Antibody Heavy Chain Variable Region Amino Acid Sequences

| Ab ID. | VH Group | VH Amino Acid Sequence | CDRH1 | CDRH2 | CDRH3 |
|---|---|---|---|---|---|
| iPS:448730 | HV-122 | QVQLQQSGPGLVKPSQTLSL TCAISGDSVSNRLATWNWIR QSPSRGLEWLGRTYYRGKW KNHYAVSVKSRITINPDTSKS QFSLQLNSVTPEDTAVYYCA RGVWIGNWFLDHWGQGTL VTVSS (SEQ ID NO: 312) | NRLATWN (SEQ ID NO: 98) | RTYYRGKWKNHYAVSVKS (SEQ ID NO: 168) | GVWIGNWFLDH (SEQ ID NO: 190) |
| iPS:449027 | HV-110 | QVQLQQSGPGLVKPSQTLSL TCAISGDSVSNKQATWNWIR QSPSRGLEWLGRTYYRGKW KNHYAVSVKSRITINPDTSKS QFSLQLNSVTPEDTAVYYCA RGMWNQNWFLDHWGQGTL VTVSS (SEQ ID NO: 300) | NKQATWN (SEQ ID NO: 100) | RTYYRGKWKNHYAVSVKS (SEQ ID NO: 168) | GMWNQNWFLDH (SEQ ID NO: 182) |
| 3574 | HV-110 | QVQLQQSGPGLVKPSQTLSL TCAISGDSVSNKQATWNWIR QSPSRGLEWLGRTYYRGKW KNHYAVSVKSRITINPDTSKS QFSLQLNSVTPEDTAVYYCA RGMWNQNWFLDHWGQGTL VTVSS (SEQ ID NO: 300) | NKQATWN (SEQ ID NO: 100) | RTYYRGKWKNHYAVSVKS (SEQ ID NO: 168) | GMWNQNWFLDH (SEQ ID NO: 182) |
| 3575 | HV-106 | QVQLQQSGPGLVKPSQTLSL TCAISGDSVSSNSATWNWIR QSPSRGLEWLGRTYYRSKW SNHYAVSVKSRITINPDTSKS QFSLQLNSVTPEDTAVYYCA RGTWKQLWFLDHWGQGTL VTVSS (SEQ ID NO: 296) | SNSATWN (SEQ ID NO: 97) | RTYYRSKWSNHYAVSVKS (SEQ ID NO: 167) | GTWKQLWFLDH (SEQ ID NO: 178) |

The anti-PAC1 antibodies or antigen-binding fragments of the invention may comprise one or more of the light chain CDRs (i.e. CDRLs) and/or heavy chain CDRs (i.e. CDRHs) presented in Tables 1A and 1B, respectively. In some embodiments, the anti-PAC1 antibodies or binding fragments thereof are derived from antibody 29G4v9, 29G4v10, or 29G4v22 (i.e. has one or more substitutions in one or more of the CDRLs and/or CDRHs of the 29G4v9, 29G4v10, or 29G4v22 antibody). For instance, in certain embodiments, the anti-PAC1 antibodies or antigen-binding fragments comprise one or more light chain CDRs selected from (i) a CDRL1 selected from SEQ ID NOs: 5 to 16, (ii) a CDRL2 of SEQ ID NO: 26, and (iii) a CDRL3 selected from SEQ ID NOs: 36 to 38, and (iv) a CDRL of (i), (ii) and (iii) that contains one or more, e.g., one, two, three, four or more amino acid substitutions (e.g., conservative amino acid substitutions), deletions or insertions of no more than five, four, three, two, or one amino acids. In these and other embodiments, the anti-PAC1 antibodies or antigen-binding fragments comprise one or more heavy chain CDRs selected from (i) a CDRH1 selected from SEQ ID NOs: 88 to 96, (ii) a CDRH2 selected from SEQ ID NOs: 106 to 166, and (iii) a CDRH3 selected from SEQ ID NOs: 171 to 177, and (iv) a CDRH of (i), (ii) and (iii) that contains one or more, e.g., one, two, three, four or more amino acid substitutions (e.g., conservative amino acid substitutions), deletions or insertions of no more than five, four, three, two, or one amino acids amino acids.

In other embodiments, the anti-PAC1 antibodies or binding fragments thereof are derived from antibody 19H8 (i.e. has one or more substitutions in one or more of the CDRLs and/or CDRHs of the 19H8 antibody). In such embodiments, the anti-PAC1 antibodies or antigen-binding fragments comprise one or more light chain CDRs selected from (i) a CDRL1 selected from SEQ ID NOs: 17 to 25, (ii) a CDRL2 selected from SEQ ID NOs: 27 to 35, and (iii) a CDRL3 selected from SEQ ID NOs: 39 to 51, and (iv) a CDRL of (i), (ii) and (iii) that contains one or more, e.g., one, two, three, four or more amino acid substitutions (e.g., conservative amino acid substitutions), deletions or insertions of no more than five, four, three, two, or one amino acids. In these and other embodiments, the anti-PAC1 antibodies or antigen-binding fragments comprise one or more heavy chain CDRs selected from (i) a CDRH1 selected from SEQ ID NOs: 97 to 105, (ii) a CDRH2 selected from SEQ ID NOs: 167 to 170, and (iii) a CDRH3 selected from SEQ ID NOs: 178 to 190, and (iv) a CDRH of (i), (ii) and (iii) that contains one or more, e.g., one, two, three, four or more amino acid substitutions (e.g., conservative amino acid substitutions), deletions or insertions of no more than five, four, three, two, or one amino acids amino acids.

In certain embodiments, the anti-PAC1 antibodies or antigen-binding fragments may comprise 1, 2, 3, 4, 5, or 6 variant forms of the CDRs listed in Tables 1A and 1B, each having at least 80%, 85%, 90% or 95% sequence identity to a CDR sequence listed in Tables 1A and 1B. In some embodiments, the anti-PAC1 antibodies or antigen-binding fragments include 1, 2, 3, 4, 5, or 6 of the CDRs listed in Tables 1A and 1B, each differing by no more than 1, 2, 3, 4 or 5 amino acids from the CDRs listed in these tables. In some embodiments, the anti-PAC1 antibodies or antigen-binding fragments of the invention comprise a CDRL1 comprising a sequence selected from SEQ ID NOs: 5 to 16 or a variant thereof having one, two, three or four amino acid substitutions; a CDRL2 comprising the sequence of SEQ ID NO: 26 or a variant thereof having one, two, three or four amino acid substitutions; a CDRL3 comprising a sequence selected from SEQ ID NOs: 36 to 38 or a variant thereof having one, two, three or four amino acid substitutions; a CDRH1 comprising a sequence selected from SEQ ID NOs: 88 to 96 or a variant thereof having one, two, three or four amino acid substitutions; a CDRH2 comprising a sequence selected from SEQ ID NOs: 106 to 166 or a variant thereof having one, two, three or four amino acid substitutions; and a CDRH3 comprising a sequence selected from SEQ ID NOs: 171 to 177 or a variant thereof having one, two, three or four amino acid substitutions. In other embodiments, the anti-PAC1 antibodies or antigen-binding fragments of the invention comprise a CDRL1 comprising a sequence selected from SEQ ID NOs: 5 to 16; a CDRL2 comprising the sequence of SEQ ID NO: 26; a CDRL3 comprising a sequence selected from SEQ ID NOs: 36 to 38; a CDRH1 comprising a sequence selected from SEQ ID NOs: 88 to 96; a CDRH2 comprising a sequence selected from SEQ ID NOs: 106 to 166; and a CDRH3 comprising a sequence selected from SEQ ID NOs: 171 to 177.

In other embodiments, the anti-PAC1 antibodies or antigen-binding fragments of the invention comprise a CDRL1 comprising a sequence selected from SEQ ID NOs: 17 to 25 or a variant thereof having one, two, three or four amino acid substitutions; a CDRL2 comprising a sequence selected from SEQ ID NOs: 27 to 35 or a variant thereof having one, two, three or four amino acid substitutions; a CDRL3 comprising a sequence selected from SEQ ID NOs: 39 to 51 or a variant thereof having one, two, three or four amino acid substitutions; a CDRH1 comprising a sequence selected from SEQ ID NOs: 97 to 105 or a variant thereof having one, two, three or four amino acid substitutions; a CDRH2 comprising a sequence selected from SEQ ID NOs: 167 to 170 or a variant thereof having one, two, three or four amino acid substitutions; and a CDRH3 comprising a sequence selected from SEQ ID NOs: 178 to 190 or a variant thereof having one, two, three or four amino acid substitutions. In other embodiments, the anti-PAC1 antibodies or antigen-binding fragments of the invention comprise a CDRL1 comprising a sequence selected from SEQ ID NOs: 17 to 25; a CDRL2 comprising a sequence selected from SEQ ID NOs: 27 to 35; a CDRL3 comprising a sequence selected from SEQ ID NOs: 39 to 51; a CDRH1 comprising a sequence selected from SEQ ID NOs: 97 to 105; a CDRH2 comprising a sequence selected from SEQ ID NOs: 167 to 170; and a CDRH3 comprising a sequence selected from SEQ ID NOs: 178 to 190.

In particular embodiments, the anti-PAC1 antibodies or antigen-binding fragments of the invention comprise a light chain variable region comprising a CDRL1, a CDRL2, and a CDRL3, wherein: (a) CDRL1, CDRL2, and CDRL3 have the sequence of SEQ ID NOs: 7, 26, and 36, respectively; (b) CDRL1, CDRL2, and CDRL3 have the sequence of SEQ ID NOs: 5, 26, and 36, respectively; (c) CDRL1, CDRL2, and CDRL3 have the sequence of SEQ ID NOs: 12, 26, and 36, respectively; or (d) CDRL1, CDRL2, and CDRL3 have the sequence of SEQ ID NOs: 13, 26, and 36, respectively.

In other particular embodiments, the anti-PAC1 antibodies or antigen-binding fragments of the invention comprise a heavy chain variable region comprising a CDRH1, a CDRH2, and a CDRH3, wherein: (a) CDRH1, CDRH2, and CDRH3 have the sequence of SEQ ID NOs: 88, 108, and 171, respectively; (b) CDRH1, CDRH2, and CDRH3 have the sequence of SEQ ID NOs: 88, 116, and 171, respectively; (c) CDRH1, CDRH2, and CDRH3 have the sequence of SEQ ID NOs: 88, 134, and 171, respectively; (d) CDRH1, CDRH2, and CDRH3 have the sequence of SEQ ID NOs: 92, 145, and 174, respectively; (e) CDRH1, CDRH2, and CDRH3 have the sequence of SEQ ID NOs: 88, 108, and 172, respectively; (f) CDRH1, CDRH2, and CDRH3 have the sequence of SEQ ID NOs: 88, 128, and 172, respectively; (g) CDRH1, CDRH2, and CDRH3 have the sequence of SEQ ID NOs: 88, 153, and 171, respectively; (i) CDRH1, CDRH2, and CDRH3 have the sequence of SEQ ID NOs: 88, 154, and 171, respectively; or (j) CDRH1, CDRH2, and CDRH3 have the sequence of SEQ ID NOs: 88, 155, and 171, respectively.

In certain embodiments, the anti-PAC1 antibodies or antigen-binding fragments of the invention comprise a light chain variable region comprising a CDRL1, a CDRL2, and a CDRL3 and a heavy chain variable region comprising a CDRH1, a CDRH2, and a CDRH3, wherein:

(a) CDRL1, CDRL2, and CDRL3 have the sequence of SEQ ID NOs: 7, 26, and 36, respectively, and CDRH1, CDRH2, and CDRH3 have the sequence of SEQ ID NOs: 88, 108, and 171, respectively;

(b) CDRL1, CDRL2, and CDRL3 have the sequence of SEQ ID NOs: 7, 26, and 36, respectively, and CDRH1, CDRH2, and CDRH3 have the sequence of SEQ ID NOs: 88, 116, and 171, respectively;

(c) CDRL1, CDRL2, and CDRL3 have the sequence of SEQ ID NOs: 5, 26, and 36, respectively, and CDRH1, CDRH2, and CDRH3 have the sequence of SEQ ID NOs: 88, 134, and 171, respectively;

(d) CDRL1, CDRL2, and CDRL3 have the sequence of SEQ ID NOs: 5, 26, and 36, respectively, and CDRH1, CDRH2, and CDRH3 have the sequence of SEQ ID NOs: 92, 145, and 174, respectively;

(e) CDRL1, CDRL2, and CDRL3 have the sequence of SEQ ID NOs: 7, 26, and 36, respectively, and CDRH1, CDRH2, and CDRH3 have the sequence of SEQ ID NOs: 88, 108, and 172, respectively;

(f) CDRL1, CDRL2, and CDRL3 have the sequence of SEQ ID NOs: 5, 26, and 36, respectively, and CDRH1, CDRH2, and CDRH3 have the sequence of SEQ ID NOs: 88, 128, and 172, respectively;

(g) CDRL1, CDRL2, and CDRL3 have the sequence of SEQ ID NOs: 7, 26, and 36, respectively, and CDRH1, CDRH2, and CDRH3 have the sequence of SEQ ID NOs: 88, 134, and 171, respectively;

(h) CDRL1, CDRL2, and CDRL3 have the sequence of SEQ ID NOs: 12, 26, and 36, respectively, and CDRH1, CDRH2, and CDRH3 have the sequence of SEQ ID NOs: 88, 153, and 171, respectively;

(i) CDRL1, CDRL2, and CDRL3 have the sequence of SEQ ID NOs: 12, 26, and 36, respectively, and CDRH1, CDRH2, and CDRH3 have the sequence of SEQ ID NOs: 88, 154, and 171, respectively; or (j) CDRL1, CDRL2, and CDRL3 have the sequence of SEQ ID NOs: 13, 26, and 36, respectively, and CDRH1, CDRH2, and CDRH3 have the sequence of SEQ ID NOs: 88, 155, and 171, respectively.

In one embodiment, the anti-PAC1 antibody or antigen-binding fragment thereof comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 7, 26, and 36, respectively, and CDRH1, CDRH2, and CDRH3 have the sequence of SEQ ID NOs: 88, 108, and 171, respectively. In another embodiment, the anti-PAC1 antibody or antigen-binding fragment thereof comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 7, 26, and 36, respectively, and CDRH1, CDRH2, and CDRH3 have the sequence of SEQ ID NOs: 88, 116, and 171, respectively. In yet another embodiment, the anti-PAC1 antibody or antigen-binding fragment thereof comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 5, 26, and 36, respectively, and CDRH1, CDRH2, and CDRH3 have the sequence of SEQ ID NOs: 88, 134, and 171, respectively. In still another embodiment, the anti-PAC1 antibody or antigen-binding fragment thereof comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 5, 26, and 36, respectively, and CDRH1, CDRH2, and CDRH3 have the sequence of SEQ ID NOs: 92, 145, and 174, respectively. In one particular embodiment, the anti-PAC1 antibody or antigen-binding fragment thereof comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 7, 26, and 36, respectively, and CDRH1, CDRH2, and CDRH3 have the sequence of SEQ ID NOs: 88, 108, and 172, respectively. In another particular embodiment, the anti-PAC1 antibody or antigen-binding fragment thereof comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 12, 26, and 36, respectively, and CDRH1, CDRH2, and CDRH3 have the sequence of SEQ ID NOs: 88, 153, and 171, respectively.

In certain embodiments, the anti-PAC1 antibodies or antigen-binding fragments of the invention comprise a light chain variable region comprising a CDRL1, a CDRL2, and a CDRL3, wherein: (a) CDRL1, CDRL2, and CDRL3 have the sequence of SEQ ID NOs: 25, 31, and 42, respectively; (b) CDRL1, CDRL2, and CDRL3 have the sequence of SEQ ID NOs: 20, 30, and 44, respectively; (c) CDRL1, CDRL2, and CDRL3 have the sequence of SEQ ID NOs: 17, 33, and 42, respectively; (d) CDRL1, CDRL2, and CDRL3 have the sequence of SEQ ID NOs: 23, 31, and 50, respectively; (e) CDRL1, CDRL2, and CDRL3 have the sequence of SEQ ID NOs: 17, 31, and 44, respectively; (f) CDRL1, CDRL2, and CDRL3 have the sequence of SEQ ID NOs: 17, 27, and 39, respectively; (g) CDRL1, CDRL2, and CDRL3 have the sequence of SEQ ID NOs: 18, 31, and 46, respectively; (h) CDRL1, CDRL2, and CDRL3 have the sequence of SEQ ID NOs: 17, 28, and 40, respectively; (i) CDRL1, CDRL2, and CDRL3 have the sequence of SEQ ID NOs: 18, 30, and 43, respectively; or (j) CDRL1, CDRL2, and CDRL3 have the sequence of SEQ ID NOs: 22, 28, and 49, respectively.

In certain other embodiments, the anti-PAC1 antibodies or antigen-binding fragments of the invention comprise a heavy chain variable region comprising a CDRH1, a CDRH2, and a CDRH3, wherein: (a) CDRH1, CDRH2, and CDRH3 have the sequence of SEQ ID NOs: 98, 168, and 190, respectively; (b) CDRH1, CDRH2, and CDRH3 have the sequence of SEQ ID NOs: 100, 168, and 182, respectively; (c) CDRH1, CDRH2, and CDRH3 have the sequence of SEQ ID NOs: 99, 168, and 187, respectively; (d) CDRH1, CDRH2, and CDRH3 have the sequence of SEQ ID NOs: 97, 167, and 178, respectively; (e) CDRH1, CDRH2, and CDRH3 have the sequence of SEQ ID NOs: 98, 168, and 189, respectively; (f) CDRH1, CDRH2, and CDRH3 have the sequence of SEQ ID NOs: 98, 168, and 179, respectively; or (g) CDRH1, CDRH2, and CDRH3 have the sequence of SEQ ID NOs: 102, 169, and 182, respectively.

In some embodiments, the anti-PAC1 antibodies or antigen-binding fragments of the invention comprise a light chain variable region comprising a CDRL1, a CDRL2, and a CDRL3 and a heavy chain variable region comprising a CDRH1, a CDRH2, and a CDRH3, wherein:

(a) CDRL1, CDRL2, and CDRL3 have the sequence of SEQ ID NOs: 25, 31, and 42, respectively, and CDRH1, CDRH2, and CDRH3 have the sequence of SEQ ID NOs: 98, 168, and 190, respectively;
(b) CDRL1, CDRL2, and CDRL3 have the sequence of SEQ ID NOs: 20, 30, and 44, respectively, and CDRH1, CDRH2, and CDRH3 have the sequence of SEQ ID NOs: 100, 168, and 182, respectively;
(c) CDRL1, CDRL2, and CDRL3 have the sequence of SEQ ID NOs: 17, 33, and 42, respectively, and CDRH1, CDRH2, and CDRH3 have the sequence of SEQ ID NOs: 99, 168, and 187, respectively;
(d) CDRL1, CDRL2, and CDRL3 have the sequence of SEQ ID NOs: 23, 31, and 50, respectively, and CDRH1, CDRH2, and CDRH3 have the sequence of SEQ ID NOs: 97, 167, and 178, respectively;
(e) CDRL1, CDRL2, and CDRL3 have the sequence of SEQ ID NOs: 17, 31, and 44, respectively, and CDRH1, CDRH2, and CDRH3 have the sequence of SEQ ID NOs: 98, 168, and 189, respectively;
(f) CDRL1, CDRL2, and CDRL3 have the sequence of SEQ ID NOs: 17, 27, and 39, respectively, and CDRH1, CDRH2, and CDRH3 have the sequence of SEQ ID NOs: 100, 168, and 182, respectively;
(g) CDRL1, CDRL2, and CDRL3 have the sequence of SEQ ID NOs: 18, 31, and 46, respectively, and CDRH1, CDRH2, and CDRH3 have the sequence of SEQ ID NOs: 98, 168, and 179, respectively;
(h) CDRL1, CDRL2, and CDRL3 have the sequence of SEQ ID NOs: 17, 28, and 40, respectively, and CDRH1, CDRH2, and CDRH3 have the sequence of SEQ ID NOs: 98, 168, and 179, respectively;
(i) CDRL1, CDRL2, and CDRL3 have the sequence of SEQ ID NOs: 18, 30, and 43, respectively, and CDRH1, CDRH2, and CDRH3 have the sequence of SEQ ID NOs: 100, 168, and 182, respectively; or
(j) CDRL1, CDRL2, and CDRL3 have the sequence of SEQ ID NOs: 22, 28, and 49, respectively, and CDRH1, CDRH2, and CDRH3 have the sequence of SEQ ID NOs: 102, 169, and 182, respectively.

In one embodiment, the anti-PAC1 antibody or antigen-binding fragment thereof comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 25, 31, and 42, respectively, and CDRH1, CDRH2, and CDRH3 have the sequence of SEQ ID NOs: 98, 168, and 190, respectively. In another embodiment, the anti-PAC1 antibody or antigen-binding fragment thereof comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 20, 30, and 44, respectively, and CDRH1, CDRH2, and CDRH3 have the sequence of SEQ ID NOs: 100, 168, and 182, respectively. In yet another embodiment, the anti-PAC1 antibody or antigen-binding fragment thereof comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 17, 33, and 42, respectively, and CDRH1, CDRH2, and CDRH3 have the sequence of SEQ ID NOs: 99, 168, and 187, respectively. In still another embodiment, the anti-PAC1 antibody or antigen-binding fragment thereof comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 23, 31, and 50, respectively, and CDRH1, CDRH2, and CDRH3 have the sequence of SEQ ID NOs: 97, 167, and 178, respectively. In one particular embodiment, the anti-PAC1 antibody or antigen-binding fragment thereof comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 17, 31, and 44, respectively, and CDRH1, CDRH2, and CDRH3 have the sequence of SEQ ID NOs: 98, 168, and 189, respectively. In another particular embodiment, the anti-PAC1 antibody or antigen-binding fragment thereof comprises a light chain variable region comprising a CDRL1, a CDRL2, and a CDRL3 and a heavy chain variable region comprising a CDRH1, a CDRH2, and a CDRH3, wherein CDRL1, CDRL2, and CDRL3 have the sequence of SEQ ID NOs: 17, 27, and 39, respectively, and CDRH1, CDRH2, and CDRH3 have the sequence of SEQ ID NOs: 100, 168, and 182, respectively.

In certain embodiments, the antibodies and antigen-binding fragments of the invention comprise an immunoglobulin heavy chain variable region (VH) and an immunoglobulin light chain variable region (VL) from an antibody that specifically binds to human PAC1, such as the antibodies described herein. The "variable region," used interchangeably herein with "variable domain" (variable region of a light chain (VL), variable region of a heavy chain (VH)), refers to the region in each of the light and heavy immunoglobulin chains which is involved directly in binding the antibody to the antigen. As discussed above, the regions of variable light and heavy chains have the same general structure and each region comprises four framework (FR) regions, the sequences of which are widely conserved, connected by three CDRs. The framework regions adopt a beta-sheet conformation and the CDRs may form loops connecting the beta-sheet structure. The CDRs in each chain are held in their three-dimensional structure by the framework regions and form, together with the CDRs from the other chain, the antigen binding site.

Thus, in some embodiments, the anti-PAC1 antibodies and antigen-binding fragments of the invention may comprise a light chain variable region selected from LV-01 to LV-15, as shown in Table 1A, and/or a heavy chain variable region selected from HV-01 to HV-105, as shown in Table 1B, and binding fragments, derivatives, and variants of these light chain and heavy chain variable regions. In other embodiments, the anti-PAC1 antibodies and antigen-binding fragments of the invention may comprise a light chain variable region selected from LV-16 to LV-36, as shown in Table 1A, and/or a heavy chain variable region selected from HV-106 to HV-122, as shown in Table 1B, and binding fragments, derivatives, and variants of these light chain and heavy chain variable regions.

Each of the light chain variable regions listed in Table 1A may be combined with any of the heavy chain variable regions listed in Table 1B to form an anti-PAC1 antibody or antigen-binding fragment thereof of the invention. Examples of such combinations include, but are not limited to: (i) LV-03 and any one of HV-03 to HV-26, HV-32 to HV-47, and HV-57 to HV-62; (ii) LV-04 and any one of HV-11 to HV-91; (iii) LV-05 and any one of HV-01, HV-03, HV-07, HV-09, and HV-10; (iv) LV-06 and any one of HV-01, HV-03, HV-07, HV-09, and HV-10; (v) LV-07 and any one of HV-01, HV-03, HV-07, HV-09, and HV-10; (vi) LV-08 and HV-01; (vii) LV-09 and HV-01; (viii) LV-10 and HV-01; (ix) LV-11 and any one of HV-92, HV-93, HV-95 to HV-97, and HV-99 to HV-101; (x) LV-12 and HV-94; (xi) LV-13 and HV-98; (xii) LV-14 and any one of HV-102 to HV-104; (xiii) LV-15 and HV-105; (xiv) LV-17 and HV-107; (xv) LV-18 and HV-108; (xvi) LV-19 and HV-109; (xvii) LV-20 and HV-110; (xviii) LV-21 and HV-110; (xix) LV-22 and HV-111; (xx) LV-23 and HV-107; (xxi) LV-24 and HV-112; (xxii) LV-25 and HV-113; (xxiii) LV-26 and HV-114; (xxiv) LV-27 and HV-106 or HV-110; (xxv) LV-28 and HV-115 or HV-118; (xxvi) LV-29 and HV-116; (xxvii) LV-30 and HV-117; (xxviii) LV-31 and HV-119; (xxix) LV-32 and HV-120; (xxx) LV-33 and HV-121; (xxxi) LV-34 and HV-122; (xxxii) LV-35 and HV-110; and (xxxiii) LV-36 and HV-110.

In certain embodiments, the anti-PACT antibodies or antigen-binding fragments of the invention comprise a light chain variable region comprising the sequence of LV-03 (SEQ ID NO: 54) and a heavy chain variable region comprising the sequence of HV-04 (SEQ ID NO: 194). In some embodiments, the anti-PACT antibodies or antigen-binding fragments of the invention comprise a light chain variable region comprising the sequence of LV-03 (SEQ ID NO: 54) and a heavy chain variable region comprising the sequence of HV-13 (SEQ ID NO: 203). In other embodiments, the anti-PACT antibodies or antigen-binding fragments of the invention comprise a light chain variable region comprising the sequence of LV-04 (SEQ ID NO: 55) and a heavy chain variable region comprising the sequence of HV-38 (SEQ ID NO: 228). In still other embodiments, the anti-PACT antibodies or antigen-binding fragments of the invention comprise a light chain variable region comprising the sequence of LV-04 (SEQ ID NO: 55) and a heavy chain variable region comprising the sequence of HV-84 (SEQ ID NO: 274). In some embodiments, the anti-PACT antibodies or antigen-binding fragments of the invention comprise a light chain variable region comprising the sequence of LV-03 (SEQ ID NO: 54) and a heavy chain variable region comprising the sequence of HV-24 (SEQ ID NO: 214). In certain embodiments, the anti-PACT antibodies or antigen-binding fragments of the invention comprise a light chain variable region comprising the sequence of LV-04 (SEQ ID NO: 55) and a heavy chain variable region comprising the sequence of HV-50 (SEQ ID NO: 240). In one embodiment, the anti-PACT antibodies or antigen-binding fragments of the invention comprise a light chain variable region comprising the sequence of LV-03 (SEQ ID NO: 54) and a heavy chain variable region comprising the sequence of HV-38 (SEQ ID NO: 228). In another embodiment, the anti-PAC1 antibodies or antigen-binding fragments of the invention comprise a light chain variable region comprising the sequence of LV-11 (SEQ ID NO: 62) and a heavy chain variable region comprising the sequence of HV-92 (SEQ ID NO: 282). In yet another embodiment, the anti-PAC1 antibodies or antigen-binding fragments of the invention comprise a light chain variable region comprising the sequence of LV-11 (SEQ ID NO: 62) and a heavy chain variable region comprising the sequence of HV-93 (SEQ ID NO: 283). In still another embodiment, the anti-PAC1 antibodies or antigen-binding fragments of the invention comprise a light chain variable region comprising the sequence of LV-12 (SEQ ID NO: 63) and a heavy chain variable region comprising the sequence of HV-94 (SEQ ID NO: 284).

In certain other embodiments, the anti-PAC1 antibodies or antigen-binding fragments of the invention comprise a light chain variable region comprising the sequence of LV-34 (SEQ ID NO: 85) and a heavy chain variable region comprising the sequence of HV-122 (SEQ ID NO: 312). In some embodiments, the anti-PAC1 antibodies or antigen-binding fragments of the invention comprise a light chain variable region comprising the sequence of LV-21 (SEQ ID NO: 72) and a heavy chain variable region comprising the sequence of HV-110 (SEQ ID NO: 300). In other embodiments, the anti-PAC1 antibodies or antigen-binding fragments of the invention comprise a light chain variable region comprising the sequence of LV-30 (SEQ ID NO: 81) and a heavy chain variable region comprising the sequence of HV-117 (SEQ ID NO: 307). In still other embodiments, the anti-PAC1 antibodies or antigen-binding fragments of the invention comprise a light chain variable region comprising the sequence of LV-27 (SEQ ID NO: 78) and a heavy chain variable region comprising the sequence of HV-106 (SEQ ID NO: 296). In some embodiments, the anti-PAC1 antibodies or antigen-binding fragments of the invention comprise a light chain variable region comprising the sequence of LV-32 (SEQ ID NO: 83) and a heavy chain variable region comprising the sequence of HV-120 (SEQ ID NO: 310). In certain embodiments, the anti-PAC1 antibodies or antigen-binding fragments of the invention comprise a light chain variable region comprising the sequence of LV-36 (SEQ ID NO: 87) and a heavy chain variable region comprising the sequence of HV-110 (SEQ ID NO: 300). In one embodiment, the anti-PAC1 antibodies or antigen-binding fragments of the invention comprise a light chain variable region comprising the sequence of LV-23 (SEQ ID NO: 74) and a heavy chain variable region comprising the sequence of HV-107 (SEQ ID NO: 297). In another embodiment, the anti-PAC1 antibodies or antigen-binding fragments of the invention comprise a light chain variable region comprising the sequence of LV-17 (SEQ ID NO: 68) and a heavy chain variable region comprising the sequence of HV-107 (SEQ ID NO: 297). In yet another embodiment, the anti-PAC1 antibodies or antigen-binding fragments of the invention comprise a light chain variable region comprising the sequence of LV-20 (SEQ ID NO: 71) and a heavy chain variable region comprising the sequence of HV-110 (SEQ ID NO: 300). In still another embodiment, the anti-PAC1 antibodies or antigen-binding fragments of the invention comprise a light chain variable region comprising the sequence of LV-26 (SEQ ID NO: 77) and a heavy chain variable region comprising the sequence of HV-114 (SEQ ID NO: 304).

In some embodiments, the anti-PAC1 antibodies or antigen-binding fragments thereof comprise a light chain variable region comprising a sequence of contiguous amino acids that differs from the sequence of a light chain variable region in Table 1A, i.e. a VL selected from LV-01 to LV-36, at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The light chain variable region in some anti-PAC1 antibodies and binding fragments comprises a sequence of amino acids that has at least 70%, at least 75%, at least 80%, at least 85%, at least 90%, at least 95%, at least 97% or at least 99% sequence identity to the amino acid sequences of SEQ ID NOs: 52 to 87 (i.e. the light chain variable regions in Table 1A).

In one embodiment, the anti-PAC1 antibody or antigen-binding fragment thereof comprises a light chain variable region comprising a sequence that is at least 90% identical to a sequence selected from SEQ ID NOs: 54-66. In another embodiment, the anti-PAC1 antibody or antigen-binding fragment thereof comprises a light chain variable region comprising a sequence that is at least 95% identical to a sequence selected from SEQ ID NOs: 54-66. In yet another embodiment, the anti-PAC1 antibody or antigen-binding fragment thereof comprises a light chain variable region comprising a sequence selected from SEQ ID NOs: 54-66. In some embodiments, the anti-PAC1 antibody or antigen-binding fragment thereof comprises a light chain variable region comprising the sequence of SEQ ID NO: 54. In other embodiments, the anti-PAC1 antibody or antigen-binding fragment thereof comprises a light chain variable region comprising the sequence of SEQ ID NO: 55. In yet other embodiments, the anti-PAC1 antibody or antigen-binding fragment thereof comprises a light chain variable region comprising the sequence of SEQ ID NO: 62. In still other embodiments, the anti-PAC1 antibody or antigen-binding fragment thereof comprises a light chain variable region comprising the sequence of SEQ ID NO: 63.

In another embodiment, the anti-PAC1 antibody or antigen-binding fragment thereof comprises a light chain variable region comprising a sequence that is at least 90% identical to a sequence selected from SEQ ID NOs: 68-87. In yet another embodiment, the anti-PAC1 antibody or antigen-binding fragment thereof comprises a light chain variable region comprising a sequence that is at least 95% identical to a sequence selected from SEQ ID NOs: 68-87. In still another embodiment, the anti-PAC1 antibody or antigen-binding fragment thereof comprises a light chain variable region comprising a sequence selected from SEQ ID NOs: 68-87. In certain embodiments, the anti-PAC1 antibody or antigen-binding fragment thereof comprises a light chain variable region comprising the sequence of SEQ ID NO: 68. In some embodiments, the anti-PAC1 antibody or antigen-binding fragment thereof comprises a light chain variable region comprising the sequence of SEQ ID NO: 71. In other embodiments, the anti-PAC1 antibody or antigen-binding fragment thereof comprises a light chain variable region comprising the sequence of SEQ ID NO: 72. In yet other embodiments, the anti-PAC1 antibody or antigen-binding fragment thereof comprises a light chain variable region comprising the sequence of SEQ ID NO: 74. In still other embodiments, the anti-PAC1 antibody or antigen-binding fragment thereof comprises a light chain variable region comprising the sequence of SEQ ID NO: 77. In certain embodiments, the anti-PAC1 antibody or antigen-binding fragment thereof comprises a light chain variable region comprising the sequence of SEQ ID NO: 78. In other embodiments, the anti-PAC1 antibody or antigen-binding fragment thereof comprises a light chain variable region comprising the sequence of SEQ ID NO: 81. In one embodiment, the anti-PAC1 antibody or antigen-binding fragment thereof comprises a light chain variable region comprising the sequence of SEQ ID NO: 83. In another embodiment, the anti-PAC1 antibody or antigen-binding fragment thereof comprises a light chain variable region comprising the sequence of SEQ ID NO: 85. In yet another embodiment, the anti-PAC1 antibody or antigen-binding fragment thereof comprises a light chain variable region comprising the sequence of SEQ ID NO: 87.

In these and other embodiments, the anti-PAC1 antibodies and antigen-binding fragments thereof comprise a heavy chain variable region comprising a sequence of contiguous amino acids that differs from the sequence of a heavy chain variable region in Table 1B, i.e., a VH selected from HV-01 to HV-122, at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The heavy chain variable region in some anti-PAC1 antibodies and antigen-binding fragments comprises a sequence of amino acids that has at least 70%, at least 75%, at least 80%, at least 85%, at least 90%, at least 95%, at least 97% or at least 99% sequence identity to the amino acid sequences of SEQ ID NOs: 191 to 312 (i.e. the heavy chain variable regions in Table 1B).

In one embodiment, the anti-PAC1 antibody or antigen-binding fragment thereof comprises a heavy chain variable region comprising a sequence that is at least 90% identical to a sequence selected from SEQ ID NOs: 191-295. In another embodiment, the anti-PAC1 antibody or antigen-binding fragment thereof comprises a heavy chain variable region comprising a sequence that is at least 95% identical to a sequence selected from SEQ ID NOs: 191-295. In yet another embodiment, the anti-PAC1 antibody or antigen-binding fragment thereof comprises a heavy chain variable region comprising a sequence selected from SEQ ID NOs: 191-295. In some embodiments, the anti-PAC1 antibody or antigen-binding fragment thereof comprises a heavy chain variable region comprising the sequence of SEQ ID NO: 194. In other embodiments, the anti-PAC1 antibody or antigen-binding fragment thereof comprises a heavy chain variable region comprising the sequence of SEQ ID NO: 203. In yet other embodiments, the anti-PAC1 antibody or antigen-binding fragment thereof comprises a heavy chain variable region comprising the sequence of SEQ ID NO: 214. In still other embodiments, the anti-PAC1 antibody or antigen-binding fragment thereof comprises a heavy chain variable region comprising the sequence of SEQ ID NO: 228. In certain embodiments, the anti-PAC1 antibody or antigen-binding fragment thereof comprises a heavy chain variable region comprising the sequence of SEQ ID NO: 240. In other embodiments, the anti-PAC1 antibody or antigen-binding fragment thereof comprises a heavy chain variable region comprising the sequence of SEQ ID NO: 274. In one embodiment, the anti-PAC1 antibody or antigen-binding fragment thereof comprises a heavy chain variable region comprising the sequence of SEQ ID NO: 282. In another embodiment, the anti-PAC1 antibody or antigen-binding fragment thereof comprises a heavy chain variable region comprising the sequence of SEQ ID NO: 283. In yet another embodiment, the anti-PAC1 antibody or antigen-binding fragment thereof comprises a heavy chain variable region comprising the sequence of SEQ ID NO: 284.

In another embodiment, the anti-PAC1 antibody or antigen-binding fragment thereof comprises a heavy chain variable region comprising a sequence that is at least 90% identical to a sequence selected from SEQ ID NOs: 296-312. In yet another embodiment, the anti-PAC1 antibody or antigen-binding fragment thereof comprises a heavy chain variable region comprising a sequence that is at least 95% identical to a sequence selected from SEQ ID NOs: 296-312. In still another embodiment, the anti-PAC1 antibody or antigen-binding fragment thereof comprises a heavy chain variable region comprising a sequence selected from SEQ ID NOs: 296-312. In some embodiments, the anti-PAC1 antibody or antigen-binding fragment thereof comprises a heavy chain variable region comprising the sequence of SEQ ID NO: 296. In other embodiments, the anti-PAC1 antibody or antigen-binding fragment thereof comprises a heavy chain variable region comprising the sequence of SEQ ID NO: 297. In yet other embodiments, the anti-PAC1 antibody or antigen-binding fragment thereof comprises a heavy chain variable region comprising the sequence of SEQ ID NO: 300. In still other embodiments, the anti-PAC1 antibody or antigen-binding fragment thereof comprises a heavy chain variable region comprising the sequence of SEQ ID NO: 304. In certain embodiments, the anti-PAC1 antibody or antigen-binding fragment thereof comprises a heavy chain variable region comprising the sequence of SEQ ID NO: 307. In other embodiments, the anti-PAC1 antibody or antigen-binding fragment thereof comprises a heavy chain variable region comprising the sequence of SEQ ID NO: 310. In one embodiment, the anti-PAC1 antibody or antigen-binding fragment thereof comprises a heavy chain variable region comprising the sequence of SEQ ID NO: 312.

The term "identity," as used herein, refers to a relationship between the sequences of two or more polypeptide molecules or two or more nucleic acid molecules, as determined by aligning and comparing the sequences. "Percent identity," as used herein, means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073. For example, sequence identity can be determined by standard methods that are commonly used to compare the similarity in position of the amino acids of two polypeptides. Using a computer program such as BLAST or FASTA, two polypeptide or two polynucleotide sequences are aligned for optimal matching of their respective residues (either along the full length of one or both sequences, or along a predetermined portion of one or both sequences). The programs provide a default opening penalty and a default gap penalty, and a scoring matrix such as PAM 250 (Dayhoff et al., in Atlas of Protein Sequence and Structure, vol. 5, supp. 3, 1978) or BLOSUM62 (Henikoff et al., 1992, Proc. Natl. Acad. Sci. U.S.A. 89:10915-10919) can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences. In calculating percent identity, the sequences being compared are aligned in a way that gives the largest match between the sequences.

The GCG program package is a computer program that can be used to determine percent identity, which package includes GAP (Devereux et al., 1984, Nucl. Acid Res. 12:387; Genetics Computer Group, University of Wisconsin, Madison, WI). The computer algorithm GAP is used to align the two polypeptides or two polynucleotides for which the percent sequence identity is to be determined. The sequences are aligned for optimal matching of their respective amino acid or nucleotide (the "matched span," as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Recommended parameters for determining percent identity for polypeptides or nucleotide sequences using the GAP program include the following:

Algorithm: Needleman et al. 1970, J. Mol. Biol. 48:443-453;

Comparison matrix: BLOSUM 62 from Henikoff et al., 1992, supra;

Gap Penalty: 12 (but with no penalty for end gaps)

Gap Length Penalty: 4

Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

The anti-PAC1 antibodies of the invention can comprise any immunoglobulin constant region. The term "constant region," used interchangeably herein with "constant domain" refers to all domains of an antibody other than the variable region. The constant region is not involved directly in binding of an antigen, but exhibits various effector functions. As described above, antibodies are divided into particular isotypes (IgA, IgD, IgE, IgG, and IgM) and subtypes (IgG1, IgG2, IgG3, IgG4, IgA1 IgA2) depending on the amino acid sequence of the constant region of their heavy chains. The light chain constant region can be, for example, a kappa- or lambda-type light chain constant region, e.g., a human kappa- or lambda-type light chain constant region, which are found in all five antibody isotypes. Examples of human immunoglobulin light chain constant region sequences are shown in the following table.

TABLE 2

Exemplary Human Immunoglobulin Light Chain Constant Regions

| Designation | SEQ ID NO: | CL Domain Amino Acid Sequence |
|---|---|---|
| Human lambda v1 | 313 | GQPKANPTVTLFPPSSEELQANKATLVCLISDFYPGAVTVAWKA DGSPVKAGVETTKPSKQSNNKYAASSYLSLTPEQWKSHRSYSC QVTHEGSTVEKTVAPTECS |
| Human lambda v2 | 314 | GQPKAAPSVTLFPPSSEELQANKATLVCLISDFYPGAVTVAWKA DSSPVKAGVETTTPSKQSNNKYAASSYLSLTPEQWKSHRSYSCQ VTHEGSTVEKTVAPTECS |
| Human lambda v3 | 315 | QPKAAPSVTLFPPSSEELQANKATLVCLISDFYPGAVTVAWKAD SSPVKAGVETTTPSKQSNNKYAASSYLSLTPEQWKSHRSYSCQV THEGSTVEKTVAPTECS |
| Human lambda v4 | 316 | GQPKAAPSVTLFPPSSEELQANKATLVCLISDFYPGAVTVAWKA DSSPVKAGVETTTPSKQSNNKYAASSYLSLTPEQWKSHKSYSCQ VTHEGSTVEKTVAPTECS |
| Human lambda v5 | 317 | GQPKAAPSVTLFPPSSEELQANKATLVCLVSDFYPGAVTVAWK ADGSPVKVGVETTKPSKQSNNKYAASSYLSLTPEQWKSHRSYS CRVTHEGSTVEKTVAPAECS |
| Human kappa v1 | 318 | TVAAPSVFIFPPSDEQLKSGTASVVCLLNNFYPREAKVQWKVDN ALQSGNSQESVTEQDSKDSTYSLSSTLTLSKADYEKHKVYACEV THQGLSSPVTKSFNRGEC |
| Human kappa v2 | 319 | RTVAAPSVFIFPPSDEQLKSGTASVVCLLNNFYPREAKVQWKVD NALQSGNSQESVTEQDSKDSTYSLSSTLTLSKADYEKHKVYACE VTHQGLSSPVTKSFNRGEC |

The heavy chain constant region of the anti-PAC1 antibodies of the invention can be, for example, an alpha-, delta-, epsilon-, gamma-, or mu-type heavy chain constant region, e.g., a human alpha-, delta-, epsilon-, gamma-, or mu-type heavy chain constant region. In some embodiments, the anti-PAC1 antibodies comprise a heavy chain constant region from an IgG1, IgG2, IgG3, or IgG4 immunoglobulin, such as a human IgG1, IgG2, IgG3, or IgG4 immunoglobulin. In one embodiment, the anti-PAC1 antibody comprises a heavy chain constant region from a human IgG1 immunoglobulin. In such embodiments, the human IgG1 immunoglobulin constant region may comprise one or more mutations to prevent glycosylation of the antibody as described in more detail herein. In another embodiment, the anti-PAC1 antibody comprises a heavy chain constant region from a human IgG2 immunoglobulin. In yet another embodiment, the anti-PAC1 antibody comprises a heavy chain constant region from a human IgG4 immunoglobulin. Examples of human IgG1, IgG2, and IgG4 heavy chain constant region sequences are shown below in Table 3.

TABLE 3

Exemplary Human Immunoglobulin Heavy Chain Constant Regions

| Ig isotype | SEQ ID NO: | Heavy Chain Constant Region Amino Acid Sequence |
|---|---|---|
| Human IgG1z | 320 | ASTKGPSVFPLAPSSKSTSGGTAALGCLVKDYFPEPVTVSWN<br>SGALTSGVHTFPAVLQSSGLYSLSSVVTVPSSSLGTQTYICNV<br>NHKPSNTKVDKKVEPKSCDKTHTCPPCPAPELLGGPSVFLFP<br>PKPKDTLMISRTPEVTCVVVDVSHEDPEVKFNWYVDGVEVH<br>NAKTKPREEQYNSTYRVVSVLTVLHQDWLNGKEYKCKVSN<br>KALPAPIEKTISKAKGQPREPQVYTLPPSREEMTKNQVSLTCL<br>VKGFYPSDIAVEWESNGQPENNYKTTPPVLDSDGSFFLYSKL<br>TVDKSRWQQGNVFSCSVMHEALHNHYTQKSLSLSPGK |
| Human IgG1za | 321 | ASTKGPSVFPLAPSSKSTSGGTAALGCLVKDYFPEPVTVSWN<br>SGALTSGVHTFPAVLQSSGLYSLSSVVTVPSSSLGTQTYICNV<br>NHKPSNTKVDKKVEPKSCDKTHTCPPCPAPELLGGPSVFLFP<br>PKPKDTLMISRTPEVTCVVVDVSHEDPEVKFNWYVDGVEVH<br>NAKTKPREEQYNSTYRVVSVLTVLHQDWLNGKEYKCKVSN<br>KALPAPIEKTISKAKGQPREPQVYTLPPSRDELTKNQVSLTCL<br>VKGFYPSDIAVEWESNGQPENNYKTTPPVLDSDGSFFLYSKL<br>TVDKSRWQQGNVFSCSVMHEALHNHYTQKSLSLSPGK |
| Human IgG1f | 322 | ASTKGPSVFPLAPSSKSTSGGTAALGCLVKDYFPEPVTVSWN<br>SGALTSGVHTFPAVLQSSGLYSLSSVVTVPSSSLGTQTYICNV<br>NHKPSNTKVDKRVEPKSCDKTHTCPPCPAPELLGGPSVFLFP<br>PKPKDTLMISRTPEVTCVVVDVSHEDPEVKFNWYVDGVEVH<br>NAKTKPREEQYNSTYRVVSVLTVLHQDWLNGKEYKCKVSN<br>KALPAPIEKTISKAKGQPREPQVYTLPPSREEMTKNQVSLTCL<br>VKGFYPSDIAVEWESNGQPENNYKTTPPVLDSDGSFFLYSKL<br>TVDKSRWQQGNVFSCSVMHEALHNHYTQKSLSLSPGK |
| Human IgG1fa | 323 | ASTKGPSVFPLAPSSKSTSGGTAALGCLVKDYFPEPVTVSWN<br>SGALTSGVHTFPAVLQSSGLYSLSSVVTVPSSSLGTQTYICNV<br>NHKPSNTKVDKRVEPKSCDKTHTCPPCPAPELLGGPSVFLFP<br>PKPKDTLMISRTPEVTCVVVDVSHEDPEVKFNWYVDGVEVH<br>NAKTKPREEQYNSTYRVVSVLTVLHQDWLNGKEYKCKVSN<br>KALPAPIEKTISKAKGQPREPQVYTLPPSRDELTKNQVSLTCL<br>VKGFYPSDIAVEWESNGQPENNYKTTPPVLDSDGSFFLYSKL<br>TVDKSRWQQGNVFSCSVMHEALHNHYTQKSLSLSPGK |
| Human IgG1z aglycosylated v1 | 324 | ASTKGPSVFPLAPSSKSTSGGTAALGCLVKDYFPEPVTVSWN<br>SGALTSGVHTFPAVLQSSGLYSLSSVVTVPSSSLGTQTYICNV<br>NHKPSNTKVDKKVEPKSCDKTHTCPPCPAPELLGGPSVFLFP<br>PKPKDTLMISRTPEVTCVVVDVSHEDPEVKFNWYVDGVEVH<br>NAKTKPREEQYGSTYRVVSVLTVLHQDWLNGKEYKCKVSN<br>KALPAPIEKTISKAKGQPREPQVYTLPPSREEMTKNQVSLTCL<br>VKGFYPSDIAVEWESNGQPENNYKTTPPVLDSDGSFFLYSKL<br>TVDKSRWQQGNVFSCSVMHEALHNHYTQKSLSLSPGK |
| Human IgG1z aglycosylated v2 | 325 | ASTKGPSVFPLAPSSKSTSGGTAALGCLVKDYFPEPVTVSWN<br>SGALTSGVHTFPAVLQSSGLYSLSSVVTVPSSSLGTQTYICNV<br>NHKPSNTKVDKKVEPKSCDKTHTCPPCPAPELLGGPSVFLFP<br>PKPKDTLMISRTPEVTCVVVDVSHEDPEVKFNWYVDGVEVH<br>NAKTKPCEEQYGSTYRCVSVLTVLHQDWLNGKEYKCKVSN<br>KALPAPIEKTISKAKGQPREPQVYTLPPSREEMTKNQVSLTCL<br>VKGFYPSDIAVEWESNGQPENNYKTTPPVLDSDGSFFLYSKL<br>TVDKSRWQQGNVFSCSVMHEALHNHYTQKSLSLSPGK |
| Human IgG2 | 326 | ASTKGPSVFPLAPCSRSTSESTAALGCLVKDYFPEPVTVSWN<br>SGALTSGVHTFPAVLQSSGLYSLSSVVTVPSSNFGTQTYTCN<br>VDHKPSNTKVDKTVERKCCVECPPCPAPPVAGPSVFLFPPKP<br>KDTLMISRTPEVTCVVVDVSHEDPEVQFNWYVDGVEVHNA<br>KTKPREEQFNSTFRVVSVLTVVHQDWLNGKEYKCKVSNKG<br>LPAPIEKTISKTKGQPREPQVYTLPPSREEMTKNQVSLTCLVK<br>GFYPSDIAVEWESNGQPENNYKTTPPMLDSDGSFFLYSKLTV<br>DKSRWQQGNVFSCSVMHEALHNHYTQKSLSLSPGK |
| Human IgG4 | 327 | ASTKGPSVFPLAPSSKSTSGGTAALGCLVKDYFPEPVTVSWN<br>SGALTSGVHTFPAVLQSSGLYSLSSVVTVPSSSLGTQTYICNV<br>NHKPSNTKVDKKVEPKSCDKTHTCPPCPAPELLGGPSVFLFP<br>PKPKDTLMISRTPEVTCVVVDVSHEDPEVKFNWYVDGVEVH |

TABLE 3-continued

| Exemplary Human Immunoglobulin Heavy Chain Constant Regions | | |
|---|---|---|
| Ig isotype | SEQ ID NO: | Heavy Chain Constant Region Amino Acid Sequence |
| | | NAKTKPCEEQYGSTYRCVSVLTVLHQDWLNGKEYKCKVSN KALPAPIEKTISKAKGQPREPQVYTLPPSREEMTKNQVSLTCL VKGFYPSDIAVEWESNGQPENNYKTTPPVLDSDGSFFLYSKL TVDKSRWQQGNVFSCSVMHEALHNHYTQKSLSLSPGK |

Each of the light chain variable regions disclosed in Table 1A and each of the heavy chain variable regions disclosed in Table 1B may be attached to the above light chain constant regions (Table 2) and heavy chain constant regions (Table 3) to form complete antibody light and heavy chains, respectively. Further, each of the so generated heavy and light chain sequences may be combined to form a complete antibody structure. It should be understood that the heavy chain and light chain variable regions provided herein can also be attached to other constant domains having different sequences than the exemplary sequences listed above.

The anti-PAC1 antibodies or antigen-binding fragments of the invention can be any of the anti-PAC1 antibodies or antigen-binding fragments disclosed herein. For example, in certain embodiments, the anti-PAC1 antibody is an anti-PAC1 antibody selected from any of the antibodies listed in Tables 9, 10, 12, 13, 14, 19, and 20. In some embodiments, the anti-PAC1 antibodies comprise a light chain variable region and/or a heavy chain variable region having one or more of the amino acid substitutions set forth in Tables 9, 10, 12, 13, 19, or 20. For instance, in one embodiment, the anti-PAC1 antibody comprises a light chain variable region comprising the sequence of SEQ ID NO: 52 with a mutation at one or more amino acid positions 27, 28, 30, 31, 32, and/or 93. In certain embodiments, the mutation is selected from Q27K, Q27R, Q27H, S28A, G30M, G30W, R31Q, R31L, R31H, R31W, R31Y, S32A, S32N, S32L, R93F, R93M, R93Y, or combinations thereof. In these and other embodiments, the anti-PAC1 antibody comprises a heavy chain variable region comprising the sequence of SEQ ID NO: 191 with a mutation at one or more amino acid positions 31, 32, 49, 52, 53, 54, 56, 57, 62, 70, 102, 103, and/or 104. In some embodiments, the mutation is selected from R31F, R31H, R31Y, R31M, R31K, F32Y, A49G, S52N, S52T, Y53F, Y53H, Y53S, D541, D54L, D54N, D54R, D54Q, D54Y, D54F, D54M, D54S, D54T, G56Q, G56N, G56R, G56H, G56A, G56S, G56T, G56D, N57A, N57F, N57G, N57S, N57Q, N57L, N57T, E62R, I70V, I70L, I70M, V102P, V102L, V102I, V102F, V102M, L103M, T104S, or combinations thereof.

In another embodiment, the anti-PAC1 antibody comprises a light chain variable region comprising the sequence of SEQ ID NO: 67 with a mutation at one or more amino acid positions 28, 30, 31, 34, 49, 50, 51, 52, 53, 91, 92, 93, 94, and/or 96. The mutation can be selected from S28Y, S28T, S28K, S28P, S28Q, S28R, S28M, S30A, S30V, R31Q, N34V, N34S, Y49F, A50V, A50G, A51G, A51S, S52Q, S52H, S52N, S52Y, S52R, S52L, S53I, S53Y, S53N, S53M, S53H, S53R, S91A, Y92I, S93G, S93Q, S93I, S93N, S93M, P94E, P94M, P94N, P94Q, P94A, P94T, P941, F96Y, or combinations thereof. In these and other embodiments, the anti-PAC1 antibody comprises a heavy chain variable region comprising the sequence of SEQ ID NO: 296 with a mutation at one or more amino acid positions 31, 32, 33, 57, 58, 60, 103, 105, 106, 107, and/or 110. In some embodiments, the mutation is selected from S31N, N32R, N32K, N32H, S33L, S33Q, S33Y, S33V, S33D, S57G, K58Q, S60K, T103M, T103Q, T103R, T103V, K105N, K105E, K105D, K1051, K105A, K1055, K105Q, Q106G, Q106E, L107D, L107N, L110M, L110F, or combinations thereof.

In certain embodiments, the anti-PAC1 antibody or antigen-binding fragment of the invention is selected from antibodies 420653, 420845, 420943, 421873, 420889, 421091, 421051, 480711, 480706, 480713, 448730, 448195, 448788, 448901, 448689, 448202, 452128, 448924, 3574, and 3575 or antigen-binding fragments thereof, the variable region and CDR sequences of which are set forth in Tables 1A and 1B. In some embodiments, the anti-PAC1 antibody is an antibody selected from 420653, 420845, 420943, 421873, 420889, 421091, 421051, 480711, 480706, and 480713 antibodies. In other embodiments, the anti-PAC1 antibody is an antibody selected from 448730, 448195, 448788, 448901, 448689, 448202, 452128, 448924, 3574, and 3575 antibodies. Full-length light chain and full-length heavy chain sequences of these exemplary human anti-PAC1 antibodies are set forth below in Tables 4A and 4B, respectively.

TABLE 4A

| Exemplary Anti-PAC1 Antibody Light Chain Sequences | | | |
|---|---|---|---|
| Antibody ID. | LC Group | Light Chain Amino Acid Sequence | Light Chain Nucleic Acid Sequence |
| 29G4 variants | | | |
| 29G4v10 | LC-01 | EIVLTQSPATLSLSPGERATLSCRA SQSVGRSLHWYQQKPGQAPRLLI KYASQSLSGIPARFSGSGSGTDFT LTISSLEPEDFAVYYCHQSSRLPFT FGPGTKVDIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 504) | GAGATCGTACTTACTCAGTCACCCGCCACA TTGTCCCTGAGCCCGGGTGAACGGGCGACC CTCAGCTGCCGAGCATCCCAGTCCGTCGGA CGATCATTGCACTGGTACCAACAAAAACCG GGCCAGGCCCCCAGACTTCTGATCAAGTAT GCGTCACAGAGCTTGTCGGGTATTCCCGCTC GCTTTTCGGGGTCGGGATCCGGGACAGATT TCACGCTCACAATCTCCTCGCTGGAACCCG AGGACTTCGCGGTCTACTATTGTCATCAGTC ATCGAGGTTGCCTTTCACGTTTGGACCAGG |

TABLE 4A-continued

Exemplary Anti-PAC1 Antibody Light Chain Sequences

| Antibody ID. | LC Group | Light Chain Amino Acid Sequence | Light Chain Nucleic Acid Sequence |
|---|---|---|---|
| | | | GACCAAGGTGGACATTAAGCGTACGGTGGC<br>TGCACCATCTGTCTTCATCTTCCCGCCATCT<br>GATGAGCAGTTGAAATCTGGAACTGCCTCT<br>GTTGTGTGCCTGCTGAATAACTTCTATCCCA<br>GAGAGGCCAAAGTACAGTGGAAGGTGGAT<br>AACGCCCTCCAATCGGGTAACTCCCAGGAG<br>AGTGTCACAGAGCAGGACAGCAAGGACAG<br>CACCTACAGCCTCAGCAGCACCCTGACGCT<br>GAGCAAAGCAGACTACGAGAAACACAAAG<br>TCTACGCCTGCGAAGTCACCCATCAGGGCC<br>TGAGCTCGCCCGTCACAAAGAGCTTCAACA<br>GGGGAGAGTGTTAG (SEQ ID NO: 537) |
| 29G4v22 | LC-02 | DIQLTQSPSFLSASVGDRVTITCRA<br>SQSIGRSLHWYQQKPGKAPKLLIK<br>YASQSLSGVPSRFSGSGSGTEFTL<br>TISSLQPEDFATYYCHQSSRLPFTF<br>GPGTKVDIKRTVAAPSVFIFPPSDE<br>QLKSGTASVVCLLNNFYPREAKV<br>QWKVDNALQSGNSQESVTEQDS<br>KDSTYSLSSTLTLSKADYEKHKV<br>YACEVTHQGLSSPVTKSFNRGEC<br>(SEQ ID NO: 505) | GATATCCAGCTCACTCAATCGCCATCATTTC<br>TCTCCGCTTCGGTAGGCGACCGGGTCACGA<br>TCACATGCAGGGCGTCGCAAAGCATTGGGA<br>GGTCGTTGCATTGGTATCAGCAGAAACCCG<br>GAAAGGCCCCGAAACTTCTGATCAAATACG<br>CATCACAAAGCTTGAGCGGTGTGCCGTCGC<br>GCTTCTCCGGTTCCGGAAGCGGAACGGAAT<br>TCACGCTTACAATCTCCTCACTGCAGCCCGA<br>GGATTTCGCGACCTATTACTGTCACCAGTCA<br>TCCAGACTCCCGTTTACTTTTGGCCCTGGGA<br>CCAAGGTGGACATTAAGCGTACGGTGGCTG<br>CACCATCTGTCTTCATCTTCCCGCCATCTGA<br>TGAGCAGTTGAAATCTGGAACTGCCTCTGTT<br>GTGTGCCTGCTGAATAACTTCTATCCCAGAG<br>AGGCCAAAGTACAGTGGAAGGTGGATAAC<br>GCCCTCCAATCGGGTAACTCCCAGGAGAGT<br>GTCACAGAGCAGGACAGCAAGGACAGCAC<br>CTACAGCCTCAGCAGCACCCTGACGCTGAG<br>CAAAGCAGACTACGAGAAACACAAAGTCTA<br>CGCCTGCGAAGTCACCCATCAGGGCCTGAG<br>CTCGCCCGTCACAAAGAGCTTCAACAGGGG<br>AGAGTGT (SEQ ID NO: 538) |
| iPS:420653 | LC-03 | EIVLTQSPATLSLSPGERATLSCRA<br>SKSVGRSLHWYQQKPGQAPRLLI<br>KYASQSLSGIPARFSGSGSGTDFT<br>LTISSLEPEDFAVYYCHQSSRLPFT<br>FGPGTKVDIKRTVAAPSVFIFPPSD<br>EQLKSGTASVVCLLNNFYPREAK<br>VQWKVDNALQSGNSQESVTEQD<br>SKDSTYSLSSTLTLSKADYEKHKV<br>YACEVTHQGLSSPVTKSFNRGEC<br>(SEQ ID NO: 506) | GAGATCGTACTTACTCAGTCACCCGCCACA<br>TTGTCCCTGAGCCCGGGTGAACGGGCGACC<br>CTCAGCTGCCGAGCATCCAAGTCCGTCGGA<br>CGATCATTGCACTGGTACCAACAAAAACCG<br>GGCCAGGCCCCCAGACTTCTGATCAAGTAT<br>GCGTCACAGAGCTTGTCGGGTATTCCCGCTC<br>GCTTTTCGGGGTCGGGATCCGGGACAGATT<br>TCACGCTCACAATCTCCTCGCTGGAACCCG<br>AGGACTTCGCGGTCTACTATTGTCATCAGTC<br>ATCGAGGTTGCCTTTCACGTTTGGACCAGG<br>GACCAAGGTGGACATTAAGCGTACGGTGGC<br>TGCACCATCTGTCTTCATCTTCCCGCCATCT<br>GATGAGCAGTTGAAATCTGGAACTGCCTCT<br>GTTGTGTGCCTGCTGAATAACTTCTATCCCA<br>GAGAGGCCAAAGTACAGTGGAAGGTGGAT<br>AACGCCCTCCAATCGGGTAACTCCCAGGAG<br>AGTGTCACAGAGCAGGACAGCAAGGACAG<br>CACCTACAGCCTCAGCAGCACCCTGACGCT<br>GAGCAAAGCAGACTACGAGAAACACAAAG<br>TCTACGCCTGCGAAGTCACCCATCAGGGCC<br>TGAGCTCGCCCGTCACAAAGAGCTTCAACA<br>GGGGAGAGTGT (SEQ ID NO: 539) |
| iPS:420845 | LC-03 | EIVLTQSPATLSLSPGERATLSCRA<br>SKSVGRSLHWYQQKPGQAPRLLI<br>KYASQSLSGIPARFSGSGSGTDFT<br>LTISSLEPEDFAVYYCHQSSRLPFT<br>FGPGTKVDIKRTVAAPSVFIFPPSD<br>EQLKSGTASVVCLLNNFYPREAK<br>VQWKVDNALQSGNSQESVTEQD<br>SKDSTYSLSSTLTLSKADYEKHKV<br>YACEVTHQGLSSPVTKSFNRGEC<br>(SEQ ID NO: 506) | GAGATCGTACTTACTCAGTCACCCGCCACA<br>TTGTCCCTGAGCCCGGGTGAACGGGCGACC<br>CTCAGCTGCCGAGCATCCAAGTCCGTCGGA<br>CGATCATTGCACTGGTACCAACAAAAACCG<br>GGCCAGGCCCCCAGACTTCTGATCAAGTAT<br>GCGTCACAGAGCTTGTCGGGTATTCCCGCTC<br>GCTTTTCGGGGTCGGGATCCGGGACAGATT<br>TCACGCTCACAATCTCCTCGCTGGAACCCG<br>AGGACTTCGCGGTCTACTATTGTCATCAGTC<br>ATCGAGGTTGCCTTTCACGTTTGGACCAGG<br>GACCAAGGTGGACATTAAGCGTACGGTGGC<br>TGCACCATCTGTCTTCATCTTCCCGCCATCT<br>GATGAGCAGTTGAAATCTGGAACTGCCTCT<br>GTTGTGTGCCTGCTGAATAACTTCTATCCCA<br>GAGAGGCCAAAGTACAGTGGAAGGTGGAT<br>AACGCCCTCCAATCGGGTAACTCCCAGGAG |

TABLE 4A-continued

Exemplary Anti-PAC1 Antibody Light Chain Sequences

| Antibody ID. | LC Group | Light Chain Amino Acid Sequence | Light Chain Nucleic Acid Sequence |
|---|---|---|---|
| | | | AGTGTCACAGAGCAGGACAGCAAGGACAG CACCTACAGCCTCAGCAGCACCCTGACGCT GAGCAAAGCAGACTACGAGAAACACAAAG TCTACGCCTGCGAAGTCACCCATCAGGGCC TGAGCTCGCCCGTCACAAAGAGCTTCAACA GGGGAGAGTGT(SEQ ID NO: 539) |
| iPS:420943 | LC-01 | EIVLTQSPATLSLSPGERATLSCRA SQSVGRSLHWYQQKPGQAPRLLI KYASQSLSGIPARFSGSGSGTDFT LTISSLEPEDFAVYYCHQSSRLPFT FGPGTKVDIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 504) | GAGATCGTACTTACTCAGTCACCCGCCACA TTGTCCCTGAGCCCGGGTGAACGGGCGACC CTCAGCTGCCGAGCATCCCAGTCCGTCGGA CGATCATTGCACTGGTACCAACAAAAACCG GGCCAGGCCCCCAGACTTCTGATCAAGTAT GCGTCACAGAGCTTGTCGGGTATTCCCGCTC GCTTTTCGGGGTCGGGATCCGGGACAGATT TCACGCTCACAATCTCCTCGCTGGAACCCG AGGACTTCGCGGTCTACTATTGTCATCAGTC ATCGAGGTTGCCTTTCACGTTTGGACCAGG GACCAAGGTGGACATTAAGCGTACGGTGGC TGCACCATCTGTCTTCATCTTCCCGCCATCT GATGAGCAGTTGAAATCTGGAACTGCCTCT GTTGTGTGCCTGCTGAATAACTTCTATCCCA GAGAGGCCAAAGTACAGTGGAAGGTGGAT AACGCCCTCCAATCGGGTAACTCCCAGGAG AGTGTCACAGAGCAGGACAGCAAGGACAG CACCTACAGCCTCAGCAGCACCCTGACGCT GAGCAAAGCAGACTACGAGAAACACAAAG TCTACGCCTGCGAAGTCACCCATCAGGGCC TGAGCTCGCCCGTCACAAAGAGCTTCAACA GGGGAGAGTGT (SEQ ID NO: 537) |
| iPS:421873 | LC-01 | EIVLTQSPATLSLSPGERATLSCRA SQSVGRSLHWYQQKPGQAPRLLI KYASQSLSGIPARFSGSGSGTDFT LTISSLEPEDFAVYYCHQSSRLPFT FGPGTKVDIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 504) | GAGATCGTACTTACTCAGTCACCCGCCACA TTGTCCCTGAGCCCGGGTGAACGGGCGACC CTCAGCTGCCGAGCATCCCAGTCCGTCGGA CGATCATTGCACTGGTACCAACAAAAACCG GGCCAGGCCCCCAGACTTCTGATCAAGTAT GCGTCACAGAGCTTGTCGGGTATTCCCGCTC GCTTTTCGGGGTCGGGATCCGGGACAGATT TCACGCTCACAATCTCCTCGCTGGAACCCG AGGACTTCGCGGTCTACTATTGTCATCAGTC ATCGAGGTTGCCTTTCACGTTTGGACCAGG GACCAAGGTGGACATTAAGCGTACGGTGGC TGCACCATCTGTCTTCATCTTCCCGCCATCT GATGAGCAGTTGAAATCTGGAACTGCCTCT GTTGTGTGCCTGCTGAATAACTTCTATCCCA GAGAGGCCAAAGTACAGTGGAAGGTGGAT AACGCCCTCCAATCGGGTAACTCCCAGGAG AGTGTCACAGAGCAGGACAGCAAGGACAG CACCTACAGCCTCAGCAGCACCCTGACGCT GAGCAAAGCAGACTACGAGAAACACAAAG TCTACGCCTGCGAAGTCACCCATCAGGGCC TGAGCTCGCCCGTCACAAAGAGCTTCAACA GGGGAGAGTGT (SEQ ID NO: 537) |
| iPS:420889 | LC-03 | EIVLTQSPATLSLSPGERATLSCRA SKSVGRSLHWYQQKPGQAPRLLI KYASQSLSGIPARFSGSGSGTDFT LTISSLEPEDFAVYYCHQSSRLPFT FGPGTKVDIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 506) | GAGATCGTACTTACTCAGTCACCCGCCACA TTGTCCCTGAGCCCGGGTGAACGGGCGACC CTCAGCTGCCGAGCATCCAAGTCCGTCGGA CGATCATTGCACTGGTACCAACAAAAACCG GGCCAGGCCCCCAGACTTCTGATCAAGTAT GCGTCACAGAGCTTGTCGGGTATTCCCGCTC GCTTTTCGGGGTCGGGATCCGGGACAGATT TCACGCTCACAATCTCCTCGCTGGAACCCG AGGACTTCGCGGTCTACTATTGTCATCAGTC ATCGAGGTTGCCTTTCACGTTTGGACCAGG GACCAAGGTGGACATTAAGCGTACGGTGGC TGCACCATCTGTCTTCATCTTCCCGCCATCT GATGAGCAGTTGAAATCTGGAACTGCCTCT GTTGTGTGCCTGCTGAATAACTTCTATCCCA GAGAGGCCAAAGTACAGTGGAAGGTGGAT AACGCCCTCCAATCGGGTAACTCCCAGGAG AGTGTCACAGAGCAGGACAGCAAGGACAG CACCTACAGCCTCAGCAGCACCCTGACGCT GAGCAAAGCAGACTACGAGAAACACAAAG TCTACGCCTGCGAAGTCACCCATCAGGGCC TGAGCTCGCCCGTCACAAAGAGCTTCAACA GGGGAGAGTGT (SEQ ID NO: 539) |

TABLE 4A-continued

Exemplary Anti-PAC1 Antibody Light Chain Sequences

| Antibody ID. | LC Group | Light Chain Amino Acid Sequence | Light Chain Nucleic Acid Sequence |
|---|---|---|---|
| iPS:421091 | LC-01 | EIVLTQSPATLSLSPGERATLSCRA SQSVGRSLHWYQQKPGQAPRLLI KYASQSLSGIPARFSGSGSGTDFT LTISSLEPEDFAVYYCHQSSRLPFT FGPGTKVDIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 504) | GAGATCGTACTTACTCAGTCACCCGCCACA TTGTCCCTGAGCCCGGGTGAACGGGCGACC CTCAGCTGCCGAGCATCCCAGTCCGTCGGA CGATCATTGCACTGGTACCAACAAAAACCG GGCCAGGCCCCCAGACTTCTGATCAAGTAT GCGTCACAGAGCTTGTCGGGTATTCCCGCTC GCTTTTCGGGGTCGGGATCCGGGACAGATT TCACGCTCACAATCTCCTCGCTGGAACCCG AGGACTTCGCGGTCTACTATTGTCATCAGTC ATCGAGGTTGCCTTTCACGTTTGGACCAGG GACCAAGGTGGACATTAAGCGTACGGTGGC TGCACCATCTGTCTTCATCTTCCCGCCATCT GATGAGCAGTTGAAATCTGGAACTGCCTCT GTTGTGTGCCTGCTGAATAACTTCTATCCCA GAGAGGCCAAAGTACAGTGGAAGGTGGAT AACGCCCTCCAATCGGGTAACTCCCAGGAG AGTGTCACAGAGCAGGACAGCAAGGACAG CACCTACAGCCTCAGCAGCACCCTGACGCT GAGCAAAGCAGACTACGAGAAACACAAAG TCTACGCCTGCGAAGTCACCCATCAGGGCC TGAGCTCGCCCGTCACAAAGAGCTTCAACA GGGGAGAGTGT (SEQ ID NO: 537) |
| iPS:421051 | LC-03 | EIVLTQSPATLSLSPGERATLSCRA SKSVGRSLHWYQQKPGQAPRLLI KYASQSLSGIPARFSGSGSGTDFT LTISSLEPEDFAVYYCHQSSRLPFT FGPGTKVDIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 506) | GAGATCGTACTTACTCAGTCACCCGCCACA TTGTCCCTGAGCCCGGGTGAACGGGCGACC CTCAGCTGCCGAGCATCCAAGTCCGTCGGA CGATCATTGCACTGGTACCAACAAAAACCG GGCCAGGCCCCCAGACTTCTGATCAAGTAT GCGTCACAGAGCTTGTCGGGTATTCCCGCTC GCTTTTCGGGGTCGGGATCCGGGACAGATT TCACGCTCACAATCTCCTCGCTGGAACCCG AGGACTTCGCGGTCTACTATTGTCATCAGTC ATCGAGGTTGCCTTTCACGTTTGGACCAGG GACCAAGGTGGACATTAAGCGTACGGTGGC TGCACCATCTGTCTTCATCTTCCCGCCATCT GATGAGCAGTTGAAATCTGGAACTGCCTCT GTTGTGTGCCTGCTGAATAACTTCTATCCCA GAGAGGCCAAAGTACAGTGGAAGGTGGAT AACGCCCTCCAATCGGGTAACTCCCAGGAG AGTGTCACAGAGCAGGACAGCAAGGACAG CACCTACAGCCTCAGCAGCACCCTGACGCT GAGCAAAGCAGACTACGAGAAACACAAAG TCTACGCCTGCGAAGTCACCCATCAGGGCC TGAGCTCGCCCGTCACAAAGAGCTTCAACA GGGGAGAGTGT (SEQ ID NO: 539) |
| iPS:480711 | LC-04 | EIVLTQSPATLSLSPGERATLSCRA SKSVGWSLHWYQQKPGQAPRLLI KYASQSLSGIPARFSGSGSGTDFT LTISSLEPEDFAVYYCHQSSRLPFT FGPGTKVDIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 507) | GAGATCGTACTTACTCAGTCACCCGCCACA TTGTCCCTGAGCCCGGGTGAACGGGCGACC CTCAGCTGCCGAGCATCCAAATCCGTCGGG TGGAGCTTGCACTGGTACCAACAAAAACCG GGCCAGGCCCCCAGACTTCTGATCAAGTAT GCGTCACAGAGCTTGTCGGGTATTCCCGCTC GCTTTTCGGGGTCGGGATCCGGGACAGATT TCACGCTCACAATCTCCTCGCTGGAACCCG AGGACTTCGCGGTCTACTATTGTCATCAGTC ATCGAGGTTGCCTTTCACGTTTGGACCAGG GACCAAGGTGGACATTAAGCGTACGGTGGC TGCACCATCTGTCTTCATCTTCCCGCCATCT GATGAGCAGTTGAAATCTGGAACTGCCTCT GTTGTGTGCCTGCTGAATAACTTCTATCCCA GAGAGGCCAAAGTACAGTGGAAGGTGGAT AACGCCCTCCAATCGGGTAACTCCCAGGAG AGTGTCACAGAGCAGGACAGCAAGGACAG CACCTACAGCCTCAGCAGCACCCTGACGCT GAGCAAAGCAGACTACGAGAAACACAAAG TCTACGCCTGCGAAGTCACCCATCAGGGCC TGAGCTCGCCCGTCACAAAGAGCTTCAACA GGGGAGAGTGT (SEQ ID NO: 540) |
| iPS:480706 | LC-04 | EIVLTQSPATLSLSPGERATLSCRA SKSVGWSLHWYQQKPGQAPRLLI KYASQSLSGIPARFSGSGSGTDFT LTISSLEPEDFAVYYCHQSSRLPFT FGPGTKVDIKRTVAAPSVFIFPPSD | GAGATCGTACTTACTCAGTCACCCGCCACA TTGTCCCTGAGCCCGGGTGAACGGGCGACC CTCAGCTGCCGAGCATCCAAATCCGTCGGG TGGAGCTTGCACTGGTACCAACAAAAACCG GGCCAGGCCCCCAGACTTCTGATCAAGTAT |

TABLE 4A-continued

| Antibody ID. | LC Group | Light Chain Amino Acid Sequence | Light Chain Nucleic Acid Sequence |
|---|---|---|---|
| Exemplary Anti-PAC1 Antibody Light Chain Sequences | | | |
| | | EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 507) | GCGTCACAGAGCTTGTCGGGTATTCCCGCTC GCTTTTCGGGGTCGGGATCCGGGACAGATT TCACGCTCACAATCTCCTCGCTGGAACCCG AGGACTTCGCGGTCTACTATTGTCATCAGTC ATCGAGGTTGCCTTTCACGTTTGGACCAGG GACCAAGGTGGACATTAAGCGTACGGTGGC TGCACCATCTGTCTTCATCTTCCCGCCATCT GATGAGCAGTTGAAATCTGGAACTGCCTCT GTTGTGTGCCTGCTGAATAACTTCTATCCCA GAGAGGCCAAAGTACAGTGGAAGGTGGAT AACGCCCTCCAATCGGGTAACTCCCAGGAG AGTGTCACAGAGCAGGACAGCAAGGACAG CACCTACAGCCTCAGCAGCACCCTGACGCT GAGCAAAGCAGACTACGAGAAACACAAAG TCTACGCCTGCGAAGTCACCCATCAGGGCC TGAGCTCGCCCGTCACAAAGAGCTTCAACA GGGGAGAGTGT (SEQ ID NO: 540) |
| iPS:480713 | LC-05 | EIVLTQSPATLSLSPGERATLSCRA SKSVGYSLHWYQQKPGQAPRLLI KYASQSLSGIPARFSGSGSGTDFT LTISSLEPEDFAVYYCHQSSRLPFT FGPGTKVDIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 508) | GAGATCGTACTTACTCAGTCACCCGCCACA TTGTCCCTGAGCCCGGGTGAACGGGCGACC CTCAGCTGCCGAGCATCCAAATCCGTCGGG TACAGCTTGCACTGGTACCAACAAAAACCG GGCCAGGCCCCCAGACTTCTGATCAAGTAT GCGTCACAGAGCTTGTCGGGTATTCCCGCTC GCTTTTCGGGGTCGGGATCCGGGACAGATT TCACGCTCACAATCTCCTCGCTGGAACCCG AGGACTTCGCGGTCTACTATTGTCATCAGTC ATCGAGGTTGCCTTTCACGTTTGGACCAGG GACCAAGGTGGACATTAAGCGTACGGTGGC TGCACCATCTGTCTTCATCTTCCCGCCATCT GATGAGCAGTTGAAATCTGGAACTGCCTCT GTTGTGTGCCTGCTGAATAACTTCTATCCCA GAGAGGCCAAAGTACAGTGGAAGGTGGAT AACGCCCTCCAATCGGGTAACTCCCAGGAG AGTGTCACAGAGCAGGACAGCAAGGACAG CACCTACAGCCTCAGCAGCACCCTGACGCT GAGCAAAGCAGACTACGAGAAACACAAAG TCTACGCCTGCGAAGTCACCCATCAGGGCC TGAGCTCGCCCGTCACAAAGAGCTTCAACA GGGGAGAGTGT (SEQ ID NO: 541) |
| 19H8 variants | | | |
| 19H8 | LC-06 | DIQMTQSPSSLSASVGDRITITCRA SQSISRYLNWYQQKPGKAPKLLIY AASSLQSGIPSRFSGSGSGTDFTLT INSLQPEDFATYFCQQSYSPPFTFG PGTKVDIKRTVAAPSVFIFPPSDEQ LKSGTASVVCLLNNFYPREAKVQ WKVDNALQSGNSQESVTEQDSK DSTYSLSSTLTLSKADYEKHKVY ACEVTHQGLSSPVTKSFNRGEC (SEQ ID NO: 509) | GACATCCAGATGACCCAGTCTCCATCCTCCC TGTCTGCATCTGTAGGAGACAGAATCACCA TCACTTGCCGGGCAAGTCAGAGCATTAGCA GGTATTTAAATTGGTATCAACAGAAACCAG GGAAAGCCCCTAAACTCCTGATCTATGCTG CATCCAGTTTGCAAAGTGGGATCCCATCAA GGTTCAGCGGCAGTGGATCTGGGACAGATT TCACTCTCACCATCAACAGTCTGCAACCTGA AGATTTTGCAACTTACTTCTGTCAACAGAGT TACAGTCCCCCATTCACTTTCGGCCCTGGGA CCAAAGTGGATATCAAACGTACGGTGGCTG CACCATCTGTCTTCATCTTCCCGCCATCTGA TGAGCAGTTGAAATCTGGAACTGCCTCTGTT GTGTGCCTGCTGAATAACTTCTATCCCAGAG AGGCCAAAGTACAGTGGAAGGTGGATAAC GCCCTCCAATCGGGTAACTCCCAGGAGAGT GTCACAGAGCAGGACAGCAAGGACAGCAC CTACAGCCTCAGCAGCACCCTGACGCTGAG CAAAGCAGACTACGAGAAACACAAAGTCTA CGCCTGCGAAGTCACCCATCAGGGCCTGAG CTCGCCCGTCACAAAGAGCTTCAACAGGGG AGAGTGT (SEQ ID NO: 542) |
| iPS:448730 | LC-07 | DIQMTQSPSSLSASVGDRITITCRA SQMIARYLNWYQQKPGKAPKLLI YASYNLQSGIPSRFSGSGSGTDFT LTINSLQPEDFATYFCQQAIINPYT FGPGTKVDIKRTVAAPSVFIFPPSD EQLKSGTASVVCLLNNFYPREAK VQWKVDNALQSGNSQESVTEQD SKDSTYSLSSTLTLSKADYEKHKV | GACATCCAGATGACCCAGTCTCCATCCTCCC TGTCTGCATCTGTAGGAGACAGAATCACCA TCACTTGCCGGGCAAGTCAGATGATTGCTC GTTACTTAAACTGGTATCAACAGAAACCAG GGAAAGCCCCTAAACTCCTGATCTACGCTT CTTACAACTTGCAAAGTGGGATCCCATCAA GGTTCAGCGGCAGTGGATCTGGGACAGATT TCACTCTCACCATCAACAGTCTGCAACCTGA |

TABLE 4A-continued

| Exemplary Anti-PAC1 Antibody Light Chain Sequences | | | |
|---|---|---|---|
| Antibody ID. | LC Group | Light Chain Amino Acid Sequence | Light Chain Nucleic Acid Sequence |
| | | YACEVTHQGLSSPVTKSFNRGEC (SEQ ID NO: 510) | AGATTTTGCAACTTACTTCTGTCAACAGGCT ATCATCAACCCATACACTTTCGGCCCTGGG ACCAAAGTGGATATCAAACGTACGGTGGCT GCACCATCTGTCTTCATCTTCCCGCCATCTG ATGAGCAGTTGAAATCTGGAACTGCCTCTG TTGTGTGCCTGCTGAATAACTTCTATCCCAG AGAGGCCAAAGTACAGTGGAAGGTGGATA ACGCCCTCCAATCGGGTAACTCCCAGGAGA GTGTCACAGAGCAGGACAGCAAGGACAGC ACCTACAGCCTCAGCAGCACCCTGACGCTG AGCAAAGCAGACTACGAGAAACACAAAGT CTACGCCTGCGAAGTCACCCATCAGGGCCT GAGCTCGCCCGTCACAAAGAGCTTCAACAG GGGAGAGTGT (SEQ ID NO: 543) |
| iPS:448195 | LC-08 | DIQMTQSPSSLSASVGDRITITCRA SQKIARYLVWYQQKPGKAPKLLI YAANMLQSGIPSRFSGSGSGTDFT LTINSLQPEDFATYFCQQSIQQPYT FGPGTKVDIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 511) | GACATCCAGATGACCCAGTCTCCATCCTCCC TGTCTGCATCTGTAGGAGACAGAATCACCA TCACTTGCCGGGCAAGTCAGAAAATTGCTC GTTACTTAGTTTGGTATCAACAGAAACCAG GGAAAGCCCCTAAACTCCTGATCTACGCTG CTAACATGTTGCAAAGTGGGATCCCATCAA GGTTCAGCGGCAGTGGATCTGGGACAGATT TCACTCTCACCATCAACAGTCTGCAACCTGA AGATTTTGCAACTTACTTCTGTCAACAGTCT ATCCAGCAGCCATACACTTTCGGCCCTGGG ACCAAAGTGGATATCAAACGTACGGTGGCT GCACCATCTGTCTTCATCTTCCCGCCATCTG ATGAGCAGTTGAAATCTGGAACTGCCTCTG TTGTGTGCCTGCTGAATAACTTCTATCCCAG AGAGGCCAAAGTACAGTGGAAGGTGGATA ACGCCCTCCAATCGGGTAACTCCCAGGAGA GTGTCACAGAGCAGGACAGCAAGGACAGC ACCTACAGCCTCAGCAGCACCCTGACGCTG AGCAAAGCAGACTACGAGAAACACAAAGT CTACGCCTGCGAAGTCACCCATCAGGGCCT GAGCTCGCCCGTCACAAAGAGCTTCAACAG GGGAGAGTGT (SEQ ID NO: 544) |
| iPS:448788 | LC-09 | DIQMTQSPSSLSASVGDRITITCRA SQSISRYLNWYQQKPGKAPKLLIY AGRILQSGIPSRFSGSGSGTDFTLT INSLQPEDFATYFCQQAIINPYTFG PGTKVDIKRTVAAPSVFIFPPSDEQ LKSGTASVVCLLNNFYPREAKVQ WKVDNALQSGNSQESVTEQDSK DSTYSLSSTLTLSKADYEKHKVY ACEVTHQGLSSPVTKSFNRGEC (SEQ ID NO: 512) | GACATCCAGATGACCCAGTCTCCATCCTCCC TGTCTGCATCTGTAGGAGACAGAATCACCA TCACTTGCCGGGCAAGTCAGAGCATTAGCA GGTATTTAAATTGGTATCAACAGAAACCAG GGAAAGCCCCTAAACTCCTGATCTACGCTG GTCGTATCTTGCAAAGTGGGATCCCATCAA GGTTCAGCGGCAGTGGATCTGGGACAGATT TCACTCTCACCATCAACAGTCTGCAACCTGA AGATTTTGCAACTTACTTCTGTCAACAGGCT ATCATCAACCCATACACTTTCGGCCCTGGG ACCAAAGTGGATATCAAACGTACGGTGGCT GCACCATCTGTCTTCATCTTCCCGCCATCTG ATGAGCAGTTGAAATCTGGAACTGCCTCTG TTGTGTGCCTGCTGAATAACTTCTATCCCAG AGAGGCCAAAGTACAGTGGAAGGTGGATA ACGCCCTCCAATCGGGTAACTCCCAGGAGA GTGTCACAGAGCAGGACAGCAAGGACAGC ACCTACAGCCTCAGCAGCACCCTGACGCTG AGCAAAGCAGACTACGAGAAACACAAAGT CTACGCCTGCGAAGTCACCCATCAGGGCCT GAGCTCGCCCGTCACAAAGAGCTTCAACAG GGGAGAGTGT (SEQ ID NO: 545) |
| iPS:448901 | LC-10 | DIQMTQSPSSLSASVGDRITITCRA SQSISRYLNWYQQKPGKAPKLLIY ASYNLQSGIPSRFSGSGSGTDFTLT INSLQPEDFATYFCQQSIQQPYTF GPGTKVDIKRTVAAPSVFIFPPSDE QLKSGTASVVCLLNNFYPREAKV QWKVDNALQSGNSQESVTEQDS KDSTYSLSSTLTLSKADYEKHKV YACEVTHQGLSSPVTKSFNRGEC (SEQ ID NO: 513) | GACATCCAGATGACCCAGTCTCCATCCTCCC TGTCTGCATCTGTAGGAGACAGAATCACCA TCACTTGCCGGGCAAGTCAGAGCATTAGCA GGTATTTAAATTGGTATCAACAGAAACCAG GGAAAGCCCCTAAACTCCTGATCTACGCTT CTTACAACTTGCAAAGTGGGATCCCATCAA GGTTCAGCGGCAGTGGATCTGGGACAGATT TCACTCTCACCATCAACAGTCTGCAACCTGA AGATTTTGCAACTTACTTCTGTCAACAGTCT ATCCAGCAGCCATACACTTTCGGCCCTGGG ACCAAAGTGGATATCAAACGTACGGTGGCT GCACCATCTGTCTTCATCTTCCCGCCATCTG ATGAGCAGTTGAAATCTGGAACTGCCTCTG TTGTGTGCCTGCTGAATAACTTCTATCCCAG |

TABLE 4A-continued

Exemplary Anti-PAC1 Antibody Light Chain Sequences

| Antibody ID. | LC Group | Light Chain Amino Acid Sequence | Light Chain Nucleic Acid Sequence |
|---|---|---|---|
| | | | AGAGGCCAAAGTACAGTGGAAGGTGGATA ACGCCCTCCAATCGGGTAACTCCCAGGAGA GTGTCACAGAGCAGGACAGCAAGGACAGC ACCTACAGCCTCAGCAGCACCCTGACGCTG AGCAAAGCAGACTACGAGAAACACAAAGT CTACGCCTGCGAAGTCACCCATCAGGGCCT GAGCTCGCCCGTCACAAAGAGCTTCAACAG GGGAGAGTGT (SEQ ID NO: 546) |
| iPS:448689 | LC-11 | DIQMTQSPSSLSASVGDRITITCRA SQYIVRYLNWYQQKPGKAPKLLI YASYNLQSGIPSRFSGSGSGTDFT LTINSLQPEDFATYFCQQAIMAPY TFGPGTKVDIKRTVAAPSVFIFPPS DEQLKSGTASVVCLLNNFYPREA KVQWKVDNALQSGNSQESVTEQ DSKDSTYSLSSTLTLSKADYEKHK VYACEVTHQGLSSPVTKSFNRGE C(SEQ ID NO: 514) | GACATCCAGATGACCCAGTCTCCATCCTCCC TGTCTGCATCTGTAGGAGACAGAATCACCA TCACTTGCCGGGCAAGTCAGTACATTGTTCG TTACTTAAACTGGTATCAACAGAAACCAGG GAAAGCCCCTAAACTCCTGATCTACGCTTCT TACAACTTGCAAAGTGGGATCCCATCAAGG TTCAGCGGCAGTGGATCTGGGACAGATTTC ACTCTCACCATCAACAGTCTGCAACCTGAA GATTTTGCAACTTACTTCTGTCAACAGGCTA TCATGGCTCCATACACTTTCGGCCCTGGGAC CAAAGTGGATATCAAACGTACGGTGGCTG CACCATCTGTCTTCATCTTCCCGCCATCTGA TGAGCAGTTGAAATCTGGAACTGCCTCTGTT GTGTGCCTGCTGAATAACTTCTATCCCAGAG AGGCCAAAGTACAGTGGAAGGTGGATAAC GCCCTCCAATCGGGTAACTCCCAGGAGAGT GTCACAGAGCAGGACAGCAAGGACAGCAC CTACAGCCTCAGCAGCACCCTGACGCTGAG CAAAGCAGACTACGAGAAACACAAAGTCTA CGCCTGCGAAGTCACCCATCAGGGCCTGAG CTCGCCCGTCACAAAGAGCTTCAACAGGGG AGAGTGT (SEQ ID NO: 547) |
| iPS:448202 | LC-12 | DIQMTQSPSSLSASVGDRITITCRA SQSISRYLNWYQQKPGKAPKLLIF AGQRLQSGIPSRFSGSGSGTDFTL TINSLQPEDFATYFCQQAIGMPYT FGPGTKVDIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 515) | GACATCCAGATGACCCAGTCTCCATCCTCCC TGTCTGCATCTGTAGGAGACAGAATCACCA TCACTTGCCGGGCAAGTCAGAGCATTAGCA GGTATTTAAATTGGTATCAACAGAAACCAG GGAAAGCCCCTAAACTCCTGATCTTCGCTG GTCAGCGTTTGCAAAGTGGGATCCCATCAA GGTTCAGCGGCAGTGGATCTGGGACAGATT TCACTCTCACCATCAACAGTCTGCAACCTGA AGATTTTGCAACTTACTTCTGTCAACAGGCT ATCGGTATGCCATACACTTTCGGCCCTGGG ACCAAAGTGGATATCAAACGTACGGTGGCT GCACCATCTGTCTTCATCTTCCCGCCATCTG ATGAGCAGTTGAAATCTGGAACTGCCTCTG TTGTGTGCCTGCTGAATAACTTCTATCCCAG AGAGGCCAAAGTACAGTGGAAGGTGGATA ACGCCCTCCAATCGGGTAACTCCCAGGAGA GTGTCACAGAGCAGGACAGCAAGGACAGC ACCTACAGCCTCAGCAGCACCCTGACGCTG AGCAAAGCAGACTACGAGAAACACAAAGT CTACGCCTGCGAAGTCACCCATCAGGGCCT GAGCTCGCCCGTCACAAAGAGCTTCAACAG GGGAGAGTGT (SEQ ID NO: 548) |
| iPS:452128 | LC-13 | DIQMTQSPSSLSASVGDRITITCRA SQYIVRYLNWYQQKPGKAPKLLI YAANMLQSGIPSRFSGSGSGTDFT LTINSLQPEDFATYFCQQAINQPY TFGPGTKVDIKRTVAAPSVFIFPPS DEQLKSGTASVVCLLNNFYPREA KVQWKVDNALQSGNSQESVIEQ DSKDSTYSLSSTLTLSKADYEKHK VYACEVTHQGLSSPVTKSFNRGE C(SEQ ID NO: 516) | GACATCCAGATGACCCAGTCTCCATCCTCCC TGTCTGCATCTGTAGGAGACAGAATCACCA TCACTTGCCGGGCAAGTCAGTACATTGTTCG TTACTTAAACTGGTATCAACAGAAACCAGG GAAAGCCCCTAAACTCCTGATCTACGCTGC TAACATGTTGCAAAGTGGGATCCCATCAAG GTTCAGCGGCAGTGGATCTGGGACAGATTT CACTCTCACCATCAACAGTCTGCAACCTGA AGATTTTGCAACTTACTTCTGTCAACAGGCT ATCAACCAGCCATACACTTTCGGCCCTGGG ACCAAAGTGGATATCAAACGTACGGTGGCT GCACCATCTGTCTTCATCTTCCCGCCATCTG ATGAGCAGTTGAAATCTGGAACTGCCTCTG TTGTGTGCCTGCTGAATAACTTCTATCCCAG AGAGGCCAAAGTACAGTGGAAGGTGGATA ACGCCCTCCAATCGGGTAACTCCCAGGAGA GTGTCACAGAGCAGGACAGCAAGGACAGC ACCTACAGCCTCAGCAGCACCCTGACGCTG AGCAAAGCAGACTACGAGAAACACAAAGT CTACGCCTGCGAAGTCACCCATCAGGGCCT |

TABLE 4A-continued

| Exemplary Anti-PAC1 Antibody Light Chain Sequences | | | |
|---|---|---|---|
| Antibody ID. | LC Group | Light Chain Amino Acid Sequence | Light Chain Nucleic Acid Sequence |
| | | | GAGCTCGCCCGTCACAAAGAGCTTCAACAG GGGAGAGTGT (SEQ ID NO: 549) |
| iPS:448924 | LC-14 | DIQMTQSPSSLSASVGDRITITCRA SQPISRYLSWYQQKPGKAPKLLIF AGQRLQSGIPSRFSGSGSGTDFTL TINSLQPEDFATYFCQQAISIPYTF GPGTKVDIKRTVAAPSVFIFPPSDE QLKSGTASVVCLLNNFYPREAKV QWKVDNALQSGNSQESVTEQDS KDSTYSLSSTLTLSKADYEKHKV YACEVTHQGLSSPVTKSFNRGEC (SEQ ID NO: 517) | GACATCCAGATGACCCAGTCTCCATCCTCCC TGTCTGCATCTGTAGGAGACAGAATCACCA TCACTTGCCGGGCAAGTCAGCCGATTTCTCG TTACTTATCTTGGTATCAACAGAAACCAGG GAAAGCCCCTAAACTCCTGATCTTCGCTGGT CAGCGTTTGCAAAGTGGGATCCCATCAAGG TTCAGCGGCAGTGGATCTGGGACAGATTTC ACTCTCACCATCAACAGTCTGCAACCTGAA GATTTTGCAACTTACTTCTGTCAACAGGCTA TCTCTATCCCATACACTTTCGGCCCTGGGAC CAAAGTGGATATCAAACGTACGGTGGCTG CACCATCTGTCTTCATCTTCCCGCCATCTGA TGAGCAGTTGAAATCTGGAACTGCCTCTGTT GTGTGCCTGCTGAATAACTTCTATCCCAGAG AGGCCAAAGTACAGTGGAAGGTGGATAAC GCCCTCCAATCGGGTAACTCCCAGGAGAGT GTCACAGAGCAGGACAGCAAGGACAGCAC CTACAGCCTCAGCAGCACCCTGACGCTGAG CAAAGCAGACTACGAGAAACACAAAGTCTA CGCCTGCGAAGTCACCCATCAGGGCCTGAG CTCGCCCGTCACAAAGAGCTTCAACAGGGG AGAGTGT (SEQ ID NO: 550) |
| 3574 | LC-06 | DIQMTQSPSSLSASVGDRITITCRA SQSISRYLNWYQQKPGKAPKLLIY AASSLQSGIPSRFSGSGSGTDFTLT INSLQPEDFATYFCQQSYSPPFTFG PGTKVDIKRTVAAPSVFIFPPSDEQ LKSGTASVVCLLNNFYPREAKVQ WKVDNALQSGNSQESVTEQDSK DSTYSLSSTLTLSKADYEKHKVY ACEVTHQGLSSPVTKSFNRGEC (SEQ ID NO: 509) | GACATCCAGATGACCCAGTCTCCATCCTCCC TGTCTGCATCTGTAGGAGACAGAATCACCA TCACTTGCCGGGCAAGTCAGAGCATTAGCA GGTATTTAAATTGGTATCAACAGAAACCAG GGAAAGCCCCTAAACTCCTGATCTATGCTG CATCCAGTTTGCAAAGTGGGATCCCATCAA GGTTCAGCGGCAGTGGATCTGGGACAGATT TCACTCTCACCATCAACAGTCTGCAACCTGA AGATTTTGCAACTTACTTCTGTCAACAGAGT TACAGTCCCCCATTCACTTTCGGCCCTGGGA CCAAAGTGGATATCAAACGTACGGTGGCTG CACCATCTGTCTTCATCTTCCCGCCATCTGA TGAGCAGTTGAAATCTGGAACTGCCTCTGTT GTGTGCCTGCTGAATAACTTCTATCCCAGAG AGGCCAAAGTACAGTGGAAGGTGGATAAC GCCCTCCAATCGGGTAACTCCCAGGAGAGT GTCACAGAGCAGGACAGCAAGGACAGCAC CTACAGCCTCAGCAGCACCCTGACGCTGAG CAAAGCAGACTACGAGAAACACAAAGTCTA CGCCTGCGAAGTCACCCATCAGGGCCTGAG CTCGCCCGTCACAAAGAGCTTCAACAGGGG AGAGTGT (SEQ ID NO: 542) |
| 3575 | LC-15 | DIQMTQSPSSLSASVGDRITITCRA SQQIARYLNWYQQKPGKAPKLLI YASYNLQSGIPSRFSGSGSGTDFT LTINSLQPEDFATYFCQQAIIQPYT FGPGTKVDIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 518) | GACATCCAGATGACCCAGTCTCCATCCTCCC TGTCTGCATCTGTAGGAGACAGAATCACCA TCACTTGCCGGGCAAGTCAGCAGATTGCTC GTTACTTAAACTGGTATCAACAGAAACCAG GGAAAGCCCCTAAACTCCTGATCTACGCTT CTTACAACTTGCAAAGTGGGATCCCATCAA GGTTCAGCGGCAGTGGATCTGGGACAGATT TCACTCTCACCATCAACAGTCTGCAACCTGA AGATTTTGCAACTTACTTCTGTCAACAGGCT ATCATCCAGCCATACACTTTCGGCCCTGGG ACCAAAGTGGATATCAAACGTACGGTGGCT GCACCATCTGTCTTCATCTTCCCGCCATCTG ATGAGCAGTTGAAATCTGGAACTGCCTCTG TTGTGTGCCTGCTGAATAACTTCTATCCCAG AGAGGCCAAAGTACAGTGGAAGGTGGATA ACGCCCTCCAATCGGGTAACTCCCAGGAGA GTGTCACAGAGCAGGACAGCAAGGACAGC ACCTACAGCCTCAGCAGCACCCTGACGCTG AGCAAAGCAGACTACGAGAAACACAAAGT CTACGCCTGCGAAGTCACCCATCAGGGCCT GAGCTCGCCCGTCACAAAGAGCTTCAACAG GGGAGAGTGT (SEQ ID NO: 551) |

TABLE 4B

Exemplary Anti-PAC1 Antibody Heavy Chain Sequences

| Antibody ID. | HC Group | Heavy Chain Amino Acid Sequence | Heavy Chain Nucleic Acid Sequence |
|---|---|---|---|
| | | 29G4 variants | |
| 29G4v10 | HC-01 | QVQLVESGGGVVQPGRSLRLSCAASGFTFSRFAMHWVRQAPGKGLEWVAVISYDGGNKYYAESVKGRFTISRDNSKNTLYLQMNSLRAEDTALFYCARGYDVLTGYPDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPCEEQYGSTYRCVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 519) | CAGGTGCAGCTGGTGGAGTCTGGGGGAGGCGTGGTCCAGCCTGGGAGGTCCCTGCGACTCTCCTGTGCAGCCTCTGGATTCACCTTCAGTAGATTTGCCATGCACTGGGTCCGCCAGGCTCCAGGCAAGGGGCTGGAGTGGGTGGCAGTTATATCATATGATGGAGGAAATAAATACTATGCAGAGTCCGTGAAGGGCCGGTTCACCATCTCCAGAGACAATTCCAAGAACACCCTGTATCTGCAAATGAACAGCCTGAGAGCTGAGGACACGGCTCTGTTTTACTGTGCGAGAGGATACGATGTTTTGACTGGTTACCCCGACTACTGGGGCCAGGGAACCCTGGTCACCGTCTCTAGTGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGTGCGAGGAGCAGTACGGCAGCACGTACCGTTGCGTCAGCGTCCTCACCGTCCTGCACCAGGACTGGCTGAATGGCAAGGAGTACAAGTGCAAGGTGTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTATAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAA (SEQ ID NO: 552) |
| 29G4v22 | HC-02 | QVQLVESGAEVVKPGASVKVSCKASGFTFSRFAMHWVRQAPGQGLEWMGVISYDGGNKYYAESVKGRVTMTRDTSTSTLYMELSSLRSEDTAVYYCARGYDVLTGYPDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYGSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 520) | CAAGTTCAGTTGGTGGAGTCTGGAGCCGAAGTAGTAAAGCCAGGAGCTTCAGTGAAAGTCTCTTGTAAAGCAAGTGGATTCACGTTTAGCCGCTTTGCCATGCATTGGGTGCGGCAAGCTCCCGGTCAGGGGTTGGAGTGGATGGGAGTTATTAGCTATGACGGGGGCAATAAGTACTACGCCGAGTCTGTTAAGGGTCGGGTCACAATGACACGGGACACCTCAACCAGTACACTCTATATGGAACTGTCTAGCCTGAGATCCGAGGACACCGCTGTGTATTATTGCGCTAGGGGGTACGATGTATTGACGGGTTATCCTGATTACTGGGGGCAGGGGACACTCGTAACCGTCTCTAGTGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACGGCAGCACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAATGGGCAGCC |

TABLE 4B-continued

Exemplary Anti-PAC1 Antibody Heavy Chain Sequences

| Antibody ID. | HC Group | Heavy Chain Amino Acid Sequence | Heavy Chain Nucleic Acid Sequence |
|---|---|---|---|
| | | | GGAGAACAACTACAAGACCACGCCTCCCGTGCTGG |
| | | | ACTCCGACGGCTCCTTCTTCCTCTATAGCAAGCTCA |
| | | | CCGTGGACAAGAGCAGGTGGCAGCAGGGGAACGTC |
| | | | TTCTCATGCTCCGTGATGCATGAGGCTCTGCACAAC |
| | | | CACTACACGCAGAAGAGCCTCTCCCTGTCTCCGGGT |
| | | | AAA (SEQ ID NO: 553) |
| iPS:420653 | HC-03 | QVQLVESGGGVVQPGRS | CAGGTGCAGCTGGTGGAGTCTGGGGGAGGCGTGGT |
| | | LRLSCAASGFTFSRFAMH | CCAGCCTGGGAGGTCCCTGCGACTCTCCTGTGCAGC |
| | | WVRQAPGKGLEWVAVIS | CTCTGGATTCACCTTCAGTAGATTTGCCATGCACTG |
| | | YIGGNKYYAESVKGRFTI | GGTCCGCCAGGCTCCAGGCAAGGGGCTGGAGTGGG |
| | | SRDNSKNTLYLQMNSLR | TGGCAGTTATATCATATATCGGAGGAAATAAATACT |
| | | AEDTALFYCARGYDVLT | ATGCAGAGTCCGTGAAGGGCCGGTTCACCATCTCC |
| | | GYPDYWGQGTLVTVSSA | AGAGACAATTCCAAGAACACCCTGTATCTGCAAAT |
| | | STKGPSVFPLAPSSKSTSG | GAACAGCCTGAGAGCTGAGGACACGGCTCTGTTTT |
| | | GTAALGCLVKDYFPEPVT | ACTGTGCGAGAGGATACGATGTTTTGACTGGTTACC |
| | | VSWNSGALTSGVHTFPA | CCGACTACTGGGGCCAGGGAACCCTGGTCACCGTC |
| | | VLQSSGLYSLSSVVTVPSS | TCTAGTGCCTCCACCAAGGGCCCATCGGTCTTCCCC |
| | | SLGTQTYICNVNHKPSNT | CTGGCACCCTCCTCCAAGAGCACCTCTGGGGGCAC |
| | | KVDKKVEPKSCDKTHTC | AGCGGCCCTGGGCTGCCTGGTCAAGGACTACTTCCC |
| | | PPCPAPELLGGPSVFLFPP | CGAACCGGTGACGGTGTCGTGGAACTCAGGCGCCC |
| | | KPKDTLMISRTPEVTCVV | TGACCAGCGGCGTGCACACCTTCCCGGCTGTCCTAC |
| | | VDVSHEDPEVKFNWYVD | AGTCCTCAGGACTCTACTCCCTCAGCAGCGTGGTGA |
| | | GVEVHNAKTKPCEEQYG | CCGTGCCCTCCAGCAGCTTGGGCACCCAGACCTACA |
| | | STYRCVSVLTVLHQDWL | TCTGCAACGTGAATCACAAGCCCAGCAACACCAAG |
| | | NGKEYKCKVSNKALPAPI | GTGGACAAGAAAGTTGAGCCCAAATCTTGTGACAA |
| | | EKTISKAKGQPREPQVYT | AACTCACACATGCCCACCGTGCCCAGCACCTGAACT |
| | | LPPSREEMTKNQVSLTCL | CCTGGGGGGACCGTCAGTCTTCCTCTTCCCCCCAAA |
| | | VKGFYPSDIAVEWESNGQ | ACCCAAGGACACCCTCATGATCTCCCGGACCCCTGA |
| | | PENNYKTTPPVLDSDGSF | GGTCACATGCGTGGTGGTGGACGTGAGCCACGAAG |
| | | FLYSKLTVDKSRWQQGN | ACCCTGAGGTCAAGTTCAACTGGTACGTGGACGGC |
| | | VFSCSVMHEALHNHYTQ | GTGGAGGTGCATAATGCCAAGACAAAGCCGTGCGA |
| | | KSLSLSPGK (SEQ ID | GGAGCAGTACGGCAGCACGTACCGTTGCGTCAGCG |
| | | NO: 521) | TCCTCACCGTCCTGCACCAGGACTGGCTGAATGGCA |
| | | | AGGAGTACAAGTGCAAGGTGTCCAACAAAGCCCTC |
| | | | CCAGCCCCCATCGAGAAAACCATCTCCAAAGCCAA |
| | | | AGGGCAGCCCCGAGAACCACAGGTGTACACCCTGC |
| | | | CCCCATCCCGGGAGGAGATGACCAAGAACCAGGTC |
| | | | AGCCTGACCTGCCTGGTCAAAGGCTTCTATCCCAGC |
| | | | GACATCGCCGTGGAGTGGGAGAGCAATGGGCAGCC |
| | | | GGAGAACAACTACAAGACCACGCCTCCCGTGCTGG |
| | | | ACTCCGACGGCTCCTTCTTCCTCTATAGCAAGCTCA |
| | | | CCGTGGACAAGAGCAGGTGGCAGCAGGGGAACGTC |
| | | | TTCTCATGCTCCGTGATGCATGAGGCTCTGCACAAC |
| | | | CACTACACGCAGAAGAGCCTCTCCCTGTCTCCGGGT |
| | | | AAA (SEQ ID NO: 554) |
| iPS:420845 | HC-04 | QVQLVESGGGVVQPGRS | CAGGTGCAGCTGGTGGAGTCTGGGGGAGGCGTGGT |
| | | LRLSCAASGFTFSRFAMH | CCAGCCTGGGAGGTCCCTGCGACTCTCCTGTGCAGC |
| | | WVRQAPGKGLEWVAVIS | CTCTGGATTCACCTTCAGTAGATTTGCCATGCACTG |
| | | YQGRNKYYAESVKGRFTI | GGTCCGCCAGGCTCCAGGCAAGGGGCTGGAGTGGG |
| | | SRDNSKNTLYLQMNSLR | TGGCAGTTATATCATATCAGGGACGCAATAAATACT |
| | | AEDTALFYCARGYDVLT | ATGCAGAGTCCGTGAAGGGCCGGTTCACCATCTCC |
| | | GYPDYWGQGTLVTVSSA | AGAGACAATTCCAAGAACACCCTGTATCTGCAAAT |
| | | STKGPSVFPLAPSSKSTSG | GAACAGCCTGAGAGCTGAGGACACGGCTCTGTTTT |
| | | GTAALGCLVKDYFPEPVT | ACTGTGCGAGAGGATACGATGTTTTGACTGGTTACC |
| | | VSWNSGALTSGVHTFPA | CCGACTACTGGGGCCAGGGAACCCTGGTCACCGTC |
| | | VLQSSGLYSLSSVVTVPSS | TCTAGTGCCTCCACCAAGGGCCCATCGGTCTTCCCC |
| | | SLGTQTYICNVNHKPSNT | CTGGCACCCTCCTCCAAGAGCACCTCTGGGGGCAC |
| | | KVDKKVEPKSCDKTHTC | AGCGGCCCTGGGCTGCCTGGTCAAGGACTACTTCCC |
| | | PPCPAPELLGGPSVFLFPP | CGAACCGGTGACGGTGTCGTGGAACTCAGGCGCCC |
| | | KPKDTLMISRTPEVTCVV | TGACCAGCGGCGTGCACACCTTCCCGGCTGTCCTAC |
| | | VDVSHEDPEVKFNWYVD | AGTCCTCAGGACTCTACTCCCTCAGCAGCGTGGTGA |
| | | GVEVHNAKTKPCEEQYG | CCGTGCCCTCCAGCAGCTTGGGCACCCAGACCTACA |
| | | STYRCVSVLTVLHQDWL | TCTGCAACGTGAATCACAAGCCCAGCAACACCAAG |
| | | NGKEYKCKVSNKALPAPI | GTGGACAAGAAAGTTGAGCCCAAATCTTGTGACAA |
| | | EKTISKAKGQPREPQVYT | AACTCACACATGCCCACCGTGCCCAGCACCTGAACT |
| | | LPPSREEMTKNQVSLTCL | CCTGGGGGGACCGTCAGTCTTCCTCTTCCCCCCAAA |
| | | VKGFYPSDIAVEWESNGQ | ACCCAAGGACACCCTCATGATCTCCCGGACCCCTGA |
| | | PENNYKTTPPVLDSDGSF | GGTCACATGCGTGGTGGTGGACGTGAGCCACGAAG |
| | | FLYSKLTVDKSRWQQGN | ACCCTGAGGTCAAGTTCAACTGGTACGTGGACGGC |
| | | VFSCSVMHEALHNHYTQ | GTGGAGGTGCATAATGCCAAGACAAAGCCGTGCGA |
| | | KSLSLSPGK (SEQ ID | GGAGCAGTACGGCAGCACGTACCGTTGCGTCAGCG |
| | | NO: 522) | TCCTCACCGTCCTGCACCAGGACTGGCTGAATGGCA |
| | | | AGGAGTACAAGTGCAAGGTGTCCAACAAAGCCCTC |

TABLE 4B-continued

Exemplary Anti-PAC1 Antibody Heavy Chain Sequences

| Antibody ID. | HC Group | Heavy Chain Amino Acid Sequence | Heavy Chain Nucleic Acid Sequence |
|---|---|---|---|
| | | | CCAGCCCCCATCGAGAAAACCATCTCCAAAGCCAA<br>AGGGCAGCCCCGAGAACCACAGGTGTACACCCTGC<br>CCCCATCCCGGGAGGAGATGACCAAGAACCAGGTC<br>AGCCTGACCTGCCTGGTCAAAGGCTTCTATCCCAGC<br>GACATCGCCGTGGAGTGGGAGAGCAATGGGCAGCC<br>GGAGAACAACTACAAGACCACGCCTCCCGTGCTGG<br>ACTCCGACGGCTCCTTCTTCCTCTATAGCAAGCTCA<br>CCGTGGACAAGAGCAGGTGGCAGCAGGGGAACGTC<br>TTCTCATGCTCCGTGATGCATGAGGCTCTGCACAAC<br>CACTACACGCAGAAGAGCCTCTCCCTGTCTCCGGGT<br>AAA (SEQ ID NO: 555) |
| iPS:420943 | HC-05 | QVQLVESGGGVVQPGRS<br>LRLSCAASGFTFSRFAMH<br>WVRQAPGKGLEWVAVIS<br>YQGNNKYYARSVKGRFT<br>ISRDNSKNTLYLQMNSLR<br>AEDTALFYCARGYDVLT<br>GYPDYWGQGTLVTVSSA<br>STKGPSVFPLAPSSKSTSG<br>GTAALGCLVKDYFPEPVT<br>VSWNSGALTSGVHTFPA<br>VLQSSGLYSLSSVVTVPSS<br>SLGTQTYICNVNHKPSNT<br>KVDKKVEPKSCDKTHTC<br>PPCPAPELLGGPSVFLFPP<br>KPKDTLMISRTPEVTCVV<br>VDVSHEDPEVKFNWYVD<br>GVEVHNAKTKPCEEQYG<br>STYRCVSVLTVLHQDWL<br>NGKEYKCKVSNKALPAPI<br>EKTISKAKGQPREPQVYT<br>LPPSREEMTKNQVSLTCL<br>VKGFYPSDIAVEWESNGQ<br>PENNYKTTPPVLDSDGSF<br>FLYSKLTVDKSRWQQGN<br>VFSCSVMHEALHNHYTQ<br>KSLSLSPGK (SEQ ID<br>NO: 523) | CAGGTGCAGCTGGTGGAGTCTGGGGGAGGCGTGGT<br>CCAGCCTGGGAGGTCCCTGCGACTCTCCTGTGCAGC<br>CTCTGGATTCACCTTCAGTAGATTTGCCATGCACTG<br>GGTCCGCCAGGCTCCAGGCAAGGGGCTGGAGTGGG<br>TGGCAGTTATATCATATCAGGGAAACAATAAATAC<br>TATGCACGCTCCGTGAAGGGCCGGTTCACCATCTCC<br>AGAGACAATTCCAAGAACACCCTGTATCTGCAAAT<br>GAACAGCCTGAGAGCTGAGGACACGGCTCTGTTTT<br>ACTGTGCGAGAGGATACGATGTTTTGACTGGTTACC<br>CCGACTACTGGGGCCAGGGAACCCTGGTCACCGTC<br>TCTAGTGCCTCCACCAAGGGCCCATCGGTCTTCCCC<br>CTGGCACCCTCCTCCAAGAGCACCTCTGGGGGCAC<br>AGCGGCCCTGGGCTGCCTGGTCAAGGACTACTTCCC<br>CGAACCGGTGACGGTGTCGTGGAACTCAGGCGCCC<br>TGACCAGCGGCGTGCACACCTTCCCGGCTGTCCTAC<br>AGTCCTCAGGACTCTACTCCCTCAGCAGCGTGGTGA<br>CCGTGCCCTCCAGCAGCTTGGGCACCCAGACCTACA<br>TCTGCAACGTGAATCACAAGCCCAGCAACACCAAG<br>GTGGACAAGAAAGTTGAGCCCAAATCTTGTGACAA<br>AACTCACACATGCCCACCGTGCCCAGCACCTGAACT<br>CCTGGGGGGACCGTCAGTCTTCCTCTTCCCCCCAAA<br>ACCCAAGGACACCCTCATGATCTCCCGGACCCCTGA<br>GGTCACATGCGTGGTGGTGGACGTGAGCCACGAAG<br>ACCCTGAGGTCAAGTTCAACTGGTACGTGGACGGC<br>GTGGAGGTGCATAATGCCAAGACAAAGCCGTGCGA<br>GGAGCAGTACGGCAGCACGTACCGTTGCGTCAGCG<br>TCCTCACCGTCCTGCACCAGGACTGGCTGAATGGCA<br>AGGAGTACAAGTGCAAGGTGTCCAACAAAGCCCTC<br>CCAGCCCCCATCGAGAAAACCATCTCCAAAGCCAA<br>AGGGCAGCCCCGAGAACCACAGGTGTACACCCTGC<br>CCCCATCCCGGGAGGAGATGACCAAGAACCAGGTC<br>AGCCTGACCTGCCTGGTCAAAGGCTTCTATCCCAGC<br>GACATCGCCGTGGAGTGGGAGAGCAATGGGCAGCC<br>GGAGAACAACTACAAGACCACGCCTCCCGTGCTGG<br>ACTCCGACGGCTCCTTCTTCCTCTATAGCAAGCTCA<br>CCGTGGACAAGAGCAGGTGGCAGCAGGGGAACGTC<br>TTCTCATGCTCCGTGATGCATGAGGCTCTGCACAAC<br>CACTACACGCAGAAGAGCCTCTCCCTGTCTCCGGGT<br>AAA (SEQ ID NO: 556) |
| iPS:421873 | HC-06 | QVQLVESGGGVVQPGRS<br>LRLSCAASGFTFSKFAMH<br>WVRQAPGKGLEWVAVIS<br>YRGGNKYYAESVKGRFTI<br>SRDNSKNTLYLQMNSLR<br>AEDTALFYCARGYDLLT<br>GYPDYWGQGTLVTVSSA<br>STKGPSVFPLAPSSKSTSG<br>GTAALGCLVKDYFPEPVT<br>VSWNSGALTSGVHTFPA<br>VLQSSGLYSLSSVVTVPSS<br>SLGTQTYICNVNHKPSNT<br>KVDKKVEPKSCDKTHTC<br>PPCPAPELLGGPSVFLFPP<br>KPKDTLMISRTPEVTCVV<br>VDVSHEDPEVKFNWYVD<br>GVEVHNAKTKPCEEQYG<br>STYRCVSVLTVLHQDWL<br>NGKEYKCKVSNKALPAPI<br>EKTISKAKGQPREPQVYT<br>LPPSREEMTKNQVSLTCL<br>VKGFYPSDIAVEWESNGQ<br>PENNYKTTPPVLDSDGSF | CAGGTGCAGCTGGTGGAGTCTGGGGGAGGCGTGGT<br>CCAGCCTGGGAGGTCCCTGCGACTCTCCTGTGCAGC<br>CTCTGGATTCACCTTCAGTAAGTTTGCCATGCACTG<br>GGTCCGCCAGGCTCCAGGCAAGGGGCTGGAGTGGG<br>TGGCAGTTATATCATATCGCGGAGGAAATAAATAC<br>TATGCAGAGTCCGTGAAGGGCCGGTTCACCATCTCC<br>AGAGACAATTCCAAGAACACCCTGTATCTGCAAAT<br>GAACAGCCTGAGAGCTGAGGACACGGCTCTGTTTT<br>ACTGTGCGAGAGGATACGATCTGTTGACTGGTTACC<br>CCGACTACTGGGGCCAGGGAACCCTGGTCACCGTC<br>TCTAGTGCCTCCACCAAGGGCCCATCGGTCTTCCCC<br>CTGGCACCCTCCTCCAAGAGCACCTCTGGGGGCAC<br>AGCGGCCCTGGGCTGCCTGGTCAAGGACTACTTCCC<br>CGAACCGGTGACGGTGTCGTGGAACTCAGGCGCCC<br>TGACCAGCGGCGTGCACACCTTCCCGGCTGTCCTAC<br>AGTCCTCAGGACTCTACTCCCTCAGCAGCGTGGTGA<br>CCGTGCCCTCCAGCAGCTTGGGCACCCAGACCTACA<br>TCTGCAACGTGAATCACAAGCCCAGCAACACCAAG<br>GTGGACAAGAAAGTTGAGCCCAAATCTTGTGACAA<br>AACTCACACATGCCCACCGTGCCCAGCACCTGAACT<br>CCTGGGGGGACCGTCAGTCTTCCTCTTCCCCCCAAA<br>ACCCAAGGACACCCTCATGATCTCCCGGACCCCTGA<br>GGTCACATGCGTGGTGGTGGACGTGAGCCACGAAG |

TABLE 4B-continued

Exemplary Anti-PAC1 Antibody Heavy Chain Sequences

| Antibody ID. | HC Group | Heavy Chain Amino Acid Sequence | Heavy Chain Nucleic Acid Sequence |
|---|---|---|---|
| | | FLYSKLTVDKSRWQQGN VFSCSVMHEALHNHYTQ KSLSLSPGK (SEQ ID NO: 524) | ACCCTGAGGTCAAGTTCAACTGGTACGTGGACGGC GTGGAGGTGCATAATGCCAAGACAAAGCCGTGCGA GGAGCAGTACGGCAGCACGTACCGTTGCGTCAGCG TCCTCACCGTCCTGCACCAGGACTGGCTGAATGGCA AGGAGTACAAGTGCAAGGTGTCCAACAAAGCCCTC CCAGCCCCCATCGAGAAAACCATCTCCAAAGCCAA AGGGCAGCCCCGAGAACCACAGGTGTACACCCTGC CCCCATCCCGGGAGGAGATGACCAAGAACCAGGTC AGCCTGACCTGCCTGGTCAAAGGCTTCTATCCCAGC GACATCGCCGTGGAGTGGGAGAGCAATGGGCAGCC GGAGAACAACTACAAGACCACGCCTCCCGTGCTGG ACTCCGACGGCTCCTTCTTCCTCTATAGCAAGCTCA CCGTGGACAAGAGCAGGTGGCAGCAGGGGAACGTC TTCTCATGCTCCGTGATGCATGAGGCTCTGCACAAC CACTACACGCAGAAGAGCCTCTCCCTGTCTCCGGGT AAA (SEQ ID NO: 557) |
| iPS:420889 | HC-07 | QVQLVESGGGVVQPGRS LRLSCAASGFTFSRFAMH WVRQAPGKGLEWVAVIS YIGGNKYYAESVKGRFTI SRDNSKNTLYLQMNSLR AEDTALFYCARGYDILTG YPDYWGQGTLVTVSSAS TKGPSVFPLAPSSKSTSGG TAALGCLVKDYFPEPVTV SWNSGALTSGVHTFPAVL QSSGLYSLSSVVTVPSSSL GTQTYICNVNHKPSNTKV DKKVEPKSCDKTHTCPPC PAPELLGGPSVFLFPPKPK DTLMISRTPEVTCVVVDV SHEDPEVKFNWYVDGVE VHNAKTKPCEEQYGSTY RCVSVLTVLHQDWLNGK EYKCKVSNKALPAPIEKTI SKAKGQPREPQVYTLPPS REEMTKNQVSLTCLVKG FYPSDIAVEWESNGQPEN NYKTTPPVLDSDGSFFLY SKLTVDKSRWQQGNVFS CSVMHEALHNHYTQKSL SLSPGK (SEQ ID NO: 525) | CAGGTGCAGCTGGTGGAGTCTGGGGGAGGCGTGGT CCAGCCTGGGAGGTCCCTGCGACTCTCCTGTGCAGC CTCTGGATTCACCTTCAGTAGATTTGCCATGCACTG GGTCCGCCAGGCTCCAGGCAAGGGGCTGGAGTGGG TGGCAGTTATATCATATATCGGAGGAAATAAATACT ATGCAGAGTCCGTGAAGGGCCGGTTCACCATCTCC AGAGACAATTCCAAGAACACCCTGTATCTGCAAAT GAACAGCCTGAGAGCTGAGGACACGGCTCTGTTTT ACTGTGCGAGAGGATACGATATCTTGACTGGTTACC CCGACTACTGGGGCCAGGGAACCCTGGTCACCGTC TCTAGTGCCTCCACCAAGGGCCCATCGGTCTTCCCC CTGGCACCCTCCTCCAAGAGCACCTCTGGGGGCAC AGCGGCCCTGGGCTGCCTGGTCAAGGACTACTTCCC CGAACCGGTGACGGTGTCGTGGAACTCAGGCGCCC TGACCAGCGGCGTGCACACCTTCCCGGCTGTCCTAC AGTCCTCAGGACTCTACTCCCTCAGCAGCGTGGTGA CCGTGCCCTCCAGCAGCTTGGGCACCCAGACCTACA TCTGCAACGTGAATCACAAGCCCAGCAACACCAAG GTGGACAAGAAAGTTGAGCCCAAATCTTGTGACAA AACTCACACATGCCCACCGTGCCCAGCACCTGAACT CCTGGGGGGACCGTCAGTCTTCCTCTTCCCCCCAAA ACCCAAGGACACCCTCATGATCTCCCGGACCCCTGA GGTCACATGCGTGGTGGTGGACGTGAGCCACGAAG ACCCTGAGGTCAAGTTCAACTGGTACGTGGACGGC GTGGAGGTGCATAATGCCAAGACAAAGCCGTGCGA GGAGCAGTACGGCAGCACGTACCGTTGCGTCAGCG TCCTCACCGTCCTGCACCAGGACTGGCTGAATGGCA AGGAGTACAAGTGCAAGGTGTCCAACAAAGCCCTC CCAGCCCCCATCGAGAAAACCATCTCCAAAGCCAA AGGGCAGCCCCGAGAACCACAGGTGTACACCCTGC CCCCATCCCGGGAGGAGATGACCAAGAACCAGGTC AGCCTGACCTGCCTGGTCAAAGGCTTCTATCCCAGC GACATCGCCGTGGAGTGGGAGAGCAATGGGCAGCC GGAGAACAACTACAAGACCACGCCTCCCGTGCTGG ACTCCGACGGCTCCTTCTTCCTCTATAGCAAGCTCA CCGTGGACAAGAGCAGGTGGCAGCAGGGGAACGTC TTCTCATGCTCCGTGATGCATGAGGCTCTGCACAAC CACTACACGCAGAAGAGCCTCTCCCTGTCTCCGGGT AAA (SEQ ID NO: 558) |
| iPS:421091 | HC-08 | QVQLVESGGGVVQPGRS LRLSCAASGFTFSRFAMH WVRQAPGKGLEWVAVIS YNGRNKYYARSVKGRFT ISRDNSKNTLYLQMNSLR AEDTALFYCARGYDILTG YPDYWGQGTLVTVSSAS TKGPSVFPLAPSSKSTSGG TAALGCLVKDYFPEPVTV SWNSGALTSGVHTFPAVL QSSGLYSLSSVVTVPSSSL GTQTYICNVNHKPSNTKV DKKVEPKSCDKTHTCPPC PAPELLGGPSVFLFPPKPK DTLMISRTPEVTCVVVDV SHEDPEVKFNWYVDGVE VHNAKTKPCEEQYGSTY RCVSVLTVLHQDWLNGK | CAGGTGCAGCTGGTGGAGTCTGGGGGAGGCGTGGT CCAGCCTGGGAGGTCCCTGCGACTCTCCTGTGCAGC CTCTGGATTCACCTTCAGTAGATTTGCCATGCACTG GGTCCGCCAGGCTCCAGGCAAGGGGCTGGAGTGGG TGGCAGTTATATCATATAACGGACGCAATAAATACT ATGCACGCTCCGTGAAGGGCCGGTTCACCATCTCCA GAGACAATTCCAAGAACACCCTGTATCTGCAAATG AACAGCCTGAGAGCTGAGGACACGGCTCTGTTTTA CTGTGCGAGAGGATACGATATCTTGACTGGTTACCC CGACTACTGGGGCCAGGGAACCCTGGTCACCGTCT CTAGTGCCTCCACCAAGGGCCCATCGGTCTTCCCCC TGGCACCCTCCTCCAAGAGCACCTCTGGGGGCACA GCGGCCCTGGGCTGCCTGGTCAAGGACTACTTCCCC GAACCGGTGACGGTGTCGTGGAACTCAGGCGCCCT GACCAGCGGCGTGCACACCTTCCCGGCTGTCCTACA GTCCTCAGGACTCTACTCCCTCAGCAGCGTGGTGAC CGTGCCCTCCAGCAGCTTGGGCACCCAGACCTACAT CTGCAACGTGAATCACAAGCCCAGCAACACCAAGG |

TABLE 4B-continued

Exemplary Anti-PAC1 Antibody Heavy Chain Sequences

| Antibody ID. | HC Group | Heavy Chain Amino Acid Sequence | Heavy Chain Nucleic Acid Sequence |
|---|---|---|---|
| | | EYKCKVSNKALPAPIEKTI<br>SKAKGQPREPQVYTLPPS<br>REEMTKNQVSLTCLVKG<br>FYPSDIAVEWESNGQPEN<br>NYKTTPPVLDSDGSFFLY<br>SKLTVDKSRWQQGNVFS<br>CSVMHEALHNHYTQKSL<br>SLSPGK (SEQ ID NO:<br>526) | TGGACAAGAAAGTTGAGCCCAAATCTTGTGACAAA<br>ACTCACACATGCCCACCGTGCCCAGCACCTGAACTC<br>CTGGGGGGACCGTCAGTCTTCCTCTTCCCCCCAAAA<br>CCCAAGGACACCCTCATGATCTCCCGGACCCCTGAG<br>GTCACATGCGTGGTGGTGGACGTGAGCCACGAAGA<br>CCCTGAGGTCAAGTTCAACTGGTACGTGGACGGCG<br>TGGAGGTGCATAATGCCAAGACAAAGCCGTGCGAG<br>GAGCAGTACGGCAGCACGTACCGTTGCGTCAGCGT<br>CCTCACCGTCCTGCACCAGGACTGGCTGAATGGCA<br>AGGAGTACAAGTGCAAGGTGTCCAACAAAGCCCTC<br>CCAGCCCCCATCGAGAAAACCATCTCCAAAGCCAA<br>AGGGCAGCCCCGAGAACCACAGGTGTACACCCTGC<br>CCCCATCCCGGGAGGAGATGACCAAGAACCAGGTC<br>AGCCTGACCTGCCTGGTCAAAGGCTTCTATCCCAGC<br>GACATCGCCGTGGAGTGGGAGAGCAATGGGCAGCC<br>GGAGAACAACTACAAGACCACGCCTCCCGTGCTGG<br>ACTCCGACGGCTCCTTCTTCCTCTATAGCAAGCTCA<br>CCGTGGACAAGAGCAGGTGGCAGCAGGGGAACGTC<br>TTCTCATGCTCCGTGATGCATGAGGCTCTGCACAAC<br>CACTACACGCAGAAGAGCCTCTCCCTGTCTCCGGGT<br>AAA (SEQ ID NO: 559) |
| iPS:421051 | HC-05 | QVQLVESGGGVVQPGRS<br>LRLSCAASGFTFSRFAMH<br>WVRQAPGKGLEWVAVIS<br>YQGNNKYYARSVKGRFT<br>ISRDNSKNTLYLQMNSLR<br>AEDTALFYCARGYDVLT<br>GYPDYWGQGTLVTVSSA<br>STKGPSVFPLAPSSKSTSG<br>GTAALGCLVKDYFPEPVT<br>VSWNSGALTSGVHTFPA<br>VLQSSGLYSLSSVVTVPSS<br>SLGTQTYICNVNHKPSNT<br>KVDKKVEPKSCDKTHTC<br>PPCPAPELLGGPSVFLFPP<br>KPKDTLMISRTPEVTCVV<br>VDVSHEDPEVKFNWYVD<br>GVEVHNAKTKPCEEQYG<br>STYRCVSVLTVLHQDWL<br>NGKEYKCKVSNKALPAPI<br>EKTISKAKGQPREPQVYT<br>LPPSREEMTKNQVSLTCL<br>VKGFYPSDIAVEWESNGQ<br>PENNYKTTPPVLDSDGSF<br>FLYSKLTVDKSRWQQGN<br>VFSCSVMHEALHNHYTQ<br>KSLSLSPGK (SEQ ID<br>NO: 523) | CAGGTGCAGCTGGTGGAGTCTGGGGGAGGCGTGGT<br>CCAGCCTGGGAGGTCCCTGCGACTCTCCTGTGCAGC<br>CTCTGGATTCACCTTCAGTAGATTTGCCATGCACTG<br>GGTCCGCCAGGCTCCAGGCAAGGGGCTGGAGTGGG<br>TGGCAGTTATATCATATCAGGGAAACAATAAATAC<br>TATGCACGCTCCGTGAAGGGCCGGTTCACCATCTCC<br>AGAGACAATTCCAAGAACACCCTGTATCTGCAAAT<br>GAACAGCCTGAGAGCTGAGGACACGGCTCTGTTTT<br>ACTGTGCGAGAGGATACGATGTTTTGACTGGTTACC<br>CCGACTACTGGGGCCAGGGAACCCTGGTCACCGTC<br>TCTAGTGCCTCCACCAAGGGCCCATCGGTCTTCCCC<br>CTGGCACCCTCCTCCAAGAGCACCTCTGGGGGCAC<br>AGCGGCCCTGGGCTGCCTGGTCAAGGACTACTTCCC<br>CGAACCGGTGACGGTGTCGTGGAACTCAGGCGCCC<br>TGACCAGCGGCGTGCACACCTTCCCGGCTGTCCTAC<br>AGTCCTCAGGACTCTACTCCCTCAGCAGCGTGGTGA<br>CCGTGCCCTCCAGCAGCTTGGGCACCCAGACCTACA<br>TCTGCAACGTGAATCACAAGCCCAGCAACACCAAG<br>GTGGACAAGAAAGTTGAGCCCAAATCTTGTGACAA<br>AACTCACACATGCCCACCGTGCCCAGCACCTGAACT<br>CCTGGGGGGACCGTCAGTCTTCCTCTTCCCCCCAAA<br>ACCCAAGGACACCCTCATGATCTCCCGGACCCCTGA<br>GGTCACATGCGTGGTGGTGGACGTGAGCCACGAAG<br>ACCCTGAGGTCAAGTTCAACTGGTACGTGGACGGC<br>GTGGAGGTGCATAATGCCAAGACAAAGCCGTGCGA<br>GGAGCAGTACGGCAGCACGTACCGTTGCGTCAGCG<br>TCCTCACCGTCCTGCACCAGGACTGGCTGAATGGCA<br>AGGAGTACAAGTGCAAGGTGTCCAACAAAGCCCTC<br>CCAGCCCCCATCGAGAAAACCATCTCCAAAGCCAA<br>AGGGCAGCCCCGAGAACCACAGGTGTACACCCTGC<br>CCCCATCCCGGGAGGAGATGACCAAGAACCAGGTC<br>AGCCTGACCTGCCTGGTCAAAGGCTTCTATCCCAGC<br>GACATCGCCGTGGAGTGGGAGAGCAATGGGCAGCC<br>GGAGAACAACTACAAGACCACGCCTCCCGTGCTGG<br>ACTCCGACGGCTCCTTCTTCCTCTATAGCAAGCTCA<br>CCGTGGACAAGAGCAGGTGGCAGCAGGGGAACGTC<br>TTCTCATGCTCCGTGATGCATGAGGCTCTGCACAAC<br>CACTACACGCAGAAGAGCCTCTCCCTGTCTCCGGGT<br>AAA (SEQ ID NO: 556) |
| iPS:480711 | HC-09 | QVQLVESGGGVVQPGRS<br>LRLSCAASGFTFSRFAMH<br>WVRQAPGKGLEWVGVIN<br>YRGHGKYYAESVKGRFT<br>VSRDNSKNTLYLQMNSL<br>RAEDTALFYCARGYDVL<br>TGYPDYWGQGTLVTVSS<br>ASTKGPSVFPLAPSSKSTS<br>GGTAALGCLVKDYFPEP<br>VTVSWNSGALTSGVHTFP<br>AVLQSSGLYSLSSVVTVP<br>SSSLGTQTYICNVNHKPS<br>NTKVDKKVEPKSCDKTH | CAGGTGCAGCTGGTGGAGTCTGGGGGAGGCGTGG<br>TCCAGCCTGGGAGGTCCCTGCGACTCTCCTGTGCAG<br>CCTCTGGATTCACCTTCAGTAGATTTGCCATGCACT<br>GGGTCCGCCAGGCTCCAGGCAAGGGGCTGGAGTGG<br>GTGGGTGTTATCAACTATCGTGGACATGGTAAATAC<br>TATGCAGAGTCCGTGAAGGGCCGGTTCACCGTGTCC<br>AGAGACAATTCCAAGAACACCCTGTATCTGCAAAT<br>GAACAGCCTGAGAGCTGAGGACACGGCTCTGTTTT<br>ACTGTGCGAGAGGATACGATGTTTTGACTGGTTACC<br>CCGACTACTGGGGCCAGGGAACCCTGGTCACCGTG<br>TCTAGTGCCTCCACCAAGGGCCCATCGGTCTTCCCC<br>CTGGCACCCTCCTCCAAGAGCACCTCTGGGGGCAC<br>AGCGGCCCTGGGCTGCCTGGTCAAGGACTACTTCCC |

TABLE 4B-continued

| Exemplary Anti-PAC1 Antibody Heavy Chain Sequences | | | |
|---|---|---|---|
| Antibody ID. | HC Group | Heavy Chain Amino Acid Sequence | Heavy Chain Nucleic Acid Sequence |
| | | TCPPCPAPELLGGPSVFLF PPKPKDTLMISRTPEVTC VVVDVSHEDPEVKFNWY VDGVEVHNAKTKPCEEQ YGSTYRCVSVLTVLHQD WLNGKEYKCKVSNKALP APIEKTISKAKGQPREPQV YTLPPSREEMTKNQVSLT CLVKGFYPSDIAVEWESN GQPENNYKTTPPVLDSDG SFFLYSKLTVDKSRWQQ GNVFSCSVMHEALHNHY TQKSLSLSPGK (SEQ ID NO: 527) | CGAACCGGTGACGGTGTCGTGGAACTCAGGCGCCC TGACCAGCGGCGTGCACACCTTCCCGGCTGTCCTAC AGTCCTCAGGACTCTACTCCCTCAGCAGCGTGGTGA CCGTGCCCTCCAGCAGCTTGGGCACCCAGACCTACA TCTGCAACGTGAATCACAAGCCCAGCAACACCAAG GTGGACAAGAAAGTTGAGCCCAAATCTTGTGACAA AACTCACACATGCCCACCGTGCCCAGCACCTGAACT CCTGGGGGGACCGTCAGTCTTCCTCTTCCCCCCAAA ACCCAAGGACACCCTCATGATCTCCCGGACCCCTGA GGTCACATGCGTGGTGGTGGACGTGAGCCACGAAG ACCCTGAGGTCAAGTTCAACTGGTACGTGGACGGC GTGGAGGTGCATAATGCCAAGACAAAGCCGTGCGA GGAGCAGTACGGCAGCACGTACCGTTGCGTCAGCG TCCTCACCGTCCTGCACCAGGACTGGCTGAATGGCA AGGAGTACAAGTGCAAGGTGTCCAACAAAGCCCTC CCAGCCCCCATCGAGAAAACCATCTCCAAAGCCAA AGGGCAGCCCCGAGAACCACAGGTGTACACCCTGC CCCCATCCCGGGAGGAGATGACCAAGAACCAGGTC AGCCTGACCTGCCTGGTCAAAGGCTTCTATCCCAGC GACATCGCCGTGGAGTGGGAGAGCAATGGGCAGCC GGAGAACAACTACAAGACCACGCCTCCCGTGCTGG ACTCCGACGGCTCCTTCTTCCTCTATAGCAAGCTCA CCGTGGACAAGAGCAGGTGGCAGCAGGGGAACGTC TTCTCATGCTCCGTGATGCATGAGGCTCTGCACAAC CACTACACGCAGAAGAGCCTCTCCCTGTCTCCGGGT AAA (SEQ ID NO: 560) |
| iPS:480706 | HC-10 | QVQLVESGGGVVQPGRS LRLSCAASGFTFSRFAMH WVRQAPGKGLEWVGVIS FSGGSKYYAESVKGRFTL SRDNSKNTLYLQMNSLR AEDTALFYCARGYDVLT GYPDYWGQGTLVTVSSA STKGPSVFPLAPSSKSTSG GTAALGCLVKDYFPEPVT VSWNSGALTSGVHTFPA VLQSSGLYSLSSVVTVPSS SLGTQTYICNVNHKPSNT KVDKKVEPKSCDKTHTC PPCPAPELLGGPSVFLFPP KPKDTLMISRTPEVTCVV VDVSHEDPEVKFNWYVD GVEVHNAKTKPCEEQYG STYRCVSVLTVLHQDWL NGKEYKCKVSNKALPAPI EKTISKAKGQPREPQVYT LPPSREEMTKNQVSLTCL VKGFYPSDIAVEWESNGQ PENNYKTTPPVLDSDGSF FLYSKLTVDKSRWQQGN VFSCSVMHEALHNHYTQ KSLSLSPGK (SEQ ID NO: 528) | CAGGTGCAGCTGGTGGAGTCTGGGGGAGGCGTGGT CCAGCCTGGGAGGTCCCTGCGACTCTCCTGTGCAGC CTCTGGATTCACCTTCAGTAGATTTGCCATGCACTG GGTCCGCCAGGCTCCAGGCAAGGGGCTGGAGTGGG TGGGTGTTATATCTTTTTCTGGAGGTTCTAAATACT ATGCAGAGTCCGTGAAGGGCCGGTTCACCTTGTCCA GAGACAATTCCAAGAACACCCTGTATCTGCAAATG AACAGCCTGAGAGCTGAGGACACGGCTCTGTTTTA CTGTGCGAGAGGATACGATGTTTTGACTGGTTACCC CGACTACTGGGGCCAGGGAACCCTGGTCACCGTGT CTAGTGCCTCCACCAAGGGCCCATCGGTCTTCCCCC TGGCACCCTCCTCCAAGAGCACCTCTGGGGGCACA GCGGCCCTGGGCTGCCTGGTCAAGGACTACTTCCCC GAACCGGTGACGGTGTCGTGGAACTCAGGCGCCCT GACCAGCGGCGTGCACACCTTCCCGGCTGTCCTACA GTCCTCAGGACTCTACTCCCTCAGCAGCGTGGTGAC CGTGCCCTCCAGCAGCTTGGGCACCCAGACCTACAT CTGCAACGTGAATCACAAGCCCAGCAACACCAAGG TGGACAAGAAAGTTGAGCCCAAATCTTGTGACAAA ACTCACACATGCCCACCGTGCCCAGCACCTGAACTC CTGGGGGGACCGTCAGTCTTCCTCTTCCCCCCAAAA CCCAAGGACACCCTCATGATCTCCCGGACCCCTGAG GTCACATGCGTGGTGGTGGACGTGAGCCACGAAGA CCCTGAGGTCAAGTTCAACTGGTACGTGGACGGCG TGGAGGTGCATAATGCCAAGACAAAGCCGTGCGAG GAGCAGTACGGCAGCACGTACCGTTGCGTCAGCGT CCTCACCGTCCTGCACCAGGACTGGCTGAATGGCA AGGAGTACAAGTGCAAGGTGTCCAACAAAGCCCTC CCAGCCCCCATCGAGAAAACCATCTCCAAAGCCAA AGGGCAGCCCCGAGAACCACAGGTGTACACCCTGC CCCCATCCCGGGAGGAGATGACCAAGAACCAGGTC AGCCTGACCTGCCTGGTCAAAGGCTTCTATCCCAGC GACATCGCCGTGGAGTGGGAGAGCAATGGGCAGCC GGAGAACAACTACAAGACCACGCCTCCCGTGCTGG ACTCCGACGGCTCCTTCTTCCTCTATAGCAAGCTCA CCGTGGACAAGAGCAGGTGGCAGCAGGGGAACGTC TTCTCATGCTCCGTGATGCATGAGGCTCTGCACAAC CACTACACGCAGAAGAGCCTCTCCCTGTCTCCGGGT AAA (SEQ ID NO: 561) |
| iPS:480713 | HC-11 | QVQLVESGGGVVQPGRS LRLSCAASGFTFSRFAMH WVRQAPGKGLEWVGVIS YTGQFKYYAESVKGRFT VSRDNSKNTLYLQMNSL RAEDTALFYCARGYDVL TGYPDYWGQGTLVTVSS ASTKGPSVFPLAPSSKSTS | CAGGTGCAGCTGGTGGAGTCTGGGGGAGGCGTGGT CCAGCCTGGGAGGTCCCTGCGACTCTCCTGTGCAGC CTCTGGATTCACCTTCAGTAGATTTGCCATGCACTG GGTCCGCCAGGCTCCAGGCAAGGGGCTGGAGTGGG TGGGTGTTATATCTCTTATACTGGACAGTTCAAATACT ATGCAGAGTCCGTGAAGGGCCGGTTCACCGTGTCC AGAGACAATTCCAAGAACACCCTGTATCTGCAAAT GAACAGCCTGAGAGCTGAGGACACGGCTCTGTTTT |

TABLE 4B-continued

Exemplary Anti-PAC1 Antibody Heavy Chain Sequences

| Antibody ID. | HC Group | Heavy Chain Amino Acid Sequence | Heavy Chain Nucleic Acid Sequence |
|---|---|---|---|
| | | GGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPCEEQYGSTYRCVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 529) | ACTGTGCGAGAGGATACGATGTTTTGACTGGTTACCCCGACTACTGGGGCCAGGGAACCCTGGTCACCGTGTCTAGTGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGTGCGAGGAGCAGTACGGCAGCACGTACCGTTGCGTCAGCGTCCTCACCGTCCTGCACCAGGACTGGCTGAATGGCAAGGAGTACAAGTGCAAGGTGTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTATAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAA (SEQ ID NO: 562) |
| 19H8 variants | | | |
| 19H8 | HC-12 | QVQLQQSGPGLVKPSQTLSLTCAISGDSVSSNSATWNWIRQSPSRGLEWLGRTYYRSKWSNHYAVSVKSRITINPDTSKSQFSLQLNSVTPEDTAVYYCARGTWKQLWFLDHWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPCEEQYGSTYRCVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 530) | CAGGTACAGCTGCAGCAGTCAGGTCCAGGACTGGTGAAGCCCTCGCAGACCCTCTCACTCACCTGTGCCATCTCCGGGGACAGTGTCTCTAGCAACAGTGCTACTTGGAACTGGATCAGGCAGTCCCCATCGAGAGGCCTTGAGTGGCTGGGAAGGACATATTACAGGTCCAAGTGGTCTAATCATTATGCAGTATCTGTGAAAAGTCGAATCACCATCAACCCCGACACGTCCAAGAGCCAGTTCTCCCTGCAGCTGAACTCTGTGACTCCCGAGGACACGGCTGTGTATTACTGTGCAAGAGGAACGTGGAAACAGCTATGGTTCCTTGACCACTGGGGCCAGGGAACCCTGGTCACCGTGTCTAGTGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGTGCGAGGAGCAGTACGGCAGCACGTACCGTTGCGTCAGCGTCCTCACCGTCCTGCACCAGGACTGGCTGAATGGCAAGGAGTACAAGTGCAAGGTGTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTATAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGCAAA (SEQ ID NO: 563) |

TABLE 4B-continued

Exemplary Anti-PAC1 Antibody Heavy Chain Sequences

| Antibody ID. | HC Group | Heavy Chain Amino Acid Sequence | Heavy Chain Nucleic Acid Sequence |
|---|---|---|---|
| iPS:448730 | HC-13 | QVQLQQSGPGLVKPSQTLSLTCAISGDSVSNRLATWNWIRQSPSRGLEWLGRTYYRGKWKNHYAVSVKSRITINPDTSKSQFSLQLNSVTPEDTAVYYCARGVWIGNWFLDHWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPCEEQYGSTYRCVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 531) | CAGGTACAGCTGCAGCAGTCAGGTCCAGGACTGGTGAAGCCCTCGCAGACCCTCTCACTCACCTGTGCCATCTCCGGGGACAGTGTCTCTAACCGTCTGGCTACTTGGAACTGGATCAGGCAGTCCCCATCGAGAGGCCTTGAGTGGCTGGGAAGGACATACTACAGGGGTAAATGGAAAAATCATTATGCAGTATCTGTGAAAAGTCGAATAACCATCAACCCCGACACGTCCAAGAGCCAGTTCTCCCTGCAGCTGAACTCTGTGACTCCCGAGGACACGGCTGTGTATTACTGTGCAAGAGGAGTTTGGATCGGTAACTGGTTCCTGGACCACTGGGGCCAGGGAACCCTGGTCACCGTGTCCTCAGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGTGCGAGGAGCAGTACGGCAGCACGTACCGTTGCGTCAGCGTCCTCACCGTCCTGCACCAGGACTGGCTGAATGGCAAGGAGTACAAGTGCAAGGTGTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTATAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAA (SEQ ID NO: 564) |
| iPS:448195 | HC-14 | QVQLQQSGPGLVKPSQTLSLTCAISGDSVSNKQATWNWIRQSPSRGLEWLGRTYYRGKWKNHYAVSVKSRITINPDTSKSQFSLQLNSVTPEDTAVYYCARGMWNQNWFLDHWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPCEEQYGSTYRCVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 532) | CAGGTACAGCTGCAGCAGTCAGGTCCAGGACTGGTGAAGCCCTCGCAGACCCTCTCACTCACCTGTGCCATCTCCGGGGACAGTGTCTCTAACAAACAGGCTACTTGGAACTGGATCAGGCAGTCCCCATCGAGAGGCCTTGAGTGGCTGGGAAGGACATACTACAGGGGTAAATGGAAAAATCATTATGCAGTATCTGTGAAAAGTCGAATAACCATCAACCCCGACACGTCCAAGAGCCAGTTCTCCCTGCAGCTGAACTCTGTGACTCCCGAGGACACGGCTGTGTATTACTGTGCAAGAGGAATGTGGAACCAGAACTGGTTCCTGGACCACTGGGGCCAGGGAACCCTGGTCACCGTGTCCTCAGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGTGCGAGGAGCAGTACGGCAGCACGTACCGTTGCGTCAGCGTCCTCACCGTCCTGCACCAGGACTGGCTGAATGGCAAGGAGTACAAGTGCAAGGTGTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACG |

TABLE 4B-continued

| Exemplary Anti-PAC1 Antibody Heavy Chain Sequences | | | |
|---|---|---|---|
| Antibody ID. | HC Group | Heavy Chain Amino Acid Sequence | Heavy Chain Nucleic Acid Sequence |
| | | | CCTCCCGTGCTGGACTCCGACGGCTCCTTCTTCCTCTATAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAA (SEQ ID NO: 565) |
| iPS:448788 | HC-15 | QVQLQQSGPGLVKPSQTLSLTCAISGDSVSSRQATWNWIRQSPSRGLEWLGRTYYRGKWKNHYAVSVKSRITINPDTSKSQFSLQLNSVTPEDTAVYYCARGMWQGNWFLDHWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPCEEQYGSTYRCVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 533) | CAGGTACAGCTGCAGCAGTCAGGTCCAGGACTGGTGAAGCCCTCGCAGACCCTCTCACTCACCTGTGCCATCTCCGGGGACAGTGTCTCTTCTCGTCAGGCTACTTGGAACTGGATCAGGCAGTCCCCATCGAGAGGCCTTGAGTGGCTGGGAAGGACATACTACAGGGGTAAATGGAAAAATCATTATGCAGTATCTGTGAAAAGTCGAATAACCATCAACCCCGACACGTCCAAGAGCCAGTTCTCCCTGCAGCTGAACTCTGTGACTCCCGAGGACACGGCTGTGTATTACTGTGCAAGAGGAATGTGGCAGGGTAACTGGTTCCTGGACCACTGGGGCCAGGGAACCCTGGTCACCGTGTCCTCAGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGTGCGAGGAGCAGTACGGCAGCACGTACCGTTGCGTCAGCGTCCTCACCGTCCTGCACCAGGACTGGCTGAATGGCAAGGAGTACAAGTGCAAGGTGTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTATAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAA (SEQ ID NO: 566) |
| iPS:448901 | HC-16 | QVQLQQSGPGLVKPSQTLSLTCAISGDSVSNRLATWNWIRQSPSRGLEWLGRTYYRGKWKNHYAVSVKSRITINPDTSKSQFSLQLNSVTPEDTAVYYCARGRWEGDWFFDHWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPCEEQYGSTYRCVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 534) | CAGGTACAGCTGCAGCAGTCAGGTCCAGGACTGGTGAAGCCCTCGCAGACCCTCTCACTCACCTGTGCCATCTCCGGGGACAGTGTCTCTAACCGTCTGGCTACTTGGAACTGGATCAGGCAGTCCCCATCGAGAGGCCTTGAGTGGCTGGGAAGGACATACTACAGGGGTAAATGGAAAAATCATTATGCAGTATCTGTGAAAAGTCGAATAACCATCAACCCCGACACGTCCAAGAGCCAGTTCTCCCTGCAGCTGAACTCTGTGACTCCCGAGGACACGGCTGTGTATTACTGTGCAAGAGGACGTTGGGAAGGTGACTGGTTCTTCGACCACTGGGGCCAGGGAACCCTGGTCACCGTGTCCTCAGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGTGCGAGGAGCAGTACGGCAGCACGTACCGTTGCGTCAGCGTCCTCACCGTCCTGCACCAGGACTGGCTGAATGGCAAGGAGTACAAGTGCAAGGTGTCCAACAAAGCCCTCCCAGCCCCCATCGAGAAAACCATC |

TABLE 4B-continued

Exemplary Anti-PAC1 Antibody Heavy Chain Sequences

| Antibody ID. | HC Group | Heavy Chain Amino Acid Sequence | Heavy Chain Nucleic Acid Sequence |
|---|---|---|---|
| | | | TCCAAAGCCAAAGGGCAGCCCCGAGAACCACAGGT |
| | | | GTACACCCTGCCCCCATCCCGGGAGGAGATGACCA |
| | | | AGAACCAGGTCAGCCTGACCTGCCTGGTCAAAGGC |
| | | | TTCTATCCCAGCGACATCGCCGTGGAGTGGGAGAG |
| | | | CAATGGGCAGCCGGAGAACAACTACAAGACCACGC |
| | | | CTCCCGTGCTGGACTCCGACGGCTCCTTCTTCCTCT |
| | | | ATAGCAAGCTCACCGTGGACAAGAGCAGGTGGCAG |
| | | | CAGGGGAACGTCTTCTCATGCTCCGTGATGCATGAG |
| | | | GCTCTGCACAACCACTACACGCAGAAGAGCCTCTC |
| | | | CCTGTCTCCGGGTAAA (SEQ ID NO: 567) |
| iPS:448689 | HC-17 | QVQLQQSGPGLVKPSQTL | CAGGTACAGCTGCAGCAGTCAGGTCCAGGACTGGT |
| | | SLTCAISGDSVSNRLATW | GAAGCCCTCGCAGACCCTCTCACTCACCTGTGCCAT |
| | | NWIRQSPSRGLEWLGRTY | CTCCGGGGACAGTGTCTCTAACCGTCTGGCTACTTG |
| | | YRGKWKNHYAVSVKSRI | GAACTGGATCAGGCAGTCCCCATCGAGAGGCCTTG |
| | | TINPDTSKSQFSLQLNSVT | AGTGGCTGGGAAGGACATACTACAGGGGTAAATGG |
| | | PEDTAVYYCARGTWNQD | AAAAATCATTATGCAGTATCTGTGAAAAGTCGAAT |
| | | WFLDHWGQGTLVTVSSA | AACCATCAACCCCGACACGTCCAAGAGCCAGTTCT |
| | | STKGPSVFPLAPSSKSTSG | CCCTGCAGCTGAACTCTGTGACTCCCGAGGACACG |
| | | GTAALGCLVKDYFPEPVT | GCTGTGTATTACTGTGCAAGAGGAACTTGGAACCA |
| | | VSWNSGALTSGVHTFPA | GGACTGGTTCCTGGACCACTGGGGCCAGGGAACCC |
| | | VLQSSGLYSLSSVVTVPSS | TGGTCACCGTGTCCTCAGCCTCCACCAAGGGCCCAT |
| | | SLGTQTYICNVNHKPSNT | CGGTCTTCCCCCTGGCACCCTCCTCCAAGAGCACCT |
| | | KVDKKVEPKSCDKTHTC | CTGGGGGCACAGCGGCCCTGGGCTGCCTGGTCAAG |
| | | PPCPAPELLGGPSVFLFPP | GACTACTTCCCCGAACCGGTGACGGTGTCGTGGAA |
| | | KPKDTLMISRTPEVTCVV | CTCAGGCGCCCTGACCAGCGGCGTGCACACCTTCCC |
| | | VDVSHEDPEVKFNWYVD | GGCTGTCCTACAGTCCTCAGGACTCTACTCCCTCAG |
| | | GVEVHNAKTKPCEEQYG | CAGCGTGGTGACCGTGCCCTCCAGCAGCTTGGGCA |
| | | STYRCVSVLTVLHQDWL | CCCAGACCTACATCTGCAACGTGAATCACAAGCCC |
| | | NGKEYKCKVSNKALPAPI | AGCAACACCAAGGTGGACAAGAAAGTTGAGCCCAA |
| | | EKTISKAKGQPREPQVYT | ATCTTGTGACAAAACTCACACATGCCCACCGTGCCC |
| | | LPPSREEMTKNQVSLTCL | AGCACCTGAACTCCTGGGGGGACCGTCAGTCTTCCT |
| | | VKGFYPSDIAVEWESNGQ | CTTCCCCCCAAAACCCAAGGACACCCTCATGATCTC |
| | | PENNYKTTPPVLDSDGSF | CCGGACCCCTGAGGTCACATGCGTGGTGGTGGACG |
| | | FLYSKLTVDKSRWQQGN | TGAGCCACGAAGACCCTGAGGTCAAGTTCAACTGG |
| | | VFSCSVMHEALHNHYTQ | TACGTGGACGGCGTGGAGGTGCATAATGCCAAGAC |
| | | KSLSLSPGK (SEQ ID | AAAGCCGTGCGAGGAGCAGTACGGCAGCACGTACC |
| | | NO: 535) | GTTGCGTCAGCGTCCTCACCGTCCTGCACCAGGACT |
| | | | GGCTGAATGGCAAGGAGTACAAGTGCAAGGTGTCC |
| | | | AACAAAGCCCTCCCAGCCCCCATCGAGAAAACCAT |
| | | | CTCCAAAGCCAAAGGGCAGCCCCGAGAACCACAGG |
| | | | TGTACACCCTGCCCCCATCCCGGGAGGAGATGACC |
| | | | AAGAACCAGGTCAGCCTGACCTGCCTGGTCAAAGG |
| | | | CTTCTATCCCAGCGACATCGCCGTGGAGTGGGAGA |
| | | | GCAATGGGCAGCCGGAGAACAACTACAAGACCACG |
| | | | CCTCCCGTGCTGGACTCCGACGGCTCCTTCTTCCTCT |
| | | | ATAGCAAGCTCACCGTGGACAAGAGCAGGTGGCAG |
| | | | CAGGGGAACGTCTTCTCATGCTCCGTGATGCATGAG |
| | | | GCTCTGCACAACCACTACACGCAGAAGAGCCTCTC |
| | | | CCTGTCTCCGGGTAAA (SEQ ID NO: 568) |
| iPS:448202 | HC-17 | QVQLQQSGPGLVKPSQTL | CAGGTACAGCTGCAGCAGTCAGGTCCAGGACTGGT |
| | | SLTCAISGDSVSNRLATW | GAAGCCCTCGCAGACCCTCTCACTCACCTGTGCCAT |
| | | NWIRQSPSRGLEWLGRTY | CTCCGGGGACAGTGTCTCTAACCGTCTGGCTACTTG |
| | | YRGKWKNHYAVSVKSRI | GAACTGGATCAGGCAGTCCCCATCGAGAGGCCTTG |
| | | TINPDTSKSQFSLQLNSVT | AGTGGCTGGGAAGGACATACTACAGGGGTAAATGG |
| | | PEDTAVYYCARGTWNQD | AAAAATCATTATGCAGTATCTGTGAAAAGTCGAAT |
| | | WFLDHWGQGTLVTVSSA | AACCATCAACCCCGACACGTCCAAGAGCCAGTTCT |
| | | STKGPSVFPLAPSSKSTSG | CCCTGCAGCTGAACTCTGTGACTCCCGAGGACACG |
| | | GTAALGCLVKDYFPEPVT | GCTGTGTATTACTGTGCAAGAGGAACTTGGAACCA |
| | | VSWNSGALTSGVHTFPA | GGACTGGTTCCTGGACCACTGGGGCCAGGGAACCC |
| | | VLQSSGLYSLSSVVTVPSS | TGGTCACCGTGTCCTCAGCCTCCACCAAGGGCCCAT |
| | | SLGTQTYICNVNHKPSNT | CGGTCTTCCCCCTGGCACCCTCCTCCAAGAGCACCT |
| | | KVDKKVEPKSCDKTHTC | CTGGGGGCACAGCGGCCCTGGGCTGCCTGGTCAAG |
| | | PPCPAPELLGGPSVFLFPP | GACTACTTCCCCGAACCGGTGACGGTGTCGTGGAA |
| | | KPKDTLMISRTPEVTCVV | CTCAGGCGCCCTGACCAGCGGCGTGCACACCTTCCC |
| | | VDVSHEDPEVKFNWYVD | GGCTGTCCTACAGTCCTCAGGACTCTACTCCCTCAG |
| | | GVEVHNAKTKPCEEQYG | CAGCGTGGTGACCGTGCCCTCCAGCAGCTTGGGCA |
| | | STYRCVSVLTVLHQDWL | CCCAGACCTACATCTGCAACGTGAATCACAAGCCC |
| | | NGKEYKCKVSNKALPAPI | AGCAACACCAAGGTGGACAAGAAAGTTGAGCCCAA |
| | | EKTISKAKGQPREPQVYT | ATCTTGTGACAAAACTCACACATGCCCACCGTGCCC |
| | | LPPSREEMTKNQVSLTCL | AGCACCTGAACTCCTGGGGGGACCGTCAGTCTTCCT |
| | | VKGFYPSDIAVEWESNGQ | CTTCCCCCCAAAACCCAAGGACACCCTCATGATCTC |
| | | PENNYKTTPPVLDSDGSF | CCGGACCCCTGAGGTCACATGCGTGGTGGTGGACG |
| | | FLYSKLTVDKSRWQQGN | TGAGCCACGAAGACCCTGAGGTCAAGTTCAACTGG |

TABLE 4B-continued

| Exemplary Anti-PAC1 Antibody Heavy Chain Sequences | | | |
|---|---|---|---|
| Antibody ID. | HC Group | Heavy Chain Amino Acid Sequence | Heavy Chain Nucleic Acid Sequence |
| | | VFSCSVMHEALHNHYTQ KSLSLSPGK (SEQ ID NO: 535) | TACGTGGACGGCGTGGAGGTGCATAATGCCAAGAC AAAGCCGTGCGAGGAGCAGTACGGCAGCACGTACC GTTGCGTCAGCGTCCTCACCGTCCTGCACCAGGACT GGCTGAATGGCAAGGAGTACAAGTGCAAGGTGTCC AACAAAGCCCTCCCAGCCCCCATCGAGAAAACCAT CTCCAAAGCCAAAGGGCAGCCCCGAGAACCACAGG TGTACACCCTGCCCCCATCCCGGGAGGAGATGACC AAGAACCAGGTCAGCCTGACCTGCCTGGTCAAAGG CTTCTATCCCAGCGACATCGCCGTGGAGTGGGAGA GCAATGGGCAGCCGGAGAACAACTACAAGACCACG CCTCCCGTGCTGGACTCCGACGGCTCCTTCTTCCTCT ATAGCAAGCTCACCGTGGACAAGAGCAGGTGGCAG CAGGGGAACGTCTTCTCATGCTCCGTGATGCATGAG GCTCTGCACAACCACTACACGCAGAAGAGCCTCTC CCTGTCTCCGGGTAAA (SEQ ID NO: 568) |
| iPS:452128 | HC-14 | QVQLQQSGPGLVKPSQTL SLTCAISGDSVSNKQATW NWIRQSPSRGLEWLGRTY YRGKWKNHYAVSVKSRI TINPDTSKSQFSLQLNSVT PEDTAVYYCARGMWNQ NWFLDHWGQGTLVTVSS ASTKGPSVFPLAPSSKSTS GGTAALGCLVKDYFPEP VTVSWNSGALTSGVHTFP AVLQSSGLYSLSSVVTVP SSSLGTQTYICNVNHKPS NTKVDKKVEPKSCDKTH TCPPCPAPELLGGPSVFLF PPKPKDTLMISRTPEVTC VVVDVSHEDPEVKFNWY VDGVEVHNAKTKPCEEQ YGSTYRCVSVLTVLHQD WLNGKEYKCKVSNKALP APIEKTISKAKGQPREPQV YTLPPSREEMTKNQVSLT CLVKGFYPSDIAVEWESN GQPENNYKTTPPVLDSDG SFFLYSKLTVDKSRWQQ GNVFSCSVMHEALHNHY TQKSLSLSPGK (SEQ ID NO: 532) | CAGGTACAGCTGCAGCAGTCAGGTCCAGGACTGGT GAAGCCCTCGCAGACCCTCTCACTCACCTGTGCCAT CTCCGGGGACAGTGTCTCTAACAAACAGGCTACTTG GAACTGGATCAGGCAGTCCCCATCGAGAGGCCTTG AGTGGCTGGGAAGGACATACTACAGGGGTAAATGG AAAAATCATTATGCAGTATCTGTGAAAAGTCGAAT AACCATCAACCCCGACACGTCCAAGAGCCAGTTCT CCCTGCAGCTGAACTCTGTGACTCCCGAGGACACG GCTGTGTATTACTGTGCAAGAGGAATGTGGAACCA GAACTGGTTCCTGGACCACTGGGGCCAGGGAACCC TGGTCACCGTGTCCTCAGCCTCCACCAAGGGCCCAT CGGTCTTCCCCCTGGCACCCTCCTCCAAGAGCACCT CTGGGGGCACAGCGGCCCTGGGCTGCCTGGTCAAG GACTACTTCCCCGAACCGGTGACGGTGTCGTGGAA CTCAGGCGCCCTGACCAGCGGCGTGCACACCTTCCC GGCTGTCCTACAGTCCTCAGGACTCTACTCCCTCAG CAGCGTGGTGACCGTGCCCTCCAGCAGCTTGGGCA CCCAGACCTACATCTGCAACGTGAATCACAAGCCC AGCAACACCAAGGTGGACAAGAAAGTTGAGCCCAA ATCTTGTGACAAAACTCACACATGCCCACCGTGCCC AGCACCTGAACTCCTGGGGGGACCGTCAGTCTTCCT CTTCCCCCCAAAACCCAAGGACACCCTCATGATCTC CCGGACCCCTGAGGTCACATGCGTGGTGGTGGACG TGAGCCACGAAGACCCTGAGGTCAAGTTCAACTGG TACGTGGACGGCGTGGAGGTGCATAATGCCAAGAC AAAGCCGTGCGAGGAGCAGTACGGCAGCACGTACC GTTGCGTCAGCGTCCTCACCGTCCTGCACCAGGACT GGCTGAATGGCAAGGAGTACAAGTGCAAGGTGTCC AACAAAGCCCTCCCAGCCCCCATCGAGAAAACCAT CTCCAAAGCCAAAGGGCAGCCCCGAGAACCACAGG TGTACACCCTGCCCCCATCCCGGGAGGAGATGACC AAGAACCAGGTCAGCCTGACCTGCCTGGTCAAAGG CTTCTATCCCAGCGACATCGCCGTGGAGTGGGAGA GCAATGGGCAGCCGGAGAACAACTACAAGACCACG CCTCCCGTGCTGGACTCCGACGGCTCCTTCTTCCTCT ATAGCAAGCTCACCGTGGACAAGAGCAGGTGGCAG CAGGGGAACGTCTTCTCATGCTCCGTGATGCATGAG GCTCTGCACAACCACTACACGCAGAAGAGCCTCTC CCTGTCTCCGGGTAAA (SEQ ID NO: 565) |
| iPS:448924 | HC-18 | QVQLQQSGPGLVKPSQTL SLTCAISGDSVSSRYATW NWIRQSPSRGLEWLGRTY YRGQWKNHYAVSVKSRI TINPDTSKSQFSLQLNSVT PEDTAVYYCA RGMWNQNWFLDHWGQ GTLVTVSSASTKGPSVFP LAPSSKSTSGGTAALGCL VKDYFPEPVTVSWNSGA LTSGVHTFPAVLQSSGLY SLSSVVTVPSSSLGTQTYI CNVNHKPSNTKVDKKVE PKSCDKTHTCPPCPAPEL LGGPSVFLFPPKPKDTLMI SRTPEVTCVVVDVSHEDP EVKFNWYVDGVEVHNA KTKPCEEQYGSTYRCVSV LTVLHQDWLNGKEYKCK | CAGGTACAGCTGCAGCAGTCAGGTCCAGGACTGGT GAAGCCCTCGCAGACCCTCTCACTCACCTGTGCCAT CTCCGGGGACAGTGTCTCTTCTCGTTACGCTACTTG GAACTGGATCAGGCAGTCCCCATCGAGAGGCCTTG AGTGGCTGGGAAGGACATACTACAGGGGTCAGTGG AAAAATCATTATGCAGTATCTGTGAAAAGTCGAAT AACCATCAACCCCGACACGTCCAAGAGCCAGTTCT CCCTGCAGCTGAACTCTGTGACTCCCGAGGACACG GCTGTGTATTACTGTGCAAGAGGAATGTGGAACCA GAACTGGTTCCTGGACCACTGGGGCCAGGGAACCC TGGTCACCGTGTCCTCAGCCTCCACCAAGGGCCCAT CGGTCTTCCCCCTGGCACCCTCCTCCAAGAGCACCT CTGGGGGCACAGCGGCCCTGGGCTGCCTGGTCAAG GACTACTTCCCCGAACCGGTGACGGTGTCGTGGAA CTCAGGCGCCCTGACCAGCGGCGTGCACACCTTCCC GGCTGTCCTACAGTCCTCAGGACTCTACTCCCTCAG CAGCGTGGTGACCGTGCCCTCCAGCAGCTTGGGCA CCCAGACCTACATCTGCAACGTGAATCACAAGCCC AGCAACACCAAGGTGGACAAGAAAGTTGAGCCCAA |

TABLE 4B-continued

Exemplary Anti-PAC1 Antibody Heavy Chain Sequences

| Antibody ID. | HC Group | Heavy Chain Amino Acid Sequence | Heavy Chain Nucleic Acid Sequence |
|---|---|---|---|
| | | VSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 536) | ATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGTGCGAGGAGCAGTACGGCAGCACGTACCGTTGCGTCAGCGTCCTCACCGTCCTGCACCAGGACTGGCTGAATGGCAAGGAGTACAAGTGCAAGGTGTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTATAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAA (SEQ ID NO: 569) |
| 3574 | HC-14 | QVQLQQSGPGLVKPSQTLSLTCAISGDSVSNKQATWNWIRQSPSRGLEWLGRTYYRGKWKNHYAVSVKSRITINPDTSKSQFSLQLNSVTPEDTAVYYCARGMWNQNWFLDHWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPCEEQYGSTYRCVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 532) | CAGGTACAGCTGCAGCAGTCAGGTCCAGGACTGGTGAAGCCCTCGCAGACCCTCTCACTCACCTGTGCCATCTCCGGGGACAGTGTCTCTAACAAACAGGCTACTTGGAACTGGATCAGGCAGTCCCCATCGAGAGGCCTTGAGTGGCTGGGAAGGACATACTACAGGGGTAAATGGAAAAATCATTATGCAGTATCTGTGAAAAGTCGAATAACCATCAACCCCGACACGTCCAAGAGCCAGTTCTCCCTGCAGCTGAACTCTGTGACTCCCGAGGACACGGCTGTGTATTACTGTGCAAGAGGAATGTGGAACCAGAACTGGTTCCTGGACCACTGGGGCCAGGGAACCCTGGTCACCGTGTCCTCAGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGTGCGAGGAGCAGTACGGCAGCACGTACCGTTGCGTCAGCGTCCTCACCGTCCTGCACCAGGACTGGCTGAATGGCAAGGAGTACAAGTGCAAGGTGTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTATAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAA (SEQ ID NO: 565) |
| 3575 | HC-12 | QVQLQQSGPGLVKPSQTLSLTCAISGDSVSSNSATWNWIRQSPSRGLEWLGRTYYRSKWSNHYAVSVKSRITINPDTSKSQFSLQLNSVTPEDTAVYYCARGTWKQLWFLDHWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTC | CAGGTACAGCTGCAGCAGTCAGGTCCAGGACTGGTGAAGCCCTCGCAGACCCTCTCACTCACCTGTGCCATCTCCGGGGACAGTGTCTCTAGCAACAGTGCTACTTGGAACTGGATCAGGCAGTCCCCATCGAGAGGCCTTGAGTGGCTGGGAAGGACATATTACAGGTCCAAGTGGTCTAATCATTATGCAGTATCTGTGAAAAGTCGAATCACCATCAACCCCGACACGTCCAAGAGCCAGTTCTCCCTGCAGCTGAACTCTGTGACTCCCGAGGACACGGCTGTGTATTACTGTGCAAGAGGAACGTGGAAACAGCTATGGTTCCTTGACCACTGGGGCCAGGGAACCCTGGTCACCGTGTCTAGTGCCTCCACCAAGGGCCCATCGGTCTTCCCCCTGGCACCCTCCTCCAAGAGCACCTCTGGGGGCACAGCGGCCCTGGGCTGCCTGGTCAAGGACT |

TABLE 4B-continued

Exemplary Anti-PAC1 Antibody Heavy Chain Sequences

| Antibody ID. | HC Group | Heavy Chain Amino Acid Sequence | Heavy Chain Nucleic Acid Sequence |
|---|---|---|---|
| | | PPCPAPELLGGPSVFLFPP KPKDTLMISRTPEVTCVV VDVSHEDPEVKFNWYVD GVEVHNAKTKPCEEQYG STYRCVSVLTVLHQDWL NGKEYKCKVSNKALPAPI EKTISKAKGQPREPQVYT LPPSREEMTKNQVSLTCL VKGFYPSDIAVEWESNGQ PENNYKTTPPVLDSDGSF FLYSKLTVDKSRWQQGN VFSCSVMHEALHNHYTQ KSLSLSPGK (SEQ ID NO: 530) | ACTTCCCCGAACCGGTGACGGTGTCGTGGAACTCA GGCGCCCTGACCAGCGGCGTGCACACCTTCCCGGCT GTCCTACAGTCCTCAGGACTCTACTCCCTCAGCAGC GTGGTGACCGTGCCCTCCAGCAGCTTGGGCACCCA GACCTACATCTGCAACGTGAATCACAAGCCCAGCA ACACCAAGGTGGACAAGAAAGTTGAGCCCAAATCT TGTGACAAAACTCACACATGCCCACCGTGCCCAGC ACCTGAACTCCTGGGGGGACCGTCAGTCTTCCTCTT CCCCCCAAAACCCAAGGACACCCTCATGATCTCCCG GACCCCTGAGGTCACATGCGTGGTGGTGGACGTGA GCCACGAAGACCCTGAGGTCAAGTTCAACTGGTAC GTGGACGGCGTGGAGGTGCATAATGCCAAGACAAA GCCGTGCGAGGAGCAGTACGGCAGCACGTACCGTT GCGTCAGCGTCCTCACCGTCCTGCACCAGGACTGGC TGAATGGCAAGGAGTACAAGTGCAAGGTGTCCAAC AAAGCCCTCCCAGCCCCCATCGAGAAAACCATCTC CAAAGCCAAAGGGCAGCCCCGAGAACCACAGGTGT ACACCCTGCCCCCATCCCGGGAGGAGATGACCAAG AACCAGGTCAGCCTGACCTGCCTGGTCAAAGGCTTC TATCCCAGCGACATCGCCGTGGAGTGGGAGAGCAA TGGGCAGCCGGAGAACAACTACAAGACCACGCCTC CCGTGCTGGACTCCGACGGCTCCTTCTTCCTCTATA GCAAGCTCACCGTGGACAAGAGCAGGTGGCAGCAG GGGAACGTCTTCTCATGCTCCGTGATGCATGAGGCT CTGCACAACCACTACACGCAGAAGAGCCTCTCCCT GTCTCCGGGCAAA (SEQ ID NO: 563) |

In certain embodiments, the anti-PAC1 antibodies of the invention may comprise a light chain selected from LC-01 to LC-05, as shown in Table 4A, and/or a heavy chain selected from HC-01 to HC-11, as shown in Table 4B, and binding fragments, derivatives, and variants of these light chains and heavy chains. In other embodiments, the anti-PAC1 antibodies of the invention may comprise a light chain selected from LC-06 to LC-15, as shown in Table 4A, and/or a heavy chain selected from HC-12 to HC-18, as shown in Table 4B, and binding fragments, derivatives, and variants of these light chains and heavy chains.

Each of the light chains listed in Table 4A may be combined with any of the heavy chains listed in Table 4B to form an anti-PAC1 antibody or antigen-binding fragment thereof of the invention. For example, in certain embodiments, the anti-PAC1 antibodies of the invention comprise a light chain comprising the sequence of LC-03 (SEQ ID NO: 506) and a heavy chain comprising the sequence of HC-03 (SEQ ID NO: 521). In some embodiments, the anti-PAC1 antibodies of the invention comprise a light chain comprising the sequence of LC-03 (SEQ ID NO: 506) and a heavy chain comprising the sequence of HC-04 (SEQ ID NO: 522). In other embodiments, the anti-PAC1 antibodies of the invention comprise a light chain comprising the sequence of LC-01 (SEQ ID NO: 504) and a heavy chain comprising the sequence of HC-05 (SEQ ID NO: 523). In still other embodiments, the anti-PAC1 antibodies of the invention comprise a light chain comprising the sequence of LC-01 (SEQ ID NO: 504) and a heavy chain comprising the sequence of HC-06 (SEQ ID NO: 524). In some embodiments, the anti-PAC1 antibodies of the invention comprise a light chain comprising the sequence of LC-03 (SEQ ID NO: 506) and a heavy chain comprising the sequence of HC-07 (SEQ ID NO: 525). In certain embodiments, the anti-PAC1 antibodies of the invention comprise a light chain comprising the sequence of LC-01 (SEQ ID NO: 504) and a heavy chain comprising the sequence of HC-08 (SEQ ID NO: 526). In one embodiment, the anti-PAC1 antibodies of the invention comprise a light chain comprising the sequence of LC-03 (SEQ ID NO: 506) and a heavy chain comprising the sequence of HC-05 (SEQ ID NO: 523). In another embodiment, the anti-PAC1 antibodies of the invention comprise a light chain comprising the sequence of LC-04 (SEQ ID NO: 507) and a heavy chain comprising the sequence of HC-09 (SEQ ID NO: 527). In yet another embodiment, the anti-PAC1 antibodies of the invention comprise a light chain comprising the sequence of LC-04 (SEQ ID NO: 507) and a heavy chain comprising the sequence of HC-10 (SEQ ID NO: 528). In still another embodiment, the anti-PAC1 antibodies of the invention comprise a light chain comprising the sequence of LC-05 (SEQ ID NO: 508) and a heavy chain comprising the sequence of HC-11 (SEQ ID NO: 529).

In certain other embodiments, the anti-PAC1 antibodies of the invention comprise a light chain comprising the sequence of LC-07 (SEQ ID NO: 510) and a heavy chain comprising the sequence of HC-13 (SEQ ID NO: 531). In some embodiments, the anti-PAC1 antibodies of the invention comprise a light chain comprising the sequence of LC-08 (SEQ ID NO: 511) and a heavy chain comprising the sequence of HC-14 (SEQ ID NO: 532). In other embodiments, the anti-PAC1 antibodies of the invention comprise a light chain comprising the sequence of LC-09 (SEQ ID NO: 512) and a heavy chain comprising the sequence of HC-15 (SEQ ID NO: 533). In still other embodiments, the anti-PAC1 antibodies of the invention comprise a light chain comprising the sequence of LC-10 (SEQ ID NO: 513) and a heavy chain comprising the sequence of HC-16 (SEQ ID NO: 534). In some embodiments, the anti-PAC1 antibodies of the invention comprise a light chain comprising the sequence of LC-11 (SEQ ID NO: 514) and a heavy chain comprising the sequence of HC-17 (SEQ ID NO: 535). In certain embodiments, the anti-PAC1 antibodies of the invention comprise a light chain comprising the sequence of LC-12 (SEQ ID NO: 515) and a heavy chain comprising the sequence of HC-17 (SEQ ID NO: 535). In one embodiment, the anti-PAC1 antibodies of the invention comprise a light chain comprising the sequence of LC-13 (SEQ ID NO: 516) and a heavy chain comprising the sequence of HC-14 (SEQ ID NO: 532). In another embodiment, the anti-PAC1 antibodies of the invention comprise a light chain comprising the sequence of LC-14 (SEQ ID NO: 517) and a heavy chain comprising the sequence of HC-18 (SEQ ID NO: 536). In yet another embodiment, the anti-PAC1 antibodies of the invention comprise a light chain comprising the sequence of LC-06 (SEQ ID NO: 509) and a heavy chain comprising the sequence of HC-14 (SEQ ID NO: 532). In still another embodiment, the anti-PAC1 antibodies of the invention comprise a light chain comprising the sequence of LC-15 (SEQ ID NO: 518) and a heavy chain comprising the sequence of HC-12 (SEQ ID NO: 530).

In some embodiments, the anti-PAC1 antibodies comprise a light chain comprising a sequence of contiguous amino acids that differs from the sequence of a light chain in Table 4A, i.e. a light chain selected from LC-01 to LC-15, at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing light chain sequences. The light chain in some anti-PAC1 antibodies comprises a sequence of amino acids that has at least 70%, at least 75%, at least 80%, at least 85%, at least 90%, at least 95%, at least 97% or at least 99% sequence identity to the amino acid sequences of SEQ ID NOs: 504 to 518 (i.e. the light chains in Table 4A).

In these and other embodiments, the anti-PAC1 antibodies comprise a heavy chain comprising a sequence of contiguous amino acids that differs from the sequence of a heavy chain in Table 4B, i.e., a heavy chain selected from HC-01 to HC-18, at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing heavy chain sequences. The heavy chain in some anti-PAC1 antibodies comprises a sequence of amino acids that has at least 70%, at least 75%, at least 80%, at least 85%, at least 90%, at least 95%, at least 97% or at least 99% sequence identity to the amino acid sequences of SEQ ID NOs: 519 to 536 (i.e. the heavy chains in Table 4B).

The anti-PAC1 antibodies or antigen-binding fragments of the invention can be monoclonal antibodies, polyclonal antibodies, recombinant antibodies, human antibodies, humanized antibodies, chimeric antibodies, or multispecific antibodies or antigen-binding fragments thereof. In certain embodiments, the anti-PAC1 antibody is a monoclonal antibody. In such embodiments, the anti-PAC1 antibody may be a chimeric antibody, a humanized antibody, or a fully human antibody having a human immunoglobulin constant domain. In these and other embodiments, the anti-PAC1 antibody is a human IgG1, IgG2, IgG3, or IgG4 antibody. Thus, the anti-PAC1 antibody may, in some embodiments, have a human IgG1, IgG2, IgG3, or IgG4 constant domain. In one embodiment, the anti-PAC1 antibody is a monoclonal human IgG1 antibody. In another embodiment, the anti-PAC1 antibody is a monoclonal human IgG2 antibody. In yet another embodiment, the anti-PAC1 antibody is a monoclonal human IgG4 antibody.

The term "monoclonal antibody" (or "mAb") as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against an individual antigenic site or epitope, in contrast to polyclonal antibody preparations that typically include different antibodies directed against different epitopes. Monoclonal antibodies may be produced using any technique known in the art, e.g., by immortalizing spleen cells harvested from an animal after completion of the immunization schedule. The spleen cells can be immortalized using any technique known in the art, e.g., by fusing them with myeloma cells to produce hybridomas. See, for example, Antibodies; Harlow and Lane, Cold Spring Harbor Laboratory Press, 1st Edition, e.g. from 1988, or 2nd Edition, e.g. from 2014. Myeloma cells for use in hybridoma-producing fusion procedures preferably are non-antibody-producing, have high fusion efficiency, and enzyme deficiencies that render them incapable of growing in certain selective media, which support the growth of only the desired fused cells (hybridomas). Examples of suitable cell lines for use in fusions with mouse cells include, but are not limited to, Sp-20, P3-X63/Ag8, P3-X63-Ag8.653, NS1/1.Ag 4 1, Sp210-Ag14, FO, NSO/U, MPC-11, MPC11-X45-GTG 1.7 and 5194/5XXO Bul. Examples of suitable cell lines used for fusions with rat cells include, but are not limited to, R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a rabbit, rat, mouse, or a transgenic animal having human immunoglobulin sequences) with a PAC1 immunogen (see, e.g., WO 2014/144632); harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds to PAC1. Another useful method for producing monoclonal antibodies is the SLAM method described in Babcook et al., Proc. Natl. Acad. Sci. USA, Vol. 93: 7843-7848, 1996.

Monoclonal antibodies secreted by a hybridoma cell line can be purified using any technique known in the art, such as protein A-Sepharose, hydroxyapatite chromatography, gel electrophoresis, dialysis, or affinity chromatography. Hybridoma supernatants or mAbs may be further screened to identify mAbs with particular properties, such as the ability to bind PAC1 (e.g. human PAC1, cynomolgus monkey PAC1, or rat PAC1); cross-reactivity to other PAC1 family members (e.g. human VPAC1 or human VPAC2); ability to block or interfere with the binding of the PACAP ligand to PAC1, or the ability to functionally block PACAP-induced activation of the PAC1 receptor, e.g., using a cAMP assay as described herein.

In some embodiments, the anti-PAC1 antibodies or antigen-binding fragments of the invention are chimeric or humanized antibodies or antigen-binding fragments thereof based upon the CDR and variable region sequences of the antibodies described herein. A chimeric antibody is an antibody composed of protein segments from different antibodies that are covalently joined to produce functional immunoglobulin light or heavy chains or binding fragments thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567 and Morrison et al., 1985, Proc. Natl. Acad. Sci. USA 81:6851-6855, both of which are hereby incorporated by reference in their entireties.

Generally, the goal of making a chimeric antibody is to create a chimera in which the number of amino acids from the intended species is maximized. One example is the "CDR-grafted" antibody, in which the antibody comprises one or more CDRs from a particular species or belonging to a particular antibody class or subclass, while the remainder of the antibody chain(s) is/are identical with or homologous to a corresponding sequence in antibodies derived from another species or belonging to another antibody class or subclass. CDR grafting is described, for example, in U.S. Pat. Nos. 6,180,370, 5,693,762, 5,693,761, 5,585,089, and 5,530,101. For use in humans, the variable region or selected CDRs from a rodent or rabbit antibody often are grafted into a human antibody, replacing the naturally-occurring variable regions or CDRs of the human antibody.

One useful type of chimeric antibody is a "humanized" antibody. Generally, a humanized antibody is produced from a monoclonal antibody raised initially in a non-human animal, such as a rodent or rabbit. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent or rabbit variable region for the corresponding regions of a human antibody (see, e.g., U.S. Pat. Nos. 5,585,089, and 5,693,762; Jones et al., 1986, Nature 321:522-525; Riechmann et al., 1988, Nature 332: 323-27; and Verhoeyen et al., 1988, Science 239:1534-1536).

In one aspect, the CDRs of the light and heavy chain variable regions of the antibodies provided herein (see, Tables 1A and 1B) are grafted to framework regions (FRs) from antibodies from the same, or a different, phylogenetic species. For example, the CDRs of the heavy and light chain variable regions listed in Tables 1A and 1B can be grafted to consensus human FRs. To create consensus human FRs, FRs from several human heavy chain or light chain amino acid sequences may be aligned to identify a consensus amino acid sequence. Alternatively, the grafted variable regions from the one heavy or light chain may be used with a constant region that is different from the constant region of that particular heavy or light chain as disclosed herein. In other embodiments, the grafted variable regions are part of a single chain Fv antibody.

In certain embodiments, the anti-PAC1 antibodies or antigen-binding fragments of the invention are fully human antibodies or antigen-binding fragments thereof. Fully human antibodies that specifically bind to human PAC1 can be generated using the immunogens or fragments thereof described in WO 2014/144632, such as polypeptides consisting of the sequence of SEQ ID NO: 1 or SEQ ID NO: 4. A "fully human antibody" is an antibody that comprises variable and constant regions derived from or indicative of human germ line immunoglobulin sequences. One specific means provided for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derived mAbs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits et al., 1993, *Proc. Natl. Acad. Sci. USA* 90:2551-2555; Jakobovits et al., 1993, Nature 362:255-258; and Bruggermann et al., 1993, Year in Immunol. 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602. Additional methods relating to transgenic mice for making human antibodies are described in U.S. Pat. Nos. 5,545,807; 6,713,610; 6,673,986; 6,162,963; 5,939,598; 5,545,807; 6,300,129; 6,255,458; 5,877,397; 5,874,299 and 5,545,806; in PCT publications WO91/10741, WO90/04036, WO 94/02602, WO 96/30498, WO 98/24893 and in EP 546073B1 and EP 546073A1.

The transgenic mice described above, referred to as "HuMab" mice, contain a human immunoglobulin gene minilocus that encodes unrearranged human heavy (mu and gamma) and kappa light chain immunoglobulin sequences, together with targeted mutations that inactivate the endogenous mu and kappa chain loci (Lonberg et al., 1994, Nature 368:856-859). Accordingly, the mice exhibit reduced expression of mouse IgM and kappa proteins and in response to immunization, the introduced human heavy and light chain transgenes undergo class switching and somatic mutation to generate high affinity human IgG kappa monoclonal antibodies (Lonberg and Huszar, 1995, Intern. Rev. Immunol. 13: 65-93; Harding and Lonberg, 1995, Ann. N.Y Acad. Sci. 764:536-546). The preparation of HuMab mice is described in detail in Taylor et al., 1992, Nucleic Acids Research 20:6287-6295; Chen et al., 1993, International Immunology 5:647-656; Tuaillon et al., 1994, J. Immunol. 152:2912-2920; Lonberg et al., 1994, Nature 368:856-859; Lonberg, 1994, Handbook of Exp. Pharmacology 113:49-101; Taylor et al., 1994, International Immunology 6:579-591; Lonberg and Huszar, 1995, Intern. Rev. Immunol. 13:65-93; Harding and Lonberg, 1995, Ann. N.Y Acad. Sci. 764:536-546; Fishwild et al., 1996, Nature Biotechnology 14:845-851; the foregoing references are hereby incorporated by reference in their entireties. See, further U.S. Pat. Nos. 5,545,806; 5,569,825; 5,625,126; 5,633,425; 5,789,650; 5,877,397; 5,661,016; 5,814,318; 5,874,299; and 5,770,429; as well as U.S. Pat. No. 5,545,807; International Publication Nos. WO 93/1227; WO 92/22646; and WO 92/03918, the disclosures of all of which are hereby incorporated by reference in their entireties. Technologies utilized for producing human antibodies in these transgenic mice are disclosed also in WO 98/24893, and Mendez et al., 1997, Nature Genetics 15:146-156, which are hereby incorporated by reference. For example, the HCo7 and HCo12 transgenic mice strains can be used to generate fully human anti-PAC1 antibodies. One particular transgenic mouse line suitable for generation of fully human anti-PAC1 antibodies is the XenoMouse® transgenic mouse line described in U.S. Pat. Nos. 6,114,598; 6,162,963; 6,833,268; 7,049,426; 7,064,244; Green et al., 1994, Nature Genetics 7:13-21; Mendez et al., 1997, Nature Genetics 15:146-156; Green and Jakobovitis, 1998, J. Ex. Med, 188:483-495; Green, 1999, Journal of Immunological Methods 231:11-23; Kellerman and Green, 2002, Current Opinion in Biotechnology 13, 593-597, all of which are hereby incorporated by reference in their entireties.

Human-derived antibodies can also be generated using phage display techniques. Phage display is described in e.g., Dower et al., WO 91/17271, McCafferty et al., WO 92/01047, and Caton and Koprowski, 1990, Proc. Natl. Acad. Sci. USA, 87:6450-6454, each of which is incorporated herein by reference in its entirety. The antibodies produced by phage technology are usually produced as antigen-binding fragments, e.g. Fv or Fab fragments, in bacteria and thus lack effector functions. Effector functions can be introduced by one of two strategies: The fragments can be engineered either into complete antibodies for expression in mammalian cells, or into bispecific antibody fragments with a second binding site capable of triggering an effector function, if desired. Typically, the Fd fragment (VH-CH1) and light chain (VL-CL) of antibodies are separately cloned by PCR and recombined randomly in combinatorial phage display libraries, which can then be selected for binding to a particular antigen. The antibody fragments are expressed on the phage surface, and selection of Fv or Fab (and therefore the phage containing the DNA encoding the antibody fragment) by antigen binding is accomplished through several rounds of antigen binding and re-amplification, a procedure termed panning. Antibody fragments specific for the antigen are enriched and finally isolated. Phage display techniques can also be used in an approach for the humanization of rodent monoclonal antibodies, called "guided selection" (see Jespers, L. S. et al., 1994, Bio/Technology 12, 899-903). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

Once cells producing anti-PAC1 antibodies according to the invention have been obtained using any of the above described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described herein to generate other anti-PAC1 antibodies or antigen-binding fragments according to the invention.

In certain embodiments, the anti-PAC1 antibodies and antigen-binding fragments of the invention may comprise one or more mutations or modifications to a constant region. For example, the heavy chain constant regions or the Fc regions of the anti-PAC1 antibodies may comprise one or more amino acid substitutions that affect the glycosylation, effector function, and/or Fcγ receptor binding of the antibody. The term "Fc region" refers to the C-terminal region of an immunoglobulin heavy chain, which may be generated by papain digestion of an intact antibody. The Fc region of an immunoglobulin generally comprises two constant domains, a CH2 domain and a CH3 domain, and optionally comprises a CH4 domain. In certain embodiments, the Fc region is an Fc region from an IgG1, IgG2, IgG3, or IgG4 immunoglobulin. In some embodiments, the Fc region comprises CH2 and CH3 domains from a human IgG1 or human IgG2 immunoglobulin. The Fc region may retain effector function, such as C1q binding, complement-dependent cytotoxicity (CDC), Fc receptor binding, antibody-dependent cell-mediated cytotoxicity (ADCC), and phagocytosis. In other embodiments, the Fc region may be modified to reduce or eliminate effector function as described in further detail below.

Unless indicated otherwise by reference to a specific sequence, throughout the present specification and claims, the numbering of the amino acid residues in an immunoglobulin heavy chain or light chain is according to AHo numbering as described in Honegger and Pluckthun, J. Mol. Biol. 309(3):657-670; 2001 or EU numbering as described in Edelman et al., Proc. Natl. Acad. USA, Vol. 63: 78-85 (1969). As used herein, the AHo numbering scheme is typically used when referring to the position of an amino acid within the variable regions, whereas the EU numbering scheme is generally used when referring to the position of an amino acid with an immunoglobulin constant region.

An amino acid substitution in an amino acid sequence is typically designated herein with a one-letter abbreviation for the amino acid residue in a particular position, followed by the numerical amino acid position relative to an original sequence of interest, which is then followed by the one-letter abbreviation for the amino acid residue substituted in. For example, "T30D" symbolizes a substitution of a threonine residue by an aspartate residue at amino acid position 30, relative to the original sequence of interest. Another example, "S218G" symbolizes a substitution of a serine residue by a glycine residue at amino acid position 218, relative to the original amino acid sequence of interest.

One of the functions of the Fc region of an immunoglobulin is to communicate to the immune system when the immunoglobulin binds its target. This is commonly referred to as "effector function." Communication leads to antibody-dependent cellular cytotoxicity (ADCC), antibody-dependent cellular phagocytosis (ADCP), and/or complement dependent cytotoxicity (CDC). ADCC and ADCP are mediated through the binding of the Fc region to Fc receptors on the surface of cells of the immune system. CDC is mediated through the binding of the Fc region with proteins of the complement system, e.g., C1q. In some embodiments, the anti-PAC1 antibodies of the invention comprise one or more amino acid substitutions in the Fc region to enhance effector function, including ADCC activity, CDC activity, ADCP activity, and/or the clearance or half-life of the antibody. Exemplary amino acid substitutions (according to the EU numbering scheme) that can enhance effector function include, but are not limited to, E233L, L234I, L234Y, L235S, G236A, S239D, F243L, F243V, P247I, D280H, K290S, K290E, K290N, K290Y, R292P, E294L, Y296W, S298A, S298D, S298V, S298G, S298T, T299A, Y300L, V305I, Q311M, K326A, K326E, K326W, A330S, A330L, A330M, A330F, I332E, D333A, E333S, E333A, K334A, K334V, A339D, A339Q, P396L, or combinations of any of the foregoing.

In other embodiments, the anti-PAC1 antibodies of the invention comprise one or more amino acid substitutions in the Fc region to reduce effector function. Exemplary amino acid substitutions (according to the EU numbering scheme) that can reduce effector function include, but are not limited to, C220S, C226S, C229S, E233P, L234A, L234V, V234A, L234F, L235A, L235E, G237A, P238S, S267E, H268Q, N297A, N297G, V309L, E318A, L328F, A330S, A331S, P331S, or combinations of any of the foregoing.

Glycosylation can contribute to the effector function of antibodies, particularly IgG1 antibodies. Thus, in some embodiments, the anti-PAC1 antibodies of the invention may comprise one or more amino acid substitutions that affect the level or type of glycosylation of the antibodies. Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

In certain embodiments, glycosylation of the anti-PAC1 antibodies described herein is increased by adding one or more glycosylation sites, e.g., to the Fc region of the antibody. Addition of glycosylation sites to the antibody can be conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody amino acid sequence may be altered through changes at the DNA level, particularly by mutating the DNA encoding the target polypeptide at preselected bases such that codons are generated that will translate into the desired amino acids.

The invention also encompasses production of antibody molecules with altered carbohydrate structure resulting in altered effector activity, including antibodies with absent or reduced fucosylation that exhibit improved ADCC activity. Various methods are known in the art to reduce or eliminate fucosylation. For example, ADCC effector activity is mediated by binding of the antibody molecule to the FcγRIII receptor, which has been shown to be dependent on the carbohydrate structure of the N-linked glycosylation at the N297 residue of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (see Yamane-Ohnuki et al., Biotechnol Bioeng. 87(5):614-22, 2004). Similar effects can be accomplished through decreasing the activity of alpha-1,6-fucosyl transferase enzyme or other enzymes in the fucosylation pathway, e.g., through siRNA or antisense RNA treatment, engineering cell lines to knockout the enzyme(s), or culturing with selective glycosylation inhibitors (see Rothman et al., Mol Immunol. 26(12):1113-23, 1989). Some host cell strains, e.g. Lec13 or rat hybridoma YB2/0 cell line naturally produce antibodies with lower fucosylation levels (see Shields et al., J Biol Chem. 277(30):26733-40, 2002 and Shinkawa et al., J Biol Chem. 278(5):3466-73, 2003). An increase in the level of bisected carbohydrate, e.g. through recombinantly producing antibody in cells that overexpress GnTIII enzyme, has also been determined to increase ADCC activity (see Umana et al., Nat Biotechnol. 17(2):176-80, 1999).

In other embodiments, glycosylation of the anti-PAC1 antibodies described herein is decreased or eliminated by removing one or more glycosylation sites, e.g., from the Fc region of the antibody. In some embodiments, the anti-PAC1 antibody is an aglycosylated human monoclonal antibody, e.g., an aglycosylated human IgG1 monoclonal antibody. Amino acid substitutions that eliminate or alter N-linked glycosylation sites can reduce or eliminate N-linked glycosylation of the antibody. In certain embodiments, the anti-PAC1 antibodies described herein comprise a heavy chain mutation at position N297 (according to the EU numbering scheme), such as N297Q, N297A, or N297G. In some embodiments, the anti-PAC1 antibodies of the invention comprise an Fc region from a human IgG1 antibody with a mutation at position N297. In one particular embodiment, the anti-PAC1 antibodies of the invention comprise an Fc region from a human IgG1 antibody with a N297G mutation. For instance, in some embodiments, the anti-PAC1 antibodies of the invention comprise a heavy chain constant region comprising the sequence of SEQ ID NO: 324.

To improve the stability of molecules comprising a N297 mutation, the Fc region of the anti-PAC1 antibodies may be further engineered. For instance, in some embodiments, one or more amino acids in the Fc region are substituted with cysteine to promote disulfide bond formation in the dimeric state. Residues corresponding to V259, A287, R292, V302, L306, V323, or I332 (according to the EU numbering scheme) of an IgG1 Fc region may thus be substituted with cysteine. Preferably, specific pairs of residues are substituted with cysteine such that they preferentially form a disulfide bond with each other, thus limiting or preventing disulfide bond scrambling. Preferred pairs include, but are not limited to, A287C and L306C, V259C and L306C, R292C and V302C, and V323C and I332C. In certain embodiments, the anti-PAC1 antibodies described herein comprise an Fc region from a human IgG1 antibody with mutations R292C and V302C. In such embodiments, the Fc region may also comprise a N297 mutation, such as a N297G mutation. In some embodiments, the anti-PAC1 antibodies of the invention comprise a heavy chain constant region comprising the sequence of SEQ ID NO: 325.

Modifications of the anti-PAC1 antibodies of the invention to increase serum half-life also may desirable, for example, by incorporation of or addition of a salvage receptor binding epitope (e.g., by mutation of the appropriate region or by incorporating the epitope into a peptide tag that is then fused to the antibody at either end or in the middle, e.g., by DNA or peptide synthesis; see, e.g., WO96/32478) or adding molecules such as PEG or other water soluble polymers, including polysaccharide polymers. The salvage receptor binding epitope preferably constitutes a region wherein any one or more amino acid residues from one or two loops of an Fc region are transferred to an analogous position in the antibody. Even more preferably, three or more residues from one or two loops of the Fc region are transferred. Still more preferred, the epitope is taken from the CH2 domain of the Fc region (e.g., an IgG Fc region) and transferred to the CH1, CH3, or VH region, or more than one such region, of the antibody. Alternatively, the epitope is taken from the CH2 domain of the Fc region and transferred to the CL region or VL region, or both, of the antibody. See International applications WO 97/34631 and WO 96/32478 for a description of Fc variants and their interaction with the salvage receptor.

The present invention includes one or more isolated polynucleotides or isolated nucleic acids encoding the anti-PAC1 antibodies or antigen-binding fragments described herein. In addition, the present invention encompasses vectors comprising the nucleic acids, host cells or cell lines comprising the nucleic acids, and methods of making the anti-PAC1 antibodies and antigen-binding fragments of the invention. The nucleic acids comprise, for example, polynucleotides that encode all or part of an antibody or antigen-binding fragment, for example, one or both chains of an antibody of the invention, or a fragment, derivative, or variant thereof, polynucleotides sufficient for use as hybridization probes, PCR primers or sequencing primers for identifying, analyzing, mutating or amplifying a polynucleotide encoding a polypeptide, anti-sense oligonucleotides for inhibiting expression of a polynucleotide, and complementary sequences of the foregoing. The nucleic acids can be any length as appropriate for the desired use or function, and can comprise one or more additional sequences, for example, regulatory sequences, and/or be part of a larger nucleic acid, for example, a vector. Nucleic acid molecules of the invention include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The nucleic acid molecules of the invention include full-length genes or cDNA molecules as well as a combination of fragments thereof. The nucleic acids of the invention can be derived from human sources as well as non-human species.

Relevant amino acid sequences from an immunoglobulin or region thereof (e.g. variable region, Fc region, etc.) or polypeptide of interest may be determined by direct protein sequencing, and suitable encoding nucleotide sequences can be designed according to a universal codon table. Alternatively, genomic or cDNA encoding monoclonal antibodies or binding fragments thereof of the invention can be isolated and sequenced from cells producing such antibodies using conventional procedures (e.g., by using oligonucleotide probes that are capable of binding specifically to genes encoding the heavy and light chains of the monoclonal antibodies).

An "isolated nucleic acid," which is used interchangeably herein with "isolated polynucleotide," is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct. In one preferred embodiment, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., Molecular Cloning: A Laboratory Manual, 2nd ed., Cold Spring Harbor Laboratory, Cold Spring Harbor, NY (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region. Unless specified otherwise, the left-hand end of any single-stranded polynucleotide sequence discussed herein is the 5' end; the left-hand direction of double-stranded polynucleotide sequences is referred to as the 5' direction. The direction of 5' to 3' production of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The present invention also includes nucleic acids that hybridize under moderately stringent conditions, and more preferably highly stringent conditions, to nucleic acids encoding polypeptides as described herein. The basic parameters affecting the choice of hybridization conditions and guidance for devising suitable conditions are set forth by Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55° C. (or other similar hybridization solutions, such as one containing about 50% formamide, with a hybridization temperature of about 42° C.), and washing conditions of about 60° C., in 0.5×SSC, 0.1% SDS. Generally, highly stringent conditions are defined as hybridization conditions as above, but with washing at approximately 68° C., 0.2×SSC, 0.1% SDS. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989).

When hybridizing a nucleic acid to a target nucleic acid of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10° C. less than the melting temperature (Tm) of the hybrid, where Tm is determined according to the following equations. For hybrids less than 18 base pairs in length, Tm (° C.)=2(# of A+T bases)+4(# of G+C bases). For hybrids above 18 base pairs in length, Tm (° C.)=81.5+16.6(log 10

[Na+])+0.41(% G+C)−(600/N), where N is the number of bases in the hybrid, and [Na+] is the concentration of sodium ions in the hybridization buffer ([Na+] for 1×SSC=0.165M). Preferably, each such hybridizing nucleic acid has a length that is at least 15 nucleotides (or more preferably at least 18 nucleotides, or at least 20 nucleotides, or at least 25 nucleotides, or at least 30 nucleotides, or at least 40 nucleotides, or most preferably at least 50 nucleotides), or at least 25% (more preferably at least 50%, or at least 60%, or at least 70%, and most preferably at least 80%) of the length of the nucleic acid of the present invention to which it hybridizes, and has at least 60% sequence identity (more preferably at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, and most preferably at least 99.5%) with the nucleic acid of the present invention to which it hybridizes, where sequence identity is determined by comparing the sequences of the hybridizing nucleic acids when aligned so as to maximize overlap and identity while minimizing sequence gaps as described in more detail above.

Variants of the anti-PAC1 antibodies and antigen-binding fragments described herein can be prepared by site-specific mutagenesis of nucleotides in the DNA encoding the polypeptide, using cassette or PCR mutagenesis or other techniques well known in the art, such as those described in Example 3, to produce DNA encoding the variant, and thereafter expressing the recombinant DNA in cell culture as outlined herein. However, antibodies or antigen-binding fragments comprising variant CDRs having up to about 100-150 residues may be prepared by in vitro synthesis using established techniques. The variants typically exhibit the same qualitative biological activity as the naturally occurring analogue, e.g., binding to antigen. Such variants include, for example, deletions and/or insertions and/or substitutions of residues within the amino acid sequences of the antibodies. Any combination of deletion, insertion, and substitution is made to arrive at the final construct, provided that the final construct possesses the desired characteristics. The amino acid changes also may alter post-translational processes of the antibody, such as changing the number or position of glycosylation sites. In certain embodiments, antibody variants are prepared with the intent to modify those amino acid residues which are directly involved in epitope binding. In other embodiments, modification of residues which are not directly involved in epitope binding or residues not involved in epitope binding in any way, is desirable, for purposes discussed herein. Mutagenesis within any of the CDR regions and/or framework regions is contemplated. Covariance analysis techniques can be employed by the skilled artisan to design useful modifications in the amino acid sequence of the antibody. See, e.g., Choulier, et al., Proteins 41:475-484, 2000; Demarest et al., J. Mol. Biol. 335:41-48, 2004; Hugo et al., Protein Engineering 16(5): 381-86, 2003; Aurora et al., US Patent Publication No. 2008/0318207 A1; Glaser et al., US Patent Publication No. 2009/0048122 A1; Urech et al., WO 2008/110348 A1; Borras et al., WO 2009/000099 A2. Such modifications determined by covariance analysis can improve potency, pharmacokinetic, pharmacodynamic, and/or manufacturability characteristics of an antibody.

Tables 4A and 4B show exemplary nucleic acid sequences encoding the full light and heavy chains, respectively, of anti-PAC1 antibodies described herein. Tables 5A and 5B show exemplary nucleic acid sequences encoding the light and heavy chain variable regions, respectively, of anti-PAC1 antibodies described herein. Polynucleotides encoding the anti-PAC1 variable regions can be used, optionally with nucleic acids encoding the light and heavy chain constant regions listed in Tables 2 and 3, respectively, to construct the antibodies and antigen-binding fragments of the invention.

TABLE 5A

Exemplary Anti-PAC1 Antibody Light Chain Variable Region Nucleic Acid Sequences

| Ab ID. | VL Group | VL Nucleic Acid Sequence | SEQ ID NO: |
|---|---|---|---|
| | | 29G4 variants | |
| 29G4v10 | LV-01 | GAGATCGTACTTACTCAGTCACCCGCCACATTGTCCCT<br>GAGCCCGGGTGAACGGGCGACCCTCAGCTGCCGAGCA<br>TCCCAGTCCGTCGGACGATCATTGCACTGGTACCAACA<br>AAAACCGGGCCAGGCCCCCAGACTTCTGATCAAGTAT<br>GCGTCACAGAGCTTGTCGGGTATTCCCGCTCGCTTTTC<br>GGGGTCGGGATCCGGGACAGATTTCACGCTCACAATC<br>TCCTCGCTGGAACCCGAGGACTTCGCGGTCTACTATTG<br>TCATCAGTCATCGAGGTTGCCTTTCACGTTTGGACCAG<br>GGACCAAGGTGGACATTAAGCGTAC | 328 |
| 29G4v22 | LV-02 | GATATCCAGCTCACTCAATCGCCATCATTTCTCTCCGC<br>TTCGGTAGGCGACCGGGTCACGATCACATGCAGGGCG<br>TCGCAAAGCATTGGGAGGTCGTTGCATTGGTATCAGC<br>AGAAACCCGGAAAGGCCCCGAAACTTCTGATCAAATA<br>CGCATCACAAAGCTTGAGCGGTGTGCCGTCGCGCTTCT<br>CCGGTTCCGGAAGCGGAACGGAATTCACGCTTACAAT<br>CTCCTCACTGCAGCCCGAGGATTTCGCGACCTATTACT<br>GTCACCAGTCATCCAGACTCCCGTTTACTTTTGGCCCT<br>GGGACCAAGGTGGACATTAAGCGTAC | 329 |
| iPS:420649; iPS:420653;<br>iPS:420657; iPS:420661;<br>iPS:420665; iPS:420672;<br>iPS:420679; iPS:420686;<br>iPS:420837; iPS:420841; | LV-03 | GAGATCGTACTTACTCAGTCACCCGCCACATTGTCCCT<br>GAGCCCGGGTGAACGGGCGACCCTCAGCTGCCGAGCA<br>TCCAAGTCCGTCGGACGATCATTGCACTGGTACCAACA<br>AAAACCGGGCCAGGCCCCCAGACTTCTGATCAAGTAT<br>GCGTCACAGAGCTTGTCGGGTATTCCCGCTCGCTTTTC | 330 |

TABLE 5A-continued

Exemplary Anti-PAC1 Antibody Light Chain Variable Region Nucleic Acid Sequences

| Ab ID. | VL Group | VL Nucleic Acid Sequence | SEQ ID NO: |
|---|---|---|---|
| iPS:420845; iPS:420849; iPS:420853; iPS:420857; iPS:420861; iPS:420865; iPS:420869; iPS:420873; iPS:420877; iPS:420881; iPS:420885; iPS:420889; iPS:420893; iPS:420897; iPS:421027; iPS:421031; iPS:421035; iPS:421039; iPS:421043; iPS:421047; iPS:421051; iPS:421055; iPS:421059; iPS:421063; iPS:421067; iPS:421071; iPS:421075; iPS:421079; iPS:421083; iPS:421087; iPS:421147; iPS:421207; iPS:421211; iPS:421215; iPS:421219; iPS:421223 | | GGGGTCGGGATCCGGGACAGATTTCACGCTCACAATC TCCTCGCTGGAACCCGAGGACTTCGCGGTCTACTATTG TCATCAGTCATCGAGGTTGCCTTTCACGTTTGGACCAG GGACCAAGGTGGACATTAAG | |
| iPS:420690; iPS:420697; iPS:420704; iPS:420711; iPS:420718; iPS:420725; iPS:420732; iPS:420739; iPS:420746; iPS:420753; iPS:420760; iPS:420767; iPS:420774; iPS:420781; iPS:420788; iPS:420795; iPS:420802; iPS:420809; iPS:420816; iPS:420823; iPS:420830; iPS:420901; iPS:420908; iPS:420915; iPS:420922; iPS:420929; iPS:420936; iPS:420943; iPS:420950; iPS:420957; iPS:420964; iPS:420971; iPS:420978; iPS:420985; iPS:420992; iPS:420999; iPS:421006; iPS:421013; iPS:421020; iPS:421091; iPS:421098; iPS:421105; iPS:421112; iPS:421119; iPS:421126; iPS:421133; iPS:421140; iPS:421163; iPS:391578; iPS:421170; iPS:421176; iPS:421182; iPS:421239; iPS:421246; iPS:421253; iPS:421260; iPS:421267; iPS:421286; iPS:421293; iPS:421300; iPS:421307; iPS:421326; iPS:421333; iPS:421340; iPS:421347; iPS:421354; iPS:421373; iPS:421380; iPS:421387; iPS:421394; iPS:421855; iPS:421861; iPS:421867; iPS:421873; iPS:421879; iPS:421885; iPS:421891; iPS:421897; iPS:421903; iPS:421909; iPS:421915 | LV-04 | GAGATCGTACTTACTCAGTCACCCGCCACATTGTCCCT GAGCCCGGGTGAACGGGCGACCCTCAGCTGCCGAGCA TCCCAGTCCGTCGGACGATCATTGCACTGGTACCAACA AAAACCGGGCCAGGCCCCCAGACTTCTGATCAAGTAT GCGTCACAGAGCTTGTCGGGTATTCCCGCTCGCTTTTC GGGGTCGGGATCCGGGACAGATTTCACGCTCACAATC TCCTCGCTGGAACCCGAGGACTTCGCGGTCTACTATTG TCATCAGTCATCGAGGTTGCCTTTCACGTTTGGACCAG GGACCAAGGTGGACATTAAG | 331 |
| iPS:421151; iPS:421227; iPS:421274; iPS:421314; iPS:421361 | LV-05 | GAGATCGTACTTACTCAGTCACCCGCCACATTGTCCCT GAGCCCGGGTGAACGGGCGACCCTCAGCTGCCGAGCA TCCCAGTCCGTCTGGCGATCATTGCACTGGTACCAACA AAAACCGGGCCAGGCCCCCAGACTTCTGATCAAGTAT GCGTCACAGAGCTTGTCGGGTATTCCCGCTCGCTTTTC GGGGTCGGGATCCGGGACAGATTTCACGCTCACAATC TCCTCGCTGGAACCCGAGGACTTCGCGGTCTACTATTG TCATCAGTCATCGAGGTTGCCTTTCACGTTTGGACCAG GGACCAAGGTGGACATTAAG | 332 |
| iPS:391478; iPS:421231; iPS:421278; iPS:421318; iPS:421365 | LV-06 | GAGATCGTACTTACTCAGTCACCCGCCACATTGTCCCT GAGCCCGGGTGAACGGGCGACCCTCAGCTGCCGAGCA TCCCAGTCCGTCGGACGAAACTTGCACTGGTACCAAC | 333 |

TABLE 5A-continued

Exemplary Anti-PAC1 Antibody Light Chain Variable Region Nucleic Acid Sequences

| Ab ID. | VL Group | VL Nucleic Acid Sequence | SEQ ID NO: |
|---|---|---|---|
| | | AAAAACCGGGCCAGGCCCCCAGACTTCTGATCAAGTA<br>TGCGTCACAGAGCTTGTCGGGTATTCCCGCTCGCTTTT<br>CGGGGTCGGGATCCGGGACAGATTTCACGCTCACAAT<br>CTCCTCGCTGGAACCCGAGGACTTCGCGGTCTACTATT<br>GTCATCAGTCATCGAGGTTGCCTTTCACGTTTGGACCA<br>GGGACCAAGGTGGACATTAAG | |
| iPS:421157; iPS:421235; iPS:421282; iPS:421322; iPS:421369 | LV-07 | GAGATCGTACTTACTCAGTCACCCGCCACATTGTCCCT<br>GAGCCCGGGTGAACGGGCGACCCTCAGCTGCCGAGCA<br>TCCCAGTCCGTCGGACGATCATTGCACTGGTACCAACA<br>AAAACCGGGCCAGGCCCCCAGACTTCTGATCAAGTAT<br>GCGTCACAGAGCTTGTCGGGTATTCCCGCTCGCTTTTC<br>GGGGTCGGGATCCGGGACAGATTTCACGCTCACAATC<br>TCCTCGCTGGAACCCGAGGACTTCGCGGTCTACTATTG<br>TCATCAGTCATCGATGTTGCCTTTCACGTTTGGACCAG<br>GGACCAAGGTGGACATTAAG | 334 |
| iPS:421189 | LV-08 | GAGATCGTACTTACTCAGTCACCCGCCACATTGTCCCT<br>GAGCCCGGGTGAACGGGCGACCCTCAGCTGCCGAGCA<br>TCCAAGTCCGTCTGGCGATCATTGCACTGGTACCAACA<br>AAAACCGGGCCAGGCCCCCAGACTTCTGATCAAGTAT<br>GCGTCACAGAGCTTGTCGGGTATTCCCGCTCGCTTTTC<br>GGGGTCGGGATCCGGGACAGATTTCACGCTCACAATC<br>TCCTCGCTGGAACCCGAGGACTTCGCGGTCTACTATTG<br>TCATCAGTCATCGAGGTTGCCTTTCACGTTTGGACCAG<br>GGACCAAGGTGGACATTAAG | 335 |
| iPS:421195 | LV-09 | GAGATCGTACTTACTCAGTCACCCGCCACATTGTCCCT<br>GAGCCCGGGTGAACGGGCGACCCTCAGCTGCCGAGCA<br>TCCAAGTCCGTCGGACGAAACTTGCACTGGTACCAAC<br>AAAAACCGGGCCAGGCCCCCAGACTTCTGATCAAGTA<br>TGCGTCACAGAGCTTGTCGGGTATTCCCGCTCGCTTTT<br>CGGGGTCGGGATCCGGGACAGATTTCACGCTCACAAT<br>CTCCTCGCTGGAACCCGAGGACTTCGCGGTCTACTATT<br>GTCATCAGTCATCGAGGTTGCCTTTCACGTTTGGACCA<br>GGGACCAAGGTGGACATTAAG | 336 |
| iPS:421201 | LV-10 | GAGATCGTACTTACTCAGTCACCCGCCACATTGTCCCT<br>GAGCCCGGGTGAACGGGCGACCCTCAGCTGCCGAGCA<br>TCCAAGTCCGTCGGACGATCATTGCACTGGTACCAACA<br>AAAACCGGGCCAGGCCCCCAGACTTCTGATCAAGTAT<br>GCGTCACAGAGCTTGTCGGGTATTCCCGCTCGCTTTTC<br>GGGGTCGGGATCCGGGACAGATTTCACGCTCACAATC<br>TCCTCGCTGGAACCCGAGGACTTCGCGGTCTACTATTG<br>TCATCAGTCATCGATGTTGCCTTTCACGTTTGGACCAG<br>GGACCAAGGTGGACATTAAG | 337 |
| iPS:480711; iPS:480706; iPS:480705; iPS:480707; iPS:480708; iPS:480712; iPS:480704; iPS:480710 | LV-11 | GAGATCGTACTTACTCAGTCACCCGCCACATTGTCCCT<br>GAGCCCGGGTGAACGGGCGACCCTCAGCTGCCGAGCA<br>TCCAAATCCGTCGGGTGGAGCTTGCACTGGTACCAAC<br>AAAAACCGGGCCAGGCCCCCAGACTTCTGATCAAGTA<br>TGCGTCACAGAGCTTGTCGGGTATTCCCGCTCGCTTTT<br>CGGGGTCGGGATCCGGGACAGATTTCACGCTCACAAT<br>CTCCTCGCTGGAACCCGAGGACTTCGCGGTCTACTATT<br>GTCATCAGTCATCGAGGTTGCCTTTCACGTTTGGACCA<br>GGGACCAAGGTGGACATTAAGCGTA | 338 |
| iPS:480713 | LV-12 | GAGATCGTACTTACTCAGTCACCCGCCACATTGTCCCT<br>GAGCCCGGGTGAACGGGCGACCCTCAGCTGCCGAGCA<br>TCCAAATCCGTCGGGTACAGCTTGCACTGGTACCAACA<br>AAAACCGGGCCAGGCCCCCAGACTTCTGATCAAGTAT<br>GCGTCACAGAGCTTGTCGGGTATTCCCGCTCGCTTTTC<br>GGGGTCGGGATCCGGGACAGATTTCACGCTCACAATC<br>TCCTCGCTGGAACCCGAGGACTTCGCGGTCTACTATTG<br>TCATCAGTCATCGAGGTTGCCTTTCACGTTTGGACCAG<br>GGACCAAGGTGGACATTAAGCGTA | 339 |
| iPS:480709 | LV-13 | GAGATCGTACTTACTCAGTCACCCGCCACATTGTCCCT<br>GAGCCCGGGTGAACGGGCGACCCTCAGCTGCCGAGCA<br>TCCAAAGCCGTCGGGTGGAGCTTGCACTGGTACCAAC<br>AAAAACCGGGCCAGGCCCCCAGACTTCTGATCAAGTA<br>TGCGTCACAGAGCTTGTCGGGTATTCCCGCTCGCTTTT<br>CGGGGTCGGGATCCGGGACAGATTTCACGCTCACAAT<br>CTCCTCGCTGGAACCCGAGGACTTCGCGGTCTACTATT | 340 |

TABLE 5A-continued

Exemplary Anti-PAC1 Antibody Light Chain Variable Region Nucleic Acid Sequences

| Ab ID. | VL Group | VL Nucleic Acid Sequence | SEQ ID NO: |
|---|---|---|---|
| | | GTCATCAGTCATCGAGGTTGCCTTTCACGTTTGGACCA GGGACCAAGGTGGACATTAAGCGTA | |
| iPS:480716; iPS:480715 iPS:480717 | LV-14 | GAGATCGTACTTACTCAGTCACCCGCCACATTGTCCCT GAGCCCGGGTGAACGGGCGACCCTCAGCTGCCGAGCA TCCAAATCAGTCGGTCAGTCTTTGCACTGGTACCAACA AAAACCGGGCCAGGCCCCCAGACTTCTGATCAAGTAT GCGTCACAGAGCTTGTCGGGTATTCCCGCTCGCTTTTC GGGGTCGGGATCCGGGACAGATTTCACGCTCACAATC TCCTCGCTGGAACCCGAGGACTTCGCGGTCTACTATTG TCATCAGTCATCGCGTTTGCCTTTCACGTTTGGACCAG GGACCAAGGTGGACATTAAGCGTA | 341 |
| iPS:480714 | LV-15 | GAGATCGTACTTACTCAGTCACCCGCCACATTGTCCCT GAGCCCGGGTGAACGGGCGACCCTCAGCTGCCGAGCA TCCCGTTCAGTCGGTCTGGCTTTGCACTGGTACCAACA AAAACCGGGCCAGGCCCCCAGACTTCTGATCAAGTAT GCGTCACAGAGCTTGTCGGGTATTCCCGCTCGCTTTTC GGGGTCGGGATCCGGGACAGATTTCACGCTCACAATC TCCTCGCTGGAACCCGAGGACTTCGCGGTCTACTATTG TCATCAGTCATCGTTCTTGCCTTTCACGTTTGGACCAG GGACCAAGGTGGACATTAAGCGTA | 342 |
| | | 19H8 variants | |
| 19H8 | LV-16 | GACATCCAGATGACCCAGTCTCCATCCTCCCTGTCTGC ATCTGTAGGAGACAGAATCACCATCACTTGCCGGGCA AGTCAGAGCATTAGCAGGTATTTAAATTGGTATCAAC AGAAACCAGGGAAAGCCCCTAAACTCCTGATCTATGC TGCATCCAGTTTGCAAAGTGGGATCCCATCAAGGTTCA GCGGCAGTGGATCTGGGACAGATTTCACTCTCACCATC AACAGTCTGCAACCTGAAGATTTTGCAACTTACTTCTG TCAACAGAGTTACAGTCCCCCATTCACTTTCGGCCCTG GGACCAAAGTGGATATCAAACGTAC | 343 |
| iPS:448202 | LV-17 | GACATCCAGATGACCCAGTCTCCATCCTCCCTGTCTGC ATCTGTAGGAGACAGAATCACCATCACTTGCCGGGCA AGTCAGAGCATTAGCAGGTATTTAAATTGGTATCAAC AGAAACCAGGGAAAGCCCCTAAACTCCTGATCTTCGC TGGTCAGCGTTTGCAAAGTGGGATCCCATCAAGGTTCA GCGGCAGTGGATCTGGGACAGATTTCACTCTCACCATC AACAGTCTGCAACCTGAAGATTTTGCAACTTACTTCTG TCAACAGGCTATCGGTATGCCATACACTTTCGGCCCTG GGACCAAAGTGGATATCAAA | 344 |
| iPS:449375 | LV-18 | GACATCCAGATGACCCAGTCTCCATCCTCCCTGTCTGC ATCTGTAGGAGACAGAATCACCATCACTTGCCGGGCA AGTCAGTACATTGTTCGTTACTTAAACTGGTATCAACA GAAACCAGGGAAAGCCCCTAAACTCCTGATCTACGCT GCTCATCATTTGCAAAGTGGGATCCCATCAAGGTTCAG CGGCAGTGGATCTGGGACAGATTTCACTCTCACCATCA ACAGTCTGCAACCTGAAGATTTTGCAACTTACTTCTGT CAACAGGCTATCCAGGAACCATACACTTTCGGCCCTG GGACCAAAGTGGATATCAAA | 345 |
| iPS:448083 | LV-19 | GACATCCAGATGACCCAGTCTCCATCCTCCCTGTCTGC ATCTGTAGGAGACAGAATCACCATCACTTGCCGGGCA AGTCAGACTATTGTTCGTTACTTAAACTGGTATCAACA GAAACCAGGGAAAGCCCCTAAACTCCTGATCTTCGCT GGTCAGCGTTTGCAAAGTGGGATCCCATCAAGGTTCA GCGGCAGTGGATCTGGGACAGATTTCACTCTCACCATC AACAGTCTGCAACCTGAAGATTTTGCAACTTACTTCTG TCAACAGGCTATCATCAACCCATACACTTTCGGCCCTG GGACCAAAGTGGATATCAAA | 346 |
| iPS:452128 | LV-20 | GACATCCAGATGACCCAGTCTCCATCCTCCCTGTCTGC ATCTGTAGGAGACAGAATCACCATCACTTGCCGGGCA AGTCAGTACATTGTTCGTTACTTAAACTGGTATCAACA GAAACCAGGGAAAGCCCCTAAACTCCTGATCTACGCT GCTAACATGTTGCAAAGTGGGATCCCATCAAGGTTCA GCGGCAGTGGATCTGGGACAGATTTCACTCTCACCATC AACAGTCTGCAACCTGAAGATTTTGCAACTTACTTCTG TCAACAGGCTATCAACCAGCCATACACTTTCGGCCCTG GGACCAAAGTGGATATCAAA | 347 |

TABLE 5A-continued

| Exemplary Anti-PAC1 Antibody Light Chain Variable Region Nucleic Acid Sequences | | | |
|---|---|---|---|
| Ab ID. | VL Group | VL Nucleic Acid Sequence | SEQ ID NO: |
| iPS:448195 | LV-21 | GACATCCAGATGACCCAGTCTCCATCCTCCCTGTCTGC ATCTGTAGGAGACAGAATCACCATCACTTGCCGGGCA AGTCAGAAAATTGCTCGTTACTTAGTTTGGTATCAACA GAAACCAGGGAAAGCCCCTAAACTCCTGATCTACGCT GCTAACATGTTGCAAAGTGGGATCCCATCAAGGTTCA GCGGCAGTGGATCTGGGACAGATTTCACTCTCACCATC AACAGTCTGCAACCTGAAGATTTTGCAACTTACTTCTG TCAACAGTCTATCCAGCAGCCATACACTTTCGGCCCTG GGACCAAAGTGGATATCAAA | 348 |
| iPS:448466 | LV-22 | GACATCCAGATGACCCAGTCTCCATCCTCCCTGTCTGC ATCTGTAGGAGACAGAATCACCATCACTTGCCGGGCA AGTCAGAGCATTAGCAGGTATTTAAATTGGTATCAAC AGAAACCAGGGAAAGCCCCTAAACTCCTGATCTTCGC TGGTCAGCGTTTGCAAAGTGGGATCCCATCAAGGTTCA GCGGCAGTGGATCTGGGACAGATTTCACTCTCACCATC AACAGTCTGCAACCTGAAGATTTTGCAACTTACTTCTG TCAACAGGCTATCCAGCAGCCATACACTTTCGGCCCTG GGACCAAAGTGGATATCAAACGT | 349 |
| iPS:448689 | LV-23 | GACATCCAGATGACCCAGTCTCCATCCTCCCTGTCTGC ATCTGTAGGAGACAGAATCACCATCACTTGCCGGGCA AGTCAGTACATTGTTCGTTACTTAAACTGGTATCAACA GAAACCAGGGAAAGCCCCTAAACTCCTGATCTACGCT TCTTACAACTTGCAAAGTGGGATCCCATCAAGGTTCAG CGGCAGTGGATCTGGGACAGATTTCACTCTCACCATCA ACAGTCTGCAACCTGAAGATTTTGCAACTTACTTCTGT CAACAGGCTATCATGGCTCCATACACTTTCGGCCCTGG GACCAAAGTGGATATCAAA | 350 |
| iPS:449034 | LV-24 | GACATCCAGATGACCCAGTCTCCATCCTCCCTGTCTGC ATCTGTAGGAGACAGAATCACCATCACTTGCCGGGCA AGTCAGCCTATTGCTCAGTACTTAAACTGGTATCAACA GAAACCAGGGAAAGCCCCTAAACTCCTGATCTACGCT GGTCGTTACTTGCAAAGTGGGATCCCATCAAGGTTCAG CGGCAGTGGATCTGGGACAGATTTCACTCTCACCATCA ACAGTCTGCAACCTGAAGATTTTGCAACTTACTTCTGT CAACAGGCTATCCAGAACCCATACACTTTCGGCCCTGG GACCAAAGTGGATATCAAA | 351 |
| iPS:448075 | LV-25 | GACATCCAGATGACCCAGTCTCCATCCTCCCTGTCTGC ATCTGTAGGAGACAGAATCACCATCACTTGCCGGGCA AGTCAGAGCATTAGCAGGTATTTAAATTGGTATCAAC AGAAACCAGGGAAAGCCCCTAAACTCCTGATCTTCGC TGGTCAGCGTTTGCAAAGTGGGATCCCATCAAGGTTCA GCGGCAGTGGATCTGGGACAGATTTCACTCTCACCATC AACAGTCTGCAACCTGAAGATTTTGCAACTTACTTCTG TCAACAGGCTATCGTTCAGCCATACACTTTCGGCCCTG GGACCAAAGTGGATATCAAA | 352 |
| iPS:448924 | LV-26 | GACATCCAGATGACCCAGTCTCCATCCTCCCTGTCTGC ATCTGTAGGAGACAGAATCACCATCACTTGCCGGGCA AGTCAGCCGATTTCTCGTTACTTATCTTGGTATCAACA GAAACCAGGGAAAGCCCCTAAACTCCTGATCTTCGCT GGTCAGCGTTTGCAAAGTGGGATCCCATCAAGGTTCA GCGGCAGTGGATCTGGGACAGATTTCACTCTCACCATC AACAGTCTGCAACCTGAAGATTTTGCAACTTACTTCTG TCAACAGGCTATCTCTATCCCATACACTTTCGGCCCTG GGACCAAAGTGGATATCAAA | 353 |
| iPS:448752; 3575 | LV-27 | GACATCCAGATGACCCAGTCTCCATCCTCCCTGTCTGC ATCTGTAGGAGACAGAATCACCATCACTTGCCGGGCA AGTCAGCAGATTGCTCGTTACTTAAACTGGTATCAACA GAAACCAGGGAAAGCCCCTAAACTCCTGATCTACGCT TCTTACAACTTGCAAAGTGGGATCCCATCAAGGTTCAG CGGCAGTGGATCTGGGACAGATTTCACTCTCACCATCA ACAGTCTGCAACCTGAAGATTTTGCAACTTACTTCTGT CAACAGGCTATCATCCAGCCATACACTTTCGGCCCTGG GACCAAAGTGGATATCAAA | 354 |
| iPS:448772; iPS:448593 | LV-28 | GACATCCAGATGACCCAGTCTCCATCCTCCCTGTCTGC ATCTGTAGGAGACAGAATCACCATCACTTGCCGGGCA AGTCAGAGCATTAGCAGGTATTTAAATTGGTATCAAC | 355 |

TABLE 5A-continued

Exemplary Anti-PAC1 Antibody Light Chain Variable Region Nucleic Acid Sequences

| Ab ID. | VL Group | VL Nucleic Acid Sequence | SEQ ID NO: |
|---|---|---|---|
| | | AGAAACCAGGGAAAGCCCCTAAACTCCTGATCTACGC TTCTTACAACTTGCAAAGTGGGATCCCATCAAGGTTCA GCGGCAGTGGATCTGGGACAGATTTCACTCTCACCATC AACAGTCTGCAACCTGAAGATTTTGCAACTTACTTCTG TCAACAGGCTATCCAGAACCCATACACTTTCGGCCCTG GGACCAAAGTGGATATCAAA | |
| iPS:448117 | LV-29 | GACATCCAGATGACCCAGTCTCCATCCTCCCTGTCTGC ATCTGTAGGAGACAGAATCACCATCACTTGCCGGGCA AGTCAGACTATTGTTCGTTACTTAAACTGGTATCAACA GAAACCAGGGAAAGCCCCTAAACTCCTGATCTTCGCT GGTCAGCGTTTGCAAAGTGGGATCCCATCAAGGTTCA GCGGCAGTGGATCTGGGACAGATTTCACTCTCACCATC AACAGTCTGCAACCTGAAGATTTTGCAACTTACTTCTG TCAACAGTCTATCCAGACTCCATACACTTTCGGCCCTG GGACCAAAGTGGATATCAAA | 356 |
| iPS:448788 | LV-30 | GACATCCAGATGACCCAGTCTCCATCCTCCCTGTCTGC ATCTGTAGGAGACAGAATCACCATCACTTGCCGGGCA AGTCAGAGCATTAGCAGGTATTTAAATTGGTATCAAC AGAAACCAGGGAAAGCCCCTAAACTCCTGATCTACGC TGGTCGTATCTTGCAAAGTGGGATCCCATCAAGGTTCA GCGGCAGTGGATCTGGGACAGATTTCACTCTCACCATC AACAGTCTGCAACCTGAAGATTTTGCAACTTACTTCTG TCAACAGGCTATCATCAACCCATACACTTTCGGCCCTG GGACCAAAGTGGATATCAAA | 357 |
| iPS:448238 | LV-31 | GACATCCAGATGACCCAGTCTCCATCCTCCCTGTCTGC ATCTGTAGGAGACAGAATCACCATCACTTGCCGGGCA AGTCAGCGTATTGCTCGTTACTTAAACTGGTATCAACA GAAACCAGGGAAAGCCCCTAAACTCCTGATCTTCGCT GGTTCTATCTTGCAAAGTGGGATCCCATCAAGGTTCAG CGGCAGTGGATCTGGGACAGATTTCACTCTCACCATCA ACAGTCTGCAACCTGAAGATTTTGCAACTTACTTCTGT CAACAGGCTATCCAGAACCCATACACTTTCGGCCCTGG GACCAAAGTGGATATCAAA | 358 |
| iPS:448901 | LV-32 | GACATCCAGATGACCCAGTCTCCATCCTCCCTGTCTGC ATCTGTAGGAGACAGAATCACCATCACTTGCCGGGCA AGTCAGAGCATTAGCAGGTATTTAAATTGGTATCAAC AGAAACCAGGGAAAGCCCCTAAACTCCTGATCTACGC TTCTTACAACTTGCAAAGTGGGATCCCATCAAGGTTCA GCGGCAGTGGATCTGGGACAGATTTCACTCTCACCATC AACAGTCTGCAACCTGAAGATTTTGCAACTTACTTCTG TCAACAGTCTATCCAGCAGCCATACACTTTCGGCCCTG GGACCAAAGTGGATATCAAA | 359 |
| iPS:448655 | LV-33 | GACATCCAGATGACCCAGTCTCCATCCTCCCTGTCTGC ATCTGTAGGAGACAGAATCACCATCACTTGCCGGGCA AGTCAGTACATTGTTCGTTACTTAAACTGGTATCAACA GAAACCAGGGAAAGCCCCTAAACTCCTGATCTACGCT TCTTACAACTTGCAAAGTGGGATCCCATCAAGGTTCAG CGGCAGTGGATCTGGGACAGATTTCACTCTCACCATCA ACAGTCTGCAACCTGAAGATTTTGCAACTTACTTCTGT CAACAGGCTATCCAGCAGCCATACACTTTCGGCCCTGG GACCAAAGTGGATATCAAA | 360 |
| iPS:448730 | LV-34 | GACATCCAGATGACCCAGTCTCCATCCTCCCTGTCTGC ATCTGTAGGAGACAGAATCACCATCACTTGCCGGGCA AGTCAGATGATTGCTCGTTACTTAAACTGGTATCAACA GAAACCAGGGAAAGCCCCTAAACTCCTGATCTACGCT TCTTACAACTTGCAAAGTGGGATCCCATCAAGGTTCAG CGGCAGTGGATCTGGGACAGATTTCACTCTCACCATCA ACAGTCTGCAACCTGAAGATTTTGCAACTTACTTCTGT CAACAGGCTATCATCAACCCATACACTTTCGGCCCTGG GACCAAAGTGGATATCAAA | 361 |
| iPS:449027 | LV-35 | GACATCCAGATGACCCAGTCTCCATCCTCCCTGTCTGC ATCTGTAGGAGACAGAATCACCATCACTTGCCGGGCA AGTCAGTACATTGTTCGTTACTTAAACTGGTATCAACA GAAACCAGGGAAAGCCCCTAAACTCCTGATCTACGGT GCTCGTAACTTGCAAAGTGGGATCCCATCAAGGTTCA GCGGCAGTGGATCTGGGACAGATTTCACTCTCACCATC AACAGTCTGCAACCTGAAGATTTTGCAACTTACTTCTG | 362 |

TABLE 5A-continued

| Exemplary Anti-PAC1 Antibody Light Chain Variable Region Nucleic Acid Sequences | | | |
|---|---|---|---|
| Ab ID. | VL Group | VL Nucleic Acid Sequence | SEQ ID NO: |
| | | TCAACAGTCTATCCAGACTCCATACACTTTCGGCCCTG GGACCAAAGTGGATATCAAA | |
| 3574 | LV-36 | GACATCCAGATGACCCAGTCTCCATCCTCCCTGTCTGC ATCTGTAGGAGACAGAATCACCATCACTTGCCGGGCA AGTCAGAGCATTAGCAGGTATTTAAATTGGTATCAAC AGAAACCAGGGAAAGCCCCTAAACTCCTGATCTATGC TGCATCCAGTTTGCAAAGTGGGATCCCATCAAGGTTCA GCGGCAGTGGATCTGGGACAGATTTCACTCTCACCATC AACAGTCTGCAACCTGAAGATTTTGCAACTTACTTCTG TCAACAGAGTTACAGTCCCCCATTCACTTTCGGCCCTG GGACCAAAGTGGATATCAAA | 363 |

TABLE 5B

| Exemplary Anti-PAC1 Antibody Heavy Chain Variable Region Nucleic Acid Sequences | | | |
|---|---|---|---|
| Ab ID. | VH Group | VH Nucleic Acid Sequence | SEQ ID NO: |
| | | 29G4 variants | |
| 29G4v10; iPS:421151; iPS:391478; iPS:421157; iPS:421189; iPS:421195; iPS:421201 | HV-01 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATGATGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCC TCAGC | 364 |
| 29G4v22 | HV-02 | CAAGTTCAGTTGGTGGAGTCTGGAGCCGAAGTAGTAAAGCCAGG AGCTTCAGTGAAAGTCTCTTGTAAAGCAAGTGGATTCACGTTTAG CCGCTTTGCCATGCATTGGGTGCGGCAAGCTCCCGGTCAGGGGTT GGAGTGGATGGGAGTTATTAGCTATGACGGGGGCAATAAGTACT ACGCCGAGTCTGTTAAGGGTCGGGTCACAATGACACGGGACACCT CAACCAGTACACTCTATATGGAACTGTCTAGCCTGAGATCCGAGG ACACCGCTGTGTATTATTGCGCTAGGGGGTACGATGTATTGACGG GTTATCCTGATTACTGGGGGCAGGGGACACTCGTAACCGTCTCTA GT | 365 |
| iPS:420649; iPS:421227; iPS:421231; iPS:421235 | HV-03 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATAACGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 366 |
| iPS:420653 | HV-04 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATATCGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 367 |
| iPS:420657 | HV-05 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATCAGGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT | 368 |

TABLE 5B-continued

Exemplary Anti-PAC1 Antibody Heavy Chain Variable Region Nucleic Acid Sequences

| Ab ID. | VH Group | VH Nucleic Acid Sequence | SEQ ID NO: |
|---|---|---|---|
| | | AGT | |
| iPS:420661 | HV-06 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATTACGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 369 |
| iPS:420665; iPS:421274; iPS:421278; iPS:421282 | HV-07 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATGATGGACGCAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 370 |
| iPS:420672 | HV-08 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATGATGGAAACAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 371 |
| iPS:420679; iPS:421314; iPS:421318; iPS:421322 | HV-09 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATGATGGAGGAAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 372 |
| iPS:420686; iPS:421361; iPS:421365; iPS:421369 | HV-10 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATGATGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 373 |
| iPS:420690; iPS:420837 | HV-11 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATAACGGACGCAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 374 |
| iPS:420697; iPS:420841 | HV-12 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATATCGGACGCAATAAATACTA TGCAGAGTCCGTGAAGGGCCGGTTCACCATCTCCAGAGACAATTC CAAGAACACCCTGTATCTGCAAATGAACAGCCTGAGAGCTGAGG ACACGGCTCTGTTTTACTGTGCGAGAGGATACGATGTTTTGACTG GTTACCCCGACTACTGGGGCCAGGGAACCCTGGTCACCGTCTCTA GT | 375 |
| iPS:420704; iPS:420845 | HV-13 | CAGGTGCAGCTGGTGGAGTCTGGGGGAGGCGTGGTCCAGCCTGG GAGGTCCCTGCGACTCTCCTGTGCAGCCTCTGGATTCACCTTCAG | 376 |

TABLE 5B-continued

| Exemplary Anti-PAC1 Antibody Heavy Chain Variable Region Nucleic Acid Sequences | | | |
|---|---|---|---|
| Ab ID. | VH Group | VH Nucleic Acid Sequence | SEQ ID NO: |
| | | TAGATTTGCCATGCACTGGGTCCGCCAGGCTCCAGGCAAGGGGCT GGAGTGGGTGGCAGTTATATCATATCAGGGACGCAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | |
| iPS:420711; iPS:420849 | HV-14 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATTACGGACGCAATAAATACTA TGCAGAGTCCGTGAAGGGCCGGTTCACCATCTCCAGAGACAATTC CAAGAACACCCTGTATCTGCAAATGAACAGCCTGAGAGCTGAGG ACACGGCTCTGTTTTACTGTGCGAGAGGATACGATGTTTTGACTG GTTACCCCGACTACTGGGGCCAGGGAACCCTGGTCACCGTCTCTA GT | 377 |
| iPS:420718; iPS:420853 | HV-15 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATAACGGAAACAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 378 |
| iPS:420725; iPS:420857 | HV-16 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATATCGGAAACAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 379 |
| iPS:420732; iPS:420861 | HV-17 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATCAGGGAAACAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 380 |
| iPS:420739; iPS:420865 | HV-18 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATTACGGAAACAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 381 |
| iPS:420746; iPS:420869 | HV-19 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATAACGGAGGAAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 382 |
| iPS:420753; iPS:420873 | HV-20 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATATCGGAGGAAATAAATACT ATGCACGCTCCGTGAAGGGCCGGTTCACCATCTCCAGAGACAATT CCAAGAACACCCTGTATCTGCAAATGAACAGCCTGAGAGCTGAG | 383 |

TABLE 5B-continued

Exemplary Anti-PAC1 Antibody Heavy Chain Variable Region Nucleic Acid Sequences

| Ab ID. | VH Group | VH Nucleic Acid Sequence | SEQ ID NO: |
|---|---|---|---|
| | | GACACGGCTCTGTTTTACTGTGCGAGAGGATACGATGTTTTGACT GGTTACCCCGACTACTGGGGCCAGGGAACCCTGGTCACCGTCTCT AGT | |
| iPS:420760; iPS:420877 | HV-21 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATCAGGGAGGAAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 384 |
| iPS:420767; iPS:420881 | HV-22 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATTACGGAGGAAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 385 |
| iPS:420774; iPS:420885 | HV-23 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATAACGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 386 |
| iPS:420781; iPS:420889 | HV-24 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATATCGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 387 |
| iPS:420788; iPS:420893 | HV-25 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATCAGGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT | 388 |
| iPS:420795; iPS:420897 | HV-26 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATTACGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 389 |
| iPS:420802 | HV-27 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATGATGGACGCAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 390 |

TABLE 5B-continued

Exemplary Anti-PAC1 Antibody Heavy Chain Variable Region Nucleic Acid Sequences

| Ab ID. | VH Group | VH Nucleic Acid Sequence | SEQ ID NO: |
|---|---|---|---|
| iPS:420809 | HV-28 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT<br>GGAGTGGGTGGCAGTTATATCATATGATGGAAACAATAAATACT<br>ATGCACGCTCCGTGAAGGGCCGGTTCACCATCTCCAGAGACAATT<br>CCAAGAACACCCTGTATCTGCAAATGAACAGCCTGAGAGCTGAG<br>GACACGGCTCTGTTTTACTGTGCGAGAGGATACGATGTTTTGACT<br>GGTTACCCCGACTACTGGGGCCAGGGAACCCTGGTCACCGTCTCT<br>AGT | 391 |
| iPS:420816 | HV-29 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT<br>GGAGTGGGTGGCAGTTATATCATATGATGGACGCAATAAATACT<br>ATGCAGAGTCCGTGAAGGGCCGGTTCACCATCTCCAGAGACAATT<br>CCAAGAACACCCTGTATCTGCAAATGAACAGCCTGAGAGCTGAG<br>GACACGGCTCTGTTTTACTGTGCGAGAGGATACGATATCTTGACT<br>GGTTACCCCGACTACTGGGGCCAGGGAACCCTGGTCACCGTCTCT<br>AGT | 392 |
| iPS:420823 | HV-30 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT<br>GGAGTGGGTGGCAGTTATATCATATGATGGAAACAATAAATACT<br>ATGCAGAGTCCGTGAAGGGCCGGTTCACCATCTCCAGAGACAATT<br>CCAAGAACACCCTGTATCTGCAAATGAACAGCCTGAGAGCTGAG<br>GACACGGCTCTGTTTTACTGTGCGAGAGGATACGATATCTTGACT<br>GGTTACCCCGACTACTGGGGCCAGGGAACCCTGGTCACCGTCTCT<br>AGT | 393 |
| iPS:420830 | HV-31 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT<br>GGAGTGGGTGGCAGTTATATCATATGATGGAGGAAATAAATACT<br>ATGCACGCTCCGTGAAGGGCCGGTTCACCATCTCCAGAGACAATT<br>CCAAGAACACCCTGTATCTGCAAATGAACAGCCTGAGAGCTGAG<br>GACACGGCTCTGTTTTACTGTGCGAGAGGATACGATATCTTGACT<br>GGTTACCCCGACTACTGGGGCCAGGGAACCCTGGTCACCGTCTCT<br>AGT | 394 |
| iPS:420901;<br>iPS:421027 | HV-32 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT<br>GGAGTGGGTGGCAGTTATATCATATAACGGACGCAATAAATACT<br>ATGCACGCTCCGTGAAGGGCCGGTTCACCATCTCCAGAGACAATT<br>CCAAGAACACCCTGTATCTGCAAATGAACAGCCTGAGAGCTGAG<br>GACACGGCTCTGTTTTACTGTGCGAGAGGATACGATGTTTTGACT<br>GGTTACCCCGACTACTGGGGCCAGGGAACCCTGGTCACCGTCTCT<br>AGT | 395 |
| iPS:420908;<br>iPS:421031 | HV-33 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT<br>GGAGTGGGTGGCAGTTATATCATATATCGGACGCAATAAATACTA<br>TGCACGCTCCGTGAAGGGCCGGTTCACCATCTCCAGAGACAATTC<br>CAAGAACACCCTGTATCTGCAAATGAACAGCCTGAGAGCTGAGG<br>ACACGGCTCTGTTTTACTGTGCGAGAGGATACGATGTTTTGACTG<br>GTTACCCCGACTACTGGGGCCAGGGAACCCTGGTCACCGTCTCTA<br>GT | 396 |
| iPS:420915;<br>iPS:421035 | HV-34 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT<br>GGAGTGGGTGGCAGTTATATCATATCAGGGACGCAATAAATACT<br>ATGCACGCTCCGTGAAGGGCCGGTTCACCATCTCCAGAGACAATT<br>CCAAGAACACCCTGTATCTGCAAATGAACAGCCTGAGAGCTGAG<br>GACACGGCTCTGTTTTACTGTGCGAGAGGATACGATGTTTTGACT<br>GGTTACCCCGACTACTGGGGCCAGGGAACCCTGGTCACCGTCTCT<br>AGT | 397 |
| iPS:420922;<br>iPS:421039 | HV-35 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT | 398 |

TABLE 5B-continued

Exemplary Anti-PAC1 Antibody Heavy Chain Variable Region Nucleic Acid Sequences

| Ab ID. | VH Group | VH Nucleic Acid Sequence | SEQ ID NO: |
|---|---|---|---|
| | | GGAGTGGGTGGCAGTTATATCATATTACGGACGCAATAAATACTATGCACGCTCCGTGAAGGGCCGGTTCACCATCTCCAGAGACAATTCCAAGAACACCCTGTATCTGCAAATGAACAGCCTGAGAGCTGAGGACACGGCTCTGTTTTACTGTGCGAGAGGATACGATGTTTTGACTGGTTACCCCGACTACTGGGGCCAGGGAACCCTGGTCACCGTCTCTAGT | |
| iPS:420929; iPS:421043 | HV-36 | CAGGTGCAGCTGGTGGAGTCTGGGGGAGGCGTGGTCCAGCCTGGGAGGTCCCTGCGACTCTCCTGTGCAGCCTCTGGATTCACCTTCAGTAGATTTGCCATGCACTGGGTCCGCCAGGCTCCAGGCAAGGGGCTGGAGTGGGTGGCAGTTATATCATATAACGGAAACAATAAATACTATGCACGCTCCGTGAAGGGCCGGTTCACCATCTCCAGAGACAATTCCAAGAACACCCTGTATCTGCAAATGAACAGCCTGAGAGCTGAGGACACGGCTCTGTTTTACTGTGCGAGAGGATACGATGTTTTGACTGGTTACCCCGACTACTGGGGCCAGGGAACCCTGGTCACCGTCTCTAGT | 399 |
| iPS:420936; iPS:421047 | HV-37 | CAGGTGCAGCTGGTGGAGTCTGGGGGAGGCGTGGTCCAGCCTGGGAGGTCCCTGCGACTCTCCTGTGCAGCCTCTGGATTCACCTTCAGTAGATTTGCCATGCACTGGGTCCGCCAGGCTCCAGGCAAGGGGCTGGAGTGGGTGGCAGTTATATCATATATCGGAAACAATAAATACTATGCACGCTCCGTGAAGGGCCGGTTCACCATCTCCAGAGACAATTCCAAGAACACCCTGTATCTGCAAATGAACAGCCTGAGAGCTGAGGACACGGCTCTGTTTTACTGTGCGAGAGGATACGATGTTTTGACTGGTTACCCCGACTACTGGGGCCAGGGAACCCTGGTCACCGTCTCTAGT | 400 |
| iPS:420943; iPS:421051 | HV-38 | CAGGTGCAGCTGGTGGAGTCTGGGGGAGGCGTGGTCCAGCCTGGGAGGTCCCTGCGACTCTCCTGTGCAGCCTCTGGATTCACCTTCAGTAGATTTGCCATGCACTGGGTCCGCCAGGCTCCAGGCAAGGGGCTGGAGTGGGTGGCAGTTATATCATATCAGGGAAACAATAAATACTATGCACGCTCCGTGAAGGGCCGGTTCACCATCTCCAGAGACAATTCCAAGAACACCCTGTATCTGCAAATGAACAGCCTGAGAGCTGAGGACACGGCTCTGTTTTACTGTGCGAGAGGATACGATGTTTTGACTGGTTACCCCGACTACTGGGGCCAGGGAACCCTGGTCACCGTCTCTAGT | 401 |
| iPS:420950; iPS:421055 | HV-39 | CAGGTGCAGCTGGTGGAGTCTGGGGGAGGCGTGGTCCAGCCTGGGAGGTCCCTGCGACTCTCCTGTGCAGCCTCTGGATTCACCTTCAGTAGATTTGCCATGCACTGGGTCCGCCAGGCTCCAGGCAAGGGGCTGGAGTGGGTGGCAGTTATATCATATTACGGAAACAATAAATACTATGCACGCTCCGTGAAGGGCCGGTTCACCATCTCCAGAGACAATTCCAAGAACACCCTGTATCTGCAAATGAACAGCCTGAGAGCTGAGGACACGGCTCTGTTTTACTGTGCGAGAGGATACGATGTTTTGACTGGTTACCCCGACTACTGGGGCCAGGGAACCCTGGTCACCGTCTCTAGT | 402 |
| iPS:420957; iPS:421059 | HV-40 | CAGGTGCAGCTGGTGGAGTCTGGGGGAGGCGTGGTCCAGCCTGGGAGGTCCCTGCGACTCTCCTGTGCAGCCTCTGGATTCACCTTCAGTAGATTTGCCATGCACTGGGTCCGCCAGGCTCCAGGCAAGGGGCTGGAGTGGGTGGCAGTTATATCATATAACGGACGCAATAAATACTATGCAGAGTCCGTGAAGGGCCGGTTCACCATCTCCAGAGACAATTCCAAGAACACCCTGTATCTGCAAATGAACAGCCTGAGAGCTGAGGACACGGCTCTGTTTTACTGTGCGAGAGGATACGATATCTTGACTGGTTACCCCGACTACTGGGGCCAGGGAACCCTGGTCACCGTCTCTAGT | 403 |
| iPS:420964; iPS:421063 | HV-41 | CAGGTGCAGCTGGTGGAGTCTGGGGGAGGCGTGGTCCAGCCTGGGAGGTCCCTGCGACTCTCCTGTGCAGCCTCTGGATTCACCTTCAGTAGATTTGCCATGCACTGGGTCCGCCAGGCTCCAGGCAAGGGGCTGGAGTGGGTGGCAGTTATATCATATATCGGACGCAATAAATACTATGCAGAGTCCGTGAAGGGCCGGTTCACCATCTCCAGAGACAATTCCAAGAACACCCTGTATCTGCAAATGAACAGCCTGAGAGCTGAGGACACGGCTCTGTTTTACTGTGCGAGAGGATACGATATCTTGACTGGTTACCCCGACTACTGGGGCCAGGGAACCCTGGTCACCGTCTCTAGT | 404 |
| iPS:420971; iPS:421067 | HV-42 | CAGGTGCAGCTGGTGGAGTCTGGGGGAGGCGTGGTCCAGCCTGGGAGGTCCCTGCGACTCTCCTGTGCAGCCTCTGGATTCACCTTCAGTAGATTTGCCATGCACTGGGTCCGCCAGGCTCCAGGCAAGGGGCTGGAGTGGGTGGCAGTTATATCATATCAGGGACGCAATAAATACTATGCAGAGTCCGTGAAGGGCCGGTTCACCATCTCCAGAGACAATTCCAAGAACACCCTGTATCTGCAAATGAACAGCCTGAGAGCTGAGGACACGGCTCTGTTTTACTGTGCGAGAGGATACGATATCTTGACT | 405 |

TABLE 5B-continued

Exemplary Anti-PAC1 Antibody Heavy Chain Variable Region Nucleic Acid Sequences

| Ab ID. | VH Group | VH Nucleic Acid Sequence | SEQ ID NO: |
|---|---|---|---|
| | | GGTTACCCCGACTACTGGGGCCAGGGAACCCTGGTCACCGTCTCT AGT | |
| iPS:420978; iPS:421071 | HV-43 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATTACGGACGCAATAAATACTA TGCAGAGTCCGTGAAGGGCCGGTTCACCATCTCCAGAGACAATTC CAAGAACACCCTGTATCTGCAAATGAACAGCCTGAGAGCTGAGG ACACGGCTCTGTTTTACTGTGCGAGAGGATACGATATCTTGACTG GTTACCCCGACTACTGGGGCCAGGGAACCCTGGTCACCGTCTCTA GT | 406 |
| iPS:420985; iPS:421075 | HV-44 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATAACGGAAACAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 407 |
| iPS:420992; iPS:421079 | HV-45 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATATCGGAAACAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 408 |
| iPS:420999; iPS:421083 | HV-46 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATCAGGGAAACAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 409 |
| iPS:421006; iPS:421087 | HV-47 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATTACGGAAACAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 410 |
| iPS:421013 | HV-48 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATGATGGACGCAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 411 |
| iPS:421020 | HV-49 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATGATGGAAACAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 412 |

TABLE 5B-continued

Exemplary Anti-PAC1 Antibody Heavy Chain Variable Region Nucleic Acid Sequences

| Ab ID. | VH Group | VH Nucleic Acid Sequence | SEQ ID NO: |
|---|---|---|---|
| iPS:421091 | HV-50 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATAACGGACGCAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 413 |
| iPS:421098 | HV-51 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATATCGGACGCAATAAATACTA TGCACGCTCCGTGAAGGGCCGGTTCACCATCTCCAGAGACAATTC CAAGAACACCCTGTATCTGCAAATGAACAGCCTGAGAGCTGAGG ACACGGCTCTGTTTTACTGTGCGAGAGGATACGATATCTTGACTG GTTACCCCGACTACTGGGGCCAGGGAACCCTGGTCACCGTCTCTA GT | 414 |
| iPS:421105 | HV-52 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATCAGGGACGCAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 415 |
| iPS:421112 | HV-53 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATTACGGACGCAATAAATACTA TGCACGCTCCGTGAAGGGCCGGTTCACCATCTCCAGAGACAATTC CAAGAACACCCTGTATCTGCAAATGAACAGCCTGAGAGCTGAGG ACACGGCTCTGTTTTACTGTGCGAGAGGATACGATATCTTGACTG GTTACCCCGACTACTGGGGCCAGGGAACCCTGGTCACCGTCTCTA GT | 416 |
| iPS:421119 | HV-54 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATAACGGAAACAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 417 |
| iPS:421126 | HV-55 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATATCGGAAACAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 418 |
| iPS:421133 | HV-56 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATCAGGGAAACAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 419 |
| iPS:421140; iPS:421147 | HV-57 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT | 420 |

TABLE 5B-continued

| Exemplary Anti-PAC1 Antibody Heavy Chain Variable Region Nucleic Acid Sequences | | | |
|---|---|---|---|
| Ab ID. | VH Group | VH Nucleic Acid Sequence | SEQ ID NO: |
| | | GGAGTGGGTGGCAGTTATATCATATTACGGAAACAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | |
| iPS:421163; iPS:421207 | HV-58 | CAGGTGCAGCTGGTGGAGTCTGGGGGAGGCGTGGTCCAGCCTGG GAGGTCCCTGCGACTCTCCTGTGCAGCCTCTGGATTCACCTTCAG TCACTTTGCCATGCACTGGGTCCGCCAGGCTCCAGGCAAGGGGCT GGAGTGGGTGGCAGTTATATCATATGATGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 421 |
| iPS:391578; iPS:421211 | HV-59 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATACGCCATGCACTGGGTCCGCCAGGCTCCAGGCAAGGGGC TGGAGTGGGTGGCAGTTATATCATATGATGGAGGAAATAAATAC TATGCAGAGTCCGTGAAGGGCCGGTTCACCATCTCCAGAGACAAT TCCAAGAACACCCTGTATCTGCAAATGAACAGCCTGAGAGCTGA GGACACGGCTCTGTTTTACTGTGCGAGAGGATACGATGTTTTGAC TGGTTACCCCGACTACTGGGGCCAGGGAACCCTGGTCACCGTCTC TAGT | 422 |
| iPS:421170; iPS:421215 | HV-60 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATTCGATGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 423 |
| iPS:421176; iPS:421219 | HV-61 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATGATGGAGCCAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 424 |
| iPS:421182; iPS:421223 | HV-62 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATGATGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATTTCTTGACT GGTTACCCCGACTACTGGGGCCAGGGAACCCTGGTCACCGTCTCT AGT | 425 |
| iPS:421239 | HV-63 | CAGGTGCAGCTGGTGGAGTCTGGGGGAGGCGTGGTCCAGCCTGG GAGGTCCCTGCGACTCTCCTGTGCAGCCTCTGGATTCACCTTCAG TCACTTTGCCATGCACTGGGTCCGCCAGGCTCCAGGCAAGGGGCT GGAGTGGGTGGCAGTTATATCATATAACGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 426 |
| iPS:421246 | HV-64 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATACGCCATGCACTGGGTCCGCCAGGCTCCAGGCAAGGGGC TGGAGTGGGTGGCAGTTATATCATATAACGGAGGAAATAAATAC TATGCAGAGTCCGTGAAGGGCCGGTTCACCATCTCCAGAGACAAT TCCAAGAACACCCTGTATCTGCAAATGAACAGCCTGAGAGCTGA GGACACGGCTCTGTTTTACTGTGCGAGAGGATACGATGTTTTGAC | 427 |

TABLE 5B-continued

Exemplary Anti-PAC1 Antibody Heavy Chain Variable Region Nucleic Acid Sequences

| Ab ID. | VH Group | VH Nucleic Acid Sequence | SEQ ID NO: |
|---|---|---|---|
| | | TGGTTACCCCGACTACTGGGGCCAGGGAACCCTGGTCACCGTCTC TAGT | |
| iPS:421253 | HV-65 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATTCAACGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 428 |
| iPS:421260 | HV-66 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATAACGGAGCCAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 429 |
| iPS:421267 | HV-67 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATAACGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATTTCTTGACT GGTTACCCCGACTACTGGGGCCAGGGAACCCTGGTCACCGTCTCT AGT | 430 |
| iPS:421286 | HV-68 | CAGGTGCAGCTGGTGGAGTCTGGGGGAGGCGTGGTCCAGCCTGG GAGGTCCCTGCGACTCTCCTGTGCAGCCTCTGGATTCACCTTCAG TCACTTTGCCATGCACTGGGTCCGCCAGGCTCCAGGCAAGGGGCT GGAGTGGGTGGCAGTTATATCATATGATGGACGCAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 431 |
| iPS:421293 | HV-69 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATACGCCATGCACTGGGTCCGCCAGGCTCCAGGCAAGGGGC TGGAGTGGGTGGCAGTTATATCATATGATGGACGCAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 432 |
| iPS:421300 | HV-70 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATTCGATGGACGCAATAAATACTA TGCAGAGTCCGTGAAGGGCCGGTTCACCATCTCCAGAGACAATTC CAAGAACACCCTGTATCTGCAAATGAACAGCCTGAGAGCTGAGG ACACGGCTCTGTTTTACTGTGCGAGAGGATACGATGTTTTGACTG GTTACCCCGACTACTGGGGCCAGGGAACCCTGGTCACCGTCTCTA GT | 433 |
| iPS:421307 | HV-71 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATGATGGACGCAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATTTCTTGACT GGTTACCCCGACTACTGGGGCCAGGGAACCCTGGTCACCGTCTCT AGT | 434 |

TABLE 5B-continued

| Ab ID. | VH Group | VH Nucleic Acid Sequence | SEQ ID NO: |
|---|---|---|---|
| | | Exemplary Anti-PAC1 Antibody Heavy Chain Variable Region Nucleic Acid Sequences | |
| iPS:421326 | HV-72 | CAGGTGCAGCTGGTGGAGTCTGGGGGAGGCGTGGTCCAGCCTGG GAGGTCCCTGCGACTCTCCTGTGCAGCCTCTGGATTCACCTTCAG TCACTTTGCCATGCACTGGGTCCGCCAGGCTCCAGGCAAGGGGCT GGAGTGGGTGGCAGTTATATCATATGATGGAGGAAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 435 |
| iPS:421333 | HV-73 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATACGCCATGCACTGGGTCCGCCAGGCTCCAGGCAAGGGGC TGGAGTGGGTGGCAGTTATATCATATGATGGAGGAAATAAATAC TATGCACGCTCCGTGAAGGGCCGGTTCACCATCTCCAGAGACAAT TCCAAGAACACCCTGTATCTGCAAATGAACAGCCTGAGAGCTGA GGACACGGCTCTGTTTTACTGTGCGAGAGGATACGATGTTTTGAC TGGTTACCCCGACTACTGGGGCCAGGGAACCCTGGTCACCGTCTC TAGT | 436 |
| iPS:421340 | HV-74 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATTCGATGGAGGAAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 437 |
| iPS:421347 | HV-75 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATGATGGAGCCAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATGTTTTGACT GGTTACCCCGACTACTGGGGCCAGGGAACCCTGGTCACCGTCTCT AGT | 438 |
| iPS:421354 | HV-76 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATGATGGAGGAAATAAATACT ATGCACGCTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATTTCTTGACT GGTTACCCCGACTACTGGGGCCAGGGAACCCTGGTCACCGTCTCT AGT | 439 |
| iPS:421373 | HV-77 | CAGGTGCAGCTGGTGGAGTCTGGGGGAGGCGTGGTCCAGCCTGG GAGGTCCCTGCGACTCTCCTGTGCAGCCTCTGGATTCACCTTCAG TCACTTTGCCATGCACTGGGTCCGCCAGGCTCCAGGCAAGGGGCT GGAGTGGGTGGCAGTTATATCATATGATGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 440 |
| iPS:421380 | HV-78 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATACGCCATGCACTGGGTCCGCCAGGCTCCAGGCAAGGGGC TGGAGTGGGTGGCAGTTATATCATATGATGGAGGAAATAAATAC TATGCAGAGTCCGTGAAGGGCCGGTTCACCATCTCCAGAGACAAT TCCAAGAACACCCTGTATCTGCAAATGAACAGCCTGAGAGCTGA GGACACGGCTCTGTTTTACTGTGCGAGAGGATACGATATCTTGAC TGGTTACCCCGACTACTGGGGCCAGGGAACCCTGGTCACCGTCTC TAGT | 441 |
| iPS:421387 | HV-79 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT | 442 |

TABLE 5B-continued

| Exemplary Anti-PAC1 Antibody Heavy Chain Variable Region Nucleic Acid Sequences | | | |
|---|---|---|---|
| Ab ID. | VH Group | VH Nucleic Acid Sequence | SEQ ID NO: |
| | | GGAGTGGGTGGCAGTTATATCATTCGATGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | |
| iPS:421394 | HV-80 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATTTGCCATGCACTGGGTCCGCCAGGCTCCAGGCAAGGGGCT GGAGTGGGTGGCAGTTATATCATATGATGGAGCCAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATCTTGACT GGTTACCCCGACTACTGGGGCCAGGGAACCCTGGTCACCGTCTCT AGT | 443 |
| iPS:421855 | HV-81 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAAGTACGCCATGCACTGGGTCCGCCAGGCTCCAGGCAAGGGGC TGGAGTGGGTGGCAGTTATATCATTCAAGGGAAGCAATAAATAC TATGCAGAGTCCGTGAAGGGCCGGTTCACCATCTCCAGAGACAAT TCCAAGAACACCCTGTATCTGCAAATGAACAGCCTGAGAGCTGA GGACACGGCTCTGTTTTACTGTGCGAGAGGATACGATCTGTTGAC TGGTTACCCCGACTACTGGGGCCAGGGAACCCTGGTCACCGTCTC TAGT | 444 |
| iPS:421861 | HV-82 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATACGCCATGCACTGGGTCCGCCAGGCTCCAGGCAAGGGGC TGGAGTGGGTGGCAGTTATATCATATCAGGGAGGAAATAAATAC TATGCAGAGTCCGTGAAGGGCCGGTTCACCATCTCCAGAGACAAT TCCAAGAACACCCTGTATCTGCAAATGAACAGCCTGAGAGCTGA GGACACGGCTCTGTTTTACTGTGCGAGAGGATACGATCTGTTGAC TGGTTACCCCGACTACTGGGGCCAGGGAACCCTGGTCACCGTCTC TAGT | 445 |
| iPS:421867 | HV-83 | CAGGTGCAGCTGGTGGAGTCTGGGGGAGGCGTGGTCCAGCCTGG GAGGTCCCTGCGACTCTCCTGTGCAGCCTCTGGATTCACCTTCAG TCACTTTGCCATGCACTGGGTCCGCCAGGCTCCAGGCAAGGGGCT GGAGTGGGTGGCAGTTATATCATTCAGCGGAAGCAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATATGTTGACT GGTTACCCCGACTACTGGGGCCAGGGAACCCTGGTCACCGTCTCT AGT | 446 |
| iPS:421873 | HV-84 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAAGTTTGCCATGCACTGGGTCCGCCAGGCTCCAGGCAAGGGGCT GGAGTGGGTGGCAGTTATATCATATCGCGGAGGAAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATCTGTTGACT GGTTACCCCGACTACTGGGGCCAGGGAACCCTGGTCACCGTCTCT AGT | 447 |
| iPS:421879 | HV-85 | CAGGTGCAGCTGGTGGAGTCTGGGGGAGGCGTGGTCCAGCCTGG GAGGTCCCTGCGACTCTCCTGTGCAGCCTCTGGATTCACCTTCAG TAGATACGCCATGCACTGGGTCCGCCAGGCTCCAGGCAAGGGGC TGGAGTGGGTGGCAGTTATATCATATAGCGGAGCCAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATCTGTTGAGC GGTTACCCCGACTACTGGGGCCAGGGAACCCTGGTCACCGTCTCT AGT | 448 |
| iPS:421885 | HV-86 | CAGGTGCAGCTGGTGGAGTCTGGGGGAGGCGTGGTCCAGCCTGG GAGGTCCCTGCGACTCTCCTGTGCAGCCTCTGGATTCACCTTCAG TCACTACGCCATGCACTGGGTCCGCCAGGCTCCAGGCAAGGGGCT GGAGTGGGTGGCAGTTATATCATTCAAGGGAGCCAATAAATACT ATGCAGAGTCCGTGAAGGGCCGGTTCACCATCTCCAGAGACAATT CCAAGAACACCCTGTATCTGCAAATGAACAGCCTGAGAGCTGAG GACACGGCTCTGTTTTACTGTGCGAGAGGATACGATCTGTTGACT | 449 |

TABLE 5B-continued

| Exemplary Anti-PAC1 Antibody Heavy Chain Variable Region Nucleic Acid Sequences | | | |
|---|---|---|---|
| Ab ID. | VH Group | VH Nucleic Acid Sequence | SEQ ID NO: |
| | | GGTTACCCCGACTACTGGGGCCAGGGAACCCTGGTCACCGTCTCT<br>AGT | |
| iPS:421891 | HV-87 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TCACTACGCCATGCACTGGGTCCGCCAGGCTCCAGGCAAGGGGCT<br>GGAGTGGGTGGCAGTTATATCATATCGCGGAGCCAATAAATACT<br>ATGCAGAGTCCGTGAAGGGCCGGTTCACCATCTCCAGAGACAATT<br>CCAAGAACACCCTGTATCTGCAAATGAACAGCCTGAGAGCTGAG<br>GACACGGCTCTGTTTTACTGTGCGAGAGGATACGATCTGTTGACT<br>GGTTACCCCGACTACTGGGGCCAGGGAACCCTGGTCACCGTCTCT<br>AGT | 450 |
| iPS:421897 | HV-88 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TCACTACGCCATGCACTGGGTCCGCCAGGCTCCAGGCAAGGGGCT<br>GGAGTGGGTGGCAGTTATATCATTCTACGGAAGCAATAAATACTA<br>TGCAGAGTCCGTGAAGGGCCGGTTCACCATCTCCAGAGACAATTC<br>CAAGAACACCCTGTATCTGCAAATGAACAGCCTGAGAGCTGAGG<br>ACACGGCTCTGTTTTACTGTGCGAGAGGATACGATTTCTTGACTG<br>GTTACCCCGACTACTGGGGCCAGGGAACCCTGGTCACCGTCTCTA<br>GT | 451 |
| iPS:421903 | HV-89 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TCACTTTGCCATGCACTGGGTCCGCCAGGCTCCAGGCAAGGGGCT<br>GGAGTGGGTGGCAGTTATATCATTCTTCGGAGGAAATAAATACTA<br>TGCAGAGTCCGTGAAGGGCCGGTTCACCATCTCCAGAGACAATTC<br>CAAGAACACCCTGTATCTGCAAATGAACAGCCTGAGAGCTGAGG<br>ACACGGCTCTGTTTTACTGTGCGAGAGGATACGATTTCTTGACTG<br>GTTACCCCGACTACTGGGGCCAGGGAACCCTGGTCACCGTCTCTA<br>GT | 452 |
| iPS:421909 | HV-90 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TCACTACGCCATGCACTGGGTCCGCCAGGCTCCAGGCAAGGGGCT<br>GGAGTGGGTGGCAGTTATATCATTCATGGGAACCAATAAATACTA<br>TGCAGAGTCCGTGAAGGGCCGGTTCACCATCTCCAGAGACAATTC<br>CAAGAACACCCTGTATCTGCAAATGAACAGCCTGAGAGCTGAGG<br>ACACGGCTCTGTTTTACTGTGCGAGAGGATACGATTTCTTGACTG<br>GTTACCCCGACTACTGGGGCCAGGGAACCCTGGTCACCGTCTCTA<br>GT | 453 |
| iPS:421915 | HV-91 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TTACTTTGCCATGCACTGGGTCCGCCAGGCTCCAGGCAAGGGGCT<br>GGAGTGGGTGGCAGTTATATCACACCGCGGAACCAATAAATACT<br>ATGCAGAGTCCGTGAAGGGCCGGTTCACCATCTCCAGAGACAATT<br>CCAAGAACACCCTGTATCTGCAAATGAACAGCCTGAGAGCTGAG<br>GACACGGCTCTGTTTTACTGTGCGAGAGGATACGATCTGTTGAGC<br>GGTTACCCCGACTACTGGGGCCAGGGAACCCTGGTCACCGTCTCT<br>AGT | 454 |
| iPS:480711 | HV-92 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT<br>GGAGTGGGTGGGTGTTATCAACTATCGTGGACATGGTAAATACTA<br>TGCAG<br>AGTCCGTGAAGGGCCGGTTCACCGTGTCCAGAGACAATTCCAAG<br>AACACCCTGTATCTGCAAATGAACAGCCTGAGAGCTGAGGACAC<br>GGCTCTGTTTTACTGTGCGAGAGGATACGATGTTTTGACTGGTTA<br>CCCCGACTACTGGGGCCAGGGAACCCTGGTCACCGTGTCTAGT | 455 |
| iPS:480706 | HV-93 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT<br>GGAGTGGGTGGGTGTTATATCTTTTTCTGGAGGTTCTAAATACTA<br>TGCAGAGTCCGTGAAGGGCCGGTTCACCTTGTCCAGAGACAATTC<br>CAAGAACACCCTGTATCTGCAAATGAACAGCCTGAGAGCTGAGG<br>ACACGGCTCTGTTTTACTGTGCGAGAGGATACGATGTTTTGACTG<br>GTTACCCCGACTACTGGGGCCAGGGAACCCTGGTCACCGTGTCTA<br>GT | 456 |

TABLE 5B-continued

Exemplary Anti-PAC1 Antibody Heavy Chain Variable Region Nucleic Acid Sequences

| Ab ID. | VH Group | VH Nucleic Acid Sequence | SEQ ID NO: |
|---|---|---|---|
| iPS:480713 | HV-94 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT<br>GGAGTGGGTGGGTGTTATCTCTTATACTGGACAGTTCAAATACTA<br>TGCAGAGTCCGTGAAGGGCCGGTTCACCGTGTCCAGAGACAATTC<br>CAAGAACACCCTGTATCTGCAAATGAACAGCCTGAGAGCTGAGG<br>ACACGGCTCTGTTTTACTGTGCGAGAGGATACGATGTTTTGACTG<br>GTTACCCCGACTACTGGGGCCAGGGAACCCTGGTCACCGTGTCTA<br>GT | 457 |
| iPS:480705 | HV-95 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT<br>GGAGTGGGTGGGTGTTATATCTTATACTGGAGCTCAGAAATACTA<br>TGCAGAGTCCGTGAAGGGCCGGTTCACCATGTCCAGAGACAATTC<br>CAAGAACACCCTGTATCTGCAAATGAACAGCCTGAGAGCTGAGG<br>ACACGGCTCTGTTTTACTGTGCGAGAGGATACGATGTTTTGACTG<br>GTTACCCCGACTACTGGGGCCAGGGAACCCTGGTCACCGTGTCTA<br>GT | 458 |
| iPS:480707 | HV-96 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT<br>GGAGTGGGTGGGTGTTATATCTTATTCTGGAGCTTCTAAATACTA<br>TGCAGAGTCCGTGAAGGGCCGGTTCACCATGTCCAGAGACAATTC<br>CAAGAACACCCTGTATCTGCAAATGAACAGCCTGAGAGCTGAGG<br>ACACGGCTCTGTTTTACTGTGCGAGAGGATACGATGTTTTGACTG<br>GTTACCCCGACTACTGGGGCCAGGGAACCCTGGTCACCGTGTCTA<br>GT | 459 |
| iPS:480708 | HV-97 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT<br>GGAGTGGGTGGCTGTTATATCTTATTCTGGAGCTTTCAAATACTA<br>TGCAGAGTCCGTGAAGGGCCGGTTCACCGTGTCCAGAGACAATTC<br>CAAGAACACCCTGTATCTGCAAATGAACAGCCTGAGAGCTGAGG<br>ACACGGCTCTGTTTTACTGTGCGAGAGGATACGATGTTTTGACTG<br>GTTACCCCGACTACTGGGGCCAGGGAACCCTGGTCACCGTGTCTA<br>GT | 460 |
| iPS:480709 | HV-98 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT<br>GGAGTGGGTGGGTGTTATAACTTATACTGGAGGTGCTAAATACTA<br>TGCAGAGTCCGTGAAGGGCCGGTTCACCATCTCCAGAGACAATTC<br>CAAGAACACCCTGTATCTGCAAATGAACAGCCTGAGAGCTGAGG<br>ACACGGCTCTGTTTTACTGTGCGAGAGGATACGATGTTTTGACTG<br>GTTACCCCGACTACTGGGGCCAGGGAACCCTGGTCACCGTGTCTA<br>GT | 461 |
| iPS:480712 | HV-99 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT<br>GGAGTGGGTGGGTGTTATCAACTTTCAGGGAACTACTAAATACTA<br>TGCAGAGTCCGTGAAGGGCCGGTTCACCATCTCCAGAGACAATTC<br>CAAGAACACCCTGTATCTGCAAATGAACAGCCTGAGAGCTGAGG<br>ACACGGCTCTGTTTTACTGTGCGAGAGGATACGATGTTTTGACTG<br>GTTACCCCGACTACTGGGGCCAGGGAACCCTGGTCACCGTGTCTA<br>GT | 462 |
| iPS:480704 | HV-100 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT<br>GGAGTGGGTGGGTGTTATATCTTATTCTGGAGATCTGAAATACTA<br>TGCAGAGTCCGTGAAGGGCCGGTTCACCGTGTCCAGAGACAATTC<br>CAAGAACACCCTGTATCTGCAAATGAACAGCCTGAGAGCTGAGG<br>ACACGGCTCTGTTTTACTGTGCGAGAGGATACGATGTTTTGACTG<br>GTTACCCCGACTACTGGGGCCAGGGAACCCTGGTCACCGTGTCTA<br>GT | 463 |
| iPS:480710 | HV-101 | CAGGTGCAGCTGGTGGAGTCTGGGGGAGGCGTGGTCCAGCCTGG<br>GAGGTCCCTGCGACTCTCCTGTGCAGCCTCTGGATTCACCTTCAG<br>TAGATTTGCCATGCACTGGGTCCGCCAGGCTCCAGGCAAGGGGCT | 464 |

TABLE 5B-continued

Exemplary Anti-PAC1 Antibody Heavy Chain Variable Region Nucleic Acid Sequences

| Ab ID. | VH Group | VH Nucleic Acid Sequence | SEQ ID NO: |
|---|---|---|---|
| | | GGAGTGGGTGGGTGTTATCAACTATTTCGGAGACGCTAAATACTATGCAGAGTCCGTGAAGGGCCGGTTCACCATCTCCAGAGACAATTCCAAGAACACCCTGTATCTGCAAATGAACAGCCTGAGAGCTGAGGACACGGCTCTGTTTTACTGTGCGAGAGGATACGATGTTTTGACTGGTTACCCCGACTACTGGGGCCAGGGAACCCTGGTCACCGTGTCTAGT | |
| iPS:480716 | HV-102 | CAGGTGCAGCTGGTGGAGTCTGGGGGAGGCGTGGTCCAGCCTGGGAGGTCCCTGAGACTCTCCTGTGCAGCCTCTGGATTCACCTTCAGTTTCTACGCCATGCACTGGGTCCGCCAGGCTCCAGGCAAGGGGCTGGAGTGGGTGGCAGTTATCTCATCTTTCGGAAGTAATAAATACTATGCAGAGTCCGTGAAGGGCCGGTTCACCATCTCCAGAGACAATTCCAAGAACACCCTGTATCTGCAAATGAACAGCCTGAGAGCTGAGGACACGGCTCTGTTTTACTGTGCGAGAGGATACGATCTGCTGACTGGTTACCCCGACTACTGGGGCCAGGGAACCCTGGTCACCGTGTCTAGT | 465 |
| iPS:480715 | HV-103 | CAGGTGCAGCTGGTGGAGTCTGGGGGAGGCGTGGTCCAGCCTGGGAGGTCCCTGCGACTCTCCTGTGCAGCCTCTGGATTCACCTTCAGTTACTACGCCATGCACTGGGTCCGCCAGGCTCCAGGCAAGGGGCTGGAGTGGGTGGCAGTTATCTCATACTCTGGAAGTAATAAATACTATGCAGAGTCCGTGAAGGGCCGGTTCACCATCTCCAGAGACAATTCCAAGAACACCCTGTATCTGCAAATGAACAGCCTGAGAGCTGAGGACACGGCTCTGTTTTACTGTGCGAGAGGATACGATCTGCTGACTGGTTACCCCGACTACTGGGGCCAGGGAACCCTGGTCACCGTGTCTAGT | 466 |
| iPS:480717 | HV-104 | CAGGTGCAGCTGGTGGAGTCTGGGGGAGGCGTGGTCCAGCCTGGGAGGTCCCTGCGACTCTCCTGTGCAGCCTCTGGATTCACCTTCAGTTACTACGCCATGCACTGGGTCCGCCAGGCTCCAGGCAAGGGGCTGGAGTGGGTGGCAGTTATCTCACATTACGGAACTAATAAATACTATGCAGAGTCCGTGAAGGGCCGGTTCACCATCTCCAGAGACAATTCCAAGAACACCCTGTATCTGCAAATGAACAGCCTGAGAGCTGAGGACACGGCTCTGTTTTACTGTGCGAGAGGATACGATCCTCTGACTGGTTACCCCGACTACTGGGGCCAGGGAACCCTGGTCACCGTGTCTAGT | 467 |
| iPS:480714 | HV-105 | CAGGTGCAGCTGGTGGAGTCTGGGGGAGGCGTGGTCCAGCCTGGGAGGTCCCTGCGACTCTCCTGTGCAGCCTCTGGATTCACCTTCAGTCATTACGCCATGCACTGGGTCCGCCAGGCTCCAGGCAAGGGGCTGGAGTGGGTGGCAGTTATCTCATACCAGGGAAGTAATAAATACTATGCAGAGTCCGTGAAGGGCCGGTTCACCATCTCCAGAGACAATTCCAAGAACACCCTGTATCTGCAAATGAACAGCCTGAGAGCTGAGGACACGGCTCTGTTTTACTGTGCGAGAGGATACGATCTGCTGACTGGTTACCCCGACTACTGGGGCCAGGGAACCCTGGTCACCGTGTCTAGT | 468 |
| | | 19H8 variants | |
| 19H8; 3575 | HV-106 | CAGGTACAGCTGCAGCAGTCAGGTCCAGGACTGGTGAAGCCCTCGCAGACCCTCTCACTCACCTGTGCCATCTCCGGGGACAGTGTCTCTAGCAACAGTGCTACTTGGAACTGGATCAGGCAGTCCCCATCGAGAGGCCTTGAGTGGCTGGGAAGGACATATTACAGGTCCAAGTGGTCTAATCATTATGCAGTATCTGTGAAAAGTCGAATAACCATCAACCCCGACACGTCCAAGAGCCAGTTCTCCCTGCAGCTGAACTCTGTGACTCCCGAGGACACGGCTGTGTATTACTGTGCAAGAGGAACGTGGAAACAGCTATGGTTCCTTGACCACTGGGGCCAGGGAACCCTGGTCACCGTCTCTAGTG | 469 |
| iPS:448202; iPS:448689 | HV-107 | CAGGTACAGCTGCAGCAGTCAGGTCCAGGACTGGTGAAGCCCTCGCAGACCCTCTCACTCACCTGTGCCATCTCCGGGGACAGTGTCTCTAACCGTCTGGCTACTTGGAACTGGATCAGGCAGTCCCCATCGAGAGGCCTTGAGTGGCTGGGAAGGACATACTACAGGGGTAAATGGAAAAATCATTATGCAGTATCTGTGAAAAGTCGAATAACCATCAACCCCGACACGTCCAAGAGCCAGTTCTCCCTGCAGCTGAACTCTGTGACTCCCGAGGACACGGCTGTGTATTACTGTGCAAGAGGAACTTGGAACCAGGACTGGTTCCTGGACCACTGGGGCCAGGGAACCCTGGTCACCGTCTCTAGT | 470 |
| iPS:449375 | HV-108 | CAGGTACAGCTGCAGCAGTCAGGTCCAGGACTGGTGAAGCCCTCGCAGACCCTCTCACTCACCTGTGCCATCTCCGGGGACAGTGTCTCTAACCGTCTGGCTACTTGGAACTGGATCAGGCAGTCCCCATCGAGAGGCCTTGAGTGGCTGGGAAGGACATACTACAGGGGTAAATGGAAAAATCATTATGCAGTATCTGTGAAAAGTCGAATAACCATCAACC | 471 |

TABLE 5B-continued

Exemplary Anti-PAC1 Antibody Heavy Chain Variable Region Nucleic Acid Sequences

| Ab ID. | VH Group | VH Nucleic Acid Sequence | SEQ ID NO: |
|---|---|---|---|
| | | CCGACACGTCCAAGAGCCAGTTCTCCCTGCAGCTGAACTCTGTGA CTCCCGAGGACACGGCTGTGTATTACTGTGCAAGAGGAACTTGGG ACCAGGACTGGTTCCTGGACCACTGGGGCCAGGGAACCCTGGTC ACCGTCTCTAGT | |
| iPS:448083 | HV-109 | CAGGTACAGCTGCAGCAGTCAGGTCCAGGACTGGTGAAGCCCTC GCAGACCCTCTCACTCACCTGTGCCATCTCCGGGGACAGTGTCTC TTCTCGTCAGGCTACTTGGAACTGGATCAGGCAGTCCCCATCGAG AGGCCTTGAGTGGCTGGGAAGGACATACTACAGGGGTAAATGGA AAAATCATTATGCAGTATCTGTGAAAAGTCGAATAACCATCAACC CCGACACGTCCAAGAGCCAGTTCTCCCTGCAGCTGAACTCTGTGA CTCCCGAGGACACGGCTGTGTATTACTGTGCAAGAGGAACTTGGG AACAGGACTGGTTCCTGGACCACTGGGGCCAGGGAACCCTGGTC ACCGTCTCTAGT | 472 |
| iPS:452128; iPS:448195; iPS:448752; iPS:449027; 3574 | HV-110 | CAGGTACAGCTGCAGCAGTCAGGTCCAGGACTGGTGAAGCCCTC GCAGACCCTCTCACTCACCTGTGCCATCTCCGGGGACAGTGTCTC TAACAAACAGGCTACTTGGAACTGGATCAGGCAGTCCCCATCGA GAGGCCTTGAGTGGCTGGGAAGGACATACTACAGGGGTAAATGG AAAAATCATTATGCAGTATCTGTGAAAAGTCGAATAACCATCAAC CCCGACACGTCCAAGAGCCAGTTCTCCCTGCAGCTGAACTCTGTG ACTCCCGAGGACACGGCTGTGTATTACTGTGCAAGAGGAATGTG GAACCAGAACTGGTTCCTGGACCACTGGGGCCAGGGAACCCTGG TCACCGTCTCTAGT | 473 |
| iPS:448466 | HV-111 | CAGGTACAGCTGCAGCAGTCAGGTCCAGGACTGGTGAAGCCCTC GCAGACCCTCTCACTCACCTGTGCCATCTCCGGGGACAGTGTCTC TAACAAACAGGCTACTTGGAACTGGATCAGGCAGTCCCCATCGA GAGGCCTTGAGTGGCTGGGAAGGACATACTACAGGGGTCAGTGG AAAAATCATTATGCAGTATCTGTGAAAAGTCGAATAACCATCAAC CCCGACACGTCCAAGAGCCAGTTCTCCCTGCAGCTGAACTCTGTG ACTCCCGAGGACACGGCTGTGTATTACTGTGCAAGAGGAACTTGG ATCGGTGACTGGTTCATGGACCACTGGGGCCAGGGAACCCTGGTC ACCGTCTCTAGT | 474 |
| iPS:449034 | HV-112 | CAGGTACAGCTGCAGCAGTCAGGTCCAGGACTGGTGAAGCCCTC GCAGACCCTCTCACTCACCTGTGCCATCTCCGGGGACAGTGTCTC TAACAAACAGGCTACTTGGAACTGGATCAGGCAGTCCCCATCGA GAGGCCTTGAGTGGCTGGGAAGGACATACTACAGGGGTAAATGG AAAAATCATTATGCAGTATCTGTGAAAAGTCGAATAACCATCAAC CCCGACACGTCCAAGAGCCAGTTCTCCCTGCAGCTGAACTCTGTG ACTCCCGAGGACACGGCTGTGTATTACTGTGCAAGAGGAACTTGG ATCCAGGACTGGTTCCTGGACCACTGGGGCCAGGGAACCCTGGTC ACCGTCTCTAGT | 475 |
| iPS:448075 | HV-113 | CAGGTACAGCTGCAGCAGTCAGGTCCAGGACTGGTGAAGCCCTC GCAGACCCTCTCACTCACCTGTGCCATCTCCGGGGACAGTGTCTC TTCTAACCATGCTACTTGGAACTGGATCAGGCAGTCCCCATCGAG AGGCCTTGAGTGGCTGGGAAGGACATACTACAGGGGTAAATGGA AAAATCATTATGCAGTATCTGTGAAAAGTCGAATAACCATCAACC CCGACACGTCCAAGAGCCAGTTCTCCCTGCAGCTGAACTCTGTGA CTCCCGAGGACACGGCTGTGTATTACTGTGCAAGAGGAACTTGGG ACCAGGACTGGTTCCTGGACCACTGGGGCCAGGGAACCCTGGTC ACCGTCTCTAGT | 476 |
| iPS:448924 | HV-114 | CAGGTACAGCTGCAGCAGTCAGGTCCAGGACTGGTGAAGCCCTC GCAGACCCTCTCACTCACCTGTGCCATCTCCGGGGACAGTGTCTC TTCTCGTTACGCTACTTGGAACTGGATCAGGCAGTCCCCATCGAG AGGCCTTGAGTGGCTGGGAAGGACATACTACAGGGGTCAGTGGA AAAATCATTATGCAGTATCTGTGAAAAGTCGAATAACCATCAACC CCGACACGTCCAAGAGCCAGTTCTCCCTGCAGCTGAACTCTGTGA CTCCCGAGGACACGGCTGTGTATTACTGTGCAAGAGGAATGTGG AACCAGAACTGGTTCCTGGACCACTGGGGCCAGGGAACCCTGGT CACCGTCTCTAGT | 477 |
| iPS:448772 | HV-115 | CAGGTACAGCTGCAGCAGTCAGGTCCAGGACTGGTGAAGCCCTC GCAGACCCTCTCACTCACCTGTGCCATCTCCGGGGACAGTGTCTC TAACAAACAGGCTACTTGGAACTGGATCAGGCAGTCCCCATCGA GAGGCCTTGAGTGGCTGGGAAGGACATACTACAGGGGTAAATGG AAAAATCATTATGCAGTATCTGTGAAAAGTCGAATAACCATCAAC CCCGACACGTCCAAGAGCCAGTTCTCCCTGCAGCTGAACTCTGTG ACTCCCGAGGACACGGCTGTGTATTACTGTGCAAGAGGAATGTG GTCTGGTGACTGGTTCCTGGACCACTGGGGCCAGGGAACCCTGGT CACCGTCTCTAGT | 478 |

TABLE 5B-continued

Exemplary Anti-PAC1 Antibody Heavy Chain Variable Region Nucleic Acid Sequences

| Ab ID. | VH Group | VH Nucleic Acid Sequence | SEQ ID NO: |
|---|---|---|---|
| iPS:448117 | HV-116 | CAGGTACAGCTGCAGCAGTCAGGTCCAGGACTGGTGAAGCCCTC<br>GCAGACCCTCTCACTCACCTGTGCCATCTCCGGGGACAGTGTCTC<br>TTCTCATGTTGCTACTTGGAACTGGATCAGGCAGTCCCCATCGAG<br>AGGCCTTGAGTGGCTGGGAAGGACATACTACAGGGGTAAATGGA<br>AAAATCATTATGCAGTATCTGTGAAAAGTCGAATAACCATCAACC<br>CCGACACGTCCAAGAGCCAGTTCTCCCTGCAGCTGAACTCTGTGA<br>CTCCCGAGGACACGGCTGTGTATTACTGTGCAAGAGGAATGTGGT<br>CTGAAGACTGGTTCCTGGACCACTGGGGCCAGGGAACCCTGGTC<br>ACCGTCTCTAGT | 479 |
| iPS:448788 | HV-117 | CAGGTACAGCTGCAGCAGTCAGGTCCAGGACTGGTGAAGCCCTC<br>GCAGACCCTCTCACTCACCTGTGCCATCTCCGGGGACAGTGTCTC<br>TTCTCGTCAGGCTACTTGGAACTGGATCAGGCAGTCCCCATCGAG<br>AGGCCTTGAGTGGCTGGGAAGGACATACTACAGGGGTAAATGGA<br>AAAATCATTATGCAGTATCTGTGAAAAGTCGAATAACCATCAACC<br>CCGACACGTCCAAGAGCCAGTTCTCCCTGCAGCTGAACTCTGTGA<br>CTCCCGAGGACACGGCTGTGTATTACTGTGCAAGAGGAATGTGGC<br>AGGGTAACTGGTTCCTGGACCACTGGGGCCAGGGAACCCTGGTC<br>ACCGTCTCTAGT | 480 |
| iPS:448593 | HV-118 | CAGGTACAGCTGCAGCAGTCAGGTCCAGGACTGGTGAAGCCCTC<br>GCAGACCCTCTCACTCACCTGTGCCATCTCCGGGGACAGTGTCTC<br>TAACCATCAGGCTACTTGGAACTGGATCAGGCAGTCCCCATCGAG<br>AGGCCTTGAGTGGCTGGGAAGGACATACTACAGGGGTAAATGGA<br>AAAATCATTATGCAGTATCTGTGAAAAGTCGAATAACCATCAACC<br>CCGACACGTCCAAGAGCCAGTTCTCCCTGCAGCTGAACTCTGTGA<br>CTCCCGAGGACACGGCTGTGTATTACTGTGCAAGAGGAACTTGGA<br>TCCAGGACTGGTTCCTGGACCACTGGGGCCAGGGAACCCTGGTCA<br>CCGTCTCTAGT | 481 |
| iPS:448238 | HV-119 | CAGGTACAGCTGCAGCAGTCAGGTCCAGGACTGGTGAAGCCCTC<br>GCAGACCCTCTCACTCACCTGTGCCATCTCCGGGGACAGTGTCTC<br>TTCTCGTGACGCTACTTGGAACTGGATCAGGCAGTCCCCATCGAG<br>AGGCCTTGAGTGGCTGGGAAGGACATACTACAGGGGTAAATGGA<br>AAAATCATTATGCAGTATCTGTGAAAAGTCGAATAACCATCAACC<br>CCGACACGTCCAAGAGCCAGTTCTCCCTGCAGCTGAACTCTGTGA<br>CTCCCGAGGACACGGCTGTGTATTACTGTGCAAGAGGACAGTGG<br>AACGAAGACTGGTTCCTGGACCACTGGGGCCAGGGAACCCTGGT<br>CACCGTCTCTAGT | 482 |
| iPS:448901 | HV-120 | CAGGTACAGCTGCAGCAGTCAGGTCCAGGACTGGTGAAGCCCTC<br>GCAGACCCTCTCACTCACCTGTGCCATCTCCGGGGACAGTGTCTC<br>TAACCGTCTGGCTACTTGGAACTGGATCAGGCAGTCCCCATCGAG<br>AGGCCTTGAGTGGCTGGGAAGGACATACTACAGGGGTAAATGGA<br>AAAATCATTATGCAGTATCTGTGAAAAGTCGAATAACCATCAACC<br>CCGACACGTCCAAGAGCCAGTTCTCCCTGCAGCTGAACTCTGTGA<br>CTCCCGAGGACACGGCTGTGTATTACTGTGCAAGAGGACGTTGGG<br>AAGGTGACTGGTTCTTCGACCACTGGGGCCAGGGAACCCTGGTCA<br>CCGTCTCTAGT | 483 |
| iPS:448655 | HV-121 | CAGGTACAGCTGCAGCAGTCAGGTCCAGGACTGGTGAAGCCCTC<br>GCAGACCCTCTCACTCACCTGTGCCATCTCCGGGGACAGTGTCTC<br>TAACAAACAGGCTACTTGGAACTGGATCAGGCAGTCCCCATCGA<br>GAGGCCTTGAGTGGCTGGGAAGGACATACTTCAGGCGTACTTGG<br>AAAAATCATTATGCAGTATCTGTGAAAAGTCGAATAACCATCAAC<br>CCCGACACGTCCAAGAGCCAGTTCTCCCTGCAGCTGAACTCTGTG<br>ACTCCCGAGGACACGGCTGTGTATTACTGTGCAAGAGGAATGTG<br>GTCTGAAGACTGGTTCCTGGACCACTGGGGCCAGGGAACCCTGGT<br>CACCGTCTCTAGT | 484 |
| iPS:448730 | HV-122 | CAGGTACAGCTGCAGCAGTCAGGTCCAGGACTGGTGAAGCCCTC<br>GCAGACCCTCTCACTCACCTGTGCCATCTCCGGGGACAGTGTCTC<br>TAACCGTCTGGCTACTTGGAACTGGATCAGGCAGTCCCCATCGAG<br>AGGCCTTGAGTGGCTGGGAAGGACATACTACAGGGGTAAATGGA<br>AAAATCATTATGCAGTATCTGTGAAAAGTCGAATAACCATCAACC<br>CCGACACGTCCAAGAGCCAGTTCTCCCTGCAGCTGAACTCTGTGA<br>CTCCCGAGGACACGGCTGTGTATTACTGTGCAAGAGGAGTTTGGA<br>TCGGTAACTGGTTCCTGGACCACTGGGGCCAGGGAACCCTGGTCA<br>CCGTCTCTAGT | 485 |

Isolated nucleic acids encoding the anti-PAC1 antibodies or antigen-binding fragments of the invention may comprise a nucleotide sequence that is at least 80% identical, at least 90% identical, at least 95% identical, or at least 98% identical to any of the nucleotide sequences listed in Tables 4A, 4B, 5A, and 5B. In some embodiments, an isolated nucleic acid encoding an anti-PAC1 antibody light chain variable region comprises a sequence that is at least 80% identical, at least 90% identical, at least 95% identical, or at least 98% identical to a sequence selected from SEQ ID NOs: 328 to 342. In other embodiments, an isolated nucleic acid encoding an anti-PAC1 antibody light chain variable region comprises a sequence that is at least 80% identical, at least 90% identical, at least 95% identical, or at least 98% identical to a sequence selected from SEQ ID NOs: 343 to 363. In certain embodiments, an isolated nucleic acid encoding an anti-PAC1 antibody light chain variable region comprises a sequence selected from SEQ ID NOs: 328 to 342. In certain other embodiments, an isolated nucleic acid encoding an anti-PAC1 antibody light chain variable region comprises a sequence selected from SEQ ID NOs: 343 to 363. In related embodiments, an isolated nucleic acid encoding an anti-PAC1 antibody heavy chain variable region comprises a sequence that is at least 80% identical, at least 90% identical, at least 95% identical, or at least 98% identical to a sequence selected from SEQ ID NOs: 364 to 468. In other related embodiments, an isolated nucleic acid encoding an anti-PAC1 antibody heavy chain variable region comprises a sequence that is at least 80% identical, at least 90% identical, at least 95% identical, or at least 98% identical to a sequence selected from SEQ ID NOs: 469 to 485. In some embodiments, an isolated nucleic acid encoding an anti-PAC1 antibody heavy chain variable region comprises a sequence selected from SEQ ID NOs: 364 to 468. In other embodiments, an isolated nucleic acid encoding an anti-PAC1 antibody heavy chain variable region comprises a sequence selected from SEQ ID NOs: 469 to 485.

In some embodiments, an isolated nucleic acid encoding an anti-PAC1 antibody light chain comprises a sequence that is at least 80% identical, at least 90% identical, at least 95% identical, or at least 98% identical to a sequence selected from SEQ ID NOs: 537 to 541. In other embodiments, an isolated nucleic acid encoding an anti-PAC1 antibody light chain comprises a sequence that is at least 80% identical, at least 90% identical, at least 95% identical, or at least 98% identical to a sequence selected from SEQ ID NOs: 542 to 551. In certain embodiments, an isolated nucleic acid encoding an anti-PAC1 antibody light chain comprises a sequence selected from SEQ ID NOs: 537 to 541. In certain other embodiments, an isolated nucleic acid encoding an anti-PAC1 antibody light chain comprises a sequence selected from SEQ ID NOs: 542 to 551. In related embodiments, an isolated nucleic acid encoding an anti-PAC1 antibody heavy chain comprises a sequence that is at least 80% identical, at least 90% identical, at least 95% identical, or at least 98% identical to a sequence selected from SEQ ID NOs: 552 to 562. In other related embodiments, an isolated nucleic acid encoding an anti-PAC1 antibody heavy chain comprises a sequence that is at least 80% identical, at least 90% identical, at least 95% identical, or at least 98% identical to a sequence selected from SEQ ID NOs: 563 to 569. In some embodiments, an isolated nucleic acid encoding an anti-PAC1 antibody heavy chain comprises a sequence selected from SEQ ID NOs: 552 to 562. In other embodiments, an isolated nucleic acid encoding an anti-PAC1 antibody heavy chain comprises a sequence selected from SEQ ID NOs: 563 to 569.

The nucleic acid sequences provided in Tables 4A, 4B, 5A, and 5B are exemplary only. As will be appreciated by those in the art, due to the degeneracy of the genetic code, an extremely large number of nucleic acids may be made, all of which encode the CDRs, variable regions, and heavy and light chains or other components of the antibodies and antigen-binding fragments described herein. Thus, having identified a particular amino acid sequence, those skilled in the art could make any number of different nucleic acids, by simply modifying the sequence of one or more codons in a way which does not change the amino acid sequence of the encoded protein.

The present invention also includes vectors comprising one or more nucleic acids encoding one or more components of the antibodies or antigen-binding fragments of the invention (e.g. variable regions, light chains, and heavy chains). The term "vector" refers to any molecule or entity (e.g., nucleic acid, plasmid, bacteriophage or virus) used to transfer protein coding information into a host cell. Examples of vectors include, but are not limited to, plasmids, viral vectors, non-episomal mammalian vectors and expression vectors, for example, recombinant expression vectors. The term "expression vector" or "expression construct" as used herein refers to a recombinant DNA molecule containing a desired coding sequence and appropriate nucleic acid control sequences necessary for the expression of the operably linked coding sequence in a particular host cell. An expression vector can include, but is not limited to, sequences that affect or control transcription, translation, and, if introns are present, affect RNA splicing of a coding region operably linked thereto. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals.

A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired. For instance, in some embodiments, signal peptide sequences may be appended/fused to the amino terminus of any of the variable region polypeptide sequences listed in Tables 1A and 1B or any of the full chain polypeptide sequences listed in Tables 4A and 4B. In certain embodiments, a signal peptide having the amino acid sequence of MDMRVPAQLLGLLLLWLRGARC (SEQ ID NO: 486) is fused to the amino terminus of any of the variable region polypeptide sequences in Tables 1A and 1B or full chain polypeptide sequences in Tables 4A and 4B. In other embodiments, a signal peptide having the amino acid sequence of MAWALLLLTLLTQGTGSWA (SEQ ID NO: 487) is fused to the amino terminus of any of the variable region polypeptide sequences in Tables 1A and 1B or full chain polypeptide sequences in Tables 4A and 4B. In still other embodiments, a signal peptide having the amino acid sequence of MTCSPLLLTLLIHCTGSWA (SEQ ID NO: 488) is fused to the amino terminus of any of the variable region polypeptide sequences in Tables 1A and 1B or full chain polypeptide sequences in Tables 4A and 4B. Other suitable signal peptide sequences that can be fused to the amino terminus of the variable region polypeptide sequences or full chain polypeptide sequences described herein include: MEAPAQLLFLLLLWLPDTTG (SEQ ID NO: 489), MEWTWRVLFLVAAATGAHS (SEQ ID NO: 490), METPAQLLFLLLLWLPDTTG (SEQ ID NO: 491), MET-PAQLLFLLLLWLPDTTG (SEQ ID NO: 492), MKHLWF-FLLLVAAPRWVLS (SEQ ID NO: 493), MEWSWVFLF-FLSVTTGVHS (SEQ ID NO: 494), MDIRAPTQLLGLLLLWLPGAKC (SEQ ID NO: 495), MDIRAPTQLLGLLLLWLPGARC (SEQ ID NO: 496), MDTRAPTQLLGLLLLWLPGATF (SEQ ID NO: 497), MDTRAPTQLLGLLLLWLPGARC (SEQ ID NO: 498), METGLRWLLLVAVLKGVQC (SEQ ID NO: 499), METGLRWLLLVAVLKGVQCQE (SEQ ID NO: 500), and MDMRAPTQLLGLLLLWLPGARC (SEQ ID NO: 501). Other signal or secretory peptides are known to those of skill in the art and may be fused to any of the variable region polypeptide chains listed in Tables 1A and 1B or full chain polypeptide sequences in Tables 4A and 4B, for example, to facilitate or optimize expression in particular host cells.

Typically, expression vectors used in the host cells to produce the anti-PAC1 antibodies and antigen-binding fragments of the invention will contain sequences for plasmid maintenance and for cloning and expression of exogenous nucleotide sequences encoding the components of the antibodies and antigen-binding fragments. Such sequences, collectively referred to as "flanking sequences," in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the polypeptide coding sequence; the oligonucleotide tag sequence encodes polyHis (such as hexaHis), FLAG, HA (hemaglutinin influenza virus), myc, or another "tag" molecule for which commercially available antibodies exist. This tag is typically fused to the polypeptide upon expression of the polypeptide, and can serve as a means for affinity purification or detection of the polypeptide from the host cell. Affinity purification can be accomplished, for example, by column chromatography using antibodies against the tag as an affinity matrix. Optionally, the tag can subsequently be removed from the purified polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using routine methods for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, CA), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, MA) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using known methods for nucleic acid synthesis.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as one or more components of the antibodies or antigen-binding fragments described herein. As a result, increased quantities of a polypeptide are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed. In certain embodiments, one or more coding regions may be operably linked to an internal ribosome binding site (IRES), allowing translation of two open reading frames from a single RNA transcript.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the invention will typically contain a promoter that is recognized by the host organism and operably linked to the molecule encoding the polypeptide. The term "operably linked" as used herein refers to the linkage of two or more nucleic acid sequences in such a manner that a nucleic acid molecule capable of directing the transcription of a given gene and/or the synthesis of a desired protein molecule is produced. For example, a control sequence in a vector that is "operably linked" to a protein coding sequence is ligated thereto so that expression of the protein coding sequence is achieved under conditions compatible with the transcriptional activity of the control sequences. More specifically, a promoter and/or enhancer sequence, including any combination of cis-acting transcriptional control elements is operably linked to a coding sequence if it stimulates or modulates the transcription of the coding sequence in an appropriate host cell or other expression system.

Promoters are non-transcribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression. A large number of promoters, recognized by a variety of potential host cells, are well known. A suitable promoter is operably linked to the DNA encoding e.g., heavy chain, light chain, or other component of the antibodies and antigen-binding fragments of the invention, by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus serotypes 2, 8, or 9), bovine papilloma virus, avian sarcoma virus, cytomegalovirus, retroviruses, hepatitis-B virus and Simian Virus 40 (SV40). Other suitable mammalian promoters include heterologous mammalian promoters, for example, heat-shock promoters and the actin promoter.

Additional specific promoters which may be of interest include, but are not limited to: SV40 early promoter (Benoist and Chambon, 1981, Nature 290:304-310); CMV promoter (Thornsen et al., 1984, Proc. Natl. Acad. U.S.A. 81:659-663); the promoter contained in the 3' long terminal repeat of Rous sarcoma virus (Yamamoto et al., 1980, Cell 22:787-797); herpes thymidine kinase promoter (Wagner et al., 1981, Proc. Natl. Acad. Sci. U.S.A. 78: 1444-1445); promoter and regulatory sequences from the metallothionine gene (Prinster et al., 1982, Nature 296:39-42); and prokaryotic promoters such as the beta-lactamase promoter (Villa-Kamaroff et al., 1978, Proc. Natl. Acad. Sci. U.S.A. 75:3727-3731); or the tac promoter (DeBoer et al., 1983, Proc. Natl. Acad. Sci. U.S.A. 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); the insulin gene control region that is active in pancreatic beta cells (Hanahan, 1985, Nature 315: 115-122); the immunoglobulin gene control region that is active in lymphoid cells (Grosschedl et al., 1984, Cell 38:647-658; Adames et al., 1985, Nature 318:533-538; Alexander et al., 1987, Mol. Cell. Biol. 7: 1436-1444); the mouse mammary tumor virus control region that is active in testicular, breast, lymphoid and mast cells (Leder et al., 1986, Cell 45:485-495); the albumin gene control region that is active in liver (Pinkert et al., 1987, Genes and Devel. 1:268-276); the alpha-feto-protein gene control region that is active in liver (Krumlauf et al., 1985, Mol. Cell. Biol. 5: 1639-1648; Hammer et al., 1987, Science 253:53-58); the alpha 1-antitrypsin gene control region that is active in liver (Kelsey et al., 1987, Genes and Devel. 1: 161-171); the beta-globin gene control region that is active in myeloid cells (Mogram et al, 1985, Nature 315:338-340; Kollias et al, 1986, Cell 46:89-94); the myelin basic protein gene control region that is active in oligodendrocyte cells in the brain (Readhead et al., 1987, Cell 48:703-712); the myosin light chain-2 gene control region that is active in skeletal muscle (Sani, 1985, Nature 314:283-286); and the gonadotropic releasing hormone gene control region that is active in the hypothalamus (Mason et al., 1986, Science 234: 1372-1378).

An enhancer sequence may be inserted into the vector to increase transcription of DNA encoding a component of the antibodies or antigen-binding fragments (e.g., light chain, heavy chain, or variable regions) by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody or antigen-binding fragment as described above. The choice of signal peptide or leader depends on the type of host cells in which the antibody or antigen-binding fragment is to be produced, and a heterologous signal sequence can replace the native signal sequence. Examples of signal peptides are described above. Other signal peptides that are functional in mammalian host cells include the signal sequence for interleukin-7 (IL-7) described in U.S. Pat. No. 4,965,195; the signal sequence for interleukin-2 receptor described in Cosman et al., 1984, Nature 312:768; the interleukin-4 receptor signal peptide described in EP Patent No. 0367 566; the type I interleukin-1 receptor signal peptide described in U.S. Pat. No. 4,968,607; and the type II interleukin-1 receptor signal peptide described in EP Patent No. 0 460 846.

The expression vectors that are provided may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art. The expression vectors can be introduced into host cells to thereby produce proteins, including antibodies and antigen-binding fragments, encoded by nucleic acids as described herein.

In certain embodiments, nucleic acids encoding the different components of the anti-PAC1 antibodies or antigen-binding fragments of the invention may be inserted into the same expression vector. For instance, the nucleic acid encoding an anti-PAC1 antibody light chain or variable region can be cloned into the same vector as the nucleic acid encoding an anti-PAC1 antibody heavy chain or variable region. In such embodiments, the two nucleic acids may be separated by an internal ribosome entry site (IRES) and under the control of a single promoter such that the light chain and heavy chain are expressed from the same mRNA transcript. Alternatively, the two nucleic acids may be under the control of two separate promoters such that the light chain and heavy chain are expressed from two separate mRNA transcripts. In some embodiments, the nucleic acid encoding the anti-PAC1 antibody light chain or variable region is cloned into one expression vector and the nucleic acid encoding the anti-PAC1 antibody heavy chain or variable region is cloned into a second expression vector. In such embodiments, a host cell may be co-transfected with both expression vectors to produce complete antibodies or antigen-binding fragments of the invention.

After the vector has been constructed and the one or more nucleic acid molecules encoding the components of the antibodies and antigen-binding fragments described herein has been inserted into the proper site(s) of the vector or vectors, the completed vector(s) may be inserted into a suitable host cell for amplification and/or polypeptide expression. Thus, the present invention encompasses an isolated host cell or cell line comprising one or more expression vectors encoding the components of the anti-PAC1 antibodies or antigen-binding fragments described herein. The term "host cell" as used herein refers to a cell that has been transformed, or is capable of being transformed, with a nucleic acid and thereby expresses a gene of interest. The term includes the progeny of the parent cell, whether or not the progeny is identical in morphology or in genetic make-up to the original parent cell, so long as the gene of interest is present. A host cell that comprises an isolated nucleic acid of the invention, preferably operably linked to at least one expression control sequence (e.g. promoter or enhancer), is a "recombinant host cell."

The transformation of an expression vector for an anti-PAC1 antibody or antigen-binding fragment into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001.

A host cell, when cultured under appropriate conditions, synthesizes an antibody or antigen-binding fragment that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Exemplary host cells include prokaryote, yeast, or higher eukaryote cells. Prokaryotic host cells include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacillus*, such as *B. subtilis* and *B. licheniformis, Pseudomonas*, and *Streptomyces*. Eukaryotic microbes such as filamentous fungi or yeast are suitable cloning or expression hosts for recombinant polypeptides. *Saccharomyces cerevisiae*, or common baker's yeast, is the most commonly used among lower eukaryotic host microorganisms. However, a number of other genera, species, and strains are commonly available and useful herein, such as *Pichia*, e.g. *P. pastoris, Schizosaccharomyces pombe; Kluyveromyces, Yarrowia; Candida; Trichoderma reesia; Neurospora crassa; Schwanniomyces*, such as *Schwanniomyces occidentalis*; and filamentous fungi, such as, e.g., *Neurospora, Penicillium, Tolypocladium*, and *Aspergillus* hosts such as *A. nidulans* and *A. niger.*

Host cells for the expression of glycosylated antibodies and antigen-binding fragments can be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection of such cells are publicly available, e.g., the L-1 variant of *Autographa californica* NPV and the Bm-5 strain of *Bombyx mori* NPV.

Vertebrate host cells are also suitable hosts, and recombinant production of antibodies and antigen-binding fragments from such cells has become routine procedure. Mammalian cell lines available as hosts for expression are well known in the art and include, but are not limited to, immortalized cell lines available from the American Type Culture Collection (ATCC), including but not limited to Chinese hamster ovary (CHO) cells, including CHOK1 cells (ATCC CCL61), DXB-11, DG-44, and Chinese hamster ovary cells/-DHFR (CHO, Urlaub et al., Proc. Natl. Acad. Sci. USA 77: 4216, 1980); monkey kidney CV1 line transformed by SV40 (COS-7, ATCC CRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, Biol. Reprod. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N.Y Acad. Sci. 383: 44-68, 1982); MRC 5 cells or FS4 cells; mammalian myeloma cells, and a number of other cell lines. In certain embodiments, cell lines may be selected through determining which cell lines have high expression levels and constitutively produce antibodies and antigen-binding fragments with PAC1 binding properties. In another embodiment, a cell line from the B cell lineage that does not make its own antibody but has a capacity to make and secrete a heterologous antibody can be selected. CHO cells are preferred host cells in some embodiments for expressing the anti-PAC1 antibodies and antigen-binding fragments of the invention.

Host cells are transformed or transfected with the above-described nucleic acids or vectors for production of anti-PAC1 antibodies or antigen-binding fragments and are cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of antibodies and antigen-binding fragments. Thus, the present invention also provides a method for producing an anti-PAC1 antibody or antigen-binding fragment thereof described herein comprising culturing a host cell comprising one or more expression vectors described herein in a culture medium under conditions permitting expression of the antibody or antigen-binding fragment encoded by the one or more expression vectors; and recovering the antibody or antigen-binding fragment from the culture medium or host cell.

The host cells used to produce the antibodies or antigen-binding fragments of the invention may be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham et al., Meth. Enz. 58: 44, 1979; Barnes et al., Anal. Biochem. 102: 255, 1980; U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinary skilled artisan.

Upon culturing the host cells, the antibody or antigen-binding fragment can be produced intracellularly, in the periplasmic space, or directly secreted into the medium. If the antibody or antigen-binding fragment is produced intracellularly, as a first step, the particulate debris, either host cells or lysed fragments, is removed, for example, by centrifugation or ultrafiltration. The antibody or antigen-binding fragment can be purified using, for example, hydroxyapatite chromatography, cation or anion exchange chromatography, or preferably affinity chromatography, using the antigen(s) of interest or protein A or protein G as an affinity ligand. Protein A can be used to purify proteins that include polypeptides that are based on human $\gamma1$, $\gamma2$, or $\gamma4$ heavy chains (Lindmark et al., J. Immunol. Meth. 62: 1-13, 1983). Protein G is recommended for all mouse isotypes and for human $\gamma3$ (Guss et al., EMBO J. 5: 1567-1575, 1986). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the protein comprises a CH3 domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the particular antibody or antigen-binding fragment to be recovered.

In certain embodiments, the invention provides a composition (e.g. a pharmaceutical composition) comprising one or a plurality of the anti-PAC1 antibodies or antigen-binding fragments of the invention (e.g. anti-PAC1 monoclonal antibodies or binding fragments thereof) together with pharmaceutically acceptable diluents, carriers, excipients, solubilizers, emulsifiers, preservatives, and/or adjuvants. The pharmaceutical compositions can be used in any of the methods described herein. Pharmaceutical compositions of the invention include, but are not limited to, liquid, frozen, and lyophilized compositions. "Pharmaceutically-acceptable" refers to molecules, compounds, and compositions that are non-toxic to human recipients at the dosages and concentrations employed and/or do not produce allergic or adverse reactions when administered to humans. In some embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. Methods and suitable materials for formulating molecules for therapeutic use are known in the pharmaceutical arts, and are described, for example, in REMINGTON'S PHARMACEUTICAL SCIENCES, 18th Edition, (A. R. Genrmo, ed.), 1990, Mack Publishing Company.

In some embodiments, the pharmaceutical composition of the invention comprises a standard pharmaceutical carrier, such as a sterile phosphate buffered saline solution, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Exemplary concentrations of the antibodies or antigen-binding fragments in the formulation may range from about 0.1 mg/ml to about 200 mg/ml or from about 0.1 mg/mL to about 50 mg/mL, or from about 0.5 mg/mL to about 25 mg/mL, or alternatively from about 2 mg/mL to about 10 mg/mL. An aqueous formulation of the antibody or antigen-binding fragment may be prepared in a pH-buffered solution, for example, at pH ranging from about 4.5 to about 6.5, or from about 4.8 to about 5.5, or alternatively about 5.0. Examples of buffers that are suitable for a pH within this range include acetate (e.g. sodium acetate), succinate (such as sodium succinate), gluconate, histidine, citrate and other organic acid buffers. The buffer concentration can be from about 1 mM to about 200 mM, or from about 10 mM to about 60 mM, depending, for example, on the buffer and the desired isotonicity of the formulation.

A tonicity agent, which may also stabilize the antibody or antigen-binding fragment, may be included in the formulation. Exemplary tonicity agents include polyols, such as mannitol, sucrose or trehalose. Preferably the aqueous formulation is isotonic, although hypertonic or hypotonic solutions may be suitable. Exemplary concentrations of the polyol in the formulation may range from about 1% to about 15% w/v.

A surfactant may also be added to the formulation to reduce aggregation of the formulated antibody or antigen-binding fragment and/or minimize the formation of particulates in the formulation and/or reduce adsorption. Exemplary surfactants include nonionic surfactants such as polysorbates (e.g. polysorbate 20 or polysorbate 80) or poloxamers (e.g. poloxamer 188). Exemplary concentrations of surfactant may range from about 0.001% to about 0.5%, or from about 0.005% to about 0.2%, or alternatively from about 0.004% to about 0.01% w/v.

In one embodiment, the formulation contains the above-identified agents (i.e. antibody or antigen-binding fragment, buffer, polyol and surfactant) and is essentially free of one or more preservatives, such as benzyl alcohol, phenol, m-cresol, chlorobutanol and benzethonium chloride. In another embodiment, a preservative may be included in the formulation, e.g., at concentrations ranging from about 0.1% to about 2%, or alternatively from about 0.5% to about 1%. One or more other pharmaceutically acceptable carriers, excipients or stabilizers such as those described in REMINGTON'S PHARMACEUTICAL SCIENCES, 18th Edition, (A. R. Genrmo, ed.), 1990, Mack Publishing Company, may be included in the formulation provided that they do not adversely affect the desired characteristics of the formulation.

Therapeutic formulations of the antibody or antigen-binding fragment are prepared for storage by mixing the antibody or antigen-binding fragment having the desired degree of purity with optional physiologically acceptable carriers, excipients or stabilizers (REMINGTON'S PHARMACEUTICAL SCIENCES, 18th Edition, (A. R. Genrmo, ed.), 1990, Mack Publishing Company), in the form of lyophilized formulations or aqueous solutions. Acceptable carriers, excipients, or stabilizers are nontoxic to recipients at the dosages and concentrations employed, and include those described above, such as buffers (e.g. phosphate, citrate, and other organic acids); antioxidants (e.g. ascorbic acid and methionine); preservatives (such as octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol; resorcinol, cyclohexanol, 3-pentanol, and m-cresol); low molecular weight (e.g. less than about 10 residues) polypeptides; proteins (such as serum albumin, gelatin, or immunoglobulins); hydrophilic polymers (e.g. polyvinylpyrrolidone); amino acids (e.g. glycine, glutamine, asparagine, histidine, arginine, or lysine); monosaccharides, disaccharides, and other carbohydrates including glucose, mannose, maltose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants, such as polysorbates (e.g. polysorbate 20 or polysorbate 80) or poloxamers (e.g. poloxamer 188); or polyethylene glycol (PEG).

In one embodiment, a suitable formulation of the invention contains an isotonic buffer such as a phosphate, acetate, or TRIS buffer in combination with a tonicity agent, such as a polyol, sorbitol, sucrose or sodium chloride, which tonicifies and stabilizes. One example of such a tonicity agent is 5% sorbitol or sucrose. In addition, the formulation could optionally include a surfactant at 0.01% to 0.02% wt/vol, for example, to prevent aggregation or improve stability. The pH of the formulation may range from 4.5 to 6.5 or 4.5 to 5.5. Other exemplary descriptions of pharmaceutical formulations for antibodies and antigen-binding fragments may be found in US Patent Publication No. 2003/0113316 and U.S. Pat. No. 6,171,586, each of which is hereby incorporated by reference in its entirety.

The formulations to be used for in vivo administration must be sterile. The compositions of the invention may be sterilized by conventional, well-known sterilization techniques. For example, sterilization is readily accomplished by filtration through sterile filtration membranes. The resulting solutions may be packaged for use or filtered under aseptic conditions and lyophilized, the lyophilized preparation being combined with a sterile solution prior to administration.

The process of freeze-drying is often employed to stabilize polypeptides for long-term storage, particularly when the polypeptide is relatively unstable in liquid compositions. A lyophilization cycle is usually composed of three steps: freezing, primary drying, and secondary drying (see Williams and Polli, Journal of Parenteral Science and Technology, Volume 38, Number 2, pages 48-59, 1984). In the freezing step, the solution is cooled until it is adequately frozen. Bulk water in the solution forms ice at this stage. The ice sublimes in the primary drying stage, which is conducted by reducing chamber pressure below the vapor pressure of the ice, using a vacuum. Finally, sorbed or bound water is removed at the secondary drying stage under reduced chamber pressure and an elevated shelf temperature. The process produces a material known as a lyophilized cake. Thereafter the cake can be reconstituted prior to use. The standard reconstitution practice for lyophilized material is to add back a volume of pure water (typically equivalent to the volume removed during lyophilization), although dilute solutions of antibacterial agents are sometimes used in the production of pharmaceuticals for parenteral administration (see Chen, Drug Development and Industrial Pharmacy, Volume 18: 1311-1354, 1992).

Excipients have been noted in some cases to act as stabilizers for freeze-dried products (see Carpenter et al., Volume 74: 225-239, 1991). For example, known excipients include polyols (including mannitol, sorbitol and glycerol); sugars (including glucose and sucrose); and amino acids (including alanine, glycine and glutamic acid). In addition, polyols and sugars are also often used to protect polypeptides from freezing- and drying-induced damage and to enhance the stability during storage in the dried state. In general, sugars, in particular disaccharides, are effective in both the freeze-drying process and during storage. Other classes of molecules, including mono- and di-saccharides and polymers such as PVP, have also been reported as stabilizers of lyophilized products.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the antibody or antigen-binding fragment, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations of the invention may be designed to be short-acting, fast-releasing, long-acting, or sustained-releasing as described herein. Thus, the pharmaceutical formulations may also be formulated for controlled release or for slow release.

Specific dosages may be adjusted depending on the disease, disorder, or condition to be treated (e.g. episodic migraine, chronic migraine, or cluster headache), the age, body weight, general health conditions, sex, and diet of the subject, dose intervals, administration routes, excretion rate, and combinations of drugs.

The anti-PAC1 antibodies or antigen-binding fragments of the invention can be administered by any suitable means, including parenteral, subcutaneous, intravenous, intraperitoneal, intrapulmonary, and intranasal, and, if desired for local treatment, intralesional administration. Parenteral administration includes intravenous, intraarterial, intraperitoneal, intramuscular, intradermal or subcutaneous administration. In addition, the antibody or antigen-binding fragment is suitably administered by pulse infusion, particularly with declining doses of the antibody or antigen-binding fragment. Preferably, the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site. The antibody or antigen-binding fragment of the invention may be administered in a physiological solution at a dose ranging between 0.01 mg/kg to 100 mg/kg at a frequency ranging from daily to weekly to monthly.

The anti-PAC1 antibodies and antigen-binding fragments described herein are useful for treating or ameliorating a condition associated with the biological activity of the PAC1 receptor in a patient in need thereof. Thus, anti-PAC1 antibodies and antigen-binding fragments of the invention for use in methods of treatment are disclosed herein. The term "patient" includes human patients and is used interchangeably with the term "subject." As used herein, the term "treating" or "treatment" is an intervention performed with the intention of preventing the development or altering the pathology of a disorder. Accordingly, "treatment" refers to both therapeutic treatment and prophylactic or preventative measures. Those in need of treatment include those already diagnosed with or suffering from the disorder or condition as well as those in which the disorder or condition is to be prevented. "Treatment" includes any indicia of success in the amelioration of an injury, pathology or condition, including any objective or subjective parameter such as abatement, remission, diminishing of symptoms, or making the injury, pathology or condition more tolerable to the patient, slowing in the rate of degeneration or decline, making the final point of degeneration less debilitating, or improving a patient's physical or mental well-being. The treatment or amelioration of symptoms can be based on objective or subjective parameters, including the results of a physical examination, self-reporting by a patient, neuropsychiatric exams, and/or a psychiatric evaluation.

Accordingly, in some embodiments, the present invention provides a method for treating or preventing a condition associated with the biological activity of the PAC1 receptor (e.g. a condition associated with PACAP-induced activation of the PAC1 receptor) in a patient in need thereof, comprising administering to the patient an effective amount of an anti-PAC1 antibody or antigen-binding fragment thereof described herein. The PACAP/PAC1 signaling pathway has been implicated in various physiological processes, including cardiovascular function, metabolic and endocrine function, inflammation, stress response, regulation of vasomotor tone, and regulation of the autonomic nervous system, particularly the balance between the sympathetic and parasympathetic systems. See, e.g., Tanida et al., Regulatory Peptides, Vol. 161: 73-80, 2010; Moody et al., Curr. Opin. Endocrinol. Diabetes Obes., Vol. 18: 61-67, 2011; and Hashimoto et al., Current Pharmaceutical Design, Vol. 17: 985-989, 2011. Conditions associated with aberrant or over-activation of the PACAP/PAC1 signaling pathway include, but are not limited to, headache conditions, such as migraine, cluster headache, tension-type headache, hemiplegic migraine, and retinal migraine; inflammatory skin conditions; chronic pain, such as neuropathic pain; anxiety disorders; irritable bowel syndrome; and vasomotor symptoms, such as hot flashes, facial flushing, sweating, and night sweats. Thus, the anti-PAC1 antibodies and antigen-binding fragments thereof of the invention can be administered to patients to prevent, ameliorate, or treat any of these conditions or disorders or other conditions associated with aberrant or excessive PAC1 receptor biological activity. In certain embodiments, the present invention provides methods for treating or preventing a headache condition (e.g. episodic migraine, chronic migraine, cluster headache, tension-type headache, hemiplegic migraine, and retinal migraine) in a patient in need thereof comprising administering to the patient an effective amount of an anti-PAC1 antibody or antigen-binding fragment thereof as described herein. In some embodiments, the present invention provides a method for inhibiting activation of the human PAC1 receptor in a patient having a headache condition comprising administering to the patient an effective amount of an anti-PAC1 antibody or antigen-binding fragment thereof described herein. In one embodiment, the patient has a migraine headache condition, such as episodic migraine or chronic migraine. In another embodiment, the patient has a cluster headache condition.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with a particular condition. In some embodiments, the effective amount is a therapeutically effective amount or a prophylactically effective amount. A "therapeutically effective amount" is an amount sufficient to remedy a disease state or symptom(s), particularly a state or symptom(s) associated with the disease state, or otherwise prevent, hinder, retard or reverse the progression of the disease state or any other undesirable symptom associated with the disease in any way whatsoever (i.e. that provides "therapeutic efficacy"). A "prophylactically effective amount" is an amount of an antibody or antigen-binding fragment that, when administered to a subject, will have the intended prophylactic effect, e.g., preventing or delaying the onset (or reoccurrence) of the condition, or reducing the likelihood of the onset (or reoccurrence) of the condition. The full therapeutic or prophylactic effect does not necessarily occur by administration of one dose, and may occur only after administration of a series of doses. Thus, a therapeutically or prophylactically effective amount may be administered in one or more administrations.

In certain embodiments, the present invention provides methods for inhibiting vasodilation in a patient in need thereof comprising administering to the patient an effective amount of an anti-PAC1 antibody or antigen-binding fragment thereof described herein. Ligands of the PAC1 receptor, such as PACAP38 and VIP, are potent vasodilators, and blocking the binding of these ligands to the PAC1 receptor can inhibit vasodilation and ameliorate conditions associated with aberrant or excessive vasodilation, such as headache conditions, hot flashes, and flushing. In one embodiment, the patient has a headache condition, such as migraine or cluster headache. In another embodiment, the patient has vasomotor symptoms (e.g. hot flashes, facial flushing, sweating, or night sweats). In a related embodiment, the patient has vasomotor symptoms associated with menopause.

In some embodiments of the methods of the invention, the headache condition to be treated, prevented or ameliorated is migraine. Thus, the present invention includes a method for treating, preventing, or ameliorating migraine in a patient in need thereof comprising administering to the patient an effective amount of an anti-PAC1 antibody or antigen-binding fragment thereof described herein. Migraine headaches are recurrent headaches lasting about 4 to about 72 hours that are characterized by unilateral, pulsating, and/or moderate to severe pain and/or pain that is exacerbated by physical activity. Migraine headaches are often accompanied by nausea, vomiting, and/or sensitivity to light (photophobia), sound (phonophobia), or smell. In some patients, an aura precedes the onset of the migraine headache. The aura is typically a visual, sensory, language, or motor disturbance that signals the headache will soon occur. The methods described herein prevent, treat, or ameliorate one or more symptoms of migraine headaches with and without aura in human patients.

PACAP38, through activation of its receptors, induces vasodilation, particularly vasodilation of the dura vasculature (Schytz et al., Neurotherapeutics, Vol. 7(2):191-196, 2010). The PACAP38/PAC1 receptor signaling cascade, in particular, has been implicated in migraine pathophysiology (Amin et al., Brain, Vol. 137: 779-794, 2014). Infusion of PACAP38, which has a higher affinity for the PAC1 receptor than the VPAC1 and VPAC2 receptors, causes migraine-like headache in migraine patients (Schytz et al., Brain 132:16-25, 2009; Amin et al., Brain, Vol. 137: 779-794, 2014; Guo et al., Cephalalgia, Vol. 37:125-135, 2017). In addition, PACAP38 levels are elevated in cranial circulation in patients experiencing a migraine attack, and the PACAP38 levels are reduced following treatment of the migraine symptoms with triptans (Tuka et al., Cephalalgia, Vol. 33, 1085-1095, 2013; Zagami et al., Ann. Clin. Transl. Neurol., Vol. 1: 1036-1040, 2014). These reports suggest that endogenous release of PACAP38 is an important trigger of migraine headache and its effects are primarily mediated through activation of the PAC1 receptor.

In some embodiments, the patients to be treated according to the methods of the invention have, suffer from, or are diagnosed with episodic migraine. Episodic migraine is diagnosed when patients with a history of migraine (e.g. at least five lifetime attacks of migraine headache) have 14 or fewer migraine headache days per month. A "migraine headache day" includes any calendar day during which a patient experiences the onset, continuation, or recurrence of a "migraine headache" with or without aura lasting greater than 30 minutes. A "migraine headache" is a headache associated with nausea or vomiting or sensitivity to light or sound and/or a headache characterized by at least two of the following pain features: unilateral pain, throbbing pain, moderate to severe pain intensity, or pain exacerbated by physical activity. In certain embodiments, patients having, suffering from, or diagnosed with episodic migraine have at least four, but less than 15 migraine headache days per month on average. In related embodiments, patients having, suffering from, or diagnosed with episodic migraine have fewer than 15 headache days per month on average. As used herein, a "headache day" is any calendar day in which the patient experiences a migraine headache as defined herein or any headache that lasts greater than 30 minutes or requires acute headache treatment.

In certain embodiments, the patients to be treated according to the methods of the invention have, suffer from, or are diagnosed with chronic migraine. Chronic migraine is diagnosed when migraine patients (i.e. patients with at least five lifetime attacks of migraine headache) have 15 or more headache days per month and at least 8 of the headache days are migraine headache days. In some embodiments, patients having, suffering from, or diagnosed with chronic migraine have 15 or more migraine headache days per month on average. In certain embodiments of the methods described herein, administration of an anti-PAC1 antibody or antigen-binding fragment of the invention prevents, reduces, or delays the progression of episodic migraine to chronic migraine in the patient.

In some embodiments, the present invention provides a method for treating, preventing, or ameliorating cluster headache in a patient in need thereof comprising administering to the patient an effective amount of an anti-PAC1 antibody or antigen-binding fragment thereof described herein. Cluster headache is a condition that involves, as its most prominent feature, recurrent, severe headaches on one side of the head, typically around the eye (see Nesbitt et al., BMJ, Vol. 344:e2407, 2012). Cluster headaches often occur periodically: spontaneous remissions interrupt active periods of pain. Cluster headaches are often accompanied by cranial autonomic symptoms, such as tearing, nasal congestion, ptosis, pupil constriction, facial blushing, sweating, and swelling around the eye, often confined to the side of the head with the pain. The average age of onset of cluster headache is ~30-50 years. It is more prevalent in males with a male to female ratio of about 2.5:1 to about 3.5:1. Sphenopalatine ganglion (SPG) stimulation has been used for the treatment of cluster headache. A neurostimulation system, which delivers low-level (but high frequency, physiologic-blocking) electrical stimulation to the SPG, has demonstrated efficacy in relieving the acute debilitating pain of cluster headache in a recent clinical trial (see Schoenen J, et al., Cephalalgia, Vol. 33(10):816-30, 2013). In view of this evidence and because PACAP is one of the major neurotransmitters in SPG, inhibition of PACAP/PAC1 signaling with an anti-PAC1 antibody or antigen-binding fragment thereof described herein is expected to have efficacy in treating cluster headache in humans.

Other conditions associated with the PACAP/PAC1 signaling pathway that may be treated according to the methods of the invention include, but are not limited to, inflammatory skin conditions, such as rosacea (see U.S. Patent Publication No. 20110229423), chronic pain syndromes, such as neuropathic pain (see Jongsma et al., Neuroreport, Vol. 12: 2215-2219, 2001; Hashimoto et al., Annals of the New York Academy of Sciences, Vol. 1070: 75-89, 2006), tension-type headaches, hemiplegic migraine, retinal migraine, anxiety disorders, such as posttraumatic stress disorder (see Hammack and May, Biol. Psychiatry, Vol. 78(3):167-177, 2015), irritable bowel syndrome, and vasomotor symptoms (e.g. hot flashes, facial flushing, sweating, and night sweats), such as those associated with menopause. In one embodiment, the condition to be treated by administering an anti-PAC1 antibody or antigen-binding fragment thereof of the invention is chronic pain. In another embodiment, the condition to be treated by administering an anti-PAC1 antibody or antigen-binding fragment thereof of the invention is neuropathic pain.

In any of the methods described herein, the treatment can comprise prophylactic treatment. Prophylactic treatment refers to treatment designed to be taken before the onset of a condition or an attack (e.g. before a migraine attack or onset of a cluster headache episode) to reduce the frequency, severity, and/or length of the symptoms (e.g. migraine or cluster headaches) in the patient.

In some embodiments, the methods of the invention for treating or preventing a headache condition in a patient comprise administering to the patient an anti-PAC1 antibody or antigen-binding fragment thereof described herein in combination with one or more agents suitable for the acute or prophylactic treatment of migraine headache or other headache disorder described herein. The term "combination therapy" as used herein encompasses the administration of the two compounds (e.g. anti-PAC1 antibody and additional agent) in a sequential manner (i.e. each compound is administered at a different time in any order) as well as administration of the two compounds in a substantially simultaneous manner. Substantially simultaneous administration includes concurrent administration and can be accomplished by administering a single formulation comprising both compounds (e.g. a single formulation comprising a fixed ratio of both compounds or a pre-filled syringe having a fixed ratio of each compound) or concurrently administering separate formulations containing each of the compounds. Thus, in certain embodiments, the methods of the invention comprise administering an anti-PAC1 antibody or antigen-binding fragment thereof described herein with a second headache therapeutic agent.

In certain embodiments, the second headache therapeutic agent may be an acute headache therapeutic agent used for the acute treatment of headaches or migraines. In some embodiments, the acute headache therapeutic agent is a serotonin (5-hydroxytryptamine; 5-HT) receptor agonist, for example a 5HT1 receptor agonist. The acute headache therapeutic agent can be an agonist of the $5HT_{1B}$, $5HT_{1D}$ and/or $5HT_{1F}$ serotonin receptors. Such serotonin receptor agonists include, but are not limited to, triptans (e.g., almotriptan, frovatriptan, rizatriptan, sumatriptan, naratriptan, eletriptan, and zolmitriptan), ergotamines (e.g., dihydroergotamine and ergotamine tartrate), and $5HT_{1F}$-selective serotonin receptor agonists, such as lasmiditan. Other suitable acute headache therapeutic agents include non-steroidal anti-inflammatory drugs (e.g., acetylsalicylic acid, ibuprofen, naproxen, indomethacin, and diclofenac), and opioids (e.g., codeine, morphine, hydrocodone, fentanyl, meperidine, and oxycodone). In one embodiment, the acute headache therapeutic agent administered in combination with an anti-PAC1 antibody or antigen-binding fragment of the invention is a triptan. In another embodiment, the acute headache therapeutic agent administered in combination with an anti-PAC1 antibody or antigen-binding fragment of the invention is an ergotamine. In yet another embodiment, the acute headache therapeutic agent administered in combination with an anti-PAC1 antibody or antigen-binding fragment of the invention is a non-steroidal anti-inflammatory drug. In still another embodiment, the acute headache therapeutic agent administered in combination with an anti-PAC1 antibody or antigen-binding fragment of the invention is an opioid.

In some embodiments, the second headache therapeutic agent is a prophylactic headache therapeutic agent used for the prophylactic treatment of headaches or migraines. In one embodiment, the prophylactic headache therapeutic agent is an antiepileptic, such as divalproex, sodium valproate, valproic acid, topiramate, or gabapentin. In another embodiment, the prophylactic headache therapeutic agent is a beta-blocker, such as propranolol, timolol, atenolol, metoprolol, or nadolol. In yet another embodiment, the prophylactic headache therapeutic agent is an anti-depressant, such as a tricyclic antidepressant (e.g. amitriptyline, nortriptyline, doxepin, and fluoxetine). In still another embodiment, the prophylactic headache therapeutic agent is onabotulinum toxin A.

In certain embodiments, the methods of the invention comprise administering an anti-PAC1 antibody or antigen-binding fragment thereof described herein with an antagonist of the calcitonin gene-related peptide (CGRP) signaling pathway (i.e. inhibits the activation or signaling of the CGRP receptor by the CGRP ligand). For example, the anti-PAC1 antibody or antigen-binding fragment of the invention can be administered in combination with a CGRP pathway antagonist to treat or prevent a headache condition (e.g. migraine or cluster headache) in a patient in need thereof. In some embodiments, the CGRP pathway antagonist is an antagonist of the human CGRP receptor. CGRP receptor antagonists include small molecule inhibitors of the CGRP receptor, such as those described in U.S. Patent Publication No. 20060142273 and U.S. Pat. Nos. 7,842,808; 7,772,244; 7,754,732; 7,569,578; 8,685,965; 8,569,291; 8,377,955; 8,372,859; 8,143,266; 7,947,677; and 7,625,901, all of which are hereby incorporated by reference in their entireties. CGRP receptor antagonists can also include peptide antagonists of the receptor, such as those described in U.S. Pat. No. 8,168,592, which is hereby incorporated by reference in its entirety. In certain embodiments, the CGRP receptor antagonist to be administered with the anti-PAC1 antibodies and antigen-binding fragments of the invention is a monoclonal antibody that specifically binds to the human CGRP receptor, such as the antibodies described in U.S. Pat. No. 9,102,731 and U.S. Patent Publication No. 20160311913, both of which are hereby incorporated by reference in their entireties. In one particular embodiment of the methods of the invention, an anti-PAC1 antibody or antigen-binding fragment thereof described herein is administered in combination with an anti-CGRP receptor monoclonal antibody comprising a light chain variable region comprising the sequence of SEQ ID NO: 502 (sequence provided below) and a heavy chain variable region comprising the sequence of SEQ ID NO: 503 (sequence provided below) to treat or prevent a headache condition (e.g. migraine or cluster headache) in a patient. In another particular embodiment of the methods of the invention, the anti-CGRP receptor monoclonal antibody administered in combination with the anti-PAC1 antibody or antigen-binding fragment of the invention to treat or prevent a headache condition (e.g. migraine or cluster headache) in a patient is erenumab.

Light chain variable region sequence for exemplary anti-CGRP receptor monoclonal antibody:

```
                                  (SEQ ID NO: 502)
QSVLTQPPSV SAAPGQKVTI SCSGSSSNIG NNYVSWYQQL

PGTAPKLLIY DNNKRPSGIP DRFSGSKSGT STTLGITGLQ

TGDEADYYCG TWDSRLSAVV FGGGTKLTVL
```

Heavy chain variable region sequence for exemplary anti-CGRP receptor monoclonal antibody:

```
                                  (SEQ ID NO: 503)
QVQLVESGGG VVQPGRSLRL SCAASGFTFS SFGMHWVRQA

PGKGLEWVAV ISFDGSIKYS VDSVKGRFTI SRDNSKNTLF

LQMNSLRAED TAVYYCARDR LNYYDSSGYY HYKYYGMAVW

GQGTTVTVSS
```

In some embodiments, the CGRP pathway antagonist to be administered with the anti-PAC1 antibody or antigen-binding fragment of the invention to treat or prevent a headache condition (e.g. migraine or cluster headache) in a patient is an antagonist of the CGRP ligand. A CGRP ligand antagonist can be a decoy or soluble CGRP receptor or other protein that binds to the CGRP ligand, such as an anti-CGRP ligand antibody. Anti-CGRP ligand antibodies are known in the art and are described, for example, in WO 2007/054809; WO 2007/076336; WO 2011/156324; and WO 2012/162243, all of which are hereby incorporated by reference in their entireties. In certain embodiments, the CGRP ligand antagonist to be administered with the anti-PAC1 antibodies and antigen-binding fragments of the invention is a monoclonal antibody that specifically binds to human α-CGRP and/or human I3-CGRP. In one embodiment, the anti-CGRP ligand antibody is fremanezumab. In another embodiment, the anti-CGRP ligand antibody is galcanezumab. In yet another embodiment, the anti-CGRP ligand antibody is eptinezumab.

The present invention also includes the use of anti-PAC1 antibodies and antigen-binding fragments in any of the methods disclosed herein. For instance, in certain embodiments, the present invention provides an anti-PAC1 antibody or antigen-binding fragment thereof described herein for use in a method for treating or preventing a headache condition in a patient in need thereof. In some such embodiments, the headache condition is migraine. The migraine may be episodic migraine or chronic migraine. In other embodiments, the headache condition is cluster headache. In some embodiments, the method for treating or preventing a headache condition comprises administering a second headache therapeutic agent in combination with the anti-PAC1 antibody or antigen-binding fragment thereof. In one embodiment, the second headache therapeutic agent is an acute headache therapeutic agent, such as a $5HT_{1B}$, $5HT_{1D}$ and/or $5HT_{1F}$ serotonin receptor agonist (e.g. a triptan or ergotamine), a non-steroidal anti-inflammatory drug, or an opioid. In another embodiment, the second headache therapeutic agent is a prophylactic headache therapeutic agent, such as an antiepileptic, a beta-blocker, an anti-depressant, onabotulinum toxin A, or a CGRP pathway antagonist. In some embodiments, the CGRP pathway antagonist is a human CGRP receptor antagonist. In one particular embodiment, the human CGRP receptor antagonist is a monoclonal antibody that specifically binds to the human CGRP receptor, such as erenumab. In other embodiments, the CGRP pathway antagonist is an antagonist of the CGRP ligand, such as a monoclonal antibody that specifically binds to human α-CGRP and/or human β-CGRP. In certain embodiments, the anti-CGRP ligand antibody is fremanezumab, galcanezumab, or eptinezumab.

In some embodiments, the present invention provides an anti-PAC1 antibody or antigen-binding fragment described herein for use in a method for inhibiting vasodilation in a patient in need thereof. In such embodiments, the patient may be diagnosed with or have a headache condition, such as migraine (e.g. episodic or chronic migraine) or cluster headache. In other embodiments, the present invention provides an anti-PAC1 antibody or antigen-binding fragment described herein for use in a method for inhibiting activation of human PAC1 receptor in a patient having a headache condition. The headache condition may be migraine (e.g. episodic or chronic migraine) or cluster headache.

The use of anti-PAC1 antibodies or antigen-binding fragments thereof for preparation of medicaments for administration according to any of the methods disclosed herein is specifically contemplated. For example, in some embodiments, the present invention encompasses the use of an anti-PAC1 antibody or antigen-binding fragment described herein in the preparation of a medicament for treating or preventing a headache condition in a patient in need thereof. In some such embodiments, the headache condition is migraine. The migraine may be episodic migraine or chronic migraine. In other embodiments, the headache condition is cluster headache. In certain embodiments, the anti-PAC1 antibody or antigen-binding fragment thereof is formulated for administration with a second headache therapeutic agent. In one embodiment, the second headache therapeutic agent is an acute headache therapeutic agent, such as a $5HT_{1B}$, $5HT_{1D}$ and/or $5HT_{1F}$ serotonin receptor agonist (e.g. a triptan or ergotamine), a non-steroidal anti-inflammatory drug, or an opioid. In another embodiment, the second headache therapeutic agent is a prophylactic headache therapeutic agent, such as an antiepileptic, a beta-blocker, an anti-depressant, onabotulinum toxin A, or a CGRP pathway antagonist. In some embodiments, the CGRP pathway antagonist is a human CGRP receptor antagonist. In one particular embodiment, the human CGRP receptor antagonist is a monoclonal antibody that specifically binds to the human CGRP receptor, such as erenumab. In other embodiments, the CGRP pathway antagonist is an antagonist of the CGRP ligand, such as a monoclonal antibody that specifically binds to human α-CGRP and/or human β-CGRP. In certain embodiments, the anti-CGRP ligand antibody is fremanezumab, galcanezumab, or eptinezumab.

In some embodiments, the present invention includes the use of an anti-PAC1 antibody or antigen-binding fragment described herein in the preparation of a medicament for inhibiting vasodilation in a patient in need thereof. In such embodiments, the patient may be diagnosed with or have a headache condition, such as migraine (e.g. episodic or chronic migraine) or cluster headache. In other embodiments, the present invention includes the use of an anti-PAC1 antibody or antigen-binding fragment described herein in the preparation of a medicament for inhibiting activation of human PAC1 receptor in a patient having a headache condition. The headache condition may be migraine (e.g. episodic or chronic migraine) or cluster headache.

The anti-PAC1 antibodies and antigen-binding fragments of the invention are also useful for detecting human PAC1 in biological samples and identification of cells or tissues that express human PAC1. For instance, the anti-PAC1 antibodies and antigen-binding fragments can be used in diagnostic assays, e.g., immunoassays to detect and/or quantify PAC1 expressed in a tissue or cell. In addition, the anti-PAC1 antibodies and antigen-binding fragments described herein can be used to inhibit PAC1 from forming a complex with PACAP, thereby modulating the biological activity of PAC1 in a cell or tissue. Such biological activity includes elevation of intracellular cAMP and vasodilation.

The anti-PAC1 antibodies and antigen-binding fragments described herein can be used for diagnostic purposes to detect, diagnose, or monitor diseases and/or conditions associated with PAC1, including migraine, cluster headache, and anxiety disorders, such as posttraumatic stress disorder. Also provided are methods for the detection of the presence of PAC1 in a sample using classical immunohistological methods known to those of skill in the art (e.g., Tijssen, 1993, Practice and Theory of Enzyme Immunoassays, Vol 15 (Eds R. H. Burdon and P. H. van Knippenberg, Elsevier, Amsterdam); Zola, 1987, Monoclonal Antibodies: A Manual of Techniques, pp. 147-158 (CRC Press, Inc.); Jalkanen et al., 1985, J. Cell. Biol. 101:976-985; Jalkanen et al., 1987, J. Cell Biol. 105:3087-3096). Examples of methods useful in the detection of the presence of PAC1 include immunoassays, such as the enzyme linked immunosorbent assay (ELISA) and the radioimmunoassay (MA), using the anti-PAC1 antibodies and antigen-binding fragments described herein. The detection of PAC1 can be performed in vivo or in vitro.

For diagnostic applications, the anti-PAC1 antibody or antigen-binding fragment can be labeled with a detectable labeling group. Suitable labeling groups include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antibody or antigen-binding fragment via spacer arms of various lengths to reduce potential steric hindrance. Various methods for labeling proteins are known in the art and may be used.

In another embodiment, the anti-PAC1 antibodies and antigen-binding fragments described herein can be used to identify a cell or cells that express PAC1. In a specific embodiment, the antibody or antigen-binding fragment is labeled with a labeling group and the binding of the labeled antibody or antigen-binding fragment to PAC1 is detected. The antibodies or antigen-binding fragments can also be used in immunoprecipitation assays in biological samples. In a further specific embodiment, the binding of the antibody or antigen-binding fragment to PAC1 is detected in vivo. In a further specific embodiment, the antibody or antigen-binding fragment is isolated and measured using techniques known in the art. See, for example, Harlow and Lane, 1988, Antibodies: A Laboratory Manual, New York: Cold Spring Harbor (ed. 1991 and periodic supplements); John E. Coligan, ed., 1993, Current Protocols In Immunology New York: John Wiley & Sons.

The following examples, including the experiments conducted and the results achieved, are provided for illustrative purposes only and are not to be construed as limiting the scope of the appended claims.

EXAMPLES

Example 1. Crystal Structure-Guided Design of Human PAC1 Antibodies

The crystal structure of a complex between the extracellular domain (ECD) of human PAC1 and the Fab fragment of a human anti-PAC1 neutralizing antibody (29G4v9) was determined. The human PAC1 ECD and anti-PAC1 Fab were separately purified and then complexed together in 1:1 molar ratio. The sample was subsequently run over gel filtration column equilibrated in 20 mM TRIS pH 7.5, 50 mM NaCl, 5 mM EDTA and concentrated to 35 mg/ml and filtered.

The sequences for the heavy chain (comprising the variable region (VH), CH1 constant region, upper hinge, and caspase III cleavage site) and the light chain (comprising the variable region (VL) and CL constant region) of the Fab fragment are listed below. The sequence of the human PAC1 ECD construct is provided below and contained amino acids 26 to 143 of human PAC1 (SEQ ID NO: 1) minus the region between amino acids 89-109.

Amino acid sequence for heavy chain of 29G4v9 Fab (comprised of VH region (amino acids: 1-120); CH1 region (amino acids: 121-218); upper hinge region (amino acids 219-221), and caspase III cleavage site (222-226):

```
                                      (SEQ ID NO: 2)
QVQLVESGGG VVQPGRSLRL SCAASGFTFS RFAMHWVRQA

PGKGLEWVAV ISYDGGNKYY AESVKGRFTI SRDNSKNTLY

LQMNSLRAED TALFYCARGY DVLTGYPDYW GQGTLVTVSS

ASTKGPSVFP LAPCSRSTSE STAALGCLVK DYFPEPVTVS

WNSGALTSGV HTFPAVLQSS GLYSLSSVVT VPSSNFGTQT

YTCNVDHKPS NTKVDKTVER KGDEVD
```

Amino acid sequence for light chain of 29G4v9 Fab (comprised of VL region (amino acids: 1-108) and CL region (amino acids: 109-214):

```
                                      (SEQ ID NO: 3)
DIQLTQSPSF LSASVGDRVT ITCRASQSIG RSLHWYQQKP

GKAPKLLIKY ASQSLSGVPS RFSGSGSGTE FTLTISSLQP

EDFATYYCHQ SSRLPFTFGP GTKVDIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

Amino acid sequence of the human PAC1 ECD construct:

```
                                      (SEQ ID NO: 4)
GSMAHSDGIF KKEQAMCLEK IQRANELMGF NDSSPGCPGM

WDNITCWKPA HVGEMVLVSC PELFRIFNPD QDMGVVSRNC

TEDGWSEPFP HYFDACGFDE YESET
```

Purified human PAC1 ECD and the anti-PAC1 Fab were initially co-crystallized using sitting drop vapor diffusion method with commercially available screens. The crystallized condition (Qiagen MPD Suite Screen #61 (134561)) was further expanded using hanging drop vapor diffusion method. Protein and crystallization buffer (0.1M Citric Acid pH 4.0, 40% MPD) were mixed 1:1 in 1111 hanging drops over a reservoir solution of crystallization buffer at 4° C. Rod-shaped crystals formed within several weeks.

The crystal was equilibrated in the crystallization buffer as cryo-protectant, and was frozen in liquid nitrogen for shipment to Lawrence Berkeley National Laboratories for data collection. The data set was collected at the Advanced Light Source Synchrotron Beamline 5.0.2 on an ADSC-Q315r CCD Detector (λ=1.000 Å). The data were integrated and scaled using HKL2000 (Otwinowski and Minor, Methods Enzymology, Vol. 276, 307-326, 1997) and were 99.8% complete to 2.00 Å with $R_{merge}$ of 0.081 (98.0% complete last shell 2.07-2.00 Å with I/σ=2.35). The crystals belong to the orthorhombic space group P21212 with unit cell dimensions of a=65.2 Å, b=177.9 Å, c=53.8 Å, α=90°, β=90°, γ=90°. The crystal structure was solved by molecular replacement using PhaserMR (Winn et al., Acta Crystallogr., Sect. D: Biol. Crystallogr., Vol. 67: 235-242, 2011). A proprietary Fab structure was used as the first search model to solve the anti-PAC1 Fab component. Subsequent molecular replacement used PDBID: 2JOD (Sun et al., Proc. Natl. Acad. Sci. USA, Vol. 104: 7875, 2007), a human PAC1 ECD NMR structure, as starting model to solve the human PAC1 ECD component. There is one ECD molecule and one Fab molecule in the asymmetric unit. The structure was refined using both Refmac5 (Winn et al., Acta Crystallogr., Sect. D: Biol. Crystallogr., Vol. 67: 235-242, 2011; Murshudov et al., Acta Crystallogr., Sect. D: Biol. Crystallogr., Vol. 67: 355-367, 2011) and Phenix.refine (Adams et al., Acta Crystallogr., Sect. D: Biol. Crystallogr., Vol. 66: 213-221, 2010), and model building was performed using the graphics program Coot (Emsley and Cowtan, Acta Crystallogr., Sect. D: Biol. Crystallogr., Vol. 2004, 60: 2126-2132, 2004).

Figure 1B:
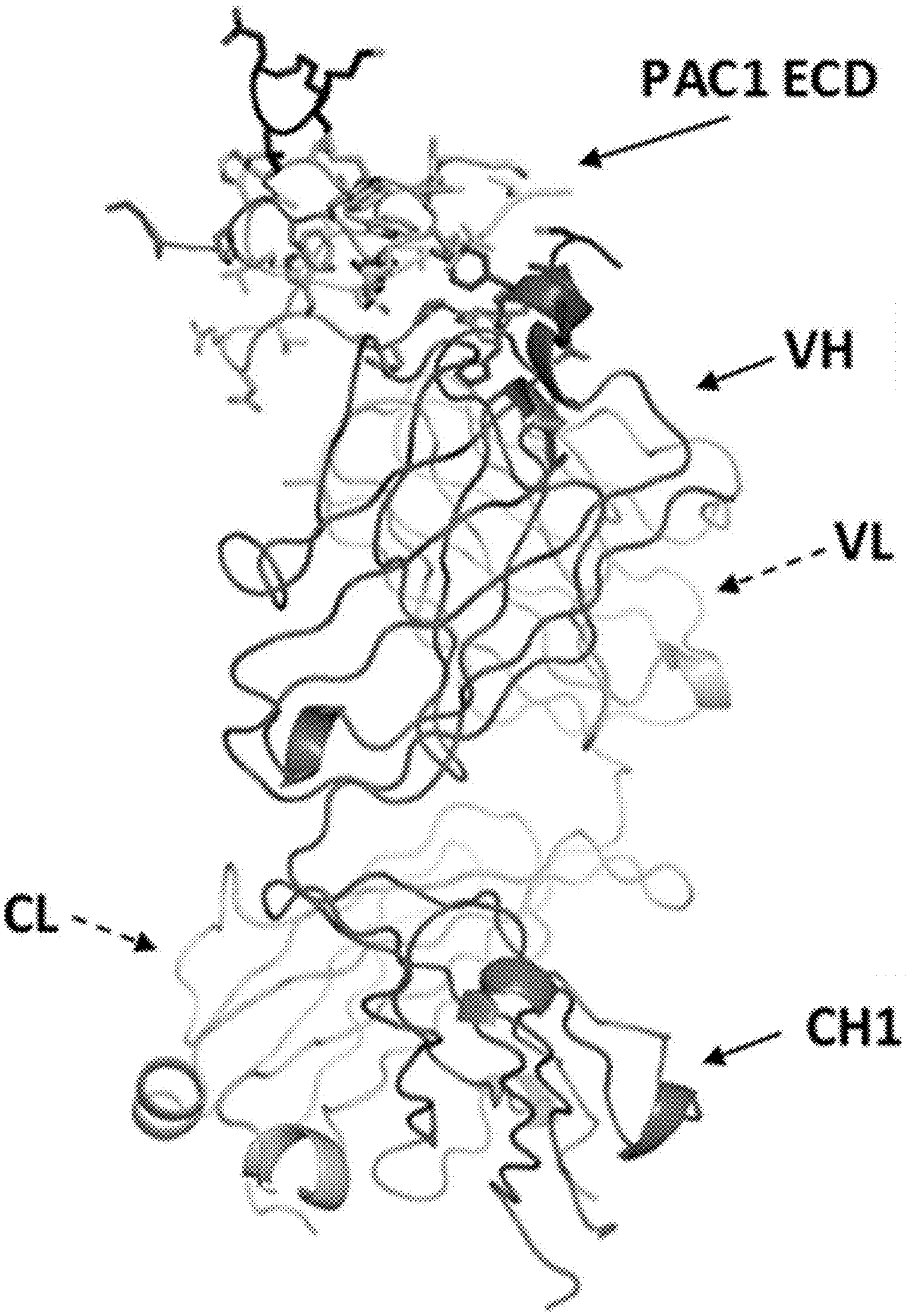
FIG. 1B is a side view of the crystal structure of the complex between human PAC1 ECD and the Fab fragment of the 29G4v9 antibody. The view depicts the structure shown in FIG. 1A rotated 90° to the left. In this view, the light chain variable region (VL) is positioned behind the heavy chain variable region (VH), and the light chain constant region (CL) is positioned behind the heavy chain CH1 constant region.

The structure of the human PAC1 ECD: anti-PAC1 Fab complex was refined to 2.00 Å with an R-factor of 20% and $R_{free}$ of 23%. A front view and side view of the structure of the complex is shown in FIGS. 1A and 1B, respectively. The interaction between the 29G4v9 Fab and the PAC1 ECD is comprised of hydrophobic, electrostatic and hydrogen bond interactions. The interaction between the 29G4v9 Fab and the PAC1 ECD has buried surface area (1613 Å 2) and shape complementarity (0.695) values that are typical for antibody-antigen interactions. All amino acids in the PAC1 ECD that contained at least one non-hydrogen atom at a distance of 5 Å or less from a non-hydrogen atom in the 29G4v9 Fab were determined to be the core interface amino acids in the PAC1 ECD. Distances of the atoms were calculated with the PyMOL program (DeLano, W. L. The PyMOL Molecular Graphics System. (Palo Alto, 2002)). The core interface amino acids in the PAC1 ECD include Asp59, Asn60, Ile61, Arg116, Asn117, Thr119, Asp121, Gly122, Trp123, Ser124, Glu125, Pro126, Phe127, Pro128, His129, Tyr130, Phe131, Asp132, and Gly135 with the amino acid position numbers relative to SEQ ID NO: 1.

Figure 2A:
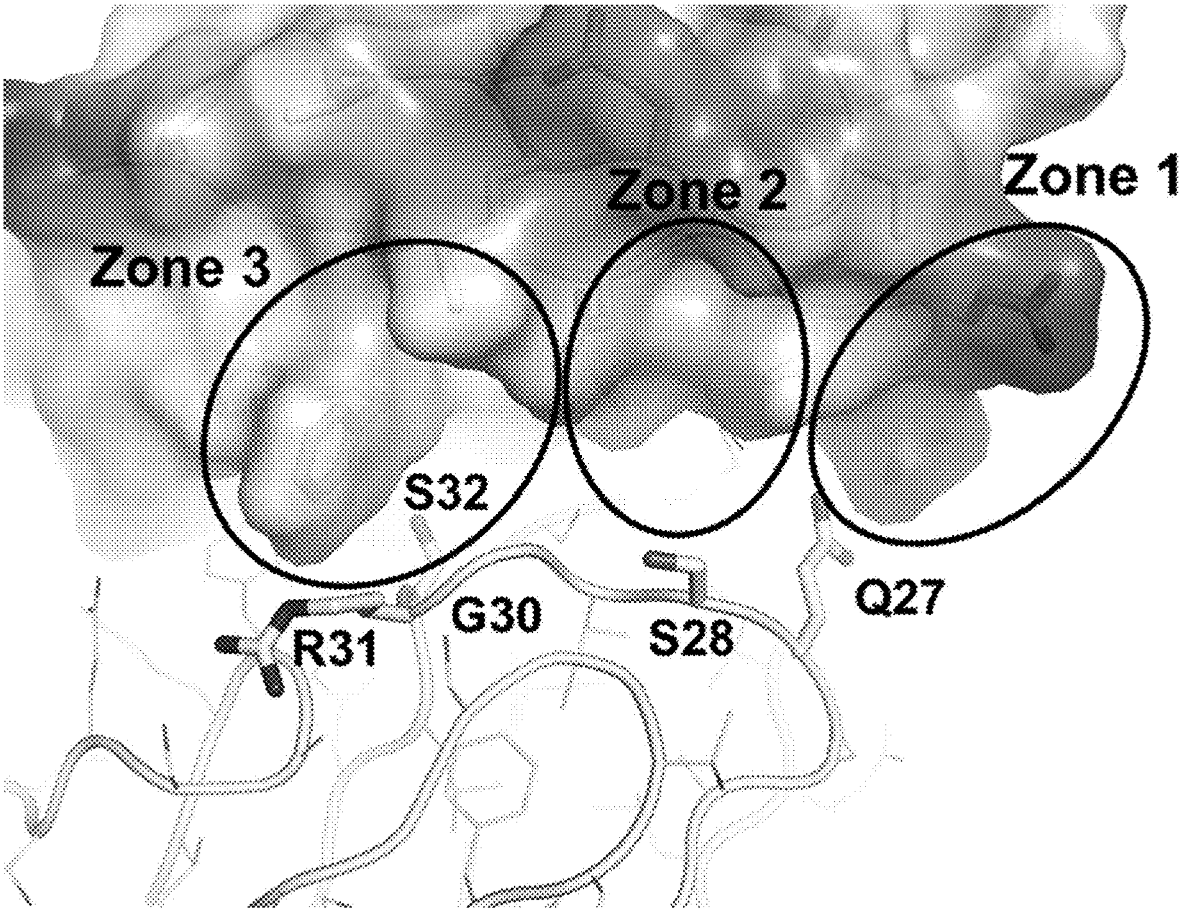
FIG. 2A is an expanded view of the interface between the human PAC1 ECD and the light chain CDR1 (amino acids 24 to 34 of SEQ ID NO: 3) of the 29G4v9 Fab. Zone 1 contains Glu120 and Asp121 residues of human PAC1 ECD (SEQ ID NO: 1), whereas Zone 3 contains the Phe127 residue of human PAC1 ECD.
Figure 2B:
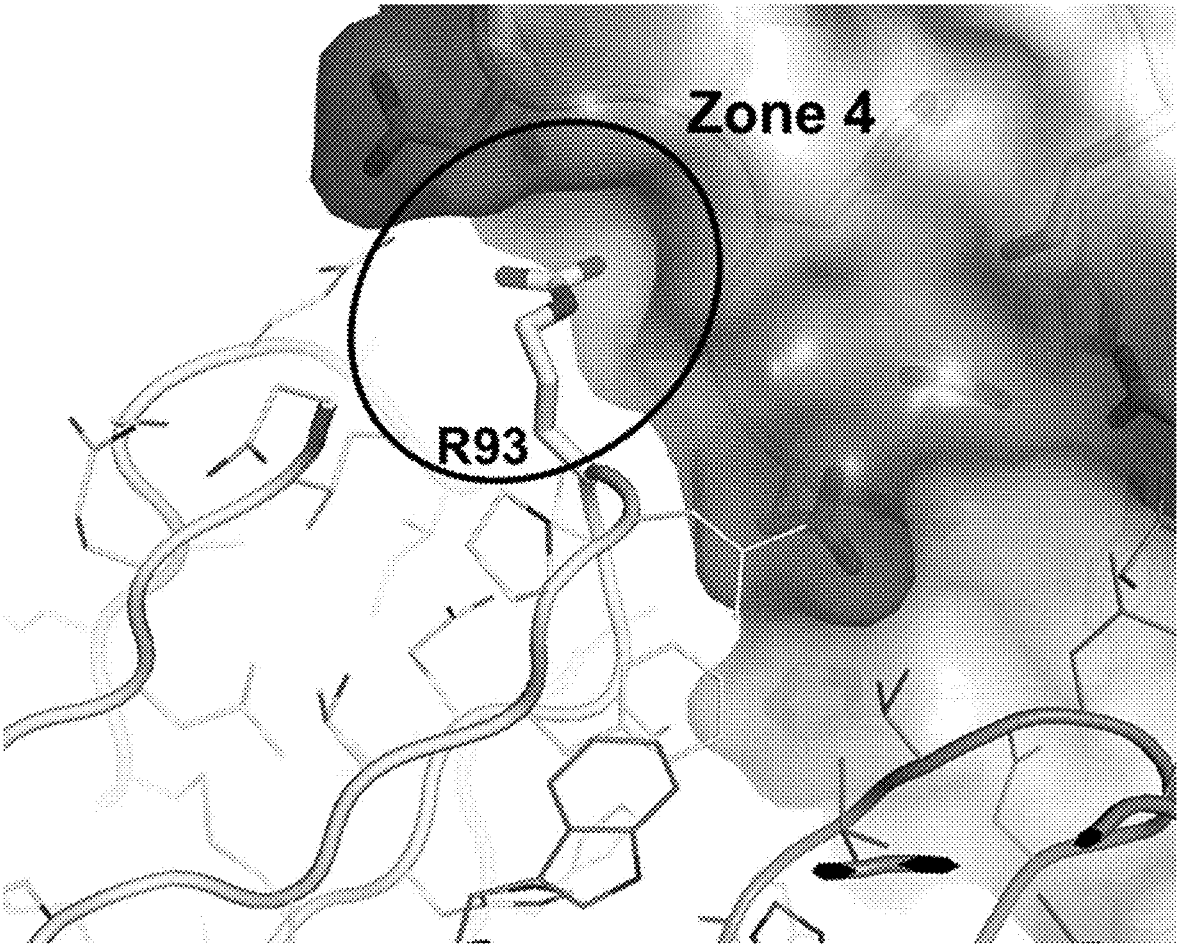
FIG. 2B is an expanded view of the interface between the human PAC1 ECD and Arg93 residue in the light chain CDR3 of the 29G4v9 Fab.

The interface between the 29G4v9 Fab and the PAC1 ECD in the crystal structure was analyzed to identify regions where the interactions between the two molecules were sub-optimal. Based on the structural analysis, mutations of the amino acids in the light and heavy chain variable regions were designed to enhance the interaction in these regions between the Fab and the PAC1 ECD to improve binding affinity and/or inhibitory potency of the antibody. In particular, analysis of the interaction between the Fab light chain and PAC1 ECD revealed four regions where mutations in the Fab light chain may possibly improve interactions with PAC1. In zone 1, a region containing PAC1 ECD amino acids Glu120 and Asp121, mutation of Gln27 in the light chain CDR1 (SEQ ID NO: 3) to lysine, tyrosine, or arginine was proposed to provide better charge complementarity or hydrogen bonding potential with the Glu120 and Asp121 PAC1 amino acids (FIG. 2A). Zone 2 is a region with positive electrostatic potential and mutation of Ser28 in the light chain CDR1 (SEQ ID NO: 3) to glutamate was proposed to provide better charge complementarity (FIG. 2A). Zone 3 is a hydrophobic region containing PAC1 ECD Phe127 residue and has hydrogen bonding potential. Gly30, Arg31, and Ser32 in the light chain CDR1 lie somewhat distant from zone 3 (FIG. 2A). Thus, multiple mutations were proposed at these three sites as summarized in Table 6 below to improve the hydrophobic or hydrogen bonding interactions between these three residues and this zone of the PAC1 ECD. Arg93 in the light chain CDR3 sits in a pocket of PAC1 residues with negative electrostatic potential (zone 4; FIG. 2B). However, due to the geometry, Arg93 does not form any direct hydrogen bonds with PAC1 residues. Mutations of Arg93 in the light chain CDR3 to glutamine, lysine, histidine, or asparagine were proposed to provide alternate charge complementarity or hydrogen bond potential with residues in the PAC1 ECD (FIG. 2B).

Figure 3A:
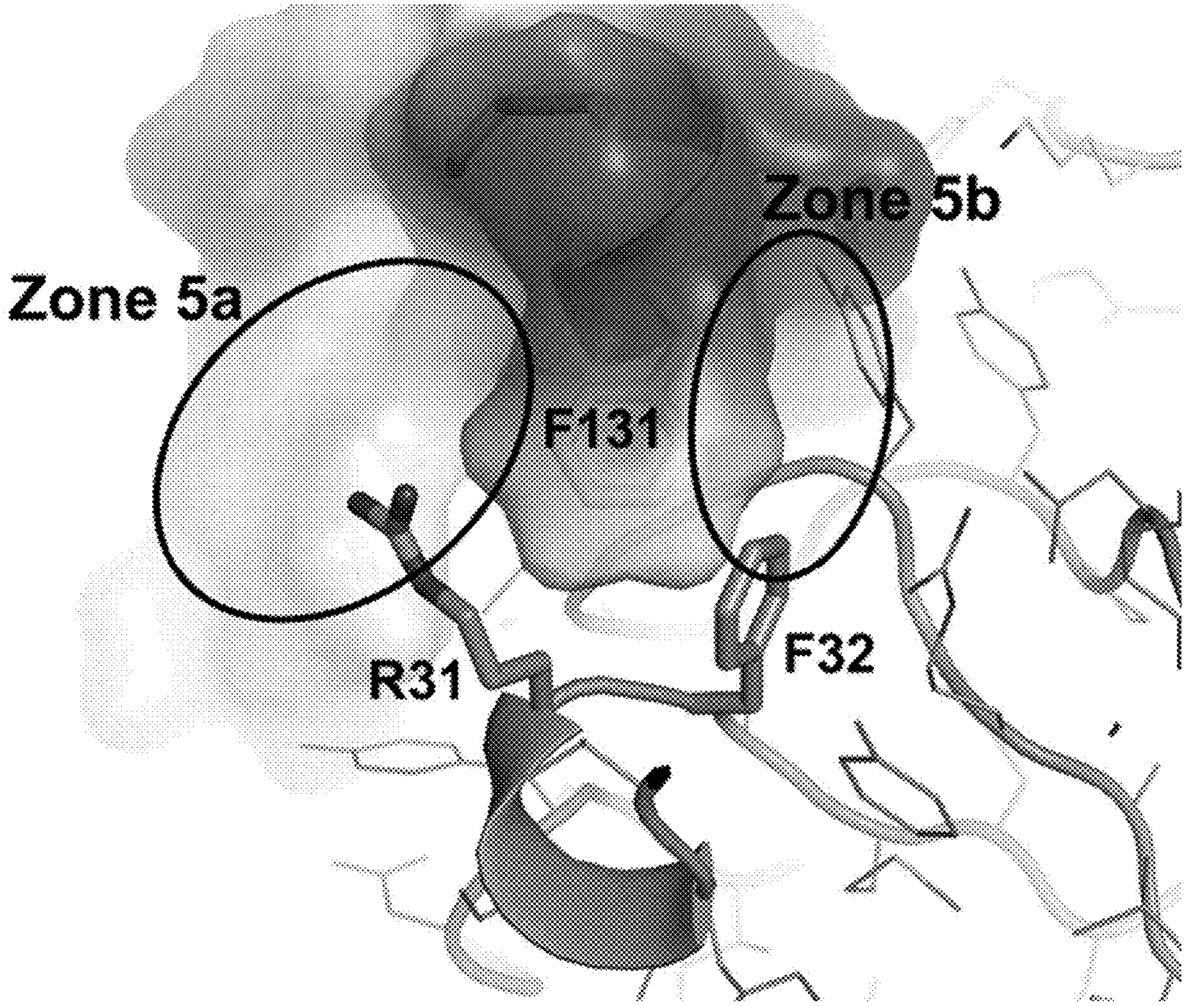
FIG. 3A is an expanded view of the interface between the human PAC1 ECD and heavy chain CDR1 amino acids Arg31 and Phe32 of the 29G4v9 Fab. The two heavy chain CDR1 amino acids lie on either side of the Phe131 residue of human PAC1 ECD.
Figure 3B:
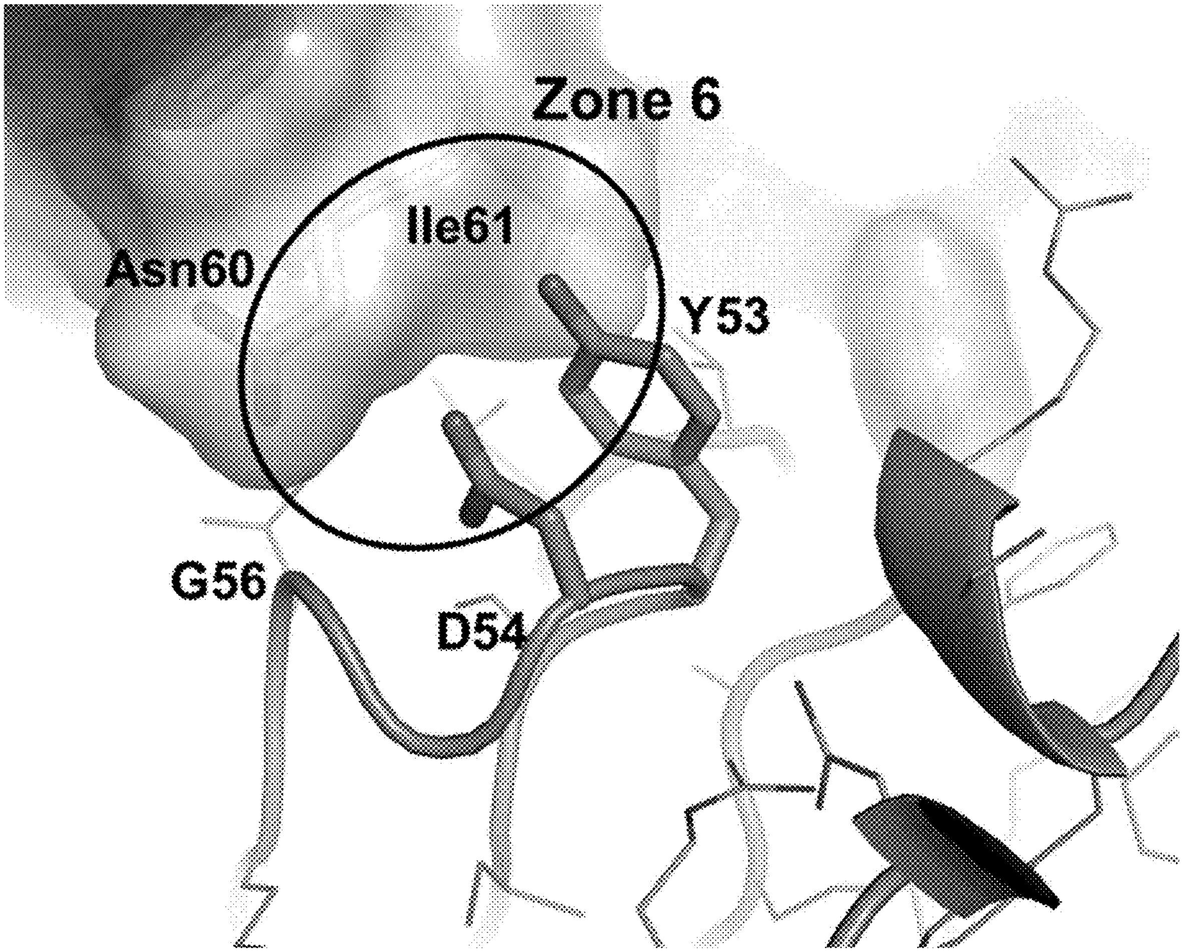
FIG. 3B is an expanded view of the interface between a region of the human PAC1 ECD containing amino acid residues Asn60 and Ile61 (relative to SEQ ID NO: 1) and heavy chain CDR2 amino acids Tyr53, Asp54, and Gly56 of the 29G4v9 Fab.
Figure 3C:
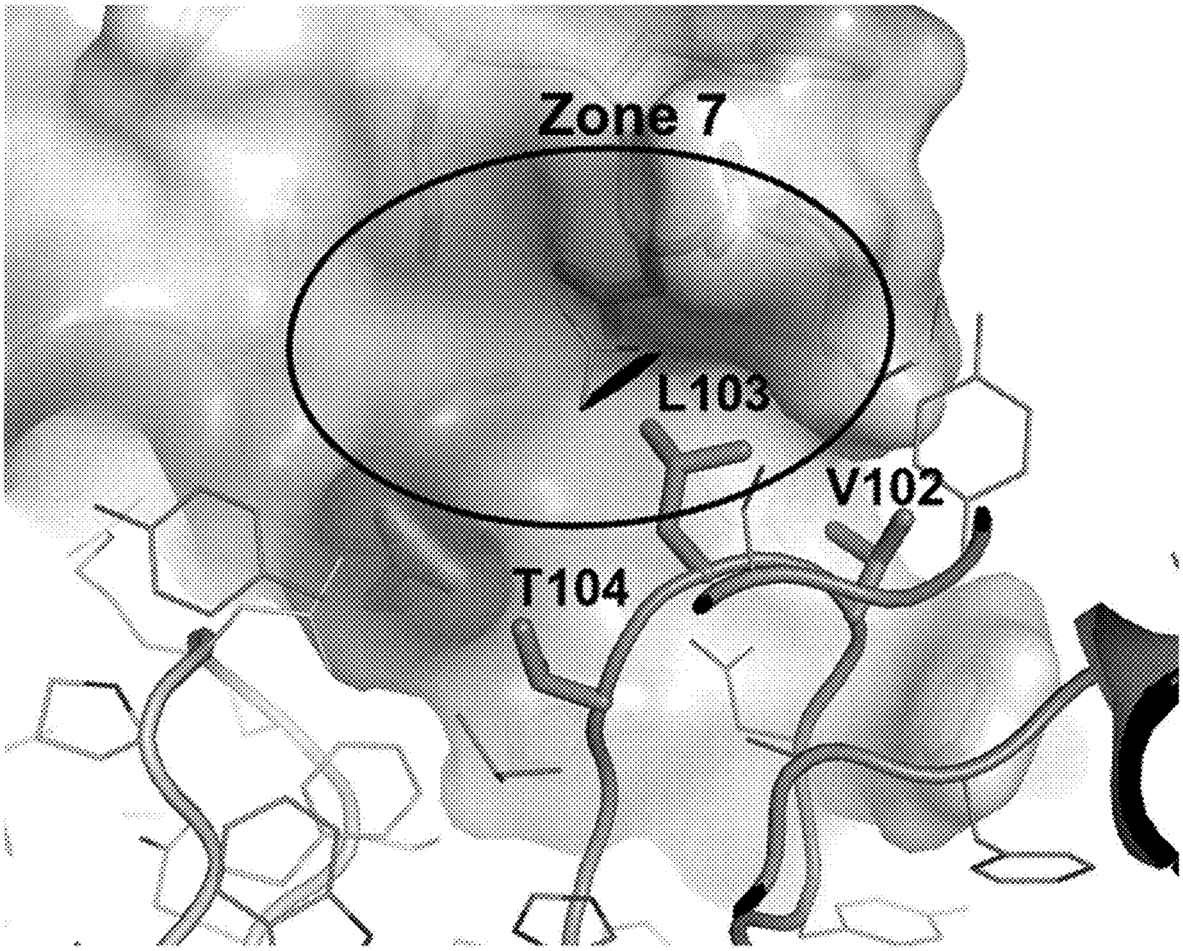
FIG. 3C is an expanded view of the interface between the human PAC1 ECD and heavy chain CDR3 amino acids Val102, Leu103, and Thr104 of the 29G4v9 Fab.

Analysis of the interaction between the 29G4v9 Fab heavy chain and PAC1 ECD revealed three main regions where mutations in the Fab heavy chain may improve interactions with the PAC1 ECD. As shown in FIG. 3A, zone 5 encompasses PAC1 amino acid Phe131, and can be divided into two sub-zones that lie on either side of Phe131. Arg31 and Phe32 in the heavy chain CDR1 lie in these sub-zones and mutations at these sites were proposed to improve the hydrophobic interactions with PAC1 Phe131 residue or provide alternate charge complementarity interactions. See Table 6 for list of mutations. In zone 6, which includes PAC1 ECD residues Asn60 and Ile61 (relative to SEQ ID NO: 1), mutation of heavy chain CDR2 residues Tyr53, Asp54 and Gly56 were proposed to improve hydrophobic interactions or provide alternate hydrogen bonding with Asn60 and Ile61 PAC1 residues (FIG. 3B). In zone 7, a region with hydrophobic residues and some negative electrostatic potential, mutations of heavy chain CDR3 residues Val102, Leu103 and Thr104 as set forth in Table 6 were proposed to improve hydrophobic interactions or provide alternate hydrogen bonding interactions (FIG. 3C).

A summary of the specific mutations proposed to improve the interaction between the anti-PAC1 antibody and the human PAC1 receptor based on the analysis of the crystal structure of the Fab/PAC1 ECD complex is provided in Table 6 below.

TABLE 6

Summary of Structure-Based Mutations in PAC1 Antibody Variable Regions

| Amino Acid Position[1] | Mutations |
|---|---|
| Light Chain | |
| Gln27 | Lys, Tyr, Arg |
| Ser28 | Glu |
| Gly30 | Leu, Val, Ile, Thr, Tyr, Phe, Met, Ala, His, Asn, Gln, Glu, Asp, Trp, Ser |
| Arg31 | Phe, Tyr, Leu, Ser, Thr, Gln, Asn |
| Ser32 | Leu, Thr, Ala, Met, Lys, Gln |
| Arg93 | Gln, Lys, His, Asn |
| Heavy Chain | |
| Arg31 | Leu, Tyr, Met, Ile, Lys |
| Phe32 | Tyr, Lys, Gln |
| Tyr53 | Gln, Leu, Ser |
| Asp54 | Tyr, Gln, Asn |
| Gly56 | Ser, Thr |
| Val102 | Phe, Tyr, Trp, Leu, Thr, Ile, Met |
| Leu103 | Asn, Gln, Phe, Met, Ser, Thr |
| Thr104 | Ser |

[1]Amino acid positions for the light chain are relative to SEQ ID NO: 3 and amino acid positions for the heavy chain are relative to SEQ ID NO: 2.

In addition to the mutations designed by analysis of the interacting amino acids between the anti-PAC1 Fab and the human PAC1 ECD as described above, an in silico affinity maturation analysis using the crystal structure was also conducted to identify additional mutations to improve the binding affinity and/or inhibitory potency of the anti-PAC1 antibody. Amino acid residues in the 29G4v9 Fab involved in binding to the human PAC1 ECD were identified by visual inspection of the crystal structure of the complex described above. These interface residues of the antibody were selected for virtual mutation to all other amino acids except for cysteine. The impact of the mutation to the antibody/PAC1 ECD binding interaction was assessed by calculating the change in binding free energy ($\Delta\Delta G_{binding}$) upon mutation of a particular residue using Discovery Studio molecular modeling software from Biovia. A negative value of $\Delta\Delta G_{binding}$ indicates that the mutation results in a stronger binding to the PAC1 ECD compared the parental molecule. These calculations identified approximately 65 mutations that led to negative value of $\Delta\Delta G_{binding}$. These 65 mutations were further narrowed down to 50 (18 in the light chain and 32 in the heavy chain) based on the visual inspection and analysis of the "modeled" structure of these variants with the PAC1 ECD. These 50 mutations predicted to increase the binding affinity of the antibody for PAC1 based on the binding free energy calculations are summarized in Table 7 below.

TABLE 7

Summary of Mutations in PAC1 Antibody Variable Regions Predicted from In Silico Analysis

| Amino Acid Position[1] | Mutations |
|---|---|
| Light Chain | |
| Gln27 | Lys, Tyr, Arg |
| Gly30 | Arg |
| Ser32 | Arg, Asn, His, Leu, Val |
| Ser91 | Lys, Thr |
| Ser92 | Gln, Ile |
| Leu94 | Arg, His, Tyr |
| Phe96 | Arg, Lys |
| Heavy Chain | |
| Phe32 | His |
| Ala33 | Ser |
| Ser52 | Ile, Gln, Met |
| Asp54 | Tyr, Gln, Asn, Ile, Leu |
| Gly55 | Ala |
| Gly56 | Arg, Asn, His, Tyr |
| Asn57 | Arg, His, Lys, Tyr |
| Lys58 | Glu |
| Glu62 | Arg |
| Gly99 | Ala |
| Tyr100 | His |
| Val102 | Ile |
| Leu103 | Arg |
| Thr104 | Ser, His |
| Gly105 | Ser, Lys |
| Tyr106 | Arg, Lys |
| Asp108 | Arg |

[1]Amino acid positions for the light chain are relative to SEQ ID NO: 3 and amino acid positions for the heavy chain are relative to SEQ ID NO: 2.

The in silico approach resulted in the identification of additional mutations, both in terms of different amino acids as well as different positions within the light and/or heavy chain, as compared with the structure-based analysis.

The mutations described in this example were incorporated into an anti-PAC1 antibody by recombinant production and tested for the ability to inhibit PACAP-induced activation of human PAC1 in an in vitro cell-based assay as described in Example 3 herein.

Example 2. Yeast Display Affinity Maturation of 29G4v10 Human PAC1 Antibody

Figure 4:
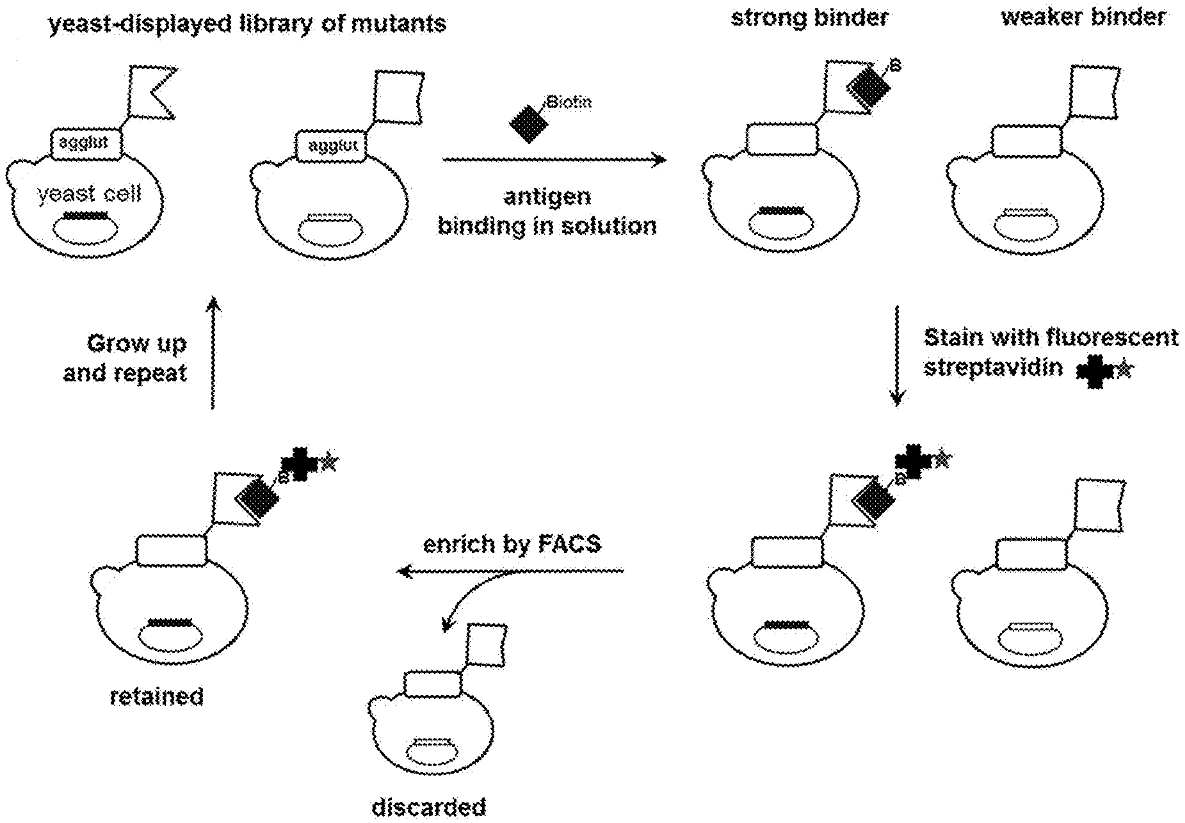
FIG. 4 is a schematic of the selection process for improved binding mutants from a yeast-displayed antibody Fab mutant library.

One powerful approach for affinity maturation involves constructing yeast-displayed libraries of antibody Fab mutants and selecting for improved binders through fluorescence-assisted cell sorting (FACS)(FIG. 4). To generate anti-PAC1 antibodies with improved inhibitory potency, the 29G4v10 antibody (VH region of SEQ ID NO: 191; VL region of SEQ ID NO: 52) was affinity matured by FACS of yeast-displayed Fab libraries. The library designs were guided by the solved co-crystal structure described in Example 1 of the complex between human PAC1 ECD and 29G4v9 Fab, the CDRs of which are nearly identical to those of 29G4v10. Structural analysis initially identified six and seven CDR positions within the light chain (LC) and heavy chain (HC) for mutagenesis, respectively, and suggested strategies for affinity enhancement. Point mutants were designed to improve hydrophobic interactions and charge complementarity, and to provide alternate hydrogen-bond interactions across the interface. See Example 1. These point mutants initiated an engineering approach that involved iterative rounds of production, characterization, and rational combination of beneficial mutations. The yeast library designs sought to complement the linear approach described in Example 1 by more comprehensively exploring mutation combinations among the 13 positions and augmenting the diversification strategy at each chosen position.

By making separate LC and HC libraries, the theoretical diversities were kept to a manageable size of $<10^7$. The LC library was designed to utilize MIX19 saturation mutagenesis at five of the six chosen positions (Gln27, Gly30, Arg31, Ser32, and Arg93 of SEQ ID NO: 52). MIX19 represents a trimer phosphoramidite (codon) mixture encoding all amino acids except for cysteine. At the remaining light chain position (Ser28 of SEQ ID NO: 52), mutation to serine, glutamate, alanine or a stop codon was employed. To explore all seven HC positions (Arg31, Phe32, Tyr53, Gly56, Val102, Leu103, and Thr104 of SEQ ID NO: 191) in one library, we designed a custom mixture of nine codons (MIX9) for diversification at five of the seven heavy chain CDR positions (Arg31, Phe32, Tyr53, Val102, and Leu103 of SEQ ID NO: 191). Custom MIX9 comprised hydrophobic amino acids, basic amino acids, and hydrogen bond donors and acceptors (e.g. F, L, Y, M, Q, H, K, R, and S). Importantly, the custom MIX9 excluded cysteine, asparagine, and tryptophan to minimize introduction of sequence liabilities that could pose downstream manufacturability risks. Mutation to glycine, alanine, serine, and threonine was performed for the remaining two heavy chain positions (Gly56 and Thr104 of SEQ ID NO: 191). In summary, for this first campaign a mutHC library with a theoretical diversity of $8.5\times10^6$ and a mutLC library with a theoretical diversity of $9.9\times10^6$ were designed, and the constructed libraries oversampled the theoretical diversities by >9-fold.

The two constructed mutHC and mutLC Fab libraries were enriched for binding to the human PAC1 ECD using FACS, increasing the stringency with each successive round by lowering the concentration of ECD used for binding (Round 1: 30 nM PAC1 ECD; Round 2: 0.67 nM PAC1 ECD; and Round 3: 0.2 nM PAC1 ECD). An identically treated 29G4v10 Fab-yeast sample was routinely used to gate specifically for yeast clones exhibiting improved binding relative to the parental Fab. A normalized binding/display ratio for each clone was calculated by dividing the median fluorescence binding signal for each clone by the median fluorescence display signal for each clone. By round 3, improved binders were enriched from the mutHC library, but not the mutLC library. An abbreviated screen of ~200 yeast clones from the mutHC Round 3 pool yielded 11 modestly improved binders (Table 8). The improved affinity variants were produced recombinantly and evaluated for in vitro functional activity as described in Example 3. Fortuitously, the aspartate isomerization site within the 29G4v10 parental Fab, a potential liability for manufacturability, was remediated in all of these 11 unique mutants.

TABLE 8

Top Improved Binders from MutHC Library Screen

| Variant Ab ID | Substitutions with respect to 29G4v10 VH sequence (SEQ ID NO: 191)[1] HC CDR1 | HC CDR2 | HC CDR3 | Yeast Binding Screen Data at 0.2 nM PAC1: Normalized Binding Signal/ Display Signal (B/D) | Mutant vs. Wild-Type B/D Ratio |
|---|---|---|---|---|---|
| iPS: 421855 | R31K; F32Y | Y53F; D54K; G56S | V102L | 0.40 | 1.86 |
| iPS: 421861 | F32Y | D54Q | V102L | 0.38 | 1.80 |
| iPS: 421867 | R31H | Y53F; D54S; G56S | V102M | 0.35 | 1.61 |
| iPS: 421873 | R31K | D54R | V102L | 0.42 | 1.95 |
| iPS: 421879 | F32Y | D54S; G56A | V102L; T104S | 0.33 | 1.56 |
| iPS: 421885 | R31H; F32Y | Y53F; D54K; G56A | V102L | 0.45 | 2.09 |
| iPS: 421891 | R31H; F32Y | D54R; G56A | V102L | 0.49 | 2.27 |
| iPS: 421897 | R31H; F32Y | Y53F; D54Y; G56S | V102F | 0.39 | 1.83 |
| iPS: 421903 | R31H | Y53F; D54F | V102F | 0.44 | 2.07 |
| iPS: 421909 | R31H; F32Y | Y53F; D54M; G56T | V102F | 0.43 | 2.01 |
| iPS: 421915 | R31Y | Y53H; D54R; G56T | V102L; T104S | 0.35 | 1.63 |
| 29G4v10 Wild-Type | — | — | — | 0.21 | 1.00 |

[1]There were no changes in the sequence of the light chain relative to the 29G4v10 antibody for any of these variants.

Figure 5:
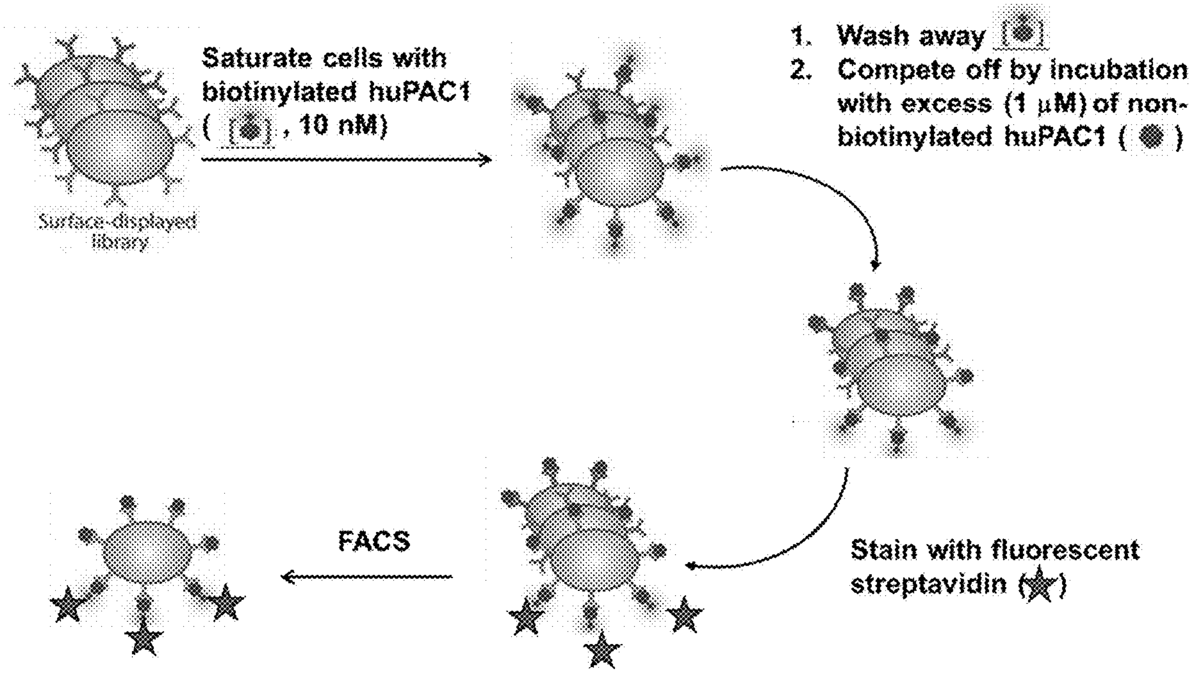
FIG. 5 is a schematic of the binding off-rate driven selection process for high affinity binding mutants from a yeast-displayed library.

To generate further affinity improvements, a chain-shuffled library that combined enriched mutations from the mutHC and mutLC sorted pools was also constructed. To improve discrimination among the top binding clones, a binding off-rate driven selection and screening strategy was implemented (FIG. 5). Yeast cells displaying the mutant Fabs were first saturated with biotinylated human PAC1 ECD and washed extensively before a prolonged incubation in buffer containing a large excess of unlabeled human PAC1 ECD (up to 24 hours). The incubation with unlabeled human PAC1 ECD, which occurred at temperatures ranging from 25° C. to 37° C., rendered dissociation events from the cells irreversible. Cells retaining the most binding to biotinylated PAC1, thereby exhibiting the slowest off-rate, were isolated by FACS after staining with a fluorescent streptavidin conjugate (FIG. 5). Yeast clones displaying Fabs exhibiting the slowest off-rates were the most highly fluorescent.

In the off-rate driven sort of the chain-shuffled library, an identically treated 29G4v10 Fab-yeast sample was employed to specifically isolate cells with greater biotinylated PAC1 binding after overnight competition with unlabeled PAC1. From two pools collected under different gating stringencies, ~600 individual yeast clones were screened using the binding off-rate assay and over 190 clones with higher remaining PAC1 binding than the parental 29G4v10 Fab were identified. Specificity of binding of these promising clones was evaluated by confirming there was no binding of the clones to the ECDs of unrelated receptors (programmed cell death protein 1 (PD1) and gastric inhibitory polypeptide receptor (GIPR)). Mutants containing additional cysteine anomalies, N-linked glycosylation, aspartate isomerization, asparagine deamidation, and tryptophan oxidation sites relative to the starting 29G4v10 sequence were also removed during the screen. The top 30 binding mutants are shown in Table 9 with sequence changes in the CDRs from parental 29G4v10 antibody and the percentage of human PAC1 ECD binding following the off-rate assay. Higher percentage association of PAC1 ECD binding indicates that the mutant Fabs have a slower off-rate.

TABLE 9

Top Improved Binders from Off-Rate Driven Screen of Chain-Shuffled Library

| | Substitutions with respect to 29G4v10 VH sequence (SEQ ID NO: 191) | | | Substitutions with respect to 29G4v10 VL sequence (SEQ ID NO: 52) | | | Secondary Screen: off-rate competition at 30° C. | |
|---|---|---|---|---|---|---|---|---|
| Clone ID | HC CDR1 | HC CDR2 | HC CDR3 | LC CDR1 | LC CDR2 | LC CDR3 | % association after off-rate | Normalized PAC1 ECD binding remaining (mutant vs. Q27K LC variant) |
| 2_C11 | R31Y; F32Y | D54S; G56S | V102L | Q27K; R31Q | — | — | 77% | 3.42 |
| 1_D07 | R31F; F32Y | Y53S; D54F; G56S | V102L | Q27K; R31Q | — | — | 56% | 2.66 |
| 2_B10 | R31H; F32Y | D54Q; G56S | V102L | Q27R; R31L; S32A | — | R93F | 54% | 2.79 |
| 2_G07 | R31Y; F32Y | Y53H; D54Y; G56T | V102P | Q27K; R31Q | — | — | 57% | 2.41 |
| 1_H04 | R31Y | Y53H; D54S; G56A | V102L; T104S | Q27K; R31Q | — | — | 52% | 2.37 |
| 1_F03 | — | — | — | Q27K; R31W | — | — | 47% | 3.23 |
| 2_E08 | — | — | — | Q27K; R31W | — | R93M | 50% | 2.29 |
| 1_F01 | R31H | D54S | V102L | Q27R; R31L; S32A | — | R93M | 50% | 2.21 |
| 2_F10 | R31H; F32Y | D54S | V102L; T104S | Q27K; G30W; R31K | — | — | 46% | 2.54 |
| 1_B08 | R31Y; F32Y | Y53S; D54R; G56S | V102L | Q27K; S28E; G30M; R31S; S32L; L33H; ΔH34[1] | — | R93M | 50% | 2.18 |
| 1_A11 | — | — | — | Q27R; S28A; G30S; R31N; S32L; L33H; ΔH34[1] | — | R93Y | 43% | 2.48 |
| 2_A10 | R31Y; F32Y | Y53S; D54M; G56T | — | Q27K; S28A; G30W; R31H; S32N | — | R93M | 55% | 1.70 |
| 2_G10 | R31M; F32Y | D54S; G56S | V102L | Q27K; R31Q | — | R93M | 49% | 2.07 |
| 2_E10 | R31K; F32Y | D54M; G56A | V102L | Q27K; R31W | — | — | 68% | 1.53 |
| 2_C05 | R31Y; F32Y | Y53S; D54R; G56S | V102L | Q27K; R31Q | — | R93M | 48% | 1.90 |
| 1_A09 | R31K; F32Y | D54S; G56A | V102L | Q27K; R31Q | — | — | 36% | 2.38 |
| 2_C02 | R31K; F32Y | Y53F; D54S; G56S | V102L; L103M | Q27K; R31W | — | R93M | 41% | 2.14 |

TABLE 9-continued

Top Improved Binders from Off-Rate Driven Screen of Chain-Shuffled Library

| | Substitutions with respect to 29G4v10 VH sequence (SEQ ID NO: 191) | | | Substitutions with respect to 29G4v10 VL sequence (SEQ ID NO: 52) | | | Secondary Screen: off-rate competition at 30° C. | |
|---|---|---|---|---|---|---|---|---|
| | | | | | | | | Normalized PAC1 ECD binding remaining |
| Clone ID | HC CDR1 | HC CDR2 | HC CDR3 | LC CDR1 | LC CDR2 | LC CDR3 | % association after off-rate | (mutant vs. Q27K LC variant) |
| 1_H06 | F32Y | D54S; G56A | V102L; T104S | Q27K; S28A; R31F | — | R93F | 38% | 2.16 |
| 2_D01 | — | — | V102L | Q27K; R31W | — | R93L | 34% | 2.10 |
| 2_B11 | R31Y; F32Y | Y53H; D54S | V102L; T104S | Q27R; R31M | — | R93M | 45% | 1.53 |
| 2_F05 | R31H; F32Y | D54S | V102L; T104S S32N | Q27R; S28A; G30F; R31G; | — | R931 | 51% | 1.54 |
| 1_F10 | R31Y | Y53H; D54S; G56A | V102L; T104S | Q27K; S28A; G30W; R31H; S32N | — | R93M | 39% | 1.96 |
| 1_D05 | R31Y; F32Y | Y53S; D54R; G56S | V102L | Q27H; S28A; G30Y; R31H; S32N | — | — | 45% | 1.82 |
| 1_E01 | R31F | Y53S; D54H; G56T | V102L; L103M; T104S | Q27K; R31W | — | — | 50% | 1.39 |
| 2_H10 | — | — | — | Q27R; S28A; G30F; R31G; S32N | — | R93M | 53% | 1.09 |
| 2_B08 | — | D54S; G56S | V102L | Q27K; S28A; G30W; R31H; S32N | — | R93M | 43% | 1.91 |
| 1_A10 | F32Y | Y53F; D54Q; G56S | V102L | Q27K; R31W | — | R93L | 49% | 1.65 |
| 1_B11 | R31M | Y53H; D54R; G56T | V102L | Q27K; R31Q | — | — | 44% | 1.65 |
| 1_D04 | R31H; F32Y | D54R; G56A | V102L | Q27K; R31Q | — | — | 37% | 2.12 |
| 1_C09 | R31H; F32Y | Y53F; D54H | — | Q27K; R31Q | — | — | 39% | 1.80 |
| 29G4v10 Wild-Type | — | — | — | — | — | — | 25% | 0.70 |
| VL Q27K variant | — | — | — | Q27K | — | — | 22% | 1.00 |

[1]The histidine residue at position 34 relative to the 29G4v10 light chain variable region sequence (SEQ ID NO: 52) is deleted in these mutants.

A set of second-generation libraries was designed to generate further affinity improvements. The first generation libraries described above focused diversification at a subset of the 29G4v10 parental antibody CDR positions that were within 4.5 Å of the PAC1 ECD in the crystal structure (Example 1). For the second generation libraries, mutagenesis in regions that were largely untouched in the first generation libraries, such as CDR2 and CDR3 of the light chain, were explored. For several positions already explored in the first generation libraries, sequencing trends were used to diversify to the limited set of neutral/beneficial mutations that had emerged after three rounds of sorting. Finally, some buried framework residues that could influence CDR conformations were targeted for limited diversification, with the mutation strategy favoring amino acids frequently found at the same position in other human VH3 and VK3 germlines.

In total, four second generation Fab libraries were designed to target 24 heavy chain CDR residues (amino acids 27, 29, 31-34, 49, 52-57, 70, 72, 77, 79, 98, 100-104, and 106 of SEQ ID NO: 191) and 17 light chain CDR residues (amino acids 27, 28, 30-32, 34, 46, 49-54, 92-94, and 96 of SEQ ID NO: 52) for diversification. The restricted diversity at many targeted positions enabled interrogation of more CDR positions within one library and co-optimization of HCDR1 with HCDR3 and LCDR1 with LCDR3. The four libraries that were constructed provided 8-24× coverage of the theoretical diversities ranging from $7\times10^6$ to $1\times10^7$.

The four constructed Fab libraries were enriched for binding to the human PAC1 ECD using FACS, as described above. By Round 3, only the mutHCDR2 and mutLCDR1-LCDR3 libraries yielded pools with equivalent or superior binding to parental 29G4v10 antibody. Therefore, these two pools were carried forward to make a mutH2/mutL1L3 chain-shuffled library for further affinity improvements. To enrich for the highest affinity mutants, 2B10, a top-performing yeast clone from the first generation libraries (Table 9), was used to set more stringent sort gates. Following an overnight off-rate competition with unlabeled PAC1 at 30° C. or 37° C., the yeast clones with significantly reduced off-rates compared to the 2B10 clone could be sorted out. A limited screen of –200 clones revealed that –100 had slower off-rates than 2B10, but most of the promising binders contained a potential asparagine deamidation liability within HCDR2. Non-specific binding to the ECDs of PD1 or GIPR was minimal for all clones screened. Applying stringent binding and sequence filters yielded ten top mutants with significantly improved PAC1 binding than the 2B10 clone (>2× higher percent association after 37° C. overnight competition) and without any potential sequence liabilities (Table 10). Sequence changes from parental 29G4v10 antibody for these top ten mutants and the percentage of human PAC1 ECD binding following the off-rate assay at 30° C. and 37° C. are shown in Table 10. Percentage association was calculated as the normalized binding after off rate assay divided by the normalized binding without the off rate assay. Higher percentage association of PAC1 ECD binding indicates that the mutant Fabs have a slower off-rate.

TABLE 10

Top Improved Binders from Off-Rate Screen of Second Generation Chain-Shuffled Library

| | Substitutions with respect to 29G4v10 VH sequence (SEQ ID NO: 191) | | | | | Substitutions with respect to 29G4v10 VL sequence (SEQ ID NO: 52) | | | % association after off-rate screen | |
|---|---|---|---|---|---|---|---|---|---|---|
| Clone ID | HC CDR1 | HC FR2 | HC CDR2 | HC FR3 | HC CDR3 | LC CDR1 | LC CDR2 | LC CDR3 | 30° C. | 37° C. |
| 30_H10 | — | — | D54S; G56A; N57F | I70V | — | Q27K; R31W | — | — | 75.8% | 63.6% |
| 30_D05 | — | A49G | S52N; D54R; G56H; N57G | I70V | — | Q27K; R31W | — | — | 74.2% | 57.9% |
| 30_F08 | — | A49G | S52T; D54T; N57A | — | — | Q27K; S28A; R31W | — | — | 67.1% | 54.6% |
| 30_A05 | — | A49G | S52N; D54F; G56D; N57A | — | — | Q27K; R31W | — | — | 65.8% | 50.5% |
| 30_E08 | — | A49G | S52N; Y53F; D54Q; G56T; N57T | — | — | Q27K; R31W | — | — | 60.9% | 46.5% |
| 37_E09 | — | A49G | D54S; G56D; N57L | I70V | — | Q27K; R31W | — | — | 73.4% | 49.2% |
| 37_F04 | — | A49G | Y53F; D54S; N57S | I70L | — | Q27K; R31W | — | — | 73.0% | 46.5% |
| 37_B06 | — | A49G | D54S; G56A; N57S | I70M | — | Q27K; R31W | — | — | 68.6% | 43.0% |
| 37_H05 | — | A49G | D54T; G56A; N57Q | I70M | — | Q27K; R31W | — | — | 64.3% | 40.2% |
| 37_A11 | — | A49G | D54T; G56Q; N57F | I70V | — | Q27K; R31Y | — | — | 64.9% | 36.6% |
| 2_B10 Control | R31H; F32Y | — | D54Q; G56S | — | V102L | Q27R; R31L; S32A | — | R93F | 53.0% | 21.5% |
| 29G4v10 Wild-Type | — | — | — | — | — | — | — | — | 10.4% | 8.5% |

As shown in Table 10, all of these top ten binding mutants contained a Q27K mutation in CDRL1 and all but one contained a R31W mutation in CDRL1. All the mutants had mutations at amino acid positions D54 and N57 in CDRH2 and most also had a mutation at amino acid position G56 in CDRH2. Conservative mutations at amino acid positions 49 and 70 in the heavy chain framework 2 (FR2) and framework 3 (FR3) regions, respectively, were also observed in many of these ten mutants.

In summary, guided by the structure of the PAC1 ECD in complex with the 29G4v9 Fab, a closely related variant of 29G4v22 and 29G4v10 anti-PAC1 neutralizing antibodies, combinatorial libraries of 29G4v10 mutants were designed and sorted for improved binding to the PAC1 ECD. To isolate the most improved binders, enriched mutations were combined through construction of CDR-shuffled and/or chain-shuffled libraries for selection under more stringent conditions. Screens of individual yeast Fab clones after sorting yielded improved binders to human PAC1 ECD with significantly slower binding off-rates as compared to the 29G4v10 parental antibody and minimal non-specific binding. A subset of the improved affinity variants were produced recombinantly and evaluated for in vitro functional activity as described in Example 3.

Example 3. In Vitro Functional Activity of Human PAC1 Antibody Variants

To evaluate the effect of the mutations in the heavy and light chain variable regions identified by the analysis of the co-crystal structure (Example 1) or the yeast display libraries (Example 2) on the inhibitory potency of the anti-PAC1 antibody, the variants were produced by recombinant expression methods as complete bivalent monoclonal antibodies and/or as monovalent Fab-Fc fusions (e.g. Fab region fused to dimeric IgG Fc region) and evaluated in a cell-based cAMP assay as described in more detail below. The light chains of the monoclonal antibodies and Fab fragments comprised the light chain variable region from the indicated antibody variant fused to a human kappa light chain constant region having the sequence of SEQ ID NO: 318 or SEQ ID NO: 319. The heavy chains of the monoclonal antibodies and Fab-Fc fusions comprised the heavy chain variable region from the indicated antibody variant fused to an aglycosylated, disulfide-stabilized human IgG1z constant region having the sequence of SEQ ID NO: 325.

PAC1 antibody variant sequences were generated by site directed mutagenesis (SDM) or by Golden Gate Assembly (GGA) in those cases where SDM was unsuccessful. Site directed mutagenesis utilized paired mutagenic primers that flanked the mutation site. Whole vector PCR reactions were carried out using double stranded plasmid DNA templates. The primers for all of the desired mutations in a particular clone were combined into a master primer mix, with one to several mutations being incorporated in an individual reaction. Following amplification, the template plasmid DNA was removed by digestion with DpnI, an endonuclease which preferentially cleaves methylated DNA. The SDM product was then transformed into competent cells for growth and screening by sequencing. The SDM reactions were performed using the QuikChange Lightning Multi Site-Directed Mutagenesis Kit (Agilent) following the manufacturer's directions.

Where SDM was unsuccessful, an alternative cloning strategy was utilized. Briefly, GGA relied upon Type II restriction enzymes and T4 DNA ligase to cut and seamlessly ligate together multiple DNA fragments. (Engler et al., PLOS One, Vol. 3(11): e3647, 2008). In this example, the multiple DNA fragments consisted of (i) a synthetic nucleic acid sequence (gBlock, Integrated DNA Technologies, Coralville, IA) encoding a Kozak consensus sequence, a signal peptide sequence and an antibody variable region sequence; (ii) an antibody constant domain fragment released from a Parts vector; and (iii) the expression vector backbone. The GGA reactions were composed of 10 ng of gBlock, 10 ng of the Part vector, 10 ng of the expression vector, 1 μl 10× Fast Digest Reaction Buffer+0.5 mM ATP (Thermo Fisher, Waltham, MA), 0.5 μl FastDigest Esp3I (Thermo Fisher, Waltham, MA), 1 μl T4 DNA Ligase (5 U/μl, Thermo Fisher, Waltham, MA) and water to 10 μl. The reactions were performed over 15 cycles consisting of a 2 minute digestion step at 37° C. and a 3 minute ligation step at 16° C. The 15 cycles were followed by a final 5 minute 37° C. digestion step and a 5 minute enzyme inactivation step at 80° C.

Following cloning, PAC1 antibody polypeptides of which the first 22 amino acids were the VK1 signal peptide (MDMRVPAQLLGLLLLWLRGARC; SEQ ID NO: 486) were generated by transiently transfecting 293 HEK cells with the corresponding cDNAs. Cells at $1.5\times10^6$ cells/ml were transfected with 0.5 mg/L DNA (0.5 mg/L PAC1 in the pTT5 vector) or (0.1 mg/L PAC1 in pTT5 vector with 0.4 mg/L empty pTT5 vector) (Durocher et al., NRCC, Nucleic Acids. Res., Vol. 30: e9, 2002) with 4 ml PEI/mg DNA in F17 media (Thermo Fisher). Yeastolate and Glucose were added to cultures 1 hour after transfection, and cells were then grown in suspension using F17 expression medium supplemented with 0.1% Kolliphor, 6 mM L-Glutamine and 50 μg/ml Geneticin for 6 days after which the conditioned media was harvested for purification.

The PAC1 antibody variants were purified from the conditioned media using protein A affinity chromatography (Mab Select SuRe, GE Healthcare Life Sciences, Little Chalfont, Buckinghamshire, UK) followed by cation exchange chromatography (SP Sepharose High Performance columns (SP HP) (GE Healthcare Life Sciences). The protein concentration of each purified pool was determined by UV absorbance at 280 nm (A280) using a NanoDrop 2000 (Thermo Fisher Scientific, Rockford, Illinois, USA). The purified pools were dialyzed against 2 L of 10 mM sodium-acetate, 9% sucrose, pH 5.2 (A52Su) using 20 kDa MWCO Slide-A-Lyzer dialysis flasks (Thermo Fisher Scientific) for 2 hours at 4° C. with gentle stirring on a stir plate. The used dialysate was decanted away, a fresh 2 L of A52Su was added and dialysis proceeded overnight. After dialysis, the samples were concentrated using 30 kDa MWCO ultrafiltration concentrators (Thermo Fisher Scientific) centrifuged at 2,000×g in a swinging-bucket rotor until each sample was approximately 40 mg/mL based on A280. The final products were analyzed for main peak purity using Caliper LabChip GXII microcapillary electrophoresis (PerkinElmer, Waltham, Massachusetts, USA) and size exclusion chromatography using an ACQUITY UPLC Protein BEH SEC column, 200 Å, 4.6×300 mm (Waters Corporation, Milford, Massachusetts, USA). The endotoxin content was measured using an Endosafe-MCS (Charles River, Wilmington, Massachusetts, USA) and 0.05 EU/mL PTS cartridges (Charles River).

The functional activity of the purified monoclonal antibodies or Fab-Fc fusion proteins was assessed using a cell-based PAC1 receptor cAMP activity assay. Both PACAP38 and PACAP27 are agonists of the PAC1 receptor, activation of which results in an increase in intracellular cAMP. The assay employed a human neuroblastoma-derived cell line (SH-SY5Y; Biedler J L et al., Cancer Res., Vol. 38: 3751-3757, 1978) obtained from ATCC (ATCC Number CRL-2266; "CRL-2266 cells"). CRL-2266 cells express human PAC1 receptor endogenously (Monaghan et al., J Neurochem., Vol. 104(1): 74-88, 2008). In addition, a CHO cell line stably expressing the rat PAC1 receptor (GenBank Accession No. NM 133511.2) or the cynomolgus monkey PAC1 receptor (NCBI Reference Sequence XP 015303041.1) was used in place of the CRL2266 cells for assays to evaluate the species cross-reactivity of the anti-PAC1 antibodies or Fab-Fc fusions at the rat and cynomolgus monkey PAC1 receptors. The LANCE Ultra cAMP assay kit (PerkinElmer, Boston, MA) was used to measure cAMP concentration.

On the day of the assay, the frozen CRL-2266 cells were thawed at 37° C. and were washed once with assay buffer. 10 μL of cell suspension containing 2,000 cells was added into 96 half-area white plates. After adding 5 μL of the anti-PAC1 variant monoclonal antibody or Fab-Fc fusion protein (10 point dose response curve: concentration range from 1 μM to 0.5 fM), the mixture was incubated for 30 min at room temperature. Then, 5 μL of human PACAP38 (10 pM final concentration) was added as an agonist and the mixture was further incubated for 15 min at room temperature. After human PACAP38 stimulation, 20 μL of detection mix was added and incubated for 45 minutes at room temperature. The plates were read on EnVision instrument (PerkinElmer, Boston, MA) at emission wavelength 665 nm. Data were processed and analyzed by Prizm (GraphPad Software Inc.) to show POC (percent of control, in which control is defined as the activity of the agonist used in the assay) as a function of the tested antagonist concentration (e.g. anti-PAC1 variant antibody or Fab-Fc fusion protein), and were fitted with standard nonlinear regression curves to yield IC50 values. POC was calculated as follows:

$$POC = 100 \times Em665 \text{ of } \frac{\text{Agonist response with antagonist} - \text{cell response without agonist and antagonist}}{\text{Agonist response without antagonist} - \text{cell response without agonist and antagonist}}$$

Monovalent Fab-Fc fusion proteins were generated with the mutations summarized in Tables 6 and 7 and tested for functional activity in the cell-based cAMP assay described above. The mutant Fab-Fc fusion proteins were segregated into two separate groups: mutations that improve inhibitory potency against the human PAC1 receptor compared to the parent molecule and mutations characterized as neutral (Table 11). Mutations were characterized as neutral if the mutation had an average potency less than 1.5× weaker than that of parent molecule, and at least one potency measurement tighter than parent molecule in same run.

TABLE 11

In vitro inhibitory potency of single mutant Fab-Fc fusion proteins

| Fab-Fc Fusion Protein ID No. | Mutations[1] | IC50 (nM) |
|---|---|---|
| Improved Potency Mutations | | |
| 29G4v10 Fab-Fc fusion parent molecule | — | 10.37 |

TABLE 11-continued

In vitro inhibitory potency of single mutant Fab-Fc fusion proteins

| Fab-Fc Fusion Protein ID No. | Mutations[1] | IC50 (nM) |
|---|---|---|
| PL-45360 | LC Q27K | 4.52 |
| PL-45362 | LC Q27R | 6.32 |
| PL-45398 | HC D54N | 1.78 |
| PL-45399 | HC D54I | 2.48 |
| PL-45400 | HC D54L | 3.11 |
| PL-45405 | HC D54Q | 3.46 |
| PL-45397 | HC D54Y | 3.62 |
| PL-45406 | HC G56R | 2.81 |
| PL-45407 | HC G56N | 7.98 |
| PL-45408 | HC G56H | 9.46 |
| PL-45402 | HC G56S | 9.49 |
| PL-45415 | HC E62R | 4.27 |
| PL-45418 | HC V102I | 9.68 |
| Neutral Mutations | | |
| 29G4v10 Fab-Fc fusion parent molecule | — | 10.37 |
| PL-45370 | LC S91T | 15.19 |
| PL-45377 | LC L94R | 11.05 |
| PL-45386 | HC R31K | 12.12 |
| PL-45401 | HC G55A | 12.58 |
| PL-45410 | HC N57R | 11.63 |
| PL-45420 | HC T104H | 11.29 |
| PL-45420 | HC T104S | 13.36 |

[1]Amino acid positions for the light chain (LC) are relative to SEQ ID NO: 52 and amino acid positions for the heavy chain (HC) are relative to SEQ ID NO: 191.

The mutations that provided increases in inhibitory potency against the human PAC1 receptor lie in three distinct regions of three dimensional space on the antibody surface. A second round of variant antibodies and Fab-Fc fusion proteins were generated by combining mutations in these three regions to potentially provide additional increases in potency. In addition, some of the neutral mutations were incorporated as they were likely to not have a significant effect on binding, but may provide mechanisms to modify antibody biophysical characteristics. The variable regions containing the desired mutations were incorporated into a bivalent monoclonal antibody having a human aglycosylated IgG1 Fc region and/or a monovalent Fab-Fc fusion protein. The aglycosylated human IgG1 antibody Fc region comprised the sequence of a human IgG1z Fc region with N297G, R292C, and V302C mutations according to EU numbering (SEQ ID NO: 325). The variant antibodies and Fab-Fc fusion proteins with combinations of mutations were evaluated for functional activity in the cell-based cAMP assay. The results are shown in Table 12 below.

TABLE 12

In vitro inhibitory potency of variant antibodies and Fab-Fc fusion proteins

| | Substitutions with respect to 29G4v10 VL sequence (SEQ ID NO: 52) | | | Substitutions with respect to 29G4v10 VH sequence (SEQ ID NO: 191) | | | mAb functional activity (bivalent target binding) | | | Fab-Fc fusion protein functional activity (monovalent target binding) | | |
|---|---|---|---|---|---|---|---|---|---|---|---|---|
| Variant Ab ID. | LC CDR1 | LC CDR2 | LC CDR3 | HC CDR1 | HC CDR2 | HC CDR3 | IC50 (SD) in nM | Fold-increase over parental (on plate)[1] | Fold-increase over parental (avg)[2] | IC50 (SD) in nM | Fold-increase over parental (on plate)[1] | Fold-increase over parental (avg)[2] |
| iPS:420649 | Q27K | — | — | — | D54N | — | 0.18 (0.04) | 6.4 | 4.3 | 0.71 (0.09) | 10.5 | 12.9 |

TABLE 12-continued

In vitro inhibitory potency of variant antibodies and Fab-Fc fusion proteins

| Variant Ab ID. | Substitutions with respect to 29G4v10 VL sequence (SEQ ID NO: 52) LC CDR1 | LC CDR2 | LC CDR3 | Substitutions with respect to 29G4v10 VH sequence (SEQ ID NO: 191) HC CDR1 | HC CDR2 | HC CDR3 | mAb functional activity (bivalent target binding) IC50 (SD) in nM | Fold-increase over parental (on plate)[1] | Fold-increase over parental (avg)[2] | Fab-Fc fusion protein functional activity (monovalent target binding) IC50 (SD) in nM | Fold-increase over parental (on plate)[1] | Fold-increase over parental (avg)[2] |
|---|---|---|---|---|---|---|---|---|---|---|---|---|
| iPS:420653 | Q27K | — | — | — | D54I | — | 0.18 (0.06) | 6.4 | 4.3 | 0.99 (0.13) | 8.1 | 9.2 |
| iPS:420657 | Q27K | — | — | — | D54Q | — | 0.29 (0.05) | 2.5 | 2.7 | 0.87 (0.23) | 9.2 | 10.4 |
| iPS:420661 | Q27K | — | — | — | D54Y | — | 0.21 (0.05) | 3.4 | 3.7 | 1.83 (0.28) | 4.4 | 5.0 |
| iPS:420665 | Q27K | — | — | — | G56R | — | 0.44 (0.19) | 1.7 | 1.8 | 1.94 (0.50) | 4.1 | 4.7 |
| iPS:420672 | Q27K | — | — | — | G56N | — | 1.04 (0.50) | 0.7 | 0.7 | 3.17 (0.97) | 2.5 | 2.9 |
| iPS:420679 | Q27K | — | — | — | E62R | — | 0.47 (0.22) | 1.6 | 1.7 | 1.34 (0.31) | 6.0 | 6.8 |
| iPS:420686 | Q27K | — | — | — | — | V102I | 0.78 (0.39) | 0.9 | 1.0 | 1.92 (0.19) | 4.2 | 4.7 |
| iPS:420690 | — | — | — | — | D54N; G56R | — | 0.16 (0.02) | 4.4 | 4.8 | 1.86 (0.17) | 3.6 | 4.9 |
| iPS:420697 | — | — | — | — | D54I; G56R | — | 0.20 (0.06) | 3.4 | 4.0 | 1.48 (0.48) | 4.5 | 6.1 |
| iPS:420704 | — | — | — | — | D54Q; G56R | — | 0.18 (0.05) | 3.7 | 4.4 | 2.00 (0.20) | 3.4 | 4.5 |
| iPS:420711 | — | — | — | — | D54Y; G56R | — | 0.45 (0.29) | 1.5 | 1.7 | 3.45 (0.13) | 1.9 | 2.6 |
| iPS:420718 | — | — | — | — | D54N; G56N | — | 0.60 (0.21) | 1.1 | 1.3 | 3.33 (0.63) | 2.0 | 2.7 |
| iPS:420725 | — | — | — | — | D54I; G56N | — | 0.56 (0.04) | 1.2 | 1.4 | 4.06 (0.58) | 1.7 | 2.2 |
| iPS:420732 | — | — | — | — | D54Q; G56N | — | 0.74 (0.18) | 0.9 | 1.1 | 1.82 (0.32) | 3.7 | 5.0 |
| iPS:420739 | — | — | — | — | D54Y; G56N | — | 0.63 (0.13) | 1.1 | 1.2 | 2.76 (0.34) | 2.9 | 3.3 |
| iPS:420746 | — | — | — | — | D54N; E62R | — | 0.18 (0.04) | 4.2 | 4.4 | 0.81 (0.13) | 9.8 | 11.3 |
| iPS:420753 | — | — | — | — | D54I; E62R | — | 0.16 (0.05) | 4.8 | 5.0 | 1.55 (0.11) | 5.1 | 5.9 |
| iPS:420760 | — | — | — | — | D54Q; E62R | — | 0.32 (0.06) | 2.4 | 2.5 | 2.70 (0.85) | 2.9 | 3.4 |
| iPS:420767 | — | — | — | — | D54Y; E62R | — | ND | ND | ND | 1.49 (0.54) | 5.3 | 6.1 |
| iPS:420774 | — | — | — | — | D54N | V102I | 0.69 (0.30) | 1.1 | 1.1 | 1.04 (0.20) | 7.6 | 8.7 |
| iPS:420781 | — | — | — | — | D54I | V102I | 0.40 (0.05) | 1.9 | 1.9 | 1.81 (0.43) | 4.4 | 5.0 |
| iPS:420788 | — | — | — | — | D54Q | V102I | 0.46 (0.17) | 1.6 | 1.7 | 1.59 (0.83) | 6.0 | 5.7 |
| iPS:420795 | — | — | — | — | D54Y | V102I | 0.50 (0.09) | 1.5 | 1.5 | 4.25 (1.91) | 2.3 | 2.1 |
| iPS:420802 | — | — | — | — | G56R; E62R | — | 0.17 (0.05) | 3.9 | 4.6 | 1.51 (0.01) | 6.4 | 6.0 |
| iPS:420809 | — | — | — | — | G56N; E62R | — | 0.77 (0.20) | 0.9 | 1.0 | 2.51 (0.28) | 3.8 | 3.6 |
| iPS:420816 | — | — | — | — | G56R | V102I | 0.50 (0.07) | 1.3 | 1.6 | 2.44 (0.43) | 3.9 | 3.7 |
| iPS:420823 | — | — | — | — | G56N | V102I | 1.41 (0.42) | 0.5 | 0.6 | 2.30 (0.42) | 4.2 | 3.9 |
| iPS:420830 | — | — | — | — | E62R | V102I | 0.91 (0.64) | 0.7 | 0.9 | 1.73 (0.16) | 5.5 | 5.3 |
| iPS:420837 | Q27K | — | — | — | D54N; G56R | — | 0.21 (0.10) | 3.2 | 3.7 | 0.67 (0.18) | 12.4 | 13.5 |
| iPS:420841 | Q27K | — | — | — | D54I; G56R | — | 0.14 (0.00) | 6.1 | 5.6 | 0.69 (0.10) | 12.0 | 13.1 |
| iPS:420845 | Q27K | — | — | — | D54Q; G56R | — | 0.12 (0.04) | 7.5 | 6.8 | 0.83 (0.14) | 10.1 | 10.9 |
| iPS:420849 | Q27K | — | — | — | D54Y; G56R | — | 0.22 (0.04) | 4.0 | 3.6 | 1.73 (0.74) | 4.8 | 5.2 |
| iPS:420853 | Q27K | — | — | — | D54N; G56N | — | 0.39 (0.06) | 2.2 | 2.0 | 1.93 (0.73) | 4.3 | 4.7 |

TABLE 12-continued

In vitro inhibitory potency of variant antibodies and Fab-Fc fusion proteins

| | Substitutions with respect to 29G4v10 VL sequence (SEQ ID NO: 52) | | | Substitutions with respect to 29G4v10 VH sequence (SEQ ID NO: 191) | | | mAb functional activity (bivalent target binding) | | | Fab-Fc fusion protein functional activity (monovalent target binding) | | |
|---|---|---|---|---|---|---|---|---|---|---|---|---|
| Variant Ab ID. | LC CDR1 | LC CDR2 | LC CDR3 | HC CDR1 | HC CDR2 | HC CDR3 | IC50 (SD) in nM | Fold-increase over parental (on plate)[1] | Fold-increase over parental (avg)[2] | IC50 (SD) in nM | Fold-increase over parental (on plate)[1] | Fold-increase over parental (avg)[2] |
| iPS:420857 | Q27K | — | — | — | D54I; G56N | — | 0.47 (0.13) | 1.8 | 1.7 | 1.94 (0.27) | 4.3 | 4.7 |
| iPS:420861 | Q27K | — | — | — | D54Q; G56N | — | 0.43 (0.01) | 2.0 | 1.8 | 1.13 (0.37) | 7.4 | 8.1 |
| iPS:420865 | Q27K | — | — | — | D54Y; G56N | — | 0.39 (0.03) | 2.2 | 2.0 | 3.23 (1.03) | 4.1 | 2.8 |
| iPS:420869 | Q27K | — | — | — | D54N; E62R | — | ND | ND | ND | 0.91 (0.06) | 14.3 | 10.0 |
| iPS:420873 | Q27K | — | — | — | D54I; E62R | — | ND | ND | ND | 1.34 (0.40) | 9.8 | 6.8 |
| iPS:420877 | Q27K | — | — | — | D54Q; E62R | — | ND | ND | ND | 1.64 (0.51) | 8.0 | 5.5 |
| iPS:420881 | Q27K | — | — | — | D54Y; E62R | — | ND | ND | ND | 1.33 (0.27) | 9.8 | 6.8 |
| iPS:420885 | Q27K | — | — | — | D54N | V102I | 0.15 (0.01) | 3.7 | 5.4 | 1.18 (0.04) | 11.1 | 7.7 |
| iPS:420889 | Q27K | — | — | — | D54I | V102I | 0.16 (0.01) | 3.4 | 4.9 | 1.87 (0.39) | 7.0 | 4.8 |
| iPS:420893 | Q27K | — | — | — | D54Q | V102I | 0.30 (0.08) | 1.8 | 2.6 | 1.58 (0.33) | 8.2 | 5.8 |
| iPS:420897 | Q27K | — | — | — | D54Y | V102I | 0.49 (0.18) | 1.1 | 1.6 | 4.05 (0.38) | 3.2 | 2.2 |
| iPS:420901 | — | — | — | — | D54N; G56R; E62R | — | ND | ND | ND | 2.06 (0.61) | 6.3 | 4.4 |
| iPS:420908 | — | — | — | — | D54I; G56R; E62R | — | ND | ND | ND | 1.46 (1.11) | 8.9 | 6.2 |
| iPS:420915 | — | — | — | — | D54Q; G56R; E62R | — | ND | ND | ND | 0.81 (0.20) | 15.9 | 11.2 |
| iPS:420922 | — | — | — | — | D54Y; G56R; E62R | — | ND | ND | ND | 1.01 (0.21) | 12.9 | 9.0 |
| iPS:420929 | — | — | — | — | D54N; G56N; E62R | — | 0.12 (0.00) | 4.5 | 6.5 | 0.84 (0.27) | 13.9 | 10.8 |
| iPS:420936 | — | — | — | — | D54I; G56N; E62R | — | 0.16 (0.01) | 3.4 | 4.9 | 1.89 (0.54) | 6.2 | 4.8 |
| iPS:420943 | — | — | — | — | D54Q; G56N; E62R | — | 0.17 (0.01) | 3.8 | 4.7 | 3.62 (1.42) | 3.2 | 2.5 |
| iPS:420950 | — | — | — | — | D54Y; G56N; E62R | — | 0.30 (0.06) | 2.1 | 2.6 | 3.45 (1.38) | 3.4 | 2.6 |
| iPS:420957 | — | — | — | — | D54N; G56R | V102I | 0.27 (0.01) | 2.3 | 2.9 | 2.83 (1.54) | 4.1 | 3.2 |
| iPS:420964 | — | — | — | — | D54I; G56R | V102I | 0.37 (0.09) | 1.7 | 2.1 | 2.86 (1.29) | 4.1 | 3.2 |
| iPS:420971 | — | — | — | — | D54Q; G56R | V102I | 0.22 (0.00) | 2.8 | 3.5 | 3.52 (1.74) | 3.3 | 2.6 |
| iPS:420978 | — | — | — | — | D54Y; G56R | V102I | 0.28 (0.01) | 2.3 | 2.8 | 5.24 (1.26) | 2.7 | 1.7 |
| iPS:420985 | — | — | — | — | D54N; G56N | V102I | ND | ND | ND | 2.86 (0.32) | 4.9 | 3.2 |
| iPS:420992 | — | — | — | — | D54I; G56N | V102I | 0.38 (0.07) | 1.6 | 2.0 | 6.18 (0.84) | 2.3 | 1.5 |
| iPS:420999 | — | — | — | — | D54Q; G56N | V102I | 0.63 (0.18) | 1.0 | 1.2 | 11.60 (1.89) | 1.2 | 0.8 |
| iPS:421006 | — | — | — | — | D54Y; G56N | V102I | 1.10 (0.17) | 0.6 | 0.7 | 13.82 (1.13) | 1.0 | 0.7 |
| iPS:421013 | — | — | — | — | G56R; E62R | V102I | 0.32 (0.03) | 2.0 | 2.4 | 2.07 (0.61) | 6.8 | 4.4 |
| iPS:421020 | — | — | — | — | G56N; E62R | V102I | 0.54 (0.01) | 1.2 | 1.5 | 2.65 (0.53) | 5.3 | 3.4 |

TABLE 12-continued

In vitro inhibitory potency of variant antibodies and Fab-Fc fusion proteins

| Variant Ab ID. | Substitutions with respect to 29G4v10 VL sequence (SEQ ID NO: 52) LC CDR1 | LC CDR2 | LC CDR3 | Substitutions with respect to 29G4v10 VH sequence (SEQ ID NO: 191) HC CDR1 | HC CDR2 | HC CDR3 | mAb functional activity (bivalent target binding) IC50 (SD) in nM | Fold-increase over parental (on plate)[1] | Fold-increase over parental (avg)[2] | Fab-Fc fusion protein functional activity (monovalent target binding) IC50 (SD) in nM | Fold-increase over parental (on plate)[1] | Fold-increase over parental (avg)[2] |
|---|---|---|---|---|---|---|---|---|---|---|---|---|
| iPS:421027 | Q27K | — | — | — | D54N; G56R; E62R | — | ND | ND | ND | 0.91 (0.41) | 12.5 | 10.0 |
| iPS:421031 | Q27K | — | — | — | D54I; G56R; E62R | — | ND | ND | ND | 0.82 (0.31) | 13.8 | 11.0 |
| iPS:421035 | Q27K | — | — | — | D54Q; G56R; E62R | — | ND | ND | ND | 1.22 | 9.3 (0.29) | 7.4 |
| iPS:421039 | Q27K | — | — | — | D54Y; G56R; E62R | — | ND | ND | ND | 2.98 (2.17) | 3.8 | 3.1 |
| iPS:421043 | Q27K | — | — | — | D54N; G56N; E62R | — | ND | ND | ND | 1.44 (0.53) | 7.9 | 6.3 |
| iPS:421047 | Q27K | — | — | — | D54I; G56N; E62R | — | 0.10 (0.00) | 6.5 | 8.1 | 1.29 (0.59) | 8.8 | 7.1 |
| iPS:421051 | Q27K | — | — | — | D54Q; G56N; E62R | — | 0.09 (0.01) | 7.0 | 8.6 | 1.80 (0.99) | 6.3 | 5.1 |
| iPS:421055 | Q27K | — | — | — | D54Y; G56N; E62R | — | 0.43 (0.04) | 1.6 | 1.8 | 1.06 (0.18) | 7.7 | 8.6 |
| iPS:421059 | Q27K | — | — | — | D54N; G56R | V102I | 0.10 (0.04) | 6.8 | 7.8 | 1.01 (0.07) | 8.1 | 9.0 |
| iPS:421063 | Q27K | — | — | — | D54I; G56R | V102I | 0.23 (0.01) | 3.0 | 3.4 | 1.12 (0.12) | 7.3 | 8.1 |
| iPS:421067 | Q27K | — | — | — | D54Q; G56R | V102I | 0.30 (0.04) | 2.3 | 2.6 | 1.49 (0.43) | 5.5 | 6.1 |
| iPS:421071 | Q27K | — | — | — | D54Y; G56R | V102I | 0.30 (0.14) | 2.3 | 2.6 | 1.18 (0.05) | 6.9 | 7.7 |
| iPS:421075 | Q27K | — | — | — | D54N; G56N | V102I | ND | ND | ND | 1.02 (0.21) | 8.0 | 8.9 |
| iPS:421079 | Q27K | — | — | — | D54I; G56N | V102I | 0.30 (0.07) | 2.2 | 2.6 | 1.21 (0.04) | 5.9 | 7.5 |
| iPS:421083 | Q27K | — | — | — | D54Q; G56N | V102I | 0.51 (0.29) | 1.3 | 1.5 | 1.73 (0.03) | 4.1 | 5.2 |
| iPS:421087 | Q27K | — | — | — | D54Y; G56N | V102I | 0.33 (0.05) | 2.3 | 2.4 | 2.38 (0.63) | 3.0 | 3.8 |
| iPS:421091 | — | — | — | — | D54N; G56R; E62R | V102I | 0.07 (0.00) | 11.4 | 11.7 | 1.41 (0.26) | 5.1 | 6.5 |
| iPS:421098 | — | — | — | — | D54I; G56R; E62R | V102I | 0.17 (0.01) | 4.6 | 4.7 | 1.26 (0.14) | 5.7 | 7.2 |
| iPS:421105 | — | — | — | — | D54Q; G56R; E62R | V102I | 0.19 (0.04) | 4.0 | 4.1 | 1.12 (0.17) | 6.4 | 8.1 |
| iPS:421112 | — | — | — | — | D54Y; G56R; E62R | V102I | 0.21 (0.01) | 3.6 | 3.7 | 1.38 (0.33) | 5.2 | 6.6 |
| iPS:421119 | — | — | — | — | D54N; G56N; E62R | V102I | 0.21 (0.00) | 3.6 | 3.7 | 1.20 (0.17) | 9.6 | 7.6 |
| iPS:421126 | — | — | — | — | D54I; G56N; E62R | V102I | 0.19 (0.01) | 4.0 | 4.1 | 1.95 (0.14) | 5.9 | 4.7 |
| iPS:421133 | — | — | — | — | D54Q; G56N; E62R | V102I | 0.29 (0.05) | 3.1 | 2.7 | 4.46 (1.18) | 2.6 | 2.0 |
| iPS:421140 | — | — | — | — | D54Y; G56N; E62R | V102I | 0.37 (0.04) | 2.4 | 2.1 | 5.48 (1.06) | 2.1 | 1.7 |
| iPS:421147 | Q27K | — | — | — | D54Y; G56N; | V102I | 1.15 (0.80) | 0.8 | 0.7 | 1.81 (0.47) | 6.4 | 5.0 |

TABLE 12-continued

| In vitro inhibitory potency of variant antibodies and Fab-Fc fusion proteins | | | | | | | | | | | | |
|---|---|---|---|---|---|---|---|---|---|---|---|---|
| | | | | | | | mAb functional activity (bivalent target binding) | | | Fab-Fc fusion protein functional activity (monovalent target binding) | | |
| | Substitutions with respect to 29G4v10 VL sequence (SEQ ID NO: 52) | | | Substitutions with respect to 29G4v10 VH sequence (SEQ ID NO: 191) | | | | | | | | |
| Variant Ab ID. | LC CDR1 | LC CDR2 | LC CDR3 | HC CDR1 | HC CDR2 | HC CDR3 | IC50 (SD) in nM | Fold-increase over parental (on plate)[1] | Fold-increase over parental (avg)[2] | IC50 (SD) in nM | Fold-increase over parental (on plate)[1] | Fold-increase over parental (avg)[2] |
| | | | | | E62R | | | | | | | |
| iPS:421151 | G30W | — | — | — | — | — | 6.66 (2.26) | 0.1 | 0.1 | 12.50 (3.25) | 0.9 | 0.7 |
| iPS:391478 | S32N | — | — | — | — | — | 6.16 (3.39) | 0.1 | 0.1 | 36.74 (9.14) | 0.3 | 0.2 |
| iPS:421157 | — | — | R93M | — | — | — | 8.04 (3.91) | 0.1 | 0.1 | 6.60 (1.31) | 2.0 | 1.4 |
| iPS:421163 | — | — | — | R31H | — | — | 14.01 (8.21) | 0.1 | 0.1 | 4.99 (0.69) | 2.6 | 1.8 |
| iPS:391578 | — | — | — | F32Y | — | — | 2.68 (1.22) | 0.3 | 0.3 | 4.91 (0.37) | 2.7 | 1.9 |
| iPS:421170 | — | — | — | — | Y53F | — | 3.18 (0.65) | 0.2 | 0.2 | 4.56 (0.87) | 2.9 | 2.0 |
| iPS:421176 | — | — | — | — | G56A | — | 3.03 (0.57) | 0.2 | 0.3 | ND | ND | ND |
| iPS:421182 | — | — | — | — | — | V102F | 1.50 (0.72) | 0.5 | 0.5 | 5.47 (0.37) | 2.4 | 1.7 |
| iPS:421189 | Q27K; G30W | — | — | — | — | — | 0.65 (0.31) | 1.1 | 1.2 | 7.48 (0.45) | 1.7 | 1.2 |
| iPS:421195 | Q27K; S32N | — | — | — | — | — | 0.65 (0.24) | 1.1 | 1.2 | 5.28 (0.46) | 1.3 | 1.7 |
| iPS:421201 | Q27K | — | R93M | — | — | — | 1.70 (0.37) | 0.4 | 0.5 | 4.63 (0.88) | 1.4 | 2.0 |
| iPS:421207 | Q27K | — | — | R31H | — | — | 3.68 (0.64) | 0.2 | 0.2 | 8.27 (1.17) | 0.8 | 1.1 |
| iPS:421211 | Q27K | — | — | F32Y | — | — | 1.67 (0.32) | 0.4 | 0.5 | 4.25 (0.21) | 1.6 | 2.1 |
| iPS:421215 | Q27K | — | — | — | Y53F | — | 1.39 (0.21) | 0.5 | 0.6 | 3.24 (0.20) | 2.0 | 2.8 |
| iPS:421219 | Q27K | — | — | — | G56A | — | 1.19 (0.51) | 0.6 | 0.7 | ND | ND | ND |
| iPS:421223 | Q27K | — | — | — | — | V102F | 0.60 (0.09) | 1.2 | 1.3 | 6.30 (0.04) | 1.1 | 1.4 |
| iPS:421227 | G30W | — | — | — | D54N | — | 0.39 (0.06) | 1.9 | 2.0 | 5.02 (1.29) | 1.3 | 1.8 |
| iPS:421231 | S32N | — | — | — | D54N | — | 0.51 (0.11) | 1.7 | 1.5 | 6.39 (1.58) | 1.1 | 1.4 |
| iPS:421235 | — | — | R93M | — | D54N | — | 1.45 (0.18) | 0.6 | 0.5 | 0.00 (0.00) | — | — |
| iPS:421239 | — | — | — | R31H | D54N | — | 3.87 (0.10) | 0.2 | 0.2 | 4.28 (0.56) | 1.6 | 2.1 |
| iPS:421246 | — | — | — | F32Y | D54N | — | 0.64 (0.17) | 1.3 | 1.2 | 3.36 (0.50) | 2.1 | 2.7 |
| iPS:421253 | — | — | — | — | Y53F; D54N | — | 0.38 (0.10) | 2.3 | 2.0 | 2.88 (0.17) | 2.4 | 3.2 |
| iPS:421260 | — | — | — | — | D54N; G56A | — | 0.43 (0.16) | 2.0 | 1.8 | 2.85 (0.12) | 2.4 | 3.2 |
| iPS:421267 | — | — | — | — | D54N | V102F | 0.23 (0.01) | 4.0 | 3.5 | 3.51 (0.16) | 2.0 | 2.6 |
| iPS:421274 | G30W | — | — | — | G56R | — | 0.61 (0.04) | 1.5 | 1.3 | 5.12 (0.45) | 1.4 | 1.8 |
| iPS:421278 | S32N | — | — | — | G56R | — | 0.90 (0.14) | 1.0 | 0.9 | 11.96 (6.93) | 1.1 | 0.8 |
| iPS:421282 | — | — | R93M | — | G56R | — | 1.12 (0.25) | 0.8 | 0.7 | 6.99 (0.40) | 1.9 | 1.3 |
| iPS:421286 | — | — | — | R31H | G56R | — | 2.92 (0.50) | 0.3 | 0.3 | 4.11 (0.38) | 3.2 | 2.2 |
| iPS:421293 | — | — | — | F32Y | G56R | — | 0.91 (0.08) | 1.0 | 0.9 | 4.30 (0.42) | 3.1 | 2.1 |

TABLE 12-continued

In vitro inhibitory potency of variant antibodies and Fab-Fc fusion proteins

| Variant Ab ID. | Substitutions with respect to 29G4v10 VL sequence (SEQ ID NO: 52) LC CDR1 | LC CDR2 | LC CDR3 | Substitutions with respect to 29G4v10 VH sequence (SEQ ID NO: 191) HC CDR1 | HC CDR2 | HC CDR3 | mAb functional activity (bivalent target binding) IC50 (SD) in nM | Fold-increase over parental (on plate)[1] | Fold-increase over parental (avg)[2] | Fab-Fc fusion protein functional activity (monovalent target binding) IC50 (SD) in nM | Fold-increase over parental (on plate)[1] | Fold-increase over parental (avg)[2] |
|---|---|---|---|---|---|---|---|---|---|---|---|---|
| iPS:421300 | — | — | — | — | Y53F; G56R | — | 1.10 (0.15) | 0.8 | 0.7 | 4.05 (0.88) | 3.3 | 2.2 |
| iPS:421307 | — | — | — | — | G56R | V102F | 0.28 (0.02) | 2.3 | 2.8 | 4.35 (0.04) | 3.0 | 2.1 |
| iPS:421314 | G30W | — | — | — | E62R | — | 0.52 (0.02) | 1.2 | 1.5 | 5.09 (0.49) | 2.6 | 1.8 |
| iPS:421318 | S32N | — | — | — | E62R | — | 0.73 (0.16) | 0.9 | 1.1 | 4.48 (0.28) | 1.7 | 2.0 |
| iPS:421322 | — | — | R93M | — | E62R | — | 1.23 (0.47) | 0.5 | 0.6 | 3.49 (0.28) | 2.2 | 2.6 |
| iPS:421326 | — | — | — | R31H | E62R | — | 3.70 (0.28) | 0.2 | 0.2 | 4.29 (0.81) | 1.8 | 2.1 |
| iPS:421333 | — | — | — | F32Y | E62R | — | 1.05 (0.08) | 0.6 | 0.7 | 1.23 (0.10) | 6.3 | 7.4 |
| iPS:421340 | — | — | — | — | Y53F; E62R | — | 0.71 (0.21) | 0.9 | 1.1 | 1.44 (0.01) | 5.4 | 6.3 |
| iPS:421347 | — | — | — | — | G56A; E62R | — | 0.71 (0.13) | 1.1 | 1.1 | 1.32 (0.45) | 5.9 | 6.9 |
| iPS:421354 | — | — | — | — | E62R | V102F | 0.53 (0.01) | 1.5 | 1.5 | 2.33 (0.67) | 2.8 | 3.9 |
| iPS:421361 | G30W | — | — | — | — | V102I | 1.29 (0.72) | 0.6 | 0.6 | 2.11 (0.11) | 3.1 | 4.3 |
| iPS:421365 | S32N | — | — | — | — | V102I | 4.46 (0.43) | 0.2 | 0.2 | 8.87 (0.57) | 0.7 | 1.0 |
| iPS:421369 | — | — | R93M | — | — | V102I | 6.43 (3.20) | 0.1 | 0.1 | 4.58 (0.38) | 1.4 | 2.0 |
| iPS:421373 | — | — | — | R31H | — | V102I | 9.82 (0.36) | 0.1 | 0.1 | 3.19 (0.13) | 2.0 | 2.8 |
| iPS:421380 | — | — | — | F32Y | — | V102I | 3.28 (0.59) | 0.2 | 0.2 | 3.09 (0.40) | 2.1 | 2.9 |
| iPS:421387 | — | — | — | — | Y53F | V102I | 1.78 (0.32) | 0.6 | 0.4 | 2.45 (0.21) | 2.7 | 3.7 |
| iPS:421394 | — | — | — | — | G56A | V102I | 2.36 (0.20) | 0.4 | 0.3 | 1.65 (0.64) | 4.0 | 5.5 |

[1]This value represents the fold-increase in IC50 as compared to the IC50 value for the 29G4v10 parental molecule formatted as either a mAb or Fab-Fc fusion protein that was run in parallel with each variant molecule.
[2]This value represents the fold-increase in IC50 as compared to the average IC50 value for the 29G4v10 parental molecule formatted as either a mAb or Fab-Fc fusion protein
ND = not determined The greatest improvements in potency were observed when the antibodies had a mutation at position Q27 (Q27K) in the light chain variable region and a mutation at position D54 (D541, D54Q, or D54N) and/or position G56 (G56R or G56N) in the heavy chain variable region. Q27 in the light chain variable region of SEQ ID NO: 52 corresponds to amino acid position 29 in AHo numbering. D54 and G56 in the heavy chain variable region of SEQ ID NO: 191 correspond to amino acid positions 61 and 66 in AHo numbering, respectively. A basic amino acid, such as lysine or arginine, at position Q27 in the light chain variable region presumably provides improved charge complementarity with acidic amino acids Glu120 and Asp121 in the PAC1 ECD (see Zone 1 in FIG. 2A). Hydrophobic residues (e.g. isoleucine) or neutral hydrophilic residues (e.g. glutamine or asparagine) at position D54 in the heavy chain variable region and basic residues (e.g. arginine) or neutral hydrophilic residues (e.g. asparagine) at position G56 in the heavy chain variable region appear to improve the hydrophobic interaction or hydrogen bonding with amino acid residues Asn60 and Ile61 in the PAC1 ECD (see Zone 6 in FIG. 3B).

The top eleven mutants from the MutHC library screen (Table 8) were formatted as aglycosylated IgG1 monoclonal antibodies and monovalent Fab-Fc molecules as described above for production and functional testing in the cAMP assay (Table 13). The modestly improved binding on yeast for this set of variants translated to improved PAC1 receptor blocking function for four out of 11 mAbs and seven out of 11 Fab-Fcs. Nevertheless, as an antibody, the iPS:421873 mutant showed about a 4-fold improvement in PAC1 blocking function compared to parental 29G4v10 antibody. Activity rankings of the mutants were largely consistent across the two formats, with the Fab-Fcs consistently showing weaker function (higher IC50 values) than the mAbs, presumably due to loss of avidity.

TABLE 13

In vitro inhibitory potency of variants from the MutHC library screen

| | Substitutions with respect to 29G4v10 VL sequence (SEQ ID NO: 52) | | | Substitutions with respect to 29G4v10 VH sequence (SEQ ID NO: 191) | | | mAb functional activity (bivalent target binding) | | | Fab-Fc fusion protein functional activity (monovalent target binding) | | |
|---|---|---|---|---|---|---|---|---|---|---|---|---|
| Variant Ab ID. | LC CDR1 | LC CDR2 | LC CDR3 | HC CDR1 | HC CDR2 | HC CDR3 | IC50 (SD) in nM | Fold-increase over parental (on plate)[1] | Fold-increase over parental (avg)[2] | IC50 (SD) in nM | Fold-increase over parental (on plate)[1] | Fold-increase over parental (avg)[2] |
| iPS:421855 | — | — | — | R31K; F32Y | Y53F; D54K G56S | V102L | 0.55 (0.11) | 1.8 | 1.4 (0.02) | 1.30 | 5.1 | 7.0 |
| iPS:421861 | — | — | — | F32Y | D54Q | V102L | 1.29 (0.22) | 0.8 | 0.6 | 3.31 (0.66) | 2.0 | 2.7 |
| iPS:421867 | — | — | — | R31H | Y53F; D54S; G56S | V102M | 5.55 (0.49) | 0.2 | 0.1 | 5.41 (0.25) | 1.2 | 1.7 |
| iPS:421873 | — | — | — | R31K | D54R | V102L | 0.25 (0.04) | 3.9 | 3.1 | 1.27 (0.03) | 5.2 | 7.1 |
| iPS:421879 | | | | F32Y | D54S; G56A | V102L; T104S | 1.60 (0.01) | 0.6 | 0.5 | 2.06 (0.75) | 3.2 | 4.4 |
| iPS:421885 | — | — | — | R31H; F32Y | Y53F; D54K; G56A | V102L | 0.72 (0.14) | 1.3 | 1.1 (0.58) | 2.51 | 2.6 | 3.6 |
| iPS:421891 | — | — | — | R31H; F32Y | D54R; G56A | V102L | 1.04 (0.09) | 0.9 | 0.8 | 2.59 (0.24) | 2.9 | 3.5 |
| iPS:421897 | — | — | — | R31H; F32Y | Y53F; D54Y; G56S | V102F | 3.42 (0.41) | 0.3 | 0.2 | 5.85 (0.71) | 1.3 | 1.6 |
| iPS:421903 | — | — | — | R31H | Y53F; D54F | V102F | 2.34 (0.98) | 0.4 | 0.3 | 4.95 (0.23) | 1.5 | 1.8 |
| iPS:421909 | — | — | — | R31H; F32Y; | Y53F; D54M; G56T | V102F | 4.10 (0.36) | 0.2 | 0.2 | 5.01 (2.10) | 1.5 | 1.8 |
| iPS:421915 | — | — | — | R31Y | Y53H; D54R; G56T | V102L; T104S | 0.80 (0.00) | 1.2 | 1.0 | 2.38 (0.69) | 3.1 | 3.8 |

[1]This value represents the fold-increase in IC50 as compared to the IC50 value for the 29G4v10 parental molecule formatted as either a mAb or Fab-Fc fusion protein that was run in parallel with each variant molecule.
[2]This value represents the fold-increase in IC50 as compared to the average IC50 value for the 29G4v10 parental molecule formatted as either a mAb or Fab-Fc fusion protein A subset of the 29G4v10 mutants from the chain-shuffled libraries (Tables 9 and 10) were converted to aglycosylated IgG1 monoclonal antibodies and tested for functional activity in the cell-based cAMP assay. The results are shown in Table 14 below.

TABLE 14

In vitro inhibitory potency of variants from chain-shuffled yeast display libraries

| | Variant Ab | Human PAC1 | | Rat PAC1 | |
|---|---|---|---|---|---|
| Clone ID | ID. | IC50 (nM) | SD | IC (nM) | SD |
| 30_D05 | iPS: 480711 | 0.07 | 0.00 | 0.17 | 0.02 |
| 37_F04 | iPS: 480706 | 0.42 | 0.01 | 0.66 | 0.08 |
| 37_A11 | iPS: 480713 | 0.50 | 0.05 | 1.22 | 0.40 |
| 37_H05 | iPS: 480705 | 0.53 | 0.25 | 1.16 | 0.34 |
| 37_B06 | iPS: 480707 | 0.59 | 0.01 | 1.17 | 0.26 |
| 30_H10 | iPS: 480708 | 0.62 | 0.02 | 1.06 | 0.13 |
| 30_F08 | iPS: 480709 | 0.77 | 0.17 | 1.82 | 0.97 |
| 30_E08 | iPS: 480712 | 0.83 | 0.33 | 1.68 | 0.92 |
| 37_E09 | iPS: 480704 | 1.36 | 0.05 | 2.74 | 1.05 |
| 30_A05 | iPS: 480710 | 1.61 | 0.20 | 3.53 | 1.00 |
| 1_D07 | iPS: 480716 | 2.51 | 0.43 | 5.22 | 2.08 |
| 2_C11 | iPS: 480715 | 3.63 | 1.04 | 7.37 | 2.73 |
| 2_G07 | iPS: 480717 | 3.92 | 0.86 | 10.77 | 0.73 |
| 2_B10 | iPS: 480714 | 10.15 | 2.12 | 41.05 | 23.77 |

TABLE 14-continued

In vitro inhibitory potency of variants from chain-shuffled yeast display libraries

| | Variant Ab | Human PAC1 | | Rat PAC1 | |
|---|---|---|---|---|---|
| Clone ID | ID. | IC50 (nM) | SD | IC (nM) | SD |
| 29G4v10 parental antibody | | 0.75 | | 84.50[2] | |
| 29G4v22 control[1] | | 4.70 | | >1000 | |

[1]29G4v22 is another anti-PAC1 neutralizing antibody that shares significant structural similarity with 29G4v10. The VL and VH sequences for 29G4v22 are provided in SEQ ID NOs: 53 and 192 respectively.
[2]Historical value obtained from a previous assay and included for comparative purposes.

When formatted as monoclonal antibodies (mAbs), 29G4v10 mutants from the second generation chain-shuffled library (Table 10) were more potent antagonists of PAC1 than mutants from the first generation chain-shuffled library (Table 9), suggesting that enhanced PAC1 blocking function is correlated with improved binding and slower binding off-rates, in particular. However, surprisingly, most of the mutants as mAbs were less active than antibody iPS:421873, the most potent mutant from the mutHC library screen (Table 13), despite their presumably enhanced binding to the human PAC1 ECD. Nevertheless, the 30_D05 mutant exhibited about a 10-fold and 67-fold improvement in function as compared to the 29G4v10 parental antibody and 29G4v22 control antibody, respectively. One common feature shared by the highly potent S8_30_D05 and iPS:421873 mAbs is the D54R mutation within HCDR2, which is absent in all of the other less potent mAb mutants. Interestingly, all of the affinity-matured variants exhibit cross-reactivity with the rat PAC1 receptor, in contrast to the 29G4v10 parental antibody and 29G4v22 control antibody (Table 14).

Example 4. In Vivo Functional Activity of Human PAC1 Antibody Variants

Maxadilan is a vasodilatory peptide and an agonist of the PAC1 receptor. When administered intradermally, maxadilan causes an increase in local dermal blood flow that can be measured by laser Doppler imaging. Inhibition of this effect by PAC1 antagonists (e.g. anti-PAC1 antibodies) can serve as a translational pharmacodynamic model of antagonism of PAC1 biological activity. A subset of the PAC1 variants that exhibited improved in vitro inhibitory potency when formatted as monoclonal antibodies from Example 3 were tested for efficacy in inhibiting PAC1 receptor activation in vivo by using a rat dermal blood flow model.

In Vivo Pharmacodynamic Model

Naive male Sprague Dawley rats aged at 8-12 weeks at the time of the study were purchased from Charles River Laboratories. All procedures in this example were conducted in compliance with the Animal Welfare Act, the Guide for the Care and Use of Laboratory Animals, and the Office of Laboratory Animal Welfare. Animals were group-housed in non-sterile, ventilated micro-isolator housing in Amgen's Assessment and Accreditation of Laboratory Animal Committee (AAALAC)-accredited facility. Animals had ad libitum access to pelleted feed (Harlan Teklad 2020X, Indianapolis, IN) and water (on-site generated reverse osmosis) via automatic watering system.

The subset of anti-PAC1 antibodies were tested in a rat maxadilan-induced increase in dermal blood flow (MIIBF) pharmacodynamic (PD) model with a laser Doppler imaging. A dosing solution of maxadilan (Bachem, H6734.0500) was prepared fresh daily by diluting maxadilan stock solution (0.5 mg/mL) in 1× phosphate-buffered saline (PBS) to a final concentration of 0.5 μg/mL. All anti-PAC1 antibodies (Abs) were prepared in 10 mM sodium-acetate, 9% sucrose, pH 5.2 (A52Su) at different concentrations, depending on the dose required for the experiment, and administered via a single bolus i.v. injection one day prior to the dermal blood flow (DBF) measurement by the laser Doppler imaging.

A laser Doppler imager (LDI-2, Moor Instruments, Ltd, Wilmington, DE) was used to measure DBF on a shaved patch of skin of the rat abdomen using a low-power laser beam generated by a 633 nm helium-neon bulb. The measurement resolution was 0.2 to 2 mm, with a scanning distance between the instrument aperture and the tissue surface of 30 cm. DBF was measured and expressed as either % change from baseline [100×(individual post-maxadilan flux-individual baseline flux)/individual baseline flux] or % DBF inhibition [Mean of vehicle % change from BL−individual antibody treated rat % change from BL)/Mean of vehicle % change from BL] to quantify the magnitude of the antibody effect.

On the test day, following anesthetization with propofol, the rat's abdominal area was shaved and each animal was placed in a supine position on a temperature-controlled circulating warm-water pad to maintain a stable body temperature during the study. After a 10 to 15 minute stabilization period, a rubber O-ring (0.925 cm inner diameter, 0-Rings West, Seattle, WA) was placed on the rat abdomen (without directly positioning it over a visible blood vessel). After placement of the O-ring on the selected area, a baseline (BL) DBF measurement was taken. After the BL scan, the PAC1 agonist maxadilan was administered by intradermal injection (20 μL of 0.5 μg/mL) at the center of the O-ring. DBF was measured 30 min following maxadilan injection, or 24±1.5 hours following antibody treatment. The O-ring defines the area of interest in which the DBF was analyzed.

All DBF results were expressed as the mean±SEM. A one-way ANOVA followed by Dunnett's Multiple Comparison Test (MCT) was used to assess the statistical significance of PAC1 Ab effects relative to vehicle treatment. A p value of <0.05 was used to determine significance between two groups.

Single Intravenous (i.v.) Dose Screening Evaluation

Figure 6:
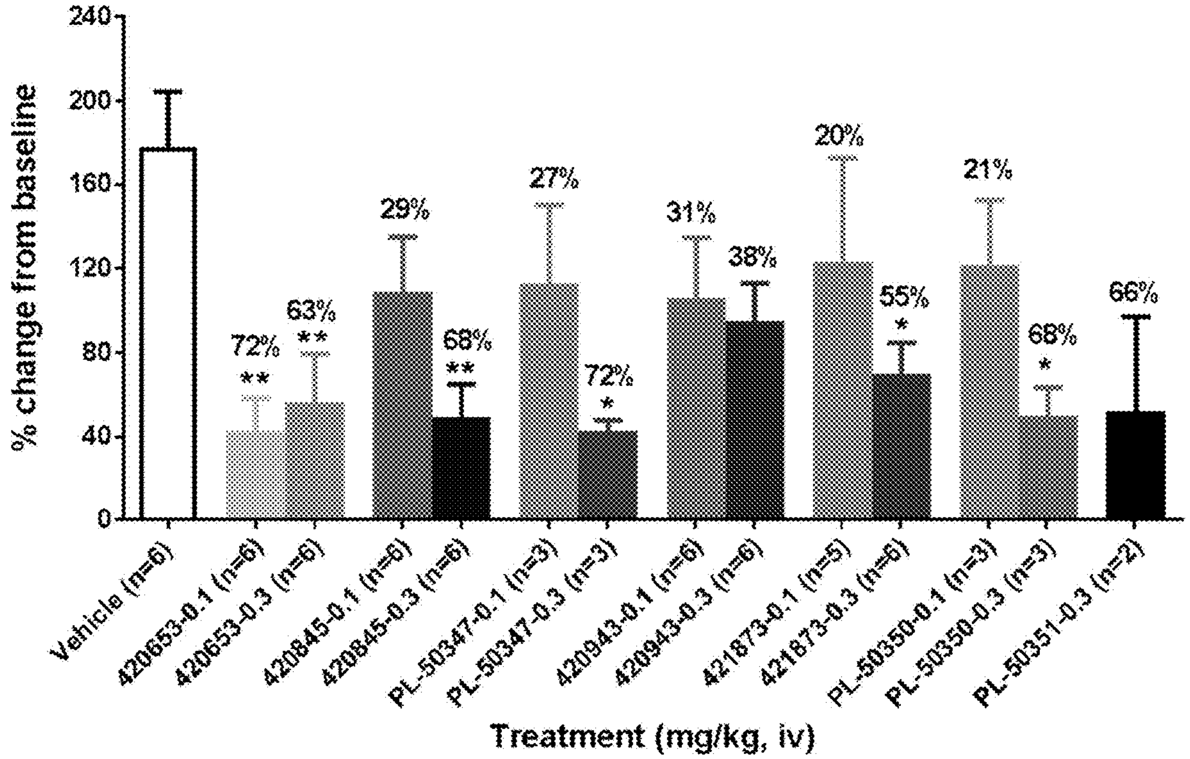
FIG. 6 shows the inhibitory effect of anti-PAC1 antibodies on maxadilan-induced increase in dermal blood flow in rats. One of seven antibodies (420653, 420845, 420943, 421873, 420889 (PL-50347), 421091 (PL-50350), and 421051 (PL-50351)) was administered to rats intravenously at a dose of 0.1 mg/kg or 0.3 mg/kg twenty-four hours prior to challenge with 10 ng maxadilan (intradermal injection). Dermal blood flow was assessed 30 minutes following maxadilan challenge with laser Doppler imaging. *$p<0.05$, **$p<0.01$ compared to the vehicle group with One-Way ANOVA followed by Dunnett's MCT.

Rats were pretreated with one of 7 different anti-PAC1 antibodies (420653, 420845, 420943, 421873, 420889 (PL-50347), 421091 (PL-50350), and 421051 (PL-50351)) 24 hours prior to maxadilan challenge (20 μl of 0.5 μg/mL) at a dose of 0.1 mg/kg or 0.3 mg/kg, which resulted in a reduction in MIIBF compared to vehicle (A52Su) treated group. At 30 min post-maxadilan treatment, there was a statistically significant inhibition in MIIBF at 0.3 mg/kg compared to the vehicle group for five of the seven antibodies tested (FIG. 6). Terminal serum concentration at 24±1.5 hours for six of the seven antibodies is listed in Table 15 below.

TABLE 15

Terminal serum concentrations for single-injection (screening) study

| Antibody ID. | Dose (mg/kg) 0.1 | 0.3 |
|---|---|---|
| 420653 (PL-50345) | 2.0 ± 0.8 | 8.9 ± 2.5 |
| 420845 (PL-50346) | 1.2 ± 0.3 | 6.4 ± 0.8 |
| 420889 (PL-50347) | 5.5 ± 3.1 | 10.7 ± 1.7 |
| 420943 (PL-50348) | 1.6 ± 0.4 | 8.9 ± 1.8 |
| 421873 (PL-50349) | 1.1 ± 0.3 | 4.4 ± 0.4 |
| 421091 (PL-50350) | 1.0 ± 0.1 | 3.0 ± 0.1 |

Dose-Response Evaluation

Figure 7A:
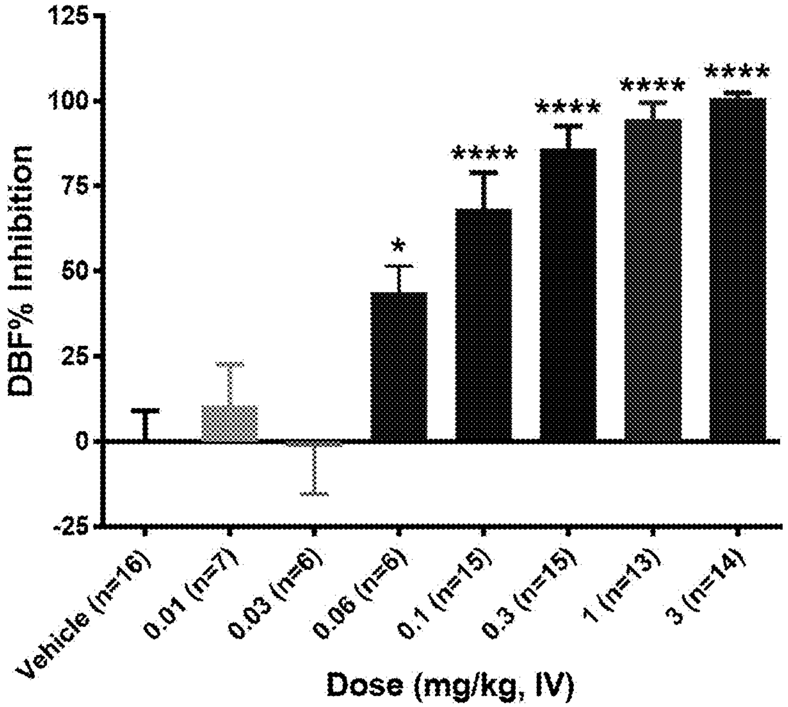
FIG. 7A shows the dose-dependent effect of anti-PAC1 antibody 420653 on maxadilan-induced increase in dermal blood flow in rats. The antibody was administered to rats intravenously at one of seven doses ranging from 0.01 mg/kg to 3 mg/kg twenty-four hours prior to challenge with 10 ng maxadilan (intradermal injection). Dermal blood flow was assessed 30 minutes following maxadilan challenge with laser Doppler imaging. *$p<0.05$, ****$p<0.0001$ compared to the vehicle group with One-Way ANOVA followed by Dunnett's MCT.
Figure 7B:
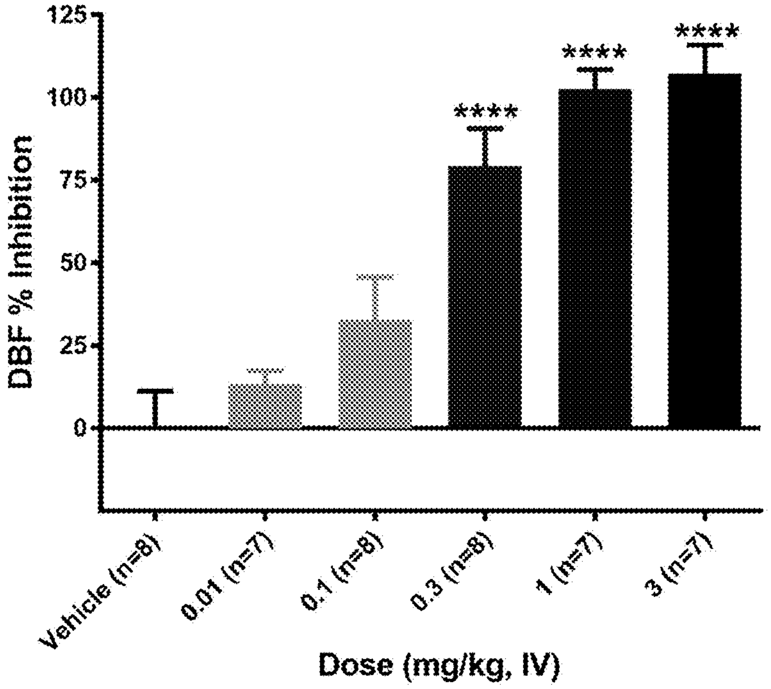
FIG. 7B shows the dose-dependent effect of anti-PAC1 antibody 420845 on maxadilan-induced increase in dermal blood flow in rats. The antibody was administered to rats intravenously at one of five doses ranging from 0.01 mg/kg to 3 mg/kg twenty-four hours prior to challenge with 10 ng maxadilan (intradermal injection). Dermal blood flow was assessed 30 minutes following maxadilan challenge with laser Doppler imaging. ****$p<0.0001$ compared to the vehicle group with One-Way ANOVA followed by Dunnett's MCT.
Figure 7C:
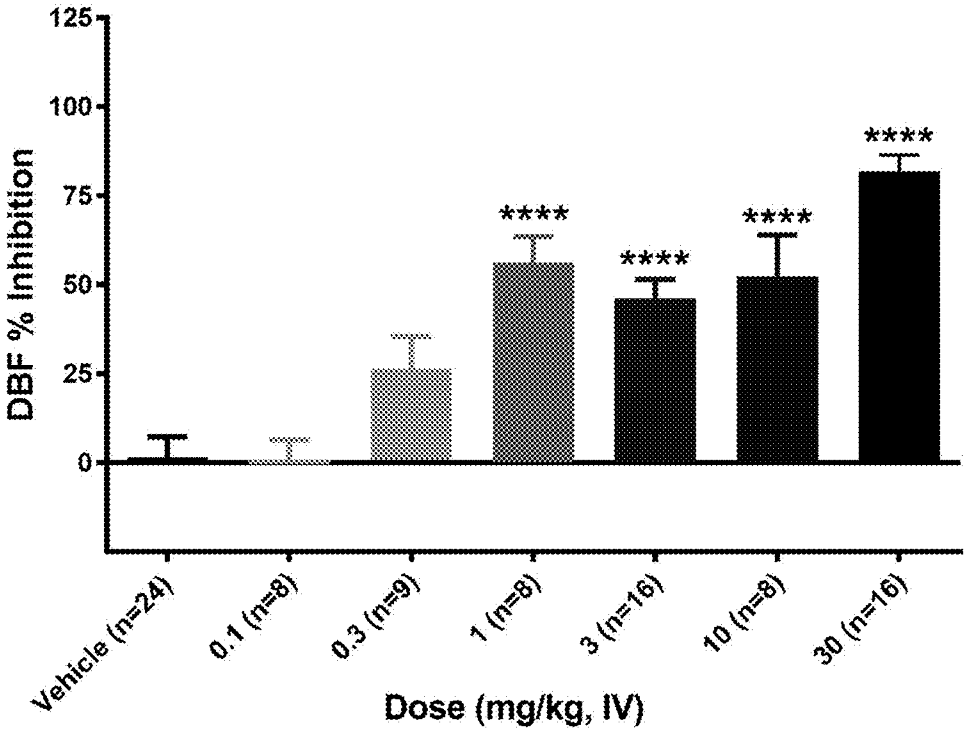
FIG. 7C shows the dose-dependent effect of anti-PAC1 antibody 420943 on maxadilan-induced increase in dermal blood flow in rats. The antibody was administered to rats intravenously at one of six doses ranging from 0.1 mg/kg to 30 mg/kg twenty-four hours prior to challenge with 10 ng maxadilan (intradermal injection). Dermal blood flow was assessed 30 minutes following maxadilan challenge with laser Doppler imaging. ****$p<0.0001$ compared to the vehicle group with One-Way ANOVA followed by Dunnett's MCT.
Figure 7D:
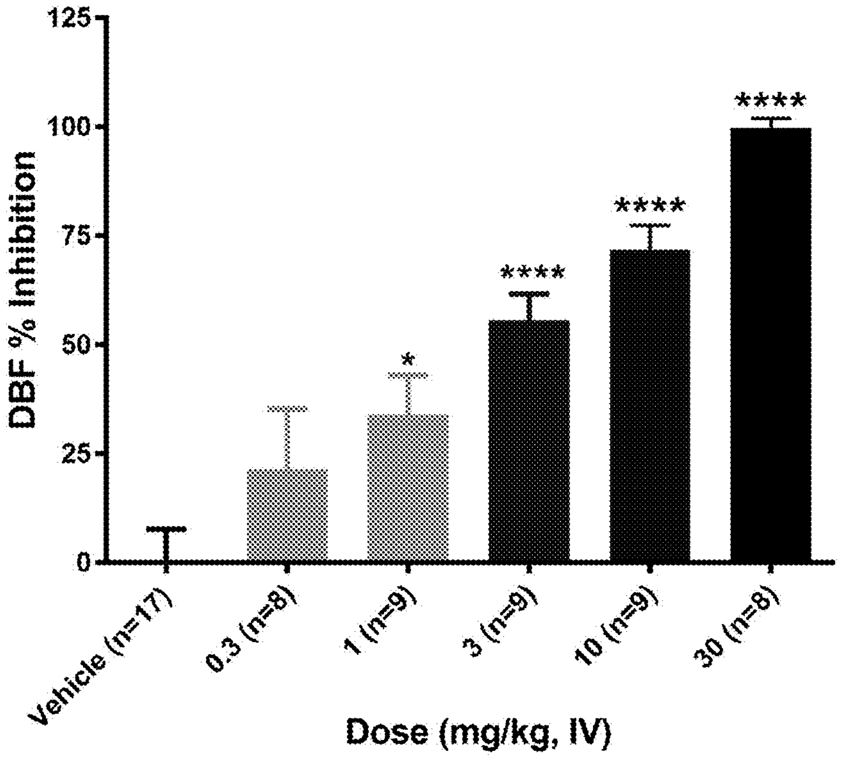
FIG. 7D shows the dose-dependent effect of anti-PAC1 antibody 421873 on maxadilan-induced increase in dermal blood flow in rats. The antibody was administered to rats intravenously at one of five doses ranging from 0.3 mg/kg to 30 mg/kg twenty-four hours prior to challenge with 10 ng maxadilan (intradermal injection). Dermal blood flow was assessed 30 minutes following maxadilan challenge with laser Doppler imaging. *$p<0.05$, ****$p<0.0001$ compared to the vehicle group with One-Way ANOVA followed by Dunnett's MCT.

Rats were pretreated with 4 different anti-PAC1 antibodies (420653, 420845, 420943, and 421873) 24 hours prior to maxadilan challenge (20 μl of 0.5 μg/mL) at a dose ranging from 0.01 mg/kg to 30 mg/kg. A dose-dependent reduction of MIIBF compared to vehicle-treated group was observed for each of the four antibodies (FIGS. 7A-7D). Ab 420653 produced a significant effect at a dose as low as 0.06 mg/kg with inhibitory effects of 44%, 68%, 86%, 95%, and 101% at 0.06, 0.1, 0.3, 1 and 3 mg/kg, respectively (FIG. 7A). Ab 420845 produced a significant effect at 0.3, 1 and 3 mg/kg with inhibition of 79% 102% and 107%, respectively (FIG. 7B). Ab 420943 and 421873 were slightly less potent than Ab 420845 and Ab 420653, but still produced a significant inhibitory effect at 1 mg/kg. The % inhibition in DBF for Ab 420943 was 56%, 46%, 52% and 81% at 1, 3, 10, 30 mg/kg, respectively (FIG. 7C). The % inhibition in DBF for Ab 421873 was 34%, 55%, 72% and 100% at 1, 3, 10, and 30 mg/kg, respectively (FIG. 7D).

The results of the experiments described in this example show that antibodies that potently inhibit ligand-induced PAC1 receptor activation in vitro also inhibit PAC1 receptor activation in vivo as assessed by the dermal blood flow assay, a model of PAC1-mediated vasodilation.

Example 5. Pharmacokinetic Characteristics of Human PAC1 Antibody Variants

Preliminary pharmacokinetic (PK) studies of four anti-PAC1 antibodies (420653, 420845, 420943, and 421873) were conducted with naïve male Sprague-Dawley rats and naïve male cynomolgus monkeys. The 29G4v10 parental antibody or the structurally related 29G4v22 antibody (VL comprising SEQ ID NO: 53 and VH comprising SEQ ID NO: 192) was evaluated as a control. The test antibodies were dosed to study animals by intravenous bolus administration. Blood samples were collected at specified time points post-dose and processed to serum. All serum specimens were stored at approximately −70° C. (±10° C.) until transferred for subsequent analysis.

To measure the amount of test antibody in serum samples from rats and cynomolgus monkeys following dosing, a colorimetric enzyme-linked immunosorbent assay (ELISA) was developed using murine monoclonal antibodies (mAb) directed against human IgG Fc (Amgen, Inc., CA, USA). Microtiter plates were coated with a murine anti-human Fc mAb at 2 μg/mL. The coated microtiter plates were blocked with I-block (Applied Biosystems, CA, USA). Assay standards (STDs) and quality controls (QCs) were prepared by spiking the test antibody into 100% serum from the studied species. STDs, QCs, blank and study samples were diluted 1:30 in assay buffer (1×PBS with 1 M NaCl, 1% BSA and 0.5% Tween 20). Diluted STDs, QCs, blank and study samples were incubated on the coated microtiter plates for 1 h at 25° C. without agitation. After a wash step, a horseradish peroxidase (HRP)-conjugated murine anti-human Fc mAb at 30 ng/mL in assay buffer was added to the microtiter plates and incubated for 1 h at 25° C. without agitation. After a final wash step, a tetramethylbenzidine (TMB) peroxide substrate solution (KPL Inc., MD, USA) was added to the microtiter plates. In the presence of HRP, TMB produced a colorimetric signal that was proportional to the quantity of bound human Fc present in the STDs, QCs and study samples. The color development duration was analyte-dependent and was stopped by addition of 2N sulfuric acid. The optical density (OD) was measured at 450 nm with reference to 650 nm using a SpectraMax 340PC microtiter plate reader (Molecular Devices, CA, USA) and SoftMax Pro software. Assay data were regressed using a logistic (auto-estimate) regression model with a weighting factor of 1/y. The assay dynamic range was from 20 ng/mL to 2000 ng/mL.

For both the rat and cynomolgus monkey PK studies, noncompartmental analysis was performed on individual serum concentration-nominal time data using Phoenix® WinNonlin® (version 6.4; Certara, NJ, USA). Individual concentration values less than the lower limit of quantification (LLOQ, 20 ng/mL) were reported as below the quantitation limit (BQL) and set to zero for the calculation of summary statistics. Mean concentration values less than the LLOQ were not reported or plotted. All concentrations values less than the LLOQ were excluded from the noncompartmental analysis. Nominal doses and nominal sampling times were used for PK analysis. The following PK parameters were estimated:

- The initial concentration ($C_0$) value after intravenous administration was estimated by back extrapolation to time zero using the first 2 observed declining concentration values.
- The area under the concentration-time curve from time zero to infinity (AUCinf) was calculated by the linear trapezoidal method.
- The terminal-phase half-life ($t_{1/2,z}$) was calculated as ln $2/\lambda_z$. $\lambda_z$ is the first-order rate constant of drug associated with the terminal portion of the curve.
- Systemic clearance (CL) was calculated as: CL=Dose/AUCinf after intravenous administration
- Volume of distribution at steady state (Vss) was estimated as: Vss=CL×MRTinf (mean residence time from time zero to infinity)

A summary of the in vitro inhibitory potency of the four antibodies as well as for the 29G4v10 parental antibody and the 29G4v22 control antibody against the human PAC1, rat PAC1, and cyno PAC1 is provided in Table 16 below. The antibodies were evaluated for the ability to inhibit ligand-induced (PACAP38 or maxadilan) activation of the PAC1 receptor from different species using the cAMP assay described in Example 3.

TABLE 16

Summary of In Vitro Inhibitory Potency for PAC1 Variant Antibodies

| | Human PAC1 (nM) | | Cyno PAC1 (nM) | | Rat PAC1 (nM) | |
|---|---|---|---|---|---|---|
| Antibody ID | PACAP38 (n = 3) | Maxadilan (n = 3) | PACAP38 (n = 3) | Maxadilan (n = 3) | PACAP38 (n = 3) | Maxadilan (n = 3) |
| 420653 | 0.24 | 0.13 | 0.13 | 0.10 | 0.21 | 0.19 |
| 420845 | 0.09 | 0.09 | 0.08 | 0.09 | 0.11 | 0.07 |
| 420943 | 0.37 | 0.20 | 0.21 | 0.17 | 5.66 | 0.69 |
| 421873 | 0.24 | 0.10 | 0.12 | 0.10 | 0.23 | 0.06 |
| 29G4v22 | 4.70 | 1.60 | 1.11 | 1.00 | >1000 | 580 |
| 29G4v10 | 0.75 | — | 0.33 | — | 84.5 | 8.75 |

Figure 8A:
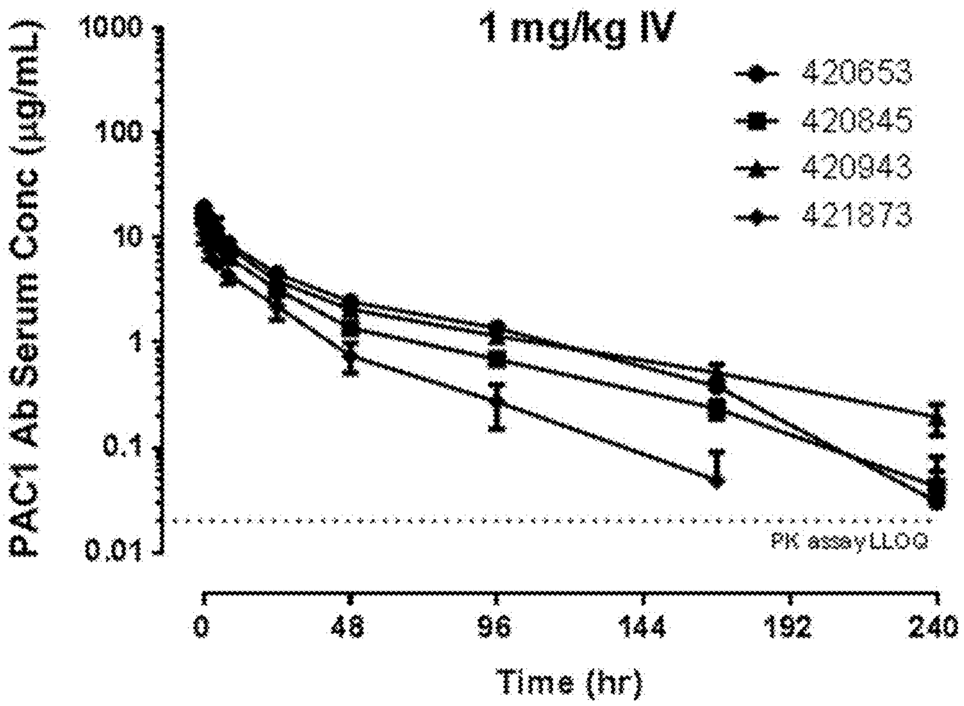
FIG. 8A is the serum concentration-time profile for anti-PAC1 antibodies 420653, 420845, 420943, and 421873 following a single intravenous dose of 1 mg/kg in rats.
Figure 8B:
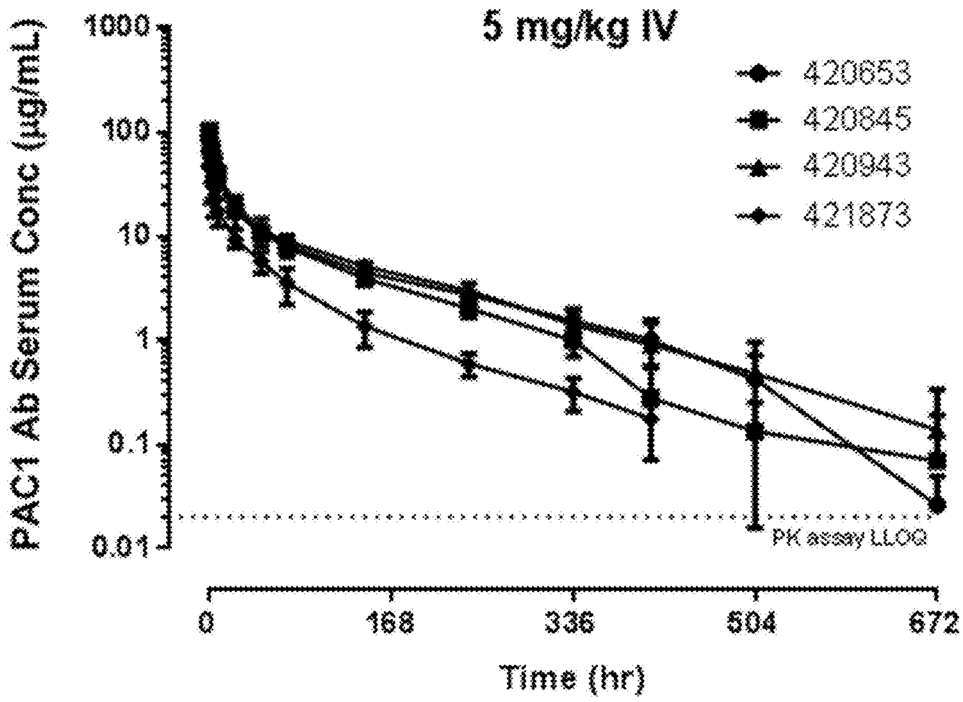
FIG. 8B is the serum concentration-time profile for anti-PAC1 antibodies 420653, 420845, 420943, and 421873 following a single intravenous dose of 5 mg/kg in rats.
Figure 8C:
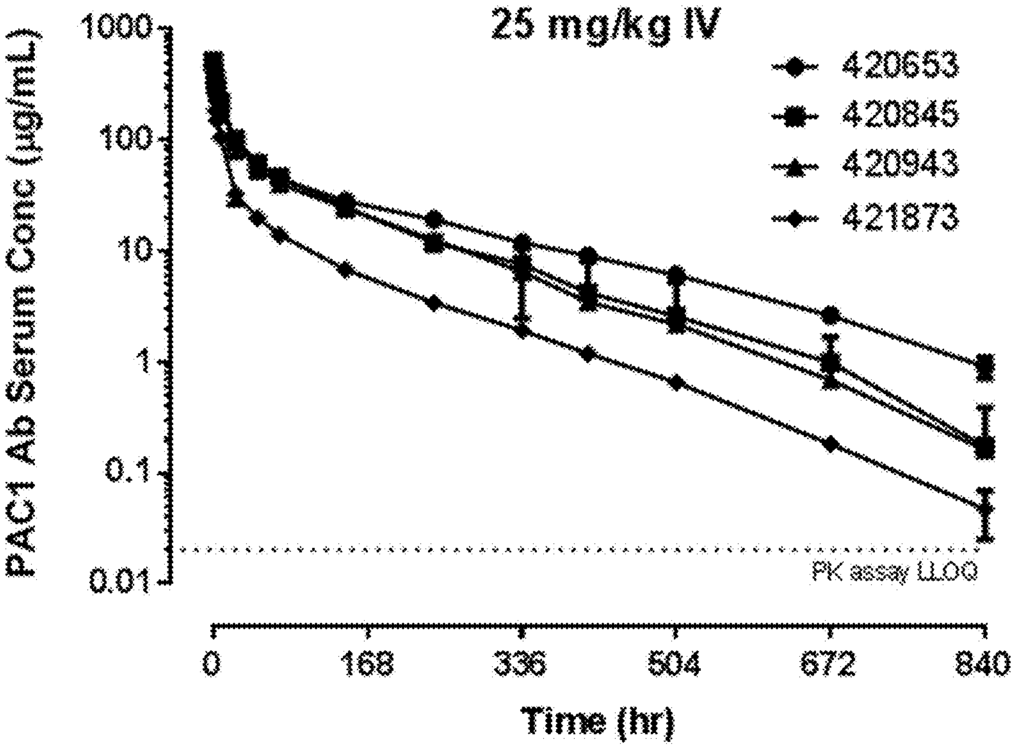
FIG. 8C is the serum concentration-time profile for anti-PAC1 antibodies 420653, 420845, 420943, and 421873 following a single intravenous dose of 25 mg/kg in rats.

Rats were administered intravenously one of the four antibodies at a dose of 1 mg/kg, 5 mg/kg, and 25 mg/kg. Blood samples were collected at various time points after dosing and antibody concentration was measured in serum samples at each of the time points using the ELISA assay described above. PK parameters for the rat study are summarized in Table 17 below and serum concentration-time profiles for each of the doses are shown in FIGS. 8A-8C.

TABLE 17

| Summary of PK Parameters for PAC1 Variant Antibodies in Rats | | | | | | | |
|---|---|---|---|---|---|---|---|
| Antibody ID | IV Dose (mg/kg) | n | $C_0$ (μg/mL) | $AUC_{0\text{-}inf}$ (μg * hr/mL) | $V_{ss}$ (mL/kg) | CL (mL/hr/kg) | $t_{1/2,z}$ (hr) |
| 420653 | 1 | 3 | 19.6 | 467 | 100 | 2.16 | 35.3 |
| | 5 | 3 | 87.1 | 2600 | 218 | 2.05 | 70.5 |
| | 25 | 2 | 462 | 16900 | 236 | 1.48 | 130 |
| 420845 | 1 | 3 | 15.7 | 305 | 141 | 3.28 | 42.2 |
| | 5 | 3 | 104 | 2420 | 171 | 2.08 | 73.2 |
| | 25 | 2 | 525 | 14800 | 179 | 1.69 | 100 |
| 420943 | 1 | 3 | 17.4 | 441 | 129 | 2.28 | 51.3 |
| | 5 | 3 | 101 | 2900 | 184 | 1.75 | 79.3 |
| | 25 | 2 | 490 | 13600 | 191 | 1.83 | 67.9 |
| 421873 | 1 | 3 | 11.2 | 179 | 156 | 5.88 | 27.9 |
| | 5 | 3 | 64.2 | 1100 | 424 | 4.73 | 110 |
| | 25 | 2 | 341 | 5300 | 383 | 4.73 | 96.8 |

Figure 9:
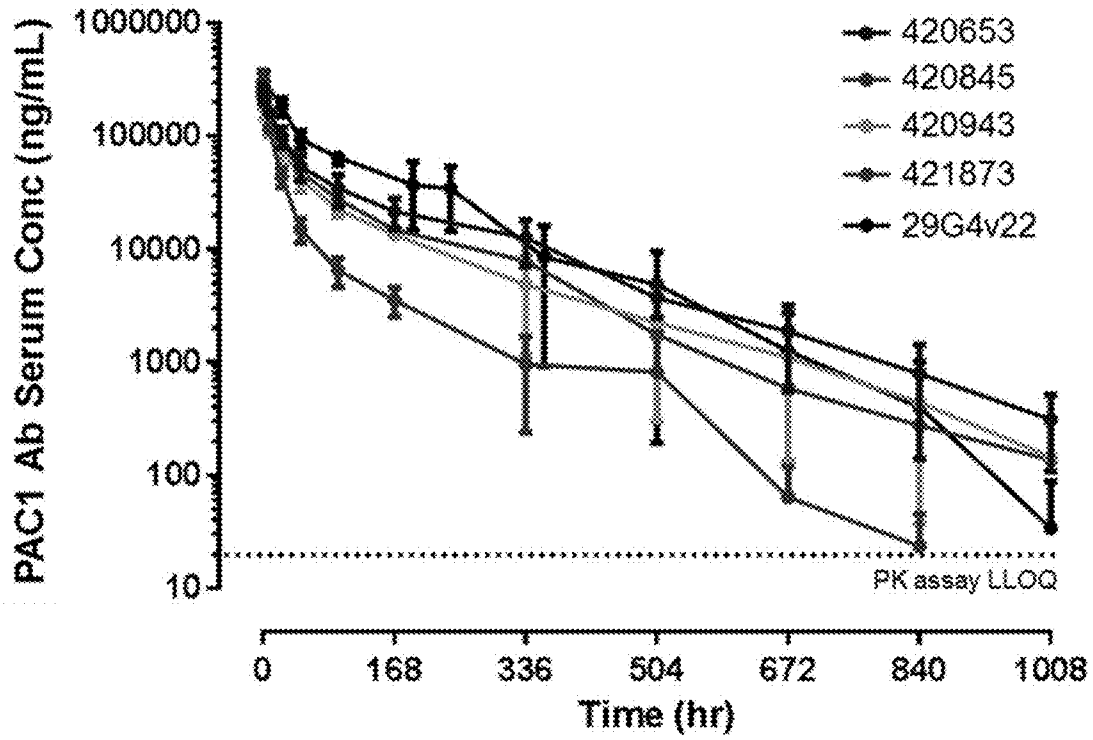
FIG. 9 is the serum concentration-time profile for anti-PAC1 antibodies 420653, 420845, 420943, 421873, and 29G4v22 following a single intravenous dose of 10 mg/kg in cynomolgus monkeys.

Cynomolgus monkeys were administered intravenously one of the four antibodies at a dose of 10 mg/kg. Blood samples were collected at various time points after dosing and antibody concentration was measured in serum samples at each of the time points using the ELISA assay described above. PK parameters for the cynomolgus monkey study are summarized in Table 18 below and the serum concentration-time profiles are shown in FIG. 9. The PK profile of the 29G4v22 antibody is show for comparison.

TABLE 18

| Summary of PK Parameters for PAC1 Variant Antibodies in Cynomolgus Monkeys | | | | | | |
|---|---|---|---|---|---|---|
| Antibody ID | n | $C_0$ (μg/mL) | $AUC_{0\text{-}inf}$ (μg * hr/mL) | $V_{ss}$ (mL/kg) | CL (mL/hr/kg) | $t_{1/2,z}$ (hr) |
| 420653 | 3 | 274 | 14800 | 110 | 0.692 | 134 |
| 420845 | 3 | 314 | 4870 | 126 | 2.09 | 85.3 |
| 420943 | 3 | 240 | 10000 | 126 | 1.00 | 107 |
| 421873 | 3 | 245 | 11800 | 96.7 | 0.849 | 92.6 |
| 29G4v22 | 6 | 312 | 24000 | 43.3 | 0.443 | 70.3 |

At this dose, all four of the PAC1 variant antibodies had a longer serum half-life than the 29G4v22 control antibody. Interestingly, although all four PAC1 variant antibodies exhibited greater in vitro inhibitory potency against the PAC1 receptor as compared with the 29G4v22 control antibody (Table 16), the PK profile for some of the variants was less favorable in cynomolgus monkeys. For example, Ab 420845 had a faster clearance rate and lower overall exposure as compared to the 29G4v22 control antibody. However, Ab 420653 had a comparable PK profile to that for the 29G4v22 control antibody (FIG. 9), suggesting that Ab 420653 could be administered at a lower dose at the same dosing frequency to achieve a similar pharmacological effect.

Example 6. Yeast Display Affinity Maturation of 19118 Human PAC1 Antibody

To generate additional anti-PAC1 antibodies with improved inhibitory potency, the 19H8 antibody (VH region of SEQ ID NO: 296; VL region of SEQ ID NO: 67) was affinity matured by FACS of yeast-displayed Fab libraries using the methods described in Example 2. The 19H8 antibody is structurally diverse from the 29G4v9, 29G4v10, and 29G4v22 antibodies, but also exhibits very potent neutralizing activity against the human PAC1 receptor.

Because no crystal structural information was available for the PAC1 ECD-19H8 Fab complex initially, a homology model was generated to identify the surface-exposed residues within each CDR loop. Because it is expected that the PAC1 ECD would make direct contacts with surface-exposed CDR residues, it was hypothesized that changing the nature of these contacts or creating new contacts through comprehensive mutagenesis could lead to improved binding of the antibody to the PAC1 ECD. To restrict theoretical diversities of each library to a manageable $10^6$-$10^7$, up to five positions per CDR were identified for MIX19 saturation mutagenesis and one separate library per CDR was constructed. Due to concerns regarding the accuracy of modeled CDRH3 loop conformations, the most solvent-exposed residues within this loop could not be reliably identified. Therefore, diversification at eight of the 11 CDR residues within CDRH3 were considered, excluding residues at the beginning and end of the loop. To narrow down the number of positions for saturation mutagenesis to five, the two tryptophans and one phenylalanine within CDRH3 was avoided, as aromatic residues are often critical mediators of protein-protein interactions. In total, six individual-CDR Fab libraries were designed to target 16 heavy chain and 15 light chain CDR residues for diversification, and the constructed libraries oversampled the theoretical diversities by 4.5 to 46-fold. A summary of the targeted positions for each CDR library is provided below:

Heavy chain CDR libraries (amino acid positions relative to SEQ ID NO: 296):

- CDRH1 library: Asp27 (located adjacent to CDRH1 in FR1), Ser31, Asn32, Ser33, and Thr35
- CDRH2 library: Tyr54, Tyr55, Ser57, Lys58, Ser60, and His62
- CDRH3 library: Thr103, Lys105, Gln106, Leu107, and Leu110

Light chain CDR libraries (amino acid positions relative to SEQ ID NO: 67):

- CDRL1 library: Ser28, Ser30, Arg31, Tyr32, and Asn34
- CDRL2 library: Tyr49 (located adjacent to CDRL2 in FR2), Ala50, Ala51, Ser52, and Ser53
- CDRL3 library: Ser91, Tyr92, Ser93, Pro94, and Phe96

The six individual-CDR Fab libraries were enriched for binding to human PAC1 ECD using FACS, increasing the stringency with each successive round by lowering the concentration of the PAC1 ECD used for binding (Round 1: 30 nM PAC1 ECD; Round 2: 0.67 nM PAC1 ECD; and Round 3: 0.2 nM PAC1 ECD). For further affinity improvements, two CDR-shuffled Fab libraries that combined enriched mutations from the individual CDR libraries (one for the heavy chain and one for the light chain) and a final chain-shuffled library that combined enriched mutations from each CDR-shuffled library were also constructed. The CDR-shuffled and chain-shuffled libraries were subjected to selections for PAC1 ECD binding under more stringent conditions using the off-rate binding selection process described in Example 2 and depicted in FIG. 5. The final off-rate sort of the chain-shuffled library suggested that most of the yeast clones within this pool were significantly improved in PAC1 ECD binding compared to parental 19H8 antibody.

Approximately 800 individual yeast clones were screened for improved binding to human PAC1 ECD. Mutant sequences with sequence liabilities (e.g. cysteine anomalies, N-linked glycosylation sites, aspartate isomerization, asparagine deamidation, and tryptophan oxidation sites) were removed. The top ~200 unique binders were advanced to a secondary screen where they were ranked by binding off-rate and evaluated for non-specific binding. In the secondary screen, >80% of the clones had slower binding off-rates than the parental 19H8 antibody, as measured by a higher association percentage of biotinylated human PAC1 ECD following an overnight competition with unlabeled PAC1 ECD at 30° C. The measurements represent lower limits on the improvement in off-rate, as biotinylated PAC1 ECD fully dissociated from parental 19H8 after only one hour of competition at 30° C. Because none of the screened clones exhibited binding to the ECDs of unrelated PD1 and GIPR receptors, to further narrow down the pool of clones, additional sequence filters were applied to remove mutants whose CDRs contained furin cleavage sites, additional tryptophan residues, and more covariance violations than the parental 19H8 antibody. An additional binding assay using a biotinylated human VPAC2 ECD to determine the degree of non-specific binding to human VPAC2, a structurally related receptor to human PAC1 receptor, was used to rank clones. The top 20 mutants exhibiting the slowest binding off-rates to human PAC1 ECD and the least amount of human VPAC2 binding among the yeast clones that entered the secondary screen are listed in Table 19 below. Higher percentage association of PAC1 ECD binding indicates that the mutant Fabs have a slower off-rate.

TABLE 19

Top Improved Binders from Yeast Display Libraries for 19H8 Parental Antibody

| | Substitutions with respect to 19H8 VH sequence (SEQ ID NO: 296) | | | Substitutions with respect to 19H8 VL sequence (SEQ ID NO: 67) | | | % human PAC1 ECD association | Biotinylated VPAC2 ECD |
|---|---|---|---|---|---|---|---|---|
| Variant Ab ID. | HC FR1-CDR1 | HC CDR2 | HC CDR3 | LC CDR1 | LC FR2-CDR2 | LC CDR3 | after off-rate competition at 30° C. | Binding (fluorescence units) |
| iPS:448202 | S31N; N32R; S33L | S57G; S60K | K105N; L107D | — | Y49F; A51G; S52Q; S53R | S91A; Y92I; S93G; P94M; F96Y | 86% | 562 |
| iPS:449375 | S31N; N32R; S33L | S57G; S60K | K105D; L107D | S28Y; S30V | S52H; S53H | S91A; Y92I; S93Q; P94E; F96Y | 80% | 506 |
| iPS:448083 | N32R; S33Q | S57G; S60K | K105E; L107D | S28T; S30V | Y49F; A51G; S52Q; S53R | S91A; Y92I; S93I; P94N; F96Y | 75% | 573 |
| iPS:452128 | S31N; N32K; S33Q | S57G; S60K | T103M; K105N; L107N | S28Y; S30V | S52N; S53M | S91A; Y92I; S93N; P94Q; F96Y | 74% | 535 |
| iPS:448195 | S31N; N32K; S33Q | S57G; S60K | T103M; K105N; L107N | S28K; S30A; N34V | S52N; S53M | Y92I; S93Q; P94Q; F96Y | 70% | 577 |
| iPS:448466 | S31N; N32K; S33Q | S57G; K58Q; S60K | K105I; Q106G; L107D; L110M | — | Y49F; A51G; S52Q; S53R | S91A; Y92I; S93Q; P94Q; F96Y | 66% | 510 |
| iPS:448689 | S31N; N32R; S33L | S57G; S60K | K105N; L107D | S28Y; S30V | A51S; S52Y; S53N | S91A; Y92I; S93M; P94A; F96Y | 66% | 596 |
| iPS:449034 | S31N; N32K; S33Q | S57G; S60K | K105I; L107D | S28P; S30A; R31Q | A51G; S52R; S53Y | S91A; Y92I; S93Q; P94N; F96Y | 65% | 519 |

TABLE 19-continued

Top Improved Binders from Yeast Display Libraries for 19H8 Parental Antibody

| | Substitutions with respect to 19H8 VH sequence (SEQ ID NO: 296) | | | Substitutions with respect to 19H8 VL sequence (SEQ ID NO: 67) | | | % human PAC1 ECD association | Biotinylated VPAC2 ECD |
|---|---|---|---|---|---|---|---|---|
| Variant Ab ID. | HC FR1-CDR1 | HC CDR2 | HC CDR3 | LC CDR1 | LC FR2-CDR2 | LC CDR3 | after off-rate competition at 30° C. | Binding (fluorescence units) |
| iPS:448568 | N32R; S33Y | S57G; S60K | T103M; K105A; Q106G; L107D; L110M | — | A51G; S52L; S53Y | S91A; Y92I; S93Q; P94T; F96Y | 63% | 620 |
| iPS:448924 | N32R; S33Y; | S57G; K58Q; S60K | T103M; K105N; L107N | S28P; N34S | Y49F; A51G; S52Q; S53R | S91A; Y92I; P94I; F96Y | 61% | 596 |
| iPS:448752 | S31N; N32K; S33Q | S57G; S60K; | T103M; K105N; L107N; | S28Q; S30A | A51S; S52Y; S53N | S91A; Y92I; S93I; P94Q; F96Y | 59% | 544 |
| iPS:448772 | S31N; N32K; S33Q | S57G; S60K | T103M; K105S; Q106G; L107D | — | A51S; S52Y; S53N | S91A; Y92I; S93Q; P94N; F96Y | 59% | 594 |
| iPS:448117 | N32H; S33V | S57G; S60K | T103M; K105S; Q106E; L107D | S28T; S30V | Y49F; A51G; S52Q; S53R | Y92I; S93Q; P94T; F96Y | 58% | 496 |
| iPS:448788 | N32R; S33Q | S57G; S60K | T103M; K105Q; Q106G; L107N | — | A51G; S52R; S53I | S91A; Y92I; S93I; P94N; F96Y | 56% | 565 |
| iPS:448593 | S31N; N32H; S33Q; | S57G; S60K | K105I; L107D | — | A51S; S52Y; S53N | S91A; Y92I; S93Q; P94N; F96Y | 54% | 544 |
| iPS:448238 | N32R; S33D | S57G; S60K | T103Q; K105N; Q106E; L107D | S28R; S30A; | Y49F; A51G; S53I | S91A; Y92I; S93Q; P94N; F96Y | 53% | 527 |
| iPS:448901 | S31N; N32R; S33L | S57G; S60K; | T103R; K105E; Q106G; L107D; L110F | — | A51S; S52Y; S53N; | Y92I; S93Q; P94Q; F96Y | 51% | 546 |
| iPS:448225 | S31N; N32R; S33L; | S57G; S60K | K105N; L107D | S28M | A50V; S53R | Y92I; S93Q; P94N; F96Y | 50% | 627 |
| iPS:448730 | S31N; N32R; S33L | S57G; S60K | T103V; K105I; Q106G; L107N | S28M; S30A | A51S; S52Y; S53N | S91A; Y92I; S93I; P94N; F96Y | 50% | 525 |
| iPS:449027 | S31N; N32K; S33Q | S57G; S60K | T103M; K105N; L107N | S28Y; S30V; | A50G; S52R; S53N | Y92I; S93Q; P94T; F96Y | 49% | 521 |
| 19H8 Wild-Type | — | — | — | — | — | — | 20% | 528 |

The improved affinity variants were produced by recombinant expression methods as complete bivalent monoclonal antibodies and/or as monovalent Fab-Fc fusions (e.g. Fab region fused to dimeric IgG Fc region) and evaluated for in vitro functional activity in the cell-based cAMP assay described in Example 3. The results of the functional assay are shown in Table 20 below.

TABLE 20

In vitro inhibitory potency of 19H8 variant antibodies and Fab-Fc fusion proteins

| Variant Ab ID. | Substitutions with respect to 19H8 VH sequence (SEQ ID NO: 296) HC FR1-CDR1 | HC CDR2 | HC CDR3 | Substitutions with respect to 19H8 VL sequence (SEQ ID NO: 67) LC CDR1 | LC FR2-CDR2 | LC CDR3 | PAC1 functional cAMP assay mAb IC50 in nM (bivalent target binding) | Fab-Fc fusion protein IC50 in nM (monovalent target binding) |
|---|---|---|---|---|---|---|---|---|
| iPS:448202 | S31N; N32R; S33L | S57G; S60K | K105N; L107D | — | Y49F; A51G; S52Q; S53R | S91A; Y92I; S93G; P94M; F96Y | 0.32 | 1.25 |
| iPS:449375 | S31N; N32R; S33L | S57G; S60K | K105D; L107D | S28Y; S30V | S52H; S53H | S91A; Y92I; S93Q; P94E; F96Y | 0.95 | 3.48 |
| iPS:448083 | N32R; S33Q | S57G; S60K | K105E; L107D | S28T; S30V | Y49F; A51G; S52Q; S53R | S91A; Y92I; S93I; P94N; F96Y | — | 3.74 |
| iPS:452128 | S31N; N32K; S33Q | S57G; S60K | T103M; K105N; L107N | S28Y; S30V | S52N; S53M | S91A; Y92I; S93N; P94Q; F96Y | 0.38 | 0.18 |
| iPS:448195 | S31N; N32K; S33Q | S57G; S60K | T103M; K105N; L107N | S28K; S30A; N34V | S52N; S53M | Y92I; S93Q; P94Q; F96Y | 0.08 | 0.26 |
| iPS:448466 | S31N; N32K; S33Q | S57G; K58Q; S60K | K105I; Q106G; L107D; L110M | — | Y49F; A51G; S52Q; S53R | S91A; Y92I; S93Q; P94Q; F96Y | 1.10 | 1.36 |
| iPS:448689 | S31N; N32R; S33L | S57G; S60K | K105N; L107D | S28Y; S30V | A51S; S52Y; S53N | S91A; Y92I; S93M; P94A; F96Y | 0.20 | 0.62 |
| iPS:449034 | S31N; N32K; S33Q | S57G; S60K | K105I; L107D | S28P; S30A; R31Q | A51G; S52R; S53Y | S91A; Y92I; S93Q; P94N; F96Y | 1.42 | 1.58 |
| iPS:448075 | S33H | S57G; S60K | K105D; L107D | — | Y49F; A51G; S52Q; S53R | S91A; Y92I; S93V; P94Q; F96Y | 2.10 | 3.69 |
| iPS:448924 | N32R; S33Y | S57G; K58Q; S60K | T103M; K105N; L107N | S28P; N34S | Y49F; A51G; S52Q; S53R | S91A; Y92I; P94I; F96Y | 0.45 | 0.21 |
| iPS:448752 | S31N; N32K S33Q; | S57G; S60K | T103M; K105N; L107N; | S28Q; S30A | A51S; S52Y; S53N | S91A; Y92I; S93I; P94Q; F96Y | — | 0.30 |
| iPS:448772 | S31N; N32K; S33Q | S57G; S60K | T103M; K105S; Q106G; L107D | — | A51S; S52Y; S53N | S91A; Y92I; S93Q; P94N; F96Y | 0.89 | 2.01 |
| iPS:448117 | N32H; S33V | S57G; S60K | T103M; K105S; Q106E; L107D | S28T; S30V | Y49F; A51G; S52Q; S53R | Y92I; S93Q; P94T; F96Y | 1.26 | 2.27 |
| iPS:448788 | N32R; S33Q | S57G; S60K | T103M; K105Q; Q106G; L107N | — | A51G; S52R; S53I | S91A; Y92I; S93I; P94N; F96Y | 0.09 | 0.37 |

TABLE 20-continued

In vitro inhibitory potency of 19H8 variant antibodies and Fab-Fc fusion proteins

| | Substitutions with respect to 19H8 VH sequence (SEQ ID NO: 296) | | | Substitutions with respect to 19H8 VL sequence (SEQ ID NO: 67) | | | PAC1 functional cAMP assay | |
|---|---|---|---|---|---|---|---|---|
| Variant Ab ID. | HC FR1-CDR1 | HC CDR2 | HC CDR3 | LC CDR1 | LC FR2-CDR2 | LC CDR3 | mAb IC50 in nM (bivalent target binding) | Fab-Fc fusion protein IC50 in nM (monovalent target binding) |
| iPS:448593 | S31N; N32H; S33Q | S57G; S60K | K105I; L107D | — | A51S; S52Y; S53N | S91A; Y92I; S93Q; P94N; F96Y | 2.79 | 20.67 |
| iPS:448238 | N32R; S33D | S57G; S60K | T103Q; K105N; Q106E; L107D | S28R; S30A | Y49F; A51G; S53I | S91A; Y92I; S93Q; P94N; F96Y | 0.65 | 1.63 |
| iPS:448901 | S31N; N32R; S33L | S57G; S60K | T103R; K105E; Q106G; L107D; L110F | — | A51S; S52Y S53N | Y92I; S93Q; P94Q; F96Y | 0.15 | 0.41 |
| iPS:448655 | S31N; N32K S33Q | Y55F; S57R; K58T; S60K | T103M; K105S; Q106E; L107D | S28Y S30V | A51S; S52Y; S53N | S91A; Y92I; S93Q; P94Q; F96Y | — | 1.34 |
| iPS:448730 | S31N; N32R; S33L | S57G; S60K | T103V; K105I; Q106G; L107N | S28M; S30A | A51S; S52Y; S53N | S91A; Y92I; S93I; P94N; F96Y | 0.08 | 0.14 |
| iPS:449027 | S31N; N32K; S33Q | S57G; S60K | T103M; K105N; L107N | S28Y; S30V | A50G; S52R; S53N | Y92I; S93Q; P94T; F96Y | — | 1.85 |
| 3574 | S31N; N32K; S33Q | S57G; S60K | T103M; K105N; L107N | — | — | — | 0.19 | — |
| 3575 | — | — | — | S28Q; S30A; | A51S; S52Y; S53N | S91A; Y92I; S93I; P94Q; F96Y | 0.14 | — |
| 19H8 Wild-Type | — | — | — | — | — | — | 0.40[1] | 8.21 |

[1]Historical value obtained from a previous assay and included for comparative purposes.

When formatted as Fab-Fc fusion proteins, the 19H8 variants exhibited a 2-fold to 58-fold increase in inhibitory potency as compared with the parental 19H8 Fab-Fc fusion protein. Many of the 19H8 variants were more potent than the 29G4v10 variants when formatted as Fab-Fc fusion proteins (compare results in Table 20 with those in Table 12 for Fab-Fc fusion proteins). When formatted as bivalent monoclonal antibodies, the 19H8 variants also exhibited potent human PAC1 neutralizing activity with IC50 values in the single digit nanomolar or picomolar range.

Example 7. In Vivo Functional Activity of a Human PAC1 Antibody Variant in Cynomolgus Monkeys To evaluate target engagement in vivo with anti-PAC1 antibody 420653, the ability of the antibody to inhibit maxadilan-induced increase in dermal blood flow in cynomolgus monkeys was assessed. Maxadilan is a selective agonist of the PAC1 receptor and can activate the receptor in rodents, cynomolgus monkeys, and humans. As described in Example 4, intradermal administration of maxadilan causes an increase in local dermal blood flow that can be measured by laser Doppler imaging. Inhibition of this effect by anti-PAC1 antibodies can serve as a translational pharmacodynamic model of antagonism of PAC1 biological activity.

Male cynomolgus monkeys between 5 and 8 years of age were used for the study. A dosing solution of maxadilan (Bachem, H6734.0500) was prepared fresh daily by diluting maxadilan stock solution (0.5 mg/mL) in 1× phosphate-buffered saline (PBS). Anti-PAC1 antibody 420653 or 29G4v22, which was tested as a control, were prepared in 10 mM sodium-acetate, 9% sucrose, 0.01% Tween-80, pH 5.2 (A52SuT) at different concentrations, depending on the dose required for the experiment, and administered via intravenous (i.v.) infusion.

A laser Doppler imager (LDI2-IR, Moor Instruments, Ltd, Wilmington, DE) was used to measure dermal blood flow (DBF) on a shaved patch of skin of either the ventral forearm or medial thigh using a low-power laser beam generated by a 633 nm helium-neon bulb. The infra-red wavelength was combined with a visible red aiming beam to give a higher weighting to blood flow in the deeper dermis (0.6 to 1 mm).

The incident light was scattered by static tissue and moving blood. Moving blood in the microvasculature caused a Doppler light shift. The shifted light from moving blood and the non-shifted light from tissue was then directed onto 2 square-law detectors. The detected intensity fluctuations were then processed to give parameters of flux (proportional to tissue blood flow) and concentration (proportional to the concentration of moving blood cells). The measurement resolution was 0.2 to 2 mm, with a scanning distance between the instrument aperture and the tissue surface of 20 to 100 cm.

DBF was measured as Flux (relative units) and expressed as % change from baseline 30 min post-maxadilan administration [100×(individual post-maxadilan flux-individual baseline flux)/individual baseline flux]. Flux units from two separate O-rings were averaged together for each test session. The inhibitory effect of the anti-PAC1 antibodies on maxadilan-induced increase in blood flow (MIIBF) from individual animals was expressed as % inhibition [100×(Mean of day 0% change from baseline−individual antibody treated animal % change from baseline)/Mean of day 0% change from baseline].

Following anesthesia and stabilization of vital signs for 15 to 20 minutes, rubber O-rings (0.925 cm inner diameter, 0-Rings West, Seattle, WA) were placed about 0.6 to 1 cm apart from each other on the pre-shaved skin of the ventral forearm or medial thigh without direct positioning over a visible vessel. The limb used for each testing session was pre-determined, with a different limb used on different testing days of the study. After placement of the O-rings on the skin, a baseline measurement was taken. After the baseline scan, a maxadilan solution of 1 ng in 20 μL vehicle (PBS) was injected intradermally at the center of the O-rings. The O-rings served as a region of interest during data analysis.

Prior to anti-PAC1 antibody administrations, the time course of MIIBF was obtained at Day 0. The maxadilan dose of 1 ng was selected based on the result of a previous maxadilan dose-response in cynomolgus monkeys. After a pre-maxadilan baseline DBF measurement, the time course of DBF response to maxadilan intradermal injection was assessed by obtaining laser Doppler scans at 5, 10, 15, 20, 25, and 30 minutes post-maxadilan application. To identify maxadilan responders and eliminate non-responders from inclusion in the study, a pre-screen procedure prior to antibody administration was implemented. Animals were considered maxadilan responders and included in the study if they had a change in DBF flow ≥60 flux units (average of post maxadilan DBF at 30 minutes−average of baseline).

Twenty-four cynomolgus monkeys identified as maxadilan responders received either antibody 420653 at a dose of 0.1 mg/kg or 3 mg/kg or antibody 29G4v22 at a dose of 10 mg/kg at Day 0. The antibodies were administered via i.v. infusion to the saphenous vein at a rate of 1 mL/min by a syringe infusion pump. Post-maxadilan DBF measurements were taken on Days 2, 4, 7, 10, 14, 21, 28, and 36 using different limbs. In each case, DBF was measured by laser Doppler imaging for 30 minutes following 1 ng maxadilan intradermal injection. Whole blood samples for pharmacokinetic (PK) analysis were collected at multiple time points including prior to antibody dosing, 30 min, 1, 2, 4, 7, 10, 14, 21, 28, 35 or 36 and 42 days post-antibody treatment.

Figure 10A:
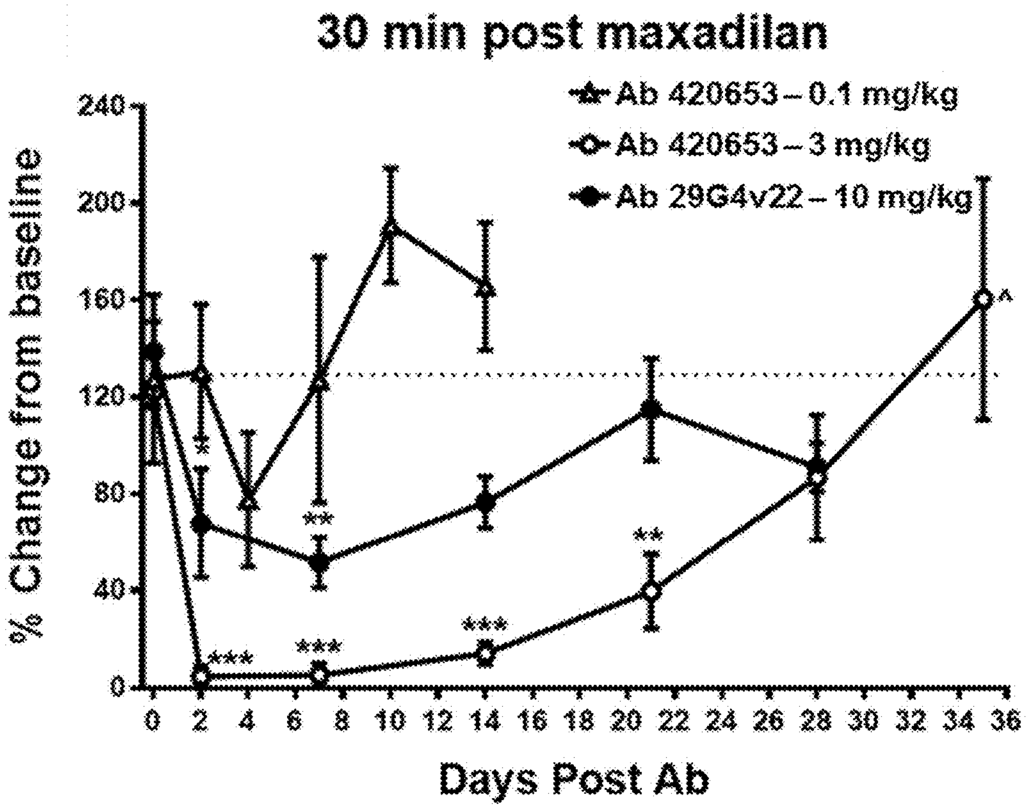
FIGS. 10A and 10B show the time-course of the inhibitory effects of anti-PAC1 antibodies 420653 and 29G4v22 on maxadilan-induced increase in dermal blood flow in cynomolgus monkeys. Twenty-four cynomolgus monkeys were given a single i.v. bolus injection of antibody 420653 at 0.1 mg/kg or 3 mg/kg or antibody 29G4v22 at 10 mg/kg at Day 0. On Days 2, 4, 7, 10, 14, 21, 28, and 36 following antibody dosing, post-maxadilan responses were measured. In each case, dermal blood flow was measured by laser Doppler imaging 30 minutes following 1 ng maxadilan intradermal injection. All data are expressed as the mean±standard error of the mean.
Figure 10B:
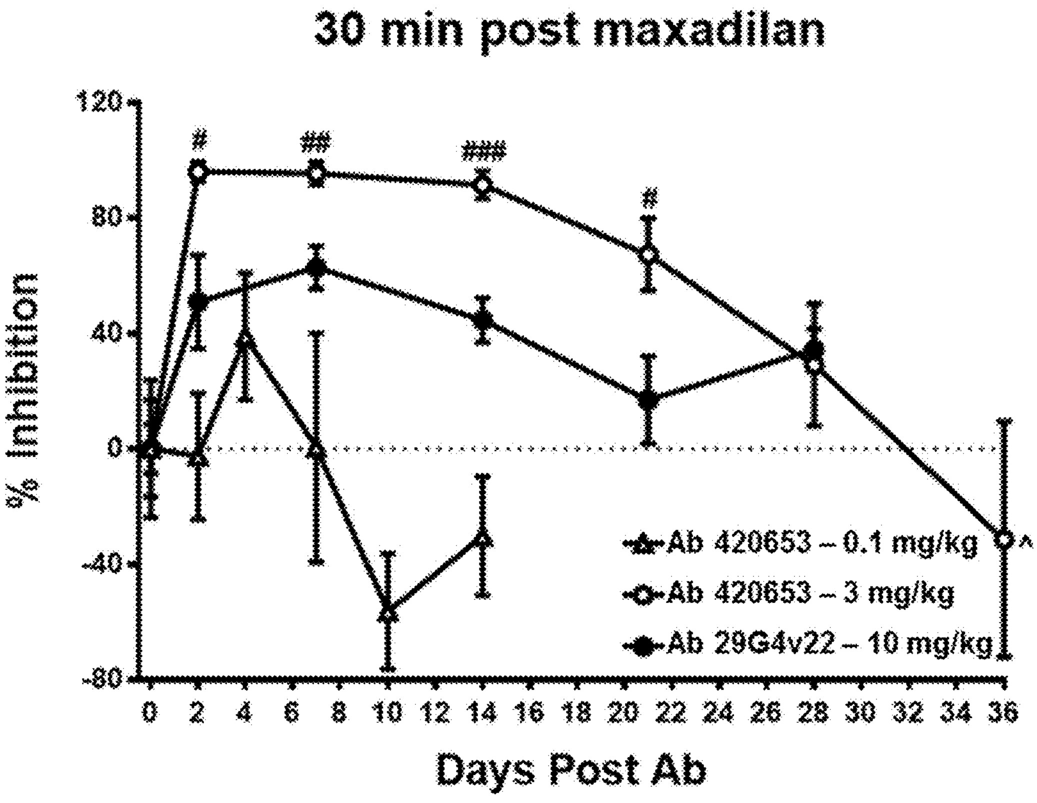

As shown in FIG. 10A, antibody 420653 at 3 mg/kg, but not 0.1 mg/kg, significantly prevented MIIBF on Day 2, Day 7, Day 14, and Day 21 (post-antibody treatment) compared to Day 0 (pre-antibody treatment) (n=8 animals/group; Bonferroni adjusted p-value=0.0087). Antibody 29G4v22 at 10 mg/kg also significantly prevented MIIBF on Day 2 and Day 7 (n=8 animals/group)(FIG. 10A). The maximum inhibitory effect of antibody 420653 at 3 mg/kg was on Day 2 with 96% inhibition, whereas at 0.1 mg/kg, antibody 420653 produced a maximum inhibition of 39% on Day 4 that was not statistically significant (FIG. 10B). Antibody 29G4v22 at 10 mg/kg produced a maximum inhibition of 63% on Day 7 (FIG. 10B). Comparison of antibody 420653 (3 mg/kg) and antibody 29G4v22 (10 mg/kg) at the same time points showed significant differences on Day 2, Day 7, Day 14 and Day 21 (FIG. 10B).

The antibody serum concentrations for antibody 420653 and antibody 29G4v22 at days when DBF measurements were taken are shown below in Table 21. The low limit of quantitation (LLOQ) or below quantitation level (BQL) was 10 ng/mL for antibody 420653 and 50 ng/mL for antibody 29G4v22.

TABLE 21

Serum Concentrations of Antibodies 420653 and 29G4v22 in Cynomolgus Monkey Following Antibody Treatment

| Dose Treatment | Dose (mg/kg) | Time Point (Days) | Serum Concentration (μg/L) Mean | SD | n |
|---|---|---|---|---|---|
| Antibody 420653 | 0.1 | 2 | 687 | 96.6 | 8 |
| | | 4 | 315 | 57.3 | 8 |
| | | 7 | 95.9 | 33.5 | 8 |
| | | 10* | 30.1 | 10.9 | 4 |
| | | 14* | LLOQ | — | 0 |
| Antibody 420653 | 3 | 2 | 36,200 | 5,010 | 8 |
| | | 7 | 14,100 | 2,170 | 8 |
| | | 14 | 5350 | 2,140 | 8 |
| | | 21* | 2,210 | 1,800 | 7 |
| | | 36* | 1,480 | — | 1 |
| Antibody 29G4v22 | 10 | 2 | 113,000 | 28,400 | 8 |
| | | 7 | 38,600 | 8,230 | 8 |
| | | 14 | 13,900 | 6,360 | 8 |
| | | 21 | 4,850 | 2,790 | 8 |
| | | 28 | 1,990 | 1,490 | 8 |

*Fewer PK data points due to some samples with LLOQ/BQL

Overall, these results demonstrate that antibody 420653 significantly attenuated MIIBF in cynomolgus monkeys when administered at a dose of 3 mg/kg. The inhibitory effect of antibody 420653 at 3 mg/kg on MIIBF was more robust than antibody 29G4v22 at a higher dose of 10 mg/kg.

All publications, patents, and patent applications discussed and cited herein are hereby incorporated by reference in their entireties. It is understood that the disclosed invention is not limited to the particular methodology, protocols and materials described as these can vary. It is also understood that the terminology used herein is for the purposes of describing particular embodiments only and is not intended to limit the scope of the appended claims.

Those skilled in the art will recognize, or be able to ascertain using no more than routine experimentation, many equivalents to the specific embodiments of the invention described herein. Such equivalents are intended to be encompassed by the following claims.

What is claimed:

1. An isolated antibody or antigen-binding fragment thereof that specifically binds to human pituitary adenylate cyclase-activating polypeptide type I receptor (PAC1), wherein the antibody or antigen-binding fragment thereof comprises a light chain variable region comprising complementarity determining regions CDRL1, CDRL2, and CDRL3 and a heavy chain variable region comprising complementarity determining regions CDRH1, CDRH2, and CDRH3, wherein CDRL1 comprises the sequence of SEQ ID NO: 7; CDRL2 comprises the sequence of SEQ ID NO: 26; CDRL3 comprises the sequence of SEQ ID NO: 36; CDRH1 comprises the sequence of SEQ ID NO: 88; CDRH2 comprises the sequence of SEQ ID NO: 116; and CDRH3 comprises the sequence of SEQ ID NO: 171.

2. The isolated antibody or antigen-binding fragment thereof of claim 1, wherein the light chain variable region comprises CDRL1, CDRL2, and CDRL3 of SEQ ID NOs: 7, 26, and 36, respectively, and the heavy chain variable region comprises CDRH1, CDRH2, and CDRH3 of SEQ ID NOs: 88, 116, and 171, respectively, and wherein the light chain variable region comprises (i) a sequence that is at least 90% identical to the sequence of SEQ ID NO: 54, (ii) a sequence that is at least 95% identical to the sequence of SEQ ID NO: 54, or (iii) the sequence of SEQ ID NO: 54.

3. The isolated antibody or antigen-binding fragment thereof of claim 1, wherein the light chain variable region comprises CDRL1, CDRL2, and CDRL3 of SEQ ID NOs: 7, 26, and 36, respectively, and the heavy chain variable region comprises CDRH1, CDRH2, and CDRH3 of SEQ ID NOs: 88, 116, and 171, respectively, and wherein the heavy chain variable region comprises (i) a sequence that is at least 90% identical to the sequence of SEQ ID NO: 203, (ii) a sequence that is at least 95% identical to the sequence of SEQ ID NO: 203, or (iii) the sequence of SEQ ID NO: 203.

4. The isolated antibody or antigen-binding fragment thereof of claim 1, wherein the light chain variable region comprises the sequence of SEQ ID NO: 54 and the heavy chain variable region comprises the sequence of SEQ ID NO: 203.

5. The isolated antibody or antigen-binding fragment thereof of claim 1, wherein the antibody or antigen-binding fragment thereof is a monoclonal antibody or antigen-binding fragment thereof.

6. The isolated antibody or antigen-binding fragment thereof of claim 5, wherein the monoclonal antibody or antigen-binding fragment thereof is a humanized antibody or antigen-binding fragment thereof or a fully human antibody or antigen-binding fragment thereof.

7. The isolated antibody or antigen-binding fragment thereof of claim 5, wherein the monoclonal antibody comprises a human constant region from is a human IgG1, IgG2, IgG3, or IgG4 antibody.

8. The isolated antibody or antigen-binding fragment thereof of claim 7, wherein the monoclonal antibody comprises a human constant region from is an aglycosylated human IgG1 antibody.

9. The isolated antibody or antigen-binding fragment thereof of claim 8, wherein the monoclonal antibody comprises a heavy chain constant region having a mutation at amino acid position N297 according to EU numbering.

10. The isolated antibody or antigen-binding fragment thereof of claim 9, wherein the mutation is N297G.

11. The isolated antibody or antigen-binding fragment thereof of claim 10, wherein the heavy chain constant region further comprises R292C and V302C mutations according to EU numbering.

12. A pharmaceutical composition comprising the isolated antibody or antigen-binding fragment thereof of claim 1 and a pharmaceutically acceptable excipient.

13. A pharmaceutical composition comprising the isolated antibody or antigen-binding fragment thereof of claim 4 and a pharmaceutically acceptable excipient.

14. An isolated antibody that specifically binds to human PAC1, wherein the antibody comprises a light chain and a heavy chain, wherein the light chain comprises the sequence of SEQ ID NO: 506 and the heavy chain comprises the sequence of SEQ ID NO: 522.

15. A pharmaceutical composition comprising the isolated antibody of claim 14 and a pharmaceutically acceptable excipient.

16. A method for inhibiting vasodilation in a patient in need thereof comprising administering to the patient an effective amount of the antibody or antigen-binding fragment thereof of claim 1.

17. A method for inhibiting activation of human PAC1 receptor in a patient having a headache condition comprising administering to the patient an effective amount of the antibody or antigen-binding fragment thereof of claim 1.

18. The method of claim 17, wherein the headache condition is migraine or cluster headache.

19. A method for ameliorating a headache condition in a patient in need thereof comprising administering to the patient an effective amount of the antibody or antigen-binding fragment thereof of claim 1.

20. The method of claim 19, wherein the headache condition is migraine or cluster headache.

* * * * *